(12) United States Patent
Hoshino et al.

(10) Patent No.: US 10,870,866 B2
(45) Date of Patent: *Dec. 22, 2020

(54) METHOD OF PRODUCING LINALOOL USING A MICROORGANISM

(71) Applicant: AJINOMOTO CO., INC., Tokyo (JP)

(72) Inventors: Yasushi Hoshino, Kanagawa (JP); Akiko Matsudaira, Kanagawa (JP); Mika Moriya, Kanagawa (JP); Nobuhisa Nitta, Kanagawa (JP); Yosuke Nishio, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/927,622

(22) Filed: Mar. 21, 2018

(65) Prior Publication Data

US 2018/0291403 A1 Oct. 11, 2018

Related U.S. Application Data

(63) Continuation of application No. PCT/JP2016/078322, filed on Sep. 26, 2016.

(30) Foreign Application Priority Data

| Sep. 25, 2015 | (JP) | ................ | 2015-188597 |
| Jun. 1, 2016 | (JP) | ................ | 2016-110490 |
| Jun. 1, 2016 | (JP) | ................ | 2016-110491 |

(51) Int. Cl.

| C12P 7/04 | (2006.01) |
| C12P 5/00 | (2006.01) |
| C12N 15/70 | (2006.01) |
| C12N 15/74 | (2006.01) |
| C12N 9/88 | (2006.01) |
| C12N 15/09 | (2006.01) |
| C12N 9/00 | (2006.01) |

(52) U.S. Cl.
CPC .......... *C12P 7/04* (2013.01); *C12N 9/00* (2013.01); *C12N 9/88* (2013.01); *C12N 15/09* (2013.01); *C12N 15/70* (2013.01); *C12N 15/74* (2013.01); *C12P 5/007* (2013.01); *C12Y 402/03025* (2013.01); *C12Y 402/03026* (2013.01)

(58) Field of Classification Search
None
See application file for complete search history.

(56) References Cited

U.S. PATENT DOCUMENTS 8,658,221 B2  2/2014  Baeuerlein et al.
2008/0274523 A1  11/2008  Renninger et al.

FOREIGN PATENT DOCUMENTS

| CN | 102071155 A | 5/2011 |
| EP | 3225691 A1 | 10/2017 |
| JP | 2005-298580 A | 10/2005 |
| JP | 2006-291007 A | 10/2006 |
| JP | 2011-506713 A | 3/2011 |
| JP | 2011-147432 A | 8/2011 |
| JP | 2013-013406 A | 1/2013 |
| JP | 2013-063063 A | 4/2013 |
| JP | 2013-143944 A | 7/2013 |
| WO | WO2017/051930 A1 | 3/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Wolff et al. Tetrahedron Letters 43 (2002) 2555-2559 (Year: 2002).*
Martin et al. Nat Biotechnol. Jul. 2003;21(7):796-802. Epub Jun. 1, 2003. (Year: 2003).*
Accession D12651. May 12, 2009. (Year: 2009).*
De Werra et al. Applied and Environmental Microbiology Jun. 2009, 75 (12) 4162-4174 (Year: 2009).*
Nakano et al. ChemBioChem 2011, 12, 2403-2407 (Year: 2011).*
Sequence Listing Validation Report dated Jun. 10, 2019 (Year: 2019).*
15927622,Computer_Readable_Form_(CRF)_for_Sequence_Listing_-_Defective,Dec. 27, 2019 (Year: 2019).*
Andreeva, I. G., et al., "Identification of *Pantoea ananatis* gene encoding membrane pyrroloquinoline quinone (PQQ)-dependent glucose dehydrogenase and pqqABCDEF operon essential for PQQ biosynthesis," FEMS Microbiol. Lett. 2011;318:55-60.
Chen, X., et al., "Characterisation of an (S)-linalool synthase from kiwifruit (*Actinidia arguta*) that catalyzes the first committed step in the production of floral lilac compounds," Functional Plant Biology 2010;37:232-243.
Partial Supplementary European Search Report for European Patent App. No. 16848716.3 (dated Feb. 13, 2019).
Nakano, C., et al., "Identification and Characterization of the Linalool/Nerolidol Synthase from *Streptomyces clavuligerus*," ChemBioChem 2011;12:2403-2407.
Dickschat, J. S., et al., "Volatiles Released by a *Streptomyces* Species Isolated from the North Sea," Chem. Biodivers. 2005;2(7):837-865.
Thanasomboon, R., et al., "Construction of synthetic *Escherichia coli* producing s-linalool," Procedia Comput. Sci. 2012;11:88-95.
Iijima, Y., et al., "The Biochemical and Molecular Basis for the Divergent Patterns in the Biosynthesis of Terpenes and Phenylpropenes in the Peltate Glands of Three Cultivars of Basil," Plant Physiol. 2004;136(3):3724-3736.

(Continued)

*Primary Examiner* — Christian L Fronda
(74) *Attorney, Agent, or Firm* — Cermak Nakajima & McGowan LLP; Shelly Guest Cermak

(57) ABSTRACT

The present invention describes an efficient method for producing linalool. The present invention provides a method for producing linalool, the method including culturing a microorganism expressing linalool synthase in a culture medium to produce linalool. The present invention also describes a microorganism able to express linalool synthase and efficiently produce linalool.

16 Claims, 29 Drawing Sheets

Specification includes a Sequence Listing.

(56) References Cited

OTHER PUBLICATIONS

Jia, J.-W., et al., "(3R)-Linalool Synthase from *Artemisia annua* L.: cDNA Isolation, Characterization, and Wound Induction," Arch. Biochem. Biophys. 1999;372(1):143-149.

Sugiura, M., et al., "Molecular Cloning and Characterization of a Linalool Synthase from Lemon Myrtle," Biosci. Biotechnol. Biochem. 2011;75(7):1245-1248.

Shimada, T., et al., "Characterization of three linalool synthase genes from Citrus unshiu Marc. and analysis of linalool-mediated resistance against *Xanthomonas citri* subsp. citri and Penicilium italicum in citrus leaves," Plant Sci. 2014;229:154-166.

Landmann, C., et al., "Cloning and functional characterization of three terpene synthases from lavender (*Lavandula angustifolia*)," Arch. Biochem. Biophys. 2007;465:417-429.

Crowell, A., et al., "Molecular cloning and characterization of a new linalool synthase," Arch. Biochem. Biophys. 2002;405:112-121.

Harada, H., et al., "Efficient synthesis of functional isoprenoids from acetoacetate through metabolic pathway-engineered *Escherichia coli*," Appl. Microbiol. Biotechnol. 2009;81:915-925.

Harada, H., "Development of efficient functional analysis of plant terpene biosynthetic genes: mainly of saquiterpene biosynthetic genes," BSJ-Review 2011;2:10-17.

Aprotosoaie, A. C., et al., "Linalool: a review on a key odorant molecule with valuable biological properties," Flavour Fragr. J. 2014;29:193-219.

Semikolenov, V. A., et al., "Linalool synthesis from alpha-pinene: kinetic peculiarities of catalytic steps," Appl. Catalyst A: General 2001;211:91-207.

Sun, M. X., et al., "Regulation of isoprenoid pathway for enhanced production of Linalool in *Saccharomyces cerevisiae*," Chinese J. Biotechnol. 2013;29(6):751-759.

Herrero, O., et al., "Engineering the *Saccharomyces cerevisiae* isoprenoid pathway for de novo production of aromatic monoterpenes in wine," Metabolic Eng. 2008;10:78-86.

Rico, J., et al., "Enhanced Production of a Plant Monoterpene by Overexpression of the 3-Hydroxy-3-Methylglutaryl Coenzyme a Reductase Catalytic Domain in *Saccharomyces cerevisiae*," Appl. Environmen. Microbiol. 2010;76 (19):6449-6454.

Carrasco, A., et al., "Lavandula angustifolia and Lavandula latifolia Essential Oils from Spain: Aromatic Profile and Bioactivities," Planta Med. 2016;82:163-170.

Eleni, M., et al., "High Quality Beramot Oil from Greece: Chemical Analysis Using Chiral Gas Chromatography and Larvicidal Activity against the West Nile Virus Vector," Molecules 2009;14(2):839-849.

Özek, T., et al., "Enantiomeric Distribution of Some Linalool Containing Essential Oils and Their Biological Activities," Rec. Nat. Prod. 2010;4:4:180-192.

International Search Report and Written Opinion for PCT Patent App. No. PCT/JP2016/078322 (dated Nov. 29, 2016) with English language translation of the ISR.

\* cited by examiner

Optimization of PMK-MVD-yidi
3471bp

FIG. 20

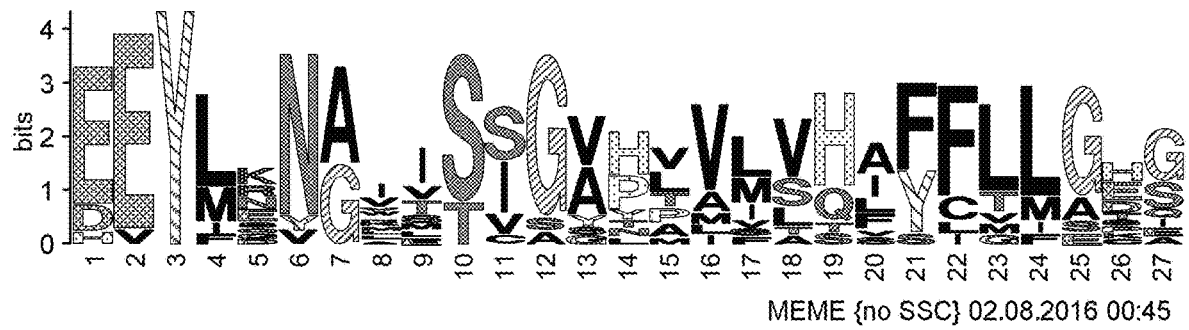

MEME {no SSC} 02.08.2016 00:45

FIG. 21

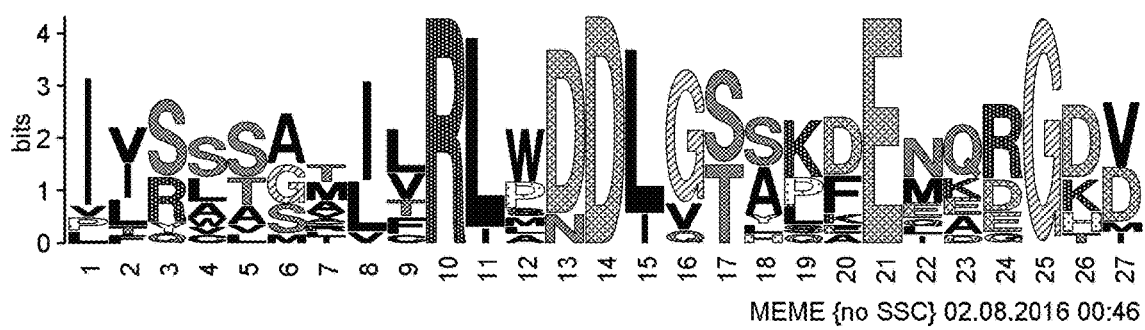

MEME {no SSC} 02.08.2016 00:46

FIG. 22

| M23 | YIIDDIFDVYGTLDELILFTETITRWDLAAMGQLPEYMKIC |
| --- | --- |
| M29 | YIIDDIFDVHGTLDELTLFTEAVNRWDIAAFETLPNYMKIC |
| M37 | YVIDDIFDTYGKMDELILFTDAIRRWDLEAMEGLPEYMKIC |
| M25 | YLIDDIFDVYGTLDELTLFTEVVNRWEIGSIEHLPDYMKIC |
| M27 | TSLDDVYDIYGTLDELQLFTDAIQRWDTESISRLPYYMQLF |
| M31 | TAIDDMYDIYGSPDELRRFTDAVNRWDTEALVDLPDYMKIC |
| M21 | YIIDDIFYVCGALDALTLFTEPINRWDLGDIDQLPEYMKIC |
| M17 | TTIDDIYDIYGTLEELQLFTVAFENWDINRLDELPEYMRLC |
| M15 | YVIDDIFDVYGELEELTIFTRVVERWDHKGLKTLPKYMRVC |
| M35 | TALDDVYDIYGTLDELQLFTHVIRRWDTESATQLPYYLQLF |
| M19 | SIIDDIYDAYGTIEELELFATAIERWDLSAIDLLPEYMKLC |
| M33 | TSLDDVYDIYGTLDELQLFTNLFERWDNASIGRLPEYLQLF |
| M39 | TVADDFFDVEGSMVDLEKLTDAVRRWDAEGLGSHSKTIFEA |

FIG.23

| | |
|---|---|
| M25 | DLHEVALRFRLLRQHGYFVSDDVFNNFKN |
| M27 | DLYFTALGFRLLRQHGFQVSQEVFDCFKN |
| M29 | DLYEVALRFRLLRQEGYHVPADVFNNFKN |
| M21 | DLQEVALRFRLLRQQGYYVSADVFNRFRN |
| M33 | DLYFTALGFRLFRQHGFKVSQEVFDRFKN |
| M35 | DLHFTSLGFRLLRQHGFNVSQGVFDCFKN |
| M23 | DLQEVALRFRLLRQEGYYVPADMFNNFRI |
| M31 | DLSTTALRFRLLRQHGYPVSSEVFDQFRS |
| M17 | DLHATALEFRLFRQHGFNVSEDVFDVFME |
| M19 | ELYYISLHFRLLRQNGYKISADVFNSFKD |
| M15 | DLHEIALRFRLLRQEGHYVQENKKGGFKD |
| M37 | DLFTAALRFRLLRHNGIQVTPEIFLKFKD |
| M39 | ELYRDSLAFWLLRVNNHWVSPSIFCWFLD |

FIG.24

| | |
|---|---|
| M23 | EIAKKDFNMVQALHQKEIVQVTKWWKDLGLTK |
| M29 | ELAKADFNMVQSIHQQELLQISKWWQDRGLAE |
| M17 | EPAKIDFNIVQAIHQEELKNVSSWWMETGLGK |
| M27 | ELAKLDFNIIQATQQEELKDLSRWWKSTCLAE |
| M33 | ELAKLNFNIVQATQQEELKALSRWWSSLGLAE |
| M25 | TVAKTDLNMVQSLHQKEVAQVSKWWKELGLCK |
| M37 | ELAILDYNQVQAQHQSELTEITRWWKQLGLVE |
| M35 | ELAKLDFNIIQATQQEELKDLSRWWNDSSLPQ |
| M21 | ELANMDFKLVQSLHQKEIVQISSWWRELGLAK |
| M31 | ELAKLDYNLVQSSYQTELKELTRWWTDLGFKE |
| M19 | TFAMLDFNILQKQHQEELRDIVRWWKNFDVPN |
| M15 | RVAEIDSIRLKSLTQGEMSQTFKWWTELGLEK |
| M39 | QLAVKNYTLRQLVYRDELAEVERWSKERGLCD |

FIG.25

| | |
|---|---|
| M21 | EEYLENGIVSSGVHLVLVHIFFLLGHG |
| M25 | EEYLKNGIISSGVNVVMVHIFFLLGEG |
| M29 | HEYLKNGVISSGVHVVLVHLFFLLGHG |
| M23 | EEYLRNGIESSGVHVALAHFFFLLGHG |
| M15 | EEYMKNGVVSSGVHLVMLHAYILLGEE |
| M37 | EEYIENGASTVGAYMVLVHLFFLIGEG |
| M31 | DEYLSNAWTSVGGPAAMVHAYFLMGCA |
| M33 | EEYFDNAFMTIGAPPVLSQAYFTLGSS |
| M27 | EEYLNNAYISIGATPVISQVFFTLATS |
| M35 | EEYLNYASITIGAPAVISQIYFMLAKS |
| M17 | EEYMQNARISISSPTIFVHFYCVFSDQ |
| M39 | DVYLGNAMTSIAAHTMVLTASCLLGPG |
| M19 | EEYMRVALLSCGYLLLSTSSFLGMEDI |

FIG.26

| | |
|---|---|
| M25 | IISSTAAILRLWDDLGSAKDENQDGDD |
| M29 | IISSTAAILRLWDDLGSAKDENQDGHD |
| M23 | IISSTATILRLWDDLGSAKDENQEGKD |
| M15 | IVSSAATILRLWDDLGSAKDENQDGTD |
| M27 | ILRLSGMLVRLPDDLGTSPFEMKRGDV |
| M35 | IIRLSGMLVRLPDDLGTLPFEMKRGDV |
| M21 | IVSSVATILRIWDDLGSAKDENQGGKD |
| M33 | ILRVSGMLVRLPDDLGTSSFEMERGDV |
| M19 | IVQASSIICRLMDDIVSHKFEQQRGHV |
| M37 | PFSAAGRIFRLWDDLGTSQEEEERGDM |
| M17 | VVRCSSSVFRLANDLVTSPDELARGDV |
| M31 | LLYWSSLITRLSDDLGTSLAEIARGDV |
| M39 | ITSLLMVLTRLLNDIQSYLKEEDEGKI |

FIG.27

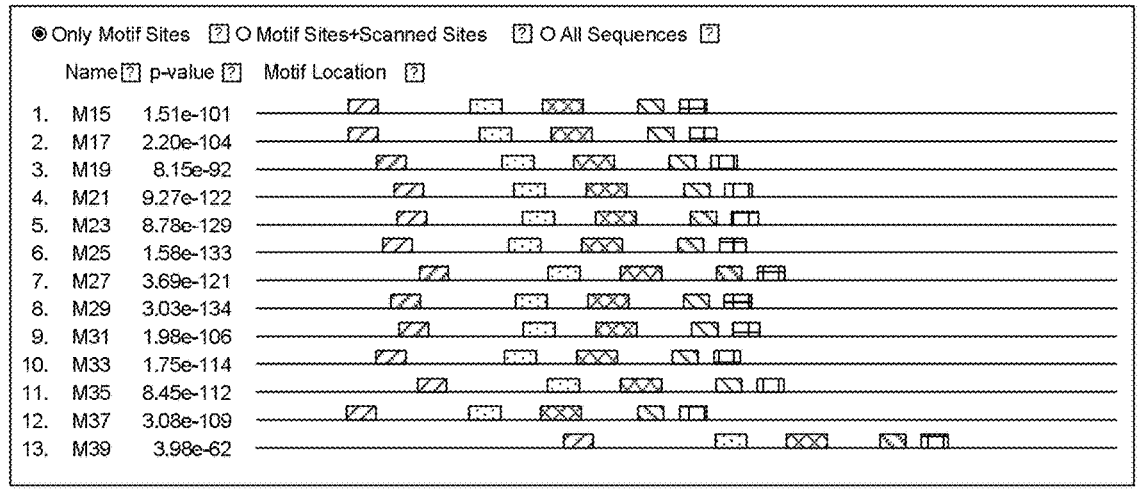

FIG.28

```
>At1LINS_M15
MANTAKRSILRNVHASVSNPSKQFHNKTSLEYLHELNIKKIKNILSANVDVPSENLEMIDVIQSLGIDLHFRQEIEQTLH
MIYKEGLQFNGDLHEIALRFRLLRQEGHYVQENKKGGFKDVVKNDVKGLTELFEASELRVEGEETLDGAREFTYSRLNEL
CSGRESHQKQEIMKSLAQPRHKTVRGLTSKRFTSMIKIAGQEDPEWLQSLLRVAEIDSIRLKSLTQGEMSQTFKWWTELG
LEKDVEKARSQPLKWHTWSMKILQDPTLTEQRLDLTKPISLVYVIDDIFDVYGELEELTIFTRVVERWDHKGLKTLPKY
MRVCFEALDMITTEISMKIYKSHGWNPTYALRQSWASLCKAFLVEAKWFNSGYLPTTEEYMKNGVVSSGVHLVMLHAYIL
LGEELTKEKVELIESNPGIVSSAATILRLWDDLGSAKDENQDGTDGSYVECYLNEYKGSTVDEARTHVAQKISRAWKRLN
RECLNPCPFSRSFSKACLNIARTVPLMYSYDDDQRLPDEYLKSLM
```

FIG.29

>At2LINS_M17

MRRSANYQPSRWDHHHLLSVENKFAKDKRVRERDLLKEKVRKMLNDEQKTYLDQLEFIDDLQKLGVSYHFEAEIDNILTS
SYKKDRTNIQESDLHATALEFRLFRQHGFNVSEDVFDVFMENCGKFDRDDIYGLISLYEASYLSTKLDKNLQIFIRPFAT
QQLRDFVDTHSNEDFGSCDMVEIVVQALDMPYYWQMRRLSTRWYIDVYGKRQNYKNLVVVEFAKIDFNIVQAIHQEELKN
VSSWWMETGLGKQLYFARDRIVENYFWTIGQIQEPQYGYVRQTMTKINALLTTI DDIYDIYGT LEELQLFTVAFENWDI
NRLDELPEYMRLCFLVIYNEVNSIACEILRTKNINVIPFLKKSWTDVSKAYLVEAKWYKSGHKPNLEEYMQNARISISSP
TIFVHFYCVFSDQLSIQVLETLSQHQQNVVRCSSSVFRLANDLVTSPDELARGDVCKSIQCYMSETGASEDKARSHVRQM
INDLWDEMNYEKMAHSSSILHHDFMETVINLARMSQCMYQYGDGHGSPEKAKIVDRVMSLLFNPIPLD

FIG.30

>Cu1LINS_M19

MLFQVSASPNKVIRINAEKESTRRSANFDPTIWGDYFLSYTGDFKESGDASVKHQELKKEIRTMLRADINKPTQTKLDLI
DDIQRLGVSYHFESEIDEILRKMHEANQDCDLGDDENVQELYYISLHFRLLRQNGYKISADVFNSFKDSNGNFKSFLKRD
IRGMLSLYEAAHLRVHGENILNEALTFTVTHLESFTSQSNTQLAAQVNRALNRPIRKSLPRLEAKHYMPIYQKDPSHNKD
LLTFAMLDFNILQKQHQEELRDIVRWWKNFDVPNKLPFIRDRVVEGYFWILGVYFEPKFLLARKILTKVISMASII DDI
YDAYG TIEELELFATAIERWDLSAIDLLPEYMKLCYCALLDAYSEFEKDLASKGILYGLPFAKESMKILVRSYIIEARW
CDQQYVPTMEEYMRVALLSCGYLLLSTSSFLGMEDIVTKEAFEWVSGNPKIVQASSIICRLMDDIVSHKFEQQRGHVASA
VECYMKQHGVSEEEAVKVFREKVGNAWKDINEELMRPPVVPMPLLERVLNLARLMDVLYQNNDSYTNPHLMKDHVAALLK
DPVFFED*

FIG.31

>Cu2LINS_M21
MAFSSKDISSDSSHIHFIPKHISKVGNRNLNNINSLLPNNKKGSINDNIGVSARLKRFTYPSEHSSNFNDDIHIKHAKKL
EVIKHILIKLGDDDSFEGLAMIDVVQRLGIDYYFQDEIELILRRQYSIFFTDGDRYNDLQEVALRFRLLRQQGYYVSADV
FNRFRNKEGEFKQNISEDINGLMSLYEASQLSIGGEDGLDEAGHFSATHLANYDLAGVVEHLLLYPYRKSLSPAKNFFHG
NFQGSEYIWILDLQELANMDFKLVQSLHQKEIVQISSWWRELGLAKKLEFAREQPVKWYVWSMACFTDPNLSWQRIELTK
PISFVYII DDIFYVCG ALDALTLFTEPINRWDLGDIDQLPEYMKICFKALNDITNEISKQGVQRSMGITLCTPLRKGVG
EVLCNAFLIEAKWFASGHLPKAEEYLENGIVSSGVHLVLVHIFFLLGHGITNETVQLIDSNPPIVSSVATILRIWDDLGS
AKDENQGGKDGSYIYYYMMEHRDLTAEDAHKHAMDKISDAWKRLNKECLSPNPFSASFTRASFNCARMVPLMYSYDDSQR
LPSLEEYIKSSLFDNLPTQGVY

FIG.32

>Cu3LINS_M23
MAFSSSSRAKLSATSHISKAPDKISKTSRPSLIEFTPSPTIYQKGCITSDNTVASPPLKHFTHTTRHPSFFDHDIQVEHS
RKLKEFKHIFSLVGGNSFEGLVMIDAVQRLRIEYLFKDEIEEILQRQYIISSTCGGHLHDLQEVALRFRLLRQEGYYVPA
DMFNNFRIKEGRFSRINVSEDIGTLMEVYEASQLSIAGEEGLDEAGHFSAKMLNECMTHLDHYHALAIGNTLRHPYHKSL
PRFMAKDVFLSNFQGERRLHVLKEIAKKDFNMVQALHQKEIVQVTKWWKDLGLTKKLPFARDQPLKWYIWSMACLTDPSL
SEQRVELTKPISLIYII DDIFDVYG TLDELILFTETITRWDLAAMGQLPEYMKICFKALDDITNEISCKVYKKHGYNPV
QSLRNAWTSLCKAFLVEAKWFASGHMPEAEEYLRNGIESSGVHVALAHFFFLLGHGITKETVELIDGNPAIISSTATILR
LWDDLGSAKDENQEGKDGSYIHYYMKEHRYSAAEEAQKSAINKISDAWKRLNKECLCPNPFSASFTRASLNLARMVPLMY
SYDDNQRLPSLEHYIKSLLFESVPTEGVY

FIG.33

>MdLINS_M25

MEFSISQSSFATSSSTPAAPEHLSSQKWSIPEDHSLLSTPLKPLNSKTKYTSSKDGIICFQNEQKLDDLRHALIKVGGEA

VESLDMIDAVQRLGLDYHFEEEIDQILQKQHIISSTTAHGAHHPTDLHEVALRFRLLRQHGYFVSDDVFNNFKNREGNFN

QMLREDIKGLMSLYEASQLSIEGEVVLEEAGKFSGHFLNSSLSHLDHHQARVVGNTLRNPHHKSLAPFMAKNFFVSSFQG

TNNRWLNILQTVAKTDLNMVQSLHQKEVAQVSKWWKELGLCKELKFARDQPIKWYIWSMACLTNPNLSDERIELTKPISF

IYLIDDIFDVYGTLDELTLFTEVVNRWEIGSIEHLPDYMKICFKALYDMTNEISCKVYQKHGWNPLHSLKKTWASLCNA

FLVEAKWFKSGHLPMAEEYLKNGIISSGVNVVMVHIFFLLGEGITNQSVEFLNGTPAIISSTAAILRLWDDLGSAKDENQ

DGDDGSYVKLYLNEHQGKTMEEAQEHVTNMISEEWKKLNKELVSPNPLPAAFTKASLNLARMVPLMYSYDDNQCLPSLDE

YMKSMLHA

FIG.34

>PfLINS_M27

MYSLRIYVAIMKKPSAKHVDNVDKKASKPSWRVSLSSSAGLRASSSLQLDVKKPADDEILTARRSGNYQPSLWDFNYLQS

LNTTQYKEVRHLKREAELIEQVKMLLEEEMEAVQQLELVDDLKNLGLSYFFEDQIKQILTFIYNEHKCFHSNSIIEAEEI

RDLYFTALGFRLLRQHGFQVSQEVFDCFKNEEGSDFKARLGDDTKGLLQLYEASFLLREGEDTLELARQYATKFLQKKVD

HELIDDNNLLSWILHSLEIPLHWRIQRLEARWFLDRYATRRDMNQIILELAKLDFNIIQATQQEELKDLSRWWKSTCLAE

KLPFVRDRLVESYFWAIALFEPHQYGYHRKVAAKIITLITSLDDVYDIYGTLDELQLFTDAIQRWDTESISRLPYYMQL

FYMVLYNFVSELAYDGLKEKGFITIPYLQRSWADLVEAYLKEAKWFYNGYVPSMEEYLNNAYISIGATPVISQVFFTLAT

SIDKPVIDSLYEYHRILRLSGMLVRLPDDLGTSPFEMKRGDVPKAIQLYMKERNATEIEAQEHVRFLIREAWKEMNTVTT

AADCPFTDDLVAATRNLGRAAQFMYLDGDGNHSQLHQRIACLLFEPYA

FIG.35

>Vv1LINS_M29

MGFSPAFYACSIPPVGPNKFTELGQSKFNNVVLVPTAQKWSIAHDHTLVYKPLRKHNHQSQHLSFTDEFYIKHAQRLDEI

RNVFSEVGEDTLEGLMMIDAIQRLGIDYHFKEEIEAVLQRQYMKASTHGESIQDLYEVALRFRLLRQEGYHVPADVFNNF

KNKEGKFKQNLSKDIKGLLALYEASQLSIEGEDILEEAQRFSSTLLNAGLEHLNHHEATVVGHTLEHPHHKSLPRFMAKS

FLKDFQGPNGWLTVLQELAKADFNMVQSIHQQELLQISKWWQDRGLAEELKFARDQPLKWHMWPMAVLPDPSLSEQRVEL

TKPISMIYII`DDIFDVHG`TLDELTLFTEAVNRWDIAAFETLPNYMKICFKTLDEITNEISNKVYKEHGWNPVDSLRKTW

VSLCNAFLVEAKWFASGHVPKAHEYLKNGVISSGVHVVLVHLFFLLGHGITRGNVDLVDDFPSIISSTAAILRLWDDLGS

AKDENQDGHDGSYIECYIKEHQGSSMENARQNVTYMISDLWKRLNKECLSQHPFSTSFTKGSLNIARMVPLMYSYDDNQS

LPHLEEHMKSLLFEAFPL

FIG.36

>Vv2LINS_M31

MELTLTSLSPLAYGALNCRKNFAMASPRMRIKQGRSELPNLTITSKIDELQVTERRSANYHPSIWDPKFIESLSTPYTNE

GYSNQLEDLKEEAKRVIKDARDTSSRLEFIDSMQRLGVAYHLEEEIKEAIDLVHLDDTTTDDLSTTALRFRLLRQHGYPV

SSEVFDQFRSKDGRFMDGISQDIAGPLSLYEASHLGVEGEDDLEEARRFSTIHLKSLVGNLESDLADQVQQSLEVPLHWR

MPRLEARNFIDIYQRRNTKNSALLELAKLDYNLVQSSYQTELKELTRWWTDLGFKEKLSFSRDRLMENYLWSMGIAPEPH

FSKSRIGLTKFICILTAI`DDMYDIYG`SPDELRRFTDAVNRWDTEALVDLPDYMKICYLAMFNFANEMAYDALRDHDLYI

LPYLKSQWLNLCTSYSMEAQWFYNGYKPSIDEYLSNAWTSVGGPAAMVHAYFLMGCATKGNLNNCLDNASNLLYWSSLIT

RLSDDLGTSLAEIARGDVAKSIQCYMIEKCISEEQARDQVEKLIRYSWKKLNEASTDSSLPKSLINSSLNMARSAQCIFQ

FGDGIGTSVGVTKDRLTSFIIKPILIEPSIKPYLDGMKMSNRR

FIG.37

>LaLINS_M33

MSININMPAAAVLRPFRCSQLHVDETRRSGNYRPSAWDSNYIQSLNSQYKEKKCLTRLEGLIEQVKELKGTKMEAVQQLE

LIDDSQNLGLSYYFQDKIKHILNLIYNDHKYFYDSEAEGMDLYFTALGFRLFRQHGFKVSQEVFDRFKNENGTYFKHDDT

KGLLQLYEASFLVREGEETLEQAREFATKSLQRKLDEDGDGIDANIESWIRHSLEIPLHWRAQRLEARWFLDAYARRPDM

NPVIFELAKLNFNIVQATQQEELKALSRWWSSLGLAEKLPFVRDRLVESYFWAIPLFEPHQYGYQRKVATKIITLITSL

DDVYDIYGTLDELQLFTNLFERWDNASIGRLPEYLQLFYFAIHNFVSEVAYDILKEKGFTSIVYLQRSWVDLLKGYLKE

AKWYNSGYTPSLEEYFDNAFMTIGAPPVLSQAYFTLGSSMEKPIIESMYEYDNILRVSGMLVRLPDDLGTSSFEMERGDV

PKSVQLYMKETNATEEEAVEHVRFLNREAWKKMNTAEAAGDSPLVSDVVAVAANLGRAAQFMYFDGDGNQSSLQQWIVSM

LFEPYA

FIG.38

>McLINS_M35

MCTIISVNHHHVAILSKPKVKLFHTKNKRSASINLPWSLSPSSSAASRPISCSISSKLYTISSAQEETRRSGNYHPSVWD

FDFIQSLDTDHYKEEKQLEREEELIMEVKKLLGAKMEATKQLELIDDLQNLGLSYFFRDEIKNILNSIYKIFQNNNSTKV

GDLHFTSLGFRLLRQHGFNVSQGVFDCFKNEHGSDFEKTLIGEDTKGVLQLYEASFLLREGEDTLEVARKFSTEFLEEKL

KAGIDGDNLSSSIGHSLEIPLHWRIQRLEERWFLDAYSRRKDMNPIIFELAKLDFNIIQATQQEELKDLSRWWNDSSLPQ

KLPFVRDRLVESYYWALGLFEAHKFGYERKTAAKIITLITALDDVYDIYGTLDELQLFTHVIRRWDTESATQLPYYLQL

FYFVLYNFVSEVAYHILKEEGFISIPFLHRAWVDLVEGYLQEAKWYYTKYTPTMEEYLNYASITIGAPAVISQIYFMLAK

SKEKPVIESFYEYDEIIRLSGMLVRLPDDLGTLPFEMKRGDVAKSIQIYMKEQNATREEAEEHVRFMIREAWKEMNTTMA

ANSDLRGDVVMAAANLGRDAQFMYLDGDGNHSQLQHRIANLLFKPYV

FIG.39

>ObLINS_M37
MASAVPLSSTPLINGDNSPLKNTHQHVEERSSKRREYLLEETARKLQRNDTESVEKLKLIDNIQRLGIGYYFEDAIDAVL
RSPFSAEEEEDLFTAALRFRLLRHNGIQVTPEIFLKFKDERGEFDESDTLGLLSLYEASNLGVTGEEILEEAMEFAEPRL
RRSLSELAAPLRSEVAQALDVPRHLRMARLEARRFIEQYGKQSDHDGDLLELAILDYNQVQAQHQSELTEITRWWKQLGL
VEKLGFGRDRALECFMWTMGILPHPKYSSSRIESAKAAALLYVI DDIFDTYGK MDELILFTDAIRRWDLEAMEGLPEYM
KICYMALYNTTNEICYRVLKDTGRIALPYLKSVWIETIEAYMVEVKWFSGGSAPKLEEYIENGASTVGAYMVLVHLFFLI
GEGLTHQNVLFFKQKPYHKPFSAAGRIFRLWDDLGTSQEEEERGDMASSIRLFMKEYKLSTVEEARSCVLEEISRLWKDL
NEGLISIKDALPLTIVKVALNIARTSQVVYKHEQHTYMLSVDNYVEALFFTPLLSS

FIG.40

>CbLINS_M39
MRESLSSSSSNTQNLFLSTSPYDTAWLALIPHPHHHHHHGRPMFEKCLQWILHNQTPQGFWAAAGDNISDTDDDVTLDCL
LSTLACLVALKRWQLAPDMIHKGLEFVNRNTERLVMKQKPSDVPRWFTIMFPAMLELAGASSLRVDFSENLNRILVELSQ
NRDDILTREEVDEKKQYSPLLLFLEALPAQSYDNDVLKQIIDKNLSNDGSLLQSPSATARAYMITGNTRCLSYLHSLTNS
CSNGGVPSFYPVDDDLHDLVMVNQLTRSGLTEHLIPEIDHLLLKVQKNYKYKKASPKSLYSIAAELYRDSLAFWLLRVNN
HWVSPSIFCWFLDDDEIRDHIETNYEEFAAVLLNVYRATDLMFSGEVQLVEARSFATKNLEKILATGNIHKTNADISSSL
HKMIEHELRVPWTARMDHVENRIWIEEIASSALWFGKSSYLRLSCFHKMSLQQLAVKNYTLRQLVYRDELAEVERWSKER
GLCDMGFCREKTGYCYYAFAASTCLPWSSDVRLVLTKAAVVITVA DDFFDVEG SMVDLEKLTDAVRRWDAEGLGSHSKT
IFEALDDLVNEVRLKCFQQNGQDIKNNLQQLWYETFHSWLMEAKWGKGLTSKPSVDVYLGNAMTSIAAHTMVLTASCLLG
PGFPVHQLWSQRRHQDITSLLMVLTRLLNDIQSYLKEEDEGKINYVWMYMIENNQASIDDSVRHVQTIINVKKQEFIQRV
LSDQHCNLPKSFKQLHFSCLKVFNMFFNSSNIFDTDTDLLLDIHEAFVSPPQVPKFKPHIKPPHQLPATLQPPHQPQQIM
VNKKKVEMVYKSYHHPFKVFTLQKKQSSGHGTMNPRASILAGPNIKLCFS

FIG. 41

>Q1XBU5|R-linalool synthase|EC 4.2.3.26|Solanum lycopersicum|TrEMBL

MVSILSNIGMMVVTFKRPSLFTSLRRRSANNIIITKHSHPISTTRRSGNYKPTMWDFQFIQSLHNPYEGDKYMKRLNKLK
KEVKKMMMTVEGSHDEELEKLELIDNLERLGVSYHFKDEIMQIMRSINININIAPPDSLYTTALKFRLLRQHGFHISQDI
LNDFKDENGNLKQSICKDTKDILNSSKDEHDNLKQSTCNNTKGLLKLYEASFLSIENESFLRNTTKSTLAHLMRYVDQNR
CGEEDNMIVELVVHALELPRHWMVPRLETRWYISIYERMSNANPLLLELAKLDFNIVQATHQQDLRILSRWWKNTGLAEK
LPFSRDILVENMFWAVGALFEPQHSYFRRLITKVIVFISII[DDIYDVYG]TLDELELFTLAIQRWDTKAMEQLPDYMKVC
YLALINIINEVAYEVLKNHDINVLPYLTKSWADLCKSYLQEAKWYHNGYKPNLEEYMDNARISIGVPMVLVHSLFLVTNQ
ITKEALDSLTNYPDIIRWSATIFRLNDDLGTSSDELKRGDVSKSIQCYMNEKGASEEEAIEHIEFLIQETWEAMNTAQSK
NSPLSETFIEVAKNITKASHFMYLHSDVKSSISKILFEPIIISNVAFALK

FIG. 42

>gi|211970992|dbj|BAG82825.1| linalool synthase [Backhousia citriodora]

MALPALFGSSLPSSIRHNQPSLFSFRHPRFCSSSSSASFSSQFILCASKTGDQEIVRRSANWQPSVWDYDYVQSLTVDYT
EDKYTKQVQRLKEEVKGLFDREMKQVAKLEFIDVVQRLGLGYHFKTEIKIALSSIHNNTEDAQLSNDLYAASLRFRLLRQ
YGCNVQQDVFQRFMNKTGTFKESLNKDVKGILGLYEASFHGMEGETVLDEAWNFASKHLKDLNLDEVPTNLASNVSHALD
MPIHWRPNRLEARWFMDMYEKQQDLIPSLLRLAKLDFNIVQSIHRKEVSNLARWWVELGANKMTFFRDRLVESYFWSCIL
VFEPQYTDFRELNTRIACMATLI[DDVYDIYG]TPEELELLTDFILRWDITDIDKLPPTIRNGFMALYNTTNKVGYRTMTK
RGINPIPYLRKLWGDECKADMKEVHWFNNGIKPTLKEYMDVAVDSIGGLILLLNSYFLTTDYLTEEGLNYVSKIPSVMHS
SAQIFRFNDDLSTSSHELARGDNSKALECYMNETGASEEIAREHIRHLVRETWKKMNKEVFEDYPFSGFGPFLSACLNLA
RASHCFYEYGDGYGLPDHQTRDHLASTIFESVSLD

FIG.43

>gi|6469618|gb|AAF13357.1|AF154125_1 (3R)-linalool synthase, partial [Artemisia annua]
GNAYMRIYSTKTTRITANATVNAADTHVRRSANYKPSSWSFDHIQSLSSKYTGDDYVARANTLKDAVKTMIRKSGNSLRT
LELVDELQRLGISYLFEEEISNLLETIYYNYYKFPENWNKINLNLKALGFRLLRQHGYHVPQEIFLNFKDKNQNLNSYLL
NDVVEMLNLYEASYHSFEDESILDDARDITTKYLKESLEKIDGSIFSSVTHALEQPLHWRVPRVEAKWFIELYEKKNGMS
PTLVELAKLDFDMVQAIHLEDLKHASRWWRDTSWDTKLTFARDLIVENFLWTIGFSYLPNFSRGRRTITKVAVMITTLD
DVYDVFGTLGELEQFTDVINRWDIKAIEQLPDYMKICFLGLYKSINDITHETLANKGFLILPYLKKAWADLCKAYLVEA
QWYHRGHIPTLNEYLDNACVSISGPVALMHVHFLTSVSSIEEIHQCIQRTENIVHYVSLIFRLADDLGTSLGEMERGDTL
KSIQLHMHETGATEPEARSYIKLLINKTWKKLNKERATVNSESSQEFIDYATNLVRMAQFMYGEGDEDFGLDVIKSHVLS
LLFTPIQGI

FIG.44

>gi|6469616|gb|AAF13356.1|AF154124_1 (3R)-linalool synthase [Artemisia annua]
MASISLFPYSILKQTSPLARGTAYNRIYSTKTTGITVDVAESHVRRSANYEPSSWSFDHIQSLSSKYTGDDCVARANTLK
ESVKTMIRKEGNLLRTLELVDELQRLGISYLFEGEISNLLETIYYNHYKFPEKWNKFDLNLKALGFRLLRQHGYHVPQEI
FLNFKDKNQNLNSYLLEDVVGMLNLYEASYHSFEDESILTEARDIATKYLKASLEKIDGSILSLVSHALDNRLHWRVPRV
ESKWFIEVYEKRVGASPTLIELAKLDFDMVQAIHLEDLKHASRWWRNTSWDTKLTFARDMLVENFLWTVGFSYLPNFSHG
RRTITKVAAMITTLDDVYDVFGTLGELEQFTDVINRWDIKAIEQLPDYMKICFFGLYNSINDITYETLATKGFLILPYI
KKAWADLCKSYLVEAQWYHRGHIPTLNEYLDNACVSISGPVALMHVHFLTSVSSTKEIHHCIERTQNIVRYVSLIFRLTD
DLGTSLGEMERGDTLKSIQLYMHETGATEPEARSYIKSLIDKTWKKLNKERAIVSSESSREFIDYATNLARMAHFMYGEG
DEDFRLDVIKSHVSSLLFTPIQGI

FIG.45

>D4N3A0|S-linalool synthase|EC 4.2.3.25|Actinidia arguta|TrEMBL

MASFNRFCVSSLLAPNNSPQISNAPRSTAVPSMPTTQKWSITEDLAFISNPSKQHNHQTGYRIFSDEFYLKHENKLKDVR

RALREVEETPLEGLVMIDTLQRLGIDYHFQGEIGALLQKQQRISTCDYPEHDLFEVSTRFRLLRQEGHNVPADVFNNFRD

KEGRFKSELSRDIRGLMSLYEASQLSIQGEDILDQAADFSSQLLSGWATNLDHHQARLVRNALTHPYHKSLATFMARNFN

YDCKGQNGWVNNLQELAKMDLTMVQSMHQKEVLQVSQWWKGRGLANELKLVRNQPLKWYMWPMAALTDPRFSEERVELTK

PISFIYII[DDIFDVYG]TLEELTLFTDAVNRWELTAVEQLPDYMKICFKALYDITNEIAYKIYKKHGRNPIDSLRRTWAS

LCNAFLEEAKWFASGNLPKAEEYLKNGIISSGMHVVTVHMFFLLGGCFTEESVNLVDEHAGITSSIATILRLSDDLGSAK

DEDQDGYDGSYLECYLKDHKGSSVENAREEVIRMISDAWKRLNEECLFPNPFSATFRKGSLNIARMVPLMYSYDDNHNLP

ILEEHMKTMLYDSSS

FIG.46

>D4N3A1|S-linalool synthase|EC 4.2.3.25|Actinidia polygama|TrEMBL

MASFHRFCVSSLLVPNNSPQISNAYRAPAVPSMPTTQKWSITEDLAFISNPSKQHNHQTGYRTFSDEFYVKREKKLKDVR

RALREVEETPLEGLVMIDTLQRLGIDYHFQGEIGALLQKQQRKSKCDYPEHDLFEVSTRFRLLRQEGHNVPADVFNHFRD

KKGRFKSELSRDIRGLMSLYEASQLSIQGEDILDQAADFSSQLLSGWATNPDHHQARLVRNALTHPYHKSLATFTARNFH

YDCKGQNGWVNNLQELAKMDLTVVQSMHQKEVLQVSQWWKDRGLANELKLVRNQPLKWYMWPMAALTDPRFSEERVELTK

PISFIYII[DDIFDVYG]TLEELTLFTDAVNRWELTAVEQLPDYMKVCFKALYDITNEIAYKIYKKHGWNPIDSLRRMWAS

LCNAFLVEAKWFASGHLPKAEEYLKNGIISSGMHVVTVHMFFLLGGCFTDESVNLVDEHAGITSSIATILRLSDDLGSAK

DEDQDGYDGSYVEYYLKDHKGSSVENAREEVIRMISDAWKRLNEECLSPNPFSATFRKGCLNIARMVPLMYSYDDNHNLP

LLEEHMKAMLYDSSS

FIG.47

>C0KWV5|S-linalool synthase|EC 4.2.3.25|Perilla frutescens var. hirtella|TrEMBL

MSSMRIYVAIMKKPSVKHVDYVDKKASKPSWRVSSSATAGLRASSSLQLDVKKPADEILTARRSGNYQPSLWDFNYLQSL

NTTHYKEERHLKREAELIEQVKMLLDEEMGAVQKLDLVDDLKNLGLSYFFEDQIKQILTFIYNEHECFRSNVEAKERDLY

FTALGFRLLRQHGFQVSQEVFDCFKNEEGSDFKASLGDDTKGLVQLYEASFLLREGEDTLELARQYATKFLQKKVDHELI

DDDSNLLSWIRHSLEIPLHWRIQRLEARWFLDAYATRHDVNPIILELAKLDFNIIQATQQEELKDLSRWWNSTCLVEKLP

FVRDRLVESYFWAIALFEPHQYGYHRKIAAKIITLITSL[DDVYDIYG]TLDELQLFTDAIQRWDTESISRLAYYMQLFYM

VLYNFVSELAYDGLKEKGFITIPYLQRSWADLVEAYLKEAKWFYNGYTPSMEEYLNNAYISIGATPVISQVFFTLATSID

KPVIESLYEYHRILRLSGMLVRLPDDLGTSPFEMKRGDVPKTIELYMKERNATEIEAQEHVRFLIREAWREMNTATAAAD

CPFTDDLVAAAANLGRAAQFMYLDGDGNHSQLHQRIASLLFEPYA

FIG.48

>C0KWV3|S-linalool synthase|EC 4.2.3.25|Perilla setoyensis|TrEMBL

MSSMRTYVAIMKKPSVEHVDNVDKKASKPSWRVSLSAGLRSSCSLQLEVKPADQILTARRSGNYQPSLWDFNYLQSLNTT

HYKEVRHLKREAELIEQVKMLLEEEMEAVQQLELVDDLKNLGLSYFFEDQIKQILTFIYNEHKCFHSNSIIEAEEIRDLY

FTALGFRLLRQHGFQISQEVFDCFKNEEGSDFKARLGDDTKGLLQLYEASFLLREGEDTLELARQYATKFLQKKVDHELI

DDNNLLSWILHSLEIPLHWRIQRLEARWFLDAYASRRDMNQIILELAKLDFNIIQATQQEELKDLSRWWKSSCLAEKLPF

VRDRLVESYFWAIALFEPHQYGYHRKIAAKIITLITSL[DDVYDIYG]TLDELQLFTDAIQRWDTESISRLPYYMQLFYMV

LYNFVPRLAYDGLKEKGFITIPYLQRSWADLVEAYLKEAKWYYNGYTPSMEEYLNNAYISIGATPVISQVFFTLATSIDK

PVIDSLYEYHRILRLSGILVRLPDDLGTSPFEMKRGDVPKAIQLYMKERNATEIEAQEHVRFLIREAWKEMNTATAAVDC

PFTDDLVTAAANLGRAAQFMYLDGDGNHSQLHQRIACLLFEPYA

SEQUENCE LISTING

<160> NUMBER OF SEQ ID NOS: 184

<210> SEQ ID NO 1
<211> LENGTH: 574
<212> TYPE: PRT
<213> ORGANISM: Actinidia arguta

<400> SEQUENCE: 1

Met Ala Ser Phe Asn Arg Phe Cys Val Ser Ser Leu Leu Ala Pro Asn
1               5                   10                  15

Asn Ser Pro Gln Ile Ser Asn Ala Pro Arg Ser Thr Ala Val Pro Ser
            20                  25                  30

Met Pro Thr Thr Gln Lys Trp Ser Ile Thr Glu Asp Leu Ala Phe Ile
        35                  40                  45

Ser Asn Pro Ser Lys Gln His Asn His Gln Thr Gly Tyr Arg Ile Phe
    50                  55                  60

Ser Asp Glu Phe Tyr Leu Lys His Glu Asn Lys Leu Lys Asp Val Arg
65                  70                  75                  80

Arg Ala Leu Arg Glu Val Glu Glu Thr Pro Leu Glu Gly Leu Val Met
                85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Arg Ile Ser Thr Cys Asp Tyr
            115                 120                 125

Pro Glu His Asp Leu Phe Glu Val Ser Thr Arg Phe Arg Leu Leu Arg
130                 135                 140

Gln Glu Gly His Asn Val Pro Ala Asp Val Phe Asn Asn Phe Arg Asp
145                 150                 155                 160

Lys Glu Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
        195                 200                 205

Thr Asn Leu Asp His His Gln Ala Arg Leu Val Arg Asn Ala Leu Thr
    210                 215                 220

His Pro Tyr His Lys Ser Leu Ala Thr Phe Met Ala Arg Asn Phe Asn
225                 230                 235                 240

Tyr Asp Cys Lys Gly Gln Asn Gly Trp Val Asn Asn Leu Gln Glu Leu
                245                 250                 255

Ala Lys Met Asp Leu Thr Met Val Gln Ser Met His Gln Lys Glu Val
            260                 265                 270

Leu Gln Val Ser Gln Trp Trp Lys Gly Arg Gly Leu Ala Asn Glu Leu
        275                 280                 285

Lys Leu Val Arg Asn Gln Pro Leu Lys Trp Tyr Met Trp Pro Met Ala
    290                 295                 300

Ala Leu Thr Asp Pro Arg Phe Ser Glu Glu Arg Val Glu Leu Thr Lys
305                 310                 315                 320

Pro Ile Ser Phe Ile Tyr Ile Ile Asp Asp Ile Phe Asp Val Tyr Gly
                325                 330                 335

Thr Leu Glu Glu Leu Thr Leu Phe Thr Asp Ala Val Asn Arg Trp Glu
            340                 345                 350

Leu Thr Ala Val Glu Gln Leu Pro Asp Tyr Met Lys Ile Cys Phe Lys
        355                 360                 365

```
Ala Leu Tyr Asp Ile Thr Asn Glu Ile Ala Tyr Lys Ile Tyr Lys Lys
        370                 375                 380

His Gly Arg Asn Pro Ile Asp Ser Leu Arg Arg Thr Trp Ala Ser Leu
385                 390                 395                 400

Cys Asn Ala Phe Leu Glu Glu Ala Lys Trp Phe Ala Ser Gly Asn Leu
                405                 410                 415

Pro Lys Ala Glu Glu Tyr Leu Lys Asn Gly Ile Ile Ser Ser Gly Met
                420                 425                 430

His Val Val Thr Val His Met Phe Phe Leu Leu Gly Gly Cys Phe Thr
                435                 440                 445

Glu Glu Ser Val Asn Leu Val Asp Glu His Ala Gly Ile Thr Ser Ser
450                 455                 460

Ile Ala Thr Ile Leu Arg Leu Ser Asp Asp Leu Gly Ser Ala Lys Asp
465                 470                 475                 480

Glu Asp Gln Asp Gly Tyr Asp Gly Ser Tyr Leu Glu Cys Tyr Leu Lys
                485                 490                 495

Asp His Lys Gly Ser Ser Val Glu Asn Ala Arg Glu Glu Val Ile Arg
                500                 505                 510

Met Ile Ser Asp Ala Trp Lys Arg Leu Asn Glu Glu Cys Leu Phe Pro
                515                 520                 525

Asn Pro Phe Ser Ala Thr Phe Arg Lys Gly Ser Leu Asn Ile Ala Arg
                530                 535                 540

Met Val Pro Leu Met Tyr Ser Tyr Asp Asp Asn His Asn Leu Pro Ile
545                 550                 555                 560

Leu Glu Glu His Met Lys Thr Met Leu Tyr Asp Ser Ser Ser
                565                 570
```

<210> SEQ ID NO 2
<211> LENGTH: 1725
<212> TYPE: DNA
<213> ORGANISM: Actinidia arguta

<400> SEQUENCE: 2

```
atggccagct tcaacaggtt ttgtgtctct tctcttcttg ctccaaacaa cagcccacaa    60
attagcaatg ctccccgctc caccgctgta ccctctatgc ctaccaccca aaaatggagc   120
atcaccgaag acctagcatt catttctaat ccctcgaaac aacacaacca tcaaaccgga   180
tatcgcattt tctctgatga gttttaccta aagcacgaaa acaaattgaa ggacgttagg   240
agagcgttaa gggaagtgga ggaaacccca ttagaaggtc tggtcatgat cgacaccctc   300
caacggctag gcattgacta ccacttccag ggggagattg agcccctact acagaaacaa   360
cagagaatat ctacttgtga ttatcccgag catgatcttt tgaggtctc tactcgcttt   420
cggctgttaa ggcaagaagg tcacaatgtg cctgcagatg tgtttaacaa cttcagagac   480
aaggagggaa ggttcaaatc agaactaagc agagacatca ggggttgat gagtttgtat   540
gaagcttcac agttaagcat acaaggagaa gacatacttg atcaagccgc agattttagt   600
tcccaactcc ttagcgggtg ggcgacaaat ctcgatcatc atcaagctag cttgtgcgt   660
aatgcactga cacatcccta tcacaagagc ctagcgacat tcatggcaag aaacttcaat   720
tatgattgca agggccaaaa tggatgggtc aataacttgc aagaactagc aaaaatggac   780
ttaactatgg ttcagtccat gcatcaaaaa gaagtccttc aagtttccca atggtggaaa   840
ggcaggggtt tggccaatga attgaagctt gtgagaaatc agccacttaa atggtacatg   900
tggccaatgg cagccctcac agatccaaga ttctcagagg aaagagttga actcacaaaa   960
```

```
ccaatctctt ttatctatat catagatgac atttttgatg tttatgggac attagaagaa      1020
ctcactctct tcacagatgc tgtcaataga tgggaactta ctgctgttga gcaactaccc      1080
gactacatga agatttgctt taaggctctt tatgacatca caaatgaaat cgcctacaag      1140
atctacaaaa agcatggacg gaaccccata gattctctgc ggagaacgtg ggcaagtttg      1200
tgcaacgcgt tcttagaaga agcaaaatgg tttgcttctg ggaacttgcc aaaggcagaa      1260
gagtacttga agaatgggat catcagttca gggatgcatg tggttacggt tcacatgttc      1320
tttctcttgg gcggttgttt caccgaagaa agtgtcaatc ttgtggatga acatgcggga      1380
attacatctt ctatagcaac aatccttcgt ctttcggatg acttgggaag tgccaaggat      1440
gaggatcaag atggctacga tggatcctat ttagaatgct atctgaagga ccacaagggc      1500
tcttcggtag agaatgcaag agaagaagtt attcgcatga tttcagatgc atggaagcgc      1560
ctcaacgagg aatgcctatt tccgaatcca ttttcagcaa ctttcaggaa gggttctctt      1620
aatatcgcaa ggatggttcc tttgatgtac agctatgatg acaatcataa cctcccaatc      1680
cttgaggagc acatgaagac aatgctctat gatagttctt cttga                      1725

<210> SEQ ID NO 3
<211> LENGTH: 1650
<212> TYPE: DNA
<213> ORGANISM: Artificial Sequence
<220> FEATURE:
<223> OTHER INFORMATION: DNA having modified codons, which encodes
      linalool synthase gene derived from Actinidia arguta (opt_AaLINS)

<400> SEQUENCE: 3
atgtccaccg ccgtgccctc tatgcccact acccaaaaat ggtctattac cgaagactta       60
gcctttatta gcaatcccag caaacaacat aatcaccaaa ccggctaccg gattttttagt      120 gacgaatttt acctgaaaca tgaaaacaaa ttgaaagatg tgcggcgcgc cttgcgtgaa      180
gttgaagaaa ccccctggaa aggcttggtg atgattgaca ctttacgcg gctgggtatt      240 gattaccact tcaaggcga aattggtgcc ttgttacaga acaacagcg cattagtacc      300 tgtgactatc ccgaacatga tttgtttgaa gtgagcactc gctttcgtct gttgcgtcaa      360
gaaggtcaca atgtgcccgc cgacgttttt aataactttc gcgataaaga agggcgtttt      420
aaatctgaac tgtcccggga tattcgcgga ttgatgtcct tatacgaagc cagtcaactg      480
agcattcagg ggaagacat tttggatcaa gccgctgact tttccagtca gttactgtct      540
ggatgggcca ccaatttaga tcatcaccaa gcccgtctgg tgcggaacgc tttgacccat      600
ccctaccaca aaagtctggc cacttttatg gctcgcaact taactacga ttgcaaaggg      660 caaaacggat gggtgaataa cctgcaggaa ttggccaaaa tggatttaac catggttcaa      720
agtatgcatc agaagaagt gctgcaagtt agccagtggt ggaaagggcg gggattggcc      780
aatgaactga aattggtgcg caaccaaccc ttgaaatggt atatgtggcc catggccgct      840
ttaaccgatc ccggttttc tgaagaacgc gtggaattga ctaaacccat ttcctttatt      900
tacattattg atgacatttt tgacgtttat ggcaccttag aagaattaac cctgtttact      960
gatgccgtga tcggtgggga attaactgct gttgaacagc tgcccgacta catgaaaatt      1020 tgtttttaaag ccttgtacga tattaccaac gaaattgctt acaaaattta caaaaaacat      1080
gggcgcaacc ccattgatag tttacgtcgg acttgggcca gcttatgcaa tgcttttctg      1140
gaagaagcca atggtttgc tagtggcaat ttgcccaaag ccgaagaata cctgaaaaac      1200
gggattatta gctctggaat gcatgtggtt accgtgcaca tgttttttctt gttaggcggt      1260
```

-continued

```
tgttttactg aagaatccgt gaatttggtt gatgaacatg ccggcattac ctccagtatt    1320
gctactattt tgcgtttatc tgatgactta ggttccgcca aagatgaaga ccaagatggc    1380
tatgacggta gctacttgga atgttacctg aaagatcata aaggtagctc tgtggaaaat    1440
gcccgtgaag aagttattcg gatgatttcc gatgcttgga aacgcttgaa tgaagaatgc    1500
ttatttccca accccttttc tgccaccttt cgcaaagggt ccttaaatat tgctcgtatg    1560
gtgcccctga tgtacagtta cgatgacaac cataacctgc ccattctgga agaacacatg    1620
aaaaccatgt tgtatgattc cagtagctaa                                     1650
```

<210> SEQ ID NO 4
<211> LENGTH: 590
<212> TYPE: PRT
<213> ORGANISM: Coriandrum sativum

<400> SEQUENCE: 4

```
Met Ala Ala Ile Thr Ile Phe Pro Leu Ser Tyr Ser Ile Lys Phe Arg
1               5                   10                  15

Arg Ser Ser Pro Cys Asn Pro Lys Asp Val Thr Ala Cys Lys Ser Val
            20                  25                  30

Ile Lys Ser Val Thr Gly Met Thr Lys Val Pro Val Pro Val Pro Glu
        35                  40                  45

Pro Ile Val Arg Arg Ser Gly Asn Tyr Lys Pro Cys Met Trp Asp Asn
    50                  55                  60

Asp Phe Leu Gln Ser Leu Lys Thr Glu Tyr Thr Gly Glu Ala Ile Asn
65                  70                  75                  80

Ala Arg Ala Ser Glu Met Lys Glu Glu Val Arg Met Ile Phe Asn Asn
                85                  90                  95

Val Val Glu Pro Leu Asn Gln Leu Glu Leu Ile Asp Gln Leu Gln Arg
            100                 105                 110

Leu Gly Leu Asp Tyr His Phe Arg Asp Glu Ile Asn His Thr Leu Lys
        115                 120                 125

Asn Val His Asn Gly Gln Lys Ser Glu Thr Trp Glu Lys Asp Leu His
    130                 135                 140

Ala Thr Ala Leu Glu Phe Arg Leu Leu Arg Gln His Gly His Tyr Ile
145                 150                 155                 160

Ser Pro Glu Gly Phe Lys Arg Phe Thr Glu Asn Gly Ser Phe Asn Lys
                165                 170                 175

Gly Ile Arg Ala Asp Val Arg Gly Leu Leu Ser Leu Tyr Glu Ala Ser
            180                 185                 190

Tyr Phe Ser Ile Glu Gly Glu Ser Leu Met Glu Glu Ala Trp Ser Phe
        195                 200                 205

Thr Ser Asn Ile Leu Lys Glu Cys Leu Glu Asn Thr Ile Asp Leu Asp
    210                 215                 220

Leu Gln Met Gln Val Arg His Ala Leu Glu Leu Pro Leu Gln Trp Arg
225                 230                 235                 240

Ile Pro Arg Phe Asp Ala Lys Trp Tyr Ile Asn Leu Tyr Gln Arg Ser
                245                 250                 255

Gly Asp Met Ile Pro Ala Val Leu Glu Phe Ala Lys Leu Asp Phe Asn
            260                 265                 270

Ile Arg Gln Ala Leu Asn Gln Glu Glu Leu Lys Asp Leu Ser Arg Trp
        275                 280                 285

Trp Ser Arg Leu Asp Met Gly Glu Lys Leu Pro Phe Ala Arg Asp Arg
    290                 295                 300
```

```
Leu Val Thr Ser Phe Phe Trp Ser Leu Gly Ile Thr Gly Glu Pro His
305                 310                 315                 320

His Arg Tyr Cys Arg Glu Val Leu Thr Lys Ile Ile Glu Phe Val Gly
                325                 330                 335

Val Tyr Asp Asp Val Tyr Asp Val Tyr Gly Thr Leu Asp Glu Leu Glu
            340                 345                 350

Leu Phe Thr Asn Val Val Lys Arg Trp Asp Thr Asn Ala Met Lys Glu
        355                 360                 365

Leu Pro Asp Tyr Met Lys Leu Cys Phe Leu Ser Leu Ile Asn Met Val
    370                 375                 380

Asn Glu Thr Thr Tyr Asp Ile Leu Lys Asp His Asn Ile Asp Thr Leu
385                 390                 395                 400

Pro His Gln Arg Lys Trp Phe Asn Asp Leu Phe Glu Arg Tyr Ile Val
                405                 410                 415

Glu Ala Arg Trp Tyr Asn Ser Gly Tyr Gln Pro Thr Leu Glu Glu Tyr
            420                 425                 430

Leu Lys Asn Gly Phe Val Ser Ile Gly Gly Pro Ile Gly Val Leu Tyr
        435                 440                 445

Ser Tyr Ile Cys Thr Glu Asp Pro Ile Lys Lys Glu Asp Leu Glu Phe
    450                 455                 460

Ile Glu Asp Leu Pro Asp Ile Val Arg Leu Thr Cys Glu Ile Phe Arg
465                 470                 475                 480

Leu Thr Asp Asp Tyr Gly Thr Ser Ser Ala Glu Leu Lys Arg Gly Asp
                485                 490                 495

Val Pro Ser Ser Ile Tyr Cys Tyr Met Ser Asp Thr Gly Val Thr Glu
            500                 505                 510

Glu Val Ser Arg Lys His Met Met Asn Leu Ile Arg Lys Lys Trp Ala
        515                 520                 525

Gln Ile Asn Lys Leu Arg Phe Ser Lys Glu Tyr Asn Asn Pro Leu Ser
    530                 535                 540

Trp Ser Phe Val Asp Ile Met Leu Asn Ile Ile Arg Ala Ala His Phe
545                 550                 555                 560

Leu Tyr Asn Thr Gly Asp Asp Gly Phe Gly Val Glu Asp Val Ala Val
                565                 570                 575

Glu Ala Thr Leu Val Ser Leu Leu Val Glu Pro Ile Pro Leu
            580                 585                 590

<210> SEQ ID NO 5
<211> LENGTH: 1773
<212> TYPE: DNA
<213> ORGANISM: Coriandrum sativum

<400> SEQUENCE: 5
atggcagcga taactatatt tccactttct tattcgatca aatttaggag atcctcccca      60
tgcaatccta agatgtgac agcctgcaag tctgtaatta aatccgtcac tggaatgact     120
aaggttcctg ttccagtacc agagcctatc gtaaggcgat cagggaacta caaaccttgc    180
atgtgggaca cgatttcttg cagtctttga aaaactgaat acaccgggga agcaatcaat    240
gcacgagctt ctgagatgaa ggaagaggtg aggatgatat taataatgt ggtcgaacca    300 ttgaatcagc ttgagctgat tgatcagttg cagagacttg gttggatta tcattttcgt    360 gatgaaatca accatacttt gaagaacgta cataatggtc agaagagtga gacttgggag    420
aaggacttgc atgctactgc tcttgaattt aggcttctta gacaacatgg acattatata    480
tcccctgagg gcttcaagag atttacagag aatgggagct tcaataaagg tatccgtgca    540
```

```
gatgtccggg gactattaag tttatatgaa gcctcgtact tttctattga aggagagtcc    600
ctgatggagg aggcttggtc ctttacaagt aacatcctta aagagtgcct cgaaaatact    660
attgatttgg atctccagat gcaagtgaga catgctttgg aacttccact acaatggagg    720
atcccgagat ttgatgcaaa gtggtacata aatttgtatc aaagaagtgg tgacatgatc    780
ccagcggttc tggaatttgc aaagttggac ttcaacatta ggcaagcgtt gaaccaagaa    840
gagcttaaag atttgtcgag gtggtggagt agattagaca tgggagagaa acttcccttt    900
gccagagata ggttggtaac atcattttc tggagtttgg ggattactgg cgagcctcat     960
cacagatatt gcagagaggt tttaaccaaa ataatagagt ttgttggtgt atacgatgat   1020
gtttatgatg tatatggtac acttgatgaa cttgaactct ttacaaatgt cgtgaagagg   1080
tgggatacaa atgcaatgaa agagctccca gactacatga agttgtgctt cctgtcattg   1140
atcaacatgg tcaatgaaac gacttacgac atcctcaagg accataacat cgatacttta   1200
ccacaccaaa gaaaatggtt caatgattta ttcgagcgtt acatagtgga ggcgaggtgg   1260
tataacagtg gataccagcc aacactagaa gaatacttga aaaatggatt tgtgtcaata   1320
ggaggcccca ttggagtgct ttactcttac atctgtactg aggatccaat caagaaagaa   1380
gatttagagt ttatcgagga ccttcctgat atagtacgat tgacatgtga aattttcgg    1440 ttaactgatg attatggaac atcttcggct gagttaaaga gaggagatgt tccatcttct   1500
atatattgct acatgtcgga tactggtgtt acggaagaag tttcccgtaa gcacatgatg   1560
aacttgatca ggaagaagtg ggcacaaatt aacaaactca gattttcaaa ggagtataat   1620
aatcctttat cgtggtcttt tgttgatatt atgttgaata taatcagggc agcccatttt   1680
ttgtataata ctggagacga tggctttggt gttgaagatg ttgcagttga agctacatta   1740
gtttcgcttc ttgtcgagcc cattcctctc taa                                1773

<210> SEQ ID NO 6
<211> LENGTH: 1659
<212> TYPE: DNA
<213> ORGANISM: Artificial Sequence
<220> FEATURE:
<223> OTHER INFORMATION: DNA having modified codons, which encodes
      linalool synthase gene derived from Coriandrum sativum
      (opt_CsLINS)

<400> SEQUENCE: 6
atgactaaag tgcccgtgcc cgtgcccgaa cccattgtgc ggcggagcgg taactataaa     60
ccctgtatgt gggataacga tttttctgcaa agcttaaaaa ccgaatatac tggcgaagcc    120
attaatgccc gtgcttctga atgaaagaa gaagtgcgga tgatttttaa caacgtggtt      180
gaacccctga ccaattggaa actgattgat caactgcagc gcctgggggtt ggactaccat    240 tttcgtgatg aaattaacca taccttgaaa aacgtgcaca acggacaaaa atccgaaacc    300
tgggaaaaag atttacacgc cactgctctg gaatttcgtt tgttacggca gcatggccac    360
tatattagcc ccgaaggttt taacggtttt accgaaaatg ggtcttttaa caaaggcatt    420
cgggccgatg tgcggggcct gttgtccctg tacgaagcta gctacttttc tattgaaggt    480
gaaagtttga tggaagaagc ctggtccttt actagtaaca ttttgaaaga atgtctggaa    540
aacaccattg atttagacct gcaaatgcag gtgcgccatg ccttggaatt accctgcaa     600 tggcgcattc cccgtttttga tgctaaatgg tacattaacc tgtaccagcg cagtggggac    660
atgattcccg ccgtgttgga atttgctaaa ctggatttta cattcgtca agccttgaac     720
```

```
caggaagaat taaaagacct gagccgctgg tggtctcgtc tggatatggg cgaaaaattg    780
ccctttgctc gggatcgctt ggtgactttcc tttttctgga gtttaggcat taccggtgaa    840
ccccatcacc ggtactgtcg cgaagttctg accaaaatta ttgaatttgt ggggtttac    900 gatgacgtgt atgacgttta cggaaccttg gatgaattgg aactgtttac taacgtggtt    960
aaacgttggg acaccaacgc catgaaagaa ttacccgatt atatgaaact gtgctttctg   1020
tccttgatta tatggtgaa cgaaaccact tacgatattc tgaaagacca taacattgat   1080
accttgcccc accaacgcaa atggtttaac gatctgtttg aacggtacat tgtggaagcc   1140
cgctggtata atagtggtta ccagcccacc ctggaagaat acttgaaaaa tgggtttgtg   1200
tccattggcg gtcccattgg agttttgtac agttacattt gtactgaaga ccccatcaaa   1260
aaagaagatt tggaatttat tgaagattta cccgacattg tgcgtctgac ctgcgaaatt   1320
tttcggctga ccgatgacta tggcacttcc agtgccgaat tgaaacgggg tgacgttccc   1380
agctctattt attgctacat gagcgatacc ggtgtgactg aagaagtttc tcggaaacat   1440
atgatgaacc tgattcgcaa aaaatgggcc caaattaaca aactgcggtt tagcaaagaa   1500
tataataacc ccttgtcctg gagttttgtg gatattatgc tgaacattat tcgcgccgct   1560
cattttctgt acaacactgg ggatgacggg tttggagttg aagatgtggc cgttgaagct   1620
accttagtga gtttactggt tgaacccatt cccttataa                          1659

<210> SEQ ID NO 7
<211> LENGTH: 900
<212> TYPE: DNA
<213> ORGANISM: Escherichia coli

<400> SEQUENCE: 7
atggactttc cgcagcaact cgaagcctgc gttaagcagg ccaaccaggc gctgagccgt     60
tttatcgccc cactgccctt tcagaacact cccgtggtcg aaaccatgca gtatggcgca    120
ttattaggtg gtaagcgcct gcgaccttc ctggtttatg ccaccggtca tatgttcggc    180
gttagcacaa acacgctgga cgcacccgct gccgccgttg agtgtatcca cgcttactca    240
ttaattcatg atgatttacc ggcaatggat gatgacgatc tgcgtcgcgg tttgccaacc    300
tgccatgtga gtttggcga agcaaacgcg attctcgctg gcgacgcttt acaaacgctg    360
gcgttctcga ttttaagcga tgccgatatg ccggaagtgt cggaccgcga cagaatttcg    420
atgatttctg aactggcgag cgccagtggt attgccggaa tgtgcggtgg tcaggcatta    480
gatttagacg cggaaggcaa acacgtacct ctggacgcgc ttgagcgtat tcatcgtcat    540
aaaaccggcg cattgattcg cgccgccgtt cgccttggtg cattaagcgc cggagataaa    600
ggacgtcgtg ctctgccggt actcgacaag tatgcagaga gcatcggcct tgccttccag    660
gttcaggatg acatcctgga tgtggtggga gatactgcaa cgttgggaaa acgccagggt    720
gccgaccagc aacttggtaa aagtacctac cctgcacttc tgggtcttga gcaagcccgg    780
aagaaagccc gggatctgat cgacgatgcc cgtcagtcgc tgaaacaact ggctgaacag    840
tcactcgata cctcggcact ggaagcgcta gcggactaca tcatccagcg taataaataa    900

<210> SEQ ID NO 8
<211> LENGTH: 900
<212> TYPE: DNA
<213> ORGANISM: Artificial Sequence
<220> FEATURE:
<223> OTHER INFORMATION: DNA having modified codons, which encodes
      farnesyl diphosphate synthase gene derived from Escherichia coli
      (ispA gene)
```

<400> SEQUENCE: 8

```
atggattttc cccagcagct ggaagcctgc gtgaaacagg ccaaccaggc cctgagccgc      60
tttatcgccc ccctgccctt tcagaacacc cccgtggtgg aaaccatgca gtacggcgcc     120
ctgctgggcg gcaaacgcct cgcccctttt ctggtgtacg ccaccggcca catgtttggc     180
gtgagcacca cacccctgga tgcccccgcc gccgccgtgg aatgcatcca cgcctacttt     240
ctgatccacg atgatctgcc cgccatggat gatgatgatc tgcgccgcgg cctgcccacc     300
tgccacgtga aatttggcga agccaacgcc atcctggccg gcgatgccct gcagaccctg     360
gcctttagca tcctgagcga tgccgatatg cccgaagtga gcgatcgcga tcgcatcagc     420
atgatcagcg aactggccag cgccagcggc atcgccggca tgtgcggcgg ccaggccctg     480
gatctggatg ccgaaggcaa acacgtgccc ctggatgccc tggaacgcat ccaccgccac     540
aaaaccggcg ccctgatccg cgccgccgtg cgcctgggcg ccctgagcgc cggcgataaa     600
ggccgccgcg ccctgcccgt gctggataaa tacgccgaaa gcatcggcct ggcctttcag     660
gtgcaggatg atatcctgga tgtggtgggc gataccgcca ccctgggcaa acgccagggc     720
gccgatcagc agctgggcaa aagcacctac cccgccctgc tgggcctgga acaggcccgc     780
aaaaaagccc gcgatctgat cgatgatgcc cgccagagcc tgaaacagct ggccgaacag     840
agcctggata ccagcgccct ggaagccctg ccgattaca tcatccagcg caacaaatag      900
```

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9

```
acgttgttgc cattgccctg ttgacaatta atcatcg                               37
```

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10

```
atgacttggt tgagtttagc tactggaatc atacaac                               37
```

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11

```
tgtgaaatta gctactggaa tcatacaac                                        29
```

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
gtagctaatt tcacacagga gactgccatg gattttcccc agcag        45

<210> SEQ ID NO 13
<211> LENGTH: 37
<212> TYPE: DNA
<213> ORGANISM: Artificial Sequence
<220> FEATURE:
<223> OTHER INFORMATION: Primer

<400> SEQUENCE: 13
atgacttggt tgagtctatt tgttgcgctg gatgatg        37

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
tgtgaaatta taagggaatg ggttcaac        28

<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
ccttataatt tcacacagga gactgccatg gattttcccc agcag        45

<210> SEQ ID NO 16
<211> LENGTH: 68
<212> TYPE: DNA
<213> ORGANISM: Artificial Sequence
<220> FEATURE:
<223> OTHER INFORMATION: Primer (gcd-attL)

<400> SEQUENCE: 16
ggtcaacatt atggggaaaa actcctcatc ctttagcgtg tgaagcctgc ttttttatac        60
taagttgg        68

<210> SEQ ID NO 17
<211> LENGTH: 68
<212> TYPE: DNA
<213> ORGANISM: Artificial Sequence
<220> FEATURE:
<223> OTHER INFORMATION: Primer (gcd-attR)

<400> SEQUENCE: 17
ttacttctgg tcgggcagcg cataggcaat cacgtaatcg cgctcaagtt agtataaaaa        60
agctgaac        68

<210> SEQ ID NO 18
<211> LENGTH: 20
<212> TYPE: DNA
<213> ORGANISM: Artificial Sequence
<220> FEATURE:
<223> OTHER INFORMATION: Primer (gcd-t1)

<400> SEQUENCE: 18
tgacaacaat ctatctgatt        20

```
<210> SEQ ID NO 19
<211> LENGTH: 20
<212> TYPE: DNA
<213> ORGANISM: Artificial Sequence
<220> FEATURE:
<223> OTHER INFORMATION: Primer (gcd-t2)

<400> SEQUENCE: 19
tgcgcctggt taagctggcg                                               20

<210> SEQ ID NO 20
<211> LENGTH: 803
<212> TYPE: PRT
<213> ORGANISM: Enterococcus faecalis

<400> SEQUENCE: 20
```

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
        195                 200                 205

Lys Asp Glu Gly Ile Arg Pro Asn Ser Ser Val Glu Lys Leu Gly Thr
    210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
                245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
        275                 280                 285

Ala Ile Gln Lys Leu Leu Ala Arg Asn Gln Leu Thr Thr Glu Glu Ile
    290                 295                 300

Asp Leu Tyr Glu Ile Asn Glu Ala Phe Ala Ala Thr Ser Ile Val Val
305                 310                 315                 320

```
Gln Arg Glu Leu Ala Leu Pro Glu Glu Lys Val Asn Ile Tyr Gly Gly
                325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Lys Tyr Gly Val
        355                 360                 365

Ala Ser Leu Cys Ile Gly Gly Leu Gly Leu Ala Met Leu Leu Glu
370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
            405                 410                 415

Lys Lys Glu Phe Glu Asn Thr Ala Leu Ser Ser Gln Ile Ala Asn His
        420                 425                 430

Met Ile Glu Asn Gln Ile Ser Glu Thr Glu Val Pro Met Gly Val Gly
            435                 440                 445

Leu His Leu Thr Val Asp Glu Thr Asp Tyr Leu Val Pro Met Ala Thr
    450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
            485                 490                 495

Val Phe Tyr Asp Val Ala Asp Ala Glu Ser Leu Ile Asp Glu Leu Gln
        500                 505                 510

Val Arg Glu Thr Glu Ile Phe Gln Gln Ala Glu Leu Ser Tyr Pro Ser
    515                 520                 525

Ile Val Lys Arg Gly Gly Gly Leu Arg Asp Leu Gln Tyr Arg Ala Phe
530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
            565                 570                 575

Phe Arg Glu Trp Phe Ala Glu Gln Lys Ile Leu Phe Ser Ile Leu Ser
        580                 585                 590

Asn Tyr Ala Thr Glu Ser Val Val Thr Met Lys Thr Ala Ile Pro Val
    595                 600                 605

Ser Arg Leu Ser Lys Gly Ser Asn Gly Arg Glu Ile Ala Glu Lys Ile
        610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
            645                 650                 655

Gly Asn Asp Thr Arg Ala Val Ser Ala Ser Cys His Ala Phe Ala Val
        660                 665                 670

Lys Glu Gly Arg Tyr Gln Gly Leu Thr Ser Trp Thr Leu Asp Gly Glu
    675                 680                 685

Gln Leu Ile Gly Glu Ile Ser Val Pro Leu Ala Leu Ala Thr Val Gly
690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
            725                 730                 735

Leu Ala Gln Asn Leu Ala Ala Leu Arg Ala Leu Val Ser Glu Gly Ile
```

```
                        740                 745                 750
Gln Lys Gly His Met Ala Leu Gln Ala Arg Ser Leu Ala Met Thr Val
            755                 760                 765

Gly Ala Thr Gly Lys Glu Val Glu Ala Val Ala Gln Gln Leu Lys Arg
        770                 775                 780

Gln Lys Thr Met Asn Gln Asp Arg Ala Leu Ala Ile Leu Asn Asp Leu
785                 790                 795                 800

Arg Lys Gln

<210> SEQ ID NO 21
<211> LENGTH: 2412
<212> TYPE: DNA
<213> ORGANISM: Enterococcus faecalis

<400> SEQUENCE: 21
atgaaaacag tagttattat tgatgcatta cgaacaccaa ttggaaaata taaaggcagc      60
ttaagtcaag taagtgccgt agacttagga acacatgtta caacacaact tttaaaaaga     120
cattccacta tttctgaaga aattgatcaa gtaatctttg gaatgttttt acaagctgga     180
aatggccaaa atcccgcacg acaaatagca ataaacagcg gtttgtctca tgaaattccc     240
gcaatgacgg ttaatgaggt ctgcggatca ggaatgaagg ccgttatttt ggcgaaacaa     300
ttgattcaat taggagaagc ggaagtttta attgctggcg ggattgagaa tatgtcccaa     360
gcacctaaat tacaacgttt taattacgaa acagaaagct acgatgcgcc ttttttctagt    420 atgatgtatg atggattaac ggatgccttt agtggtcagg caatgggctt aactgctgaa     480
aatgtggccg aaaagtatca tgtaactaga gaagagcaag atcaatttct tgtacattca     540
caattaaaag cagctcaagc acaagcagaa gggatattcg ctgacgaaat agccccatta     600
gaagtatcag gaacgcttgt ggagaaagat gaagggattc gccctaattc gagcgttgag     660
aagctaggaa cgcttaaaac agttttaaa gaagacggta ctgtaacagc agggaatgca      720
tcaaccatta tgatggggc ttctgctttg attattgctt cacaagaata tgccgaagca      780
cacggtcttc cttatttagc tattattcga gacagtgtgg aagtcggtat tgatccagcc     840
tatatgggaa tttcgccgat taaagccatt caaaaactgt tagcgcgcaa tcaacttact     900
acggaagaaa ttgatctgta tgaaatcaac gaagcatttg cagcaacttc aatcgtggtc     960
caaagagaac tggctttacc agaggaaaag gtcaacattt atggtggcgg tatttcatta    1020
ggtcatgcga ttggtgccac aggtgctcgt ttattaacga gtttaagtta tcaattaaat    1080
caaaaagaaa gaaatatgg agtggcttct ttatgtatcg gcggtggctt aggactcgct    1140
atgctactag agagacctca gcaaaaaaaa acagccgat tttatcaaat gagtcctgag     1200
gaacgcctgg cttctcttct taatgaaggc cagatttctg ctgatacaaa aaagaatt     1260 gaaaatacgg ctttatcttc gcagattgcc aatcatatga ttgaaaatca atcagtgaa     1320 acagaagtgc cgatgggcgt tggcttacat ttaacagtgg acgaaactga ttatttggta    1380
ccaatggcga cagaagagcc ctcagttatt gcggctttga gtaatggtgc aaaaatagca    1440
caaggattta aaacagtgaa tcaacaacgc ttaatgcgtg acaaatcgt tttttacgat     1500 gttgcagatc ccgagtcatt gattgataaa ctacaagtaa gagaagcgga agttttcaa     1560 caagcagagt taagttatcc atctatcgtt aaacggggcg gcggcttaag agatttgcaa     1620
tatcgtactt ttgatgaatc atttgtatct gtcgactttt tagtagatgt taaggatgca    1680
atgggggcaa atatcgttaa cgctatgttg gaaggtgtgg ccgagttgtt ccgtgaatgg    1740
```

-continued

```
tttgcggagc aaaagatttt attcagtatt ttaagtaatt atgccacgga gtcggttgtt   1800
acgatgaaaa cggctattcc agtttcacgt ttaagtaagg ggagcaatgg ccgggaaatt   1860
gctgaaaaaa ttgttttagc ttcacgctat gcttcattag atccttatcg ggcagtcacg   1920
cataacaaag gaatcatgaa tggcattgaa gctgtagttt tagctacagg aaatgataca   1980
cgcgctgtta gcgcttcttg tcatgctttt gcggtgaagg aaggtcgcta ccaaggcttg   2040
actagttgga cgctggatgg cgaacaacta attggtgaaa tttcagttcc gcttgcttta   2100
gccacggttg gcggtgccac aaaagtctta cctaaatctc aagcagctgc tgatttgtta   2160
gcagtgacgg atgcaaaaga actaagtcga gtagtagcgg ctgttggttt ggcacaaaat   2220
ttagcggcgt tacgggcctt agtctctgaa ggaattcaaa aaggacacat ggctctacaa   2280
gcacgttctt tagcgatgac ggtcggagct actggtaaag aagttgaggc agtcgctcaa   2340
caattaaaac gtcaaaaaac gatgaaccaa gaccgagcca tggctatttt aaatgattta   2400
agaaaacaat aa                                                       2412
```

<210> SEQ ID NO 22
<211> LENGTH: 2412
<212> TYPE: DNA
<213> ORGANISM: Artificial Sequence
<220> FEATURE:
<223> OTHER INFORMATION: DNA having modified codons, which encodes mvaE derived from Enterococcus faecalis

<400> SEQUENCE: 22

```
atgaaaaccg tggttattat cgatgcgctg cgcacgccga ttggtaaata taaaggcagc     60
ctgtctcaag tgagcgccgt tgatctgggt acgcatgtga ccacgcagct gctgaaacgt    120
cacagcacca tctctgaaga aattgatcag gtgatctttg gtaacgttct gcaagccggt   180
aatggtcaga atccggcacg tcagattgca atcaacagtg gcctgagcca tgaaattccg    240
gcgatgaccg tgaatgaagt ttgcggtagc ggcatgaaag cggttattct ggccaaacag    300
ctgatccagc tgggtgaagc ggaagtgctg attgccggcg gtatcgaaaa catgagtcag    360
gcaccgaaac tgcaacgttt taattatgaa accgaaagct acgatgcccc ggtcagctct    420
atgatgtatg atggcctgac cgatgcattt agcggtcagg cgatgggcct gacggcagaa    480
aacgtggcgg aaaaatacca tgttacccgc gaagaacagg atcagttttc tgttcacagt    540
cagctgaaag cggcccaggc ccaggcagaa ggtattttcg ccgatgaaat cgcaccgctg    600
gaagtgtctg gtacgctggt tgaaaaagat gaaggcattc gtccgaatag tagcgtggaa    660
aaactgggca ccctgaaaac ggtgttcaaa gaagatggca ccgttacggc gggcaatgca    720
agcaccatca atgatggtgc gagtgccctg attatcgcga ccaggaata tgcagaagcg     780 catggcctgc cgtacctggc cattatccgc gattctgtgg aagttggtat tgatccggca    840
tatatgggca ttagtccgat caaagcgatt cagaaactgc tggcccgtaa ccagctgacc    900
accgaagaaa ttgatctgta cgaaatcaat gaagcgtttg cagcgaccag tattgtggtt    960
cagcgcgaac tggccctgcc ggaagaaaaa gttaacattt atggcggtgg catcagcctg   1020
ggtcacgcaa ttggtgccac cggtgcacgt ctgctgacca gtctgagcta tcagctgaat   1080
cagaaagaga aaaatacgg tgtggcaagc ctgtgtattg tggcggtct gggtctggcc    1140 atgctgctgg aacgtccgca gcagaagaaa actctcgtt tttaccagat gagtccggaa    1200
gaacgtctgg ccagtctgct gaacgaaggc cagattagcg cagataccaa aaagaattc   1260 gaaaatacgg cactgtctag tcagatcgcg aaccatatga ttgaaaatca gatcagcgaa   1320
```

-continued

```
accgaagtgc cgatgggtgt tggcctgcac ctgaccgtgg atgaaacgga ttatctggtt      1380
ccgatggcga cggaagaacc gagcgttatt gccgcactgt ctaacggtgc aaaaatcgcg      1440
cagggcttta aaccgtgaaa tcagcagcgt ctgatgcgcg ccagattgt gttctacgat       1500 gttgcggatc cggaaagcct gatcgataaa ctgcaagtgc gcgaagccga agttttcag       1560 caggcagaac tgagctatcc gtctattgtg aaacgtggcg gtggcctgcg cgatctgcaa      1620
taccgtacct ttgatgaaag tttcgtgagc gttgatttcc tggtggatgt taaagatgcc     1680
atgggtgcaa acatcgtgaa tgcgatgctg aaggcgttg ccgaactgtt tcgtgaatgg      1740
ttcgcggaac agaaaatcct gttttctatc ctgagtaact acgcgaccga aagcgtggtt     1800
accatgaaaa cggccattcc tgtgagccgc ctgtctaaag gtagtaatgg ccgtgaaatt     1860
gcggaaaaaa tcgttctggc gagccgctat gcctctctgg atccgtaccg tgccgtgacc     1920
cataacaaag gtattatgaa tggcatcgaa gcagtggttc tggcgaccgg taacgatacc    1980
cgtgccgtgt ctgcaagttg ccatgcattc gcagttaaag aaggtcgtta tcagggcctg    2040
accagctgga cgctggatgg tgaacagctg atcggcgaaa tttctgtgcc gctggccctg    2100
gcaaccgtgg gtggcgcgac gaaagttctg ccgaaaagcc aggcggccgc agatctgctg    2160
gcggtgaccg atgcaaaaga actgtctcgc gtggttgcgg ccgttggtct ggcacagaat    2220
ctggcagcgc tgcgtgcgct ggtgtctgaa ggtattcaga aaggccacat ggcactgcaa    2280
gcccgtagtc tggccatgac cgtgggtgca acgggcaaag aagtggaagc agttgcgcag    2340
cagctgaaac gccagaaaac catgaaccag gatcgtgcca tggcaatcct gaatgatctg    2400
cgcaaacagt aa                                                          2412
```

<210> SEQ ID NO 23
<211> LENGTH: 383
<212> TYPE: PRT
<213> ORGANISM: Enterococcus faecalis

<400> SEQUENCE: 23

```
Met Thr Ile Gly Ile Asp Lys Ile Ser Phe Phe Val Pro Pro Tyr Tyr
1               5                  10                   15

Ile Asp Met Thr Ala Leu Ala Glu Ala Arg Asn Val Asp Pro Gly Lys
            20                 25                   30

Phe His Ile Gly Ile Gly Gln Asp Gln Met Ala Val Asn Pro Ile Ser
        35                 40                   45

Gln Asp Ile Val Thr Phe Ala Ala Asn Ala Ala Glu Ala Ile Leu Thr
    50                 55                   60

Lys Glu Asp Lys Glu Ala Ile Asp Met Val Ile Val Gly Thr Glu Ser
65                 70                   75                   80

Ser Ile Asp Glu Ser Lys Ala Ala Ala Val Val Leu His Arg Leu Met
                85                   90                   95

Gly Ile Gln Pro Phe Ala Arg Ser Phe Glu Ile Lys Glu Ala Cys Tyr
            100                 105                  110

Gly Ala Thr Ala Gly Leu Gln Leu Ala Lys Asn His Val Ala Leu His
        115                 120                  125

Pro Asp Lys Lys Val Leu Val Val Ala Ala Asp Ile Ala Lys Tyr Gly
    130                 135                  140

Leu Asn Ser Gly Gly Glu Pro Thr Gln Gly Ala Gly Ala Val Ala Met
145                 150                  155                  160

Leu Val Ala Ser Glu Pro Arg Ile Leu Ala Leu Lys Glu Asp Asn Val
                165                  170                  175
```

```
Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380

<210> SEQ ID NO 24
<211> LENGTH: 1152
<212> TYPE: DNA
<213> ORGANISM: Enterococcus faecalis

<400> SEQUENCE: 24
atgacaattg ggattgataa aattagtttt tttgtgcccc cttattatat tgatatgacg    60
gcactggctg aagccagaaa tgtagaccct ggaaaatttc atattggtat tgggcaagac   120
caaatggcgg tgaacccaat cagccaagat attgtgacat ttgcagccaa tgccgcagaa   180
gcgatcttga ccaagaaga taagaggcc attgatatgg tgattgtcgg gactgagtcc   240
agtatcgatg agtcaaaagc ggccgcagtt gtcttacatc gtttaatggg gattcaacct   300
ttcgctcgct ctttcgaaat caaggaagct tgttacggag caacagcagg cttacagtta   360
gctaagaatc acgtagcctt acatccagat aaaaaagtct tggtcgtagc ggcagatatt   420
gcaaaatatg gcttaaattc tggcggtgag cctacacaag agctggggc ggttgcaatg   480 ttagttgcta gtgaaccgcg cattttggct ttaaagagg ataatgtgat gctgacgcaa   540
gatatctatg acttttggcg tccaacaggc caccgtatc ctatggtcga tggtcctttg   600
tcaaacgaaa cctacatcca atcttttgcc caagtctggg atgaacataa aaacgaacc   660 ggtcttgatt ttgcagatta tgatgccttta gcgttccata ttccttacac aaaaatgggc   720
aaaaaagcct tattagcaaa aatctccgac caaactgaag cagaacagga acgaattta   780 gcccgttatg aagaaagtat cgtctatagt cgtcgcgtag aaacttgta tacgggttca   840 ctttatctgg gactcatttc ccttttagaa aatgcaacga ctttaaccgc aggcaatcaa   900
attggtttat tcagttatgg ttctggtgct gtcgctgaat ttttcactgg tgaattagta   960
```

```
gctggttatc aaaatcattt acaaaaagaa actcatttag cactgctgga taatcggaca      1020
gaactttcta tcgctgaata tgaagccatg tttgcagaaa ctttagacac agacattgat      1080
caaacgttag aagatgaatt aaaatatagt atttctgcta ttaataatac cgttcgttct      1140
tatcgaaact aa                                                         1152
```

<210> SEQ ID NO 25
<211> LENGTH: 1152
<212> TYPE: DNA
<213> ORGANISM: Artificial Sequence
<220> FEATURE:
<223> OTHER INFORMATION: DNA having modified codons, which encodes mvaS
      derived from Enterococcus faecalis

<400> SEQUENCE: 25

```
atgaccattg gtatcgataa aattagcttt ttcgtgccgc cgtattacat cgatatgacg       60
gcgctggccg aagcacgtaa cgttgatccg ggcaaatttc atattggcat cggtcaggat      120
cagatggcgt tgaacccgat ttctcaggat atcgttacct tcgcggccaa tgcagcggaa      180
gcaattctga cgaaagaaga taaagaagcg attgatatgg tgatcgttgg caccgaaagc      240
tctatcgatg aaagtaaagc cgcagcggtg gttctgcacc gtctgatggg cattcagccg      300
tttgcgcgca gcttcgaaat caaagaagcc tgctatggcg cgaccgccgg tctgcaactg      360
gccaaaaacc atgtggcact gcacccggat aaaaaagttc tggtggttgc cgcagatatt      420
gcgaaatacg gtctgaatag cggcggtgaa ccgacccagg gtgcaggtgc cgtggcaatg      480
ctggttgcat ctgaaccgcg tattctggcg ctgaaagaag ataacgtgat gctgacccag      540
gatatctatg atttttggcg tccgaccggt catccgtacc cgatggtgga tggcccgctg      600
agtaatgaaa cctatattca gagcttcgcc caggtttggg atgaacataa aaaacgtacg      660
ggtctggatt ttgcggatta tgatgcactg gcgttccaca ttccgtacac caaaatgggc      720
aaaaaagcgc tgctggccaa atcagcgat cagacggaag ccgaacagga acgtattctg      780
gcacgctatg aagaaagcat cgtgtactct cgtcgcgttg caacctgta taccggttct      840 ctgtacctgg gcctgattag tctgctggaa aacgcgacca cgctgacggc cggcaatcag      900
atcggtctgt tttcttatgg cagtggtgcc gtggcagaat ttttcaccgg tgaactggtt      960
gccggctacc agaaccatct gcaaaaagaa acccacctgg ccctgctgga taatcgcacg     1020
gaactgtcta ttgcagaata tgaagcaatg tttgcgaaaa ccctggatac ggatatcgat     1080
cagaccctgg aagatgaact gaaatatagt attagcgcga tcaacaatac ggtgcgtagt     1140
taccgcaatt aa                                                         1152
```

<210> SEQ ID NO 26
<211> LENGTH: 40
<212> TYPE: DNA
<213> ORGANISM: Artificial Sequence
<220> FEATURE:
<223> OTHER INFORMATION: Primer for amplifying a fragment comprising
      Para composed of araC and ara BAD promoters from E.coli

<400> SEQUENCE: 26

```
tgaattcgag ctcggtaccc actcttcctt tttcaatatt                              40
```

<210> SEQ ID NO 27
<211> LENGTH: 40
<212> TYPE: DNA
<213> ORGANISM: Artificial Sequence
<220> FEATURE:
<223> OTHER INFORMATION: Primer for amplifying a fragment comprising Para composed of araC and ara BAD promoters from E.coli

<400> SEQUENCE: 27
ataataacca cggttttcat tttttataac ctccttagag                    40

<210> SEQ ID NO 28
<211> LENGTH: 40
<212> TYPE: DNA
<213> ORGANISM: Artificial Sequence
<220> FEATURE:
<223> OTHER INFORMATION: Primer for amplifying a fragment comprising
      EFmvaE gene

<400> SEQUENCE: 28
ctctaaggag gttataaaaa atgaaaaccg tggttattat                    40

<210> SEQ ID NO 29
<211> LENGTH: 55
<212> TYPE: DNA
<213> ORGANISM: Artificial Sequence
<220> FEATURE:
<223> OTHER INFORMATION: Primer for amplifying a fragment comprising
      EFmvaE gene

<400> SEQUENCE: 29
ttatcgatac caatggtcat gtttttttac ctcctttact gtttgcgcag atcat    55

<210> SEQ ID NO 30
<211> LENGTH: 55
<212> TYPE: DNA
<213> ORGANISM: Artificial Sequence
<220> FEATURE:
<223> OTHER INFORMATION: Primer for amplifying a fragment comprising
      EFmvaS gene

<400> SEQUENCE: 30
atgatctgcg caaacagtaa aggaggtaaa aaaacatgac cattggtatc gataa    55

<210> SEQ ID NO 31
<211> LENGTH: 40
<212> TYPE: DNA
<213> ORGANISM: Artificial Sequence
<220> FEATURE:
<223> OTHER INFORMATION: Primer for amplifying a fragment comprising
      EFmvaS gene

<400> SEQUENCE: 31
cagcggaact ggcggctccc ttaattgcgg taactacgca                    40

<210> SEQ ID NO 32
<211> LENGTH: 40
<212> TYPE: DNA
<213> ORGANISM: Artificial Sequence
<220> FEATURE:
<223> OTHER INFORMATION: Primer for amplifying a fragment comprising
      Ttrp

<400> SEQUENCE: 32
tgcgtagtta ccgcaattaa gggagccgcc agttccgctg                    40

<210> SEQ ID NO 33
<211> LENGTH: 38
<212> TYPE: DNA
<213> ORGANISM: Artificial Sequence
<220> FEATURE:
<223> OTHER INFORMATION: Primer for amplifying a fragment comprising
      Ttrp

<400> SEQUENCE: 33
gtcgactcta gaggatccct aatgagaatt agtcaaat                                    38

<210> SEQ ID NO 34
<211> LENGTH: 42
<212> TYPE: DNA
<213> ORGANISM: Artificial Sequence
<220> FEATURE:
<223> OTHER INFORMATION: Primer (Linker-F)

<400> SEQUENCE: 34
agctttaggg ataacagggt aatctcgagc tgcaggcatg ca                               42

<210> SEQ ID NO 35
<211> LENGTH: 42
<212> TYPE: DNA
<213> ORGANISM: Artificial Sequence
<220> FEATURE:
<223> OTHER INFORMATION: Primer (Linker-R)

<400> SEQUENCE: 35
agcttgcatg cctgcagctc gagattaccc tgttatccct aa                               42

<210> SEQ ID NO 36
<211> LENGTH: 55
<212> TYPE: DNA
<213> ORGANISM: Artificial Sequence
<220> FEATURE:
<223> OTHER INFORMATION: Primer (lldD5' CAS)

<400> SEQUENCE: 36
tttttaagct ttagggataa cagggtaatc tcgagattta agcggctgc tttac                  55

<210> SEQ ID NO 37
<211> LENGTH: 43
<212> TYPE: DNA
<213> ORGANISM: Artificial Sequence
<220> FEATURE:
<223> OTHER INFORMATION: Primer (lldD3' CAS)

<400> SEQUENCE: 37
tttttaagct tgcatgcctg cagtatttaa tagaatcagg tag                              43

<210> SEQ ID NO 38
<211> LENGTH: 54
<212> TYPE: DNA
<213> ORGANISM: Artificial Sequence
<220> FEATURE:
<223> OTHER INFORMATION: Primer (phoC5' CAS)

<400> SEQUENCE: 38
tttttaagct ttagggataa cagggtaatc tcgagtggat aacctcatgt aaac                  54

<210> SEQ ID NO 39
<211> LENGTH: 44
<212> TYPE: DNA
<213> ORGANISM: Artificial Sequence
<220> FEATURE:
<223> OTHER INFORMATION: Primer (phoC3' CAS)

<400> SEQUENCE: 39
tttttaagct tgcatgcctg cagttgatgt ctgattatct ctga                             44

<210> SEQ ID NO 40

-continued

<211> LENGTH: 54
<212> TYPE: DNA
<213> ORGANISM: Artificial Sequence
<220> FEATURE:
<223> OTHER INFORMATION: Primer (pstS5' CAS)

<400> SEQUENCE: 40
tttttaagct ttagggataa cagggtaatc tcgagagcct ctcacgcgtg aatc       54

<210> SEQ ID NO 41
<211> LENGTH: 44
<212> TYPE: DNA
<213> ORGANISM: Artificial Sequence
<220> FEATURE:
<223> OTHER INFORMATION: Primer (pstS3' CAS)

<400> SEQUENCE: 41
tttttaagct tgcatgcctg cagaggggag aaaagtcagg ctaa       44

<210> SEQ ID NO 42
<211> LENGTH: 33
<212> TYPE: DNA
<213> ORGANISM: Artificial Sequence
<220> FEATURE:
<223> OTHER INFORMATION: Primer (n67)

<400> SEQUENCE: 42
tgcgaagacg tcctcgtgaa gaaggtgttg ctg       33

<210> SEQ ID NO 43
<211> LENGTH: 36
<212> TYPE: DNA
<213> ORGANISM: Artificial Sequence
<220> FEATURE:
<223> OTHER INFORMATION: Primer (n68)

<400> SEQUENCE: 43
tgcgaagggc ccgttgtgt ctcaaaatct ctgatg       36

<210> SEQ ID NO 44
<211> LENGTH: 70
<212> TYPE: DNA
<213> ORGANISM: Artificial Sequence
<220> FEATURE:
<223> OTHER INFORMATION: Primer (ampH-attL-phi80)

<400> SEQUENCE: 44
atgcgcactc cttacgtact ggctctactg gtttctttgc gaaaggtcat ttttcctgaa       60
tatgctcaca       70

<210> SEQ ID NO 45
<211> LENGTH: 64
<212> TYPE: DNA
<213> ORGANISM: Artificial Sequence
<220> FEATURE:
<223> OTHER INFORMATION: Primer (ampH-attR-phi80)

<400> SEQUENCE: 45
ttaaggaatc gcctggacca tcatcggcga gccgttctga cgtttgttga cagctggtcc       60
aatg       64

<210> SEQ ID NO 46
<211> LENGTH: 68
<212> TYPE: DNA
<213> ORGANISM: Artificial Sequence
<220> FEATURE:
<223> OTHER INFORMATION: Primer (DampC-phL)

<400> SEQUENCE: 46
ctgatgaact gtcacctgaa tgagtgctga tgaaaatata gaaaggtcat ttttcctgaa    60
tatgctca    68

<210> SEQ ID NO 47
<211> LENGTH: 64
<212> TYPE: DNA
<213> ORGANISM: Artificial Sequence
<220> FEATURE:
<223> OTHER INFORMATION: Primer (DampC-phR)

<400> SEQUENCE: 47
attcgccagc ataacgatgc cgctgttgag ctgaggaaca cgtttgttga cagctggtcc    60
aatg    64

<210> SEQ ID NO 48
<211> LENGTH: 18
<212> TYPE: DNA
<213> ORGANISM: Artificial Sequence
<220> FEATURE:
<223> OTHER INFORMATION: Primer (ampH-t1)

<400> SEQUENCE: 48
gcgaagccct ctccgttg    18

<210> SEQ ID NO 49
<211> LENGTH: 21
<212> TYPE: DNA
<213> ORGANISM: Artificial Sequence
<220> FEATURE:
<223> OTHER INFORMATION: Primer (ampH-t2)

<400> SEQUENCE: 49
agccagtcag cctcatcagc g    21

<210> SEQ ID NO 50
<211> LENGTH: 21
<212> TYPE: DNA
<213> ORGANISM: Artificial Sequence
<220> FEATURE:
<223> OTHER INFORMATION: Primer (ampC-t1)

<400> SEQUENCE: 50
gattcccact tcaccgagcc g    21

<210> SEQ ID NO 51
<211> LENGTH: 21
<212> TYPE: DNA
<213> ORGANISM: Artificial Sequence
<220> FEATURE:
<223> OTHER INFORMATION: Primer (ampC-t2)

<400> SEQUENCE: 51
ggcaggtatg gtgctctgac g    21

<210> SEQ ID NO 52
<211> LENGTH: 64
<212> TYPE: DNA
<213> ORGANISM: Artificial Sequence
<220> FEATURE:
<223> OTHER INFORMATION: Primer (crtE-attRphi80)

```
<400> SEQUENCE: 52
atgacggtct gcgcaaaaaa acacgttcat ctcactcgcg cgtttgttga cagctggtcc      60
aatg                                                                   64

<210> SEQ ID NO 53
<211> LENGTH: 68
<212> TYPE: DNA
<213> ORGANISM: Artificial Sequence
<220> FEATURE:
<223> OTHER INFORMATION: Primer (crtZ-attLphi80)

<400> SEQUENCE: 53
atgttgtgga tttggaatgc cctgatcgtt tcgttaccg gaaaggtcat ttttcctgaa       60
tatgctca                                                               68

<210> SEQ ID NO 54
<211> LENGTH: 21
<212> TYPE: DNA
<213> ORGANISM: Artificial Sequence
<220> FEATURE:
<223> OTHER INFORMATION: Primer (crtZ-test)

<400> SEQUENCE: 54
ccgtgtggtt ctgaaagccg a                                                21

<210> SEQ ID NO 55
<211> LENGTH: 21
<212> TYPE: DNA
<213> ORGANISM: Artificial Sequence
<220> FEATURE:
<223> OTHER INFORMATION: Primer (crtE-test)

<400> SEQUENCE: 55
cgttgccgta aatgtatccg t                                                21

<210> SEQ ID NO 56
<211> LENGTH: 27
<212> TYPE: DNA
<213> ORGANISM: Artificial Sequence
<220> FEATURE:
<223> OTHER INFORMATION: Primer (phL-test)

<400> SEQUENCE: 56
ggatgtaaac cataacactc tgcgaac                                          27

<210> SEQ ID NO 57
<211> LENGTH: 25
<212> TYPE: DNA
<213> ORGANISM: Artificial Sequence
<220> FEATURE:
<223> OTHER INFORMATION: Primer (phR-test)

<400> SEQUENCE: 57
gattggtggt tgaattgtcc gtaac                                            25

<210> SEQ ID NO 58
<211> LENGTH: 3471
<212> TYPE: DNA
<213> ORGANISM: Artificial Sequence
<220> FEATURE:
<223> OTHER INFORMATION: Sequence of the chemically synthesized DNA
      fragment retaining artificial KDyI operon with optimized codons

<400> SEQUENCE: 58
```

```
gcatgcagga ggtatgaatg tcagagttgc gtgccttcag tgccccaggg aaagcgttac    60
tcgctggtgg atatttagtt ttagatacaa aatatgaagc atttgtagtc ggattatcgg   120
cacgtatgca cgctgtagcc catccttacg gttcattgca agggtctgat aagtttgaag   180
tgcgtgtgaa aagtaaacaa tttaaagatg gggagtggct gtaccatata agtcctaaaa   240
gtggcttcat tcctgtttcg ataggcggat ctaagaaccc tttcattgaa aaagttatcg   300
ctaacgtatt tagctacttt aaacctaaca tggacgacta ctgcaatcgt aacttgttcg   360
ttattgatat tttctctgat gatgcctacc attctcagga ggatagcgtt accgaacatc   420
gtggcaaccg ccgtttgagt tttcattcgc accgtattga agaagttccc aaaacagggc   480
tgggctcctc ggcaggttta gtcacagttt aactacagc tttggcctcc ttttttgtat   540
cggacctgga aaataatgta gacaaatatc gtgaagttat tcataattta gcacaagttg   600
ctcattgtca agctcagggt aaaattggaa gcgggtttga tgtagcggcg gcagcatatg   660
gatctatccg ttatcgccgt ttcccacccg cattaatctc taatttgcca gatattggaa   720
gtgctactta cggcagtaaa ctggcgcatt tggttgatga agaagactgg aatattacga   780
ttaaaagtaa ccatttacct tcgggattaa ctttatggat gggcgatatt aagaatggtt   840
cagaaacagt aaaactggtc cagaaggtaa aaaattggta tgattcgcat atgccagaaa   900
gcctcaaaat atatacagaa ctcgatcatg caaattctcg ttttatggat ggactctcta   960
aactcgatcg cttacacgag actcatgacg attacagcga tcagatattt gagtctcttg  1020
agcgtaatga ctgtacctgt caaaagtatc ctgaaatcac agaagttcgt gatgcagttg  1080
ccacaattcg tcgttccttt cgtaaaataa ctaaagaatc tggtgccgat atcgaacctc  1140
ccgtacaaac tagcttattg gatgattgcc agaccttaaa aggagttctt acttgcttaa  1200
tacctggtgc tggtggttat gacgccattg cagtgattac taagcaagat gttgatcttc  1260
gtgctcaaac cgctaatgac aaacgttttt ctaaggttca atggctggat gtaactcagg  1320
ctgactgggg tgttcgtaaa gaaaaagatc cggaaactta tcttgataaa taactgcaga  1380
ggaggtatga atgaccgttt acacagcatc cgttaccgca cccgtcaaca tcgcaaccct  1440
taagtattgg gggaaacgtg acacgaagtt gaatctgccc accaattcgt ccatatcagt  1500
gactttatcg caagatgacc tccgtacgtt gacctctgcg gctactgcac ctgagtttga  1560
acgcgacact ttgtggttaa atggagaacc acacagcatc gacaatgaac gtactcaaaa  1620
ttgtctgcgc gacctccgcc aattacgtaa ggaaatggaa tcgaaggacg cctcattgcc  1680
cacattatct caatggaaac tccacattgt ctccgaaaat aactttccta cagcagctgg  1740
tttagcttcc tccgctgctg ctttgctgc attggtctct gcaattgcta agttatacca  1800
attaccacag tcaacttcag aaatatctcg tatagcacgt aagggggtctg gttcagcttg  1860 tcgttcgttg tttggcggat acgtggcctg ggaaatggga aaagctgaag atggtcatga  1920
ttccatggca gtacaaatcg cagacagctc tgactggcct cagatgaaag catgtgtcct  1980
tgttgtcagc gatattaaaa aggatgtgag ttccactcag ggtatgcaat tgaccgtggc  2040
aacctccgaa ctctttaaag aacgtattga acatgtcgta ccaaagcgtt ttgaagtcat  2100
gcgtaaagcc attgttgaaa agatttcgc caccttgca aaggaaacaa tgatggattc  2160
caactctttc catgccacat gtttggactc tttccctcca atattctaca tgaatgacac  2220
ttccaagcgt atcatcagtt ggtgccacac cattaatcag ttttacggag aaacaatcgt  2280
tgcatacacg tttgatgcag gtccaaatgc tgtgttgtac tacttagctg aaaatgagtc  2340
gaaactcttt gcatttatct ataaattgtt tggctctgtt cctggatggg acaagaaatt  2400
```

```
tactactgag cagcttgagg ctttcaacca tcaatttgaa tcatctaact ttactgcacg    2460
tgaattggat cttgagttgc aaaaggatgt tgcccgtgtg attttaactc aagtcggttc    2520
aggcccacaa gaaacaaacg aatctttgat tgacgcaaag actggtctcc caaggaata     2580 aggatccagg aggtatgaat gactgccgac aacaatagta tgccccatgg tgcagtatct    2640
agttacgcca aattagtgca aaaccaaaca cctgaagaca ttttggaaga gtttcctgaa    2700
attattccat tacaacaacg tcctaatacc cgctctagtg agacgtcaaa tgacgaaagc    2760
ggagaaacat gttttctgg tcatgatgag gagcaaatta agttaatgaa tgaaaattgt     2820
attgttttgg attgggacga taatgctatt ggtgccggca ccaagaaagt ttgtcattta    2880
atggaaaata ttgaaaaggg tttacttcat cgtgcattct ccgtctttat tttcaatgaa    2940
caaggtgaat tacttttaca caacgtgcc actgaaaaaa taactttccc tgatctttgg     3000
actaacacat gctgctctca tccactttgt attgatgacg aattaggttt gaagggtaag    3060
ctcgacgata agattaaggg cgctattact gcggcggtgc gtaaactcga tcatgaatta    3120
ggtattccag aagatgaaac taagacacgt ggtaagtttc acttttaaa ccgtatccat     3180 tacatggcac aagcaatga accatggggt gaacatgaaa ttgattacat cctcttttat    3240
aagatcaacg ctaaagaaaa cttgactgtc aacccaaacg tcaatgaagt tcgtgacttc    3300
aaatgggttt caccaaatga tttgaaaact atgtttgctg acccaagtta caagtttacg    3360
ccttggttta agattatttg cgagaattac ttattcaact ggtgggagca attagatgac    3420
ctttctgaag tggaaaatga ccgtcaaatt catcgtatgc tctaaggtac c              3471

<210> SEQ ID NO 59
<211> LENGTH: 2931
<212> TYPE: DNA
<213> ORGANISM: Pantoea anantis
<220> FEATURE:
<221> NAME/KEY: CDS
<222> LOCATION: (301)..(2691)

<400> SEQUENCE: 59
gcgtctggcg atctcattcc ctttacgctt taaccttctt tatctcctgg cactattgaa       60
tcatatcggc aaggccccat taacaccctc taaagtattg ccttagatgc gttgttaaga     120
gctttaagcc aaaaaaatca aaactcatac caatttgct ataacattta acagatatgg      180
atcatcacgc ttcagggaag agcgaaataa gaatgccttt catcttttgt actttatgac     240
tgacaacaat ctatctgatt gttttcctga gttttctggc aacgaaatga ggtcaacatt     300 atg ggg aaa aac tcc tca tcc ttt agc gtg gtc cgt ttt tta acg gtg       348
Met Gly Lys Asn Ser Ser Ser Phe Ser Val Val Arg Phe Leu Thr Val
1               5                   10                  15 ctg ttc gcc gtg cta acg ggt gcg ttc atg tta att ggt ggt atc tgg       396
Leu Phe Ala Val Leu Thr Gly Ala Phe Met Leu Ile Gly Gly Ile Trp
            20                  25                  30 ctg gcc acg atc ggt ggt tcc tgg tac tac atc atc ggc ggt gca gcc       444
Leu Ala Thr Ile Gly Gly Ser Trp Tyr Tyr Ile Ile Gly Gly Ala Ala
        35                  40                  45 atg ctg ctt acc gct ttc ctg ctg tgg cga cgt aac agc gct gcc ctg       492
Met Leu Leu Thr Ala Phe Leu Leu Trp Arg Arg Asn Ser Ala Ala Leu
    50                  55                  60 gtt gtc tat gcg ctc tta ctg ctg gct acg ctg gcc tgg ggc gtt tgg       540
Val Val Tyr Ala Leu Leu Leu Ala Thr Leu Ala Trp Gly Val Trp
65                  70                  75                  80 gaa gtc ggc acc gac ttc tgg gca ctg gca ccg cgt acc gac gta ctg       588
Glu Val Gly Thr Asp Phe Trp Ala Leu Ala Pro Arg Thr Asp Val Leu
```

|     |     |     |     |     |     |     |     |     |     |     |     |     |     |     |     |
|---|---|---|---|---|---|---|---|---|---|---|---|---|---|---|---|
| Glu | Val | Gly | Thr | Asp | Phe | Trp | Ala | Leu | Ala | Pro | Arg | Thr | Asp | Val | Leu |
|     |     |     |     | 85  |     |     |     | 90  |     |     |     |     | 95  |     |     |

```
gtg atc ttt ggc gtc tgg ctg gtg ttg ccc ttt gtc tat cgc ggc tta    636
Val Ile Phe Gly Val Trp Leu Val Leu Pro Phe Val Tyr Arg Gly Leu
        100                 105                 110 tac cag ccg ggt aaa ggc gca ctg ggt gcc atg ggc gta gcg ctg gtt    684
Tyr Gln Pro Gly Lys Gly Ala Leu Gly Ala Met Gly Val Ala Leu Val
        115                 120                 125 gcc agt gca gcg gtg tta acc tat tcc gtc ttt aat gat cca caa gtg    732
Ala Ser Ala Ala Val Leu Thr Tyr Ser Val Phe Asn Asp Pro Gln Val
    130                 135                 140 gtt aac ggt gca tta ccg gca aca gcg gat aat gcg cct cag gca cag    780
Val Asn Gly Ala Leu Pro Ala Thr Ala Asp Asn Ala Pro Gln Ala Gln
145                 150                 155                 160 ccg ttg agc aat att gct gat ggt gac tgg ccg gcc tat gcg cgc gat    828
Pro Leu Ser Asn Ile Ala Asp Gly Asp Trp Pro Ala Tyr Ala Arg Asp
                165                 170                 175 cag caa ggg acg cgc ttc tcg ccg ctc aag cag atc aac cac gac aat    876
Gln Gln Gly Thr Arg Phe Ser Pro Leu Lys Gln Ile Asn His Asp Asn
            180                 185                 190 gtg aaa gaa ctg cag gtt gcc tgg caa ttc cag acc ggt gat atg aaa    924
Val Lys Glu Leu Gln Val Ala Trp Gln Phe Gln Thr Gly Asp Met Lys
        195                 200                 205 cgc cca agc gat ccg ggc gaa att acc gat gaa gtg acg cca atc aag    972
Arg Pro Ser Asp Pro Gly Glu Ile Thr Asp Glu Val Thr Pro Ile Lys
    210                 215                 220 att cgc gac acg ctg tat ctt tgc acg cca cat cag att tta ttt gct    1020
Ile Arg Asp Thr Leu Tyr Leu Cys Thr Pro His Gln Ile Leu Phe Ala
225                 230                 235                 240 ctg gat gcg gcc acc ggc aag caa aag tgg aag ttt gat ccc ggc ctg    1068
Leu Asp Ala Ala Thr Gly Lys Gln Lys Trp Lys Phe Asp Pro Gly Leu
                245                 250                 255 aaa acc aac cca acc ttc cag cac gtg acc tgt cgt ggt gtg tca tac    1116
Lys Thr Asn Pro Thr Phe Gln His Val Thr Cys Arg Gly Val Ser Tyr
            260                 265                 270 cac gaa ttc cct gca gcg aag gat gcg tcc aat acc cag cct gcg ctg    1164
His Glu Phe Pro Ala Ala Lys Asp Ala Ser Asn Thr Gln Pro Ala Leu
        275                 280                 285 tgc tcg cgt cgt atc tac ctg cca gtc aat gac ggg cgt ttg ttc gcg    1212
Cys Ser Arg Arg Ile Tyr Leu Pro Val Asn Asp Gly Arg Leu Phe Ala
    290                 295                 300 ctg gat gcg gaa acc ggt gaa cgc tgc ccg gcc ttt ggt aac aac ggt    1260
Leu Asp Ala Glu Thr Gly Glu Arg Cys Pro Ala Phe Gly Asn Asn Gly
305                 310                 315                 320 gag ctg gat ctg cag cac aag cag ccg gtc aca acg cca ggc atg tat    1308
Glu Leu Asp Leu Gln His Lys Gln Pro Val Thr Thr Pro Gly Met Tyr
                325                 330                 335 gag cca acc tcg cca ccg gtg att act gac acc acc att gtg atg gct    1356
Glu Pro Thr Ser Pro Pro Val Ile Thr Asp Thr Thr Ile Val Met Ala
            340                 345                 350 ggc gcg gta acc gat aac ttt tca acc cgt gaa cct tca ggc gcc atc    1404
Gly Ala Val Thr Asp Asn Phe Ser Thr Arg Glu Pro Ser Gly Ala Ile
        355                 360                 365 cgt ggc ttt gat gtg aac acc ggt aag ctg ttg tgg gtg ttc gat ccg    1452
Arg Gly Phe Asp Val Asn Thr Gly Lys Leu Leu Trp Val Phe Asp Pro
370                 375                 380 ggc gcg aaa gat cct aac gcg att ccg gcg gat gaa cac acg ttc acc    1500
Gly Ala Lys Asp Pro Asn Ala Ile Pro Ala Asp Glu His Thr Phe Thr
                385                 390                 395                 400
```

| | |
|---|---|
| atg aac tcc cct aac tcg tgg gca cct gcg gtt tac gat ccg aag ctg<br>Met Asn Ser Pro Asn Ser Trp Ala Pro Ala Val Tyr Asp Pro Lys Leu<br>405 410 415 | 1548 |
| gat atc gtt tac ctg cca atg ggg gtg acc acg ccg gat atc tgg ggc<br>Asp Ile Val Tyr Leu Pro Met Gly Val Thr Thr Pro Asp Ile Trp Gly<br>420 425 430 | 1596 |
| ggc aac cgc aca cct gag cag gaa cgt tat gcc agc agc gtg ctg gcg<br>Gly Asn Arg Thr Pro Glu Gln Glu Arg Tyr Ala Ser Ser Val Leu Ala<br>435 440 445 | 1644 |
| ctg aac gcg acg acc ggt aag ctg gtg tgg tca tat cag act gtg cat<br>Leu Asn Ala Thr Thr Gly Lys Leu Val Trp Ser Tyr Gln Thr Val His<br>450 455 460 | 1692 |
| cac gat ctg tgg gat atg gac ctg cct tcg cag ccg acg ctg gcg gat<br>His Asp Leu Trp Asp Met Asp Leu Pro Ser Gln Pro Thr Leu Ala Asp<br>465 470 475 480 | 1740 |
| att acc gat aaa gac ggt aat acc gtg ccg gtt atc tat gcc cct gcc<br>Ile Thr Asp Lys Asp Gly Asn Thr Val Pro Val Ile Tyr Ala Pro Ala<br>485 490 495 | 1788 |
| aaa acc ggg aac atc ttt gtt ctg gat cgc cgc aca ggt aaa act gtg<br>Lys Thr Gly Asn Ile Phe Val Leu Asp Arg Arg Thr Gly Lys Thr Val<br>500 505 510 | 1836 |
| gtt ccg gcc ccg gaa acc cct gtt ccg cag ggc gca gct aag ggc gac<br>Val Pro Ala Pro Glu Thr Pro Val Pro Gln Gly Ala Ala Lys Gly Asp<br>515 520 525 | 1884 |
| cat gtc tca gct aca cag cct tac tct gaa ctg acc ttc cgt ccg aaa<br>His Val Ser Ala Thr Gln Pro Tyr Ser Glu Leu Thr Phe Arg Pro Lys<br>530 535 540 | 1932 |
| cag aac ctg acg gat aag gac atg tgg ggc gcg acg atg tat gac cag<br>Gln Asn Leu Thr Asp Lys Asp Met Trp Gly Ala Thr Met Tyr Asp Gln<br>545 550 555 560 | 1980 |
| ctg gtg tgc cgc gtg att ttc aaa cgt ctg cgc tac gaa ggt ccg ttc<br>Leu Val Cys Arg Val Ile Phe Lys Arg Leu Arg Tyr Glu Gly Pro Phe<br>565 570 575 | 2028 |
| acg cca cct tct gag cag ggc acc ctg gtc ttc ccg ggc aac ctg ggc<br>Thr Pro Pro Ser Glu Gln Gly Thr Leu Val Phe Pro Gly Asn Leu Gly<br>580 585 590 | 2076 |
| atg ttt gaa tgg ggc ggc att tcc gtt gat ccg cat cgt cag att gcg<br>Met Phe Glu Trp Gly Gly Ile Ser Val Asp Pro His Arg Gln Ile Ala<br>595 600 605 | 2124 |
| att gct aac cca atg gcg ctg ccg ttc gtg tct aag ctg atc cca cgc<br>Ile Ala Asn Pro Met Ala Leu Pro Phe Val Ser Lys Leu Ile Pro Arg<br>610 615 620 | 2172 |
| ggt ccg ggt aat ccg gaa gag cca cca aaa ggc gca acg ggc ggt tca<br>Gly Pro Gly Asn Pro Glu Glu Pro Pro Lys Gly Ala Thr Gly Gly Ser<br>625 630 635 640 | 2220 |
| ggt act gaa acc ggt att cag ccg cag tac ggt gtg cca tat ggc gtt<br>Gly Thr Glu Thr Gly Ile Gln Pro Gln Tyr Gly Val Pro Tyr Gly Val<br>645 650 655 | 2268 |
| gaa ctg aat ccg ttc ctg tca cct ttt ggt ctg ccg tgt aaa caa cct<br>Glu Leu Asn Pro Phe Leu Ser Pro Phe Gly Leu Pro Cys Lys Gln Pro<br>660 665 670 | 2316 |
| gca tgg ggt tat gtt tct gct gtt gac ctg aaa acc aac gaa gtg gtg<br>Ala Trp Gly Tyr Val Ser Ala Val Asp Leu Lys Thr Asn Glu Val Val<br>675 680 685 | 2364 |
| tgg aaa caa cgt att ggt acc gtt cgt gac agc tca cct gta ccg ctg<br>Trp Lys Gln Arg Ile Gly Thr Val Arg Asp Ser Ser Pro Val Pro Leu<br>690 695 700 | 2412 |
| ccc ttt aaa atg ggt atg cca atg ctg ggc gga ccg gtt gcc acc gca<br>Pro Phe Lys Met Gly Met Pro Met Leu Gly Gly Pro Val Ala Thr Ala<br>705 710 715 720 | 2460 |

```
ggc aaa gtg ttc ttt att ggc gca acg gct gat aac tac ctg cgc gct    2508
Gly Lys Val Phe Phe Ile Gly Ala Thr Ala Asp Asn Tyr Leu Arg Ala
            725                 730                 735 ttc agc acc gac acc ggt gaa ctc ttg tgg cag gcg ctg cca gcc        2556
Phe Ser Thr Asp Thr Gly Glu Leu Leu Trp Gln Ala Arg Leu Pro Ala
            740                 745                 750 ggt ggt cag gca acg cca atg acc tat gaa gtt aac ggc aag caa tac    2604
Gly Gly Gln Ala Thr Pro Met Thr Tyr Glu Val Asn Gly Lys Gln Tyr
            755                 760                 765 gtt gtg att gct gcc ggt ggc cat ggt tca ttc ggc acc aag ctg ggc    2652
Val Val Ile Ala Ala Gly Gly His Gly Ser Phe Gly Thr Lys Leu Gly
            770                 775                 780 gat tac gtg att gcc tat gcg ctg ccc gac cag aag taa ttaacacctg     2701
Asp Tyr Val Ile Ala Tyr Ala Leu Pro Asp Gln Lys
785             790                 795 aacagaggcg gactccggtc cgccttttt tatgcctgct atctgccctg tgcttttgcg    2761
cgtggggagc gccagcttaa ccaggcgcac agcccatga ccatgcaggt ggccagaaat    2821
actggccgca ttccccacgc gccaccaatc accccaccaa aaagggggacc actgacctgg   2881 ccgatatact gcgccgacgt cgaatagccg agcatgcgcc ccacctgcac               2931
```

<210> SEQ ID NO 60
<211> LENGTH: 796
<212> TYPE: PRT
<213> ORGANISM: Pantoea anantis

<400> SEQUENCE: 60

```
Met Gly Lys Asn Ser Ser Phe Ser Val Val Arg Phe Leu Thr Val
1               5                   10                  15

Leu Phe Ala Val Leu Thr Gly Ala Phe Met Leu Ile Gly Gly Ile Trp
            20                  25                  30

Leu Ala Thr Ile Gly Gly Ser Trp Tyr Tyr Ile Ile Gly Gly Ala Ala
            35                  40                  45

Met Leu Leu Thr Ala Phe Leu Leu Trp Arg Arg Asn Ser Ala Ala Leu
    50                  55                  60

Val Val Tyr Ala Leu Leu Leu Ala Thr Leu Ala Trp Gly Val Trp
65                  70                  75                  80

Glu Val Gly Thr Asp Phe Trp Ala Leu Ala Pro Arg Thr Asp Val Leu
                85                  90                  95

Val Ile Phe Gly Val Trp Leu Val Leu Pro Phe Val Tyr Arg Gly Leu
            100                 105                 110

Tyr Gln Pro Gly Lys Gly Ala Leu Gly Ala Met Gly Val Ala Leu Val
            115                 120                 125

Ala Ser Ala Ala Val Leu Thr Tyr Ser Val Phe Asn Asp Pro Gln Val
    130                 135                 140

Val Asn Gly Ala Leu Pro Ala Thr Ala Asp Asn Ala Pro Gln Ala Gln
145                 150                 155                 160

Pro Leu Ser Asn Ile Ala Asp Gly Asp Trp Pro Ala Tyr Ala Arg Asp
                165                 170                 175

Gln Gln Gly Thr Arg Phe Ser Pro Leu Lys Gln Ile Asn His Asp Asn
            180                 185                 190

Val Lys Glu Leu Gln Val Ala Trp Gln Phe Gln Thr Gly Asp Met Lys
            195                 200                 205

Arg Pro Ser Asp Pro Gly Glu Ile Thr Asp Glu Val Thr Pro Ile Lys
    210                 215                 220
```

```
Ile Arg Asp Thr Leu Tyr Leu Cys Thr Pro His Gln Ile Leu Phe Ala
225                 230                 235                 240

Leu Asp Ala Ala Thr Gly Lys Gln Lys Trp Lys Phe Asp Pro Gly Leu
            245                 250                 255

Lys Thr Asn Pro Thr Phe Gln His Val Thr Cys Arg Gly Val Ser Tyr
        260                 265                 270

His Glu Phe Pro Ala Ala Lys Asp Ala Ser Asn Thr Gln Pro Ala Leu
    275                 280                 285

Cys Ser Arg Arg Ile Tyr Leu Pro Val Asn Asp Gly Arg Leu Phe Ala
290                 295                 300

Leu Asp Ala Glu Thr Gly Glu Arg Cys Pro Ala Phe Gly Asn Asn Gly
305                 310                 315                 320

Glu Leu Asp Leu Gln His Lys Gln Pro Val Thr Thr Pro Gly Met Tyr
                325                 330                 335

Glu Pro Thr Ser Pro Pro Val Ile Thr Asp Thr Thr Ile Val Met Ala
            340                 345                 350

Gly Ala Val Thr Asp Asn Phe Ser Thr Arg Glu Pro Ser Gly Ala Ile
                355                 360                 365

Arg Gly Phe Asp Val Asn Thr Gly Lys Leu Leu Trp Val Phe Asp Pro
370                 375                 380

Gly Ala Lys Asp Pro Asn Ala Ile Pro Ala Asp Glu His Thr Phe Thr
385                 390                 395                 400

Met Asn Ser Pro Asn Ser Trp Ala Pro Ala Val Tyr Asp Pro Lys Leu
                405                 410                 415

Asp Ile Val Tyr Leu Pro Met Gly Val Thr Thr Pro Asp Ile Trp Gly
            420                 425                 430

Gly Asn Arg Thr Pro Glu Gln Glu Arg Tyr Ala Ser Ser Val Leu Ala
                435                 440                 445

Leu Asn Ala Thr Thr Gly Lys Leu Val Trp Ser Tyr Gln Thr Val His
450                 455                 460

His Asp Leu Trp Asp Met Asp Leu Pro Ser Gln Pro Thr Leu Ala Asp
465                 470                 475                 480

Ile Thr Asp Lys Asp Gly Asn Thr Val Pro Val Ile Tyr Ala Pro Ala
                485                 490                 495

Lys Thr Gly Asn Ile Phe Val Leu Asp Arg Arg Thr Gly Lys Thr Val
            500                 505                 510

Val Pro Ala Pro Glu Thr Pro Val Pro Gln Gly Ala Ala Lys Gly Asp
                515                 520                 525

His Val Ser Ala Thr Gln Pro Tyr Ser Glu Leu Thr Phe Arg Pro Lys
530                 535                 540

Gln Asn Leu Thr Asp Lys Asp Met Trp Gly Ala Thr Met Tyr Asp Gln
545                 550                 555                 560

Leu Val Cys Arg Val Ile Phe Lys Arg Leu Arg Tyr Glu Gly Pro Phe
                565                 570                 575

Thr Pro Pro Ser Glu Gln Gly Thr Leu Val Phe Pro Gly Asn Leu Gly
            580                 585                 590

Met Phe Glu Trp Gly Gly Ile Ser Val Asp Pro His Arg Gln Ile Ala
                595                 600                 605

Ile Ala Asn Pro Met Ala Leu Pro Phe Val Ser Lys Leu Ile Pro Arg
            610                 615                 620

Gly Pro Gly Asn Pro Glu Glu Pro Pro Lys Gly Ala Thr Gly Gly Ser
625                 630                 635                 640

Gly Thr Glu Thr Gly Ile Gln Pro Gln Tyr Gly Val Pro Tyr Gly Val
```

```
                    645                 650                 655
Glu Leu Asn Pro Phe Leu Ser Pro Phe Gly Leu Pro Cys Lys Gln Pro
                660                 665                 670

Ala Trp Gly Tyr Val Ser Ala Val Asp Leu Lys Thr Asn Glu Val Val
            675                 680                 685

Trp Lys Gln Arg Ile Gly Thr Val Arg Asp Ser Ser Pro Val Pro Leu
        690                 695                 700

Pro Phe Lys Met Gly Met Pro Met Leu Gly Gly Pro Val Ala Thr Ala
705                 710                 715                 720

Gly Lys Val Phe Phe Ile Gly Ala Thr Ala Asp Asn Tyr Leu Arg Ala
                725                 730                 735

Phe Ser Thr Asp Thr Gly Glu Leu Leu Trp Gln Ala Arg Leu Pro Ala
            740                 745                 750

Gly Gly Gln Ala Thr Pro Met Thr Tyr Glu Val Asn Gly Lys Gln Tyr
        755                 760                 765

Val Val Ile Ala Ala Gly Gly His Gly Ser Phe Gly Thr Lys Leu Gly
770                 775                 780

Asp Tyr Val Ile Ala Tyr Ala Leu Pro Asp Gln Lys
                790                 795
785

<210> SEQ ID NO 61
<211> LENGTH: 333
<212> TYPE: PRT
<213> ORGANISM: Streptomyces clavuligerus

<400> SEQUENCE: 61

Met Gly Ser Leu Met Gln Glu Phe Glu Phe Ala Val Pro Ala Pro Ser
1               5                   10                  15

Arg Val Ser Pro Asp Leu Ala Arg Ala Arg Ala Arg His Leu Asp Trp
            20                  25                  30

Val His Ala Met Asp Leu Val Arg Gly Glu Glu Ala Arg Arg Arg Tyr
        35                  40                  45

Glu Phe Ser Cys Val Ala Asp Ile Gly Ala Tyr Gly Tyr Pro His Ala
    50                  55                  60

Thr Gly Ala Asp Leu Asp Leu Cys Val Asp Val Leu Gly Trp Thr Phe
65                  70                  75                  80

Leu Phe Asp Asp Gln Phe Asp Ala Gly Asp Gly Arg Glu Arg Asp Ala
                85                  90                  95

Leu Ala Val Cys Ala Glu Leu Thr Asp Leu Leu Trp Lys Gly Thr Ala
            100                 105                 110

Ala Thr Ala Ala Ser Pro Pro Ile Val Val Ala Phe Ser Asp Cys Trp
        115                 120                 125

Glu Arg Met Arg Ala Gly Met Ser Asp Ala Trp Arg Arg Arg Thr Val
    130                 135                 140

His Glu Trp Val Asp Tyr Leu Ala Gly Trp Pro Thr Lys Leu Ala Asp
145                 150                 155                 160

Arg Ala His Gly Ala Val Leu Asp Pro Ala His Leu Arg Ala Arg
                165                 170                 175

His Arg Thr Ile Cys Cys Arg Pro Leu Phe Ala Leu Ala Glu Arg Val
            180                 185                 190

Gly Gly Tyr Glu Val Pro Arg Arg Ala Trp His Ser Ser Arg Leu Asp
        195                 200                 205

Gly Met Arg Phe Thr Thr Ser Asp Ala Val Ile Gly Met Asn Glu Leu
    210                 215                 220
```

```
His Ser Phe Glu Lys Asp Arg Ala Gln Gly His Ala Asn Leu Val Leu
225                 230                 235                 240

Ser Leu Val His His Gly Gly Leu Thr Gly Pro Glu Ala Val Thr Arg
            245                 250                 255

Val Cys Asp Leu Val Gln Gly Ser Ile Glu Ser Phe Leu Arg Leu Arg
            260                 265                 270

Ser Gly Leu Pro Glu Leu Gly Arg Ala Leu Gly Val Glu Gly Ala Val
            275                 280                 285

Leu Asp Arg Tyr Ala Asp Ala Leu Ser Ala Phe Cys Arg Gly Tyr His
            290                 295                 300

Asp Trp Gly Arg Gly Ala Ser Arg Tyr Thr Thr Arg Asp His Pro Gly
305                 310                 315                 320

Asp Leu Gly Leu Glu Asn Leu Val Ala Arg Ser Ser Gly
                325                 330
```

<210> SEQ ID NO 62
<211> LENGTH: 1002
<212> TYPE: DNA
<213> ORGANISM: Streptomyces clavuligerus

<400> SEQUENCE: 62

```
ttggggtcat tgatgcagga attcgaattc gcggtgcccg cgccgagccg tgtcagtccg      60
gatctcgccc gcgcgagggc ccgtcatctc gactgggtcc acgccatgga cctggtgcgc     120
ggcgaggagg ccaggcggcg ttacgagttc tcctgtgtgg ccgacatcgg cgcctatgga     180
tatccgcacg cgaccggtgc ggacctggat ctctgcgtcg acgtcctcgg gtggaccttc     240
ctcttcgacg atcaattcga cgccggggac gggcgggagc gggacgcttt ggcggtctgc     300
gcggagctga cggacctgtt gtggaagggg acggcggcca cggcggcctc gccgccgatc     360
gtggtggcgt tcagcgactg ctgggagcgg atgcgggcgg gcatgtcgga cgcgtggcgg     420
cggcggacgg tccatgagtg ggtggactat ctggcgggct ggcccaccaa gctcgccgac     480
cgcgcgcacg gcgccgtcct ggacccggcc gcgcatctgc gcgcgcggca ccggacgatc     540
tgctgccgcc cgctcttcgc cctggcggaa cgggtcgggg ggtacgaggt cccgcggcgg     600
gcctggcact ccagccggct cgacgggatg cggttcacca cgtccgatgc ggtgatcggc     660
atgaacgagc tccactcgtt cgagaaggac cgggcgcagg ccacgccaa cctcgtcctg     720
agcctcgtgc accacggcgg actcaccggg ccggaggccg tcacccgggt gtgcgacctg     780
gtccagggct cgatcgagtc cttcctgcga ctgcggtccg ggctgccgga gctgggccgg     840
gccctcggtg tcgaggggc cgtgctcgac cggtacgccg acgcgctgtc cgcgttctgc     900
cgcgggtacc acgactgggg tcgcggcgcc tcgcggtaca ccacccgcga tcaccccggc     960
gatctcggac tggagaatct cgtcgcccgg tcgtcgggct ga                       1002
```

<210> SEQ ID NO 63
<211> LENGTH: 1002
<212> TYPE: DNA
<213> ORGANISM: Artificial Sequence
<220> FEATURE:
<223> OTHER INFORMATION: DNA having modified codons, which encodes linalool synthase gene derived from Streptomyces clavuligerus (opt_ScLINS)

<400> SEQUENCE: 63

```
atgggttctc tgatgcagga atttgaattt gctgtgcccg ctccctctcg cgttagcccc      60
gatttagccc gtgctcgtgc tcgtcatctg gattgggttc atgccatgga cttagttcgg     120
```

```
ggtgaagaag cccggcgccg ttatgaattt agctgtgtgg ctgatattgg cgcctatggt    180
tacccccatg ccaccggcgc tgatctggac ttgtgcgtgg atgttttggg ttggaccttt    240
ttatttgatg accaatttga tgctggagac ggtcgtgaac gtgatgctct ggctgtgtgt    300
gccgaattga ccgacttgtt atggaaagga accgctgcta ctgctgctag ccccccccatt    360 gtggttgcct tttctgattg ctgggaacgg atgcgggctg gtatgagtga cgcttggcgg    420
cgccgtaccg tgcatgaatg ggttgattat ttggccgggt ggcccactaa attagccgat    480
cgtgctcacg gagctgtgtt agaccccgct gctcatctgc gtgctcgtca ccgtaccatt    540
tgttgccgcc ccctgtttgc cttggctgaa cgtgtgggag gttacgaagt tcccgtcgt     600 gcttggcatt ccagtcgttt ggatggtatg cggtttacca cttccgacgc cgtgattggt    660
atgaacgaac tgcatagttt tgaaaaagat cgtgctcaag gcacgccaa cttagtgctg     720 tccttggttc atcacggagg attgaccgga cccgaagctg tgactcgtgt ttgtgattta    780
gttcagggct ccattgaatc ctttttgcgg ctgcgcagtg ggttacccga actgggacgt    840
gctctgggag tggaaggagc tgttttggat cggtacgccg acgctttaag cgcttttttgc   900 cgcgggtatc atgattgggg gcgtggagcc tctcggtaca ccactcgcga tcaccccggc   960
gacttgggtt tagaaaattt ggtggcccgc agctctggct aa                     1002
```

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64

```
gtgtgaaatt agccagagct gcgggccacc                                      30
```

<210> SEQ ID NO 65
<211> LENGTH: 44
<212> TYPE: DNA
<213> ORGANISM: Artificial Sequence
<220> FEATURE:
<223> OTHER INFORMATION: Primer

<400> SEQUENCE: 65

```
tggctaattt cacacaggag actgccatgg attttcccca gcag                       44
```

<210> SEQ ID NO 66
<211> LENGTH: 33
<212> TYPE: DNA
<213> ORGANISM: Artificial Sequence
<220> FEATURE:
<223> OTHER INFORMATION: Primer

<400> SEQUENCE: 66

```
atgacttggt tgagtttagc cagagctgcg ggc                                   33
```

<210> SEQ ID NO 67
<211> LENGTH: 37
<212> TYPE: DNA
<213> ORGANISM: Artificial Sequence
<220> FEATURE:
<223> OTHER INFORMATION: Primer

<400> SEQUENCE: 67

```
acgttgttgc cattgccctg tttgcaatta atcatcg                               37
```

<210> SEQ ID NO 68
<211> LENGTH: 36
<212> TYPE: DNA
<213> ORGANISM: Artificial Sequence
<220> FEATURE:
<223> OTHER INFORMATION: Primer

<400> SEQUENCE: 68
atgacttggt tgagtttata agggaatggg ttcaac 36

<210> SEQ ID NO 69
<211> LENGTH: 567
<212> TYPE: PRT
<213> ORGANISM: Artemisia annua

<400> SEQUENCE: 69

| | | | | | | | | | | | | | | | |
|---|---|---|---|---|---|---|---|---|---|---|---|---|---|---|---|
| Gly | Asn | Ala | Tyr | Met | Arg | Ile | Tyr | Ser | Thr | Lys | Thr | Thr | Arg | Ile | Thr |
| 1 | | | | 5 | | | | | 10 | | | | | 15 | |
| Ala | Asn | Ala | Thr | Val | Asn | Ala | Ala | Asp | Thr | His | Val | Arg | Arg | Ser | Ala |
| | | | 20 | | | | | 25 | | | | | 30 | | |
| Asn | Tyr | Lys | Pro | Ser | Ser | Trp | Ser | Phe | Asp | His | Ile | Gln | Ser | Leu | Ser |
| | | | 35 | | | | 40 | | | | | 45 | | | |
| Ser | Lys | Tyr | Thr | Gly | Asp | Asp | Tyr | Val | Ala | Arg | Ala | Asn | Thr | Leu | Lys |
| 50 | | | | | 55 | | | | | 60 | | | | | |
| Asp | Ala | Val | Lys | Thr | Met | Ile | Arg | Lys | Ser | Gly | Asn | Ser | Leu | Arg | Thr |
| 65 | | | | | 70 | | | | | 75 | | | | | 80 |
| Leu | Glu | Leu | Val | Asp | Glu | Leu | Gln | Arg | Leu | Gly | Ile | Ser | Tyr | Leu | Phe |
| | | | | 85 | | | | | 90 | | | | | 95 | |
| Glu | Glu | Glu | Ile | Ser | Asn | Leu | Leu | Glu | Thr | Ile | Tyr | Tyr | Asn | Tyr | Tyr |
| | | | | 100 | | | | | 105 | | | | | 110 | |
| Lys | Phe | Pro | Glu | Asn | Trp | Asn | Lys | Ile | Asn | Leu | Asn | Leu | Lys | Ala | Leu |
| | | | 115 | | | | | 120 | | | | | 125 | | |
| Gly | Phe | Arg | Leu | Leu | Arg | Gln | His | Gly | Tyr | His | Val | Pro | Gln | Glu | Ile |
| | 130 | | | | | 135 | | | | | 140 | | | | |
| Phe | Leu | Asn | Phe | Lys | Asp | Lys | Asn | Gln | Asn | Leu | Asn | Ser | Tyr | Leu | Leu |
| 145 | | | | | 150 | | | | | 155 | | | | | 160 |
| Asn | Asp | Val | Val | Glu | Met | Leu | Asn | Leu | Tyr | Glu | Ala | Ser | Tyr | His | Ser |
| | | | | 165 | | | | | 170 | | | | | 175 | |
| Phe | Glu | Asp | Glu | Ser | Ile | Leu | Asp | Asp | Ala | Arg | Asp | Ile | Thr | Thr | Lys |
| | | | 180 | | | | | 185 | | | | | 190 | | |
| Tyr | Leu | Lys | Glu | Ser | Leu | Glu | Lys | Ile | Asp | Gly | Ser | Ile | Phe | Ser | Ser |
| | | | 195 | | | | | 200 | | | | | 205 | | |
| Val | Thr | His | Ala | Leu | Glu | Gln | Pro | Leu | His | Trp | Arg | Val | Pro | Arg | Val |
| | 210 | | | | | 215 | | | | | 220 | | | | |
| Glu | Ala | Lys | Trp | Phe | Ile | Glu | Leu | Tyr | Glu | Lys | Lys | Asn | Gly | Met | Ser |
| 225 | | | | | 230 | | | | | 235 | | | | | 240 |
| Pro | Thr | Leu | Val | Glu | Leu | Ala | Lys | Leu | Asp | Phe | Asp | Met | Val | Gln | Ala |
| | | | | 245 | | | | | 250 | | | | | 255 | |
| Ile | His | Leu | Glu | Asp | Leu | Lys | His | Ala | Ser | Arg | Trp | Trp | Arg | Asp | Thr |
| | | | 260 | | | | | 265 | | | | | 270 | | |
| Ser | Trp | Asp | Thr | Lys | Leu | Thr | Phe | Ala | Arg | Asp | Leu | Ile | Val | Glu | Asn |
| | | | 275 | | | | | 280 | | | | | 285 | | |
| Phe | Leu | Trp | Thr | Ile | Gly | Phe | Ser | Tyr | Leu | Pro | Asn | Phe | Ser | Arg | Gly |
| | 290 | | | | | 295 | | | | | 300 | | | | |
| Arg | Arg | Thr | Ile | Thr | Lys | Val | Ala | Val | Met | Ile | Thr | Thr | Leu | Asp | Asp |
| 305 | | | | | 310 | | | | | 315 | | | | | 320 |

Val Tyr Asp Val Phe Gly Thr Leu Gly Glu Leu Glu Gln Phe Thr Asp
            325                 330                 335

Val Ile Asn Arg Trp Asp Ile Lys Ala Ile Glu Gln Leu Pro Asp Tyr
        340                 345                 350

Met Lys Ile Cys Phe Leu Gly Leu Tyr Lys Ser Ile Asn Asp Ile Thr
            355                 360                 365

His Glu Thr Leu Ala Asn Lys Gly Phe Leu Ile Leu Pro Tyr Leu Lys
        370                 375                 380

Lys Ala Trp Ala Asp Leu Cys Lys Ala Tyr Leu Val Glu Ala Gln Trp
385                 390                 395                 400

Tyr His Arg Gly His Ile Pro Thr Leu Asn Glu Tyr Leu Asp Asn Ala
            405                 410                 415

Cys Val Ser Ile Ser Gly Pro Val Ala Leu Met His Val His Phe Leu
            420                 425                 430

Thr Ser Val Ser Ser Ile Glu Glu Ile His Gln Cys Ile Gln Arg Thr
        435                 440                 445

Glu Asn Ile Val His Tyr Val Ser Leu Ile Phe Arg Leu Ala Asp Asp
        450                 455                 460

Leu Gly Thr Ser Leu Gly Glu Met Glu Arg Gly Asp Thr Leu Lys Ser
465                 470                 475                 480

Ile Gln Leu His Met His Glu Thr Gly Ala Thr Glu Pro Glu Ala Arg
            485                 490                 495

Ser Tyr Ile Lys Leu Leu Ile Asn Lys Thr Trp Lys Lys Leu Asn Lys
            500                 505                 510

Glu Arg Ala Thr Val Asn Ser Glu Ser Ser Gln Glu Phe Ile Asp Tyr
        515                 520                 525

Ala Thr Asn Leu Val Arg Met Ala Gln Phe Met Tyr Gly Glu Gly Asp
        530                 535                 540

Glu Asp Phe Gly Leu Asp Val Ile Lys Ser His Val Leu Ser Leu Leu
545                 550                 555                 560

Phe Thr Pro Ile Gln Gly Ile
            565

<210> SEQ ID NO 70
<211> LENGTH: 1704
<212> TYPE: DNA
<213> ORGANISM: Artemisia annua

<400> SEQUENCE: 70
ggtaatgctt acatgcgaat atattcaaca aaaaccacaa gaataactgc caatgcaact      60
gtcaatgcag ctgacaccca cgtaaggcga tcagcaaatt acaaaccatc atcatggtca     120
tttgatcata ttcagtcact ctctagtaaa tacacgggag atgattacgt ggcaagagca     180
aatactttga aggacgcagt gaagacgatg atacgaaaat caggaaattc gttgagaact     240
ctggagctag ttgatgagtt gcaaagatta ggaatctcgt atcttttga ggaggaaata      300 agtaatctct tggaaacgat ttactacaat tactataaat ttcctgaaaa ttggaataag     360
atcaatttga accttaaggc tcttggcttt cgattactga dacaacatgg ttatcatgtt     420
cctcaagaga tatttctcaa ctttaaggac aagaatcaaa atcttaattc atatttactc     480
aacgatgttg tggaaatgct caacctgtat gaggcatctt atcattcgtt cgaggatgaa     540
agcatattgg acgacgctag agacatcaca accaaatatc tcaaagaaag cttggagaag     600
attgacggga gtatcttttc atcagtaact catgctttgg agcaaccgct gcattggagg     660
gtaccgagag ttgaggcgaa gtggtttatt gaactatatg agaaaagaa tggcatgagt     720

```
cccacattag tcgagcttgc gaaattggat ttcgatatgg tccaggctat ccatcttgag      780
gatctaaaac acgcatcaag gtggtggaga gatacaagtt gggataccaa gttaaccttt      840
gcaagggact tgatagtgga gaatttcttg tggacaattg gtttcagtta cttaccaaac      900
tttagtcgtg ggaggagaac aataactaag gtggccgtta tgattactac tctcgatgat      960
gtctatgatg tgtttggtac tttgggcgaa ctagaacaat tcactgatgt tataaacaga     1020
tgggatataa aggcgattga acaactccca gattatatga agatatgttt cttaggactt     1080
tacaagtcga taaatgatat cacgcatgaa actttggcaa acaaaggatt cctcattctt     1140
ccatatttaa agaaagcatg ggcagatcta tgtaaggcgt acctagtaga agctcaatgg     1200
taccaccgtg acatatacc aacactgaac gagtacttgg acaatgcttg tgtatcgata     1260
tcaggacctg tagcacttat gcatgtccac ttttttaacat cagttagttc aatcgaagaa     1320
atccatcaat gcatacaaag aactgagaat atagttcact atgtatcact tatcttccga     1380
cttgctgatg acttggggac atcattaggt gaaatggaaa gaggtgatac tctaaaatca     1440
atccagttgc acatgcatga gaccggtgct actgaaccag aagctagaag ttatataaaa     1500
ttgttaatca acaaaacatg gaagaaactt aacaaagaac gagcaactgt taactccgaa     1560
tcttcacagg agtttattga ttatgcaaca aaccttgtta gaatggctca attcatgtac     1620
ggtgaaggag acgaggattt tggtctagat gtgattaaat ctcatgtatt atcattgttg     1680
tttactccaa tccaagggat ataa                                            1704

<210> SEQ ID NO 71
<211> LENGTH: 1623
<212> TYPE: DNA
<213> ORGANISM: Artificial Sequence
<220> FEATURE:
<223> OTHER INFORMATION: DNA having modified codons, which encodes
      linalool synthase gene derived from Artemisia annua (opt_AnLINS)

<400> SEQUENCE: 71
atgcggcgga gtgctaacta caaaccctct tcttggtcct tgatcacat tcagtccctg       60 tccagtaaat acaccggaga cgattatgtg gcccgcgcta ataccttgaa agatgccgtt      120
aaaactatga ttcgtaaatc cggcaatagt ttacggacct tagaactggt ggacgaactg      180
caacgtttgg gtatttccta tttgtttgaa gaagaaatta gtaacttgct ggaaaccatt      240
tactacaact actacaaatt tcccgaaaac tggaacaaaa ttaacttgaa cctgaaagcc      300
ttagggtttc gtctgttgcg gcaacatgga tatcacgtgc cccaggaaat ttttctgaac      360
tttaaagata aaaaccagaa cttgaatagt tacttactga acgacgtggt tgaaatgctg      420
aatttgtatg aagctagcta ccattctttt gaagatgaat ccattttgga tgacgcccgg      480
gacattacca ctaaatacct gaaagaatcc ttggaaaaaa ttgatggcag tattttagt      540 agtgtgaccc atgctttaga acaacccctg cactggcgcg tgccccgtgt tgaagccaaa      600
tggtttattg aactgtacga aaagaaaaat ggcatgagtc ccaccttagt ggaactggcc      660
aaattggatt ttgacatggt tcaggctatt catttagaag atctgaaaca cgccagccgg      720
tggtggcgcg atacctcttg ggacaccaaa ttaacttttg cccgtgatct gattgtggaa      780
aattttctgt ggaccattgg ctttagctat ttgcccaact tttctcgggg tcggcgcacc      840
attactaaag tggccgttat gattaccact ttagatgacg tgtacgatgt ttttgggacc      900
ttgggagaac tggaacaatt tactgatgtg attaatcgtt gggacattaa agctattgaa      960
cagttgcccg attatatgaa aatttgtttt ctggggctgt acaaaagtat taacgacatt     1020
```

-continued

```
acccatgaaa ctctggccaa caaaggattt ttgattctgc cctacctgaa aaaagcctgg    1080
gctgatttgt gtaaagccta tttagtggaa gctcaatggt accatcgcgg tcacattccc    1140
accttgaacg aatacttaga taatgcttgc gtgagcattt ctgggcccgt ggccttaatg    1200
catgttcact ttctgacctc cgttagctct attgaagaaa ttcatcaatg cattcagcgc    1260
actgaaaata ttgtgcacta tgttagcctg attttcgtt tggccgatga cttaggcacc     1320
tctctgggtg aaatggaacg gggggatact ctgaaatcca ttcaattgca tatgcacgaa    1380
accggagcca ctgaacccga agctcggagt tacattaaat tgctgattaa caaaacctgg    1440
aaaaaattga ataagaacg cgccactgtg aacagcgaat ccagtcaaga atttattgat     1500
tacgccacca acttagttcg catggctcag tttatgtacg gcgaaggtga tgaagacttt    1560
ggcttggatg tgattaaatc ccatgttctg agtctgttgt ttaccccat tcaaggtatt     1620 taa                                                                  1623
```

<210> SEQ ID NO 72
<211> LENGTH: 594
<212> TYPE: PRT
<213> ORGANISM: Backhousia citriodora

<400> SEQUENCE: 72

```
Met Ala Leu Pro Ala Leu Phe Gly Ser Ser Leu Pro Ser Ser Ile Arg
1               5                   10                  15

His Asn Gln Pro Ser Leu Phe Ser Phe Arg His Pro Arg Phe Cys Ser
            20                  25                  30

Ser Ser Ser Ala Ser Phe Ser Gln Phe Ile Leu Cys Ala Ser
        35                  40                  45

Lys Thr Gly Asp Gln Glu Ile Val Arg Arg Ser Ala Asn Trp Gln Pro
50                  55                  60

Ser Val Trp Asp Tyr Asp Tyr Val Gln Ser Leu Thr Val Asp Tyr Thr
65                  70                  75                  80

Glu Asp Lys Tyr Thr Lys Gln Val Gln Arg Leu Lys Glu Glu Val Lys
                85                  90                  95

Gly Leu Phe Asp Arg Glu Met Lys Gln Val Ala Lys Leu Glu Phe Ile
            100                 105                 110

Asp Val Val Gln Arg Leu Gly Leu Gly Tyr His Phe Lys Thr Glu Ile
        115                 120                 125

Lys Ile Ala Leu Ser Ser Ile His Asn Asn Thr Glu Asp Ala Gln Leu
130                 135                 140

Ser Asn Asp Leu Tyr Ala Ala Ser Leu Arg Phe Arg Leu Leu Arg Gln
145                 150                 155                 160

Tyr Gly Cys Asn Val Gln Gln Asp Val Phe Gln Arg Phe Met Asn Lys
                165                 170                 175

Thr Gly Thr Phe Lys Glu Ser Leu Asn Lys Asp Val Lys Gly Ile Leu
            180                 185                 190

Gly Leu Tyr Glu Ala Ser Phe His Gly Met Glu Gly Thr Val Leu
        195                 200                 205

Asp Glu Ala Trp Asn Phe Ala Ser Lys His Leu Lys Asp Leu Asn Leu
210                 215                 220

Asp Glu Val Pro Thr Asn Leu Ala Ser Asn Val Ser His Ala Leu Asp
225                 230                 235                 240

Met Pro Ile His Trp Arg Pro Asn Arg Leu Glu Ala Arg Trp Phe Met
                245                 250                 255
```

Asp Met Tyr Glu Lys Gln Gln Asp Leu Ile Pro Ser Leu Leu Arg Leu
          260                 265                 270

Ala Lys Leu Asp Phe Asn Ile Val Gln Ser Ile His Arg Lys Glu Val
            275                 280                 285

Ser Asn Leu Ala Arg Trp Trp Val Glu Leu Gly Ala Asn Lys Met Thr
        290                 295                 300

Phe Phe Arg Asp Arg Leu Val Glu Ser Tyr Phe Trp Ser Cys Ile Leu
305                 310                 315                 320

Val Phe Glu Pro Gln Tyr Thr Asp Phe Arg Glu Leu Asn Thr Arg Ile
                325                 330                 335

Ala Cys Met Ala Thr Leu Ile Asp Asp Val Tyr Asp Ile Tyr Gly Thr
            340                 345                 350

Pro Glu Glu Leu Glu Leu Leu Thr Asp Phe Ile Leu Arg Trp Asp Ile
        355                 360                 365

Thr Asp Ile Asp Lys Leu Pro Pro Thr Ile Arg Asn Gly Phe Met Ala
370                 375                 380

Leu Tyr Asn Thr Thr Asn Lys Val Gly Tyr Arg Thr Met Thr Lys Arg
385                 390                 395                 400

Gly Ile Asn Pro Ile Pro Tyr Leu Arg Lys Leu Trp Gly Asp Glu Cys
                405                 410                 415

Lys Ala Asp Met Lys Glu Val His Trp Phe Asn Asn Gly Ile Lys Pro
            420                 425                 430

Thr Leu Lys Glu Tyr Met Asp Val Ala Val Asp Ser Ile Gly Gly Leu
        435                 440                 445

Ile Leu Leu Leu Asn Ser Tyr Phe Leu Thr Thr Asp Tyr Leu Thr Glu
450                 455                 460

Glu Gly Leu Asn Tyr Val Ser Lys Ile Pro Ser Val Met His Ser Ser
465                 470                 475                 480

Ala Gln Ile Phe Arg Phe Asn Asp Asp Leu Ser Thr Ser Ser His Glu
                485                 490                 495

Leu Ala Arg Gly Asp Asn Ser Lys Ala Leu Glu Cys Tyr Met Asn Glu
            500                 505                 510

Thr Gly Ala Ser Glu Glu Ile Ala Arg Glu His Ile Arg His Leu Val
        515                 520                 525

Arg Glu Thr Trp Lys Lys Met Asn Lys Glu Val Phe Glu Asp Tyr Pro
530                 535                 540

Phe Ser Gly Phe Gly Pro Phe Leu Ser Ala Cys Leu Asn Leu Ala Arg
545                 550                 555                 560

Ala Ser His Cys Phe Tyr Glu Tyr Gly Asp Gly Tyr Gly Leu Pro Asp
                565                 570                 575

His Gln Thr Arg Asp His Leu Ala Ser Thr Ile Phe Glu Ser Val Ser
            580                 585                 590

Leu Asp

<210> SEQ ID NO 73
<211> LENGTH: 1785
<212> TYPE: DNA
<213> ORGANISM: Backhousia citriodora

<400> SEQUENCE: 73
atggctcttc ctgctctttt tggaagctcc ctcccctcct caatccgcca taaccaaccc      60
tctctctttt cctttagaca ccctcgcttc tgctcctcct cctcttccgc ctccttcagc     120
agccagttta ttttatgcgc ttcgaagact ggggatcaag agattgtgag acgttccgcg     180

```
aattggcaac ctagcgtctg ggactacgac tatgtgcagt cacttactgt tgattacacg    240
gaggataaat ataccaaaca agtccaaagg ttaaaggaag aagtcaaggg tttattcgat    300
agggagatga aacaggtagc caagctcgag ttcatagatg tggttcaaag actaggactt    360
ggataccatt tcaagaccga gataaaaatt gctctcagtt ccattcataa caacaccgaa    420
gatgcgcaac tttcgaatga tctctatgct gcttcccttc gattccgact actcagacaa    480
tatggatgta acgtgcagca agatgtgttt caaggttta tgaacaagac gggcacattc     540
aaggaatcac tcaataagga tgtgaagggg attcttggtc tttatgaagc ttcttttcac    600
ggaatggaag gtgaaaccgt actcgatgaa gcttggaact ttgcttctaa gcatctgaag    660
gatctaaacc tcgacgaagt tcccaccaat ttggcgagca acgtgagtca tgcattagac    720
atgccgattc attggaggcc aaacagacta gaggctcggt ggttcatgga catgtacgag    780
aaacagcaag acttgatccc ctctttgctg cgattggcta attagactt caatatagtg      840 cagtcgatcc acaggaagga agttagcaat cttgcaaggt ggtgggttga acttggggcg    900
aacaagatga ccttctttag ggacaggctg gtggaaagct atttttggag ttgtatactt    960
gttttcgaac ctcaatatac agatttcaga gaactaaata caaggattgc ttgcatggcg    1020
acacttatcg atgatgttta cgatatatat gggactccgg aagagcttga actcttaaca    1080
gatttcattc tcaggtggga catcacagat atcgataagc ttcctccaac aataaggaac    1140
ggtttcatgg ccttatacaa cacgaccaac aaagttgggt atcggacgat gacaaagcga    1200
ggaatcaatc ccatcccttac cttgcgtaaa ttgtggggcg atgaatgcaa ggcggacatg    1260
aaggaggtcc attggttcaa taatggcatt aaaccgacgc tgaaggagta catggacgtt    1320
gcggtggatt caatcggagg gctgattttg ctgttgaata gctacttcct aaccacagac    1380
tatttgacgg aagagggact taattacgtg tcgaaaatcc caagtgtcat gcattcttct    1440
gcccagatct ttcgattcaa cgatgatctc agtacatcat cgcatgaatt ggcacgagga    1500
gacaactcta aggcgctaga atgctacatg aacgaaactg cgcttcgga agagatcgcg     1560 cgggaacata tcaggcatct ggtccgggag acctggaaga agatgaacaa agaagtgttt    1620
gaggactacc cattttccgg gttcgggcct tttcttagtg cctgtctaaa cttggctcga    1680
gcttctcatt gcttttacga gtatggagac ggatatggcc ttcccgatca ccaaaccagg    1740
gaccatcttg cgtcaactat attcgaatct gtgtcccttg attag                     1785
```

<210> SEQ ID NO 74
<211> LENGTH: 1620
<212> TYPE: DNA
<213> ORGANISM: Artificial Sequence
<220> FEATURE:
<223> OTHER INFORMATION: DNA having modified codons, which encodes
      linalool synthase gene derived from Backhousia citriodora
      (opt_BcLINS)

<400> SEQUENCE: 74

```
atgcgtcgct ccgctaactg gcagccctcc gtgtgggatt atgattatgt tcaaagcctg     60
accgtggact ataccgaaga caaatacacc aaacaagtgc agcggctgaa agaagaagtt    120
aaaggtttgt ttgatcgcga aatgaaacaa gtggccaaat tggaatttat tgacgtggtt    180
cagcgcttgg ggctgggata ccattttaaa actgaaatta aaattgcctt gtccagtatt    240
cacaataaca ccgaagatgc tcaattgagc aatgacttat atgccgcttc tttacggttt    300
cgcttgttac gtcaatacgg ttgtaacgtg caacaggatg ttttttcagcg gtttatgaac    360 aaaccggga cttttaaaga atccctgaac aaaagacgtta aaggtattct ggggttgtat    420
```

-continued

```
gaagccagtt ttcatggaat ggaaggcgaa accgtgttgg atgaagcctg gaactttgct      480
tccaaacacc tgaaagatct gaacctggac gaagtgccca ccaatctggc ctccaacgtt      540
agtcatgctt tggatatgcc cattcactgg cgccccaatc gtttggaagc ccgttggttt      600
atggatatgt acgaaaaaca acaggacctg attcccagtc tgttgcggct ggctaaattg      660
gattttaaca ttgtgcaatc cattcatcgc aaagaagtta gtaatttagc ccgttggtgg      720
gtggaactgg gggctaacaa aatgaccttt tccgtgatc ggctggttga aagctacttt       780
tggtcttgta ttttggtgtt tgaaccccag tacaccgact tcgggaatt aaatactcgc       840 attgcctgca tggctaccct gattgatgac gtgtatgata tttacggcac tcccgaagaa      900
ctggaactgc tgaccgattt tattctgcgc tgggacatta ctgatattga caaactgccc      960
cccaccattc gtaatggttt tatggccttg tataatacca ctaacaaagt gggttaccgt     1020
accatgacta aacgggggat taatcccatt ccctatttac ggaaactgtg gggagatgaa     1080
tgtaaagccg acatgaaaga agtgcattgg tttaataacg ggattaaacc caccttaaaa     1140
gaatacatgg atgtggccgt tgactccatt ggcggtctga ttttgctgct gaatagttat     1200
tttctgacca ctgattactt gaccgaagaa ggcttaaact atgtgtccaa aattcccagt     1260
gttatgcata gctctgccca aatttttcgg tttaatgatg acttgagcac ctccagtcac     1320
gaattagccc gcggagataa ttctaaagct ttggaatgct acatgaacga aactggcgcc     1380
tccgaagaaa ttgctcggga acatattcgc cacttagttc gtgaaacctg aagaaaatg     1440 aacaaagaag tgtttgaaga ttaccccttt agcggctttg gtcccttttt gtctgcctgt     1500
ttgaacttag cccgcgctag ccattgcttt tatgaatacg gggatggata cggcttgccc     1560
gatcatcaaa ctcgtgacca cttagccagt accattttg aaagcgtgtc tttagattaa      1620
```

<210> SEQ ID NO 75
<211> LENGTH: 27
<212> TYPE: DNA
<213> ORGANISM: Artificial Sequence
<220> FEATURE:
<223> OTHER INFORMATION: Primer

<400> SEQUENCE: 75
tgtgaaatta aataccttga atggggg      27

<210> SEQ ID NO 76
<211> LENGTH: 45
<212> TYPE: DNA
<213> ORGANISM: Artificial Sequence
<220> FEATURE:
<223> OTHER INFORMATION: Primer

<400> SEQUENCE: 76
gtatttaatt tcacacagga gactgccatg gattttcccc agcag      45

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
tgtgaaatta atctaaagac acgctttc      28

<210> SEQ ID NO 78

<211> LENGTH: 45
<212> TYPE: DNA
<213> ORGANISM: Artificial Sequence
<220> FEATURE:
<223> OTHER INFORMATION: Primer

<400> SEQUENCE: 78
tagattaatt tcacacagga gactgccatg gattttcccc agcag    45

<210> SEQ ID NO 79
<211> LENGTH: 56
<212> TYPE: DNA
<213> ORGANISM: Artificial Sequence
<220> FEATURE:
<223> OTHER INFORMATION: Primer

<400> SEQUENCE: 79
aaggaattat aaccaaatgt ccaccgccgt gccctctatg cccactaccc aaaaat    56

<210> SEQ ID NO 80
<211> LENGTH: 55
<212> TYPE: DNA
<213> ORGANISM: Artificial Sequence
<220> FEATURE:
<223> OTHER INFORMATION: Primer

<400> SEQUENCE: 80
ggcatggagg acatattagc tactggaatc atacaacatg gttttcatgt gttct    55

<210> SEQ ID NO 81
<211> LENGTH: 55
<212> TYPE: DNA
<213> ORGANISM: Artificial Sequence
<220> FEATURE:
<223> OTHER INFORMATION: Primer

<400> SEQUENCE: 81
tctagagtcg acgtcccctg ttgacaatta atcatcggct cgtataatgt gtgga    55

<210> SEQ ID NO 82
<211> LENGTH: 55
<212> TYPE: DNA
<213> ORGANISM: Artificial Sequence
<220> FEATURE:
<223> OTHER INFORMATION: Primer

<400> SEQUENCE: 82
atccaatgtg aggttctatt tgttgcgctg gatgatgtaa tcggccaggg cttcc    55

<210> SEQ ID NO 83
<211> LENGTH: 45
<212> TYPE: DNA
<213> ORGANISM: Artificial Sequence
<220> FEATURE:
<223> OTHER INFORMATION: Primer

<400> SEQUENCE: 83
ttggaacatt gtgttcagcc catggctgtc tcccgccatt gctaa    45

<210> SEQ ID NO 84
<211> LENGTH: 45
<212> TYPE: DNA
<213> ORGANISM: Artificial Sequence
<220> FEATURE:
<223> OTHER INFORMATION: Primer

<400> SEQUENCE: 84
ttgttcccgg tacaacttag ccaccaactc cttgagaatg accac       45

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
ggaggattgg gttaccctca gtgtg       25

<210> SEQ ID NO 86
<211> LENGTH: 25
<212> TYPE: DNA
<213> ORGANISM: Artificial Sequence
<220> FEATURE:
<223> OTHER INFORMATION: Primer

<400> SEQUENCE: 86
cgccatatca atcccaacgc tctgg       25

<210> SEQ ID NO 87
<211> LENGTH: 299
<212> TYPE: PRT
<213> ORGANISM: Escherichia coli

<400> SEQUENCE: 87

```
Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Ala Val Glu Cys Ile His Ala Tyr Ser
65                  70                  75                  80

Leu Ile His Asp Asp Leu Pro Ala Met Asp Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240
```

```
Ala Asp Gln Gln Leu Gly Lys Ser Thr Tyr Pro Ala Leu Leu Gly Leu
            245                 250                 255

Glu Gln Ala Arg Lys Lys Ala Arg Asp Leu Ile Asp Asp Ala Arg Gln
        260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295

<210> SEQ ID NO 88
<211> LENGTH: 299
<212> TYPE: PRT
<213> ORGANISM: Artificial Sequence
<220> FEATURE:
<223> OTHER INFORMATION: Mutant farnesyl diphosphate synthase derived
      from Escherichia coli whose 80th serine residue of the enzyme is
      substituted with a phenilalanine (ispA* (S80F))

<400> SEQUENCE: 88

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Phe
65                  70                  75                  80

Leu Ile His Asp Asp Leu Pro Ala Met Asp Asp Asp Asp Leu Arg Arg
            85                  90                  95

Gly Leu Pro Thr Cys His Val Lys Phe Gly Glu Ala Asn Ala Ile Leu
        100                 105                 110

Ala Gly Asp Ala Leu Gln Thr Leu Ala Phe Ser Ile Leu Ser Asp Ala
    115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
            165                 170                 175

Ile His Arg His Lys Thr Gly Ala Leu Ile Arg Ala Ala Val Arg Leu
        180                 185                 190

Gly Ala Leu Ser Ala Gly Asp Lys Gly Arg Arg Ala Leu Pro Val Leu
    195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
            245                 250                 255

Glu Gln Ala Arg Lys Lys Ala Arg Asp Leu Ile Asp Asp Ala Arg Gln
        260                 265                 270

Ser Leu Lys Gln Leu Ala Glu Gln Ser Leu Asp Thr Ser Ala Leu Glu
        275                 280                 285
```

Ala Leu Ala Asp Tyr Ile Ile Gln Arg Asn Lys
    290                 295

<210> SEQ ID NO 89
<211> LENGTH: 1575
<212> TYPE: DNA
<213> ORGANISM: Arabidopsis thaliana

<400> SEQUENCE: 89

| | | | | | | |
|---|---|---|---|---|---|---|
| atggcaaata | ctgctaaaag | atcgatcttg | agaaacgtcc | atgcttcagt | ttctaaccct | 60 |
| tcgaagcagt | ttcataataa | gacatcctta | gaatatttac | acgagttgaa | tatcaagaag | 120 |
| atcaagaata | tactaagtgc | aaacgtagat | gttccatccg | agaacctgga | gatgatcgat | 180 |
| gtcattcaaa | gtttaggcat | tgatctccat | tttcgacaag | agatcgagca | aacccttcac | 240 |
| atgatttaca | agaaggcct | ccaattcaac | ggtgatctcc | atgagatagc | gcttcgcttt | 300 |
| cgattgctga | gacaagaggg | tcactatgtt | caagaaaaca | gaagggtgg | atttaaagac | 360 |
| gtagtaaaaa | atgacgtcaa | gggtctaaca | gaattgtttg | aagcttctga | gctccgtgta | 420 |
| gaaggtgaag | aaacactcga | cggtgcgaga | gaattcacat | atagccgcct | taatgaactt | 480 |
| tgctcaggta | gagaaagtca | tcaaaagcaa | gagataatga | agtctttggc | gcaacctcgc | 540 |
| cacaaaaccg | taagaggatt | aacgtccaag | aggttcacaa | gcatgatcaa | aatcgcgggt | 600 |
| caagaagatc | cagaatggtt | acagtctcta | ttacgagtgg | cggagatcga | ttccattagg | 660 |
| ctaaagtcat | tgactcaagg | agaaatgtct | caaacattta | aatggtggac | agaacttggt | 720 |
| ttagaaaaag | atgtggagaa | ggcaagaagc | cagccgttaa | aatggcatac | gtggtccatg | 780 |
| aaaattcttc | aagatccgac | cttaaccgaa | caaaggcttg | atcttaccaa | accaatatcg | 840 |
| cttgttatg | ttatagatga | catttttcgat | gtctatgggg | agctagaaga | actaaccatc | 900 |
| ttcacacgag | ttgttgagag | atgggatcat | aaggggctta | gacgctacc | caaatacatg | 960 |
| agggtttgtt | ttgaagctct | agatatgatc | acaacggaga | ttagcatgaa | gatctacaaa | 1020 |
| tcacatggtt | ggaacccgac | atacgctctt | cgacaatcgt | gggcaagttt | gtgtaaagca | 1080 |
| ttcttggtag | aagcaaagtg | gtttaattcg | ggttacttac | ccaccactga | agagtatatg | 1140 |
| aagaatgggg | ttgtgagttc | aggtgttcat | ttagtgatgc | ttcatgccta | tatcttgtta | 1200 |
| ggcgaagaac | taacaaaaga | gaaagtcgaa | ctaatagaga | gtaacccggg | gattgtatca | 1260 |
| tctgcagcta | caattctcag | gctctgggat | gatctcggaa | gtgccaagga | tgagaaccaa | 1320 |
| gatggaactg | atggatcata | tgtagagtgt | tacctgaacg | agtacaaggg | atcaactgtt | 1380 |
| gatgaagcaa | gaacacatgt | tgcccagaag | atatctagag | catggaaacg | cttgaacagg | 1440 |
| gagtgtctga | atccatgtcc | attctcaaga | tcattctcaa | aagcttgtct | caacattgca | 1500 |
| agaacagttc | ctttaatgta | cagctatgat | gatgatcaac | gacttcccga | cgaatatctc | 1560 |
| aagtctctaa | tgtaa | | | | | 1575 |

<210> SEQ ID NO 90
<211> LENGTH: 1644
<212> TYPE: DNA
<213> ORGANISM: Arabidopsis thaliana

<400> SEQUENCE: 90

| | | | | | | |
|---|---|---|---|---|---|---|
| atgcgtcgtt | ctgcgaacta | tcagccttct | cgttgggacc | atcaccatct | cctctcggtc | 60 |
| gaaaataaat | ttgcgaaaga | taaagggta | cgagagagag | atttgttgaa | ggaaaaagtg | 120 |
| agaaagatgc | tcaatgatga | gcaaaagact | tatcttgacc | aattggagtt | cattgacgat | 180 |

-continued

| | |
|---|---|
| ctacaaaaac tcggggtttc ttatcatttt gaagcggaaa tcgacaacat tttaacatct | 240 |
| tcttataaaa aagatagaac aaacatccag gagagtgacc tacatgccac cgcactcgag | 300 |
| ttccgacttt tcaggcaaca tggtttcaat gtttcagaag atgtattcga tgttttcatg | 360 |
| gaaaattgtg ggaagtttga ccgtgatgat atatatggtt taatatctct ttacgaagca | 420 |
| tcatatcttt cgacaaaatt ggataaaaac ctgcaaatat tcatcagacc ttttgctaca | 480 |
| caacaactca gagactttgt tgatactcat agtaatgaag attttgggtc gtgtgacatg | 540 |
| gtggaaattg tggtccaagc gttggatatg ccctactatt ggcaaatgag aaggctatcc | 600 |
| accagatggt acatagatgt gtatggaaaa agacaaaatt ataagaacct tgtcgtcgtt | 660 |
| gaatttgcca agattgattt caacatcgta caagctattc atcaagagga actcaaaaac | 720 |
| gtttccagct ggtggatgga gacaggttta ggtaagcaac tctactttgc aagagacaga | 780 |
| atagtggaga attatttctg gacgattgga caaatccaag agcctcaata cggatacgtt | 840 |
| cgacaaacaa tgacgaaaat aaatgcactc cttactacaa ttgatgatat ctacgatatc | 900 |
| tatggcactc ttgaagaact tcagcttttc actgtcgcgt ttgaaaactg ggatataaat | 960 |
| cgtcttgatg aactccccga gtacatgagg ttgtgttttc ttgttatata caatgaagtc | 1020 |
| aatagcattg catgtgagat tctcagaact aaaaatatca acgtgatccc attcctcaaa | 1080 |
| aaatcttgga cagatgtatc caaagcgtat ttagtagaag caaagtggta caaaagtggt | 1140 |
| cacaaaccaa atttggaaga gtacatgcaa aatgctcgga tttcaatctc gtccccaacg | 1200 |
| atatttgttc acttctactg cgtattctcc gaccagctct ctattcaggt cttggagact | 1260 |
| ttgtcccaac accaacaaaa cgtcgtccga tgctcctcct cagtgttccg tctagccaac | 1320 |
| gaccttgtaa cctcaccgga tgaattggcg agaggagacg tctgcaaatc catccaatgt | 1380 |
| tacatgagtg aaactggagc atcagaggat aaggcgcgtt cgcatgttcg acagatgatc | 1440 |
| aatgacttgt gggatgaaat gaattatgag aaaatggcac atagctcttc gatactccat | 1500 |
| catgatttta tggaaacagt gataaatttg gcacgcatgt ctcaatgcat gtatcaatat | 1560 |
| ggcgatggcc atggctctcc cgaaaaagcc aaaatcgttg atcgtgtcat gtccttactc | 1620 |
| ttcaatccga ttcctttaga ttga | 1644 |

<210> SEQ ID NO 91
<211> LENGTH: 1698
<212> TYPE: DNA
<213> ORGANISM: Citrus unshiu

<400> SEQUENCE: 91

| | |
|---|---|
| atgttgtttc aagtttcagc ctctcctaat aaagttatcc gaataaatgc cgagaaagaa | 60 |
| tctactcgtc gttcggcaaa ttttgatcct accatttggg gggattattt cctttcatat | 120 |
| actggtgact tcaaggaaag tggtgatgct agcgtgaagc atcaagagct gaagaaagaa | 180 |
| attagaacga tgctaagagc tgatatcaac aagcctacgc agactaaaac tggatttgatt | 240 |
| gatgacattc agcgtttagg agtgtcttat cattttgaaa gtgagattga tgaaatcttg | 300 |
| cgaaaaatgc atgaggctaa ccaagattgt gatcttggcg atgatgaaaa tgttcaggag | 360 |
| ctctattata tctctcttca ttttcgatta cttagacaaa atggctataa aatttctgct | 420 |
| gatgtcttta acagcttcaa ggatagcaat gggaacttca agtctttcct taaaagagat | 480 |
| attcggggaa tgttaagcct gtatgaagcg gcacatctca gggtacatgg agaaaatata | 540 |
| ctcaacgaag cacttacttt cactgtcact caccttgagt catttacaag ccaatccaac | 600 |
| actcaacttg cggctcaagt caatcgtgcc ctcaatcgac ctattcgcaa aagcttacca | 660 |

```
aggctagagg caaaacacta catgccaatc tatcagaaag acccttcaca caacaaagat      720
ctattaacct ttgccatgtt agatttcaac atacttcaga acaacacca agaagaactc      780 agagatatcg taaggtggtg gaaaaatttt gatgttccca ataagctacc tttcataaga     840
gacagagtgg tggagggcta tttctggatt ttgggagtat attttgagcc aaaattttta     900
ttggctagaa aaattctaac caaagtgata tcaatggctt caattattga tgacatttat     960
gatgcttatg gtacaataga agaacttgag cttttttgcca cagcaattga gaggtgggat    1020
ctcagtgcca tagatctgct tcctgagtac atgaagttgt gctattgcgc tctcctggat    1080
gcttacagcg aatttgagaa agatttggcc agcaaaggaa tattgtacgg cctaccttt     1140 gctaaagaat cgatgaagat tttggtgaga agttacatca tcgaagctag atggtgtgac   1200
caacaatatg taccgacaat ggaggaatac atgcgcgttg cactactttc atgtggctac    1260
ttactgttat caacatcttc atttctggga atggaagata ttgtaacaaa agaagccttt    1320
gaatgggtat ccggcaaccc taaaatcgtt caggcttcct caataatttg cagactcatg    1380
gatgacattg tctctcataa gtttgagcaa cagagaggac atgtggcctc agctgttgaa   1440
tgctacatga agcagcatgg agtttctgag gaagaggcag ttaaagtgtt tcgggagaaa    1500
gttgggaatg cgtggaaaga tataaatgag gagctcatga gaccacctgt tgttcctatg   1560
cctttgctcg aacgggttct taatcttgct cgtttaatgg atgtgctgta ccaaaataat    1620
gattcctata caaatcctca cttgatgaaa gatcatgtag ccgcattgct taaggatcct   1680
gttttctttg aagactag                                                  1698

<210> SEQ ID NO 92
<211> LENGTH: 1746
<212> TYPE: DNA
<213> ORGANISM: Citrus unshiu

<400> SEQUENCE: 92
atggctttct cttccaaaga tatttcgtct gattcatccc acattcactt tattccaaaa     60
cacatatcaa aagttggcaa ccgaaacctc aataacatta attctttgct gcctaataat    120
aaaaagggca gcattaatga taacataggt gtttctgccc ggttgaaacg ttcacttat    180 cccagtgaac actccagtaa ttttaatgac gacattcaca ttaagcatgc gaaaaaactg     240
gaggtaatca agcacatact tatcaaacta ggagatgacg attcttttga aggattggcc    300
atgattgatg tcgttcaacg cctagggatt gattactatt ttcaagatga gattgaacta    360
attctacgaa ggcagtatag catatttttc actgatggtg atcgctataa tgaccttcaa    420
gaggttgccc ttcgctttcg actgttgaga caacaaggtt actatgtgtc tgcagatgtt    480
tttaacaggt tcagaaacaa agaagggag tttaaacaga atataagtga agacatcaat    540
ggattgatga gcttatacga ggcctcacag ctaagtattg gaggagaaga tgggcttgat    600
gaagctggac actttagtgc gacacatctt gctaattatg atctagcggg agtagttgag    660
catctgttgc tgtatcccta tcgcaaaagc ttgtcccgg ccaaaaactt tttccatggc     720
aattttcaag gcagtgaata tatttggata ctggatttgc aagaactagc gaatatggat    780
ttcaaattgg tccaatcctt acaccaaaag gaaattgtgc aaatatccag ttggtggaga   840
gagctcggtt tggctaagaa gttgaatttt gcaagagagc aaccagttaa atggtatgtg    900
tggtcaatgg catgtttcac ggatccaaac ttgtcgtggc aaaggataga gctcacaaaa    960
cccatctcct tcgtctacat tattgacgac atttttttatg tttgtggagc actcgatgcc   1020
```

```
ctcacccttt tcacagaacc cattaataga tgggatcttg gggacattga tcaattgcca    1080
gagtacatga agatatgttt caaggctctt aacgatatca ctaatgaaat cagcaaacaa    1140
ggtgtacaaa ggagcatggg tataaccctg tgcactcctt tgcgaaaggg cgtgggggaa    1200
gttttgtgca acgcgttcct aatagaggca aaatggtttg cttccgggca cttgcctaag    1260
gctgaagagt acttggaaaa tgggattgtt agttcagggg tacacttggt acttgtgcac    1320
attttctttc tcctgggtca tggcatcacc aatgaaacag tgcaactcat tgacagcaac    1380
ccacccattg tatcatccgt cgcaacaatt cttcgaattt gggatgactt gggaagtgct    1440
aaggatgaaa atcaaggcgg caaagatgga tcatatatat attactacat gatggaacac    1500
cgagacttaa cggctgaaga tgcacacaag catgccatgg ataagatttc agatgcatgg    1560
aagcgcctaa acaaggaatg cctctcccca aatccatttt cagcatcttt cacaagggct    1620
tcttttaact gtgccagaat ggttcctttg atgtacagct atgatgacag ccaacggctt    1680
ccgagcctcg aggagtatat taagtcctcc ctttttgata atttgcctac tcaaggagtg    1740
tactag                                                              1746

<210> SEQ ID NO 93
<211> LENGTH: 1767
<212> TYPE: DNA
<213> ORGANISM: Citrus unshiu

<400> SEQUENCE: 93
atggctttct cttccagttc tagagctaag ttgtctgcta cctcccacat ttcaaaggct      60
ccagataaga tttcaaaaac tagcaggcct agcctcattg aatttactcc ttcgcctact     120
atctatcaaa aagggtgcat tactagtgac aatacagtcg cttctcctcc ccttaaacac     180
ttcacccaca caactagaca ccccagcttc ttcgatcatg atattcaagt cgaacattct     240
cggaaattga aggaattcaa gcatatattt agcctagtcg ggggaaattc ttttgaagga     300
ttagtcatga ttgatgctgt tcaacggcta cgcattgagt accttttcaa agatgagatt     360
gaagaaattt tacaaaggca atatatcata tcttccactt gtggtggtca cctccatgat     420
cttcaagagg ttgcccttcg ctttcggttg ctgagacaag aaggttacta cgtgcctgcg     480
gatatgttta caactttag gatcaaggaa gggagattca gccggatcaa cgtaagtgaa     540
gacataggga cattgatgga agtatatgaa gcttcgcagc taagtatagc aggcgaagaa     600
gggcttgacg aagccggaca ctttagtgcg aagatgctca atgagtgcat gacacatctt     660
gatcactatc atgctctagc tatcgggaat actttgaggc atccatacca caaaagcttg     720
cccagattta tggccaaaga cgttttcctt agcaatttcc aaggtgaacg cagattgcat     780
gttttaaaag aaatagcgaa aaaagatttc aacatggtac aggccttaca ccaaaaagag     840
attgttcaag taaccaaatg gtggaaagac ctcggtttga ctaagaagtt gccgtttgca     900
agagaccaac cacttaaatg gtacatttgg tctatggctt gcctcacaga tccaagcttg     960
tcagagcaaa gagttgagct cacaaaaccc atatccctca tctacattat tgacgacata    1020
tttgatgttt atgggacgct tgatgaactt attctcttca cagaaactat tactagatgg    1080
gatcttgccg ctatgggtca attgcctgag tacatgaaga tatgtttcaa agctcttgac    1140
gatattacta acgaaatcag ctgcaaggtc tataagaagc atgggtataa cccagtacag    1200
tccctccgaa atgcgtggac aagtttgtgc aaagcatttc tagtggaagc gaaatggttt    1260
gcttctggac acatgcctga ggctgaagaa tacttgagga tgggattga gagttcagga     1320 gtacatgtgg cactggcgca cttttttttt ctcctaggtc atggtataac taaggaaacg    1380
```

```
gtggagctta ttgacggtaa cccggccata atatcatcaa ccgcaacaat tcttcggctc    1440
tgggatgact tgggaagtgc aaaggatgag aatcaagaag gtaaggatgg atcttacatc    1500
cattactaca tgaaggaaca ccgatattct gccgccgaag aggcacaaaa aagtgctatc    1560
aataaaattt cagacgcatg gaagcggctc aacaaagaat gcctctgccc aaatccattc    1620
tcagcatctt tcacgagggc ttctctcaat cttgcaagaa tggtcccctt gatgtacagt    1680
tacgatgaca ccaacgcct accaagcctc gaacattaca ttaagtccct actctttgaa    1740
agcgtaccta ctgaaggagt ttattaa                                       1767

<210> SEQ ID NO 94
<211> LENGTH: 1704
<212> TYPE: DNA
<213> ORGANISM: Malus domestica

<400> SEQUENCE: 94
atggaatttt ctatttccca gtcctccttt gcgacctcgt cttctactcc agctgctccg      60 gaacaccta gttctcaaaa atggagcatc cccgaagatc acagtttgct ttctactccc     120
ttaaaaccgc ttaactccaa aacgaagtat acttcatcta aggatggcat aatttgtttc     180
cagaatgaac aaaaactgga cgacttaagg catgcattga taaaagtggg aggagaagca     240
gttgaaagtt tggacatgat cgatgcggtt caacggctag gtctagacta ccactttgaa     300
gaagaaattg accaaattct ccaaaagcaa catataatat ctagtactac tgctcatggt     360
gctcaccatc ccaccgacct acatgaagtc gctctccgct ttcgactact caggcagcat     420
ggttacttcg tctctgatga tgtgtttaac aacttcaaga acagagaagg aaatttcaat     480
caaatgttaa gggaagacat caaggggttg atgagtttgt atgaagcttc acagctaagt     540
atagagggtg aagttgtact tgaagaagct ggaaagttta gtggccattt cctaaattca     600
tcactgtcac atctcgatca tcaccaggcc agagttgttg aaacacatt gagaaatcct     660 catcacaaaa gcttggcccc attcatggcc aagaactttt ttgtctctag cttccaagga     720
acaaataata gatggctaaa tatattacaa actgtagcaa aaacagattt aaatatggtc     780
cagtcccttc accagaaaga agttgctcaa gtttccaaat ggtggaaaga gctgggattg     840
tgtaaggagt gaagtttgc aagagaccaa cctattaaat ggtacatttg gtccatggct     900
tgcctaacaa atccaaactt gtcagatgag aggattgagc tcacaaaacc tatctcattt     960
atctatttga ttgatgacat ttttgacgtt tacgggacgc ttgatgaact cactcttttc    1020
acggaggttg tcaatagatg ggaaattggt tctatagagc acttaccgga ctacatgaag    1080
atatgcttca aggctcttta cgatatgacg aatgaaatca gctgtaaggt ctatcaaaag    1140 cacgggatgga acccattgca ttcgctaaag aagacgtggg ctagtctgtg caatgcattt    1200
ttagtggaag caaaatggtt caaatctggg cacttgccta tggctgaaga gtacttgaag    1260
aatggaatta tttcttctgg ggtgaatgtg gtgatggtcc acattttctt tctgtttgggt    1320 gaaggtataa ccaatcaaag tgtggagttc ttgaatggca ctccagccat tatatcttca    1380
acggcagcaa ttcttcggct ttgggacgac ttgggaagtg ccaaggatga gaatcaagat    1440
ggggacgacg ggtcatatgt aaagttgtat ttaaatgaac atcaaggcaa gaccatggag    1500
gaagcacaag aacatgttac aaatatgatt tcagaagaat ggaagaagct gaacaaagaa    1560
ttggtgtctc ctaatccact tcccgcggca ttcacaaagg cttccctaaa tctcgcaaga    1620
atggtgccat tgatgtatag ctacgacgac aaccagtgcc ttccatctct tgacgagtac    1680
```

```
atgaaatcga tgcttcatgc atga                                      1704
```

<210> SEQ ID NO 95
<211> LENGTH: 1824
<212> TYPE: DNA
<213> ORGANISM: Perilla frutescens var. crispa

<400> SEQUENCE: 95

```
atgtatagct tgagaatata tgtagcgatc atgaaaaagc catcagctaa acatgttgac    60
aacgtcgaca agaaagcttc aaagccgtcg tggcgtgtct cactctcttc gagtgcgggt   120
ctccgagctt cttcctcctt acaactcgat gtaaaaaagc ccgctgatga tgaaattctg   180
acggcccgac gctctggcaa ctaccagcct tccctttggg atttcaacta ccttcaatct   240
ctcaacacta ctcagtataa ggaagtgagg cacttgaaaa gggaagcaga gctgattgag   300
caagtgaaga tgctgctgga agaagaaatg gaggcagttc aacaattgga gttggttgat   360
gacttgaaaa atctgggatt gtcttatttt tttgaagacc aaattaagca gatcttaacg   420
tttatatata atgagcataa atgtttccac agtaatagta ttattgaagc ggaggaaatt   480
agggatttgt atttcacagc tcttggattc agactcctca gacaacatgg tttccaagtc   540
tctcaagagg tatttgattg tttcaagaac gaggagggta gtgatttcaa agcaaggctt   600
ggtgacgata caaaggatt gctgcaactc tacgaagcct ctttcctatt gagagaaggt   660
gaagatacac tggagctagc aaggcaatat gccaccaaat ttctccagaa aaagttgat   720
catgaattaa ttgacgacaa taatctatta tcatggattc tccattcttt ggagatcccg   780
cttcactgga ggattcagag gctggaggca agatggttct tagatcgtta cgcgacgaga   840
cgagacatga atcaaatcat tcttgagctc gccaaactcg acttcaatat tattcaagca   900
acacaacagg aagaactcaa agatctctca aggtggtgga agagtacatg tctggctgag   960
aaacttccat tcgtgaggga taggcttgtg aaagctact tttgggccat tgctctcttt  1020
gaacctcatc aatatggata tcacagaaaa gttgctgcca agattattac actaataaca  1080
tctttagatg atgtttacga tatctatggt acattagacg aactacaact atttacagac  1140
gcgattcaaa gatgggatac tgaatcaata agccgccttc catattatat gcaattattt  1200
tatatggtac tctacaactt tgtttcggag ctggcttacg atggtctcaa ggagaagggt  1260
ttcatcacca tcccatattt acagagatcg tgggcagatt tggttgaagc atatttaaaa  1320
gaggcaaagt ggttctacaa tggatatgta ccaagcatgg aagaatatct caacaacgcc  1380
tacatttcaa taggggctac tcccgtaatt tctcaagttt tcttcacatt agcaacctcc  1440
attgacaaac cagtgatcga cagcttgtac gaataccacc gcatacttcg cctctctgga  1500
atgcttgtaa ggcttcctga tgatttagga acatcaccgt ttgagatgaa gagaggcgac  1560
gtgccgaaag caatccagtt gtacatgaag gaaagaaatg ctaccgagat agaggctcaa  1620
gaacacgtga ggtttctgat tcgtgaggcg tggaaggaga tgaacacggt aacgacggcg  1680
gccgattgtc cgtttacgga tgatttggtt gcagcgacac gtaatcttgg tagggcggca  1740
cagtttatgt atctcgacgg agatggtaac cactctcaat tacatcagcg gattgcgtgc  1800
ctactgttcg agccatatgc atga                                        1824
```

<210> SEQ ID NO 96
<211> LENGTH: 1734
<212> TYPE: DNA
<213> ORGANISM: Vitis vinifera

<400> SEQUENCE: 96

```
atgggattct ctcctgcctt ttacgcttgc tccattcctc cagttggtcc taacaaattc        60
acagagctag gccagtccaa attcaacaat gttgtgcttg tgcctactgc tcagaaatgg       120
agcattgccc acgaccacac cttggtttat aagcccttaa gaaagcataa tcatcaatct       180
caacatctca gctttactga tgaattttac atcaagcatg cacaaagatt ggatgaaatt       240
agaaacgtat tcagtgaagt tggagaggat acgctggaag gtttgatgat gattgatgcc       300
atacaaaggt tgggcattga ctaccacttc aagaggaaa ttgaagcagt tctacagaga        360
cagtatatga aagccagcac tcacggtgag agcattcagg atctctacga ggttgctctt      420
cgttttcggc tattgagaca agaaggttac catgtgcctg cagatgtgtt taacaacttc       480
aagaacaagg aggggaagtt taaacaaaat ctcagcaaag acatcaaggg attgttggct      540
ttatatgaag cttcacaact gagtatagaa ggagaagata tcctcgagga agcccaaaga      600
ttcagcagca cgctccttaa cgcagggttg gaacatctta atcaccacga agctacagtt      660
gttgggcata cactggagca tccccatcat aagagcttgc caaggttcat ggccaaaagc      720
ttccttaagg acttccaggg accaaatgga tggctgactg tcttgcaaga acttgcaaaa      780
gcggatttca atatggttca atccatacat cagcaggaat tacttcaaat ttcgaaatgg      840
tggcaagacc gaggtttggc tgaggagttg aaatttgcaa gagaccaacc actgaaatgg      900
cacatgtggc ccatggcagt actccccgat ccaagcttgt cagagcaaag ggttgagctc      960
acaaaaccca tctctatgat ctatataatc gatgacattt ttgatgttca tggaacgctt     1020
gatgagctca ctctctttac agaagctgtc aatagatggg atatagctgc tttcgagacg     1080
ctaccaaact acatgaagat atgcttcaag actctagatg aaatcacaaa tgaaatcagc     1140
aacaaggtct acaaagagca cgggtggaac ccagtagact cgctacggaa gacgtgggtg     1200
agtttatgca atgcgtttct agtagaagcc aaatggtttg cctctgggca tgtgccaaag     1260
gcccacgagt acttgaaaaa cggggtcatc agttcagggg tacatgtggt gcttgttcac     1320
ttgttctttc tcttgggcca tggcataacc aggggaaatg tggatcttgt ggatgacttc     1380
cccagcatca tatcttccac agctgccatt cttcgtcttt gggacgacct gggaagcgcc     1440
aaggatgaga atcaagatgg ccacgacggg tcatacatcg agtgctacat taggaacac      1500 caaggctctt ccatggaaaa tgcacggcaa aatgtgacct atatgatttc agacttatgg     1560
aagcgcctca caaggagtg cctctctcag catccatttt caactttctt tacaaagggt      1620
tcccttaaca ttgcaaggat ggttcctttg atgtacagtt atgatgacaa tcagagtctt     1680
ccacaccttg aggaacatat gaagtccctc ctctttgaag catttcccct gtag            1734
```

<210> SEQ ID NO 97
<211> LENGTH: 1809
<212> TYPE: DNA
<213> ORGANISM: Vitis vinifera

<400> SEQUENCE: 97

```
atggaactaa ccctcacatc cctctcaccc ttggcctatg gtgccctcaa ttgtcgtaaa        60
aattttgcca tggcatcccc aagaatgaga atcaagcaag ggagatcaga attgcccaac      120
ctcacaatca cttcgaagat tgatgagtta caagtgaccg aaaggcgatc ggctaattac      180
catcctagca tttgggaccc caaatttatt gagtccttaa gcactcccta tacgaatgag      240
ggctattcca accaattaga ggacttgaag gaagaagcta aaagggtaat taaggacgct      300
agagacactt cctcccgatt agagttcatt gattcgatgc aacggtttggg agtggcttac      360
```

```
catttggagg aggagatcaa agaggctatt gatcttgttc atttggatga taccactacc    420
gatgatcttt ccacaactgc actccgattt agacttctac gacaacacgg ctatccagtt    480
agctcagagg tgtttgatca attcagaagt aaagatggga gattcatgga tggcatcagc    540
caggatattg ctgggccttt gagtttgtat gaagcttccc atcttggagt cgagggagaa    600
gatgacttgg aagaagccag gaggttcagt actatacatt tgaagtcact ggttgggaat    660
ttggagagtg atttagctga ccaagtgcag cagtccctgg aagttccctt acactggaga    720
atgccaaggc tagaagcccg aaacttcatc gatatctacc aaaggcgcaa tacgaagaac    780
tctgctctcc ttgagctagc caagctggac tacaatctag tgcaatcatc atatcagacg    840
gagttgaagg agctaacaag gtggtggacg gacttgggat taaggagaa gctaagtttt    900
tctcgggatc gattgatgga gaactatttg tggtcaatgg ggatcgctcc tgagccccac    960
ttctccaaaa gcaggatagg actcaccaaa ttcatatgca tattaacagc catagatgac   1020
atgtatgaca tatatggatc accgatgag cttcgacgtt ttacagatgc tgtgaatcga   1080
tgggatactg aggcactggt ggaccttcca gattacatga agatatgtta cttggccatg   1140
ttcaactttg ctaatgaaat ggcctacgat gcattaagag atcacgacct atatatttta   1200
ccctatctta aaagtcagtg gctaaatctc tgtacatcct actcaatgga agctcaatgg   1260
ttttacaatg ggtataagcc aagcatcgat gaatacttaa gcaatgcctg gacttccgta   1320
gggggtcctg cagccatggt ccatgcctat tttctaatgg gttgtgccac caagggaaac   1380
ttgaacaatt gtttagacaa tgcctctaat ctactttatt ggtcatctct tattactcga   1440
cttagcgatg atttgggaac ttcttttagcc gagattgcga gaggcgacgt ggcaaaatct   1500
atccaatgtt acatgattga aaaatgtata tccgaagaac aagctcgaga tcaagtagag   1560
aagcttatac gttactcatg gaaaaagttg aatgaagcaa gtactgatag ctctctccca   1620
aagtccttaa taaattcatc attgaacatg gcgcgatcag ctcaatgtat ttttcaattt   1680
ggagatggaa tcggtacatc agttggggtg accaaagatc gattgacatc attcattatc   1740
aagccaatat tgatagaacc aagcattaaa ccctatcttg atggcatgaa gatgagcaac   1800
agaagatga                                                          1809

<210> SEQ ID NO 98
<211> LENGTH: 1695
<212> TYPE: DNA
<213> ORGANISM: Lavandula angustifolia

<400> SEQUENCE: 98
atgtcgatca atatcaacat gcctgcagcc gccgtcctcc gccctttcg ctgctcacaa     60
ctacatgtcg atgaaacccg acgctccgga aactaccgcc cctcggcttg ggattccaac    120
tacatccaat ctctcaattc tcagtataag gaaaagaagt gcttgacaag gctagaaggg    180
ctgattgagc aagtgaagga actgaagggg acaaaaatgg aggctgttca acaattggag    240
ttgattgatg actcgcagaa tctgggatta tcatattatt ttcaagataa aattaaacat    300
atcttgaatt tgatatataa tgatcacaaa tatttttacg atagtgaagc tgaaggaatg    360
gatttgtatt ttacagctct tggatttaga ctctttagac aacatggttt taaagtctcc    420
caagaagtat ttgatcgttt caagaacgag aatggtacgt atttcaagca cgacgataca    480
aagggattgt tgcagctcta cgaagcatca ttcctagtgc gagaaggcga agagacactc    540
gaacaagcac gagaatttgc caccaaatcc ctacaaagaa aacttgatga ggatggtgat    600
ggaattgacg ccaatatcga atcatggatc cgccactctc tggagatccc acttcattgg    660
```

```
agggctcaga ggctagaggc gagatggttc ctagatgctt atgcgagaag gcccgacatg    720
aaccccgtta tcttcgagct tgctaaactc aacttcaata ttgtccaagc aacacaacaa    780
gaagaattga agctctctc gaggtggtgg agtagtttag gcctagctga aaaactccca     840
tttgtgaggg ataggcttgt ggaaagctac ttttgggcta ttccactctt tgagcctcat    900
caatatggat atcaaagaaa agtggccacc aagatcataa ccctaatcac atctttagac    960
gatgtttacg atatctatgg cacgttagat gaattgcaac tatttacgaa cttatttgaa   1020
agatgggata atgcatcaat cggccgactt cctgaatact tgcaattgtt ctatttcgca   1080
atccacaact ttgtttccga ggtggcttac gacattctca agaaaaggg tttcactagt    1140 attgtatatt tacagagatc gtgggtggat ttgctaaaag gatacctaaa agaggcaaag   1200
tggtacaata gtggatacac gccaagcctc gaggaatatt tcgacaacgc attcatgaca   1260
atagggcccc ctccggtact atcgcaagct tatttcacat taggaagctc gatggagaaa   1320
ccgatcatcg agagcatgta cgaatatgac aacatacttc gcgtttcggg aatgctcgtg   1380
aggcttcccg atgacctagg aacatcatcg ttcgagatgg agagaggcga cgtgccgaaa   1440
tcggtccagc tatacatgaa ggaaacaaat gctacggagg aggaggcggt ggagcacgtg   1500 aggttttga atcgggaggc gtggaagaag atgaacacgg cggaggcggc cggtgattct    1560
ccgttagtga gtgacgtggt ggcggtggcg gcgaatcttg aagggcggc gcagtttatg    1620 tatttcgacg gagatggtaa ccagtctagt ttgcagcagt ggattgtgag catgctgttc   1680
gagccgtacg catga                                                    1695

<210> SEQ ID NO 99
<211> LENGTH: 1821
<212> TYPE: DNA
<213> ORGANISM: Mentha citrata

<400> SEQUENCE: 99
atgtgtacta ttattagcgt aaatcatcat catgtggcga tccttagcaa gcctaaagta     60
aaacttttcc acaccaaaaa caagagatca gcttcaatta atctcccatg gagtctctct    120
ccttcttcat ccgccgcctc tcgccccatc agttgttcta tctcctcaaa actatatacc    180
atcagttcgg ctcaggagga aacccgacgt tccggaaact accacccttc agtttgggat    240
tttgatttca ttcaatctct cgacactgat cactataagg aggagaagca gttagagagg    300
gaggaagagc tgatcatgga ggtgaagaag ttgttggggg caaaaatgga ggcaactaag    360
cagttggagt tgattgatga cttgcagaat ttgggattgt cttatttttt ccagagacgag   420 attaagaata tcttgaattc tatatataaa attttccaaa ataataatag tactaaagta    480
ggggatttgc atttcacgtc tcttggattc aggctcctcc ggcagcatgg tttcaacgtt    540
tcacaaggag tatttgattg cttcaagaac gagcatggta gcgatttcga gaaaccccta    600
attggggaag atacgaaagg agtgctgcaa ctttacgaag catcattcct tttgagagaa    660
ggtgaagata cattggaggt agctagaaaa ttctccaccg aatttctcga ggaaaaactc    720
aaagccggaa tcgatggtga taatctatca tcatcgattg ccattctttt ggagatccct    780
cttcactgga ggattcaaag actagaggaa agatggttct tagatgctta ctcaaggagg    840
aaagacatga accctatcat tttcgagctc gccaaactcg acttcaatat tattcaagca    900
acgcagcaag aagaactcaa agatctctca aggtggtgga atgattcaag cctacctcaa    960
aaactcccat tgtgagggga taggctggtg gaaagctact attgggccct tgggttgttt   1020
```

| | |
|---|---|
| gaggctcaca aatttggata tgaaagaaaa actgctgcaa agattattac cctaattaca | 1080 |
| gctcttgatg atgtttatga tatttatggc acactcgacg agctccaact atttacacac | 1140 |
| gtcattcgaa gatgggatac tgaatcagcc acccaacttc cttattactt gcaattattc | 1200 |
| tatttcgtac tatacaactt tgtttccgag gtggcgtacc acattctaaa ggaagagggt | 1260 |
| ttcatcagca tcccatttct acacagagcg tgggtggatt tggttgaagg atatttacaa | 1320 |
| gaggcaaagt ggtactacac taaatataca ccaaccatgg aagaatattt gaactatgcc | 1380 |
| agcatcacaa tagggctcc tgcagtaata tcccaaattt attttatgct agccaaatcg | 1440 |
| aaagagaaac cggtgatcga gagttttttac gaatacgacg aaataattcg cctttcggga | 1500 |
| atgctcgtga ggcttcccga tgacctagga acactaccgt tgagatgaa gagaggcgac | 1560 |
| gtggcgaaat caatccagat ttacatgaag aacagaatg caacacggga agaagcagaa | 1620 |
| gaacacgtga ggtttatgat tagggaggcg tggaaggaga tgaacacaac tatggcggcg | 1680 |
| aattctgatt tgagaggtga tgtggttatg gctgcagcta atcttggaag ggatgcacag | 1740 |
| tttatgtatc tcgacggaga cggtaaccac tctcagttac aacaccggat tgcgaacttg | 1800 |
| ctgttcaagc catatgtctg a | 1821 |

<210> SEQ ID NO 100
<211> LENGTH: 1608
<212> TYPE: DNA
<213> ORGANISM: Ocimum basilicum

<400> SEQUENCE: 100

| | |
|---|---|
| atggcatccg cagtgcctct aagttcaact cctctcatca acggggataa ctctccgctt | 60 |
| aaaaacacac atcaacacgt ggaggagagg agcagcaaga ggagagaata tctgctggag | 120 |
| gaaacgcgc gaaaactgca gagaaacgac accgaatcgg tggagaaact caagctcatc | 180 |
| gacaacatcc aacggctggg aatcggctac tattttgagg atgccatcga cgccgtactc | 240 |
| cgctcgcctt tctccgccga agaagaagaa gacctcttca ccgctgctct gcgcttccgc | 300 |
| ttgctccgcc acaatggcat ccaagtcacc cctgaaatat tcctaaaatt caaggacgag | 360 |
| agaggagaat tcgacgaatc ggacacgcta gggttactga gcttgtacga agcgtcaaat | 420 |
| ttgggggtta caggagaaga gatactggag gaggctatgg agttcgcgga gcctcgcctg | 480 |
| agacgatcac tgtcagagct ggcggcgccg cttcgtagtg aggtggcgca agccctagat | 540 |
| gtgccgaggc atctgagaat ggcgaggttg gaagccagac gattcatcga gcagtatggt | 600 |
| aaacagagcg atcatgatgg agacctttg gagctagcaa ttttggatta taatcaagtt | 660 |
| caggctcaac accaatccga actcactgaa attaccaggt ggtggaagca actgggtttg | 720 |
| gtggaaaagt tgggtttcgg tagagacaga gcgttggagt gctttatgtg gaccatgggg | 780 |
| atcctacctc accctaaata ctcttcttct agaatagaat cagccaaggc agctgctctt | 840 |
| ctgtacgtca tcgatgatat tttcgatacc tatggcaaaa tggacgaact catcctcttc | 900 |
| accgacgcaa ttcgaagatg ggatttggaa gcaatggagg tctacccga gtacatgaaa | 960 |
| atatgctaca tggcgttgta caacaccacc aatgaaatat gctacagagt gctcaaggat | 1020 |
| actggacgga tcgccctccc atacctcaaa tctgtgtgga tagagactat tgaagcttat | 1080 |
| atggtggagg tgaagtggtt cagtggtgga agtgccccaa agttggaaga atacattgag | 1140 |
| aatggggcat caactgtagg ggcatacatg gttcttgtcc acctattctt tctcattgga | 1200 |
| gaaggtctca cccaccaaaa tgtcctattt ttcaaacaaa aacccatca caagcctttc | 1260 |
| tccgccgccg gccggatttt tcgcctttgg gacgatcttg gaacttctca ggaggaggaa | 1320 |

```
gaacgaggag atatggcgtc aagtatacgg ttatttatga aagagtacaa gttgtcgacg    1380
gtagaggagg ctagaagttg cgttttggaa gagatatccc gtttatggaa ggatcttaat    1440
gaagggctca tcagtataaa ggacgccttg ccattaacca tagtcaaagt cgcacttaac    1500
attgcacgaa cttctcaagt tgtatacaag cacgaacaac atacatatat gttgagtgtt    1560
gataattacg tggaagccct cttcttcact cctcttcttt cttcttag                1608
```

<210> SEQ ID NO 101
<211> LENGTH: 2550
<212> TYPE: DNA
<213> ORGANISM: Clarkia breweri

<400> SEQUENCE: 101

```
atgagagaat cattgtcttc ttcatcatct aatactcaga atttgtttct ctcaacttca      60
ccttatgaca ctgcttggct cgcccttatc cctcatcctc atcatcacca tcaccatggc     120
cgacccatgt ttgaaaaatg tctgcaatgg attctccata accagacacc acaaggtttc     180
tgggcagcag ctggtgacaa tatttccgac accgacgatg acgtcaccct ggattgtctt     240
ctatcaacct tggcttgctt agttgcactc aaaaggtggc agcttgctcc cgacatgatt     300
cataaaggat tggaatttgt aaatagaaac acagagagac ttgtaatgaa gcagaagccg     360
agcgacgttc ctcgttggtt caccatcatg ttcccggcga tgctcgagct tgccggagct     420
tccagtctcc gagtcgattt cagcgagaat cttaacagaa tcttggtgga actatctcaa     480
aatagggatg atattctcac aagggaggaa gttgatgaga agaagcaata ctcaccattg     540
ctactatttc tagaagcatt gcctgcacaa tcctatgaca atgatgttct aaagcaaatt     600
atagacaaga acttgagcaa tgatggttct ttattgcaat cgccttctgc tacagcaaga     660
gcatacatga taacaggaaa taccagatgc ttatcgtatc tacactcttt aacaaatagc     720
tgctctaatg gaggagtacc atcattctat cctgttgacg acgacctcca tgatcttgtc     780
atggtgaatc aactgacaag gtcgggtttg actgaacatc tcatcccgga gattgaccac     840
cttctactca aagttcaaaa gaactacaaa tacaaaaaag catcaccaaa atcattgtat     900
agcattgctg cggaactata cagggattca ttagcatttt ggttgcttcg agtcaataat     960
cactgggtat caccatcaat ttttgttgg ttttttagatg acgacgaaat ccgtgatcac    1020
atcgaaacaa actacgagga atttgctgcc gtgcttctta atgtgtatcg agctaccgat    1080
cttatgttct ccggcgaagt ccaacttgtc gaagcaagat ctttcgctac caagaatctt    1140 gagaaatat tagcaacagg aaacatacat aaaactaatg cagatatctc atctagtttg    1200
cataagatga tcgaacacga actaagagtt ccttggaccg caagaatgga ccatgttgaa    1260
aatcgaattt ggatcgaaga aatagcttcc agtgctttat ggtttggaaa atcatcctac    1320
cttaggttat cttgctttca caagatgagt ttacagcaac tcgcggtgaa aaattatacg    1380
cttcgacaat tggtttaccg agacgagctt gcggaagttg agaggtggtc taagaaaga    1440 gggctatgtg acatgggatt tgtagagag aaaaccgggt attgttacta cgcatttgcg    1500
gcaagtactt gtctgccgtg gagttccgac gtgaggctgg tcctgaccaa ggcggcagtt    1560
gtcattacag tggccgatga tttctttgat gtcgaaggat ctatggttga tctcgaaaaa    1620
ttaacggatg cagttcggag gtgggatgcg aagggttag gcagccacag caagacaata    1680
tttgaagccc tggatgatct tgtaaatgaa gttagactca agtgtttcca acaaaatgga    1740
caagacatca aaaacaatct ccaacaatta tggtatgaaa cattccattc atggcttatg    1800
```

| | |
|---|---|
| gaagctaagt ggggaaaggg gttaacaagt aaaccatctg tagatgtgta tcttggaaat | 1860 |
| gcaatgacat ccatagcagc tcacaccatg gtccttacag catcctgtct tctaggtccc | 1920 |
| ggtttcccgg ttcaccaact atggtcgcaa aggcgccacc aggacattac atccttgctc | 1980 |
| atggtcttga ctcgcttgct aaatgacatt caatccctact tgaaagaaga agacgaagga | 2040 |
| aaaataaact atgtatggat gtacatgatc gagaacaatc aagcgtcgat agatgactcg | 2100 |
| gttcgacacg tccagacgat aatcaatgta aaaaagcaag aattcatcca acgtgttcta | 2160 |
| tcggatcaac attgcaatct cccaaagtca ttcaagcagc tccatttctc ctgcctcaaa | 2220 |
| gtattcaaca tgttcttcaa ctcctccaac attttcgaca ctgataccga ccttcttctt | 2280 |
| gacattcacg aagcttttgt ttctccacca caagttccca aattcaaacc ccacatcaag | 2340 |
| ccacctcatc agcttccagc aacacttcag ccacctcatc agccccaaca ataatggtc | 2400 |
| aataagaaga aggtggaaat ggtttacaaa agctatcatc atccattcaa ggttttcacc | 2460 |
| ttgcagaaga aacaaagttc gggacatggt acaatgaatc caagggctag tatcttagca | 2520 |
| ggacccaaca tcaaactatg tttcagttaa | 2550 |

<210> SEQ ID NO 102
<211> LENGTH: 1575
<212> TYPE: DNA
<213> ORGANISM: Artificial Sequence
<220> FEATURE:
<223> OTHER INFORMATION: DNA having modified codons, which encodes linalool synthase gene derived from Arabitopsis thaliana (At1LINS)

<400> SEQUENCE: 102

| | |
|---|---|
| atggcgaaca cggcgaagcg tagtatcctg cgtaatgtcc atgcgagcgt tagcaacccg | 60 |
| agtaagcagt ttcataataa gacgagtctg gaatacctgc atgaactgaa cattaaaaag | 120 |
| atcaagaaca ttctgagcgc caatgttgac gtgccgagcg aaaatctgga atgatcgat | 180 |
| gtgattcaga gcctgggcat tgacctgcat tttcgccagg aaattgaaca gacccctgcac | 240 |
| atgatctaca aagaaggcct gcagtttaat ggcgatctgc atgaaattgc cctgcgtttt | 300 |
| cgtctgctgc gtcaggaagg ccactacgtc caggaaaaata aaaagggcgg ctttaaagat | 360 |
| gttgtgaaga atgacgtgaa aggcctgacg gaactgtttg aagcgagcga actgcgcgtc | 420 |
| gaaggcgaag aaacgctgga cggcgcccgc gaatttacct acagccgcct gaatgaactg | 480 |
| tgtagcggcc gcgaaagcca tcagaagcag gaaattatga aaagcctggc ccagcccgt | 540 |
| cacaaaacgg ttcgcggcct gacgagcaag cgctttacca gcatgattaa atcgcgggc | 600 |
| caggaagatc ccgaatggct gcagagcctg ctgcgcgtgg ccgaaatcga cagcattcgc | 660 |
| ctgaagagcc tgacccaggg cgaaatgagc cagacgtta aatggtggac cgaactgggc | 720 |
| ctggaaaagg atgttgaaaa agcgcgcagc agccgctga gtggcatac gtggagcatg | 780 |
| aaaattctgc aggatccgac cctgacggaa cagcgcctgg acctgaccaa gcccatcagc | 840 |
| ctggtctacg ttatcgatga cattttttgat gtctacggcg aactggaaga actgaccatc | 900 |
| tttacgcgcg tcgttgaacg ctgggaccat aaaggcctga gaccctgcc caaatacatg | 960 |
| cgcgttttgtt ttgaagcgct ggatatgatc accacggaaa ttagcatgaa atctacaag | 1020 |
| agccacggct ggaatcccac ctacgccctg cgccagagct gggccagcct gtgcaaggcg | 1080 |
| tttctggtgg aagccaaatg gtttaatagc ggctacctgc ccaccacgga gaatacatg | 1140 |
| aagaatggcg tggtcagcag cggcgtgcat ctggtcatgc tgcacgcgta cattctgctg | 1200 |
| ggcgaagaac tgacgaaaga aaaggtcgaa ctgattgaaa gcaatccggg catcgttagc | 1260 |

-continued

```
agcgcggcca ccattctgcg tctgtgggat gacctgggta gcgccaagga cgaaaatcag    1320
gatggcacgg acggcagcta cgttgaatgt tacctgaatg aatacaaagg cagcacggtt    1380
gatgaagcgc gcacccacgt ggcccagaag attagccgcg cgtggaaacg cctgaatcgc    1440
gaatgtctga atccgtgccc ctttagccgc agctttagca aagcgtgcct gaatatcgcc    1500
cgcacggtgc ccctgatgta tagttatgat gatgaccagc gtctgcccga tgagtatctg    1560
aaaagcctga tgtaa                                                     1575
```

<210> SEQ ID NO 103
<211> LENGTH: 524
<212> TYPE: PRT
<213> ORGANISM: Arabidopsis thaliana

<400> SEQUENCE: 103

```
Met Ala Asn Thr Ala Lys Arg Ser Ile Leu Arg Asn Val His Ala Ser
1               5                   10                  15

Val Ser Asn Pro Ser Lys Gln Phe His Asn Lys Thr Ser Leu Glu Tyr
            20                  25                  30

Leu His Glu Leu Asn Ile Lys Lys Ile Lys Asn Ile Leu Ser Ala Asn
        35                  40                  45

Val Asp Val Pro Ser Glu Asn Leu Glu Met Ile Asp Val Ile Gln Ser
    50                  55                  60

Leu Gly Ile Asp Leu His Phe Arg Gln Glu Ile Glu Gln Thr Leu His
65                  70                  75                  80

Met Ile Tyr Lys Glu Gly Leu Gln Phe Asn Gly Asp Leu His Glu Ile
                85                  90                  95

Ala Leu Arg Phe Arg Leu Leu Arg Gln Glu Gly His Tyr Val Gln Glu
            100                 105                 110

Asn Lys Lys Gly Gly Phe Lys Asp Val Val Lys Asn Asp Val Lys Gly
        115                 120                 125

Leu Thr Glu Leu Phe Glu Ala Ser Glu Leu Arg Val Glu Gly Glu Glu
    130                 135                 140

Thr Leu Asp Gly Ala Arg Glu Phe Thr Tyr Ser Arg Leu Asn Glu Leu
145                 150                 155                 160

Cys Ser Gly Arg Glu Ser His Gln Lys Gln Glu Ile Met Lys Ser Leu
                165                 170                 175

Ala Gln Pro Arg His Lys Thr Val Arg Gly Leu Thr Ser Lys Arg Phe
            180                 185                 190

Thr Ser Met Ile Lys Ile Ala Gly Gln Glu Asp Pro Glu Trp Leu Gln
        195                 200                 205

Ser Leu Leu Arg Val Ala Glu Ile Asp Ser Ile Arg Leu Lys Ser Leu
    210                 215                 220

Thr Gln Gly Glu Met Ser Gln Thr Phe Lys Trp Trp Thr Glu Leu Gly
225                 230                 235                 240

Leu Glu Lys Asp Val Glu Lys Ala Arg Ser Gln Pro Leu Lys Trp His
                245                 250                 255

Thr Trp Ser Met Lys Ile Leu Gln Asp Pro Thr Leu Thr Glu Gln Arg
            260                 265                 270

Leu Asp Leu Thr Lys Pro Ile Ser Leu Val Tyr Val Ile Asp Asp Ile
        275                 280                 285

Phe Asp Val Tyr Gly Glu Leu Glu Glu Leu Thr Ile Phe Thr Arg Val
    290                 295                 300

Val Glu Arg Trp Asp His Lys Gly Leu Lys Thr Leu Pro Lys Tyr Met
305                 310                 315                 320
```

```
Arg Val Cys Phe Glu Ala Leu Asp Met Ile Thr Thr Glu Ile Ser Met
                325                 330                 335
Lys Ile Tyr Lys Ser His Gly Trp Asn Pro Thr Tyr Ala Leu Arg Gln
            340                 345                 350
Ser Trp Ala Ser Leu Cys Lys Ala Phe Leu Val Glu Ala Lys Trp Phe
        355                 360                 365
Asn Ser Gly Tyr Leu Pro Thr Thr Glu Glu Tyr Met Lys Asn Gly Val
    370                 375                 380
Val Ser Ser Gly Val His Leu Val Met Leu His Ala Tyr Ile Leu Leu
385                 390                 395                 400
Gly Glu Glu Leu Thr Lys Glu Lys Val Glu Leu Ile Glu Ser Asn Pro
                405                 410                 415
Gly Ile Val Ser Ser Ala Ala Thr Ile Leu Arg Leu Trp Asp Asp Leu
            420                 425                 430
Gly Ser Ala Lys Asp Glu Asn Gln Asp Gly Thr Asp Gly Ser Tyr Val
        435                 440                 445
Glu Cys Tyr Leu Asn Glu Tyr Lys Gly Ser Thr Val Asp Glu Ala Arg
    450                 455                 460
Thr His Val Ala Gln Lys Ile Ser Arg Ala Trp Lys Arg Leu Asn Arg
465                 470                 475                 480
Glu Cys Leu Asn Pro Cys Pro Phe Ser Arg Ser Phe Ser Lys Ala Cys
                485                 490                 495
Leu Asn Ile Ala Arg Thr Val Pro Leu Met Tyr Ser Tyr Asp Asp Asp
            500                 505                 510
Gln Arg Leu Pro Asp Glu Tyr Leu Lys Ser Leu Met
        515                 520
```

<210> SEQ ID NO 104
<211> LENGTH: 1644
<212> TYPE: DNA
<213> ORGANISM: Artificial Sequence
<220> FEATURE:
<223> OTHER INFORMATION: DNA having modified codons, which encodes
      linalool synthase gene derived from Arabitopsis thaliana (At2LINS)

<400> SEQUENCE: 104

```
atgcgtcgta gtgcgaatta ccagccgagt cgttgggacc atcatcacct gctgagtgtg      60
gagaataagt ttgcgaagga caagcgtgtc cgcgaacgcg acctgctgaa agaaaaggtt     120
cgcaaaatgc tgaatgacga acagaagacc tacctggatc agctggaatt tattgatgac     180
ctgcagaaac tgggcgtcag ctaccatttt gaagccgaaa ttgataatat cctgaccagc     240
agctacaaaa aggaccgcac gaatatccag gaaagcgatc tgcatgccac ggcgctggaa     300
tttcgcctgt ttcgccagca cggctttaat gttagcgaag atgtgtttga cgtctttatg     360
gaaaattgtg gcaagtttga ccgcgatgac atctacggcc tgattagcct gtacgaagcc     420
agctacctga gcaccaaact ggataagaat ctgcagattt ttattcgtcc ctttgccacc     480
cagcagctgc gtgattttgt tgacacgcat agcaatgaag attttggcag ctgcgacatg     540
gtggaaattg ttgtgcaggc cctggacatg ccctactact ggcagatgcg ccgcctgagc     600
acccgttggt acatcgatgt gtacggcaaa cgccagaatt acaagaatct ggtcgttgtg     660
gaatttgcca aaatcgactt taatattgtg caggcgatcc accaggaaga actgaaaaat     720
gtcagcagtt ggtggatgga accggcctg ggcaagcagc tgtactttgc gcgcgatcgc     780
attgtcgaaa attactttg acgattggc cagatccagg aaccgcagta cggctacgtt     840
```

-continued

```
cgccagacca tgacgaagat caatgccctg ctgaccacga ttgatgacat ctacgatatt    900
tacggcaccc tggaagaact gcagctgttt acggttgcgt ttgaaaattg ggatattaat    960
cgcctggacg aactgccgga atacatgcgc ctgtgttttc tggttatcta caatgaagtg   1020
aatagcattg cctgcgaaat cctgcgcacc aagaacatca acgtgatccc ctttctgaaa   1080
aagagctgga cggacgtgag caaagcctac ctggtcgaag cgaaatggta caagagcggc   1140
cataagccga atctggaaga atacatgcag aatgcgcgca ttagcatcag cagccccacc   1200
atctttgtcc attttactg tgttttagc gatcagctga gcatccaggt gctggaaacg     1260
ctgagccagc accagcagaa tgtcgttcgc tgcagcagca gcgttttttcg cctggccaat    1320 gatctggtga ccagccccga tgaactggcc cgcggcgatg tgtgtaaaag cattcagtgc   1380
tacatgagcg aaacgggtgc cagcgaagat aaggcccgca gccatgtccg ccagatgatc   1440
aatgatctgt gggacgaaat gaattacgaa aaaatggccc acagcagcag cattctgcat   1500
cacgacttta tggaaaccgt tatcaatctg cgcgcgcatga gccagtgtat gtaccagtac   1560
ggtgatggtc atggcagccc cgaaaaagcc aaaatcgtgg accgtgtgat gagcctgctg   1620
tttaacccta tcccgctgga ctaa                                          1644
```

<210> SEQ ID NO 105
<211> LENGTH: 547
<212> TYPE: PRT
<213> ORGANISM: Arabidopsis thaliana

<400> SEQUENCE: 105

```
Met Arg Arg Ser Ala Asn Tyr Gln Pro Ser Arg Trp Asp His His
1               5                   10                  15

Leu Leu Ser Val Glu Asn Lys Phe Ala Lys Asp Lys Arg Val Arg Glu
                20                  25                  30

Arg Asp Leu Leu Lys Glu Lys Val Arg Lys Met Leu Asn Asp Glu Gln
            35                  40                  45

Lys Thr Tyr Leu Asp Gln Leu Glu Phe Ile Asp Asp Leu Gln Lys Leu
        50                  55                  60

Gly Val Ser Tyr His Phe Glu Ala Glu Ile Asp Asn Ile Leu Thr Ser
65                  70                  75                  80

Ser Tyr Lys Lys Asp Arg Thr Asn Ile Gln Glu Ser Asp Leu His Ala
                85                  90                  95

Thr Ala Leu Glu Phe Arg Leu Phe Arg Gln His Gly Phe Asn Val Ser
            100                 105                 110

Glu Asp Val Phe Asp Val Phe Met Glu Asn Cys Gly Lys Phe Asp Arg
        115                 120                 125

Asp Asp Ile Tyr Gly Leu Ile Ser Leu Tyr Glu Ala Ser Tyr Leu Ser
    130                 135                 140

Thr Lys Leu Asp Lys Asn Leu Gln Ile Phe Ile Arg Pro Phe Ala Thr
145                 150                 155                 160

Gln Gln Leu Arg Asp Phe Val Asp Thr His Ser Asn Glu Asp Phe Gly
                165                 170                 175

Ser Cys Asp Met Val Glu Ile Val Gln Ala Leu Asp Met Pro Tyr
            180                 185                 190

Tyr Trp Gln Met Arg Arg Leu Ser Thr Arg Trp Tyr Ile Asp Val Tyr
        195                 200                 205

Gly Lys Arg Gln Asn Tyr Lys Asn Leu Val Val Glu Phe Ala Lys
    210                 215                 220

Ile Asp Phe Asn Ile Val Gln Ala Ile His Gln Glu Glu Leu Lys Asn
```

```
         225                 230                 235                 240
Val Ser Ser Trp Trp Met Glu Thr Gly Leu Gly Lys Gln Leu Tyr Phe
                245                 250                 255

Ala Arg Asp Arg Ile Val Glu Asn Tyr Phe Trp Thr Ile Gly Gln Ile
            260                 265                 270

Gln Glu Pro Gln Tyr Gly Tyr Val Arg Gln Thr Met Thr Lys Ile Asn
        275                 280                 285

Ala Leu Leu Thr Thr Ile Asp Asp Ile Tyr Asp Ile Tyr Gly Thr Leu
    290                 295                 300

Glu Glu Leu Gln Leu Phe Thr Val Ala Phe Glu Asn Trp Asp Ile Asn
305                 310                 315                 320

Arg Leu Asp Glu Leu Pro Glu Tyr Met Arg Leu Cys Phe Leu Val Ile
                325                 330                 335

Tyr Asn Glu Val Asn Ser Ile Ala Cys Glu Ile Leu Arg Thr Lys Asn
            340                 345                 350

Ile Asn Val Ile Pro Phe Leu Lys Lys Ser Trp Thr Asp Val Ser Lys
        355                 360                 365

Ala Tyr Leu Val Glu Ala Lys Trp Tyr Lys Ser Gly His Lys Pro Asn
    370                 375                 380

Leu Glu Glu Tyr Met Gln Asn Ala Arg Ile Ser Ile Ser Pro Thr
385                 390                 395                 400

Ile Phe Val His Phe Tyr Cys Val Phe Ser Asp Gln Leu Ser Ile Gln
                405                 410                 415

Val Leu Glu Thr Leu Ser Gln His Gln Gln Asn Val Val Arg Cys Ser
            420                 425                 430

Ser Ser Val Phe Arg Leu Ala Asn Asp Leu Val Thr Ser Pro Asp Glu
        435                 440                 445

Leu Ala Arg Gly Asp Val Cys Lys Ser Ile Gln Cys Tyr Met Ser Glu
    450                 455                 460

Thr Gly Ala Ser Glu Asp Lys Ala Arg Ser His Val Arg Gln Met Ile
465                 470                 475                 480

Asn Asp Leu Trp Asp Glu Met Asn Tyr Glu Lys Met Ala His Ser Ser
                485                 490                 495

Ser Ile Leu His His Asp Phe Met Glu Thr Val Ile Asn Leu Ala Arg
            500                 505                 510

Met Ser Gln Cys Met Tyr Gln Tyr Gly Asp Gly His Gly Ser Pro Glu
        515                 520                 525

Lys Ala Lys Ile Val Asp Arg Val Met Ser Leu Leu Phe Asn Pro Ile
    530                 535                 540

Pro Leu Asp
545

<210> SEQ ID NO 106
<211> LENGTH: 1698
<212> TYPE: DNA
<213> ORGANISM: Artificial Sequence
<220> FEATURE:
<223> OTHER INFORMATION: DNA having modified codons, which encodes
      linalool synthase gene derived from Citrus unshiu (CulLINS)

<400> SEQUENCE: 106
atgctgtttc aggtgagcgc cagtcccaat aaggtgatcc gtattaacgc cgagaaggag      60
agtacccgtc gtagtgccaa ctttgacccg acgatttggg gcgattactt tctgagctac     120
accggcgatt ttaaagaaag cggcgacgcc agcgtcaagc atcaggaact gaaaaaggaa     180
```

-continued

| | |
|---|---|
| attcgcacga tgctgcgcgc ggatatcaat aaacccaccc agacgaagct ggacctgatt | 240 |
| gatgacatcc agcgcctggg cgtgagctac cattttgaaa gcgaaattga cgaaatcctg | 300 |
| cgcaaaatgc acgaagccaa tcaggattgt gacctgggcg atgacgaaaa tgtgcaggaa | 360 |
| ctgtactaca ttagcctgca ttttcgcctg ctgcgccaga atggctacaa aatcagcgcg | 420 |
| gatgtcttta atagctttaa ggacagcaat ggcaatttta aaagctttct gaagcgcgat | 480 |
| attcgcggca tgctgagcct gtacgaagcc gcgcatctgc gcgttcacgg cgaaaatatc | 540 |
| ctgaatgaag ccctgacctt tacggtgacc cacctggaaa gctttacgag ccagagcaat | 600 |
| acgcagctgg cggcccaggt taatcgtgcc ctgaatcgcc cgattcgcaa agcctgccc | 660 |
| cgcctggaag cgaagcatta catgccgatc taccagaaag atcccagcca caataaggac | 720 |
| ctgctgacgt ttgcgatgct ggattttaat attctgcaga acagcacca ggaagaactg | 780 |
| cgcgatatcg tgcgttggtg gaaaaatttt gacgtcccga ataagctgcc ctttattcgc | 840 |
| gaccgcgttg tggaaggcta cttttggatc ctgggcgtct actttgaacc gaagtttctg | 900 |
| ctggcccgca aaattctgac caaggttatc agcatggcca gcattatcga tgacatttac | 960 |
| gatgcgtacg gcacgatcga agaactggaa ctgtttgcca ccgcgattga acgctgggat | 1020 |
| ctgagcgcga tcgacctgct gccccgaatac atgaaactgt gttactgcgc cctgctggat | 1080 |
| gcgtacagcg aatttgaaaa agacctggcc agcaagggca ttctgtacgg cctgccgttt | 1140 |
| gcgaaagaaa gcatgaagat cctggtgcgc agctacatta tcgaagcccg ctggtgtgat | 1200 |
| cagcagtacg ttcccacgat ggaagaatac atgcgtgtgg ccctgctgag ctgtggttac | 1260 |
| ctgctgctga gcacgagcag ctttctgggc atggaagaca ttgttaccaa gaagcctttt | 1320 |
| gaatgggtca gcggcaatcc gaagattgtt caggcgagca gcattatctg tcgcctgatg | 1380 |
| gatgacatcg tgagccataa atttgaacag cagcgcggtc atgttgccag cgccgtggaa | 1440 |
| tgctacatga agcagcatgg cgtgagcgaa gaagaagccg tgaaagtctt tcgcgaaaag | 1500 |
| gtcggcaatg cgtggaaaga tatcaatgaa gaactgatgc gcccgcccgt tgttcccatg | 1560 |
| cctctgctgg aacgcgtcct gaatctggcc cgcctgatgg atgttctgta ccagaataat | 1620 |
| gacagctaca ccaatccgca cctgatgaag gaccatgttg ccgccctgct gaaagaccct | 1680 |
| gtgtttttg aggactaa | 1698 |

<210> SEQ ID NO 107
<211> LENGTH: 565
<212> TYPE: PRT
<213> ORGANISM: Citrus unshiu

<400> SEQUENCE: 107

Met Leu Phe Gln Val Ser Ala Ser Pro Asn Lys Val Ile Arg Ile Asn
1               5                   10                  15

Ala Glu Lys Glu Ser Thr Arg Arg Ser Ala Asn Phe Asp Pro Thr Ile
            20                  25                  30

Trp Gly Asp Tyr Phe Leu Ser Tyr Thr Gly Asp Phe Lys Glu Ser Gly
        35                  40                  45

Asp Ala Ser Val Lys His Gln Glu Leu Lys Lys Glu Ile Arg Thr Met
    50                  55                  60

Leu Arg Ala Asp Ile Asn Lys Pro Thr Gln Thr Lys Leu Asp Leu Ile
65                  70                  75                  80

Asp Asp Ile Gln Arg Leu Gly Val Ser Tyr His Phe Glu Ser Glu Ile
                85                  90                  95

Asp Glu Ile Leu Arg Lys Met His Glu Ala Asn Gln Asp Cys Asp Leu

```
            100                 105                 110
Gly Asp Asp Glu Asn Val Gln Glu Leu Tyr Tyr Ile Ser Leu His Phe
            115                 120                 125
Arg Leu Leu Arg Gln Asn Gly Tyr Lys Ile Ser Ala Asp Val Phe Asn
            130                 135                 140
Ser Phe Lys Asp Ser Asn Gly Asn Phe Lys Ser Phe Leu Lys Arg Asp
145                 150                 155                 160
Ile Arg Gly Met Leu Ser Leu Tyr Glu Ala Ala His Leu Arg Val His
                    165                 170                 175
Gly Glu Asn Ile Leu Asn Glu Ala Leu Thr Phe Thr Val Thr His Leu
                    180                 185                 190
Glu Ser Phe Thr Ser Gln Ser Asn Thr Gln Leu Ala Ala Gln Val Asn
            195                 200                 205
Arg Ala Leu Asn Arg Pro Ile Arg Lys Ser Leu Pro Arg Leu Glu Ala
            210                 215                 220
Lys His Tyr Met Pro Ile Tyr Gln Lys Asp Pro Ser His Asn Lys Asp
225                 230                 235                 240
Leu Leu Thr Phe Ala Met Leu Asp Phe Asn Ile Leu Gln Lys Gln His
                    245                 250                 255
Gln Glu Glu Leu Arg Asp Ile Val Arg Trp Trp Lys Asn Phe Asp Val
            260                 265                 270
Pro Asn Lys Leu Pro Phe Ile Arg Asp Arg Val Val Glu Gly Tyr Phe
            275                 280                 285
Trp Ile Leu Gly Val Tyr Phe Glu Pro Lys Phe Leu Leu Ala Arg Lys
            290                 295                 300
Ile Leu Thr Lys Val Ile Ser Met Ala Ser Ile Ile Asp Asp Ile Tyr
305                 310                 315                 320
Asp Ala Tyr Gly Thr Ile Glu Glu Leu Glu Leu Phe Ala Thr Ala Ile
                    325                 330                 335
Glu Arg Trp Asp Leu Ser Ala Ile Asp Leu Leu Pro Glu Tyr Met Lys
            340                 345                 350
Leu Cys Tyr Cys Ala Leu Leu Asp Ala Tyr Ser Glu Phe Glu Lys Asp
            355                 360                 365
Leu Ala Ser Lys Gly Ile Leu Tyr Gly Leu Pro Phe Ala Lys Glu Ser
            370                 375                 380
Met Lys Ile Leu Val Arg Ser Tyr Ile Ile Glu Ala Arg Trp Cys Asp
385                 390                 395                 400
Gln Gln Tyr Val Pro Thr Met Glu Glu Tyr Met Arg Val Ala Leu Leu
            405                 410                 415
Ser Cys Gly Tyr Leu Leu Leu Ser Thr Ser Ser Phe Leu Gly Met Glu
            420                 425                 430
Asp Ile Val Thr Lys Glu Ala Phe Glu Trp Val Ser Gly Asn Pro Lys
            435                 440                 445
Ile Val Gln Ala Ser Ser Ile Ile Cys Arg Leu Met Asp Asp Ile Val
            450                 455                 460
Ser His Lys Phe Glu Gln Gln Arg Gly His Val Ala Ser Ala Val Glu
465                 470                 475                 480
Cys Tyr Met Lys Gln His Gly Val Ser Glu Glu Ala Val Lys Val
                    485                 490                 495
Phe Arg Glu Lys Val Gly Asn Ala Trp Lys Asp Ile Asn Glu Glu Leu
            500                 505                 510
Met Arg Pro Pro Val Val Pro Met Pro Leu Leu Glu Arg Val Leu Asn
            515                 520                 525
```

```
Leu Ala Arg Leu Met Asp Val Leu Tyr Gln Asn Asn Asp Ser Tyr Thr
    530                 535                 540

Asn Pro His Leu Met Lys Asp His Val Ala Ala Leu Leu Lys Asp Pro
545                 550                 555                 560

Val Phe Phe Glu Asp
            565
```

<210> SEQ ID NO 108
<211> LENGTH: 1746
<212> TYPE: DNA
<213> ORGANISM: Artificial Sequence
<220> FEATURE:
<223> OTHER INFORMATION: DNA having modified codons, which encodes linalool synthase gene derived from Citrus unshiu (Cu2LINS)

<400> SEQUENCE: 108

| | | |
|---|---|---|
| atggcgttta gcagcaagga catcagtagc gacagcagtc acattcattt tatcccgaag | 60 |
| cacatcagta aggttggtaa tcgtaacctg aataatatta atagcctgct gccgaacaac | 120 |
| aaaaagggca gcatcaacga taacatcggc gtcagcgccc gcctgaaacg ctttacctac | 180 |
| cccagcgaac atagcagcaa ctttaacgat gacatccata tcaagcacgc caaaaagctg | 240 |
| gaagttatta acacattct gatcaagctg ggcgatgacg atagctttga aggcctggcg | 300 |
| atgattgacg ttgtgcagcg cctgggcatc gactactact ttcaggatga aattgaactg | 360 |
| atcctgcgtc gccagtacag cattttcttt acggacggcg atcgctacaa tgatctgcag | 420 |
| gaagttgcgc tgcgttttcg tctgctgcgt cagcagggct actacgtgag cgcggacgtc | 480 |
| tttaatcgct ttcgcaacaa agaaggcgaa tttaagcaga acatcagcga agatatcaat | 540 |
| ggcctgatga cctgtacga agcgagccag ctgagcatcg gcggcgaaga tggcctggat | 600 |
| gaagccggcc attttagcgc cacccacctg gcgaattacg atctggcggg cgtcgttgaa | 660 |
| catctgctgc tgtacccgta ccgcaaaagc ctgagccccg ccaagaattt ctttcacggc | 720 |
| aattttcagg gcagcgaata catttggatc ctggacctgc aggaactggc gaatatggat | 780 |
| tttaaactgg tgcagagcct gcatcagaag gaaattgtcc agatcagcag ttggtggcgc | 840 |
| gaactgggcc tggcgaaaaa gctggaattt gcccgcgaac agccggttaa atggtacgtt | 900 |
| tggagcatgg cctgttttac cgacccgaat ctgagctggc agcgcattga actgacgaaa | 960 |
| cccatcagct ttgtttacat catcgacgat atctttacg tgtgtggtgc cctggatgcc | 1020 |
| ctgaccctgt ttacggaacc gattaatcgc tgggatctgg cgacatcga tcagctgccc | 1080 |
| gaatacatga agatttgttt taaggcgctg aacgatatca ccaatgaaat cagcaaacag | 1140 |
| ggcgtgcagc gcagcatggg cattaccctg tgtacgccgc tgcgtaaggg cgttggcgaa | 1200 |
| gtgctgtgca atgcctttct gatcgaagcc aaatggtttg cgagcggcca tctgcccaag | 1260 |
| gcggaagaat acctggaaaa tggcattgtc agcagcggcg ttcatctggt gctggtccac | 1320 |
| atttctcttc tgctgggcca cggcatcacc aatgaaacgg tccagctgat tgatagcaat | 1380 |
| ccgcccatcg tcagcagcgt tgcgacgatt ctgcgcatct gggacgatct gggcagcgcc | 1440 |
| aaagacgaaa tcagggcgg caaggatggc agctacattt actactacat gatggaacac | 1500 |
| cgcgacctga ccgccgaaga tgcgcataaa cacgcgatgg acaagatcag cgatgcctgg | 1560 |
| aaacgcctga ataaggaatg tctgagcccg aatcccttta gcgccagctt tacgcgcgcg | 1620 |
| agctttaatt gcgcccgcat ggtgccgctg atgtacagct acgacgatag ccagcgcctg | 1680 |
| cccagcctgg aagaatacat taagagcagt ctgtttgaca atctgcctac gcagggtgtt | 1740 |

-continued

```
tactaa                                                                    1746
```

<210> SEQ ID NO 109
<211> LENGTH: 581
<212> TYPE: PRT
<213> ORGANISM: Citrus unshiu

<400> SEQUENCE: 109

| Met | Ala | Phe | Ser | Ser | Lys | Asp | Ile | Ser | Asp | Ser | Ser | His | Ile | His |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Ile | Pro | Lys | His | Ile | Ser | Lys | Val | Gly | Asn | Arg | Asn | Leu | Asn | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Ile Asn Ser Leu Leu Pro Asn Asn Lys Lys Gly Ser Ile Asn Asp Asn
            35                  40                  45

Ile Gly Val Ser Ala Arg Leu Lys Arg Phe Thr Tyr Pro Ser Glu His
 50                  55                  60

Ser Ser Asn Phe Asn Asp Asp Ile His Ile Lys His Ala Lys Lys Leu
65                  70                  75                  80

Glu Val Ile Lys His Ile Leu Ile Lys Leu Gly Asp Asp Asp Ser Phe
                85                  90                  95

Glu Gly Leu Ala Met Ile Asp Val Val Gln Arg Leu Gly Ile Asp Tyr
            100                 105                 110

Tyr Phe Gln Asp Glu Ile Glu Leu Ile Leu Arg Arg Gln Tyr Ser Ile
        115                 120                 125

Phe Phe Thr Asp Gly Asp Arg Tyr Asn Asp Leu Gln Glu Val Ala Leu
    130                 135                 140

Arg Phe Arg Leu Leu Arg Gln Gln Gly Tyr Tyr Val Ser Ala Asp Val
145                 150                 155                 160

Phe Asn Arg Phe Arg Asn Lys Glu Gly Glu Phe Lys Gln Asn Ile Ser
                165                 170                 175

Glu Asp Ile Asn Gly Leu Met Ser Leu Tyr Glu Ala Ser Gln Leu Ser
            180                 185                 190

Ile Gly Gly Glu Asp Gly Leu Asp Glu Ala Gly His Phe Ser Ala Thr
        195                 200                 205

His Leu Ala Asn Tyr Asp Leu Ala Gly Val Val Glu His Leu Leu Leu
    210                 215                 220

Tyr Pro Tyr Arg Lys Ser Leu Ser Pro Ala Lys Asn Phe His Gly
225                 230                 235                 240

Asn Phe Gln Gly Ser Glu Tyr Ile Trp Ile Leu Asp Leu Gln Glu Leu
                245                 250                 255

Ala Asn Met Asp Phe Lys Leu Val Gln Ser Leu His Gln Lys Glu Ile
            260                 265                 270

Val Gln Ile Ser Ser Trp Trp Arg Glu Leu Gly Leu Ala Lys Lys Leu
        275                 280                 285

Glu Phe Ala Arg Glu Gln Pro Val Lys Trp Tyr Val Trp Ser Met Ala
    290                 295                 300

Cys Phe Thr Asp Pro Asn Leu Ser Trp Gln Arg Ile Glu Leu Thr Lys
305                 310                 315                 320

Pro Ile Ser Phe Val Tyr Ile Ile Asp Asp Ile Phe Tyr Val Cys Gly
                325                 330                 335

Ala Leu Asp Ala Leu Thr Leu Phe Thr Glu Pro Ile Asn Arg Trp Asp
            340                 345                 350

Leu Gly Asp Ile Asp Gln Leu Pro Glu Tyr Met Lys Ile Cys Phe Lys
        355                 360                 365

```
Ala Leu Asn Asp Ile Thr Asn Glu Ile Ser Lys Gln Gly Val Gln Arg
        370                 375                 380

Ser Met Gly Ile Thr Leu Cys Thr Pro Leu Arg Lys Gly Val Gly Glu
385                 390                 395                 400

Val Leu Cys Asn Ala Phe Leu Ile Glu Ala Lys Trp Phe Ala Ser Gly
                405                 410                 415

His Leu Pro Lys Ala Glu Glu Tyr Leu Glu Asn Gly Ile Val Ser Ser
            420                 425                 430

Gly Val His Leu Val Leu Val His Ile Phe Phe Leu Leu Gly His Gly
        435                 440                 445

Ile Thr Asn Glu Thr Val Gln Leu Ile Asp Ser Asn Pro Pro Ile Val
450                 455                 460

Ser Ser Val Ala Thr Ile Leu Arg Ile Trp Asp Asp Leu Gly Ser Ala
465                 470                 475                 480

Lys Asp Glu Asn Gln Gly Lys Asp Gly Ser Tyr Ile Tyr Tyr Tyr
                485                 490                 495

Met Met Glu His Arg Asp Leu Thr Ala Glu Ala His Lys His Ala
            500                 505                 510

Met Asp Lys Ile Ser Asp Ala Trp Lys Arg Leu Asn Lys Glu Cys Leu
        515                 520                 525

Ser Pro Asn Pro Phe Ser Ala Ser Phe Thr Arg Ala Ser Phe Asn Cys
530                 535                 540

Ala Arg Met Val Pro Leu Met Tyr Ser Tyr Asp Asp Ser Gln Arg Leu
545                 550                 555                 560

Pro Ser Leu Glu Glu Tyr Ile Lys Ser Ser Leu Phe Asp Asn Leu Pro
                565                 570                 575

Thr Gln Gly Val Tyr
            580

<210> SEQ ID NO 110
<211> LENGTH: 1767
<212> TYPE: DNA
<213> ORGANISM: Artificial Sequence
<220> FEATURE:
<223> OTHER INFORMATION: DNA having modified codons, which encodes
      linalool synthase gene derived from Citrus unshiu (Cu3LINS)

<400> SEQUENCE: 110
atggcgttta gtagcagtag ccgtgcgaag ctgagtgcga cgagtcacat tagcaaagcc    60
cctgataaga ttagcaagac gagccgtccg agcctgattg aatttacgcc gagccccacc   120
atttaccaga aaggctgtat cacgagcgat aataccgtcg cgagcccgcc cctgaagcat   180
tttacgcaca ccacgcgcca tcccagcttt tcgatcacg acattcaggt cgaacatagc   240
cgcaagctga aggaatttaa gcatatcttt agcctggttg cgggcaatag ctttgaaggc   300
ctggtgatga ttgatgccgt ccagcgcctg cgcatcgaat acctgtttaa ggacgaaatt   360
gaagaaatcc tgcagcgcca gtacattatc agcagcacgt gtggtggcca tctgcacgat   420
ctgcaggaag ttgcgctgcg ctttcgcctg ctgcgccagg aaggctacta cgtgccggcc   480
gatatgttta caactttcg catcaaagaa ggccgcttta gccgcattaa tgtcagcgaa   540
gacatcggca ccctgatgga agtttacgaa gcgagccagc tgagcatcgc cggcgaagaa   600
ggcctggatg aagccggcca ctttagcgcg aagatgctga tgaatgcat gacgcatctg   660 gaccattacc acgccctggc gatcggcaat ccctgcgcc atccgtacca caaaagcctg   720
ccccgcttta tggccaagga tgtgtttctg agcaattttc agggcgaacg ccgcctgcac   780
```

```
gtgctgaagg aaatcgcgaa aaaggacttt aacatggtcc aggccctgca tcagaaggaa     840
atcgttcagg tgacgaaatg gtggaaggat ctgggcctga ccaaaaagct gccgtttgcg     900
cgcgaccagc ccctgaaatg gtacatttgg agcatggcct gtctgacgga tccgagcctg     960
agcgaacagc gcgtggaact gaccaagccc attagcctga tctacattat cgatgacatc    1020
tttgatgtct acggcacgct ggacgaactg attctgttta ccgaaacgat cacgcgttgg    1080
gacctggcgg ccatgggtca gctgccggaa tacatgaaaa tttgttttaa ggcgctggat    1140
gacattacga atgaaatcag ctgcaaagtt tacaaaaagc acggctacaa tccggtgcag    1200
agcctgcgca atgcgtggac cagcctgtgc aaagcctttc tggttgaagc caagtggttt    1260
gcgagcggcc atatgcccga agccgaagaa tacctgcgca atggcatcga aagcagcggc    1320
gtccatgttg ccctggcgca cttttctctt ctgctgggcc acggcattac gaaagaaacc    1380
gtggaactga tcgatggcaa tcccgcgatt atcagcagca cggccaccat tctgcgtctg    1440
tgggatgacc tgggtagcgc caaagatgaa atcaggaag gcaaggacgg cagctacatc     1500
cactactaca tgaaagaaca tcgctacagc gccgcgaag aagcccagaa agcgcgatt      1560 aataagatca gcgacgcctg gaaacgcctg aataaggaat gtctgtgccc gaatcccttt    1620
agcgccagct ttacgcgtgc cagcctgaat ctggcccgta tggttccgct gatgtacagc    1680
tacgatgaca atcagcgcct gcccagcctg gaacattaca ttaagagcct gctgtttgag    1740
agcgtgccta cggagggcgt ctactaa                                        1767

<210> SEQ ID NO 111
<211> LENGTH: 588
<212> TYPE: PRT
<213> ORGANISM: Citrus unshiu

<400> SEQUENCE: 111

Met Ala Phe Ser Ser Ser Arg Ala Lys Leu Ser Ala Thr Ser His
1               5                   10                  15

Ile Ser Lys Ala Pro Asp Lys Ile Ser Lys Thr Ser Arg Pro Ser Leu
                20                  25                  30

Ile Glu Phe Thr Pro Ser Pro Thr Ile Tyr Gln Lys Gly Cys Ile Thr
            35                  40                  45

Ser Asp Asn Thr Val Ala Ser Pro Leu Lys His Phe Thr His Thr
    50                  55                  60

Thr Arg His Pro Ser Phe Phe Asp His Asp Ile Gln Val Glu His Ser
65                  70                  75                  80

Arg Lys Leu Lys Glu Phe Lys His Ile Phe Ser Leu Val Gly Gly Asn
                85                  90                  95

Ser Phe Glu Gly Leu Val Met Ile Asp Ala Val Gln Arg Leu Arg Ile
            100                 105                 110

Glu Tyr Leu Phe Lys Asp Glu Ile Glu Ile Leu Gln Arg Gln Tyr
        115                 120                 125

Ile Ile Ser Ser Thr Cys Gly Gly His Leu His Asp Leu Gln Glu Val
    130                 135                 140

Ala Leu Arg Phe Arg Leu Leu Arg Gln Glu Gly Tyr Tyr Val Pro Ala
145                 150                 155                 160

Asp Met Phe Asn Asn Phe Arg Ile Lys Glu Gly Arg Phe Ser Arg Ile
                165                 170                 175

Asn Val Ser Glu Asp Ile Gly Thr Leu Met Glu Val Tyr Glu Ala Ser
            180                 185                 190

Gln Leu Ser Ile Ala Gly Glu Glu Gly Leu Asp Glu Ala Gly His Phe
```

```
              195                 200                 205
Ser Ala Lys Met Leu Asn Glu Cys Met Thr His Leu Asp His Tyr His
210                 215                 220

Ala Leu Ala Ile Gly Asn Thr Leu Arg His Pro Tyr His Lys Ser Leu
225                 230                 235                 240

Pro Arg Phe Met Ala Lys Asp Val Phe Leu Ser Asn Phe Gln Gly Glu
                245                 250                 255

Arg Arg Leu His Val Leu Lys Glu Ile Ala Lys Asp Phe Asn Met
            260                 265                 270

Val Gln Ala Leu His Gln Lys Glu Ile Val Gln Val Thr Lys Trp Trp
        275                 280                 285

Lys Asp Leu Gly Leu Thr Lys Lys Leu Pro Phe Ala Arg Asp Gln Pro
290                 295                 300

Leu Lys Trp Tyr Ile Trp Ser Met Ala Cys Leu Thr Asp Pro Ser Leu
305                 310                 315                 320

Ser Glu Gln Arg Val Glu Leu Thr Lys Pro Ile Ser Leu Ile Tyr Ile
                325                 330                 335

Ile Asp Asp Ile Phe Asp Val Tyr Gly Thr Leu Asp Glu Leu Ile Leu
            340                 345                 350

Phe Thr Glu Thr Ile Thr Arg Trp Asp Leu Ala Ala Met Gly Gln Leu
        355                 360                 365

Pro Glu Tyr Met Lys Ile Cys Phe Lys Ala Leu Asp Asp Ile Thr Asn
370                 375                 380

Glu Ile Ser Cys Lys Val Tyr Lys Lys His Gly Tyr Asn Pro Val Gln
385                 390                 395                 400

Ser Leu Arg Asn Ala Trp Thr Ser Leu Cys Lys Ala Phe Leu Val Glu
                405                 410                 415

Ala Lys Trp Phe Ala Ser Gly His Met Pro Glu Ala Glu Glu Tyr Leu
            420                 425                 430

Arg Asn Gly Ile Glu Ser Ser Gly Val His Val Ala Leu Ala His Phe
        435                 440                 445

Phe Phe Leu Leu Gly His Gly Ile Thr Lys Glu Thr Val Glu Leu Ile
450                 455                 460

Asp Gly Asn Pro Ala Ile Ile Ser Ser Thr Ala Thr Ile Leu Arg Leu
465                 470                 475                 480

Trp Asp Asp Leu Gly Ser Ala Lys Asp Glu Asn Gln Glu Gly Lys Asp
                485                 490                 495

Gly Ser Tyr Ile His Tyr Tyr Met Lys Glu His Arg Tyr Ser Ala Ala
            500                 505                 510

Glu Glu Ala Gln Lys Ser Ala Ile Asn Lys Ile Ser Asp Ala Trp Lys
        515                 520                 525

Arg Leu Asn Lys Glu Cys Leu Cys Pro Asn Pro Phe Ser Ala Ser Phe
530                 535                 540

Thr Arg Ala Ser Leu Asn Leu Ala Arg Met Val Pro Leu Met Tyr Ser
545                 550                 555                 560

Tyr Asp Asp Asn Gln Arg Leu Pro Ser Leu Glu His Tyr Ile Lys Ser
                565                 570                 575

Leu Leu Phe Glu Ser Val Pro Thr Glu Gly Val Tyr
            580                 585

<210> SEQ ID NO 112
<211> LENGTH: 1704
<212> TYPE: DNA
<213> ORGANISM: Artificial Sequence
```

<220> FEATURE:
<223> OTHER INFORMATION: DNA having modified codons, which encodes linalool synthase gene derived from Malus domestica (MdLINS)

<400> SEQUENCE: 112

```
atggagttta gcattagcca gagtagtttt gcgaccagta gcagcacgcc cgccgccct      60
gagcacctga gcagccagaa gtggagtatt cccgaagatc atagcctgct gagcaccccg     120
ctgaaaccgc tgaatagcaa aaccaagtac acgagcagca aggacggcat catttgtttt     180
cagaacgaac agaagctgga tgacctgcgc catgcgctga ttaaggttgg cggcgaagcc     240
gtggaaagcc tggatatgat cgacgcggtt cagcgcctgg gcctggatta ccactttgaa     300
gaagaaattg accagatcct gcagaaacag catattatca gcagcacgac cgcccatggt     360
gcccatcacc ccaccgatct gcatgaagtt gccctgcgtt tcgtctgct gcgtcagcac      420
ggctactttg tgagcgatga cgtctttaac aactttaaga accgcgaagg caactttaat     480
cagatgctgc gcgaagacat taagggcctg atgagcctgt acgaagcgag ccagctgagc     540
atcgaaggcg aagttgtgct ggaagaagcc ggcaaattta gcggccattt tctgaatagc     600
agcctgagcc acctggatca tcaccaggcg cgcgtcgttg caataccct gcgcaatccc      660
catcacaaaa gcctggcccc gtttatggcg aagaatttct tgtcagcag ctttcagggc      720
acgaataatc gctggctgaa tattctgcag accgtggcga aacggatct gaatatggtc      780
cagagcctgc atcagaagga agtcgcccag gttagcaaat ggtggaagga actgggcctg     840
tgtaaagaac tgaagtttgc gcgcgatcag cccattaaat ggtacatctg gagcatggcc     900
tgcctgacca tcccaatct gagcgacgaa cgcatcgaac tgacgaagcc gattagcttt     960
atctacctga ttgatgacat ctttgatgtg tacggcaccc tggacgaact gaccctgttt    1020
acggaagtgg tcaatcgctg ggaaattggc agcatcgaac cctgccgga ttacatgaaa    1080
atttgtttta aggcgctgta cgacatgacc aatgaaatca gctgcaaagt ctaccagaag    1140
catggctgga atcccctgca cagcctgaaa agacgtggg ccagcctgtg caatgcgttt     1200
ctggttgaag ccaaatggtt taagagcggc catctgccga tggccgaaga atacctgaaa    1260
aatggcatta tcagcagcgg cgtcaatgtt gtgatggttc acattttctt tctgctgggc    1320
gaaggcatca ccaatcagag cgtggaattt ctgaatggca ccccggcgat tatcagcagc    1380
accgcggcca ttctgcgcct gtgggatgac ctgggtagcg ccaaggatga aaatcaggac    1440
ggcgatgacg gcagctacgt caaactgtac ctgaatgaac atcagggcaa gaccatggaa    1500
gaagcccagg aacacgttac gaatatgatc agcgaagaat ggaaaaagct gaataaagaa    1560
ctggtgagcc ccaatcccct gcccgcggcc tttaccaagg ccagcctgaa tctggcccgc    1620
atggttccgc tgatgtacag ctacgacgat aatcagtgtc tgccgagtct ggatgagtac    1680
atgaagagta tgctgcacgc ctaa                                          1704
```

<210> SEQ ID NO 113
<211> LENGTH: 567
<212> TYPE: PRT
<213> ORGANISM: Malus domestica

<400> SEQUENCE: 113

```
Met Glu Phe Ser Ile Ser Gln Ser Ser Phe Ala Thr Ser Ser Ser Thr
  1               5                  10                  15

Pro Ala Ala Pro Glu His Leu Ser Ser Gln Lys Trp Ser Ile Pro Glu
             20                  25                  30

Asp His Ser Leu Leu Ser Thr Pro Leu Lys Pro Leu Asn Ser Lys Thr
```

```
            35                  40                  45
Lys Tyr Thr Ser Ser Lys Asp Gly Ile Ile Cys Phe Gln Asn Glu Gln
 50                  55                  60

Lys Leu Asp Asp Leu Arg His Ala Leu Ile Lys Val Gly Gly Glu Ala
 65                  70                  75                  80

Val Glu Ser Leu Asp Met Ile Asp Ala Val Gln Arg Leu Gly Leu Asp
                 85                  90                  95

Tyr His Phe Glu Glu Glu Ile Asp Gln Ile Leu Gln Lys Gln His Ile
                100                 105                 110

Ile Ser Ser Thr Thr Ala His Gly Ala His His Pro Thr Asp Leu His
            115                 120                 125

Glu Val Ala Leu Arg Phe Arg Leu Leu Arg Gln His Gly Tyr Phe Val
            130                 135                 140

Ser Asp Asp Val Phe Asn Asn Phe Lys Asn Arg Glu Gly Asn Phe Asn
145                 150                 155                 160

Gln Met Leu Arg Glu Asp Ile Lys Gly Leu Met Ser Leu Tyr Glu Ala
                165                 170                 175

Ser Gln Leu Ser Ile Glu Gly Glu Val Val Leu Glu Glu Ala Gly Lys
                180                 185                 190

Phe Ser Gly His Phe Leu Asn Ser Ser Leu Ser His Leu Asp His His
            195                 200                 205

Gln Ala Arg Val Val Gly Asn Thr Leu Arg Asn Pro His His Lys Ser
210                 215                 220

Leu Ala Pro Phe Met Ala Lys Asn Phe Phe Val Ser Ser Phe Gln Gly
225                 230                 235                 240

Thr Asn Asn Arg Trp Leu Asn Ile Leu Gln Thr Val Ala Lys Thr Asp
                245                 250                 255

Leu Asn Met Val Gln Ser Leu His Gln Lys Glu Val Ala Gln Val Ser
                260                 265                 270

Lys Trp Trp Lys Glu Leu Gly Leu Cys Lys Glu Leu Lys Phe Ala Arg
            275                 280                 285

Asp Gln Pro Ile Lys Trp Tyr Ile Trp Ser Met Ala Cys Leu Thr Asn
290                 295                 300

Pro Asn Leu Ser Asp Glu Arg Ile Glu Leu Thr Lys Pro Ile Ser Phe
305                 310                 315                 320

Ile Tyr Leu Ile Asp Asp Ile Phe Asp Val Tyr Gly Thr Leu Asp Glu
                325                 330                 335

Leu Thr Leu Phe Thr Glu Val Val Asn Arg Trp Glu Ile Gly Ser Ile
                340                 345                 350

Glu His Leu Pro Asp Tyr Met Lys Ile Cys Phe Lys Ala Leu Tyr Asp
            355                 360                 365

Met Thr Asn Glu Ile Ser Cys Lys Val Tyr Gln Lys His Gly Trp Asn
            370                 375                 380

Pro Leu His Ser Leu Lys Lys Thr Trp Ala Ser Leu Cys Asn Ala Phe
385                 390                 395                 400

Leu Val Glu Ala Lys Trp Phe Lys Ser Gly His Leu Pro Met Ala Glu
                405                 410                 415

Glu Tyr Leu Lys Asn Gly Ile Ile Ser Ser Gly Val Asn Val Val Met
                420                 425                 430

Val His Ile Phe Phe Leu Leu Gly Glu Gly Ile Thr Asn Gln Ser Val
            435                 440                 445

Glu Phe Leu Asn Gly Thr Pro Ala Ile Ile Ser Ser Thr Ala Ala Ile
450                 455                 460
```

```
Leu Arg Leu Trp Asp Asp Leu Gly Ser Ala Lys Asp Glu Asn Gln Asp
465                 470                 475                 480

Gly Asp Asp Gly Ser Tyr Val Lys Leu Tyr Leu Asn Glu His Gln Gly
                485                 490                 495

Lys Thr Met Glu Glu Ala Gln Glu His Val Thr Asn Met Ile Ser Glu
            500                 505                 510

Glu Trp Lys Lys Leu Asn Lys Glu Leu Val Ser Pro Asn Pro Leu Pro
        515                 520                 525

Ala Ala Phe Thr Lys Ala Ser Leu Asn Leu Ala Arg Met Val Pro Leu
    530                 535                 540

Met Tyr Ser Tyr Asp Asp Asn Gln Cys Leu Pro Ser Leu Asp Glu Tyr
545                 550                 555                 560

Met Lys Ser Met Leu His Ala
                565
```

<210> SEQ ID NO 114
<211> LENGTH: 1824
<212> TYPE: DNA
<213> ORGANISM: Artificial Sequence
<220> FEATURE:
<223> OTHER INFORMATION: DNA having modified codons, which encodes linalool synthase gene derived from Perilla frutescens var. crispa (PfLINS)

<400> SEQUENCE: 114

```
atgtatagcc tgcgtattta tgtggcgatt atgaaaaagc ccagtgcgaa gcatgttgac      60
aatgtggaca agaaagcgag taagcctagc tggcgcgtta gcctgagcag cagcgcgggc     120
ctgcgtgcca gcagcagcct gcagctggat gtgaaaaagc cggcggatga tgaaatcctg     180
acggcccgcc gcagcggtaa ttaccagccc agcctgtggg actttaatta cctgcagagc     240
ctgaatacca cgcagtacaa agaagtgcgc catctgaagc gcgaagcgga actgattgaa     300
caggtcaaaa tgctgctgga agaagaaatg gaagccgtcc agcagctgga actggttgat     360
gacctgaaga atctgggcct gagctacttt ttcgaagatc agattaaaca gatcctgacg     420
tttatctaca cgaacataaa gtgttttcac agcaatagca ttatcgaagc ggaagaaatt     480
cgcgacctgt actttacggc cctgggtttt cgtctgctgc gtcagcatgg ctttcaggtt     540
agccaggaag tgtttgattg ctttaagaat gaagaaggca gcgactttaa agcccgtctg     600
ggtgatgaca ccaagggcct gctgcagctg tacgaagcca gctttctgct gcgcgaaggc     660
gaagatacgc tggaactggc cgccagtac gcgaccaaat ttctgcagaa aaaggtggac     720
cacgaactga tcgatgacaa taatctgctg agctggattc tgcatagcct ggaaatcccg     780
ctgcactggc gcattcagcg cctggaagcg cgctggtttc tggatcgcta cgccacgcgt     840
cgcgacatga atcagattat cctggaactg gcgaaactgg atttaatat tatccaggcc     900 acgcagcagg aagaactgaa agacctgagc cgttggtgga gagcaccctg tctggcggaa     960
aaactgccgt tgtgcgcga tcgcctggtc gaaagctact ttgggccat gcgctgtttt    1020 gaacccatc agtacggcta ccaccgcaaa gtcgccgcga agattatcac cctgatcacg    1080
agcctggatg acgtttacga tatttacggc accctggacg aactgcagct gtttacggat    1140
gcgatccagc gctgggacac cgaaagcatt agccgcctgc cctactacat gcagctgttt    1200
tacatggttc tgtacaattt tgtgagcgaa ctggcctacg atggcctgaa agaaaagggc    1260
tttattacca ttccctacct gcagcgtagc tgggcggacc tggtggaagc gtacctgaaa    1320
gaagccaagt ggtttacaa tggctacgtc cccagcatgg aagaatacct gaataatgcg    1380
```

```
tacattagca ttggtgccac cccggtcatc agccaggttt tctttaccct ggccacgagc    1440
attgataaac ccgtcatcga cagcctgtac gaataccatc gcattctgcg tctgagcggt    1500
atgctggttc gcctgcccga tgacctgggt acgagcccct ttgaaatgaa acgcggcgat    1560
gttccgaagg cgatccagct gtacatgaaa gaacgcaatg cgacggaaat cgaagcccag    1620
gaacacgttc gctttctgat tcgcgaagcc tggaaggaaa tgaataccgt taccacggcc    1680
gcggattgcc cctttaccga tgacctggtt gcggccaccc gtaatctggg tcgtgccgcg    1740
cagtttatgt acctggatgg cgacggtaac cacagtcagc tgcaccagcg tatcgcctgc    1800
ctgctgtttg aaccctatgc ctaa                                           1824
```

<210> SEQ ID NO 115
<211> LENGTH: 607
<212> TYPE: PRT
<213> ORGANISM: Perilla frutescens var.crispa

<400> SEQUENCE: 115

```
Met Tyr Ser Leu Arg Ile Tyr Val Ala Ile Met Lys Lys Pro Ser Ala
1               5                   10                  15

Lys His Val Asp Asn Val Asp Lys Lys Ala Ser Lys Pro Ser Trp Arg
            20                  25                  30

Val Ser Leu Ser Ser Ser Ala Gly Leu Arg Ala Ser Ser Ser Leu Gln
        35                  40                  45

Leu Asp Val Lys Lys Pro Ala Asp Asp Glu Ile Leu Thr Ala Arg Arg
    50                  55                  60

Ser Gly Asn Tyr Gln Pro Ser Leu Trp Asp Phe Asn Tyr Leu Gln Ser
65                  70                  75                  80

Leu Asn Thr Thr Gln Tyr Lys Glu Val Arg His Leu Lys Arg Glu Ala
                85                  90                  95

Glu Leu Ile Glu Gln Val Lys Met Leu Leu Glu Glu Met Glu Ala
            100                 105                 110

Val Gln Gln Leu Glu Leu Val Asp Asp Leu Lys Asn Leu Gly Leu Ser
        115                 120                 125

Tyr Phe Phe Glu Asp Gln Ile Lys Gln Ile Leu Thr Phe Ile Tyr Asn
    130                 135                 140

Glu His Lys Cys Phe His Ser Asn Ser Ile Ile Glu Ala Glu Ile
145                 150                 155                 160

Arg Asp Leu Tyr Phe Thr Ala Leu Gly Phe Arg Leu Leu Arg Gln His
                165                 170                 175

Gly Phe Gln Val Ser Gln Glu Val Phe Asp Cys Phe Lys Asn Glu Glu
            180                 185                 190

Gly Ser Asp Phe Lys Ala Arg Leu Gly Asp Asp Thr Lys Gly Leu Leu
        195                 200                 205

Gln Leu Tyr Glu Ala Ser Phe Leu Leu Arg Glu Gly Glu Asp Thr Leu
    210                 215                 220

Glu Leu Ala Arg Gln Tyr Ala Thr Lys Phe Leu Gln Lys Lys Val Asp
225                 230                 235                 240

His Glu Leu Ile Asp Asp Asn Asn Leu Leu Ser Trp Ile Leu His Ser
                245                 250                 255

Leu Glu Ile Pro Leu His Trp Arg Ile Gln Arg Leu Glu Ala Arg Trp
            260                 265                 270

Phe Leu Asp Arg Tyr Ala Thr Arg Arg Asp Met Asn Gln Ile Ile Leu
        275                 280                 285
```

| | | | | | | | | | | | | | | |
|---|---|---|---|---|---|---|---|---|---|---|---|---|---|---|
|Glu|Leu|Ala|Lys|Leu|Asp|Phe|Asn|Ile|Ile|Gln|Ala|Thr|Gln|Gln|Glu|
| |290| | | |295| | | |300| | | | | |

Glu Leu Lys Asp Leu Ser Arg Trp Trp Lys Ser Thr Cys Leu Ala Glu
305                 310                 315                 320

Lys Leu Pro Phe Val Arg Asp Arg Leu Val Glu Ser Tyr Phe Trp Ala
                325                 330                 335

Ile Ala Leu Phe Glu Pro His Gln Tyr Gly Tyr His Arg Lys Val Ala
                340                 345                 350

Ala Lys Ile Ile Thr Leu Ile Thr Ser Leu Asp Asp Val Tyr Asp Ile
            355                 360                 365

Tyr Gly Thr Leu Asp Glu Leu Gln Leu Phe Thr Asp Ala Ile Gln Arg
370                 375                 380

Trp Asp Thr Glu Ser Ile Ser Arg Leu Pro Tyr Tyr Met Gln Leu Phe
385                 390                 395                 400

Tyr Met Val Leu Tyr Asn Phe Val Ser Glu Leu Ala Tyr Asp Gly Leu
                405                 410                 415

Lys Glu Lys Gly Phe Ile Thr Ile Pro Tyr Leu Gln Arg Ser Trp Ala
                420                 425                 430

Asp Leu Val Glu Ala Tyr Leu Lys Glu Ala Lys Trp Phe Tyr Asn Gly
            435                 440                 445

Tyr Val Pro Ser Met Glu Glu Tyr Leu Asn Asn Ala Tyr Ile Ser Ile
450                 455                 460

Gly Ala Thr Pro Val Ile Ser Gln Val Phe Phe Thr Leu Ala Thr Ser
465                 470                 475                 480

Ile Asp Lys Pro Val Ile Asp Ser Leu Tyr Glu Tyr His Arg Ile Leu
                485                 490                 495

Arg Leu Ser Gly Met Leu Val Arg Leu Pro Asp Asp Leu Gly Thr Ser
                500                 505                 510

Pro Phe Glu Met Lys Arg Gly Asp Val Pro Lys Ala Ile Gln Leu Tyr
            515                 520                 525

Met Lys Glu Arg Asn Ala Thr Glu Ile Glu Ala Gln Glu His Val Arg
530                 535                 540

Phe Leu Ile Arg Glu Ala Trp Lys Glu Met Asn Thr Val Thr Thr Ala
545                 550                 555                 560

Ala Asp Cys Pro Phe Thr Asp Asp Leu Val Ala Ala Thr Arg Asn Leu
                565                 570                 575

Gly Arg Ala Ala Gln Phe Met Tyr Leu Asp Gly Asp Gly Asn His Ser
            580                 585                 590

Gln Leu His Gln Arg Ile Ala Cys Leu Leu Phe Glu Pro Tyr Ala
            595                 600                 605

<210> SEQ ID NO 116
<211> LENGTH: 1734
<212> TYPE: DNA
<213> ORGANISM: Artificial Sequence
<220> FEATURE:
<223> OTHER INFORMATION: DNA having modified codons, which encodes linalool synthase gene derived from Vitis vinifera (Vv1LINS)

<400> SEQUENCE: 116

```
atgggtttta gtcctgcctt ttatgcgtgt agtatccctc ccgttggtcc gaacaagttt      60
accgagctgg gtcagagcaa gtttaacaat gttgtgctgg ttccgaccgc ccagaaatgg     120
agcattgcgc atgatcacac gctggtgtac aaacccctgc gcaagcataa tcaccagagc     180
cagcatctga gctttaccga tgaattttac attaagcacg cgcagcgcct ggacgaaatc     240
```

```
cgcaatgtct ttagcgaagt tggcgaagac acgctggaag gcctgatgat gattgatgcc    300
atccagcgcc tgggcatcga ctaccatttt aaagaagaaa tcgaagccgt cctgcagcgc    360
cagtacatga aggcgagcac ccacggcgaa agcattcagg atctgtacga agttgccctg    420
cgttttcgtc tgctgcgtca ggaaggctac catgtgccgg ccgatgtctt taacaacttt    480
aagaacaagg aaggcaaatt taagcagaat ctgagcaaag acatcaaggg cctgctggcc    540
ctgtacgaag cgagccagct gagcattgaa ggcgaagata tcctggaaga agcccagcgc    600
tttagcagca ccctgctgaa tgcgggcctg aacaccctga tcatcacga agccaccgtc    660 gttggccata cgctggaaca cccgcatcac aaaagcctgc cccgctttat ggcgaaaagc    720
tttctgaagg attttcaggg ccccaatggc tggctgacgg tcctgcagga actggccaaa    780
gcggacttta atatggttca gagcattcat cagcaggaac tgctgcagat cagcaaatgg    840
tggcaggatc gcggcctggc cgaagaactg aaatttgcgc gcgaccagcc gctgaagtgg    900
cacatgtggc cgatggccgt tctgcccgac cctagcctga cgaacagcg tgtggaactg    960 accaaaccga ttagcatgat ctacatcatc gatgacatct ttgatgtgca tggcacgctg   1020
gacgaactga ccctgtttac ggaagccgtc aatcgctggg acattgccgc gtttgaaacc   1080
ctgcccaact acatgaagat ttgttttaag accctggatg aaatcacgaa cgaaatcagc   1140
aacaaggttt acaaggaaca cggctggaat ccggttgata gcctgcgcaa acgtgggtg    1200 agcctgtgca atgcgtttct ggtcgaagcc aagtggtttg cgagcggcca tgtgcccaaa   1260
gcccacgaat acctgaagaa tggcgttatt agcagcggcg tgcatgtggt cctggtccac   1320 ctgttttttcc tgctgggcca tggcatcacc cgcggcaatg ttgacctggt ggatgacttt   1380
ccgagcatta tcagcagcac cgcggccatt ctgcgtctgt gggatgacct gggtagcgcg   1440
aaagatgaaa atcaggatgg ccatgacggc agctacattg aatgttacat caaggaacac   1500
cagggcagca gcatggaaaa tgcccgccag aatgttacgt acatgattag cgatctgtgg   1560
aaacgcctga ataaggaatg cctgagccag cacccgttta gcaccagctt tacgaaaggc   1620
agcctgaata tcgcccgcat ggtgcccctg atgtacagct acgatgacaa tcagagcctg   1680
ccccatctgg aggagcacat gaagagtctg ctgtttgaag cgtttcccct gtaa          1734
```

<210> SEQ ID NO 117
<211> LENGTH: 577
<212> TYPE: PRT
<213> ORGANISM: Vitis vinifera

<400> SEQUENCE: 117

```
Met Gly Phe Ser Pro Ala Phe Tyr Ala Cys Ser Ile Pro Pro Val Gly
1               5                   10                  15

Pro Asn Lys Phe Thr Glu Leu Gly Gln Ser Lys Phe Asn Asn Val Val
            20                  25                  30

Leu Val Pro Thr Ala Gln Lys Trp Ser Ile Ala His Asp His Thr Leu
        35                  40                  45

Val Tyr Lys Pro Leu Arg Lys His Asn His Gln Ser Gln His Leu Ser
    50                  55                  60

Phe Thr Asp Glu Phe Tyr Ile Lys His Ala Gln Arg Leu Asp Glu Ile
65                  70                  75                  80

Arg Asn Val Phe Ser Glu Val Gly Glu Asp Thr Leu Glu Gly Leu Met
                85                  90                  95

Met Ile Asp Ala Ile Gln Arg Leu Gly Ile Asp Tyr His Phe Lys Glu
            100                 105                 110
```

-continued

Glu Ile Glu Ala Val Leu Gln Arg Gln Tyr Met Lys Ala Ser Thr His
        115                 120                 125
Gly Glu Ser Ile Gln Asp Leu Tyr Glu Val Ala Leu Arg Phe Arg Leu
130                 135                 140
Leu Arg Gln Glu Gly Tyr His Val Pro Ala Asp Val Phe Asn Asn Phe
145                 150                 155                 160
Lys Asn Lys Glu Gly Lys Phe Lys Gln Asn Leu Ser Lys Asp Ile Lys
                165                 170                 175
Gly Leu Leu Ala Leu Tyr Glu Ala Ser Gln Leu Ser Ile Glu Gly Glu
            180                 185                 190
Asp Ile Leu Glu Glu Ala Gln Arg Phe Ser Ser Thr Leu Leu Asn Ala
        195                 200                 205
Gly Leu Glu His Leu Asn His His Glu Ala Thr Val Val Gly His Thr
    210                 215                 220
Leu Glu His Pro His His Lys Ser Leu Pro Arg Phe Met Ala Lys Ser
225                 230                 235                 240
Phe Leu Lys Asp Phe Gln Gly Pro Asn Gly Trp Leu Thr Val Leu Gln
                245                 250                 255
Glu Leu Ala Lys Ala Asp Phe Asn Met Val Gln Ser Ile His Gln Gln
            260                 265                 270
Glu Leu Leu Gln Ile Ser Lys Trp Trp Gln Asp Arg Gly Leu Ala Glu
        275                 280                 285
Glu Leu Lys Phe Ala Arg Asp Gln Pro Leu Lys Trp His Met Trp Pro
    290                 295                 300
Met Ala Val Leu Pro Asp Pro Ser Leu Ser Glu Gln Arg Val Glu Leu
305                 310                 315                 320
Thr Lys Pro Ile Ser Met Ile Tyr Ile Ile Asp Asp Ile Phe Asp Val
                325                 330                 335
His Gly Thr Leu Asp Glu Leu Thr Leu Phe Thr Glu Ala Val Asn Arg
            340                 345                 350
Trp Asp Ile Ala Ala Phe Glu Thr Leu Pro Asn Tyr Met Lys Ile Cys
        355                 360                 365
Phe Lys Thr Leu Asp Glu Ile Thr Asn Glu Ile Ser Asn Lys Val Tyr
    370                 375                 380
Lys Glu His Gly Trp Asn Pro Val Asp Ser Leu Arg Lys Thr Trp Val
385                 390                 395                 400
Ser Leu Cys Asn Ala Phe Leu Val Glu Ala Lys Trp Phe Ala Ser Gly
                405                 410                 415
His Val Pro Lys Ala His Glu Tyr Leu Lys Asn Gly Val Ile Ser Ser
            420                 425                 430
Gly Val His Val Val Leu Val His Leu Phe Phe Leu Leu Gly His Gly
        435                 440                 445
Ile Thr Arg Gly Asn Val Asp Leu Val Asp Asp Phe Pro Ser Ile Ile
    450                 455                 460
Ser Ser Thr Ala Ala Ile Leu Arg Leu Trp Asp Asp Leu Gly Ser Ala
465                 470                 475                 480
Lys Asp Glu Asn Gln Asp Gly His Asp Gly Ser Tyr Ile Glu Cys Tyr
                485                 490                 495
Ile Lys Glu His Gln Gly Ser Ser Met Glu Asn Ala Arg Gln Asn Val
            500                 505                 510
Thr Tyr Met Ile Ser Asp Leu Trp Lys Arg Leu Asn Lys Glu Cys Leu
        515                 520                 525
Ser Gln His Pro Phe Ser Thr Ser Phe Thr Lys Gly Ser Leu Asn Ile

```
                530               535               540
Ala Arg Met Val Pro Leu Met Tyr Ser Tyr Asp Asp Asn Gln Ser Leu
545                 550               555                 560

Pro His Leu Glu Glu His Met Lys Ser Leu Leu Phe Glu Ala Phe Pro
                565               570                 575

Leu
```

<210> SEQ ID NO 118
<211> LENGTH: 1809
<212> TYPE: DNA
<213> ORGANISM: Artificial Sequence
<220> FEATURE:
<223> OTHER INFORMATION: DNA having modified codons, which encodes
      linalool synthase gene derived from Vitis vinifera (Vv2LINS)

<400> SEQUENCE: 118

```
atggaactga ccctgacgag tctgagcccg ctggcgtatg gtgccctgaa ctgccgtaag    60
aactttgcga tggcgagtcc ccgtatgcgc attaagcagg gccgcagcga actgccgaat   120
ctgacgatta ccagcaaaat cgacgaactg caggtgaccg aacgccgcag cgcgaattac   180
cacccgagca tttgggatcc caaatttatc gaaagcctga gcacgcccta caccaatgaa   240
ggctacagca atcagctgga agatctgaaa gaagaagcca agcgcgtcat taaagatgcg   300
cgcgacacga gcagccgcct ggaatttatc gacagcatgc agcgcctggg cgtggcctac   360
catctggaag aagaaattaa ggaagcgatc gatctggtcc acctggatga caccacgacc   420
gatgacctga gcaccacggc cctgcgtttt cgtctgctgc gtcagcatgg ttacccggtc   480
agcagcgaag tttttgatca gtttcgcagc aaagatggcc gctttatgga cggcattagc   540
caggatattg cgggtcctct gagcctgtac gaagccagcc atctgggcgt tgaaggcgaa   600
gatgacctgg aagaagcccg ccgctttagc accatccacc tgaagagcct ggtgggcaat   660
ctggaaagcg atctggcgga ccaggtgcag cagagcctgg aagtcccccct gcactggcgt   720 atgcctcgtc tggaagcccg caattttatt gacatctacc agcgtcgcaa taccaagaat   780
agcgccctgc tggaactggc gaaactggat acaatctggt tcagagcag ctaccagacg   840 gaactgaaag aactgacgcg ttggtggacc gacctgggct taaagaaaaa gctgagcttt   900
agccgcgatc gcctgatgga aaattacctg tggagcatgg gcattgcgcc ggaaccccat   960
tttagcaaga gccgcatcgg cctgaccaaa tttatttgta tcctgacggc cattgatgac  1020
atgtacgaca tctacggcag cccggatgaa ctgcgccgct ttaccgacgc cgtcaatcgc  1080
tgggatacga aagcgctggt tgatctgccc gactacatga agatttgtta cctggccatg  1140
tttaactttg cgaatgaaat ggcctacgat gcgctgcgcg atcatgacct gtacatcctg  1200
ccgtacctga agagccagtg gctgaatctg tgcaccagct acagcatgga agcccagtgg  1260
ttttacaatg gctacaaacc gagcattgat gaataccctga gcaatgcctg gaccagcgtt  1320
ggcggcccgg cggccatggt gcacgcctac tttctgatgg gctgtgcgac gaagggcaat  1380
ctgaataatt gcctggacaa tgcgagcaat ctgctgtact ggagcagcct gatcacgcgt  1440
ctgagcgatg acctgggtac gagcctggcg gaaattgccc gcggcgatgt cgccaagagc  1500
atccagtgtt acatgattga aaatgcatc agcgaagaac aggcgcgcga ccaggttgaa  1560
aagctgattc gctacagctg gaaaagctg aatgaagcca gcacggatag cagcctgccg  1620
aaaagcctga tcaatagcag cctgaatatg gcccgcagcg cgcagtgcat ttttcagttt  1680
ggtgatggta ttggtacgag cgttggcgtg accaaggatc gcctgacgag ctttattatc  1740
```

```
aaacccattc tgattgaacc gagcattaag ccctacctgg atggcatgaa gatgagtaac    1800
cgccgctaa                                                            1809
```

<210> SEQ ID NO 119
<211> LENGTH: 602
<212> TYPE: PRT
<213> ORGANISM: Vitis vinifera

<400> SEQUENCE: 119

```
Met Glu Leu Thr Leu Thr Ser Leu Ser Pro Leu Ala Tyr Gly Ala Leu
1               5                   10                  15

Asn Cys Arg Lys Asn Phe Ala Met Ala Ser Pro Arg Met Arg Ile Lys
            20                  25                  30

Gln Gly Arg Ser Glu Leu Pro Asn Leu Thr Ile Thr Ser Lys Ile Asp
        35                  40                  45

Glu Leu Gln Val Thr Glu Arg Arg Ser Ala Asn Tyr His Pro Ser Ile
50                  55                  60

Trp Asp Pro Lys Phe Ile Glu Ser Leu Ser Thr Pro Tyr Thr Asn Glu
65                  70                  75                  80

Gly Tyr Ser Asn Gln Leu Glu Asp Leu Lys Glu Glu Ala Lys Arg Val
                85                  90                  95

Ile Lys Asp Ala Arg Asp Thr Ser Ser Arg Leu Glu Phe Ile Asp Ser
            100                 105                 110

Met Gln Arg Leu Gly Val Ala Tyr His Leu Glu Glu Glu Ile Lys Glu
        115                 120                 125

Ala Ile Asp Leu Val His Leu Asp Asp Thr Thr Thr Asp Asp Leu Ser
130                 135                 140

Thr Thr Ala Leu Arg Phe Arg Leu Leu Arg Gln His Gly Tyr Pro Val
145                 150                 155                 160

Ser Ser Glu Val Phe Asp Gln Phe Arg Ser Lys Asp Gly Arg Phe Met
                165                 170                 175

Asp Gly Ile Ser Gln Asp Ile Ala Gly Pro Leu Ser Leu Tyr Glu Ala
            180                 185                 190

Ser His Leu Gly Val Glu Gly Glu Asp Asp Leu Glu Glu Ala Arg Arg
        195                 200                 205

Phe Ser Thr Ile His Leu Lys Ser Leu Val Gly Asn Leu Glu Ser Asp
210                 215                 220

Leu Ala Asp Gln Val Gln Gln Ser Leu Glu Val Pro Leu His Trp Arg
225                 230                 235                 240

Met Pro Arg Leu Glu Ala Arg Asn Phe Ile Asp Ile Tyr Gln Arg Arg
                245                 250                 255

Asn Thr Lys Asn Ser Ala Leu Leu Glu Leu Ala Lys Leu Asp Tyr Asn
            260                 265                 270

Leu Val Gln Ser Ser Tyr Gln Thr Glu Leu Lys Glu Leu Thr Arg Trp
        275                 280                 285

Trp Thr Asp Leu Gly Phe Lys Glu Lys Leu Ser Phe Ser Arg Asp Arg
290                 295                 300

Leu Met Glu Asn Tyr Leu Trp Ser Met Gly Ile Ala Pro Glu Pro His
305                 310                 315                 320

Phe Ser Lys Ser Arg Ile Gly Leu Thr Lys Phe Ile Cys Ile Leu Thr
                325                 330                 335

Ala Ile Asp Asp Met Tyr Asp Ile Tyr Gly Ser Pro Asp Glu Leu Arg
            340                 345                 350

Arg Phe Thr Asp Ala Val Asn Arg Trp Asp Thr Glu Ala Leu Val Asp
```

```
              355                 360                 365
Leu Pro Asp Tyr Met Lys Ile Cys Tyr Leu Ala Met Phe Asn Phe Ala
    370                 375                 380

Asn Glu Met Ala Tyr Asp Ala Leu Arg Asp His Asp Leu Tyr Ile Leu
385                 390                 395                 400

Pro Tyr Leu Lys Ser Gln Trp Leu Asn Leu Cys Thr Ser Tyr Ser Met
                405                 410                 415

Glu Ala Gln Trp Phe Tyr Asn Gly Tyr Lys Pro Ser Ile Asp Glu Tyr
            420                 425                 430

Leu Ser Asn Ala Trp Thr Ser Val Gly Gly Pro Ala Ala Met Val His
        435                 440                 445

Ala Tyr Phe Leu Met Gly Cys Ala Thr Lys Gly Asn Leu Asn Asn Cys
    450                 455                 460

Leu Asp Asn Ala Ser Asn Leu Leu Tyr Trp Ser Ser Leu Ile Thr Arg
465                 470                 475                 480

Leu Ser Asp Asp Leu Gly Thr Ser Leu Ala Glu Ile Ala Arg Gly Asp
                485                 490                 495

Val Ala Lys Ser Ile Gln Cys Tyr Met Ile Glu Lys Cys Ile Ser Glu
            500                 505                 510

Glu Gln Ala Arg Asp Gln Val Glu Lys Leu Ile Arg Tyr Ser Trp Lys
        515                 520                 525

Lys Leu Asn Glu Ala Ser Thr Asp Ser Ser Leu Pro Lys Ser Leu Ile
    530                 535                 540

Asn Ser Ser Leu Asn Met Ala Arg Ser Ala Gln Cys Ile Phe Gln Phe
545                 550                 555                 560

Gly Asp Gly Ile Gly Thr Ser Val Gly Val Thr Lys Asp Arg Leu Thr
                565                 570                 575

Ser Phe Ile Ile Lys Pro Ile Leu Ile Glu Pro Ser Ile Lys Pro Tyr
            580                 585                 590

Leu Asp Gly Met Lys Met Ser Asn Arg Arg
        595                 600

<210> SEQ ID NO 120
<211> LENGTH: 1695
<212> TYPE: DNA
<213> ORGANISM: Artificial Sequence
<220> FEATURE:
<223> OTHER INFORMATION: DNA having modified codons, which encodes
      linalool synthase gene derived from Lavandula angustifolia
      (LaLINS)

<400> SEQUENCE: 120
atgagtatca acattaacat gcccgccgcc gccgttctgc gtccgtttcg ttgtagtcag    60
ctgcacgtcg atgagacccg ccgtagtggc aattaccgcc cgagcgcctg ggacagcaat   120
tacatccaga gcctgaatag ccagtacaag gaaagaaat gtctgacgcg cctggaaggc   180
ctgattgaac aggttaaaga actgaagggc accaaaatgg aagcggtgca gcagctggaa   240
ctgatcgatg acagccagaa tctgggcctg agctactact tcaggataa gatcaagcat   300 atcctgaacc tgatctacaa cgaccacaag tactttttacg atagcgaagc cgaaggcatg   360
gacctgtact ttacggcgct gggctttcgc ctgtttcgcc agcatggctt taaggttagc   420
caggaagtgt ttgatcgctt taagaacgaa aacggcacct actttaagca cgatgacacg   480
aaaggcctgc tgcagctgta cgaagccagc tttctggttc gcgaaggcga agaaaccctg   540
gaacaggccc gcgaatttgc gacgaagagc ctgcagcgca aactggatga agacggcgat   600
```

```
ggcattgatg cgaatatcga aagctggatt cgccatagcc tggaaattcc gctgcattgg      660
cgtgcccagc gtctggaagc ccgttggttt ctggatgcct acgcccgccg ccctgatatg      720
aatcccgtca tctttgaact ggccaagctg aactttaaca tcgttcaggc cacgcagcag      780
gaagaactga aagccctgag ccgttggtgg agcagcctgg gcctggccga aaaactgccc      840
tttgtgcgcg accgcctggt cgaaagttac ttttgggcca tcccgctgtt tgaacccat       900 cagtacggct accagcgcaa ggtggcgacc aaaattatca ccctgatcac gagcctggat      960
gacgtctacg acatttacgg caccctggat gaactgcagc tgtttacgaa cctgtttgaa     1020
cgctgggata tgccagcat cggccgcctg ccggaatacc tgcagctgtt ttactttgcc      1080
attcacaatt ttgtcagcga agttgcgtac gacatcctga agaaaaggg ctttaccagc      1140 attgtgtacc tgcagcgcag ctgggtcgat ctgctgaagg gctacctgaa ggaagccaaa     1200
tggtacaata gcggctacac cccgagcctg gaagaatact ttgataatgc ctttatgacg     1260
attggtgccc ctccggtgct gagccaggcc tactttaccc tgggcagcag catggaaaaa     1320
cccattatcg aaagcatgta cgaatacgac aatatcctgc gcgttagcgg tatgctggtt     1380
cgcctgcccg atgacctggg tacgagcagc tttgaaatgg aacgcggcga tgtccccaag     1440
agcgttcagc tgtacatgaa agaaaccaat gccacggaag aagaagccgt ggaacatgtc     1500
cgctttctga atcgcgaagc ctggaaaaag atgaatacgg ccgaagcggc cggtgacagc     1560
cccctggtca gcgatgttgt tgcggttgcg gccaatctgg gtcgtgccgc gcagtttatg     1620
tactttgacg gcgatggtaa ccagagtagc ctgcagcagt ggattgtcag tatgctgttt     1680
gaaccgtatg cctaa                                                      1695

<210> SEQ ID NO 121
<211> LENGTH: 564
<212> TYPE: PRT
<213> ORGANISM: Lavandula angustifolia

<400> SEQUENCE: 121

Met Ser Ile Asn Ile Asn Met Pro Ala Ala Ala Val Leu Arg Pro Phe
1               5                   10                  15

Arg Cys Ser Gln Leu His Val Asp Glu Thr Arg Arg Ser Gly Asn Tyr
            20                  25                  30

Arg Pro Ser Ala Trp Asp Ser Asn Tyr Ile Gln Ser Leu Asn Ser Gln
        35                  40                  45

Tyr Lys Glu Lys Lys Cys Leu Thr Arg Leu Glu Gly Leu Ile Glu Gln
    50                  55                  60

Val Lys Glu Leu Lys Gly Thr Lys Met Glu Ala Val Gln Gln Leu Glu
65                  70                  75                  80

Leu Ile Asp Asp Ser Gln Asn Leu Gly Leu Ser Tyr Tyr Phe Gln Asp
                85                  90                  95

Lys Ile Lys His Ile Leu Asn Leu Ile Tyr Asn Asp His Lys Tyr Phe
            100                 105                 110

Tyr Asp Ser Glu Ala Glu Gly Met Asp Leu Tyr Phe Thr Ala Leu Gly
        115                 120                 125

Phe Arg Leu Phe Arg Gln His Gly Phe Lys Val Ser Gln Glu Val Phe
    130                 135                 140

Asp Arg Phe Lys Asn Glu Asn Gly Thr Tyr Phe Lys His Asp Asp Thr
145                 150                 155                 160

Lys Gly Leu Leu Gln Leu Tyr Glu Ala Ser Phe Leu Val Arg Glu Gly
                165                 170                 175
```

Glu Glu Thr Leu Glu Gln Ala Arg Glu Phe Ala Thr Lys Ser Leu Gln
            180                 185                 190

Arg Lys Leu Asp Glu Asp Gly Asp Gly Ile Asp Ala Asn Ile Glu Ser
        195                 200                 205

Trp Ile Arg His Ser Leu Glu Ile Pro Leu His Trp Arg Ala Gln Arg
    210                 215                 220

Leu Glu Ala Arg Trp Phe Leu Asp Ala Tyr Ala Arg Arg Pro Asp Met
225                 230                 235                 240

Asn Pro Val Ile Phe Glu Leu Ala Lys Leu Asn Phe Asn Ile Val Gln
                245                 250                 255

Ala Thr Gln Gln Glu Glu Leu Lys Ala Leu Ser Arg Trp Trp Ser Ser
            260                 265                 270

Leu Gly Leu Ala Glu Lys Leu Pro Phe Val Arg Asp Arg Leu Val Glu
        275                 280                 285

Ser Tyr Phe Trp Ala Ile Pro Leu Phe Glu Pro His Gln Tyr Gly Tyr
    290                 295                 300

Gln Arg Lys Val Ala Thr Lys Ile Ile Thr Leu Ile Thr Ser Leu Asp
305                 310                 315                 320

Asp Val Tyr Asp Ile Tyr Gly Thr Leu Asp Glu Leu Gln Leu Phe Thr
                325                 330                 335

Asn Leu Phe Glu Arg Trp Asp Asn Ala Ser Ile Gly Arg Leu Pro Glu
            340                 345                 350

Tyr Leu Gln Leu Phe Tyr Phe Ala Ile His Asn Phe Val Ser Glu Val
        355                 360                 365

Ala Tyr Asp Ile Leu Lys Glu Lys Gly Phe Thr Ser Ile Val Tyr Leu
    370                 375                 380

Gln Arg Ser Trp Val Asp Leu Leu Lys Gly Tyr Leu Lys Glu Ala Lys
385                 390                 395                 400

Trp Tyr Asn Ser Gly Tyr Thr Pro Ser Leu Glu Glu Tyr Phe Asp Asn
                405                 410                 415

Ala Phe Met Thr Ile Gly Ala Pro Pro Val Leu Ser Gln Ala Tyr Phe
            420                 425                 430

Thr Leu Gly Ser Ser Met Glu Lys Pro Ile Ile Glu Ser Met Tyr Glu
        435                 440                 445

Tyr Asp Asn Ile Leu Arg Val Ser Gly Met Leu Val Arg Leu Pro Asp
    450                 455                 460

Asp Leu Gly Thr Ser Ser Phe Glu Met Glu Arg Gly Asp Val Pro Lys
465                 470                 475                 480

Ser Val Gln Leu Tyr Met Lys Glu Thr Asn Ala Thr Glu Glu Glu Ala
                485                 490                 495

Val Glu His Val Arg Phe Leu Asn Arg Glu Ala Trp Lys Lys Met Asn
            500                 505                 510

Thr Ala Glu Ala Ala Gly Asp Ser Pro Leu Val Ser Asp Val Val Ala
        515                 520                 525

Val Ala Ala Asn Leu Gly Arg Ala Ala Gln Phe Met Tyr Phe Asp Gly
    530                 535                 540

Asp Gly Asn Gln Ser Ser Leu Gln Gln Trp Ile Val Ser Met Leu Phe
545                 550                 555                 560

Glu Pro Tyr Ala

<210> SEQ ID NO 122
<211> LENGTH: 1821
<212> TYPE: DNA
<213> ORGANISM: Artificial Sequence
<220> FEATURE:
<223> OTHER INFORMATION: DNA having modified codons, which encodes linalool synthase gene derived from Mentha citrata (McLINS)

<400> SEQUENCE: 122

```
atgtgtacca tcattagcgt caatcatcat catgtcgcca tcctgagcaa gccgaaggtc      60
aagctgtttc ataccaagaa taagcgcagc gccagcatca atctgccgtg gagcctgagc     120
cctagcagca gcgcggccag ccgcccgatt agctgtagca tcagcagcaa actgtacacc     180
atcagcagcg cccaggaaga aacgcgccgc agcggcaatt accatcccag cgtttgggat     240
tttgactttta ttcagagcct ggataccgac cactacaagg aagaaaaaca gctggaacgc     300
gaagaagaac tgatcatgga agtgaaaaag ctgctgggcg cgaagatgga agccacgaaa     360
cagctggaac tgattgatga cctgcagaat ctgggcctga gctacttttt ccgcgacgaa     420
atcaagaaca tcctgaacag catctacaag atctttcaga caacaatag caccaaggtt     480
ggcgatctgc attttacgag cctgggtttt cgtctgctgc gtcagcacgg ctttaatgtt     540
agccagggcg tgtttgattg ctttaaaaat gaacatggca gcgactttga aaagaccctg     600
atcggcgaag atacgaaagg cgtgctgcag ctgtacgaag cgagctttct gctgcgcgaa     660
ggcgaagata ccctggaagt cgcccgcaaa tttagcacgg aatttctgga gaaaaaactg     720
aaggcgggca ttgatggcga caatctgagc agcagcattg ccatagcct ggaaatcccg     780
ctgcactggc gcattcagcg cctggaagaa cgctggtttc tggatgccta cagccgtcgc     840
aaggacatga atcccattat ctttgaactg gcgaaactgg actttaatat tatccaggcc     900
acccagcagg aagaactgaa ggatctgagc cgttggtgga tgacagcag cctgccgcag     960
aaactgccct tgtccgcga tcgcctggtt gaaagctact actgggcgct gggcctgttt    1020
gaagcccata gtttggcta cgaacgcaag acggccgcga aaattatcac cctgatcacg    1080
gcgctggatg acgtgtacga tatttacggc accctggacg aactgcagct gtttacgcac    1140
gtcattcgcc gctgggacac ggaaagcgcc acccagctgc cgtactacct gcagctgttt    1200
tactttgtcc tgtacaattt tgtcagcgaa gttgcgtacc atattctgaa agaagaaggc    1260
tttattagca tccccttcct gcaccgcgcg tgggtggatc tggtcgaagg ctacctgcag    1320
gaagccaagt ggtactacac caaatacacc ccgacgatgg aagaatacct gaattacgcc    1380
agcattacca ttggtgcccc ggccgttatt agccagatct actttatgct ggcgaaaagc    1440
aaggaaaaac cggtgatcga aagcttttac gaatacgacg aaattattcg tctgagcggt    1500
atgctggttc gcctgcccga tgacctgggt accctgccct ttgaaatgaa gcgcggcgat    1560
gttgccaaaa gcattcagat ctacatgaag gaacagaatg cgacgcgcga agaagccgaa    1620
gaacacgtgc gctttatgat cgcgaagcg tggaaagaaa tgaataccac gatggccgcg    1680
aatagcgatc tgcgcggcga cgttgtgatg gcggccgcca atctgggtcg tgatgcccag    1740
tttatgtacc tggatggcga cggtaatcat agtcagctgc agcaccgcat cgccaatctg    1800
ctgtttaagc cctacgtcta a                                              1821
```

<210> SEQ ID NO 123
<211> LENGTH: 606
<212> TYPE: PRT
<213> ORGANISM: Mentha citrata

<400> SEQUENCE: 123

```
Met Cys Thr Ile Ile Ser Val Asn His His Val Ala Ile Leu Ser
1               5                   10                  15
```

```
Lys Pro Lys Val Lys Leu Phe His Thr Lys Asn Lys Arg Ser Ala Ser
                20                  25                  30

Ile Asn Leu Pro Trp Ser Leu Ser Pro Ser Ser Ala Ala Ser Arg
        35                  40                  45

Pro Ile Ser Cys Ser Ile Ser Ser Lys Leu Tyr Thr Ile Ser Ser Ala
    50                  55                  60

Gln Glu Glu Thr Arg Arg Ser Gly Asn Tyr His Pro Ser Val Trp Asp
65                  70                  75                  80

Phe Asp Phe Ile Gln Ser Leu Asp Thr Asp His Tyr Lys Glu Glu Lys
                85                  90                  95

Gln Leu Glu Arg Glu Glu Glu Leu Ile Met Glu Val Lys Lys Leu Leu
            100                 105                 110

Gly Ala Lys Met Glu Ala Thr Lys Gln Leu Glu Leu Ile Asp Asp Leu
            115                 120                 125

Gln Asn Leu Gly Leu Ser Tyr Phe Phe Arg Asp Glu Ile Lys Asn Ile
130                 135                 140

Leu Asn Ser Ile Tyr Lys Ile Phe Gln Asn Asn Asn Ser Thr Lys Val
145                 150                 155                 160

Gly Asp Leu His Phe Thr Ser Leu Gly Phe Arg Leu Leu Arg Gln His
                165                 170                 175

Gly Phe Asn Val Ser Gln Gly Val Phe Asp Cys Phe Lys Asn Glu His
            180                 185                 190

Gly Ser Asp Phe Glu Lys Thr Leu Ile Gly Glu Asp Thr Lys Gly Val
            195                 200                 205

Leu Gln Leu Tyr Glu Ala Ser Phe Leu Leu Arg Glu Gly Glu Asp Thr
210                 215                 220

Leu Glu Val Ala Arg Lys Phe Ser Thr Glu Phe Leu Glu Glu Lys Leu
225                 230                 235                 240

Lys Ala Gly Ile Asp Gly Asp Asn Leu Ser Ser Ser Ile Gly His Ser
                245                 250                 255

Leu Glu Ile Pro Leu His Trp Arg Ile Gln Arg Leu Glu Glu Arg Trp
            260                 265                 270

Phe Leu Asp Ala Tyr Ser Arg Arg Lys Asp Met Asn Pro Ile Ile Phe
            275                 280                 285

Glu Leu Ala Lys Leu Asp Phe Asn Ile Ile Gln Ala Thr Gln Gln Glu
290                 295                 300

Glu Leu Lys Asp Leu Ser Arg Trp Trp Asn Asp Ser Ser Leu Pro Gln
305                 310                 315                 320

Lys Leu Pro Phe Val Arg Asp Arg Leu Val Glu Ser Tyr Tyr Trp Ala
                325                 330                 335

Leu Gly Leu Phe Glu Ala His Lys Phe Gly Tyr Glu Arg Lys Thr Ala
            340                 345                 350

Ala Lys Ile Ile Thr Leu Ile Thr Ala Leu Asp Asp Val Tyr Asp Ile
            355                 360                 365

Tyr Gly Thr Leu Asp Glu Leu Gln Leu Phe Thr His Val Ile Arg Arg
370                 375                 380

Trp Asp Thr Glu Ser Ala Thr Gln Leu Pro Tyr Tyr Leu Gln Leu Phe
385                 390                 395                 400

Tyr Phe Val Leu Tyr Asn Phe Val Ser Glu Val Ala Tyr His Ile Leu
                405                 410                 415

Lys Glu Glu Gly Phe Ile Ser Ile Pro Phe Leu His Arg Ala Trp Val
            420                 425                 430

Asp Leu Val Glu Gly Tyr Leu Gln Glu Ala Lys Trp Tyr Tyr Thr Lys
```

```
              435                 440                 445
Tyr Thr Pro Thr Met Glu Glu Tyr Leu Asn Tyr Ala Ser Ile Thr Ile
    450                 455                 460

Gly Ala Pro Ala Val Ile Ser Gln Ile Tyr Phe Met Leu Ala Lys Ser
465                 470                 475                 480

Lys Glu Lys Pro Val Ile Glu Ser Phe Tyr Glu Tyr Asp Glu Ile Ile
                485                 490                 495

Arg Leu Ser Gly Met Leu Val Arg Leu Pro Asp Asp Leu Gly Thr Leu
            500                 505                 510

Pro Phe Glu Met Lys Arg Gly Asp Val Ala Lys Ser Ile Gln Ile Tyr
        515                 520                 525

Met Lys Glu Gln Asn Ala Thr Arg Glu Glu Ala Glu Glu His Val Arg
    530                 535                 540

Phe Met Ile Arg Glu Ala Trp Lys Glu Met Asn Thr Thr Met Ala Ala
545                 550                 555                 560

Asn Ser Asp Leu Arg Gly Asp Val Val Met Ala Ala Asn Leu Gly
                565                 570                 575

Arg Asp Ala Gln Phe Met Tyr Leu Asp Gly Asp Gly Asn His Ser Gln
            580                 585                 590

Leu Gln His Arg Ile Ala Asn Leu Leu Phe Lys Pro Tyr Val
        595                 600                 605

<210> SEQ ID NO 124
<211> LENGTH: 1608
<212> TYPE: DNA
<213> ORGANISM: Artificial Sequence
<220> FEATURE:
<223> OTHER INFORMATION: DNA having modified codons, which encodes
      linalool synthase gene derived from Ocimum basilicum (Ob1LINS)

<400> SEQUENCE: 124
atggcgagtg cggtcccccct gagtagtacg ccccctgatta acggcgacaa tagtcccctg      60 aaaaatccc accagcatgt tgaggagcgc agcagcaaac gtcgcgaata cctgctggaa       120
gaaaccgcgc gcaagctgca gcgcaatgac acggaaagcg ttgaaaaact gaagctgatt      180
gataatatcc agcgcctggg cattggctac tactttgaag atgccattga tgcggtgctg      240
cgcagcccct ttagcgccga agaagaagaa gacctgttta ccgcggccct gcgttttcgt      300
ctgctgcgtc ataatggcat tcaggtcacc ccggaaatct ttctgaaatt taaggatgaa      360
cgcggcgaat ttgacgaaag cgatacgctg ggcctgctga gcctgtacga agcgagcaat      420
ctgggcgtga ccggcgaaga aatcctggaa gaagcgatgg aatttgcgga accccgtctg      480
cgccgcagcc tgagcgaact ggccgcgccc ctgcgcagcg aagtcgccca ggccctggat      540
gttccccgtc acctgcgcat ggcccgtctg gaagcccgcc gctttattga acagtacggc      600
aaacagagcg atcatgacgg cgatctgctg gaactggcga ttctggacta caatcaggtc      660
caggcccagc accagagcga actgaccgaa atcacgcgtt ggtggaaaca gctgggcctg      720
gttgaaaaac tgggttttgg tcgcgatcgc gccctggaat gttttatgtg gacgatgggc      780
attctgccgc atcccaaata cagcagcagc cgtattgaaa gcgccaaggc ggccgccctg      840
ctgtacgtta ttgatgacat ctttgacacc tacggcaaaa tggatgaact gattctgttt      900
acggacgcga tccgccgctg ggatctggaa gccatggaag gcctgcccga atacatgaag      960
atttgttaca tggcgctgta caataccacg aatgaaattt gctaccgcgt tctgaaagat     1020
accggtcgta ttgccctgcc ttacctgaag agcgtgtgga ttgaaaccat cgaagcgtac     1080
```

```
atggtcgaag ttaaatggtt tagcggcggc agcgccccca agctggaaga atacattgaa   1140
aatggtgcca gcaccgtggg tgcctacatg gtgctggtcc acctgttttt cctgatcggc   1200
gaaggcctga cccaccagaa tgtcctgttt ttcaaacaga agccgtacca caaacccttt   1260
agcgccgcgg tcgtattttt tcgtctgtgg gatgacctgg gcacgagcca ggaagaagaa   1320
gaacgcggcg atatggcgag cagcatccgc ctgtttatga agaatacaa gctgagcacc   1380 gtggaagaag cccgcagctg cgtcctggaa gaaattagcc gcctgtgcaa agacctgaat   1440
gaaggcctga ttagcatcaa agatgccctg ccgctgacca ttgttaaggt ggcgctgaat   1500
atcgcccgca cgagccaggt tgtgtacaag catgaacagc acacctacat gctgagtgtt   1560
gacaattatg tggaagccct gttttttacg ccctgctga gtagttaa              1608
```

<210> SEQ ID NO 125
<211> LENGTH: 535
<212> TYPE: PRT
<213> ORGANISM: Ocimum basilicum

<400> SEQUENCE: 125

```
Met Ala Ser Ala Val Pro Leu Ser Ser Thr Pro Leu Ile Asn Gly Asp
1               5                   10                  15

Asn Ser Pro Leu Lys Asn Thr His Gln His Val Glu Glu Arg Ser Ser
                20                  25                  30

Lys Arg Arg Glu Tyr Leu Leu Glu Glu Thr Ala Arg Lys Leu Gln Arg
            35                  40                  45

Asn Asp Thr Glu Ser Val Glu Lys Leu Lys Leu Ile Asp Asn Ile Gln
        50                  55                  60

Arg Leu Gly Ile Gly Tyr Tyr Phe Glu Asp Ala Ile Asp Ala Val Leu
65                  70                  75                  80

Arg Ser Pro Phe Ser Ala Glu Glu Glu Asp Leu Phe Thr Ala Ala
                85                  90                  95

Leu Arg Phe Arg Leu Leu Arg His Asn Gly Ile Gln Val Thr Pro Glu
            100                 105                 110

Ile Phe Leu Lys Phe Lys Asp Glu Arg Gly Glu Phe Asp Glu Ser Asp
        115                 120                 125

Thr Leu Gly Leu Leu Ser Leu Tyr Glu Ala Ser Asn Leu Gly Val Thr
130                 135                 140

Gly Glu Glu Ile Leu Glu Glu Ala Met Glu Phe Ala Glu Pro Arg Leu
145                 150                 155                 160

Arg Arg Ser Leu Ser Glu Leu Ala Ala Pro Leu Arg Ser Glu Val Ala
                165                 170                 175

Gln Ala Leu Asp Val Pro Arg His Leu Arg Met Ala Arg Leu Glu Ala
            180                 185                 190

Arg Arg Phe Ile Glu Gln Tyr Gly Lys Gln Ser Asp His Asp Gly Asp
        195                 200                 205

Leu Leu Glu Leu Ala Ile Leu Asp Tyr Asn Gln Val Gln Ala Gln His
210                 215                 220

Gln Ser Glu Leu Thr Glu Ile Thr Arg Trp Trp Lys Gln Leu Gly Leu
225                 230                 235                 240

Val Glu Lys Leu Gly Phe Gly Arg Asp Arg Ala Leu Glu Cys Phe Met
                245                 250                 255

Trp Thr Met Gly Ile Leu Pro His Pro Lys Tyr Ser Ser Arg Ile
            260                 265                 270

Glu Ser Ala Lys Ala Ala Ala Leu Leu Tyr Val Ile Asp Asp Ile Phe
        275                 280                 285
```

Asp Thr Tyr Gly Lys Met Asp Glu Leu Ile Leu Phe Thr Asp Ala Ile
    290                 295                 300

Arg Arg Trp Asp Leu Glu Ala Met Glu Gly Leu Pro Glu Tyr Met Lys
305                 310                 315                 320

Ile Cys Tyr Met Ala Leu Tyr Asn Thr Thr Asn Glu Ile Cys Tyr Arg
                325                 330                 335

Val Leu Lys Asp Thr Gly Arg Ile Ala Leu Pro Tyr Leu Lys Ser Val
                340                 345                 350

Trp Ile Glu Thr Ile Glu Ala Tyr Met Val Glu Val Lys Trp Phe Ser
                355                 360                 365

Gly Gly Ser Ala Pro Lys Leu Glu Glu Tyr Ile Glu Asn Gly Ala Ser
    370                 375                 380

Thr Val Gly Ala Tyr Met Val Leu Val His Leu Phe Phe Leu Ile Gly
385                 390                 395                 400

Glu Gly Leu Thr His Gln Asn Val Leu Phe Phe Lys Gln Lys Pro Tyr
                405                 410                 415

His Lys Pro Phe Ser Ala Ala Gly Arg Ile Phe Arg Leu Trp Asp Asp
                420                 425                 430

Leu Gly Thr Ser Gln Glu Glu Glu Arg Gly Asp Met Ala Ser Ser
    435                 440                 445

Ile Arg Leu Phe Met Lys Glu Tyr Lys Leu Ser Thr Val Glu Glu Ala
450                 455                 460

Arg Ser Cys Val Leu Glu Glu Ile Ser Arg Leu Trp Lys Asp Leu Asn
465                 470                 475                 480

Glu Gly Leu Ile Ser Ile Lys Asp Ala Leu Pro Leu Thr Ile Val Lys
                485                 490                 495

Val Ala Leu Asn Ile Ala Arg Thr Ser Gln Val Val Tyr Lys His Glu
                500                 505                 510

Gln His Thr Tyr Met Leu Ser Val Asp Asn Tyr Val Glu Ala Leu Phe
                515                 520                 525

Phe Thr Pro Leu Leu Ser Ser
    530                 535

<210> SEQ ID NO 126
<211> LENGTH: 2550
<212> TYPE: DNA
<213> ORGANISM: Artificial Sequence
<220> FEATURE:
<223> OTHER INFORMATION: DNA having modified codons, which encodes
      linalool synthase gene derived from Clarkia breweri (CbLINS)

<400> SEQUENCE: 126
atgcgtgaga gcctgagcag tagcagtagc aataccccaga acctgttctct gagtacgagt     60 ccttacgata cggcgtggct ggccctgatt ccgcatcccc atcaccatca ccatcacggc      120
cgccctatgt ttgaaaaatg tctgcagtgg attctgcaca atcagacccc gcagggtttt      180
tgggcggccg cgggtgataa tatcagcgac accgatgacg atgtgacgct ggactgtctg      240
ctgagcaccc tggcctgcct ggttgccctg aaacgttggc agctggcccc ggatatgatt      300
cataagggcc tggaatttgt caatcgcaat accgaacgcc tggttatgaa gcagaaaccg      360
agcgacgtgc cccgctggtt tacgatcatg tttccggcca tgctggaact ggccggtgcc      420
agcagcctgc gcgtcgattt tagcgaaaat ctgaatcgca ttctggttga actgagccag      480
aatcgcgacg atatcctgac ccgcgaagaa gtggatgaaa gaaacagta cagcccgctg      540 ctgctgtttc tggaagccct gcccgcgcag agctacgaca tgatgttcct gaaacagatt      600

```
atcgataaga atctgagcaa tgacggcagc ctgctgcaga gccccagcgc cacggcccgt    660
gcctacatga tcaccggcaa tacgcgctgt ctgagctacc tgcatagcct gacgaatagc    720
tgcagcaatg gcggcgttcc gagcttttac cccgtggacg atgacctgca cgacctggtc    780
atggttaatc agctgacccg cagcggcctg acggaacatc tgattccgga atcgatcac    840 ctgctgctga aggtgcagaa aaattacaag tacaaaaagg ccagccccaa aagcctgtac    900
agcattgcgg ccgaactgta ccgcgatagc ctggcgtttt ggctgctgcg cgttaataat    960
cattgggtga gcccgagcat cttttgttgg tttctggatg acgatgaaat tcgcgaccac   1020
atcgaaacca attacgaaga attttgcggcc gtgctgctga atgtctaccg cgccacggat   1080
ctgatgttta gcggcgaagt tcagctggtt aagcccgca gctttgcgac caaaaatctg    1140
gaaaagattc tggccaccgg caatatccat aaaacgaatg cggacattag cagcagcctg   1200
cataagatga tcgaacatga actgcgtgtg ccttggaccg cccgtatgga tcacgtcgaa   1260
aatcgcattt ggatcgaaga aattgccagc agcgcgctgt ggtttggcaa aagcagctac   1320
ctgcgcctga gctgctttca taaaatgagc ctgcagcagc tggccgttaa gaattacacc   1380
ctgcgccagc tggtctaccg cgacgaactg gcggaagttg aacgctggag caaagaacgc   1440
ggcctgtgtg atatgggctt tgccgcgaa aagaccggct actgttacta cgcctttgcc    1500
gccagcacct gtctgccctg gagcagcgat gtccgtctgg ttctgaccaa gcggccgtt    1560 gtgatcacgg tggcggacga tttctttgat gtcgaaggca gcatggttga tctggaaaaa    1620
ctgacggatg cggtccgccg ctgggatgcc gaaggcctgg gcagccacag caagacgatt   1680
tttgaggccc tggacgatct ggtgaatgaa gtccgcctga atgttttca gcagaatggc     1740 caggacatca gaataatctc gcagcagctg tggtacgaaa cctttcatag ctggctgatg   1800
gaagcgaaat ggggcaaggg cctgaccagc aaaccgagcg tggatgtcta cctgggcaat   1860
gccatgacga gcattgcggc ccacaccatg gttctgaccg ccagctgtct gctgggtccc   1920
ggttttccgg tgcatcagct gtggagccag cgtcgccacc aggatatcac cagcctgctg   1980
atggtgctga cgcgcctgct gaatgacatt cagagctacc tgaaagaaga agatgaaggc   2040
aagatcaact acgtttggat gtacatgatc gaaaacaatc aggccagcat cgacgatagc   2100
gttcgccatg tgcagacgat catcaacgtt aaaaagcagg aatttatcca gcgcgtgctg   2160
agcgatcagc attgtaatct gccgaaaagc tttaagcagc tgcactttag ctgcctgaaa   2220
gtgtttaaca tgtttttcaa cagcagcaac atctttgaca ccgatacgga cctgctgctg   2280
gatatccatg aagcctttgt gagcccgccc caggtcccga gtttaaaacc ccatattaag   2340
ccgccccacc agctgcccgc caccctgcag ccgccccacc agcccagca gatcatggtc    2400 aacaaaaaga agtcgaaat ggtttacaag agctaccatc accccttaa ggttttacg     2460 ctgcagaaga aacagagcag cggccacggc acgatgaatc cccgtgcgag tatcctggcc   2520
ggtccgaata tcaaactgtg ctttagttaa                                    2550
```

<210> SEQ ID NO 127
<211> LENGTH: 849
<212> TYPE: PRT
<213> ORGANISM: Clarkia breweri

<400> SEQUENCE: 127

Met Arg Glu Ser Leu Ser Ser Ser Ser Asn Thr Gln Asn Leu Phe
1               5                   10                  15

Leu Ser Thr Ser Pro Tyr Asp Thr Ala Trp Leu Ala Leu Ile Pro His

```
                  20                  25                  30
Pro His His His His His Gly Arg Pro Met Phe Glu Lys Cys Leu
             35                  40                  45
Gln Trp Ile Leu His Asn Gln Thr Pro Gln Gly Phe Trp Ala Ala
         50                  55                  60
Gly Asp Asn Ile Ser Asp Thr Asp Asp Val Thr Leu Asp Cys Leu
 65                  70                  75                  80
Leu Ser Thr Leu Ala Cys Leu Val Ala Leu Lys Arg Trp Gln Leu Ala
                 85                  90                  95
Pro Asp Met Ile His Lys Gly Leu Glu Phe Val Asn Arg Asn Thr Glu
            100                 105                 110
Arg Leu Val Met Lys Gln Lys Pro Ser Asp Val Pro Arg Trp Phe Thr
            115                 120                 125
Ile Met Phe Pro Ala Met Leu Glu Leu Ala Gly Ala Ser Ser Leu Arg
            130                 135                 140
Val Asp Phe Ser Glu Asn Leu Asn Arg Ile Leu Val Glu Leu Ser Gln
145                 150                 155                 160
Asn Arg Asp Asp Ile Leu Thr Arg Glu Glu Val Asp Glu Lys Lys Gln
                165                 170                 175
Tyr Ser Pro Leu Leu Leu Phe Leu Glu Ala Leu Pro Ala Gln Ser Tyr
            180                 185                 190
Asp Asn Asp Val Leu Lys Gln Ile Ile Asp Lys Asn Leu Ser Asn Asp
            195                 200                 205
Gly Ser Leu Leu Gln Ser Pro Ser Ala Thr Ala Arg Ala Tyr Met Ile
            210                 215                 220
Thr Gly Asn Thr Arg Cys Leu Ser Tyr Leu His Ser Leu Thr Asn Ser
225                 230                 235                 240
Cys Ser Asn Gly Gly Val Pro Ser Phe Tyr Pro Val Asp Asp Leu
                245                 250                 255
His Asp Leu Val Met Val Asn Gln Leu Thr Arg Ser Gly Leu Thr Glu
            260                 265                 270
His Leu Ile Pro Glu Ile Asp His Leu Leu Leu Lys Val Gln Lys Asn
            275                 280                 285
Tyr Lys Tyr Lys Lys Ala Ser Pro Lys Ser Leu Tyr Ser Ile Ala Ala
            290                 295                 300
Glu Leu Tyr Arg Asp Ser Leu Ala Phe Trp Leu Leu Arg Val Asn Asn
305                 310                 315                 320
His Trp Val Ser Pro Ser Ile Phe Cys Trp Phe Leu Asp Asp Glu
                325                 330                 335
Ile Arg Asp His Ile Glu Thr Asn Tyr Glu Glu Phe Ala Ala Val Leu
            340                 345                 350
Leu Asn Val Tyr Arg Ala Thr Asp Leu Met Phe Ser Gly Glu Val Gln
            355                 360                 365
Leu Val Glu Ala Arg Ser Phe Ala Thr Lys Asn Leu Glu Lys Ile Leu
            370                 375                 380
Ala Thr Gly Asn Ile His Lys Thr Asn Ala Asp Ile Ser Ser Ser Leu
385                 390                 395                 400
His Lys Met Ile Glu His Glu Leu Arg Val Pro Trp Thr Ala Arg Met
                405                 410                 415
Asp His Val Glu Asn Arg Ile Trp Ile Glu Glu Ile Ala Ser Ser Ala
            420                 425                 430
Leu Trp Phe Gly Lys Ser Ser Tyr Leu Arg Leu Ser Cys Phe His Lys
            435                 440                 445
```

```
Met Ser Leu Gln Gln Leu Ala Val Lys Asn Tyr Thr Leu Arg Gln Leu
    450                 455                 460

Val Tyr Arg Asp Glu Leu Ala Glu Val Glu Arg Trp Ser Lys Glu Arg
465                 470                 475                 480

Gly Leu Cys Asp Met Gly Phe Cys Arg Glu Lys Thr Gly Tyr Cys Tyr
                485                 490                 495

Tyr Ala Phe Ala Ala Ser Thr Cys Leu Pro Trp Ser Ser Asp Val Arg
                500                 505                 510

Leu Val Leu Thr Lys Ala Ala Val Ile Thr Val Ala Asp Asp Phe
            515                 520                 525

Phe Asp Val Glu Gly Ser Met Val Asp Leu Glu Lys Leu Thr Asp Ala
530                 535                 540

Val Arg Arg Trp Asp Ala Glu Gly Leu Gly Ser His Ser Lys Thr Ile
545                 550                 555                 560

Phe Glu Ala Leu Asp Asp Leu Val Asn Glu Val Arg Leu Lys Cys Phe
                565                 570                 575

Gln Gln Asn Gly Gln Asp Ile Lys Asn Asn Leu Gln Gln Leu Trp Tyr
                580                 585                 590

Glu Thr Phe His Ser Trp Leu Met Glu Ala Lys Trp Gly Lys Gly Leu
            595                 600                 605

Thr Ser Lys Pro Ser Val Asp Val Tyr Leu Gly Asn Ala Met Thr Ser
610                 615                 620

Ile Ala Ala His Thr Met Val Leu Thr Ala Ser Cys Leu Leu Gly Pro
625                 630                 635                 640

Gly Phe Pro Val His Gln Leu Trp Ser Gln Arg Arg His Gln Asp Ile
                645                 650                 655

Thr Ser Leu Leu Met Val Leu Thr Arg Leu Leu Asn Asp Ile Gln Ser
                660                 665                 670

Tyr Leu Lys Glu Glu Asp Glu Gly Lys Ile Asn Tyr Val Trp Met Tyr
            675                 680                 685

Met Ile Glu Asn Asn Gln Ala Ser Ile Asp Asp Ser Val Arg His Val
            690                 695                 700

Gln Thr Ile Ile Asn Val Lys Lys Gln Glu Phe Ile Gln Arg Val Leu
705                 710                 715                 720

Ser Asp Gln His Cys Asn Leu Pro Lys Ser Phe Lys Gln Leu His Phe
                725                 730                 735

Ser Cys Leu Lys Val Phe Asn Met Phe Phe Asn Ser Ser Asn Ile Phe
                740                 745                 750

Asp Thr Asp Thr Asp Leu Leu Leu Asp Ile His Glu Ala Phe Val Ser
                755                 760                 765

Pro Pro Gln Val Pro Lys Phe Lys Pro His Ile Lys Pro Pro His Gln
770                 775                 780

Leu Pro Ala Thr Leu Gln Pro Pro His Gln Pro Gln Ile Met Val
785                 790                 795                 800

Asn Lys Lys Lys Val Glu Met Val Tyr Lys Ser Tyr His His Pro Phe
                805                 810                 815

Lys Val Phe Thr Leu Gln Lys Lys Gln Ser Ser Gly His Gly Thr Met
                820                 825                 830

Asn Pro Arg Ala Ser Ile Leu Ala Gly Pro Asn Ile Lys Leu Cys Phe
                835                 840                 845

Ser
```

-continued

```
<210> SEQ ID NO 128
<211> LENGTH: 43
<212> TYPE: DNA
<213> ORGANISM: Artificial Sequence
<220> FEATURE:
<223> OTHER INFORMATION: Primer

<400> SEQUENCE: 128
cacaaggaga ctgccatggc gaacacggcg aagcgtagta tcc            43

<210> SEQ ID NO 129
<211> LENGTH: 44
<212> TYPE: DNA
<213> ORGANISM: Artificial Sequence
<220> FEATURE:
<223> OTHER INFORMATION: Primer

<400> SEQUENCE: 129
gtctcctgtg tgaaattaca tcaggctttt cagatactca tcgg           44

<210> SEQ ID NO 130
<211> LENGTH: 44
<212> TYPE: DNA
<213> ORGANISM: Artificial Sequence
<220> FEATURE:
<223> OTHER INFORMATION: Primer

<400> SEQUENCE: 130
cacaaggaga ctgccatgcg tcgtagtgcg aattaccagc cgag           44

<210> SEQ ID NO 131
<211> LENGTH: 43
<212> TYPE: DNA
<213> ORGANISM: Artificial Sequence
<220> FEATURE:
<223> OTHER INFORMATION: Primer

<400> SEQUENCE: 131
gtctcctgtg tgaaattagt ccagcgggat agggttaaac agc            43

<210> SEQ ID NO 132
<211> LENGTH: 48
<212> TYPE: DNA
<213> ORGANISM: Artificial Sequence
<220> FEATURE:
<223> OTHER INFORMATION: Primer

<400> SEQUENCE: 132
cacaaggaga ctgccatgga gtttagcatt agccagagta gttttgcg       48

<210> SEQ ID NO 133
<211> LENGTH: 45
<212> TYPE: DNA
<213> ORGANISM: Artificial Sequence
<220> FEATURE:
<223> OTHER INFORMATION: Primer

<400> SEQUENCE: 133
gtctcctgtg tgaaattagg cgtgcagcat actcttcatg tactc          45

<210> SEQ ID NO 134
<211> LENGTH: 42
<212> TYPE: DNA
<213> ORGANISM: Artificial Sequence
<220> FEATURE:
<223> OTHER INFORMATION: Primer
```

```
<400> SEQUENCE: 134
cacaaggaga ctgccatgta tagcctgcgt atttatgtgg cg                    42

<210> SEQ ID NO 135
<211> LENGTH: 46
<212> TYPE: DNA
<213> ORGANISM: Artificial Sequence
<220> FEATURE:
<223> OTHER INFORMATION: Primer

<400> SEQUENCE: 135
gtctcctgtg tgaaattagg catagggttc aaacagcagg caggcg                46

<210> SEQ ID NO 136
<211> LENGTH: 44
<212> TYPE: DNA
<213> ORGANISM: Artificial Sequence
<220> FEATURE:
<223> OTHER INFORMATION: Primer

<400> SEQUENCE: 136
cacaaggaga ctgccatggg ttttagtcct gccttttatg cgtg                  44

<210> SEQ ID NO 137
<211> LENGTH: 46
<212> TYPE: DNA
<213> ORGANISM: Artificial Sequence
<220> FEATURE:
<223> OTHER INFORMATION: Primer

<400> SEQUENCE: 137
gtctcctgtg tgaaattaca ggggaaacgc ttcaaacagc agactc                46

<210> SEQ ID NO 138
<211> LENGTH: 45
<212> TYPE: DNA
<213> ORGANISM: Artificial Sequence
<220> FEATURE:
<223> OTHER INFORMATION: Primer

<400> SEQUENCE: 138
cacaaggaga ctgccatgga actgaccctg acgagtctga gcccg                 45

<210> SEQ ID NO 139
<211> LENGTH: 46
<212> TYPE: DNA
<213> ORGANISM: Artificial Sequence
<220> FEATURE:
<223> OTHER INFORMATION: Primer

<400> SEQUENCE: 139
gtctcctgtg tgaaattagc ggcggttact catcttcatg ccatcc                46

<210> SEQ ID NO 140
<211> LENGTH: 43
<212> TYPE: DNA
<213> ORGANISM: Artificial Sequence
<220> FEATURE:
<223> OTHER INFORMATION: Primer

<400> SEQUENCE: 140
cacaaggaga ctgccatgtg taccatcatt agcgtcaatc atc                   43

<210> SEQ ID NO 141
<211> LENGTH: 45
```

```
<212> TYPE: DNA
<213> ORGANISM: Artificial Sequence
<220> FEATURE:
<223> OTHER INFORMATION: Primer

<400> SEQUENCE: 141
gtctcctgtg tgaaattaga cgtagggctt aaacagcaga ttggc          45

<210> SEQ ID NO 142
<211> LENGTH: 45
<212> TYPE: DNA
<213> ORGANISM: Artificial Sequence
<220> FEATURE:
<223> OTHER INFORMATION: Primer

<400> SEQUENCE: 142
cacaaggaga ctgccatggc gagtgcggtc ccctgagta gtacg           45

<210> SEQ ID NO 143
<211> LENGTH: 47
<212> TYPE: DNA
<213> ORGANISM: Artificial Sequence
<220> FEATURE:
<223> OTHER INFORMATION: Primer

<400> SEQUENCE: 143
gtctcctgtg tgaaattaac tactcagcag gggcgtaaaa aacaggg        47

<210> SEQ ID NO 144
<211> LENGTH: 45
<212> TYPE: DNA
<213> ORGANISM: Artificial Sequence
<220> FEATURE:
<223> OTHER INFORMATION: Primer

<400> SEQUENCE: 144
cacaaggaga ctgccatgcg tgagagcctg agcagtagca gtagc          45

<210> SEQ ID NO 145
<211> LENGTH: 44
<212> TYPE: DNA
<213> ORGANISM: Artificial Sequence
<220> FEATURE:
<223> OTHER INFORMATION: Primer

<400> SEQUENCE: 145
gtctcctgtg tgaaattaac taaagcacag tttgatattc ggac           44

<210> SEQ ID NO 146
<211> LENGTH: 34
<212> TYPE: DNA
<213> ORGANISM: Artificial Sequence
<220> FEATURE:
<223> OTHER INFORMATION: Primer

<400> SEQUENCE: 146
ggcagtctcc ttgtgtgaaa ttgttatccg ctca                      34

<210> SEQ ID NO 147
<211> LENGTH: 35
<212> TYPE: DNA
<213> ORGANISM: Artificial Sequence
<220> FEATURE:
<223> OTHER INFORMATION: Primer

<400> SEQUENCE: 147
```

```
tttcacacag gagactgcca tggattttcc ccagc                               35

<210> SEQ ID NO 148
<211> LENGTH: 41
<212> TYPE: DNA
<213> ORGANISM: Artificial Sequence
<220> FEATURE:
<223> OTHER INFORMATION: Primer

<400> SEQUENCE: 148
atgtccaccg ccgtgccctc tatgcccact acccaaaaat g                       41

<210> SEQ ID NO 149
<211> LENGTH: 42
<212> TYPE: DNA
<213> ORGANISM: Artificial Sequence
<220> FEATURE:
<223> OTHER INFORMATION: Primer

<400> SEQUENCE: 149
gcaggtcgac tctagctatt tgttgcgctg gatgatgtaa tc                      42

<210> SEQ ID NO 150
<211> LENGTH: 40
<212> TYPE: DNA
<213> ORGANISM: Artificial Sequence
<220> FEATURE:
<223> OTHER INFORMATION: Primer

<400> SEQUENCE: 150
ggtacccggg gatcctctag agatcgttta gatccgaagg                         40

<210> SEQ ID NO 151
<211> LENGTH: 40
<212> TYPE: DNA
<213> ORGANISM: Artificial Sequence
<220> FEATURE:
<223> OTHER INFORMATION: Primer

<400> SEQUENCE: 151
cacggcggtg gacattgtat gtcctcctgg acttcgtggt                         40

<210> SEQ ID NO 152
<211> LENGTH: 8564
<212> TYPE: DNA
<213> ORGANISM: Artificial Sequence
<220> FEATURE:
<223> OTHER INFORMATION: DNA encoding pVK9-P0480-optAaLINS-ispA*

<400> SEQUENCE: 152
gaggtctgcc tcgtgaagaa ggtgttgctg actcatacca ggcctgaatc gccccatcat   60
ccagccagaa agtgagggag ccacggttga tgagagcttt gttgtaggtg acggggatc   120 ttttctacgg ggtctgacgc tcagtggaac gaaaactcac gttaagggat tttggtcatg   180
agattatcaa aaaggatcat gcgagcaacc tccataagat cagctaggcg atctttggga   240
gcagtccttg tcgcgttacg aggtgagccg gtggggaacc gttagctgcc tatggtgtga   300 gccccctag agagcttcaa gagcaatcag cccgacctag aaaggaggcc aagagagaga   360
cctacggggg gaaccgtttt ctgcctacga gatgggcaca ttactgggaa gctttacggc   420
gtcctcgtgg aagttcaatg cccgcagact taagtgctct attcacggtc tgacgtgaca   480
cgctaaattc agacatagct tcattgattg tcggccacga gccagtctct ccctcaacag   540
tcataaacca acctgcaatg gtcaagcgat ttcctttagc tttcctagct tgtcgttgac   600
```

```
tggacttagc tagttttttct cgctgtgctc gggcgtactc actgtttggg tctttccagc    660
gttctgcggc cttttaccg ccacgtcttc ccatagtggc cagagcttt cgccctcggc      720
tgctctgcgt ctctgtctga cgagcaggga cgactggctg cctttagcg acgtagccgc    780
gcacacgtcg cgccatcgtc tggcggtcac gcatcggcgg cagatcaggc tcacggccgt    840
ctgctccgac cgcctgagcg acggtgtagg cacgctcgta ggcgtcgatg atcttggtgt    900
cttttaggcg ctcaccagcc gcttttaact ggtatcccac agtcaaagcg tggcgaaaag    960
ccgtctcatc acgggcggca cgccctggag cagtccagag gacacggacg ccgtcgatca   1020
gctctccaga cgcttcagcg gcgctcggca ggcttgcttc aagcgtggca agtgcttttg   1080
cttccgcagt ggcttttctt gccgcttcga tacgtgcccg tccgctagaa aactcctgct   1140
catagcgttt tttaggtttt tctgtgcctg agatcatgcg agcaacctcc ataagatcag   1200
ctaggcgatc cacgcgattg tgctgggcat gccagcggta cgcggtggga tcgtcggaga   1260
cgtgcagtgg ccaccggctc agcctatgtg aaaaagcctg gtcagcgccg aaaacgcggg   1320
tcatttcctc ggtcgttgca gccagcaggc gcatattcgg gctgctcatg cctgctgcgg   1380
catacaccga atcaatgagc cagatagagct ggcatttccc gctcagtgga ttcacgccga   1440
tccaagctgg cgcttttcc aggcgtgccc agcgctccaa aatcgcgtag acctcggggt    1500
ttacgtgctc gattttcccg ccggcctggt ggctcggcac atcaatgtcc aggacaagca   1560
cggctgcgtg ctgcgcgtgc gtcagagcaa catactggca ccgggcaagc gattttgaac   1620
caactcggta taacttcggc tgtgtttctc ccgtgtccgg gtctttgatc caagcgctgg   1680
cgaagtcgcg ggtcttgctg ccctggaaat tttctctgcc caggtgagcg aggaattcgc   1740
ggcggtcttc gctcgtccag ccacgtgatc gcagcgcgag ctcgggatgg gtgtcgaaca   1800
gatcagcgga aaatttccag gccggtgtgt caatgtctcg tgaatccgct agagtcattt   1860
ttgagcgctt tctcccaggt ttggactggg ggttagccga cgccctgtga gttaccgctc   1920
acggggcgtt caacattttt caggtattcg tgcagcttat cgcttcttgc cgcctgtgcg   1980
cttttttcgac gcgcgacgct gctgccgatt cggtgcaggt ggtggcggcg ctgacacgtc   2040
ctgggcggcc acgccacac gaaacgcggc atttacgatg tttgtcatgc ctgcgggcac    2100
cgcgccacga tcgcggataa ttctcgctgc cgcttccagc tctgtgacga ccatggccaa   2160
aatttcgctc gggggacgca cttccagcgc catttgcgac ctagccgcct ccagctcctc   2220
ggcgtggcgt ttgttggcgc gctcgcggct ggctgcggca cgacacgcat ctgagcaata   2280
ttttgcgcgc cgtcctcgcg ggtcaggccg gggaggaatc aggccaccgc agtaggcgca   2340
actgattcga tcctccacta ctgtgcgtcc tcctggcgct gccgagcacg cagctcgtca   2400
gccagctcct caagatccgc cacgagagtt tctaggtcgc tcgcggcact ggcccagtct   2460
cgtgatgctg gcgcgtccgt cgtatcgaga gctcggaaaa atccgatcac cgttttaaa   2520
tcgacggcag catcgagcgc gtcggactcc agcgcgacat cagagagatc catagctgat   2580
gattcgggcc aattttggta cttcgtcgtg aaggtcatga caccattata acgaacgttc   2640
gttaaagttt ttggcggaaa atcacgcggc acgaaaattt tcacgaagcg ggactttgcg   2700
cagctcaggg gtgctaaaaa ttttgtatcg cacttgattt ttccgaaaga cagattatct   2760
gcaaacggtg tgtcgtattt ctggcttggt ttttaaaaaa tctggaatcg aaaatttgcg   2820
gggcgaccga gaagtttttt acaaaaggca aaaactttt cgggatcagc taggcgatcc    2880
acgcgattgt gctgggcatg ccagcggtac gcggtgggat cgtcggagac gtgcagtggc   2940
```

-continued

```
caccggctca gcctatgtga aaaagcctgg tcagcgccga aaacgcgggt catttcctcg    3000
gtcgttgcag ccagcaggcg catattcggg ctgctcatgc ctgctgcggc ataccggga    3060
tcggaccagt tggtgatttt gaacttttgc tttgccacgg aacggtctgc gttgtcggga    3120
agatgcgtga tctgatcctt caactcagca aaagttcgat ttattcaaca aagccacgtt    3180
gtgtctcaaa atctctgatg ttacattgca caagataaaa atatatcatc atgaacaata    3240
aaactgtctg cttacataaa cagtaataca aggggtgtta tgagccatat tcaacgggaa    3300
acgtcttgct cgaagccgcg attaaattcc aacatggatg ctgatttata tgggtataaa    3360
tgggctcgcg ataatgtcgg gcaatcaggt gcgacaatct atcgattgta tgggaagccc    3420
gatgcgccag agttgtttct gaaacatggc aaaggtagcg ttgccaatga tgttacagat    3480
gagatggtca gactaaactg gctgacggaa tttatgcctc ttccgaccat caagcatttt    3540
atccgtactc ctgatgatgc atggttactc accactgcga tccccgggaa aacagcattc    3600
caggtattag aagaatatcc tgattcaggt gaaaatattg ttgatgcgct ggcagtgttc    3660
ctgcgccggt tgcattcgat tcctgttttgt aattgtcctt ttaacagcga tcgcgtattt    3720
cgtctcgctc aggcgcaatc acgaatgaat aacggtttgg ttgatgcgag tgattttgat    3780
gacgagcgta atggctggcc tgttaacaa gtctggaaag aaatgcataa gcttttgcca    3840
ttctcaccgg attcagtcgt cactcatggt gatttctcac ttgataacct tattttgac    3900
gaggggaaat taataggttg tattgatgtt ggacgagtcg gaatcgcaga ccgataccag    3960
gatcttgcca tcctatggaa ctgcctcggt gagttttctc cttcattaca gaaacggctt    4020
tttcaaaaat atggtattga taatcctgat atgaataaat tgcagtttca tttgatgctc    4080
gatgagtttt tctaatcaga attggttaat tggttgtaac actggcagag cattacgctg    4140
acttgacggg acggcggctt tgttaataa atcgcattcg ccattcaggc tgcgcaactg    4200
ttgggaaggg cgatcggtgc gggcctcttc gctattacgc cagctggcga aggggggatg    4260
tgctgcaagg cgattaagtt gggtaacgcc agggttttcc cagtcacgac gttgtaaaac    4320
gacggccagt gaattcgagc tcggtacccg gggatcctct agagatcgtt tagatccgaa    4380
ggaaaacgtc gaaaagcaat ttgcttttcg acgccccacc ccgcgcgttt tagcgtgtca    4440
gtagacgcgt agggtaagtg gggtagcggc ttgttagata tcttgaaatc ggctttcaac    4500
agcattgatt tcgatgtatt tagctggccg ttaccctgcg aatgtccaca gggtagctgg    4560
tagtttgaaa atcaacgccg ttgcccttag gattcagtaa ctggcacatt ttgtaatgcg    4620
ctagatctgt gtgcccagtc ttccaggctg cttatcacag tgaaagcaaa accaattcgt    4680
ggctgcgaaa gtcgtagcca ccacgaagtc caggaggaca tacaatgtcc accgccgtgc    4740
cctctatgcc cactacccaa aaatggtcta ttaccgaaga cttagccttt attagcaatc    4800
ccagcaaaca acataatcac caaaccggct accggatttt tagtgacgaa ttttacctga    4860
aacatgaaaa caaattgaaa gatgtgcggc gcgccttgcg tgaagttgaa gaaacccccc    4920
tggaaggctt ggtgatgatt gacactttac agcggctggg tattgattac cactttcaag    4980
gcgaaattgg tgccttgtta cagaaacaac agcgcattag tacctgtgac tatcccgaac    5040
atgatttgtt tgaagtgagc actcgctttc gtctgttgcg tcaagaaggt cacaatgtgc    5100
ccgccgacgt ttttaataac tttcgcgata agaagggcg ttttaaatct gaactgtccc    5160
gggatattcg cggattgatg tccttatacg aagccagtca actgagcatt caggggaag    5220
acattttgga tcaagccgct gacttttcca gtcagttact gtctggatgg ccaccaatt    5280
tagatcatca ccaagcccgt ctggtgcgga acgctttgac ccatccctac cacaaaagtc    5340
```

| | |
|---|---|
| tggccacttt tatggctcgc aactttaact acgattgcaa agggcaaaac ggatgggtga | 5400 |
| ataacctgca ggaattggcc aaaatggatt taaccatggt tcaaagtatg catcagaaag | 5460 |
| aagtgctgca agttagccag tggtggaaag ggcggggatt ggccaatgaa ctgaaattgg | 5520 |
| tgcgcaacca acccttgaaa tggtatatgt ggcccatggc cgctttaacc gatcccggt | 5580 |
| tttctgaaga acgcgtggaa ttgactaaac ccatttcctt tatttacatt attgatgaca | 5640 |
| tttttgacgt ttatggcacc ttagaagaat taaccctgtt tactgatgcc gtgaatcggt | 5700 |
| gggaattaac tgctgttgaa cagctgcccg actacatgaa aatttgtttt aaagccttgt | 5760 |
| acgatattac caacgaaatt gcttacaaaa tttacaaaaa acatgggcgc aaccccattg | 5820 |
| atagtttacg tcggacttgg gccagcttat gcaatgcttt tctggaagaa gccaaatggt | 5880 |
| ttgctagtgg caatttgccc aaagccgaag aatacctgaa aaacgggatt attagctctg | 5940 |
| gaatgcatgt ggttaccgtg cacatgtttt tcttgttagg cggttgtttt actgaagaat | 6000 |
| ccgtgaattt ggttgatgaa catgccggca ttacctccag tattgctact attttgcgtt | 6060 |
| tatctgatga cttaggttcc gccaaagatg aagaccaaga tggctatgac ggtagctact | 6120 |
| tggaatgtta cctgaaagat cataaaggta gctctgtgga aaatgcccgt gaagaagtta | 6180 |
| ttcggatgat ttccgatgct tggaaacgct tgaatgaaga atgcttattt cccaacccct | 6240 |
| tttctgccac ctttcgcaaa gggtccttaa atattgctcg tatggtgccc ctgatgtaca | 6300 |
| gttacgatga caaccataac ctgcccattc tggaagaaca catgaaaacc atgttgtatg | 6360 |
| attccagtag ctaatttcac acaggagact gccatggatt ttccccagca gctggaagcc | 6420 |
| tgcgtgaaac aggccaacca ggccctgagc cgctttatcg ccccccctgcc ctttcagaac | 6480 |
| accccgtgg tggaaaccat gcagtacggc gccctgctgg gcggcaaacg cctgcgcccc | 6540 |
| tttctggtgt acgccaccgg ccacatgttt ggcgtgagca ccaacaccct ggatgcccc | 6600 |
| gccgccgccg tggaatgcat ccacgcctac tttctgatcc acgatgatct gcccgccatg | 6660 |
| gatgatgatg atctgcgccg cggcctgccc acctgccacg tgaaatttgg cgaagccaac | 6720 |
| gccatcctgg ccggcgatgc cctgcagacc ctggccttta gcatcctgag cgatgccgat | 6780 |
| atgcccgaag tgagcgatcg cgatcgcatc agcatgatca gcgaactggc cagcgccagc | 6840 |
| ggcatcgccg gcatgtgcgg cggccaggcc ctggatctgg atgccgaagg caaacacgtg | 6900 |
| cccctggatg ccctggaacg catccaccgc cacaaaaccg gcgccctgat ccgcgccgcc | 6960 |
| gtgcgcctgg gcgccctgag cgccggcgat aaaggccgcc gcgccctgcc cgtgctggat | 7020 |
| aaatacgccg aaagcatcgg cctggccttt caggtgcagg atgatatcct ggatgtggtg | 7080 |
| ggcgataccg ccaccctggg caaacgccag ggcgccgatc agcagctggg caaaagcacc | 7140 |
| tacccccgcc tgctgggcct ggaacaggcc cgcaaaaaag cccgcgatct gatcgatgat | 7200 |
| gcccgccaga gcctgaaaca gctggccgaa cagagcctgg ataccagcgc cctggaagcc | 7260 |
| ctggccgatt acatcatcca gcgcaacaaa tagctagagt cgacctgcag gcatgcaagc | 7320 |
| ttggcgtaat catggtcata gctgtttcct gtgtgaaatt gttatccgct cacaattcca | 7380 |
| cacaacatac gagccggaag cataaagtgt aaagcctggg gtgcctaatg agtgagctaa | 7440 |
| ctcacattaa ttgcgttgcg ctcactgccc gctttccagt cgggaaacct gtcgtgccag | 7500 |
| ctgcattaat gaatcggcca acgcgcgggg agaggcggtt tgcgtattgg cgaacttttg | 7560 |
| ctgagttgaa ggatcagatc acgcatcttc ccgacaacgc agaccgttcc gtggcaaagc | 7620 |
| aaaagttcaa aatcagtaac cgtcagtgcc gataagttca aagttaaacc tggtgttgat | 7680 |

```
accaacattg aaacgctgat cgaaaacgcg ctgaaaaacg ctgctgaatg tgcgagcttc    7740
ttccgcttcc tcgctcactg actcgctgcg ctcggtcgtt cggctgcggc gagcggtatc    7800
agctcactca aaggcggtaa tacggttatc cacagaatca ggggataacg caggaaagaa    7860
catgtgagca aaaggccagc aaaaggccag gaaccgtaaa aaggccgcgt tgctggcgtt    7920
tttccatagg ctccgccccc ctgacgagca tcacaaaaat cgacgctcaa gtcagaggtg    7980
gcgaaacccg acaggactat aaagatacca ggcgtttccc cctggaagct ccctcgtgcg    8040
ctctcctgtt ccgaccctgc cgcttaccgg atacctgtcc gcctttctcc cttcgggaag    8100
cgtggcgctt tctcaatgct cacgctgtag gtatctcagt tcggtgtagg tcgttcgctc    8160
caagctgggc tgtgtgcacg aaccccccgt tcagcccgac cgctgcgcct tatccggtaa    8220
ctatcgtctt gagtccaacc cggtaagaca cgacttatcg ccactggcag cagccactgg    8280
taacaggatt agcagagcga ggtatgtagg cggtgctaca gagttcttga agtggtggcc    8340
taactacggc tacactagaa ggacagtatt tggtatctgc gctctgctga agccagttac    8400
cttcggaaaa agagttggta gctcttgatc cggcaaacaa accaccgctg gtagcggtgg    8460
tttttttgtt tgcaagcagc agattacgcg cagaaaaaaa ggatctcaag aagatccttt    8520
gatcttttct acgggtctg acgctcagtg aacgatccg tcga                      8564
```

<210> SEQ ID NO 153
<211> LENGTH: 55
<212> TYPE: DNA
<213> ORGANISM: Artificial Sequence
<220> FEATURE:
<223> OTHER INFORMATION: Primer

<400> SEQUENCE: 153
tctagagtcg acgtcccctg ttgacaatta atcatcggct cgtataatgt gtgga    55

<210> SEQ ID NO 154
<211> LENGTH: 54
<212> TYPE: DNA
<213> ORGANISM: Artificial Sequence
<220> FEATURE:
<223> OTHER INFORMATION: Primer

<400> SEQUENCE: 154
tccaatgtga ggttttagct actggaatca tacaacatgg ttttcatgtg ttct    54

<210> SEQ ID NO 155
<211> LENGTH: 57
<212> TYPE: DNA
<213> ORGANISM: Artificial Sequence
<220> FEATURE:
<223> OTHER INFORMATION: Primer

<400> SEQUENCE: 155
aaggaattat aaccaaatgt ccaccgccgt gccctctatg cccactaccc aaaaatg    57

<210> SEQ ID NO 156
<211> LENGTH: 55
<212> TYPE: DNA
<213> ORGANISM: Artificial Sequence
<220> FEATURE:
<223> OTHER INFORMATION: Primer

<400> SEQUENCE: 156
gatggggaag tttaggctag cctatttgtt gcgctggatg atgtaatcgg ccagg    55

```
<210> SEQ ID NO 157
<211> LENGTH: 25
<212> TYPE: DNA
<213> ORGANISM: Artificial Sequence
<220> FEATURE:
<223> OTHER INFORMATION: Primer

<400> SEQUENCE: 157
ggaggattgg gttaccctca gtgtg                                      25

<210> SEQ ID NO 158
<211> LENGTH: 25
<212> TYPE: DNA
<213> ORGANISM: Artificial Sequence
<220> FEATURE:
<223> OTHER INFORMATION: Primer

<400> SEQUENCE: 158
cgccatatca atcccaacgc tctgg                                      25

<210> SEQ ID NO 159
<211> LENGTH: 44
<212> TYPE: DNA
<213> ORGANISM: Artificial Sequence
<220> FEATURE:
<223> OTHER INFORMATION: Primer

<400> SEQUENCE: 159
ggaatattaa gcttggtacc atgtccaccg ccgtgccctc tatg                 44

<210> SEQ ID NO 160
<211> LENGTH: 42
<212> TYPE: DNA
<213> ORGANISM: Artificial Sequence
<220> FEATURE:
<223> OTHER INFORMATION: Primer

<400> SEQUENCE: 160
gtggatccga gctcggtacc ctatttgttg cgctggatga tg                   42

<210> SEQ ID NO 161
<211> LENGTH: 609
<212> TYPE: PRT
<213> ORGANISM: Solanum lycopersicum

<400> SEQUENCE: 161

Met Val Ser Ile Leu Ser Asn Ile Gly Met Met Val Val Thr Phe Lys
1               5                   10                  15

Arg Pro Ser Leu Phe Thr Ser Leu Arg Arg Ser Ala Asn Asn Ile
            20                  25                  30

Ile Ile Thr Lys His Ser His Pro Ile Ser Thr Thr Arg Arg Ser Gly
        35                  40                  45

Asn Tyr Lys Pro Thr Met Trp Asp Phe Gln Phe Ile Gln Ser Leu His
    50                  55                  60

Asn Pro Tyr Glu Gly Asp Lys Tyr Met Lys Arg Leu Asn Lys Leu Lys
65                  70                  75                  80

Lys Glu Val Lys Lys Met Met Met Thr Val Glu Gly Ser His Asp Glu
                85                  90                  95

Glu Leu Glu Lys Leu Glu Leu Ile Asp Asn Leu Glu Arg Leu Gly Val
            100                 105                 110

Ser Tyr His Phe Lys Asp Glu Ile Met Gln Ile Met Arg Ser Ile Asn
        115                 120                 125
```

```
Ile Asn Ile Asn Ile Ala Pro Pro Asp Ser Leu Tyr Thr Thr Ala Leu
    130                 135                 140

Lys Phe Arg Leu Leu Arg Gln His Gly Phe His Ile Ser Gln Asp Ile
145                 150                 155                 160

Leu Asn Asp Phe Lys Asp Glu Asn Gly Asn Leu Lys Gln Ser Ile Cys
                165                 170                 175

Lys Asp Thr Lys Asp Ile Leu Asn Ser Ser Lys Asp Glu His Asp Asn
            180                 185                 190

Leu Lys Gln Ser Thr Cys Asn Asn Thr Lys Gly Leu Leu Lys Leu Tyr
                195                 200                 205

Glu Ala Ser Phe Leu Ser Ile Glu Asn Glu Ser Phe Leu Arg Asn Thr
    210                 215                 220

Thr Lys Ser Thr Leu Ala His Leu Met Arg Tyr Val Asp Gln Asn Arg
225                 230                 235                 240

Cys Gly Glu Glu Asp Asn Met Ile Val Glu Leu Val Val His Ala Leu
                245                 250                 255

Glu Leu Pro Arg His Trp Met Val Pro Arg Leu Glu Thr Arg Trp Tyr
            260                 265                 270

Ile Ser Ile Tyr Glu Arg Met Ser Asn Ala Asn Pro Leu Leu Leu Glu
            275                 280                 285

Leu Ala Lys Leu Asp Phe Asn Ile Val Gln Ala Thr His Gln Gln Asp
    290                 295                 300

Leu Arg Ile Leu Ser Arg Trp Trp Lys Asn Thr Gly Leu Ala Glu Lys
305                 310                 315                 320

Leu Pro Phe Ser Arg Asp Ile Leu Val Glu Asn Met Phe Trp Ala Val
                325                 330                 335

Gly Ala Leu Phe Glu Pro Gln His Ser Tyr Phe Arg Arg Leu Ile Thr
            340                 345                 350

Lys Val Ile Val Phe Ile Ser Ile Ile Asp Asp Ile Tyr Asp Val Tyr
            355                 360                 365

Gly Thr Leu Asp Glu Leu Glu Leu Phe Thr Leu Ala Ile Gln Arg Trp
    370                 375                 380

Asp Thr Lys Ala Met Glu Gln Leu Pro Asp Tyr Met Lys Val Cys Tyr
385                 390                 395                 400

Leu Ala Leu Ile Asn Ile Ile Asn Glu Val Ala Tyr Glu Val Leu Lys
                405                 410                 415

Asn His Asp Ile Asn Val Leu Pro Tyr Leu Thr Lys Ser Trp Ala Asp
            420                 425                 430

Leu Cys Lys Ser Tyr Leu Gln Glu Ala Lys Trp Tyr His Asn Gly Tyr
    435                 440                 445

Lys Pro Asn Leu Glu Glu Tyr Met Asp Asn Ala Arg Ile Ser Ile Gly
    450                 455                 460

Val Pro Met Val Leu Val His Ser Leu Phe Leu Val Thr Asn Gln Ile
465                 470                 475                 480

Thr Lys Glu Ala Leu Asp Ser Leu Thr Asn Tyr Pro Asp Ile Ile Arg
                485                 490                 495

Trp Ser Ala Thr Ile Phe Arg Leu Asn Asp Asp Leu Gly Thr Ser Ser
            500                 505                 510

Asp Glu Leu Lys Arg Gly Asp Val Ser Lys Ser Ile Gln Cys Tyr Met
            515                 520                 525

Asn Glu Lys Gly Ala Ser Glu Glu Ala Ile Glu His Ile Glu Phe
    530                 535                 540

Leu Ile Gln Glu Thr Trp Glu Ala Met Asn Thr Ala Gln Ser Lys Asn
```

```
                        545                 550                 555                 560

Ser Pro Leu Ser Glu Thr Phe Ile Glu Val Ala Lys Asn Ile Thr Lys
                565                 570                 575

Ala Ser His Phe Met Tyr Leu His Ser Asp Val Lys Ser Ser Ile Ser
            580                 585                 590

Lys Ile Leu Phe Glu Pro Ile Ile Ile Ser Asn Val Ala Phe Ala Leu
        595                 600                 605

Lys

<210> SEQ ID NO 162
<211> LENGTH: 594
<212> TYPE: PRT
<213> ORGANISM: Backhousia citriodora

<400> SEQUENCE: 162

Met Ala Leu Pro Ala Leu Phe Gly Ser Ser Leu Pro Ser Ser Ile Arg
1               5                   10                  15

His Asn Gln Pro Ser Leu Phe Ser Phe Arg His Pro Arg Phe Cys Ser
            20                  25                  30

Ser Ser Ser Ser Ala Ser Phe Ser Ser Gln Phe Ile Leu Cys Ala Ser
        35                  40                  45

Lys Thr Gly Asp Gln Glu Ile Val Arg Arg Ser Ala Asn Trp Gln Pro
    50                  55                  60

Ser Val Trp Asp Tyr Asp Tyr Val Gln Ser Leu Thr Val Asp Tyr Thr
65                  70                  75                  80

Glu Asp Lys Tyr Thr Lys Gln Val Gln Arg Leu Lys Glu Glu Val Lys
                85                  90                  95

Gly Leu Phe Asp Arg Glu Met Lys Gln Val Ala Lys Leu Glu Phe Ile
            100                 105                 110

Asp Val Val Gln Arg Leu Gly Leu Gly Tyr His Phe Lys Thr Glu Ile
        115                 120                 125

Lys Ile Ala Leu Ser Ser Ile His Asn Asn Thr Glu Asp Ala Gln Leu
    130                 135                 140

Ser Asn Asp Leu Tyr Ala Ala Ser Leu Arg Phe Arg Leu Leu Arg Gln
145                 150                 155                 160

Tyr Gly Cys Asn Val Gln Gln Asp Val Phe Gln Arg Phe Met Asn Lys
                165                 170                 175

Thr Gly Thr Phe Lys Glu Ser Leu Asn Lys Asp Val Lys Gly Ile Leu
            180                 185                 190

Gly Leu Tyr Glu Ala Ser Phe His Gly Met Glu Gly Glu Thr Val Leu
        195                 200                 205

Asp Glu Ala Trp Asn Phe Ala Ser Lys His Leu Lys Asp Leu Asn Leu
    210                 215                 220

Asp Glu Val Pro Thr Asn Leu Ala Ser Asn Val Ser His Ala Leu Asp
225                 230                 235                 240

Met Pro Ile His Trp Arg Pro Asn Arg Leu Glu Ala Arg Trp Phe Met
                245                 250                 255

Asp Met Tyr Glu Lys Gln Gln Asp Leu Ile Pro Ser Leu Leu Arg Leu
            260                 265                 270

Ala Lys Leu Asp Phe Asn Ile Val Gln Ser Ile His Arg Lys Glu Val
        275                 280                 285

Ser Asn Leu Ala Arg Trp Trp Val Glu Leu Gly Ala Asn Lys Met Thr
    290                 295                 300

Phe Phe Arg Asp Arg Leu Val Glu Ser Tyr Phe Trp Ser Cys Ile Leu
```

```
              305                 310                 315                 320
Val Phe Glu Pro Gln Tyr Thr Asp Phe Arg Glu Leu Asn Thr Arg Ile
                    325                 330                 335

Ala Cys Met Ala Thr Leu Ile Asp Asp Val Tyr Asp Ile Tyr Gly Thr
                340                 345                 350

Pro Glu Glu Leu Glu Leu Leu Thr Asp Phe Ile Leu Arg Trp Asp Ile
                355                 360                 365

Thr Asp Ile Asp Lys Leu Pro Pro Thr Ile Arg Asn Gly Phe Met Ala
370                 375                 380

Leu Tyr Asn Thr Thr Asn Lys Val Gly Tyr Arg Thr Met Thr Lys Arg
385                 390                 395                 400

Gly Ile Asn Pro Ile Pro Tyr Leu Arg Lys Leu Trp Gly Asp Glu Cys
                405                 410                 415

Lys Ala Asp Met Lys Glu Val His Trp Phe Asn Asn Gly Ile Lys Pro
                420                 425                 430

Thr Leu Lys Glu Tyr Met Asp Val Ala Val Asp Ser Ile Gly Gly Leu
                435                 440                 445

Ile Leu Leu Leu Asn Ser Tyr Phe Leu Thr Thr Asp Tyr Leu Thr Glu
450                 455                 460

Glu Gly Leu Asn Tyr Val Ser Lys Ile Pro Ser Val Met His Ser Ser
465                 470                 475                 480

Ala Gln Ile Phe Arg Phe Asn Asp Asp Leu Ser Thr Ser Ser His Glu
                485                 490                 495

Leu Ala Arg Gly Asp Asn Ser Lys Ala Leu Glu Cys Tyr Met Asn Glu
                500                 505                 510

Thr Gly Ala Ser Glu Glu Ile Ala Arg Glu His Ile Arg His Leu Val
                515                 520                 525

Arg Glu Thr Trp Lys Lys Met Asn Lys Glu Val Phe Glu Asp Tyr Pro
                530                 535                 540

Phe Ser Gly Phe Gly Pro Phe Leu Ser Ala Cys Leu Asn Leu Ala Arg
545                 550                 555                 560

Ala Ser His Cys Phe Tyr Glu Tyr Gly Asp Gly Tyr Gly Leu Pro Asp
                565                 570                 575

His Gln Thr Arg Asp His Leu Ala Ser Thr Ile Phe Glu Ser Val Ser
                580                 585                 590

Leu Asp

<210> SEQ ID NO 163
<211> LENGTH: 567
<212> TYPE: PRT
<213> ORGANISM: Artemisia annua

<400> SEQUENCE: 163

Gly Asn Ala Tyr Met Arg Ile Tyr Ser Thr Lys Thr Thr Arg Ile Thr
1               5                   10                  15

Ala Asn Ala Thr Val Asn Ala Ala Asp Thr His Val Arg Ser Ala
                20                  25                  30

Asn Tyr Lys Pro Ser Ser Trp Ser Phe Asp His Ile Gln Ser Leu Ser
            35                  40                  45

Ser Lys Tyr Thr Gly Asp Asp Tyr Val Ala Arg Ala Asn Thr Leu Lys
        50                  55                  60

Asp Ala Val Lys Thr Met Ile Arg Lys Ser Gly Asn Ser Leu Arg Thr
65                  70                  75                  80

Leu Glu Leu Val Asp Glu Leu Gln Arg Leu Gly Ile Ser Tyr Leu Phe
```

```
                    85                  90                  95
Glu Glu Glu Ile Ser Asn Leu Leu Glu Thr Ile Tyr Tyr Asn Tyr Tyr
                100                 105                 110

Lys Phe Pro Glu Asn Trp Asn Lys Ile Asn Leu Asn Leu Lys Ala Leu
            115                 120                 125

Gly Phe Arg Leu Leu Arg Gln His Gly Tyr His Val Pro Gln Glu Ile
        130                 135                 140

Phe Leu Asn Phe Lys Asp Lys Asn Gln Asn Leu Asn Ser Tyr Leu Leu
145                 150                 155                 160

Asn Asp Val Val Glu Met Leu Asn Leu Tyr Glu Ala Ser Tyr His Ser
                165                 170                 175

Phe Glu Asp Glu Ser Ile Leu Asp Asp Ala Arg Asp Ile Thr Thr Lys
            180                 185                 190

Tyr Leu Lys Glu Ser Leu Glu Lys Ile Asp Gly Ser Ile Phe Ser Ser
        195                 200                 205

Val Thr His Ala Leu Glu Gln Pro Leu His Trp Arg Val Pro Arg Val
    210                 215                 220

Glu Ala Lys Trp Phe Ile Glu Leu Tyr Glu Lys Lys Asn Gly Met Ser
225                 230                 235                 240

Pro Thr Leu Val Glu Leu Ala Lys Leu Asp Phe Asp Met Val Gln Ala
                245                 250                 255

Ile His Leu Glu Asp Leu Lys His Ala Ser Arg Trp Trp Arg Asp Thr
            260                 265                 270

Ser Trp Asp Thr Lys Leu Thr Phe Ala Arg Asp Leu Ile Val Glu Asn
        275                 280                 285

Phe Leu Trp Thr Ile Gly Phe Ser Tyr Leu Pro Asn Phe Ser Arg Gly
290                 295                 300

Arg Arg Thr Ile Thr Lys Val Ala Val Met Ile Thr Thr Leu Asp Asp
305                 310                 315                 320

Val Tyr Asp Val Phe Gly Thr Leu Gly Glu Leu Glu Gln Phe Thr Asp
                325                 330                 335

Val Ile Asn Arg Trp Asp Ile Lys Ala Ile Glu Gln Leu Pro Asp Tyr
            340                 345                 350

Met Lys Ile Cys Phe Leu Gly Leu Tyr Lys Ser Ile Asn Asp Ile Thr
        355                 360                 365

His Glu Thr Leu Ala Asn Lys Gly Phe Leu Ile Leu Pro Tyr Leu Lys
    370                 375                 380

Lys Ala Trp Ala Asp Leu Cys Lys Ala Tyr Leu Val Glu Ala Gln Trp
385                 390                 395                 400

Tyr His Arg Gly His Ile Pro Thr Leu Asn Glu Tyr Leu Asp Asn Ala
                405                 410                 415

Cys Val Ser Ile Ser Gly Pro Val Ala Leu Met His Val His Phe Leu
            420                 425                 430

Thr Ser Val Ser Ser Ile Glu Glu Ile His Gln Cys Ile Gln Arg Thr
        435                 440                 445

Glu Asn Ile Val His Tyr Val Ser Leu Ile Phe Arg Leu Ala Asp Asp
    450                 455                 460

Leu Gly Thr Ser Leu Gly Glu Met Glu Arg Gly Asp Thr Leu Lys Ser
465                 470                 475                 480

Ile Gln Leu His Met His Glu Thr Gly Ala Thr Glu Pro Glu Ala Arg
                485                 490                 495

Ser Tyr Ile Lys Leu Leu Ile Asn Lys Thr Trp Lys Lys Leu Asn Lys
            500                 505                 510
```

```
Glu Arg Ala Thr Val Asn Ser Glu Ser Ser Gln Glu Phe Ile Asp Tyr
            515                 520                 525

Ala Thr Asn Leu Val Arg Met Ala Gln Phe Met Tyr Gly Glu Gly Asp
            530                 535                 540

Glu Asp Phe Gly Leu Asp Val Ile Lys Ser His Val Leu Ser Leu Leu
545                 550                 555                 560

Phe Thr Pro Ile Gln Gly Ile
                565
```

<210> SEQ ID NO 164
<211> LENGTH: 583
<212> TYPE: PRT
<213> ORGANISM: Artemisia annua

<400> SEQUENCE: 164

```
Met Ala Ser Ile Ser Leu Phe Pro Tyr Ser Ile Leu Lys Gln Thr Ser
1               5                   10                  15

Pro Leu Ala Arg Gly Thr Ala Tyr Asn Arg Ile Tyr Ser Thr Lys Thr
            20                  25                  30

Thr Gly Ile Thr Val Asp Val Ala Glu Ser His Val Arg Arg Ser Ala
            35                  40                  45

Asn Tyr Glu Pro Ser Ser Trp Ser Phe Asp His Ile Gln Ser Leu Ser
50                  55                  60

Ser Lys Tyr Thr Gly Asp Asp Cys Val Ala Arg Ala Asn Thr Leu Lys
65                  70                  75                  80

Glu Ser Val Lys Thr Met Ile Arg Lys Glu Gly Asn Leu Leu Arg Thr
                85                  90                  95

Leu Glu Leu Val Asp Glu Leu Gln Arg Leu Gly Ile Ser Tyr Leu Phe
            100                 105                 110

Glu Gly Glu Ile Ser Asn Leu Leu Glu Thr Ile Tyr Tyr Asn His Tyr
            115                 120                 125

Lys Phe Pro Glu Lys Trp Asn Lys Phe Asp Leu Asn Leu Lys Ala Leu
130                 135                 140

Gly Phe Arg Leu Leu Arg Gln His Gly Tyr His Val Pro Gln Glu Ile
145                 150                 155                 160

Phe Leu Asn Phe Lys Asp Lys Asn Gln Asn Leu Asn Ser Tyr Leu Leu
                165                 170                 175

Glu Asp Val Val Gly Met Leu Asn Leu Tyr Glu Ala Ser Tyr His Ser
            180                 185                 190

Phe Glu Asp Glu Ser Ile Leu Thr Glu Ala Arg Asp Ile Ala Thr Lys
            195                 200                 205

Tyr Leu Lys Ala Ser Leu Glu Lys Ile Asp Gly Ser Ile Leu Ser Leu
210                 215                 220

Val Ser His Ala Leu Asp Asn Arg Leu His Trp Arg Val Pro Arg Val
225                 230                 235                 240

Glu Ser Lys Trp Phe Ile Glu Val Tyr Glu Lys Arg Val Gly Ala Ser
                245                 250                 255

Pro Thr Leu Ile Glu Leu Ala Lys Leu Asp Phe Asp Met Val Gln Ala
            260                 265                 270

Ile His Leu Glu Asp Leu Lys His Ala Ser Arg Trp Trp Arg Asn Thr
            275                 280                 285

Ser Trp Asp Thr Lys Leu Thr Phe Ala Arg Asp Met Leu Val Glu Asn
290                 295                 300

Phe Leu Trp Thr Val Gly Phe Ser Tyr Leu Pro Asn Phe Ser His Gly
```

```
              305                 310                 315                 320
        Arg Arg Thr Ile Thr Lys Val Ala Ala Met Ile Thr Thr Leu Asp Asp
                        325                 330                 335

Val Tyr Asp Val Phe Gly Thr Leu Gly Glu Leu Glu Gln Phe Thr Asp
                        340                 345                 350

Val Ile Asn Arg Trp Asp Ile Lys Ala Ile Glu Gln Leu Pro Asp Tyr
                        355                 360                 365

Met Lys Ile Cys Phe Phe Gly Leu Tyr Asn Ser Ile Asn Asp Ile Thr
                        370                 375                 380

Tyr Glu Thr Leu Ala Thr Lys Gly Phe Leu Ile Leu Pro Tyr Ile Lys
        385                 390                 395                 400

Lys Ala Trp Ala Asp Leu Cys Lys Ser Tyr Leu Val Glu Ala Gln Trp
                        405                 410                 415

Tyr His Arg Gly His Ile Pro Thr Leu Asn Glu Tyr Leu Asp Asn Ala
                        420                 425                 430

Cys Val Ser Ile Ser Gly Pro Val Ala Leu Met His Val His Phe Leu
                        435                 440                 445

Thr Ser Val Ser Ser Thr Lys Glu Ile His His Cys Ile Glu Arg Thr
                        450                 455                 460

Gln Asn Ile Val Arg Tyr Val Ser Leu Ile Phe Arg Leu Thr Asp Asp
        465                 470                 475                 480

Leu Gly Thr Ser Leu Gly Glu Met Glu Arg Gly Asp Thr Leu Lys Ser
                        485                 490                 495

Ile Gln Leu Tyr Met His Glu Thr Gly Ala Thr Glu Pro Glu Ala Arg
                        500                 505                 510

Ser Tyr Ile Lys Ser Leu Ile Asp Lys Thr Trp Lys Lys Leu Asn Lys
                        515                 520                 525

Glu Arg Ala Ile Val Ser Ser Glu Ser Ser Arg Glu Phe Ile Asp Tyr
                        530                 535                 540

Ala Thr Asn Leu Ala Arg Met Ala His Phe Met Tyr Gly Glu Gly Asp
        545                 550                 555                 560

Glu Asp Phe Arg Leu Asp Val Ile Lys Ser His Val Ser Ser Leu Leu
                        565                 570                 575

Phe Thr Pro Ile Gln Gly Ile
                        580

<210> SEQ ID NO 165
<211> LENGTH: 574
<212> TYPE: PRT
<213> ORGANISM: Actinidia arguta

<400> SEQUENCE: 165

Met Ala Ser Phe Asn Arg Phe Cys Val Ser Ser Leu Leu Ala Pro Asn
        1               5                   10                  15

Asn Ser Pro Gln Ile Ser Asn Ala Pro Arg Ser Thr Ala Val Pro Ser
                        20                  25                  30

Met Pro Thr Thr Gln Lys Trp Ser Ile Thr Glu Asp Leu Ala Phe Ile
                        35                  40                  45

Ser Asn Pro Ser Lys Gln His Asn His Gln Thr Gly Tyr Arg Ile Phe
                        50                  55                  60

Ser Asp Glu Phe Tyr Leu Lys His Glu Asn Lys Leu Lys Asp Val Arg
        65                  70                  75                  80

Arg Ala Leu Arg Glu Val Glu Glu Thr Pro Leu Glu Gly Leu Val Met
                        85                  90                  95
```

```
Ile Asp Thr Leu Gln Arg Leu Gly Ile Asp Tyr His Phe Gln Gly Glu
            100                 105                 110

Ile Gly Ala Leu Leu Gln Lys Gln Gln Arg Ile Ser Thr Cys Asp Tyr
            115                 120                 125

Pro Glu His Asp Leu Phe Glu Val Ser Thr Arg Phe Arg Leu Leu Arg
            130                 135                 140

Gln Glu Gly His Asn Val Pro Ala Asp Val Phe Asn Asn Phe Arg Asp
145                 150                 155                 160

Lys Glu Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
            195                 200                 205

Thr Asn Leu Asp His His Gln Ala Arg Leu Val Arg Asn Ala Leu Thr
            210                 215                 220

His Pro Tyr His Lys Ser Leu Ala Thr Phe Met Ala Arg Asn Phe Asn
225                 230                 235                 240

Tyr Asp Cys Lys Gly Gln Asn Gly Trp Val Asn Asn Leu Gln Glu Leu
                245                 250                 255

Ala Lys Met Asp Leu Thr Met Val Gln Ser Met His Gln Lys Glu Val
            260                 265                 270

Leu Gln Val Ser Gln Trp Trp Lys Gly Arg Gly Leu Ala Asn Glu Leu
            275                 280                 285

Lys Leu Val Arg Asn Gln Pro Leu Lys Trp Tyr Met Trp Pro Met Ala
            290                 295                 300

Ala Leu Thr Asp Pro Arg Phe Ser Glu Glu Arg Val Glu Leu Thr Lys
305                 310                 315                 320

Pro Ile Ser Phe Ile Tyr Ile Ile Asp Asp Ile Phe Asp Val Tyr Gly
                325                 330                 335

Thr Leu Glu Glu Leu Thr Leu Phe Thr Asp Ala Val Asn Arg Trp Glu
            340                 345                 350

Leu Thr Ala Val Glu Gln Leu Pro Asp Tyr Met Lys Ile Cys Phe Lys
            355                 360                 365

Ala Leu Tyr Asp Ile Thr Asn Glu Ile Ala Tyr Lys Ile Tyr Lys Lys
            370                 375                 380

His Gly Arg Asn Pro Ile Asp Ser Leu Arg Arg Thr Trp Ala Ser Leu
385                 390                 395                 400

Cys Asn Ala Phe Leu Glu Glu Ala Lys Trp Phe Ala Ser Gly Asn Leu
                405                 410                 415

Pro Lys Ala Glu Glu Tyr Leu Lys Asn Gly Ile Ile Ser Ser Gly Met
            420                 425                 430

His Val Val Thr Val His Met Phe Phe Leu Leu Gly Gly Cys Phe Thr
            435                 440                 445

Glu Glu Ser Val Asn Leu Val Asp Glu His Ala Gly Ile Thr Ser Ser
            450                 455                 460

Ile Ala Thr Ile Leu Arg Leu Ser Asp Asp Leu Gly Ser Ala Lys Asp
465                 470                 475                 480

Glu Asp Gln Asp Gly Tyr Asp Gly Ser Tyr Leu Glu Cys Tyr Leu Lys
                485                 490                 495

Asp His Lys Gly Ser Ser Val Glu Asn Ala Arg Glu Glu Val Ile Arg
            500                 505                 510

Met Ile Ser Asp Ala Trp Lys Arg Leu Asn Glu Glu Cys Leu Phe Pro
```

515                 520                 525
Asn Pro Phe Ser Ala Thr Phe Arg Lys Gly Ser Leu Asn Ile Ala Arg
                530                 535                 540

Met Val Pro Leu Met Tyr Ser Tyr Asp Asp Asn His Asn Leu Pro Ile
545                 550                 555                 560

Leu Glu Glu His Met Lys Thr Met Leu Tyr Asp Ser Ser Ser
                565                 570

<210> SEQ ID NO 166
<211> LENGTH: 574
<212> TYPE: PRT
<213> ORGANISM: Actinidia polygama

<400> SEQUENCE: 166

Met Ala Ser Phe His Arg Phe Cys Val Ser Ser Leu Leu Val Pro Asn
1               5                   10                  15

Asn Ser Pro Gln Ile Ser Asn Ala Tyr Arg Ala Pro Ala Val Pro Ser
                20                  25                  30

Met Pro Thr Thr Gln Lys Trp Ser Ile Thr Glu Asp Leu Ala Phe Ile
            35                  40                  45

Ser Asn Pro Ser Lys Gln His Asn His Gln Thr Gly Tyr Arg Thr Phe
    50                  55                  60

Ser Asp Glu Phe Tyr Val Lys Arg Glu Lys Lys Leu Lys Asp Val Arg
65                  70                  75                  80

Arg Ala Leu Arg Glu Val Glu Thr Pro Leu Glu Gly Leu Val Met
                85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Gln Arg Lys Ser Lys Cys Asp Tyr
        115                 120                 125

Pro Glu His Asp Leu Phe Glu Val Ser Thr Arg Phe Arg Leu Leu Arg
    130                 135                 140

Gln Glu Gly His Asn Val Pro Ala Asp Val Phe Asn His Phe Arg Asp
145                 150                 155                 160

Lys Lys Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
        195                 200                 205

Thr Asn Pro Asp His His Gln Ala Arg Leu Val Arg Asn Ala Leu Thr
    210                 215                 220

His Pro Tyr His Lys Ser Leu Ala Thr Phe Thr Ala Arg Asn Phe His
225                 230                 235                 240

Tyr Asp Cys Lys Gly Gln Asn Gly Trp Val Asn Asn Leu Gln Glu Leu
                245                 250                 255

Ala Lys Met Asp Leu Thr Val Val Gln Ser Met His Gln Lys Glu Val
            260                 265                 270

Leu Gln Val Ser Gln Trp Trp Lys Asp Arg Gly Leu Ala Asn Glu Leu
        275                 280                 285

Lys Leu Val Arg Asn Gln Pro Leu Lys Trp Tyr Met Trp Pro Met Ala
    290                 295                 300

Ala Leu Thr Asp Pro Arg Phe Ser Glu Glu Arg Val Glu Leu Thr Lys
305                 310                 315                 320

-continued

```
Pro Ile Ser Phe Ile Tyr Ile Ile Asp Asp Ile Phe Asp Val Tyr Gly
            325                 330                 335

Thr Leu Glu Glu Leu Thr Leu Phe Thr Asp Ala Val Asn Arg Trp Glu
        340                 345                 350

Leu Thr Ala Val Glu Gln Leu Pro Asp Tyr Met Lys Val Cys Phe Lys
    355                 360                 365

Ala Leu Tyr Asp Ile Thr Asn Glu Ile Ala Tyr Lys Ile Tyr Lys Lys
370                 375                 380

His Gly Trp Asn Pro Ile Asp Ser Leu Arg Arg Met Trp Ala Ser Leu
385                 390                 395                 400

Cys Asn Ala Phe Leu Val Glu Ala Lys Trp Phe Ala Ser Gly His Leu
                405                 410                 415

Pro Lys Ala Glu Glu Tyr Leu Lys Asn Gly Ile Ile Ser Ser Gly Met
            420                 425                 430

His Val Val Thr Val His Met Phe Phe Leu Leu Gly Gly Cys Phe Thr
        435                 440                 445

Asp Glu Ser Val Asn Leu Val Asp Glu His Ala Gly Ile Thr Ser Ser
    450                 455                 460

Ile Ala Thr Ile Leu Arg Leu Ser Asp Asp Leu Gly Ser Ala Lys Asp
465                 470                 475                 480

Glu Asp Gln Asp Gly Tyr Asp Gly Ser Tyr Val Glu Tyr Tyr Leu Lys
                485                 490                 495

Asp His Lys Gly Ser Ser Val Glu Asn Ala Arg Glu Glu Val Ile Arg
            500                 505                 510

Met Ile Ser Asp Ala Trp Lys Arg Leu Asn Glu Glu Cys Leu Ser Pro
        515                 520                 525

Asn Pro Phe Ser Ala Thr Phe Arg Lys Gly Cys Leu Asn Ile Ala Arg
    530                 535                 540

Met Val Pro Leu Met Tyr Ser Tyr Asp Asp Asn His Asn Leu Pro Leu
545                 550                 555                 560

Leu Glu Glu His Met Lys Ala Met Leu Tyr Asp Ser Ser Ser
                565                 570

<210> SEQ ID NO 167
<211> LENGTH: 604
<212> TYPE: PRT
<213> ORGANISM: Perilla frutescens var. hirtella

<400> SEQUENCE: 167

Met Ser Ser Met Arg Ile Tyr Val Ala Ile Met Lys Lys Pro Ser Val
1               5                   10                  15

Lys His Val Asp Tyr Val Asp Lys Lys Ala Ser Lys Pro Ser Trp Arg
            20                  25                  30

Val Ser Ser Ala Thr Ala Gly Leu Arg Ala Ser Ser Ser Leu Gln
        35                  40                  45

Leu Asp Val Lys Lys Pro Ala Asp Glu Ile Leu Thr Ala Arg Arg Ser
    50                  55                  60

Gly Asn Tyr Gln Pro Ser Leu Trp Asp Phe Asn Tyr Leu Gln Ser Leu
65                  70                  75                  80

Asn Thr Thr His Tyr Lys Glu Glu Arg His Leu Lys Arg Glu Ala Glu
                85                  90                  95

Leu Ile Glu Gln Val Lys Met Leu Leu Asp Glu Glu Met Gly Ala Val
            100                 105                 110

Gln Lys Leu Asp Leu Val Asp Asp Leu Lys Asn Leu Gly Leu Ser Tyr
        115                 120                 125
```

-continued

Phe Phe Glu Asp Gln Ile Lys Gln Ile Leu Thr Phe Ile Tyr Asn Glu
    130                 135                 140

His Glu Cys Phe Arg Ser Asn Val Glu Ala Lys Glu Arg Asp Leu Tyr
145                 150                 155                 160

Phe Thr Ala Leu Gly Phe Arg Leu Leu Arg Gln His Gly Phe Gln Val
                165                 170                 175

Ser Gln Glu Val Phe Asp Cys Phe Lys Asn Glu Glu Gly Ser Asp Phe
            180                 185                 190

Lys Ala Ser Leu Gly Asp Asp Thr Lys Gly Leu Val Gln Leu Tyr Glu
                195                 200                 205

Ala Ser Phe Leu Leu Arg Glu Gly Glu Asp Thr Leu Glu Leu Ala Arg
210                 215                 220

Gln Tyr Ala Thr Lys Phe Leu Gln Lys Lys Val Asp His Glu Leu Ile
225                 230                 235                 240

Asp Asp Asp Ser Asn Leu Leu Ser Trp Ile Arg His Ser Leu Glu Ile
                245                 250                 255

Pro Leu His Trp Arg Ile Gln Arg Leu Glu Ala Arg Trp Phe Leu Asp
                260                 265                 270

Ala Tyr Ala Thr Arg His Asp Val Asn Pro Ile Ile Leu Glu Leu Ala
                275                 280                 285

Lys Leu Asp Phe Asn Ile Ile Gln Ala Thr Gln Gln Glu Glu Leu Lys
    290                 295                 300

Asp Leu Ser Arg Trp Trp Asn Ser Thr Cys Leu Val Glu Lys Leu Pro
305                 310                 315                 320

Phe Val Arg Asp Arg Leu Val Glu Ser Tyr Phe Trp Ala Ile Ala Leu
                325                 330                 335

Phe Glu Pro His Gln Tyr Gly Tyr His Arg Lys Ile Ala Ala Lys Ile
                340                 345                 350

Ile Thr Leu Ile Thr Ser Leu Asp Asp Val Tyr Asp Ile Tyr Gly Thr
            355                 360                 365

Leu Asp Glu Leu Gln Leu Phe Thr Asp Ala Ile Gln Arg Trp Asp Thr
    370                 375                 380

Glu Ser Ile Ser Arg Leu Ala Tyr Tyr Met Gln Leu Phe Tyr Met Val
385                 390                 395                 400

Leu Tyr Asn Phe Val Ser Glu Leu Ala Tyr Asp Gly Leu Lys Glu Lys
                405                 410                 415

Gly Phe Ile Thr Ile Pro Tyr Leu Gln Arg Ser Trp Ala Asp Leu Val
                420                 425                 430

Glu Ala Tyr Leu Lys Glu Ala Lys Trp Phe Tyr Asn Gly Tyr Thr Pro
            435                 440                 445

Ser Met Glu Glu Tyr Leu Asn Asn Ala Tyr Ile Ser Ile Gly Ala Thr
    450                 455                 460

Pro Val Ile Ser Gln Val Phe Phe Thr Leu Ala Thr Ser Ile Asp Lys
465                 470                 475                 480

Pro Val Ile Glu Ser Leu Tyr Glu Tyr His Arg Ile Leu Arg Leu Ser
                485                 490                 495

Gly Met Leu Val Arg Leu Pro Asp Asp Leu Gly Thr Ser Pro Phe Glu
                500                 505                 510

Met Lys Arg Gly Asp Val Pro Lys Thr Ile Glu Leu Tyr Met Lys Glu
    515                 520                 525

Arg Asn Ala Thr Glu Ile Glu Ala Gln Glu His Val Arg Phe Leu Ile
530                 535                 540

```
Arg Glu Ala Trp Arg Glu Met Asn Thr Ala Thr Ala Ala Asp Cys
545                 550                 555                 560

Pro Phe Thr Asp Asp Leu Val Ala Ala Ala Asn Leu Gly Arg Ala
                565                 570                 575

Ala Gln Phe Met Tyr Leu Asp Gly Asp Gly Asn His Ser Gln Leu His
            580                 585                 590

Gln Arg Ile Ala Ser Leu Leu Phe Glu Pro Tyr Ala
        595                 600

<210> SEQ ID NO 168
<211> LENGTH: 603
<212> TYPE: PRT
<213> ORGANISM: Perilla setoensis

<400> SEQUENCE: 168

Met Ser Ser Met Arg Thr Tyr Val Ala Ile Met Lys Lys Pro Ser Val
1               5                   10                  15

Glu His Val Asp Asn Val Asp Lys Lys Ala Ser Lys Pro Ser Trp Arg
                20                  25                  30

Val Ser Leu Ser Ala Gly Leu Arg Ser Ser Cys Ser Leu Gln Leu Glu
            35                  40                  45

Val Lys Pro Ala Asp Gln Ile Leu Thr Ala Arg Arg Ser Gly Asn Tyr
50                  55                  60

Gln Pro Ser Leu Trp Asp Phe Asn Tyr Leu Gln Ser Leu Asn Thr Thr
65                  70                  75                  80

His Tyr Lys Glu Val Arg His Leu Lys Arg Glu Ala Glu Leu Ile Glu
                85                  90                  95

Gln Val Lys Met Leu Leu Glu Glu Met Glu Ala Val Gln Gln Leu
                100                 105                 110

Glu Leu Val Asp Asp Leu Lys Asn Leu Gly Leu Ser Tyr Phe Phe Glu
            115                 120                 125

Asp Gln Ile Lys Gln Ile Leu Thr Phe Ile Tyr Asn Glu His Lys Cys
        130                 135                 140

Phe His Ser Asn Ser Ile Ile Glu Ala Glu Glu Ile Arg Asp Leu Tyr
145                 150                 155                 160

Phe Thr Ala Leu Gly Phe Arg Leu Leu Arg Gln His Gly Phe Gln Ile
                165                 170                 175

Ser Gln Glu Val Phe Asp Cys Phe Lys Asn Glu Glu Gly Ser Asp Phe
            180                 185                 190

Lys Ala Arg Leu Gly Asp Asp Thr Lys Gly Leu Leu Gln Leu Tyr Glu
        195                 200                 205

Ala Ser Phe Leu Leu Arg Glu Gly Glu Asp Thr Leu Glu Leu Ala Arg
210                 215                 220

Gln Tyr Ala Thr Lys Phe Leu Gln Lys Val Asp His Glu Leu Ile
225                 230                 235                 240

Asp Asp Asn Asn Leu Leu Ser Trp Ile Leu His Ser Leu Glu Ile Pro
                245                 250                 255

Leu His Trp Arg Ile Gln Arg Leu Glu Ala Arg Trp Phe Leu Asp Ala
            260                 265                 270

Tyr Ala Ser Arg Arg Asp Met Asn Gln Ile Ile Leu Glu Leu Ala Lys
        275                 280                 285

Leu Asp Phe Asn Ile Ile Gln Ala Thr Gln Gln Glu Glu Leu Lys Asp
290                 295                 300

Leu Ser Arg Trp Trp Lys Ser Ser Cys Leu Ala Glu Lys Leu Pro Phe
305                 310                 315                 320
```

```
Val Arg Asp Arg Leu Val Glu Ser Tyr Phe Trp Ala Ile Ala Leu Phe
            325                 330                 335

Glu Pro His Gln Tyr Gly Tyr His Arg Lys Ile Ala Ala Lys Ile Ile
            340                 345                 350

Thr Leu Ile Thr Ser Leu Asp Asp Val Tyr Asp Ile Tyr Gly Thr Leu
            355                 360                 365

Asp Glu Leu Gln Leu Phe Thr Asp Ala Ile Gln Arg Trp Asp Thr Glu
            370                 375                 380

Ser Ile Ser Arg Leu Pro Tyr Tyr Met Gln Leu Phe Tyr Met Val Leu
385                 390                 395                 400

Tyr Asn Phe Val Pro Arg Leu Ala Tyr Asp Gly Leu Lys Glu Lys Gly
                405                 410                 415

Phe Ile Thr Ile Pro Tyr Leu Gln Arg Ser Trp Ala Asp Leu Val Glu
                420                 425                 430

Ala Tyr Leu Lys Glu Ala Lys Trp Tyr Tyr Asn Gly Tyr Thr Pro Ser
            435                 440                 445

Met Glu Glu Tyr Leu Asn Asn Ala Tyr Ile Ser Ile Gly Ala Thr Pro
            450                 455                 460

Val Ile Ser Gln Val Phe Phe Thr Leu Ala Thr Ser Ile Asp Lys Pro
465                 470                 475                 480

Val Ile Asp Ser Leu Tyr Glu Tyr His Arg Ile Leu Arg Leu Ser Gly
                485                 490                 495

Ile Leu Val Arg Leu Pro Asp Asp Leu Gly Thr Ser Pro Phe Glu Met
                500                 505                 510

Lys Arg Gly Asp Val Pro Lys Ala Ile Gln Leu Tyr Met Lys Glu Arg
            515                 520                 525

Asn Ala Thr Glu Ile Glu Ala Gln His Val Arg Phe Leu Ile Arg
            530                 535                 540

Glu Ala Trp Lys Glu Met Asn Thr Ala Thr Ala Ala Val Asp Cys Pro
545                 550                 555                 560

Phe Thr Asp Asp Leu Val Thr Ala Ala Ala Asn Leu Gly Arg Ala Ala
                565                 570                 575

Gln Phe Met Tyr Leu Asp Gly Asp Gly Asn His Ser Gly Leu His Gln
            580                 585                 590

Arg Ile Ala Cys Leu Leu Phe Glu Pro Tyr Ala
            595                 600

<210> SEQ ID NO 169
<211> LENGTH: 547
<212> TYPE: PRT
<213> ORGANISM: Arabidopsis thaliana

<400> SEQUENCE: 169

Met Arg Arg Ser Ala Asn Tyr Gln Pro Ser Arg Trp Asp His His His
1               5                   10                  15

Leu Leu Ser Val Glu Asn Lys Phe Ala Lys Asp Lys Arg Val Arg Glu
            20                  25                  30

Arg Asp Leu Leu Lys Glu Lys Val Arg Lys Met Leu Asn Asp Glu Gln
        35                  40                  45

Lys Thr Tyr Leu Asp Gln Leu Glu Phe Ile Asp Asp Leu Gln Lys Leu
    50                  55                  60

Gly Val Ser Tyr His Phe Glu Ala Glu Ile Asp Asn Ile Leu Thr Ser
65                  70                  75                  80

Ser Tyr Lys Lys Asp Arg Thr Asn Ile Gln Glu Ser Asp Leu His Ala
```

```
                    85                  90                  95
Thr Ala Leu Glu Phe Arg Leu Phe Arg Gln His Gly Phe Asn Val Ser
                100                 105                 110
Glu Asp Val Phe Asp Val Phe Met Glu Asn Cys Gly Lys Phe Asp Arg
                115                 120                 125
Asp Asp Ile Tyr Gly Leu Ile Ser Leu Tyr Glu Ala Ser Tyr Leu Ser
            130                 135                 140
Thr Lys Leu Asp Lys Asn Leu Gln Ile Phe Ile Arg Pro Phe Ala Thr
145                 150                 155                 160
Gln Gln Leu Arg Asp Phe Val Asp Thr His Ser Asn Glu Asp Phe Gly
                165                 170                 175
Ser Cys Asp Met Val Glu Ile Val Gln Ala Leu Asp Met Pro Tyr
                180                 185                 190
Tyr Trp Gln Met Arg Arg Leu Ser Thr Arg Trp Tyr Ile Asp Val Tyr
                195                 200                 205
Gly Lys Arg Gln Asn Tyr Lys Asn Leu Val Val Glu Phe Ala Lys
            210                 215                 220
Ile Asp Phe Asn Ile Val Gln Ala Ile His Gln Glu Leu Lys Asn
225                 230                 235                 240
Val Ser Ser Trp Trp Met Glu Thr Gly Leu Gly Lys Gln Leu Tyr Phe
                245                 250                 255
Ala Arg Asp Arg Ile Val Glu Asn Tyr Phe Trp Thr Ile Gly Gln Ile
                260                 265                 270
Gln Glu Pro Gln Tyr Gly Tyr Val Arg Gln Thr Met Thr Lys Ile Asn
            275                 280                 285
Ala Leu Leu Thr Thr Ile Asp Asp Ile Tyr Asp Ile Tyr Gly Thr Leu
            290                 295                 300
Glu Glu Leu Gln Leu Phe Thr Val Ala Phe Glu Asn Trp Asp Ile Asn
305                 310                 315                 320
Arg Leu Asp Glu Leu Pro Glu Tyr Met Arg Leu Cys Phe Leu Val Ile
                325                 330                 335
Tyr Asn Glu Val Asn Ser Ile Ala Cys Glu Ile Leu Arg Thr Lys Asn
                340                 345                 350
Ile Asn Val Ile Pro Phe Leu Lys Lys Ser Trp Thr Asp Val Ser Lys
            355                 360                 365
Ala Tyr Leu Val Glu Ala Lys Trp Tyr Lys Ser Gly His Lys Pro Asn
            370                 375                 380
Leu Glu Glu Tyr Met Gln Asn Ala Arg Ile Ser Ile Ser Ser Pro Thr
385                 390                 395                 400
Ile Phe Val His Phe Tyr Cys Val Phe Ser Asp Gln Leu Ser Ile Gln
                405                 410                 415
Val Leu Glu Thr Leu Ser Gln His Gln Asn Val Val Arg Cys Ser
                420                 425                 430
Ser Ser Val Phe Arg Leu Ala Asn Asp Leu Val Thr Ser Pro Asp Glu
            435                 440                 445
Leu Ala Arg Gly Asp Val Cys Lys Ser Ile Gln Cys Tyr Met Ser Glu
            450                 455                 460
Thr Gly Ala Ser Glu Asp Lys Ala Arg Ser His Val Arg Gln Met Ile
465                 470                 475                 480
Asn Asp Leu Trp Asp Glu Met Asn Tyr Glu Lys Met Ala His Ser Ser
                485                 490                 495
Ser Ile Leu His His Asp Phe Met Glu Thr Val Ile Asn Leu Ala Arg
            500                 505                 510
```

```
Met Ser Gln Cys Met Tyr Gln Tyr Gly Asp Gly His Gly Ser Pro Glu
        515                 520                 525

Lys Ala Lys Ile Val Asp Arg Val Met Ser Leu Leu Phe Asn Pro Ile
        530                 535                 540

Pro Leu Asp
545

<210> SEQ ID NO 170
<211> LENGTH: 1644
<212> TYPE: DNA
<213> ORGANISM: Arabidopsis thaliana

<400> SEQUENCE: 170
atgcgtcgtt ctgcgaacta tcagccttct cgttgggacc atcaccatct cctctcggtc      60
gaaaataaat ttgcgaaaga taaagggta cgagagagag atttgttgaa ggaaaaagtg     120
agaaagatgc tcaatgatga gcaaaagact tatcttgacc aattggagtt cattgacgat     180
ctacaaaaac tcggggttc ttatcatttt gaagcggaaa tcgacaacat tttaacatct     240
tcttataaaa aagatagaac aaacatccag gagagtgacc tacatgccac cgcactcgag     300
ttccgacttt tcaggcaaca tggtttcaat gtttcagaag atgtattcga tgttttcatg     360
gaaaattgtg ggaagtttga ccgtgatgat atatatggtt taatatctct ttacgaagca     420
tcatatcttt cgacaaaatt ggataaaaac ctgcaaatat tcatcagacc ttttgctaca     480
caacaactca gagactttgt tgatactcat agtaatgaag attttgggtc gtgtgacatg     540
gtggaaattg tggtccaagc gttggatatg ccctactatt ggcaaatgag aaggctatcc     600
accagatggt acatagatgt gtatggaaaa agacaaaatt ataagaaccct tgtcgtcgtt     660 gaatttgcca agattgattt caacatcgta caagctattc atcaagagga actcaaaaac     720
gtttccagct ggtggatgga acaggtttta ggtaagcaac tctactttgc aagagacaga     780
atagtggaga ttattttctg gacgattgga caaatccaag agcctcaata cggatacgtt     840
cgacaaacaa tgacgaaaat aaatgcactc cttactacaa ttgatgatat ctacgatatc     900
tatggcactc ttgaagaact tcagcttttc actgtcgcgt ttgaaaactg ggatataaat     960
cgtcttgatg aactccccga gtacatgagg ttgtgttttc ttgttatata caatgaagtc    1020
aatagcattg catgtgagat tctcagaact aaaaatatca acgtgatccc attcctcaaa    1080
aaatcttgga cagatgtatc caaagcgtat ttagtagaag caaagtggta caaaagtggt    1140
cacaaaccaa atttggaaga gtacatgcaa aatgctcgga tttcaatctc gtccccaacg    1200
atatttgttc acttctactg cgtattctcc gaccagctct ctattcaggt cttggagact    1260
ttgtcccaac accaacaaaa cgtcgtccga tgctcctcct cagtgttccg tctagccaac    1320
gaccttgtaa cctcaccgga tgaattggcg agaggagacg tctgcaaatc catccaatgt    1380
tacatgagtg aaactggagc atcagaggat aaggcgcgtt cgcatgttcg acagatgatc    1440
aatgacttgt gggatgaaat gaattatgag aaaatggcac atagctcttc gatactccat    1500
catgatttta tggaaacagt gataaatttg gcacgcatgt ctcaatgcat gtatcaatat    1560
ggcgatggcc atggctctcc cgaaaaagcc aaaatcgttg atcgtgtcat gtccttactc    1620
ttcaatccga ttcctttaga ttga                                            1644

<210> SEQ ID NO 171
<211> LENGTH: 1644
<212> TYPE: DNA
<213> ORGANISM: Artificial Sequence
```

<220> FEATURE:
<223> OTHER INFORMATION: DNA having modified codons, which encodes linalool synthase gene derived from Arabidopsis thaliana

<400> SEQUENCE: 171

```
atgcgtcgta gtgcgaatta ccagccgagt cgttgggacc atcatcacct gctgagtgtg      60
gagaataagt ttgcgaagga caagcgtgtc cgcgaacgcg acctgctgaa agaaaaggtt     120
cgcaaaatgc tgaatgacga acagaagacc tacctggatc agctggaatt tattgatgac     180
ctgcagaaac tgggcgtcag ctaccatttt gaagccgaaa ttgataatat cctgaccagc     240
agctacaaaa aggaccgcac gaatatccag gaaagcgatc tgcatgccac ggcgctggaa     300
tttcgcctgt ttcgccagca cggctttaat gttagcgaag atgtgtttga cgtctttatg     360
gaaaattgtg gcaagtttga ccgcgatgac atctacggcc tgattagcct gtacgaagcc     420
agctacctga gcaccaaact ggataagaat ctgcagattt ttattcgtcc ctttgccacc     480
cagcagctgc gtgattttgt tgacacgcat agcaatgaag attttggcag ctgcgacatg     540
gtggaaattg ttgtgcaggc cctggacatg ccctactact ggcagatgcg ccgcctgagc     600
acccgttggt acatcgatgt gtacggcaaa cgccagaatt acaagaatct ggtcgttgtg     660
gaatttgcca aaatcgactt taatattgtg caggcgatcc accaggaaga actgaaaaat     720
gtcagcagtt ggtggatgga aaccggcctg gcaagcagc tgtactttgc gcgcgatcgc     780
attgtcgaaa attacttttg acgattggc cagatccagg aaccgcagta cggctacgtt     840
cgccagacca tgacgaagat caatgccctg ctgaccacga ttgatgacat ctacgatatt     900
tacggcaccc tggaagaact gcagctgttt acggttgcgt ttgaaaattg ggatattaat     960
cgcctggacg aactgccgga atacatgcgc ctgtgttttc tggttatcta caatgaagtg    1020
aatagcattg cctgcgaaat cctgcgcacc aagaacatca cgtgatccc ctttctgaaa    1080
aagagctgga cggacgtgag caaagcctac ctggtcgaag cgaaatggta caagagcggc    1140
cataagccga atctggaaga atacatgcag aatgcgcgca ttagcatcag cagccccacc    1200
atctttgtcc attttactg tgtttttagc gatcagctga gcatccaggt gctggaaacg    1260
ctgagccagc accagcagaa tgtcgttcgc tgcagcagca gcgttttcg cctggccaat    1320
gatctggtga ccagccccga tgaactggcc cgcggcgatg tgtgtaaaag cattcagtgc    1380
tacatgagcg aaacgggtgc cagcgaagat aaggcccgca gccatgtccg ccagatgatc    1440
aatgatctgt gggacgaaat gaattacgaa aaaatggccc acagcagcag cattctgcat    1500
cacgacttta tggaaaccgt tatcaatctg gcgcgcatga gccagtgtat gtaccagtac    1560
ggtgatggtc atggcagccc cgaaaaagcc aaaatcgtgg accgtgtgat gagcctgctg    1620
tttaacccta tcccgctgga ctaa                                            1644
```

<210> SEQ ID NO 172
<211> LENGTH: 607
<212> TYPE: PRT
<213> ORGANISM: Perilla frutescens var. crispa

<400> SEQUENCE: 172

```
Met Tyr Ser Leu Arg Ile Tyr Val Ala Ile Met Lys Lys Pro Ser Ala
1               5                   10                  15

Lys His Val Asp Asn Val Asp Lys Lys Ala Ser Lys Pro Ser Trp Arg
            20                  25                  30

Val Ser Leu Ser Ser Ser Ala Gly Leu Arg Ala Ser Ser Ser Leu Gln
        35                  40                  45
```

```
Leu Asp Val Lys Lys Pro Ala Asp Asp Glu Ile Leu Thr Ala Arg Arg
 50                  55                  60

Ser Gly Asn Tyr Gln Pro Ser Leu Trp Asp Phe Asn Tyr Leu Gln Ser
 65                  70                  75                  80

Leu Asn Thr Thr Gln Tyr Lys Glu Val Arg His Leu Lys Arg Glu Ala
                 85                  90                  95

Glu Leu Ile Glu Gln Val Lys Met Leu Leu Glu Glu Glu Met Glu Ala
                100                 105                 110

Val Gln Gln Leu Glu Leu Val Asp Asp Leu Lys Asn Leu Gly Leu Ser
                115                 120                 125

Tyr Phe Phe Glu Asp Gln Ile Lys Gln Ile Leu Thr Phe Ile Tyr Asn
        130                 135                 140

Glu His Lys Cys Phe His Ser Asn Ser Ile Ile Glu Ala Glu Glu Ile
145                 150                 155                 160

Arg Asp Leu Tyr Phe Thr Ala Leu Gly Phe Arg Leu Leu Arg Gln His
                165                 170                 175

Gly Phe Gln Val Ser Gln Glu Val Phe Asp Cys Phe Lys Asn Glu Glu
                180                 185                 190

Gly Ser Asp Phe Lys Ala Arg Leu Gly Asp Asp Thr Lys Gly Leu Leu
                195                 200                 205

Gln Leu Tyr Glu Ala Ser Phe Leu Leu Arg Glu Gly Glu Asp Thr Leu
        210                 215                 220

Glu Leu Ala Arg Gln Tyr Ala Thr Lys Phe Leu Gln Lys Lys Val Asp
225                 230                 235                 240

His Glu Leu Ile Asp Asp Asn Asn Leu Leu Ser Trp Ile Leu His Ser
                245                 250                 255

Leu Glu Ile Pro Leu His Trp Arg Ile Gln Arg Leu Glu Ala Arg Trp
                260                 265                 270

Phe Leu Asp Arg Tyr Ala Thr Arg Arg Asp Met Asn Gln Ile Ile Leu
        275                 280                 285

Glu Leu Ala Lys Leu Asp Phe Asn Ile Ile Gln Ala Thr Gln Gln Glu
        290                 295                 300

Glu Leu Lys Asp Leu Ser Arg Trp Trp Lys Ser Thr Cys Leu Ala Glu
305                 310                 315                 320

Lys Leu Pro Phe Val Arg Asp Arg Leu Val Glu Ser Tyr Phe Trp Ala
                325                 330                 335

Ile Ala Leu Phe Glu Pro His Gln Tyr Gly Tyr His Arg Lys Val Ala
                340                 345                 350

Ala Lys Ile Ile Thr Leu Ile Thr Ser Leu Asp Asp Val Tyr Asp Ile
            355                 360                 365

Tyr Gly Thr Leu Asp Glu Leu Gln Leu Phe Thr Asp Ala Ile Gln Arg
        370                 375                 380

Trp Asp Thr Glu Ser Ile Ser Arg Leu Pro Tyr Tyr Met Gln Leu Phe
385                 390                 395                 400

Tyr Met Val Leu Tyr Asn Phe Val Ser Glu Leu Ala Tyr Asp Gly Leu
                405                 410                 415

Lys Glu Lys Gly Phe Ile Thr Ile Pro Tyr Leu Gln Arg Ser Trp Ala
                420                 425                 430

Asp Leu Val Glu Ala Tyr Leu Lys Glu Ala Lys Trp Phe Tyr Asn Gly
                435                 440                 445

Tyr Val Pro Ser Met Glu Glu Tyr Leu Asn Asn Ala Tyr Ile Ser Ile
        450                 455                 460

Gly Ala Thr Pro Val Ile Ser Gln Val Phe Phe Thr Leu Ala Thr Ser
```

|  |  |  | 465 |  |  |  | 470 |  |  |  | 475 |  |  |  | 480 |  |
| --- | --- | --- | --- | --- | --- | --- | --- | --- | --- | --- | --- | --- | --- | --- | --- | --- |
| Ile | Asp | Lys | Pro | Val | Ile | Asp | Ser | Leu | Tyr | Glu | Tyr | His | Arg | Ile | Leu |  |
|  |  |  |  | 485 |  |  |  |  | 490 |  |  |  |  | 495 |  |  |

| Arg | Leu | Ser | Gly | Met | Leu | Val | Arg | Leu | Pro | Asp | Asp | Leu | Gly | Thr | Ser |
| --- | --- | --- | --- | --- | --- | --- | --- | --- | --- | --- | --- | --- | --- | --- | --- |
|  |  |  | 500 |  |  |  |  | 505 |  |  |  |  | 510 |  |  |

| Pro | Phe | Glu | Met | Lys | Arg | Gly | Asp | Val | Pro | Lys | Ala | Ile | Gln | Leu | Tyr |
| --- | --- | --- | --- | --- | --- | --- | --- | --- | --- | --- | --- | --- | --- | --- | --- |
|  |  | 515 |  |  |  |  | 520 |  |  |  |  | 525 |  |  |  |

| Met | Lys | Glu | Arg | Asn | Ala | Thr | Glu | Ile | Glu | Ala | Gln | Glu | His | Val | Arg |
| --- | --- | --- | --- | --- | --- | --- | --- | --- | --- | --- | --- | --- | --- | --- | --- |
|  | 530 |  |  |  |  | 535 |  |  |  |  | 540 |  |  |  |  |

| Phe | Leu | Ile | Arg | Glu | Ala | Trp | Lys | Glu | Met | Asn | Thr | Val | Thr | Thr | Ala |
| --- | --- | --- | --- | --- | --- | --- | --- | --- | --- | --- | --- | --- | --- | --- | --- |
| 545 |  |  |  |  | 550 |  |  |  |  | 555 |  |  |  |  | 560 |

| Ala | Asp | Cys | Pro | Phe | Thr | Asp | Asp | Leu | Val | Ala | Ala | Thr | Arg | Asn | Leu |
| --- | --- | --- | --- | --- | --- | --- | --- | --- | --- | --- | --- | --- | --- | --- | --- |
|  |  |  |  | 565 |  |  |  |  | 570 |  |  |  |  | 575 |  |

| Gly | Arg | Ala | Ala | Gln | Phe | Met | Tyr | Leu | Asp | Gly | Asp | Gly | Asn | His | Ser |
| --- | --- | --- | --- | --- | --- | --- | --- | --- | --- | --- | --- | --- | --- | --- | --- |
|  |  |  | 580 |  |  |  |  | 585 |  |  |  |  | 590 |  |  |

| Gln | Leu | His | Gln | Arg | Ile | Ala | Cys | Leu | Leu | Phe | Glu | Pro | Tyr | Ala |
| --- | --- | --- | --- | --- | --- | --- | --- | --- | --- | --- | --- | --- | --- | --- |
|  |  | 595 |  |  |  |  | 600 |  |  |  |  | 605 |  |  |

<210> SEQ ID NO 173
<211> LENGTH: 1824
<212> TYPE: DNA
<213> ORGANISM: Perilla frutescens var. crispa

<400> SEQUENCE: 173

| | |
|---|---|
| atgtatagct tgagaatata tgtagcgatc atgaaaaagc catcagctaa acatgttgac | 60 |
| aacgtcgaca agaaagcttc aaagccgtcg tggcgtgtct cactctcttc gagtgcgggt | 120 |
| ctccgagctt cttcctcctt acaactcgat gtaaaaaagc ccgctgatga tgaaattctg | 180 |
| acggcccgac gctctggcaa ctaccagcct ccctttggg atttcaacta ccttcaatct | 240 |
| ctcaacacta ctcagtataa ggaagtgagg cacttgaaaa gggaagcaga gctgattgag | 300 |
| caagtgaaga tgctgctgga agaagaaatg gaggcagttc aacaattgga gttggttgat | 360 |
| gacttgaaaa atctgggatt gtcttatttt tttgaagacc aaattaagca gatcttaacg | 420 |
| tttatatata atgagcataa atgtttccac agtaatagta ttattgaagc ggaggaaatt | 480 |
| agggatttgt atttcacagc tcttggattc agactcctca gacaacatgg tttccaagtc | 540 |
| tctcaagagg tatttgattg tttcaagaac gaggagggta gtgatttcaa agcaaggctt | 600 |
| ggtgacgata caaaaggatt gctgcaactc tacgaagcct ctttcctatt gagagaaggt | 660 |
| gaagatacac tggagctagc aaggcaatat gccaccaaat ttctccagaa aaaagttgat | 720 |
| catgaattaa ttgacgacaa taatctatta tcatggattc tccattcttt ggagatcccg | 780 |
| cttcactgga ggattcagag gctggaggca agatggttct tagatcgtta cgcgacgaga | 840 |
| cgagacatga atcaaatcat tcttgagctc gccaaactcg acttcaatat tattcaagca | 900 |
| acacaacagg aagaactcaa agatctctca aggtggtgga gagtacatg tctggctgag | 960 |
| aaacttccat tcgtgaggga taggcttgtg aaaagctact tttgggccat tgctctcttt | 1020 |
| gaacctcatc aatatggata tcacagaaaa gttgctgcca agattattac actaataaca | 1080 |
| tctttagatg atgtttacga tatctatggt acattagacg aactacaact atttacagac | 1140 |
| gcgattcaaa gatgggatac tgaatcaata agccgccttc catattatat gcaattattt | 1200 |
| tatatggtac tctacaactt tgtttcggag ctggcttacg atggtctcaa ggagaagggt | 1260 |
| ttcatccacca tccatatttt acagagatcg tgggcagatt tggttgaagc atatttaaaa | 1320 |
| gaggcaaagt ggttctacaa tggatatgta ccaagcatgg aagaatatct caacaacgcc | 1380 |

```
tacatttcaa tagggctac tcccgtaatt tctcaagttt tcttcacatt agcaacctcc    1440
attgacaaac cagtgatcga cagcttgtac gaataccacc gcatacttcg cctctctgga    1500
atgcttgtaa ggcttcctga tgatttagga acatcaccgt ttgagatgaa gagaggcgac    1560
gtgccgaaag caatccagtt gtacatgaag gaaagaaatg ctaccgagat agaggctcaa    1620
gaacacgtga ggtttctgat tcgtgaggcg tggaaggaga tgaacacggt aacgacggcg    1680
gccgattgtc cgtttacgga tgatttggtt gcagcgacac gtaatcttgg tagggcggca    1740
cagtttatgt atctcgacgg agatggtaac cactctcaat tacatcagcg gattgcgtgc    1800
ctactgttcg agccatatgc atga                                           1824
```

<210> SEQ ID NO 174
<211> LENGTH: 1824
<212> TYPE: DNA
<213> ORGANISM: Artificial Sequence
<220> FEATURE:
<223> OTHER INFORMATION: DNA having modified codons, which encodes
    linalool synthase gene derived from Pereilla frutescens var.
    crispa

<400> SEQUENCE: 174

```
atgtatagcc tgcgtattta tgtggcgatt atgaaaaagc ccagtgcgaa gcatgttgac      60
aatgtggaca agaaagcgag taagcctagc tggcgcgtta gcctgagcag cagcgcgggc     120
ctgcgtgcca gcagcagcct gcagctggat gtgaaaaagc cggcggatga tgaaatcctg     180
acggcccgcc gcagcggtaa ttaccagccc agcctgtggg actttaatta cctgcagagc     240
ctgaatacca cgcagtacaa agaagtgcgc catctgaagc gcgaagcgga actgattgaa     300
caggtcaaaa tgctgctgga agaagaaatg gaagccgtcc agcagctgga actggttgat     360
gacctgaaga atctgggcct gagctacttt ttcgaagatc agattaaaca gatcctgacg     420
tttatctaca cgaacataa gtgttttcac agcaatagca ttatcgaagc ggaagaaatt     480
cgcgacctgt actttacggc cctgggtttt cgtctgctgc gtcagcatgg ctttcaggtt     540
agccaggaag tgtttgattg ctttaagaat gaagaaggca gcgactttaa agcccgtctg     600
ggtgatgaca ccaagggcct gctgcagctg tacgaagcca gctttctgct gcgcgaaggc     660
gaagatacgc tggaactggc cgccagtac gcgaccaaat ttctgcagaa aaaggtggac     720
cacgaactga tcgatgacaa taatctgctg agctggattc tgcatagcct ggaaatcccg     780
ctgcactggc gcattcagcg cctggaagcg cgctggtttc tggatcgcta cgccacgcgt     840
cgcgacatga atcagattat cctggaactg gcgaaactgg attttaatat tatccaggcc     900
acgcagcagg aagaactgaa agacctgagc cgttggtgga agagcacctg tctggcggaa     960
aaactgccgt ttgtgcgcga tcgcctggtc gaaagctact ttgggccat tgcgctgttt    1020 gaacccatc agtacggcta ccaccgcaaa gtcgccgcga agattatcac cctgatcacg    1080
agcctggatg acgtttacga tatttacggc accctggacg aactgcagct gtttacggat    1140
gcgatccagc gctgggacac cgaaagcatt agccgcctgc cctactacat gcagctgttt    1200
tacatggttc tgtacaattt tgtgagcgaa ctggcctacg atggcctgaa agaaagggc    1260 tttattacca ttccctacct gcagcgtagc tgggcggacc tggtggaagc gtacctgaaa    1320
gaagccaagt ggttttacaa tggctacgtc cccagcatgg aagaatacct gaataatgcg    1380
tacattagca ttggtgccac cccggtcatc agccaggttt cttttacct ggccacgagc    1440 attgataaac ccgtcatcga cagcctgtac gaataccatc gcattctgcg tctgagcggt    1500
```

```
atgctggttc gcctgcccga tgacctgggt acgagcccct ttgaaatgaa acgcggcgat    1560
gttccgaagg cgatccagct gtacatgaaa gaacgcaatg cgacggaaat cgaagcccag    1620
gaacacgttc gctttctgat tcgcgaagcc tggaaggaaa tgaataccgt taccacggcc    1680
gcggattgcc cctttaccga tgacctggtt gcggccaccc gtaatctggg tcgtgccgcg    1740
cagtttatgt acctggatgg cgacggtaac cacagtcagc tgcaccagcg tatcgcctgc    1800
ctgctgtttg aaccctatgc ctaa                                           1824
```

<210> SEQ ID NO 175
<211> LENGTH: 602
<212> TYPE: PRT
<213> ORGANISM: Vitis vinifera

<400> SEQUENCE: 175

```
Met Glu Leu Thr Leu Thr Ser Leu Ser Pro Leu Ala Tyr Gly Ala Leu
1               5                   10                  15

Asn Cys Arg Lys Asn Phe Ala Met Ala Ser Pro Arg Met Arg Ile Lys
            20                  25                  30

Gln Gly Arg Ser Glu Leu Pro Asn Leu Thr Ile Thr Ser Lys Ile Asp
        35                  40                  45

Glu Leu Gln Val Thr Glu Arg Arg Ser Ala Asn Tyr His Pro Ser Ile
    50                  55                  60

Trp Asp Pro Lys Phe Ile Glu Ser Leu Ser Thr Pro Tyr Thr Asn Glu
65                  70                  75                  80

Gly Tyr Ser Asn Gln Leu Glu Asp Leu Lys Glu Ala Lys Arg Val
                85                  90                  95

Ile Lys Asp Ala Arg Asp Thr Ser Ser Arg Leu Glu Phe Ile Asp Ser
                100                 105                 110

Met Gln Arg Leu Gly Val Ala Tyr His Leu Glu Glu Ile Lys Glu
            115                 120                 125

Ala Ile Asp Leu Val His Leu Asp Asp Thr Thr Thr Asp Asp Leu Ser
    130                 135                 140

Thr Thr Ala Leu Arg Phe Arg Leu Leu Arg Gln His Gly Tyr Pro Val
145                 150                 155                 160

Ser Ser Glu Val Phe Asp Gln Phe Arg Ser Lys Asp Gly Arg Phe Met
                165                 170                 175

Asp Gly Ile Ser Gln Asp Ile Ala Gly Pro Leu Ser Leu Tyr Glu Ala
                180                 185                 190

Ser His Leu Gly Val Glu Gly Glu Asp Asp Leu Glu Glu Ala Arg Arg
            195                 200                 205

Phe Ser Thr Ile His Leu Lys Ser Leu Val Gly Asn Leu Glu Ser Asp
    210                 215                 220

Leu Ala Asp Gln Val Gln Gln Ser Leu Glu Val Pro Leu His Trp Arg
225                 230                 235                 240

Met Pro Arg Leu Glu Ala Arg Asn Phe Ile Asp Ile Tyr Gln Arg Arg
                245                 250                 255

Asn Thr Lys Asn Ser Ala Leu Leu Glu Leu Ala Lys Leu Asp Tyr Asn
            260                 265                 270

Leu Val Gln Ser Ser Tyr Gln Thr Glu Leu Lys Glu Leu Thr Arg Trp
        275                 280                 285

Trp Thr Asp Leu Gly Phe Lys Glu Lys Leu Ser Phe Ser Arg Asp Arg
    290                 295                 300

Leu Met Glu Asn Tyr Leu Trp Ser Met Gly Ile Ala Pro Glu Pro His
305                 310                 315                 320
```

```
Phe Ser Lys Ser Arg Ile Gly Leu Thr Lys Phe Ile Cys Ile Leu Thr
                325                 330                 335

Ala Ile Asp Asp Met Tyr Asp Ile Tyr Gly Ser Pro Asp Glu Leu Arg
            340                 345                 350

Arg Phe Thr Asp Ala Val Asn Arg Trp Asp Thr Glu Ala Leu Val Asp
        355                 360                 365

Leu Pro Asp Tyr Met Lys Ile Cys Tyr Leu Ala Met Phe Asn Phe Ala
    370                 375                 380

Asn Glu Met Ala Tyr Asp Ala Leu Arg Asp His Asp Leu Tyr Ile Leu
385                 390                 395                 400

Pro Tyr Leu Lys Ser Gln Trp Leu Asn Leu Cys Thr Ser Tyr Ser Met
                405                 410                 415

Glu Ala Gln Trp Phe Tyr Asn Gly Tyr Lys Pro Ser Ile Asp Glu Tyr
            420                 425                 430

Leu Ser Asn Ala Trp Thr Ser Val Gly Gly Pro Ala Ala Met Val His
        435                 440                 445

Ala Tyr Phe Leu Met Gly Cys Ala Thr Lys Gly Asn Leu Asn Asn Cys
    450                 455                 460

Leu Asp Asn Ala Ser Asn Leu Leu Tyr Trp Ser Ser Leu Ile Thr Arg
465                 470                 475                 480

Leu Ser Asp Asp Leu Gly Thr Ser Leu Ala Glu Ile Ala Arg Gly Asp
                485                 490                 495

Val Ala Lys Ser Ile Gln Cys Tyr Met Ile Glu Lys Cys Ile Ser Glu
            500                 505                 510

Glu Gln Ala Arg Asp Gln Val Glu Lys Leu Ile Arg Tyr Ser Trp Lys
        515                 520                 525

Lys Leu Asn Glu Ala Ser Thr Asp Ser Ser Leu Pro Lys Ser Leu Ile
    530                 535                 540

Asn Ser Ser Leu Asn Met Ala Arg Ser Ala Gln Cys Ile Phe Gln Phe
545                 550                 555                 560

Gly Asp Gly Ile Gly Thr Ser Val Gly Val Thr Lys Asp Arg Leu Thr
                565                 570                 575

Ser Phe Ile Ile Lys Pro Ile Leu Ile Glu Pro Ser Ile Lys Pro Tyr
            580                 585                 590

Leu Asp Gly Met Lys Met Ser Asn Arg Arg
        595                 600
```

<210> SEQ ID NO 176
<211> LENGTH: 1809
<212> TYPE: DNA
<213> ORGANISM: Vitis vinifera

<400> SEQUENCE: 176

```
atggaactaa ccctcacatc cctctcaccc ttggcctatg gtgccctcaa ttgtcgtaaa      60
aattttgcca tggcatcccc aagaatgaga atcaagcaag ggagatcaga attgcccaac     120
ctcacaatca cttcgaagat tgatgagtta caagtgaccg aaaggcgatc ggctaattac     180
catcctagca tttgggaccc caaatttatt gagtccttaa gcactcccta tacgaatgag     240
ggctattcca accaattaga ggacttgaag gaagaagcta aagggtaat  taaggacgct     300 agagacactt cctcccgatt agagttcatt gattcgatgc aacggttggg agtggcttac     360
catttggagg aggagatcaa agaggctatt gatcttgttc atttggatga taccactacc     420
gatgatcttt ccacaactgc actccgattt agacttctac gacaacacgg ctatccagtt     480
```

```
agctcagagg tgtttgatca attcagaagt aaagatggga gattcatgga tggcatcagc    540
caggatattg ctgggccttt gagtttgtat gaagcttccc atcttggagt cgagggagaa    600
gatgacttgg aagaagccag gaggttcagt actatacatt tgaagtcact ggttgggaat    660
ttggagagtg atttagctga ccaagtgcag cagtccctgg aagttccctt acactggaga    720
atgccaaggc tagaagcccg aaacttcatc gatatctacc aaaggcgcaa tacgaagaac    780
tctgctctcc ttgagctagc caagctggac tacaatctag tgcaatcatc atatcagacg    840
gagttgaagg agctaacaag gtggtggacg gacttgggat ttaaggagaa gctaagtttt    900
tctcgggatc gattgatgga gaactatttg tggtcaatgg ggatcgctcc tgagccccac    960
ttctccaaaa gcaggatagg actcaccaaa ttcatatgca tattaacagc catagatgac   1020
atgtatgaca tatatggatc accggatgag cttcgacgtt ttacagatgc tgtgaatcga   1080
tgggatactg aggcactggt ggaccttcca gattacatga agatatgtta cttggccatg   1140
ttcaactttg ctaatgaaat ggcctacgat gcattaagag atcacgacct atatatttta   1200
ccctatctta aaagtcagtg gctaaatctc tgtacatcct actcaatgga agctcaatgg   1260
ttttacaatg ggtataagcc aagcatcgat gaatacttaa gcaatgcctg gacttccgta   1320
gggggtcctg cagccatggt ccatgcctat tttctaatgg ggttgtgccac caagggaaac   1380
ttgaacaatt gtttagacaa tgcctctaat ctactttatt ggtcatctct tattactcga   1440
cttagcgatg atttgggaac ttcttttagcc gagattgcga gaggcgacgt ggcaaaatct   1500
atccaatgtt acatgattga aaaatgtata tccgaagaac aagctcgaga tcaagtagag   1560
aagcttatac gttactcatg gaaaaagttg aatgaagcaa gtactgatag ctctctccca   1620
aagtccttaa taaattcatc attgaacatg gcgcgatcag ctcaatgtat ttttcaattt   1680
ggagatggaa tcgtacatc agttggggtg accaaagatc gattgacatc attcattatc   1740
aagccaatat tgatagaacc aagcattaaa ccctatcttg atggcatgaa gatgagcaac   1800
agaagatga                                                          1809

<210> SEQ ID NO 177
<211> LENGTH: 1809
<212> TYPE: DNA
<213> ORGANISM: Artificial Sequence
<220> FEATURE:
<223> OTHER INFORMATION: DNA having modified codons, which encodes
      linalool synthase gene derived from Vitis vinifera

<400> SEQUENCE: 177
atggaactga ccctgacgag tctgagcccg ctggcgtatg gtgccctgaa ctgccgtaag     60
aactttgcga tggcgagtcc ccgtatgcgc attaagcagg ccgcagcga actgccgaat    120
ctgacgatta ccagcaaaat cgacgaactg caggtgaccg aacgccgcag cgcgaattac    180
caccccgagca tttgggatcc caaatttatc gaaagcctga gcacgcccta ccaatgaa    240
ggctacagca atcagctgga agatctgaaa gaagaagcca agcgcgtcat taaagatgcg    300
cgcgacacga gcagccgcct ggaatttatc gacagcatgc agcgcctggg cgtggcctac    360
catctggaag aagaaattaa ggaagcgatc gatctggtcc acctggatga caccacgacc    420
gatgacctga gcaccacggc cctgcgtttt cgtctgctgc gtcagcatgg ttacccggtc    480
agcagcgaag ttttgatca gtttcgcagc aaagatggcc gctttatgga cggcattagc    540
caggatattg cgggtcctct gagcctgtac gaagccagcc atctgggcgt gaaggcgaa     600
gatgacctgg aagaagcccg ccgctttagc accatccacc tgaagagcct ggtgggcaat    660
```

```
ctggaaagcg atctggcgga ccaggtgcag cagagcctgg aagtccccct gcactggcgt    720
atgcctcgtc tggaagcccg caatttttatt gacatctacc agcgtcgcaa taccaagaat    780
agcgccctgc tggaactggc gaaactggat tacaatctgg ttcagagcag ctaccagacg    840
gaactgaaag aactgacgcg ttggtggacc gacctgggct taaagaaaa gctgagcttt    900
agccgcgatc gcctgatgga aaattacctg tggagcatgg gcattgcgcc ggaacccat    960
tttagcaaga gccgcatcgg cctgaccaaa tttatttgta tcctgacggc cattgatgac   1020
atgtacgaca tctacggcag cccggatgaa ctgcgccgct taccgacgc cgtcaatcgc   1080
tgggatacgg aagcgctggt tgatctgccc gactacatga agatttgtta cctggccatg   1140
tttaactttg cgaatgaaat ggcctacgat gcgctgcgcg atcatgacct gtacatcctg   1200
ccgtacctga agagccagtg gctgaatctg tgcaccagct acagcatgga agcccagtgg   1260
ttttacaatg gctacaaacc gagcattgat gaatacctga gcaatgcctg gaccagcgtt   1320
ggcggcccgg cggccatggt gcacgcctac tttctgatgg gctgtgcgac gaagggcaat   1380
ctgaataatt gcctggacaa tgcgagcaat ctgctgtact ggagcagcct gatcacgcgt   1440
ctgagcgatg acctgggtac gagcctggcg gaaattgccc gcggcgatgt cgccaagagc   1500
atccagtgtt acatgattga aaatgcatc agcgaagaac aggcgcgcga ccaggttgaa   1560
aagctgattc gctacagctg gaaaaagctg aatgaagcca gcacggatag cagcctgccg   1620
aaaagcctga tcaatagcag cctgaatatg cccgcagcg cgcagtgcat tttttcagttt   1680
ggtgatggta ttggtacgag cgttggcgtg accaaggatc gcctgacgag ctttattatc   1740
aaacccattc tgattgaacc gagcattaag ccctacctgg atggcatgaa gatgagtaac   1800
cgccgctaa                                                            1809
```

<210> SEQ ID NO 178
<211> LENGTH: 606
<212> TYPE: PRT
<213> ORGANISM: Mentha citrata

<400> SEQUENCE: 178

```
Met Cys Thr Ile Ile Ser Val Asn His His Val Ala Ile Leu Ser
1               5                   10                  15

Lys Pro Lys Val Lys Leu Phe His Thr Lys Asn Lys Arg Ser Ala Ser
            20                  25                  30

Ile Asn Leu Pro Trp Ser Leu Ser Pro Ser Ser Ala Ala Ser Arg
            35                  40                  45

Pro Ile Ser Cys Ser Ile Ser Lys Leu Tyr Thr Ile Ser Ser Ala
    50                  55                  60

Gln Glu Glu Thr Arg Arg Ser Gly Asn Tyr His Pro Ser Val Trp Asp
65                  70                  75                  80

Phe Asp Phe Ile Gln Ser Leu Asp Thr Asp His Tyr Lys Glu Glu Lys
                85                  90                  95

Gln Leu Glu Arg Glu Glu Glu Leu Ile Met Glu Val Lys Lys Leu Leu
            100                 105                 110

Gly Ala Lys Met Glu Ala Thr Lys Gln Leu Glu Leu Ile Asp Asp Leu
        115                 120                 125

Gln Asn Leu Gly Leu Ser Tyr Phe Phe Arg Asp Glu Ile Lys Asn Ile
    130                 135                 140

Leu Asn Ser Ile Tyr Lys Ile Phe Gln Asn Asn Asn Ser Thr Lys Val
145                 150                 155                 160

Gly Asp Leu His Phe Thr Ser Leu Gly Phe Arg Leu Leu Arg Gln His
```

```
                   165                 170                 175
Gly Phe Asn Val Ser Gln Gly Val Phe Asp Cys Phe Lys Asn Glu His
                180                 185                 190
Gly Ser Asp Phe Glu Lys Thr Leu Ile Gly Glu Asp Thr Lys Gly Val
                195                 200                 205
Leu Gln Leu Tyr Glu Ala Ser Phe Leu Leu Arg Glu Gly Glu Asp Thr
            210                 215                 220
Leu Glu Val Ala Arg Lys Phe Ser Thr Glu Phe Leu Glu Glu Lys Leu
225                 230                 235                 240
Lys Ala Gly Ile Asp Gly Asp Asn Leu Ser Ser Ile Gly His Ser
                245                 250                 255
Leu Glu Ile Pro Leu His Trp Arg Ile Gln Arg Leu Glu Glu Arg Trp
                260                 265                 270
Phe Leu Asp Ala Tyr Ser Arg Arg Lys Asp Met Asn Pro Ile Ile Phe
            275                 280                 285
Glu Leu Ala Lys Leu Asp Phe Asn Ile Ile Gln Ala Thr Gln Gln Glu
            290                 295                 300
Glu Leu Lys Asp Leu Ser Arg Trp Trp Asn Asp Ser Ser Leu Pro Gln
305                 310                 315                 320
Lys Leu Pro Phe Val Arg Asp Arg Leu Val Glu Ser Tyr Tyr Trp Ala
                325                 330                 335
Leu Gly Leu Phe Glu Ala His Lys Phe Gly Tyr Glu Arg Lys Thr Ala
                340                 345                 350
Ala Lys Ile Ile Thr Leu Ile Thr Ala Leu Asp Asp Val Tyr Asp Ile
            355                 360                 365
Tyr Gly Thr Leu Asp Glu Leu Gln Leu Phe Thr His Val Ile Arg Arg
            370                 375                 380
Trp Asp Thr Glu Ser Ala Thr Gln Leu Pro Tyr Tyr Leu Gln Leu Phe
385                 390                 395                 400
Tyr Phe Val Leu Tyr Asn Phe Val Ser Glu Val Ala Tyr His Ile Leu
                405                 410                 415
Lys Glu Glu Gly Phe Ile Ser Ile Pro Phe Leu His Arg Ala Trp Val
                420                 425                 430
Asp Leu Val Glu Gly Tyr Leu Gln Glu Ala Lys Trp Tyr Tyr Thr Lys
            435                 440                 445
Tyr Thr Pro Thr Met Glu Glu Tyr Leu Asn Tyr Ala Ser Ile Thr Ile
            450                 455                 460
Gly Ala Pro Ala Val Ile Ser Gln Ile Tyr Phe Met Leu Ala Lys Ser
465                 470                 475                 480
Lys Glu Lys Pro Val Ile Glu Ser Phe Tyr Glu Tyr Asp Glu Ile Ile
                485                 490                 495
Arg Leu Ser Gly Met Leu Val Arg Leu Pro Asp Asp Leu Gly Thr Leu
                500                 505                 510
Pro Phe Glu Met Lys Arg Gly Asp Val Ala Lys Ser Ile Gln Ile Tyr
            515                 520                 525
Met Lys Glu Gln Asn Ala Thr Arg Glu Glu Ala Glu Glu His Val Arg
            530                 535                 540
Phe Met Ile Arg Glu Ala Trp Lys Glu Met Asn Thr Thr Met Ala Ala
545                 550                 555                 560
Asn Ser Asp Leu Arg Gly Asp Val Val Met Ala Ala Ala Asn Leu Gly
                565                 570                 575
Arg Asp Ala Gln Phe Met Tyr Leu Asp Gly Asp Gly Asn His Ser Gln
            580                 585                 590
```

Leu Gln His Arg Ile Ala Asn Leu Leu Phe Lys Pro Tyr Val
        595                 600                 605

<210> SEQ ID NO 179
<211> LENGTH: 1821
<212> TYPE: DNA
<213> ORGANISM: Mentha citrata

<400> SEQUENCE: 179

```
atgtgtacta ttattagcgt aaatcatcat catgtggcga tccttagcaa gcctaaagta      60
aaacttttcc acaccaaaaa caagagatca gcttcaatta atctcccatg gagtctctct     120
ccttcttcat ccgccgcctc tcgccccatc agttgttcta tctcctcaaa actatatacc     180
atcagttcgg ctcaggagga aacccgacgt tccggaaact accacccttc agtttgggat     240
tttgatttca ttcaatctct cgacactgat cactataagg aggagaagca gttagagagg     300
gaggaagagc tgatcatgga ggtgaagaag ttgttggggg caaaaatgga ggcaactaag     360
cagttggagt tgattgatga cttgcagaat ttgggattgt cttattttt ccagacgag       420
attaagaata tcttgaattc tatatataaa attttccaaa ataataatag tactaaagta     480
ggggatttgc atttcacgtc tcttggattc aggctcctcc ggcagcatgg tttcaacgtt     540
tcacaaggag tatttgattg cttcaagaac gagcatggta gcgatttcga gaaaccccta     600
attgggaag atacgaaagg agtgctgcaa ctttacgaag catcattcct tttgagagaa       660
ggtgaagata cattggaggt agctagaaaa ttctccaccg aatttctcga ggaaaaactc     720
aaaagccgga tcgatggtga taatctatca tcatcgattg ccattctttt ggagatccct     780
cttcactgga ggattcaaag actagaggaa agatggttct tagatgctta ctcaaggagg     840
aaagacatga accctatcat tttcgagctc gccaaactcg acttcaatat tattcaagca     900
acgcagcaag aagaactcaa agatctctca aggtggtgga atgattcaag cctacctcaa     960
aaactcccat ttgtgaggga taggctggtg gaaagctact attgggccct tgggttgttt    1020
gaggctcaca aatttggata tgaaagaaaa actgctgcaa agattattac cctaattaca    1080
gctcttgatg atgtttatga tatttatggc acactcgacg agctccaact atttacacac    1140
gtcattcgaa gatgggatac tgaatcagcc acccaacttc cttattactt gcaattattc    1200
tatttcgtac tatacaactt tgttttccgag gtggcgtacc acattctaaa ggaagagggt    1260
ttcatcagca tcccatttct acacagagcg tgggtggatt tggttgaagg atatttacaa    1320
gaggcaaagt ggtactacac taaatataca ccaaccatgg aagaatattt gaactatgcc    1380
agcatcacaa tagggcgctcc tgcagtaata tcccaaattt attttatgct agccaaatcg    1440
aaagagaaac cggtgatcga gagttttttac gaatacgacg aaataattcg cctttcggga    1500
atgctcgtga ggcttcccga tgacctagga acactaccgt tgagatgaa gagaggcgac      1560
gtggcgaaat caatccagat ttacatgaag gaacagaatg caaacgggga agaagcagaa    1620
gaacacgtga ggtttatgat tagggaggcg tggaaggaga tgaacacaac tatggcggcg    1680
aattctgatt tgagaggtga tgtggttatg gctgcagcta atcttggaag ggatgcacag    1740
tttatgtatc tcgacggaga cggtaaccac tctcagttac aacaccggat tgcgaacttg    1800
ctgttcaagc catatgtctg a                                              1821
```

<210> SEQ ID NO 180
<211> LENGTH: 1821
<212> TYPE: DNA
<213> ORGANISM: Artificial Sequence
<220> FEATURE:
<223> OTHER INFORMATION: DNA having modified codons, which encodes linalool synthase gene derived from Mentha citrata

<400> SEQUENCE: 180

```
atgtgtacca tcattagcgt caatcatcat catgtcgcca tcctgagcaa gccgaaggtc      60
aagctgtttc ataccaagaa taagcgcagc gccagcatca atctgccgtg gagcctgagc     120
cctagcagca gcgcggccag ccgcccgatt agctgtagca tcagcagcaa actgtacacc     180
atcagcagcg cccaggaaga aacgcgccgc agcggcaatt accatcccag cgtttgggat     240
tttgactttta ttcagagcct ggataccgac cactacaagg aagaaaaaca gctggaacgc     300
gaagaagaac tgatcatgga agtgaaaaag ctgctgggcg cgaagatgga agccacgaaa     360
cagctggaac tgattgatga cctgcagaat ctgggcctga gctactttt ccgcgacgaa      420
atcaagaaca tcctgaacag catctacaag atctttcaga caacaatag caccaaggtt      480
ggcgatctgc attttacgag cctgggtttt cgtctgctgc gtcagcacgg ctttaatgtt     540
agccagggcg tgtttgattg ctttaaaaat gaacatggca gcgactttga aaagaccctg     600
atcggcgaag atacgaaagg cgtgctgcag ctgtacgaag cgagctttct gctgcgcgaa     660
ggcgaagata ccctggaagt cgcccgcaaa tttagcacgg aatttctgga gaaaaaactg     720
aaggcgggca ttgatggcga caatctgagc agcagcattg ccatagcct ggaaatcccg      780
ctgcactggc gcattcagcg cctggaagaa cgctggtttc tggatgccta cagccgtcgc     840
aaggacatga atcccattat ctttgaactg gcgaaactgg actttaatat tatccaggcc     900
acccagcagg aagaactgaa ggatctgagc cgttggtgga atgacagcag cctgccgcag     960
aaactgccct tgtccgcga tcgcctggtt gaaagctact actgggcgct gggcctgttt    1020
gaagcccata gtttggcta cgaacgcaag acggccgcga aaattatcac cctgatcacg    1080
gcgctggatg acgtgtacga tatttacggc accctggacg aactgcagct gtttacgcac    1140
gtcattcgcc gctgggacac ggaaagcgcc acccagctgc cgtactacct gcagctgttt    1200
tactttgtcc tgtacaattt tgtcagcgaa gttgcgtacc atattctgaa agaagaaggc    1260
tttattagca tcccctttct gcaccgcgcg tgggtggatc tggtcgaagg ctacctgcag    1320
gaagccaagt ggtactacac caaatacacc ccgacgatgg aagaatacct gaattacgcc    1380
agcattacca ttggtgcccc ggccgttatt agccagatct actttatgct ggcgaaaagc    1440
aaggaaaaac cggtgatcga aagcttttac gaatacgacg aaattattcg tctgagcggt    1500
atgctggttc gcctgcccga tgacctgggt accctgccct ttgaaatgaa gcgcggcgat    1560
gttgccaaaa gcattcagat ctacatgaag gaacagaatg cgacgcgcga agaagccgaa    1620
gaacacgtgc gctttatgat tcgcgaagcg tggaaagaaa tgaataccac gatggccgcg    1680
aatagcgatc tgcgcggcga cgttgtgatg gcggccgcca atctgggtcg tgatgcccag    1740
tttatgtacc tggatggcga cggtaatcat agtcagctgc agcaccgcat cgccaatctg    1800
ctgtttaagc cctacgtcta a                                             1821
```

<210> SEQ ID NO 181
<211> LENGTH: 535
<212> TYPE: PRT
<213> ORGANISM: Ocimum basilicum

<400> SEQUENCE: 181

```
Met Ala Ser Ala Val Pro Leu Ser Ser Thr Pro Leu Ile Asn Gly Asp
1               5                   10                  15
```

```
Asn Ser Pro Leu Lys Asn Thr His Gln His Val Glu Glu Arg Ser Ser
                20                  25                  30

Lys Arg Arg Glu Tyr Leu Leu Glu Glu Thr Ala Arg Lys Leu Gln Arg
            35                  40                  45

Asn Asp Thr Glu Ser Val Glu Lys Leu Lys Leu Ile Asp Asn Ile Gln
 50                  55                  60

Arg Leu Gly Ile Gly Tyr Tyr Phe Glu Asp Ala Ile Asp Ala Val Leu
 65                  70                  75                  80

Arg Ser Pro Phe Ser Ala Glu Glu Glu Asp Leu Phe Thr Ala Ala
                85                  90                  95

Leu Arg Phe Arg Leu Leu Arg His Asn Gly Ile Gln Val Thr Pro Glu
            100                 105                 110

Ile Phe Leu Lys Phe Lys Asp Glu Arg Gly Glu Phe Asp Glu Ser Asp
            115                 120                 125

Thr Leu Gly Leu Leu Ser Leu Tyr Glu Ala Ser Asn Leu Gly Val Thr
    130                 135                 140

Gly Glu Glu Ile Leu Glu Glu Ala Met Glu Phe Ala Glu Pro Arg Leu
145                 150                 155                 160

Arg Arg Ser Leu Ser Glu Leu Ala Ala Pro Leu Arg Ser Glu Val Ala
                165                 170                 175

Gln Ala Leu Asp Val Pro Arg His Leu Arg Met Ala Arg Leu Glu Ala
            180                 185                 190

Arg Arg Phe Ile Glu Gln Tyr Gly Lys Gln Ser Asp His Asp Gly Asp
            195                 200                 205

Leu Leu Glu Leu Ala Ile Leu Asp Tyr Asn Gln Val Gln Ala Gln His
    210                 215                 220

Gln Ser Glu Leu Thr Glu Ile Thr Arg Trp Trp Lys Gln Leu Gly Leu
225                 230                 235                 240

Val Glu Lys Leu Gly Phe Gly Arg Asp Arg Ala Leu Glu Cys Phe Met
                245                 250                 255

Trp Thr Met Gly Ile Leu Pro His Pro Lys Tyr Ser Ser Ser Arg Ile
            260                 265                 270

Glu Ser Ala Lys Ala Ala Ala Leu Leu Tyr Val Ile Asp Asp Ile Phe
            275                 280                 285

Asp Thr Tyr Gly Lys Met Asp Glu Leu Ile Leu Phe Thr Asp Ala Ile
    290                 295                 300

Arg Arg Trp Asp Leu Glu Ala Met Glu Gly Leu Pro Glu Tyr Met Lys
305                 310                 315                 320

Ile Cys Tyr Met Ala Leu Tyr Asn Thr Thr Asn Glu Ile Cys Tyr Arg
                325                 330                 335

Val Leu Lys Asp Thr Gly Arg Ile Ala Leu Pro Tyr Leu Lys Ser Val
            340                 345                 350

Trp Ile Glu Thr Ile Glu Ala Tyr Met Val Glu Val Lys Trp Phe Ser
            355                 360                 365

Gly Gly Ser Ala Pro Lys Leu Glu Glu Tyr Ile Glu Asn Gly Ala Ser
    370                 375                 380

Thr Val Gly Ala Tyr Met Val Leu Val His Leu Phe Phe Leu Ile Gly
385                 390                 395                 400

Glu Gly Leu Thr His Gln Asn Val Leu Phe Phe Lys Gln Lys Pro Tyr
                405                 410                 415

His Lys Pro Phe Ser Ala Ala Gly Arg Ile Phe Arg Leu Trp Asp Asp
            420                 425                 430

Leu Gly Thr Ser Gln Glu Glu Glu Glu Arg Gly Asp Met Ala Ser Ser
```

|     |     |     |     | 435 |     |     |     |     | 440 |     |     |     |     | 445 |
| --- | --- | --- | --- | --- | --- | --- | --- | --- | --- | --- | --- | --- | --- | --- |
| Ile | Arg | Leu | Phe | Met | Lys | Glu | Tyr | Lys | Leu | Ser | Thr | Val | Glu | Glu | Ala |
| 450 |     |     |     |     | 455 |     |     |     |     | 460 |     |     |     |     |     |

Arg Ser Cys Val Leu Glu Glu Ile Ser Arg Leu Trp Lys Asp Leu Asn
465                 470                 475                 480

Glu Gly Leu Ile Ser Ile Lys Asp Ala Leu Pro Leu Thr Ile Val Lys
                    485                 490                 495

Val Ala Leu Asn Ile Ala Arg Thr Ser Gln Val Val Tyr Lys His Glu
            500                 505                 510

Gln His Thr Tyr Met Leu Ser Val Asp Asn Tyr Val Glu Ala Leu Phe
        515                 520                 525

Phe Thr Pro Leu Leu Ser Ser
530                 535

```
<210> SEQ ID NO 182
<211> LENGTH: 1608
<212> TYPE: DNA
<213> ORGANISM: Ocimum basilicum

<400> SEQUENCE: 182
```

| | | | | |
|---|---|---|---|---|
| atggcatccg | cagtgcctct | aagttcaact | cctctcatca | acggggataa | ctctccgctt |   60 |
| aaaaacacac | atcaacacgt | ggaggagagg | agcagcaaga | ggagagaata | tctgctggag |  120 |
| gaaacggcgc | gaaaactgca | gagaaacgac | accgaatcgg | tggagaaact | caagctcatc |  180 |
| gacaacatcc | aacggctggg | aatcggctac | tattttgagg | atgccatcga | cgccgtactc |  240 |
| cgctcgcctt | tctccgccga | agaagaagaa | gacctcttca | ccgctgctct | gcgcttccgc |  300 |
| ttgctccgcc | acaatggcat | ccaagtcacc | cctgaaatat | tcctaaaatt | caaggacgag |  360 |
| agaggagaat | cgacgaatc | ggacacgcta | gggttactga | gcttgtacga | agcgtcaaat |  420 |
| ttggggtta | caggagaaga | gatactggag | gaggctatgg | agttcgcgga | gcctcgcctg |  480 |
| agacgatcac | tgtcagagct | ggcggcgccg | cttcgtagtg | aggtggcgca | agccctagat |  540 |
| gtgccgaggc | atctgagaat | ggcgaggttg | gaagccagac | gattcatcga | gcagtatggt |  600 |
| aaacagagcg | atcatgatgg | agaccttttg | gagctagcaa | ttttggatta | taatcaagtt |  660 |
| caggctcaac | accaatccga | actcactgaa | attaccaggt | ggtggaagca | actgggtttg |  720 |
| gtggaaaagt | tgggttttcgg | tagagacaga | gcgttggagt | gctttatgtg | gaccatgggg |  780 |
| atcctacctc | accctaaata | ctcttcttct | agaatagaat | cagccaaggc | agctgctctt |  840 |
| ctgtacgtca | tcgatgatat | tttcgatacc | tatggcaaaa | tggacgaact | catcctcttc |  900 |
| accgacgcaa | ttcgaagatg | ggatttggaa | gcaatggagg | gtctacccga | gtacatgaaa |  960 |
| atatgctaca | tggcgttgta | caacaccacc | aatgaaatat | gctacagagt | gctcaaggat | 1020 |
| actggacgga | tcgccctccc | atacctcaaa | tctgtgtgga | tagagactat | tgaagcttat | 1080 |
| atggtggagg | tgaagtggtt | cagtggtgga | agtgccccaa | agttgaagaa | atacattgag | 1140 |
| aatgggcat | caactgtagg | ggcatacatg | gttcttgtcc | acctattctt | tctcattgga | 1200 |
| gaaggtctca | cccaccaaaa | tgtcctattt | tcaaacaaaa | accctatca | caagcctttc | 1260 |
| tccgccgccg | gccggatttt | tcgcctttgg | gacgatcttg | gaacttctca | ggaggaggaa | 1320 |
| gaacgaggag | atatggcgtc | aagtatacgg | ttatttatga | aagagtacaa | gttgtcgacg | 1380 |
| gtagaggagg | ctagaagttg | cgttttggaa | gagatatccc | gtttatggaa | ggatcttaat | 1440 |
| gaagggctca | tcagtataaa | ggacgccttg | ccattaacca | tagtcaaagt | cgcacttaac | 1500 |
| attgcacgaa | cttctcaagt | tgtatacaag | cacgaacaac | atacatatat | gttgagtgtt | 1560 |

```
gataattacg tggaagccct cttcttcact cctcttcttt cttcttag        1608
```

<210> SEQ ID NO 183
<211> LENGTH: 1608
<212> TYPE: DNA
<213> ORGANISM: Artificial Sequence
<220> FEATURE:
<223> OTHER INFORMATION: DNA having modified codons, which encodes
      linalool synthase gene derived from Ocimum basilicum

<400> SEQUENCE: 183

```
atggcgagtg cggtcccct  gagtagtacg cccctgatta acggcgacaa tagtcccctg      60
aaaaatacc  accagcatgt tgaggagcgc agcagcaaac gtcgcgaata cctgctggaa     120
gaaaccgcgc gcaagctgca cgcaatgac  acggaaagcg ttgaaaaact gaagctgatt     180
gataatatcc agcgcctggg cattggctac tactttgaag atgccattga tgcggtgctg     240
cgcagcccct ttagcgccga agaagaagaa gacctgttta ccgcggccct gcgttttcgt     300
ctgctgcgtc ataatggcat tcaggtcacc ccggaaatct ttctgaaatt taaggatgaa     360
cgcggcgaat ttgacgaaag cgatacgctg gcctgctga  gcctgtacga agcgagcaat     420
ctgggcgtga ccggcgaaga aatcctggaa gaagcgatgg aatttgcgga accccgtctg     480
cgccgcagcc tgagcgaact ggccgcgccc ctgcgcagcg aagtcgccca ggccctggat     540
gttccccgtc acctgcgcat ggcccgtctg gaagcccgcc gctttattga acagtacggc     600
aaacagagcg atcatgacgg cgatctgctg gaactggcga ttctggacta caatcaggtc     660
caggcccagc accagagcga actgaccgaa atcacgcgtt ggtggaaaca gctgggcctg     720
gttgaaaaac tgggttttgg tcgcgatcgc gccctggaat gttttatgtg gacgatgggc     780
attctgccgc atcccaaata cagcagcagc cgtattgaaa cgccaaggc  ggccgccctg     840
ctgtacgtta ttgatgacat cttt gacacc tacggcaaaa tggatgaact gattctgttt     900
acggacgcga tccgccgctg ggatctggaa gccatggaag cctgcccga  atacatgaag     960
atttgttaca tggcgctgta caataccacg aatgaaattt gctaccgcgt tctgaaagat    1020
accggtcgta ttgccctgcc ttacctgaag agcgtgtgga ttgaaaccat cgaagcgtac    1080
atggtcgaag ttaaatggtt tagcggcggc agcgccccca gctggaaga  atacattgaa    1140
aatggtgcca gcaccgtggg tgcctacatg gtgctggtcc acctgttttt cctgatcggc    1200
gaaggcctga cccaccagaa tgtcctgttt ttcaaacaga gccgtacca  caaacccttt    1260
agcgccgcgg tcgtattttt tcgtctgtgg gatgacctgg cacgagcca  ggaagaagaa    1320
gaacgcggcg atatggcgag cagcatccgc ctgtttatga agaatacaa  gctgagcacc    1380
gtggaagaag cccgcagctg cgtcctggaa gaaattagcc gcctgtggaa agacctgaat    1440
gaaggcctga ttagcatcaa agatgccctg ccgctgacca ttgttaaggt ggcgctgaat    1500
atcgcccgca cgagccaggt tgtgtacaag catgaacagc acacctacat gctgagtgtt    1560
gacaattatg tggaagccct gttttttacg cccctgctga gtagttaa              1608
```

<210> SEQ ID NO 184
<211> LENGTH: 8
<212> TYPE: PRT
<213> ORGANISM: Artificial Sequence
<220> FEATURE:
<223> OTHER INFORMATION: amino acid sequence of motif contained in
      linalool synthase
<220> FEATURE:
<221> NAME/KEY: misc_feature
<222> LOCATION: (3)..(3)

```
<223> OTHER INFORMATION: XXa is arbitrary amino acid
<220> FEATURE:
<221> NAME/KEY: misc_feature
<222> LOCATION: (4)..(4)
<223> OTHER INFORMATION: XXa is Phe or Tyr
<220> FEATURE:
<221> NAME/KEY: misc_feature
<222> LOCATION: (5)..(5)
<223> OTHER INFORMATION: XXa is Asp or Tyr
<220> FEATURE:
<221> NAME/KEY: misc_feature
<222> LOCATION: (6)..(6)
<223> OTHER INFORMATION: XXa is arbitrary amino acid
<220> FEATURE:
<221> NAME/KEY: misc_feature
<222> LOCATION: (7)..(7)
<223> OTHER INFORMATION: XXa is arbitrary amino acid

<400> SEQUENCE: 184

Asp Asp Xaa Xaa Xaa Xaa Xaa Gly
1               5
```

US 10,870,866 B2

METHOD OF PRODUCING LINALOOL USING A MICROORGANISM

This application is a Continuation of, and claims priority under 35 U.S.C. § 120 to, International Application No. PCT/JP2016/078322, filed Sep. 26, 2016, and claims priority therethrough under 35 U.S.C. § 119 to Japanese Patent Application No. 2015-188597, filed Sep. 25, 2015, Japanese Patent Application No. 2016-110490, filed Jun. 1, 2016, and Japanese Patent Application No. 2016-110491, filed Jun. 1, 2016, the entireties of which are incorporated by reference herein. Also, the Sequence Listing filed electronically herewith is hereby incorporated by reference (File name: 2018-03-21T_US-578 Seq List; File size: 341 KB; Date recorded: Mar. 21, 2018).

BACKGROUND OF THE INVENTION

Field of the Invention

The present invention relates to a method for producing linalool, and a microorganism used in the method.

Brief Description of the Related Arts

The aromatic substance linalool is a monoterpene alcohol that is found in the essential oils of various plants, including lavender and orange. Linalool is used to scent products such as perfumes, cosmetics, shampoos, and soaps, and is also used as an additive to provide flavor to food and beverages. Furthermore, linalool is used as a raw material in other monoterpene-based aromatic materials, and is an important compound as an intermediate of vitamin A or E. Linalool exists as enantiomers, including licareol, or (3R)-(−)-linalool ((3R)-3,7-dimethylocta-1,6-diene-3-ol, R-linalool), and coriandrol, or (3S)-(+)-linalool ((3S)-3,7-dimethylocta-1,6-diene-3-ol, S-linalool). It has been reported that the licareol and the coriandrol each provide distinct odors; licareol smells like woody lavender, and coriandrol smells like sweet *citrus* similar to petitgrain. These two enantiomers also have distinct odor thresholds, and licareol shows a lower threshold by approximately nine times as compared to coriandrol (for example, see Ana Clara Aprotosoaie, Monica Hancianu, Irina-Iuliana Costache Anca Miron, Flavour and Fragrance Journal, 2014, 29, 193-219).

Linalool as a flavor component has been well-studied, revealing relatively many biological activities such as sedative activity, anti-inflammatory activity, and antioxidant activity. In recent years, there has been an increase in health consciousness, a desire for functional food and beverages containing ingredients derived from plants. As a result, the function of linalool has become appealing, and products containing linalool have been developed. The desire for such food and beverages is expected to continue to increase, and therefore the demand for linalool will also increase. For this reason, establishing a method for efficiently producing linalool is in demand.

Linalool is synthesized by linalool synthase with geranyl diphosphate (GPP). GPP, a common precursor of monoterpene, is produced by condensation of isopentenyl diphosphate (IPP) and dimethylallyl diphosphate (DMAPP). DMAPP is an isomer of isopentenyl diphosphate. As a biosynthetic pathway for IPP and DMAPP, there are known a mevalonate pathway and a non-mevalonate pathway (MEP pathway). The mevalonate pathway is present in eukaryotes, such as plants, animals, yeasts, and the like, and some actinomycete and archaea. On the other hand, the MEP pathway is present in bacteria and plastids of plants. Conventionally, essential oils of plants including linalool are produced by extraction from plants using various extraction methods, Such as, for example, steam distillation and distillation under reduced pressure. (Japanese Patent Application Laid-open No. 2005-298580A and Japanese Patent Application Laid-open No. 2006-291007A, respectively. Furthermore, Japanese Patent Application Laid-open No. 2011-506713A describes a method of extracting a plant component by treating a mixture of a plant material and a solvent with an ultra-high-temperature. Meanwhile, a production method by chemical synthesis has also been reported, and for example, V. A. Semikolenov, I. I. Ilyna, and I. L. Simakova, Applied Catalysis A, General, 2001, 211: 91-107 describes a method for producing linalool by chemical synthesis using a catalyst and the raw material α-pinene. Moreover, recently, linalool production in yeast and *Escherichia coli* using a gene recombination technique has been reported (for example, see Chinese Patent Application Laid-open No. 102071155 and Sun M X, Liu J D, Du G C, Zhou J, and Chen J., Chin J Biotech, 2013, 29(6): 751-759, Herrero O, Ramon D, and Orejas M, Metab Eng, 2008, 10, 78-86, Rico J, Pardo E, and Orejas M, Appl Environ Microbiol, 2010, 76, 6449-6454, and Ratana Thanasomboon, Dujduan Waraho, Supapon Cheevadhanarak, and Asawin Meechaia, Procedia Computer Science 11 (2012) 88-95). However, the amount of linalool produced by genetic recombinant yeast is only a trace amount, and thus it cannot necessarily be said that this is an efficient production method.

SUMMARY OF THE INVENTION

The present invention describes a method of efficiently producing linalool and a microorganism able to express linalool synthase and efficiently produce linalool. The present invention specifically describes a method of producing linalool efficiently by culturing a bacterium expressing linalool synthase in a culture medium, wherein the linalool synthase is native to an actinomycete or a plant.

It is an aspect of the present invention to provide a method for producing linalool, the method comprising culturing a bacterium in a culture medium so that it is able to produce and casue accumulation of linalool, and collecting linalool from the culture medium or the bacterium; wherein said bacterium expresses linalool synthase; and wherein said linalool synthase has a property selected from the group consisting of: (a) amino acid sequence of said linalool synthase has at least one motif represented by the following formula $DDX_1[F/Y][D/Y]X_2X_3G$ (SEQ ID NO: 184), wherein, D represents aspartic acid, F represents phenylalanine, Y represents tyrosine, G represents glycine, $X_1$, $X_2$, and $X_3$ each independently represent an arbitrary amino acid, [F/Y] represents F or Y, and [D/Y] represents D or Y), (b) said linalool synthase is native to a plant or a microorganism, and (c) combinations thereof.

It is a further aspect of the present invention to provide the method as described above, wherein $X_1$ is selected from the group consisting of isoleucine (I), valine (V), methionine (M), and phenylalanine (F); $X_2$ is selected from the group consisting of valine (V), isoleucine (I), alanine (A), and threonine (T); and/or $X_3$ is selected from the group consisting of tyrosine (Y), cysteine (C), histidine (H), glutamic acid (E), and phenylalanine (F).

It is a further aspect of the present invention to provide the method as described above, wherein the linalool synthase is native to an actinomycete or a plant belonging to the genus

*Actinidia, Coriandrum, Artemisia, Backhousia, Arabidopsis, Citrus, Malta, Perilla, Vitis, Lavandula, Mentha, Ocimum,* or *Clarkia.*

It is a further aspect of the present invention to provide the method as described above, wherein the actinomycete is a bacterium belonging to the genus *Streptomyces.*

It is a further aspect of the present invention to provide the method as described above, wherein the linalool synthase is native to *Actinidia arguta, Coriandrum sativum, Artemisia annua, Backhousia citriodora, Arabidopsis thaliana, Citrus unshiu, Malus domestica, Perilla frutescens* var. *crispa, Vitis vinifera, Lavandula angustifolia, Mentha citrata, Ocimum basilicum, Clarkia breweri,* or *Streptomyces clavuligerus.*

It is a further aspect of the present invention to provide the method as described above, wherein the bacterium comprises a heterologous expression unit comprising a polynucleotide encoding the linalool synthase and a promoter operably linked thereto.

It is a further aspect of the present invention to provide the method as described above, wherein the polynucleotide is selected from the group consisting of (a1) a polynucleotide that comprises (i1) a nucleotide sequence represented by SEQ ID NO: 2, (ii1) a nucleotide sequence consisting of nucleotide residues at positions 79 to 1725 in the nucleotide sequence represented by SEQ ID NO: 2, or (iii1) a nucleotide sequence represented by SEQ ID NO: 3; (b1) a polynucleotide that comprises a nucleotide sequence having an identity of 90% or more to the nucleotide sequence of (i1), (ii1), or (iii1), and encodes a protein having a linalool synthase activity; (c1) a polynucleotide that hybridizes under stringent conditions with a polynucleotide comprising a nucleotide sequence complementary to the nucleotide sequence of (i1), (ii1), or (iii1), and encodes a protein having a linalool synthase activity; (a2) a polynucleotide that comprises (i2) a nucleotide sequence represented by SEQ ID NO: 5, (ii2) a nucleotide sequence consisting of nucleotide residues at positions 115 to 1773 in the nucleotide sequence represented by SEQ ID NO: 5, or (iii2) a nucleotide sequence represented by SEQ ID NO: 6; (b2) a polynucleotide that comprises a nucleotide sequence having an identity of 90% or more to the nucleotide sequence of (i2), (ii2), or (iii2), and encodes a protein having a linalool synthase activity; (c2) a polynucleotide that hybridizes under stringent conditions with a polynucleotide comprising a nucleotide sequence complementary to the nucleotide sequence of (i2), (ii2), or (iii2), and encodes a protein having a linalool synthase activity; (a3) a polynucleotide that comprises (i3) a nucleotide sequence represented by SEQ ID NO: 62 or (ii3) a nucleotide sequence represented by SEQ ID NO: 63; (b3) a polynucleotide that comprises a nucleotide sequence having an identity of 90% or more to the nucleotide sequence of (i3) or (ii3), and encodes a protein having a linalool synthase activity; (c3) a polynucleotide that hybridizes under stringent conditions with a polynucleotide comprising a nucleotide sequence complementary to the nucleotide sequence of (i3) or (ii3), and encodes a protein having a linalool synthase activity; (a4) a polynucleotide that comprises (i4) a nucleotide sequence represented by SEQ ID NO: 70, (ii4) a nucleotide sequence consisting of nucleotide residues at positions 85 to 1704 in the nucleotide sequence represented by SEQ ID NO: 70, or (iii4) a nucleotide sequence represented by SEQ ID NO: 71; (b4) a polynucleotide that comprises a nucleotide sequence having an identity of 90% or more to the nucleotide sequence of (i4), (ii4), or (iii4), and encodes a protein having a linalool synthase activity; (c4) a polynucleotide that hybridizes under stringent conditions with a polynucleotide comprising a nucleotide sequence complementary to the nucleotide sequence of (i4), (ii4), or (iii4), and encodes a protein having a linalool synthase activity; (a5) a polynucleotide that comprises (i5) a nucleotide sequence represented by SEQ ID NO: 73, (ii5) a nucleotide sequence consisting of nucleotide residues at positions 169 to 1785 in the nucleotide sequence represented by SEQ ID NO: 73, or (iii5) a nucleotide sequence represented by SEQ ID NO: 74; (b5) a polynucleotide that comprises a nucleotide sequence having an identity of 90% or more to the nucleotide sequence of (i5), (ii5), or (iii5), and encodes a protein having a linalool synthase activity; (c5) a polynucleotide that hybridizes under stringent conditions with a polynucleotide comprising a nucleotide sequence complementary to the nucleotide sequence of (i5), (ii5), or (iii5), and encodes a protein having a linalool synthase activity; (a6) a polynucleotide that comprises (i6) a nucleotide sequence represented by SEQ ID NO: 89 (M1) or (ii6) a nucleotide sequence represented by SEQ ID NO: 102 (M14); (b6) a polynucleotide that comprises a nucleotide sequence having an identity of 90% or more to the nucleotide sequence of (i6) or (ii6), and encodes a protein having a linalool synthase activity; (c6) a polynucleotide that hybridizes under stringent conditions with a polynucleotide comprising a nucleotide sequence complementary to the nucleotide sequence of (i6) or (ii6), and encodes a protein having a linalool synthase activity; (a7) a polynucleotide that comprises (i7) a nucleotide sequence represented by SEQ ID NO: 90 (M2) or (ii7) a nucleotide sequence represented by SEQ ID NO: 104 (M16); (b7) a polynucleotide that comprises a nucleotide sequence having an identity of 90% or more to the nucleotide sequence of (i7) or (ii7), and encodes a protein having a linalool synthase activity; (c7) a polynucleotide that hybridizes under stringent conditions with a polynucleotide comprising a nucleotide sequence complementary to the nucleotide sequence of (i7) or (ii7), and encodes a protein having a linalool synthase activity; (a8) a polynucleotide that comprises (i8) a nucleotide sequence represented by SEQ ID NO: 91 (M3) or (ii8) a nucleotide sequence represented by SEQ ID NO: 106 (M18); (b8) a polynucleotide that comprises a nucleotide sequence having an identity of 90% or more to the nucleotide sequence of (i8) or (ii8), and encodes a protein having a linalool synthase activity; (c8) a polynucleotide that hybridizes under stringent conditions with a polynucleotide comprising a nucleotide sequence complementary to the nucleotide sequence of (i8) or (ii8), and encodes a protein having a linalool synthase activity; (a9) a polynucleotide that comprises (i9) a nucleotide sequence represented by SEQ ID NO: 92 (M4) or (ii9) a nucleotide sequence represented by SEQ ID NO: 108 (M20); (b9) a polynucleotide that comprises a nucleotide sequence having an identity of 90% or more to the nucleotide sequence of (i9) or (ii9), and encodes a protein having a linalool synthase activity; (c9) a polynucleotide that hybridizes under stringent conditions with a polynucleotide comprising a nucleotide sequence complementary to the nucleotide sequence of (i9) or (ii9), and encodes a protein having a linalool synthase activity; (a10) a polynucleotide that comprises (i10) a nucleotide sequence represented by SEQ ID NO: 93 (M5) or (ii10) a nucleotide sequence represented by SEQ ID NO: 110 (M22); (b10) a polynucleotide that comprises a nucleotide sequence having an identity of 90% or more to the nucleotide sequence of (i10) or (ii10), and encodes a protein having a linalool synthase activity; (c10) a polynucleotide that hybridizes under stringent conditions with a polynucleotide comprising a nucleotide sequence complementary to the nucleotide sequence of (i10) or (ii10), and encodes a protein having a linalool synthase activity; (a11) a polynucleotide that comprises (i11) a nucleotide sequence represented by SEQ ID NO: 94 (M6) or (ii11) a nucleotide sequence represented by SEQ ID NO: 112 (M24); (b11) a polynucleotide that comprises a nucleotide sequence having an identity of 90% or more to the nucleotide sequence of (i11) or (ii11), and encodes a protein having a linalool synthase activity; (c11) a polynucleotide that hybridizes under stringent conditions with a polynucleotide comprising a nucleotide sequence complementary to the nucleotide sequence of (i11) or (ii11), and encodes a protein having a linalool synthase activity; (a12) a polynucleotide that comprises (i12) a nucleotide sequence represented by SEQ ID NO: 95 (M7) or (ii12) a nucleotide sequence represented by SEQ ID NO: 114 (M26); (b12) a polynucleotide that comprises a nucleotide sequence having an identity of 90% or more to the nucleotide sequence of (i12) or (ii12), and encodes a protein having a linalool synthase activity; (c12) a polynucleotide that hybridizes under stringent conditions with a polynucleotide comprising a nucleotide sequence complementary to the nucleotide sequence of (i12) or (ii12), and encodes a protein having a linalool synthase activity; (a13) a polynucleotide that comprises (i13) a nucleotide sequence represented by SEQ ID NO: 96 (M8) or (ii13) a nucleotide sequence represented by SEQ ID NO: 116 (M28); (b13) a polynucleotide that comprises a nucleotide sequence having an identity of 90% or more to the nucleotide sequence of (i13) or (ii13), and encodes a protein having a linalool synthase activity; (c13) a polynucleotide that hybridizes under stringent conditions with a polynucleotide comprising a nucleotide sequence complementary to the nucleotide sequence of (i13) or (ii13), and encodes a protein having a linalool synthase activity; (a14) a polynucleotide that comprises (i14) a nucleotide sequence represented by SEQ ID NO: 97 (M9) or (ii14) a nucleotide sequence represented by SEQ ID NO: 118 (M30); (b14) a polynucleotide that comprises a nucleotide sequence having an identity of 90% or more to the nucleotide sequence of (i14) or (ii14), and encodes a protein having a linalool synthase activity; (c14) a polynucleotide that hybridizes under stringent conditions with a polynucleotide comprising a nucleotide sequence complementary to the nucleotide sequence of (i14) or (ii14), and encodes a protein having a linalool synthase activity; (a15) a polynucleotide that comprises (i15) a nucleotide sequence represented by SEQ ID NO: 98 (M10) or (ii15) a nucleotide sequence represented by SEQ ID NO: 120 (M32); (b15) a polynucleotide that comprises a nucleotide sequence having an identity of 90% or more to the nucleotide sequence of (i15) or (ii15), and encodes a protein having a linalool synthase activity; (c15) a polynucleotide that hybridizes under stringent conditions with a polynucleotide comprising a nucleotide sequence complementary to the nucleotide sequence of (i15) or (ii15), and encodes a protein having a linalool synthase activity; (a16) a polynucleotide that comprises (i16) a nucleotide sequence represented by SEQ ID NO: 99 (M11) or (ii16) a nucleotide sequence represented by SEQ ID NO: 122 (M34); (b16) a polynucleotide that comprises a nucleotide sequence having an identity of 90% or more to the nucleotide sequence of (i16) or (ii16), and encodes a protein having a linalool synthase activity; (c16) a polynucleotide that hybridizes under stringent conditions with a polynucleotide comprising a nucleotide sequence complementary to the nucleotide sequence of (i16) or (ii16), and encodes a protein having a linalool synthase activity; (a17) a polynucleotide that comprises (i17) a nucleotide sequence represented by SEQ ID NO: 100 (M12) or (ii17) a nucleotide sequence represented by SEQ ID NO: 124 (M36); (b17) a polynucleotide that comprises a nucleotide sequence having an identity of 90% or more to the nucleotide sequence of (i17) or (ii17), and encodes a protein having a linalool synthase activity; (c17) a polynucleotide that hybridizes under stringent conditions with a polynucleotide comprising a nucleotide sequence complementary to the nucleotide sequence of (i17) or (ii17), and encodes a protein having a linalool synthase activity; (a18) a polynucleotide that comprises (i18) a nucleotide sequence represented by SEQ ID NO: 101 (M13) or (ii18) a nucleotide sequence represented by SEQ ID NO: 126 (M38); (b18) a polynucleotide that comprises a nucleotide sequence having an identity of 90% or more to the nucleotide sequence of (i18) or (ii18), and encodes a protein having a linalool synthase activity; (c18) a polynucleotide that hybridizes under stringent conditions with a polynucleotide comprising a nucleotide sequence complementary to the nucleotide sequence of (i18) or (ii18), and encodes a protein having a linalool synthase activity; (a19) a polynucleotide that comprises (i19) a nucleotide sequence represented by SEQ ID NO: 170 or (ii19) a nucleotide sequence represented by SEQ ID NO: 171; (b19) a polynucleotide that comprises a nucleotide sequence having an identity of 90% or more to the nucleotide sequence of (i19) or (ii19), and encodes a protein having a linalool synthase activity; (c19) a polynucleotide that hybridizes under stringent conditions with a polynucleotide comprising a nucleotide sequence complementary to the nucleotide sequence of (i19) or (ii19), and encodes a protein having a linalool synthase activity; (a20) a polynucleotide that comprises (i20) a nucleotide sequence represented by SEQ ID NO: 173 or (ii20) a nucleotide sequence represented by SEQ ID NO: 174; (b20) a polynucleotide that comprises a nucleotide sequence having an identity of 90% or more to the nucleotide sequence of (i20) or (ii20), and encodes a protein having a linalool synthase activity; (c20) a polynucleotide that hybridizes under stringent conditions with a polynucleotide comprising a nucleotide sequence complementary to the nucleotide sequence of (i20) or (ii20), and encodes a protein having a linalool synthase activity; (a21) a polynucleotide that comprises (i21) a nucleotide sequence represented by SEQ ID NO: 176 or (ii21) a nucleotide sequence represented by SEQ ID NO: 177; (b21) a polynucleotide that comprises a nucleotide sequence having an identity of 90% or more to the nucleotide sequence of (i21) or (ii21), and encodes a protein having a linalool synthase activity; (c21) a polynucleotide that hybridizes under stringent conditions with a polynucleotide comprising a nucleotide sequence complementary to the nucleotide sequence of (i21) or (ii21), and encodes a protein having a linalool synthase activity; (a22) a polynucleotide that comprises (i22) a nucleotide sequence represented by SEQ ID NO: 179 or (ii22) a nucleotide sequence represented by SEQ ID NO: 180; (b22) a polynucleotide that comprises a nucleotide sequence having an identity of 90% or more to the nucleotide sequence of (i22) or (ii22), and encodes a protein having a linalool synthase activity; (c22) a polynucleotide that hybridizes under stringent conditions with a polynucleotide comprising a nucleotide sequence complementary to the nucleotide sequence of (i22) or (ii22), and encodes a protein having a linalool synthase activity; (a23) a polynucleotide that comprises (i23) a nucleotide sequence represented by SEQ ID NO: 182 or (ii23) a nucleotide sequence represented by SEQ ID NO: 183; (b23) a polynucleotide that comprises a nucleotide sequence having an identity of 90% or more to the nucleotide sequence of (i23) or (ii23), and encodes a protein having a linalool synthase activity; (c23) a polynucleotide that hybridizes under stringent conditions with a polynucleotide comprising a nucleotide sequence complementary to the nucleotide sequence of (i23) or (ii23), and encodes a protein having a linalool synthase activity; and (a24) combinations thereof.

It is a further aspect of the present invention to provide the method as described above, wherein the linalool synthase is a protein selected from the group consisting of (A1) a protein that comprises (i1') a full-length amino acid sequence represented by SEQ ID NO: 1 or (ii1') an amino acid sequence consisting of amino acid residues at positions 27 to 574 in the amino acid sequence represented by SEQ ID NO: 1; (B1) a protein that comprises an amino acid sequence having an identity of 90% or more to the amino acid sequence of (i1') or (ii1'), and has a linalool synthase activity; (C1) a protein that comprises an amino acid sequence having a deletion, substitution, addition, or insertion of one or several amino acids in the amino acid sequence of (i1') or (ii1'), and has a linalool synthase activity; (A2) a protein that comprises (i2') a full-length amino acid sequence represented by SEQ ID NO: 4 or (ii2') an amino acid sequence consisting of amino acid residues at positions 39 to 590 in the amino acid sequence represented by SEQ ID NO: 4; (B2) a protein that comprises an amino acid sequence having an identity of 90% or more to the amino acid sequence of (i2') or (ii2'), and has a linalool synthase activity; (C2) a protein that comprises an amino acid sequence having a deletion, substitution, addition, or insertion of one or several amino acids in the amino acid sequence of (i2') or (ii2'), and has a linalool synthase activity; (A3) a protein that comprises (i3') a full-length amino acid sequence represented by SEQ ID NO: 61; (B3) a protein that comprises an amino acid sequence having an identity of 90% or more to the amino acid sequence of (i3'), and has a linalool synthase activity; (C3) a protein that comprises an amino acid sequence having a deletion, substitution, addition, or insertion of one or several amino acids in the amino acid sequence of (i3'), and has a linalool synthase activity; (A4) a protein that comprises (i4') a full-length amino acid sequence represented by SEQ ID NO: 69 or (ii4') an amino acid sequence consisting of amino acid residues at positions 29 to 567 in the amino acid sequence represented by SEQ ID NO: 69; (B4) a protein that comprises an amino acid sequence having an identity of 90% or more to the amino acid sequence of (i4') or (ii4'), and has a linalool synthase activity; (C4) a protein that comprises an amino acid sequence having a deletion, substitution, addition, or insertion of one or several amino acids in the amino acid sequence of (i4') or (ii4'), and has a linalool synthase activity; (A5) a protein that comprises (i5') a full-length amino acid sequence represented by SEQ ID NO: 72 or (ii5') an amino acid sequence consisting of amino acid residues at positions 57 to 594 in the amino acid sequence represented by SEQ ID NO: 72; (B5) a protein that comprises an amino acid sequence having an identity of 90% or more to the amino acid sequence of (i5') or (ii5'), and has a linalool synthase activity; (C5) a protein that comprises an amino acid sequence having a deletion, substitution, addition, or insertion of one or several amino acids in the amino acid sequence of (i5') or (ii5'), and has a linalool synthase activity; (A6) a protein that comprises (i6') an amino acid sequence consisting of a full-length amino acid sequence represented by SEQ ID NO: 103 (M15); (B6) a protein that comprises an amino acid sequence having an identity of 90% or more to the amino acid sequence of (i6'), and has a linalool synthase activity; (C6) a protein that comprises an amino acid sequence having a deletion, substitution, addition, or insertion of one or several amino acids in the amino acid sequence of (i6'), and has a linalool synthase activity; (A7) a protein that comprises (i7') an amino acid sequence consisting of a full-length amino acid sequence represented by SEQ ID NO: 105 (M17); (B7) a protein that comprises an amino acid sequence having an identity of 90% or more to the amino acid sequence of (i7'), and has a linalool synthase activity; (C7) a protein that comprises an amino acid sequence having a deletion, substitution, addition, or insertion of one or several amino acids in the amino acid sequence of (i7'), and has a linalool synthase activity; (A8) a protein that comprises (i8') an amino acid sequence consisting of a full-length amino acid sequence represented by SEQ ID NO: 107 (M19); (B8) a protein that comprises an amino acid sequence having an identity of 90% or more to the amino acid sequence of (i8'), and has a linalool synthase activity; (C8) a protein that comprises an amino acid sequence having a deletion, substitution, addition, or insertion of one or several amino acids in the amino acid sequence of (i8'), and has a linalool synthase activity; (A9) a protein that comprises (i9') a full-length amino acid sequence represented by SEQ ID NO: 109 (M21); (B9) a protein that comprises an amino acid sequence having an identity of 90% or more to the amino acid sequence of (i9'), and has a linalool synthase activity; (C9) a protein that comprises an amino acid sequence having a deletion, substitution, addition, or insertion of one or several amino acids in the amino acid sequence of (i9'), and has a linalool synthase activity; (A10) a protein that comprises (i10') an amino acid sequence consisting of a full-length amino acid sequence represented by SEQ ID NO: 111 (M23); (B10) a protein that comprises an amino acid sequence having an identity of 90% or more to the amino acid sequence of (i10'), and has a linalool synthase activity; (C10) a protein that comprises an amino acid sequence having a deletion, substitution, addition, or insertion of one or several amino acids in the amino acid sequence of (i10'), and has a linalool synthase activity; (A11) a protein that comprises (i11') a full-length amino acid sequence represented by SEQ ID NO: 113 (M25); (B11) a protein that comprises an amino acid sequence having an identity of 90% or more to the amino acid sequence of (i11'), and has a linalool synthase activity; (C11) a protein that comprises an amino acid sequence having a deletion, substitution, addition, or insertion of one or several amino acids in the amino acid sequence of (i11'), and has a linalool synthase activity; (A12) a protein that comprises (i12') a full-length amino acid sequence represented by SEQ ID NO: 115 (M27); (B12) a protein that comprises an amino acid sequence having an identity of 90% or more to the amino acid sequence of (i12'), and has a linalool synthase activity; (C12) a protein that comprises an amino acid sequence having a deletion, substitution, addition, or insertion of one or several amino acids in the amino acid sequence of (i12'), and has a linalool synthase activity; (A13) a protein that comprises (i13') a full-length amino acid sequence represented by SEQ ID NO: 117 (M29); (B13) a protein that comprises an amino acid sequence having an identity of 90% or more to the amino acid sequence of (i13'), and has a linalool synthase activity; (C13) a protein that comprises an amino acid sequence having a deletion, substitution, addition, or insertion of one or several amino acids in the amino acid sequence of (i13'), and has a linalool synthase activity; (A14) a protein that comprises (i14') a full-length amino acid sequence represented by SEQ ID NO: 119 (M31); (B14) a protein that comprises an amino acid sequence having an identity of 90% or more to the amino acid sequence of (i14'), and has a linalool synthase activity; (C14) a protein that comprises an amino acid sequence having a deletion, substitution, addition, or insertion of one or several amino acids in the amino acid sequence of (i14'), and has a linalool synthase activity; (A15) a protein that comprises (i15') a full-length amino acid sequence represented by SEQ ID NO: 121 (M33); (B15) a protein that comprises an amino acid sequence having an identity of 90% or more to the (i15') amino acid sequence and has a linalool synthase activity; (C15) a protein that comprises an amino acid sequence having a deletion, substitution, addition, or insertion of one or several amino acids in the amino acid sequence of (i15'), and has a linalool synthase activity; (A16) a protein that comprises (i16') a full-length amino acid sequence represented by SEQ ID NO: 123 (M35); (B16) a protein that comprises an amino acid sequence having an identity of 90% or more to the amino acid sequence of (i16'), and has a linalool synthase activity; (C16) a protein that comprises an amino acid sequence having a deletion, substitution, addition, or insertion of one or several amino acids in the amino acid sequence of (i16'), and has a linalool synthase activity; (A17) a protein that comprises (i17') a full-length amino acid sequence represented by SEQ ID NO: 125 (M37); (B17) a protein that comprises an amino acid sequence having an identity of 90% or more to the amino acid sequence of (i17'), and has a linalool synthase activity; (C17) a protein that comprises an amino acid sequence having a deletion, substitution, addition, or insertion of one or several amino acids in the amino acid sequence of (i17'), and has a linalool synthase activity; (A18) a protein that comprises (i18') a full-length amino acid sequence represented by SEQ ID NO: 127 (M39); (B18) a protein that comprises an amino acid sequence having an identity of 90% or more to the amino acid sequence of (i18'), and has a linalool synthase activity; (C18) a protein that comprises an amino acid sequence having a deletion, substitution, addition, or insertion of one or several amino acids in the amino acid sequence of (i18'), and has a linalool synthase activity; (A19) a protein that comprises (i19') an amino acid sequence consisting of a full-length amino acid sequence represented by SEQ ID NO: 161; (B19) a protein that comprises an amino acid sequence having an identity of 90% or more to the amino acid sequence of (i19'), and has a linalool synthase activity; (C19) a protein that comprises an amino acid sequence having a deletion, substitution, addition, or insertion of one or several amino acids in the amino acid sequence of (i19'), and has a linalool synthase activity; (A20) a protein that comprises (i20') a full-length amino acid sequence represented by SEQ ID NO: 162; (B20) a protein that comprises an amino acid sequence having an identity of 90% or more to the amino acid sequence of (i20'), and has a linalool synthase activity; (C20) a protein that comprises an amino acid sequence having a deletion, substitution, addition, or insertion of one or several amino acids in the amino acid sequence of (i20'), and has a linalool synthase activity; (A21) a protein that comprises (i21') an amino acid sequence consisting of a full-length amino acid sequence represented by SEQ ID NO: 163; (B21) a protein that comprises an amino acid sequence having an identity of 90% or more to the amino acid sequence of (i21'), and has a linalool synthase activity; (C21) a protein that comprises an amino acid sequence having a deletion, substitution, addition, or insertion of one or several amino acids in the amino acid sequence of (i21'), and has a linalool synthase activity; (A22) a protein that comprises (i22') a full-length amino acid sequence represented by SEQ ID NO: 164; (B22) a protein that comprises an amino acid sequence having an identity of 90% or more to the amino acid sequence of (i22'), and has a linalool synthase activity; (C22) a protein that comprises an amino acid sequence having a deletion, substitution, addition, or insertion of one or several amino acids in the amino acid sequence of (i22'), and has a linalool synthase activity; (A23) a protein that comprises (i23') a full-length amino acid sequence represented by SEQ ID NO: 165; (B23) a protein that comprises an amino acid sequence having an identity of 90% or more to the amino acid sequence of (i23'), and has a linalool synthase activity; (C23) a protein that comprises an amino acid sequence having a deletion, substitution, addition, or insertion of one or several amino acids in the amino acid sequence of (i23'), and has a linalool synthase activity; (A24) a protein that comprises (i24') a full-length amino acid sequence represented by SEQ ID NO: 166; (B24) a protein that comprises an amino acid sequence having an identity of 90% or more to the amino acid sequence of (i24'), and has a linalool synthase activity; (C24) a protein that comprises an amino acid sequence having a deletion, substitution, addition, or insertion of one or several amino acids in the amino acid sequence of (i24'), and has a linalool synthase activity; (A25) a protein that comprises (i25') a full-length amino acid sequence represented by SEQ ID NO: 167; (B25) a protein that comprises an amino acid sequence having an identity of 90% or more to the amino acid sequence of (i25'), and has a linalool synthase activity; (C25) a protein that comprises an amino acid sequence having a deletion, substitution, addition, or insertion of one or several amino acids in the amino acid sequence of (i25'), and has a linalool synthase activity; (A26) a protein that comprises (i26') a full-length amino acid sequence represented by SEQ ID NO: 168; (B26) a protein that comprises an amino acid sequence having an identity of 90% or more to the amino acid sequence of (i26'), and has a linalool synthase activity; (C26) a protein that comprises an amino acid sequence having a deletion, substitution, addition, or insertion of one or several amino acids in the amino acid sequence of (i26'), and has a linalool synthase activity; (A27) a protein that comprises (i27') a full-length amino acid sequence represented by SEQ ID NO: 169; (B27) a protein that comprises an amino acid sequence having an identity of 90% or more to the amino acid sequence of (i27'), and has a linalool synthase activity; (C27) a protein that comprises an amino acid sequence having a deletion, substitution, addition, or insertion of one or several amino acids in the amino acid sequence of (i27'), and has a linalool synthase activity; (A28) a protein that comprises (i28') a full-length amino acid sequence represented by SEQ ID NO: 172; (B28) a protein that comprises an amino acid sequence having an identity of 90% or more to the amino acid sequence of (i28'), and has a linalool synthase activity; (C28) a protein that comprises an amino acid sequence having a deletion, substitution, addition, or insertion of one or several amino acids in the amino acid sequence of (i28'), and has a linalool synthase activity; (A29) a protein that comprises (i29') a full-length amino acid sequence represented by SEQ ID NO: 175; (B29) a protein that comprises an amino acid sequence having an identity of 90% or more to the amino acid sequence of (i29'), and has a linalool synthase activity; (C29) a protein that comprises an amino acid sequence having a deletion, substitution, addition, or insertion of one or several amino acids in the amino acid sequence of (i29'), and has a linalool synthase activity; (A30) a protein that comprises (i30') a full-length amino acid sequence represented by SEQ ID NO: 178; (B30) a protein that comprises an amino acid sequence having an identity of 90% or more to the amino acid sequence of (i30'), and has a linalool synthase activity;

(C30) a protein that comprises an amino acid sequence having a deletion, substitution, addition, or insertion of one or several amino acids in the amino acid sequence of (i30'), and has a linalool synthase activity; (A31) a protein that comprises (i31') a full-length amino acid sequence represented by SEQ ID NO: 181; (B31) a protein that comprises an amino acid sequence having an identity of 90% or more to the amino acid sequence of (i31'), and has a linalool synthase activity; (C31) a protein that comprises an amino acid sequence having a deletion, substitution, addition, or insertion of one or several amino acids in the amino acid sequence of (i31'), and has a linalool synthase activity; and (A32) combinations thereof.

It is a further aspect of the present invention to provide the method as described above, wherein the bacterium expresses geranyl diphosphate synthase.

It is a further aspect of the present invention to provide the method as described above, wherein the bacterium has an ability to synthesize dimethylallyl diphosphate via a methylerythritol phosphate pathway.

It is a further aspect of the present invention to provide the method as described above, wherein the bacterium has an ability to synthesize dimethylallyl diphosphate via a mevalonate pathway.

It is a further aspect of the present invention to provide the method as described above, wherein the bacterium belongs to the family Enterobacteriaceae, is a coryneform bacterium, or is a bacterium of blue-green algae.

It is a further aspect of the present invention to provide the method as described above, wherein the bacterium belongs to the genus *Escherichia*, *Pantoea*, *Synechocystis*, or *Corynebacterium*.

It is a further aspect of the present invention to provide the method as described above, wherein the bacterium is *Escherichia coli*, *Pantoea ananatis*, *Synechocystis* sp., or *Corynebacterium glutamicum*.

It is a further aspect of the present invention to provide the method as described above, wherein a 2-ketogluconate formation pathway is blocked in the bacterium.

It is a further aspect of the present invention to provide the method as described above, wherein the 2-ketogluconate formation pathway is blocked by reduction of a glucose dehydrogenase activity.

It is a further aspect of the present invention to provide the method as described above, wherein a glucose dehydrogenase gene is disrupted in the bacterium.

It is a further aspect of the present invention to provide the method as described above, wherein the polynucleotide is selected from the group consisting of (x) a polynucleotide that comprises [i] a nucleotide sequence represented by SEQ ID NO: 59 or [ii] a nucleotide sequence consisting of nucleotide residues at positions 301 to 2691 in the nucleotide sequence represented by SEQ ID NO: 59; (y) a polynucleotide that comprises a nucleotide sequence having an identity of 90% or more to the nucleotide sequence of [i] or [ii], and encodes a protein having a glucose dehydrogenase activity; (z) a polynucleotide that hybridizes under stringent conditions with a polynucleotide comprising a nucleotide sequence complementary to the nucleotide sequence of [i] or [ii], and encodes a protein having a glucose dehydrogenase activity; and (z') combinations thereof.

It is a further aspect of the present invention to provide the method as described above, wherein the glucose dehydrogenase is a protein selected from the group consisting of (X) a protein that comprises a full-length amino acid sequence represented by SEQ ID NO: 60; (Y) a protein that comprises an amino acid sequence having an identity of 90% or more to the amino acid sequence represented by SEQ ID NO: 60, and has a glucose dehydrogenase activity; (Z) a protein that comprises an amino acid sequence having a deletion, substitution, addition, or insertion of one or several amino acids in the amino acid sequence represented by SEQ ID NO: 60, and has a glucose dehydrogenase activity; and (Z') combinations thereof.

It is a further aspect of the present invention to provide the method as described above, wherein an amount of linalool accumulated in the culture medium is 200 mg/L or more.

It is a further aspect of the present invention to provide the method as described above, wherein an amount of linalool accumulated in the culture medium is 500 mg/L or more.

It is an aspect of the present invention to provide a bacterium expressing linalool synthase native to an actinomycete or a plant belonging the genus *Actinidia*, *Coriandrum*, *Artemisia*, *Backhousia*, *Arabidopsis*, *Citrus*, *Malus*, *Perilla*, *Vitis*, *Lavandula*, *Mentha*, *Ocimum*, or *Clarkia*.

It is a further aspect of the present invention to provide the bacterium as described above, wherein the linalool synthase is native to *Actinidia arguta*, *Coriandrum sativum*, *Artemisia annua*, *Backhousia citriodora*, *Arabidopsis thaliana*, *Citrus unshiu*, *Malus domestica*, *Perilla frutescens* var. *crispa*, *Vitis vinifera*, *Lavandula angustifolia*, *Mentha citrata*, *Ocimum basilicum*, *Clarkia breweri*, or *Streptomyces clavuligerus*.

It is a further aspect of the present invention to provide the bacterium as described above, wherein the microorganism comprises a heterologous expression unit comprising a polynucleotide encoding the linalool synthase and a promoter operably linked to the polynucleotide.

It is an aspect of the present invention to provide a bacterium as described above, wherein the polynucleotide is selected from the group consisting of (a1) a polynucleotide that comprises (i1) a nucleotide sequence represented by SEQ ID NO: 2, (ii1) a nucleotide sequence consisting of nucleotide residues at positions 79 to 1725 in the nucleotide sequence represented by SEQ ID NO: 2, or (iii1) a nucleotide sequence represented by SEQ ID NO: 3; (b1) a polynucleotide that comprises a nucleotide sequence having an identity of 90% or more to the nucleotide sequence of (i1), (ii1), or (iii1), and encodes a protein having a linalool synthase activity; (c1) a polynucleotide that hybridizes under stringent conditions with a polynucleotide comprising a nucleotide sequence complementary to the nucleotide sequence of (i1), (ii1), or (iii1), and encodes a protein having a linalool synthase activity; (a2) a polynucleotide that comprises (i2) a nucleotide sequence represented by SEQ ID NO: 5, (ii2) a nucleotide sequence consisting of nucleotide residues at positions 115 to 1773 in the nucleotide sequence represented by SEQ ID NO: 5, or (iii2) a nucleotide sequence represented by SEQ ID NO: 6; (b2) a polynucleotide that comprises a nucleotide sequence having an identity of 90% or more to the nucleotide sequence of (i2), (ii2), or (iii2), and encodes a protein having a linalool synthase activity; (c2) a polynucleotide that hybridizes under stringent conditions with a polynucleotide comprising a nucleotide sequence complementary to the nucleotide sequence of (i2), (ii2), or (iii2), and encodes a protein having a linalool synthase activity; (a3) a polynucleotide that comprises (i3) a nucleotide sequence represented by SEQ ID NO: 62 or (ii3) a nucleotide sequence represented by SEQ ID NO: 63; (b3) a polynucleotide that comprises a nucleotide sequence having an identity of 90% or more to the nucleotide sequence of (i3) or (ii3), and encodes a protein having a linalool synthase activity; (c3) a polynucleotide that hybridizes under stringent conditions with a polynucleotide comprising a nucleotide sequence complementary to the nucleotide sequence of (i3) or (ii3), and encodes a protein having a linalool synthase activity; (a4) a polynucleotide that comprises (i4) a nucleotide sequence represented by SEQ ID NO: 70, (ii4) a nucleotide sequence consisting of nucleotide residues at positions 85 to 1704 in the nucleotide sequence represented by SEQ ID NO: 70, or (iii4) a nucleotide sequence represented by SEQ ID NO: 71; (b4) a polynucleotide that comprises a nucleotide sequence having an identity of 90% or more to the nucleotide sequence of (i4), (ii4), or (iii4), and encodes a protein having a linalool synthase activity; (c4) a polynucleotide that hybridizes under stringent conditions with a polynucleotide comprising a nucleotide sequence complementary to the nucleotide sequence of (i4), (ii4), or (iii4), and encodes a protein having a linalool synthase activity; (a5) a polynucleotide that comprises (i5) a nucleotide sequence represented by SEQ ID NO: 73, (ii5) a nucleotide sequence consisting of nucleotide residues at positions 169 to 1785 in the nucleotide sequence represented by SEQ ID NO: 73, or (iii5) a nucleotide sequence represented by SEQ ID NO: 74; (b5) a polynucleotide that comprises a nucleotide sequence having an identity of 90% or more to the nucleotide sequence of (i5), (ii5), or (iii5), and encodes a protein having a linalool synthase activity; (c5) a polynucleotide that hybridizes under stringent conditions with a polynucleotide comprising a nucleotide sequence complementary to the nucleotide sequence of (i5), (ii5), or (iii5), and encodes a protein having a linalool synthase activity; (a6) a polynucleotide that comprises (i6) a nucleotide sequence represented by SEQ ID NO: 89 (M1) or (ii6) a nucleotide sequence represented by SEQ ID NO: 102 (M14); (b6) a polynucleotide that comprises a nucleotide sequence having an identity of 90% or more to the nucleotide sequence of (i6) or (ii6), and encodes a protein having a linalool synthase activity; (c6) a polynucleotide that hybridizes under stringent conditions with a polynucleotide comprising a nucleotide sequence complementary to the nucleotide sequence of (i6) or (ii6), and encodes a protein having a linalool synthase activity; (a7) a polynucleotide that comprises (i7) a nucleotide sequence represented by SEQ ID NO: 90 (M2) or (ii7) a nucleotide sequence represented by SEQ ID NO: 104 (M16); (b7) a polynucleotide that comprises a nucleotide sequence having an identity of 90% or more to the nucleotide sequence of (i7) or (ii7), and encodes a protein having a linalool synthase activity; (c7) a polynucleotide that hybridizes under stringent conditions with a polynucleotide comprising a nucleotide sequence complementary to the nucleotide sequence of (i7) or (ii7), and encodes a protein having a linalool synthase activity; (a8) a polynucleotide that comprises (i8) a nucleotide sequence represented by SEQ ID NO: 91 (M3) or (ii8) a nucleotide sequence represented by SEQ ID NO: 106 (M18); (b8) a polynucleotide that comprises a nucleotide sequence having an identity of 90% or more to the nucleotide sequence of (i8) or (ii8), and encodes a protein having a linalool synthase activity; (c8) a polynucleotide that hybridizes under stringent conditions with a polynucleotide comprising a nucleotide sequence complementary to the nucleotide sequence of (i8) or (ii8), and encodes a protein having a linalool synthase activity; (a9) a polynucleotide that comprises (i9) a nucleotide sequence represented by SEQ ID NO: 92 (M4) or (ii9) a nucleotide sequence represented by SEQ ID NO: 108 (M20); (b9) a polynucleotide that comprises a nucleotide sequence having an identity of 90% or more to the nucleotide sequence of (i9) or (ii9), and encodes a protein having a linalool synthase activity; (c9) a polynucleotide that hybridizes under stringent conditions with a polynucleotide comprising a nucleotide sequence complementary to the nucleotide sequence of (i9) or (ii9), and encodes a protein having a linalool synthase activity; (a10) a polynucleotide that comprises (i10) a nucleotide sequence represented by SEQ ID NO: 93 (M5) or (ii10) a nucleotide sequence represented by SEQ ID NO: 110 (M22); (b10) a polynucleotide that comprises a nucleotide sequence having an identity of 90% or more to the nucleotide sequence of (i10) or (ii10), and encodes a protein having a linalool synthase activity; (c10) a polynucleotide that hybridizes under stringent conditions with a polynucleotide comprising a nucleotide sequence complementary to the nucleotide sequence of (i10) or (ii10), and encodes a protein having a linalool synthase activity; (a11) a polynucleotide that comprises (i11) a nucleotide sequence represented by SEQ ID NO: 94 (M6) or (ii11) a nucleotide sequence represented by SEQ ID NO: 112 (M24); (b11) a polynucleotide that comprises a nucleotide sequence having an identity of 90% or more to the nucleotide sequence of (i11) or (ii11), and encodes a protein having a linalool synthase activity; (c11) a polynucleotide that hybridizes under stringent conditions with a polynucleotide comprising a nucleotide sequence complementary to the nucleotide sequence of (i11) or (ii11), and encodes a protein having a linalool synthase activity; (a12) a polynucleotide that comprises (i12) a nucleotide sequence represented by SEQ ID NO: 95 (M7) or (ii12) a nucleotide sequence represented by SEQ ID NO: 114 (M26); (b12) a polynucleotide that comprises a nucleotide sequence having an identity of 90% or more to the nucleotide sequence of (i12) or (ii12), and encodes a protein having a linalool synthase activity; (c12) a polynucleotide that hybridizes under stringent conditions with a polynucleotide comprising a nucleotide sequence complementary to the nucleotide sequence of (i12) or (ii12), and encodes a protein having a linalool synthase activity; (a13) a polynucleotide that comprises (i13) a nucleotide sequence represented by SEQ ID NO: 96 (M8) or (ii13) a nucleotide sequence represented by SEQ ID NO: 116 (M28); (b13) a polynucleotide that comprises a nucleotide sequence having an identity of 90% or more to the nucleotide sequence of (i13) or (ii13), and encodes a protein having a linalool synthase activity; (c13) a polynucleotide that hybridizes under stringent conditions with a polynucleotide comprising a nucleotide sequence complementary to the nucleotide sequence of (i13) or (ii13), and encodes a protein having a linalool synthase activity; (a14) a polynucleotide that comprises (i14) a nucleotide sequence represented by SEQ ID NO: 97 (M9) or (ii14) a nucleotide sequence represented by SEQ ID NO: 118 (M30); (b14) a polynucleotide that comprises a nucleotide sequence having an identity of 90% or more to the nucleotide sequence of (i14) or (ii14), and encodes a protein having a linalool synthase activity; (c14) a polynucleotide that hybridizes under stringent conditions with a polynucleotide comprising a nucleotide sequence complementary to the nucleotide sequence of (i14) or (ii14), and encodes a protein having a linalool synthase activity; (a15) a polynucleotide that comprises (i15) a nucleotide sequence represented by SEQ ID NO: 98 (M10) or (ii15) a nucleotide sequence represented by SEQ ID NO: 120 (M32); (b15) a polynucleotide that comprises a nucleotide sequence having an identity of 90% or more to the nucleotide sequence of (i15) or (ii15), and encodes a protein having a linalool synthase activity; (c15) a polynucleotide that hybridizes under stringent conditions with a polynucleotide comprising a nucleotide sequence complementary to the nucleotide sequence of (i15) or (ii15), and encodes a protein having a linalool synthase activity; (a16) a polynucleotide that comprises (i16) a nucleotide sequence represented by SEQ ID NO: 99 (M11) or (ii16) a nucleotide sequence represented by SEQ ID NO: 122 (M34); (b16) a polynucleotide that comprises a nucleotide sequence having an identity of 90% or more to the nucleotide sequence of (i16) or (ii16), and encodes a protein having a linalool synthase activity; (c16) a polynucleotide that hybridizes under stringent conditions with a polynucleotide comprising a nucleotide sequence complementary to the nucleotide sequence of (i16) or (ii16), and encodes a protein having a linalool synthase activity; (a17) a polynucleotide that comprises (i17) a nucleotide sequence represented by SEQ ID NO: 100 (M12) or (ii17) a nucleotide sequence represented by SEQ ID NO: 124 (M36); (b17) a polynucleotide that comprises a nucleotide sequence having an identity of 90% or more to the nucleotide sequence of (i17) or (ii17), and encodes a protein having a linalool synthase activity; (c17) a polynucleotide that hybridizes under stringent conditions with a polynucleotide comprising a nucleotide sequence complementary to the nucleotide sequence of (i17) or (ii17), and encodes a protein having a linalool synthase activity; (a18) a polynucleotide that comprises (i18) a nucleotide sequence represented by SEQ ID NO: 101 (M13) or (ii18) a nucleotide sequence represented by SEQ ID NO: 126 (M38); (b18) a polynucleotide that comprises a nucleotide sequence having an identity of 90% or more to the nucleotide sequence of (i18) or (ii18), and encodes a protein having a linalool synthase activity; (c18) a polynucleotide that hybridizes under stringent conditions with a polynucleotide comprising a nucleotide sequence complementary to the nucleotide sequence of (i18) or (ii18), and encodes a protein having a linalool synthase activity; (a19) a polynucleotide that comprises (i19) a nucleotide sequence represented by SEQ ID NO: 170 or (ii19) a nucleotide sequence represented by SEQ ID NO: 171; (b19) a polynucleotide that comprises a nucleotide sequence having an identity of 90% or more to the nucleotide sequence of (i19) or (ii19), and encodes a protein having a linalool synthase activity; (c19) a polynucleotide that hybridizes under stringent conditions with a polynucleotide comprising a nucleotide sequence complementary to the nucleotide sequence of (i19) or (ii19), and encodes a protein having a linalool synthase activity; (a20) a polynucleotide that comprises (i20) a nucleotide sequence represented by SEQ ID NO: 173 or (ii20) a nucleotide sequence represented by SEQ ID NO: 174; (b20) a polynucleotide that comprises a nucleotide sequence having an identity of 90% or more to the nucleotide sequence of (i20) or (ii20), and encodes a protein having a linalool synthase activity; (c20) a polynucleotide that hybridizes under stringent conditions with a polynucleotide comprising a nucleotide sequence complementary to the nucleotide sequence of (i20) or (ii20), and encodes a protein having a linalool synthase activity; (a21) a polynucleotide that comprises (i21) a nucleotide sequence represented by SEQ ID NO: 176 or (ii21) a nucleotide sequence represented by SEQ ID NO: 177; (b21) a polynucleotide that comprises a nucleotide sequence having an identity of 90% or more to the nucleotide sequence of (i21) or (ii21), and encodes a protein having a linalool synthase activity; (c21) a polynucleotide that hybridizes under stringent conditions with a polynucleotide comprising a nucleotide sequence complementary to the nucleotide sequence of (i21) or (ii21), and encodes a protein having a linalool synthase activity; (a22) a polynucleotide that comprises (i22) a nucleotide sequence represented by SEQ ID NO: 179 or (ii22) a nucleotide sequence represented by SEQ ID NO: 180; (b22) a polynucleotide that comprises a nucleotide sequence having an identity of 90% or more to the nucleotide sequence of (i22) or (ii22), and encodes a protein having a linalool synthase activity; (c22) a polynucleotide that hybridizes under stringent conditions with a polynucleotide comprising a nucleotide sequence complementary to the nucleotide sequence of (i22) or (ii22), and encodes a protein having a linalool synthase activity; (a23) a polynucleotide that comprises (i23) a nucleotide sequence represented by SEQ ID NO: 182 or (ii23) a nucleotide sequence represented by SEQ ID NO: 183; (b23) a polynucleotide that comprises a nucleotide sequence having an identity of 90% or more to the nucleotide sequence of (i23) or (ii23), and encodes a protein having a linalool synthase activity; (c23) a polynucleotide that hybridizes under stringent conditions with a polynucleotide comprising a nucleotide sequence complementary to the nucleotide sequence of (i23) or (ii23), and encodes a protein having a linalool synthase activity; and (a24) combinations thereof.

It is a further aspect of the present invention to provide the bacterium as described above, wherein the bacterium belongs to the genus *Escherichia, Pantoea, Synechocystis,* or *Corynebacterium.*

BRIEF DESCRIPTION OF THE DRAWINGS

FIG. 20 shows a diagram illustrating the sequence logo of motif 4.

FIG. 21 shows a diagram illustrating the sequence logo of motif 5.

FIG. 22 shows a diagram illustrating the alignment of motif 1.

FIG. 23 shows a diagram illustrating the alignment of motif 2.

FIG. 24 shows a diagram illustrating the alignment of motif 3.

FIG. 25 shows a diagram illustrating the alignment of motif 4.

FIG. 26 shows a diagram illustrating the alignment of motif 5.

FIG. 27 shows a diagram illustrating the distribution of input sequences of motifs 1 to 5.

FIG. 28 is a diagram illustrating the distribution of motif 1 in linalool synthase (SEQ ID NO: 103: M15).

FIG. 29 is a diagram illustrating the distribution of motif 1 in linalool synthase (SEQ ID NO: 105: M17).

FIG. 30 is a diagram illustrating the distribution of motif 1 in linalool synthase (SEQ ID NO: 107: M19).

FIG. 31 is a diagram illustrating the distribution of motif 1 in linalool synthase (SEQ ID NO: 109: M21).

FIG. 32 is a diagram illustrating the distribution of motif 1 in linalool synthase (SEQ ID NO: 111: M23).

FIG. 33 is a diagram illustrating the distribution of motif 1 in linalool synthase (SEQ ID NO: 113: M25).

FIG. 34 is a diagram illustrating the distribution of motif 1 in linalool synthase (SEQ ID NO: 115: M27).

FIG. 35 is a diagram illustrating the distribution of motif 1 in linalool synthase (SEQ ID NO: 117: M29).

FIG. 36 is a diagram illustrating the distribution of motif 1 in linalool synthase (SEQ ID NO: 119: M31).

FIG. 37 is a diagram illustrating the distribution of motif 1 in linalool synthase (SEQ ID NO: 121: M33).

FIG. 38 is a diagram illustrating the distribution of motif 1 in linalool synthase (SEQ ID NO: 123: M35).

FIG. 39 is a diagram illustrating the distribution of motif 1 in linalool synthase (SEQ ID NO: 125: M37).

FIG. 40 is a diagram illustrating the distribution of motif 1 in linalool synthase (SEQ ID NO: 127: M39).

FIG. 41 is a diagram illustrating the distribution of motif 1 in linalool synthase (SEQ ID NO: 161).

FIG. 42 is a diagram illustrating the distribution of motif 1 in linalool synthase (SEQ ID NO: 162).

FIG. 43 is a diagram illustrating the distribution of motif 1 in linalool synthase (SEQ ID NO: 163).

FIG. 44 is a diagram illustrating the distribution of motif 1 in linalool synthase (SEQ ID NO: 164).

FIG. 45 is a diagram illustrating the distribution of motif 1 in linalool synthase (SEQ ID NO: 165).

FIG. 46 is a diagram illustrating the distribution of motif 1 in linalool synthase (SEQ ID NO: 166).

FIG. 47 is a diagram illustrating the distribution of motif 1 in linalool synthase (SEQ ID NO: 167).

FIG. 48 is a diagram illustrating the distribution of motif 1 in linalool synthase (SEQ ID NO: 168).

DESCRIPTION OF THE PREFERRED EMBODIMENTS

Figure 1:
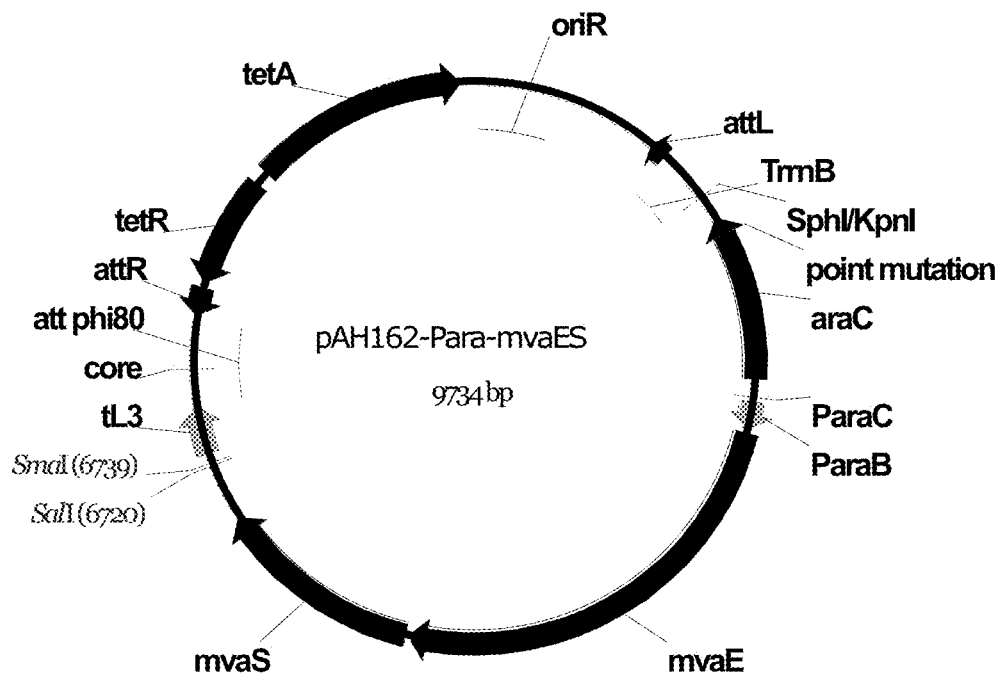
FIG. 1 shows a pAH162-Para-mvaES plasmid possessing an mvaES operon native to *E. faecalis* under control of *E. coli* Para promoter and a repressor gene araC.

The present invention provides a method of producing linalool.

The method as described herein includes the steps of culturing a microorganism expressing linalool synthase in a culture medium to produce linalool. The linalool synthase is can have at least one motif as described herein and the linalool synthase can be derived from a plant or a microorganism.

Linalool is an isoprenoid compound represented by $C_{10}H_{18}O$. Linalool has been assigned CAS number: 78-70-6, R-linalool has been assigned CAS number: 126-91-0, and S-linalool has been assigned CAS number: 126-90-9.

The linalool synthase refers to one or more enzymes involved in synthesis of linalool from geranyl diphosphate (GPP).

Linalool synthase may have at least one motif represented by the following formula:

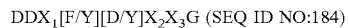

$DDX_1[F/Y][D/Y]X_2X_3G$ (SEQ ID NO:184)

In the formula, D represents aspartic acid. [F/Y] represents phenylalanine (F) or tyrosine (Y). [D/Y] represents D or Y. $X_1$, $X_2$, X, and $X_3$ each independently represent an arbitrary amino acid. Examples of $X_1$ can include isoleucine (I), valine (V), methionine (M), and F, I or V is preferable. Examples of $X_2$ can include V, I, alanine (A), and threonine (T), and V are particular examples. Examples of $X_3$ can include Y, cysteine (C), histidine (H), glutamic acid (E), and F, and Y are particular examples.

Linalool synthase may have one or a plurality of the motif, and a particular example is that linalool synthase has one motif.

Examples of the motif can include as follows:
a combination in which $X_1$ is I, [F/Y] is F, [D/Y] is D, $X_2$ is V, and $X_3$ is Y;
a combination in which $X_1$ is I, [F/Y] is F, [D/Y] is D, $X_2$ is V, and $X_3$ is Y;
a combination in which $X_1$ is I, [F/Y] is F, [D/Y] is D, $X_2$ is V, and $X_3$ is H;
a combination in which $X_1$ is I, [F/Y] is F, [D/Y] is D, $X_2$ is T, and $X_3$ is Y;
a combination in which $X_1$ is I, [F/Y] is F, [D/Y] is Y, $X_2$ is V, and $X_3$ is C;
a combination in which $X_1$ is I, [F/Y] is Y, [D/Y] is D, $X_2$ is I, and $X_3$ is Y;
a combination in which $X_1$ is I, [F/Y] is Y, [D/Y] is D, $X_2$ is A, and $X_3$ is Y;
a combination in which $X_1$ is I, [F/Y] is Y, [D/Y] is D, $X_2$ is V, and $X_3$ is Y;
a combination in which $X_1$ is V, [F/Y] is Y, [D/Y] is D, $X_2$ is I, and $X_3$ is Y;
a combination in which $X_1$ is V, [F/Y] is Y, [D/Y] is D, $X_2$ is V, and $X_3$ is F;
a combination in which $X_1$ is M, [F/Y] is Y, [D/Y] is D, $X_2$ is I, and $X_3$ is Y; and
a combination in which $X_1$ is F, [F/Y] is F, [D/Y] is D, $X_2$ is V, and $X_3$ is E.

The linalool synthase may be native to any living substance in which it exists natively. Examples of living substances having native linalool synthase can include plants belonging to the genera *Actinidia, Coriandrum, Artemisia, Backhousia, Fragaria, Clarkia, Arabidopsis, Citrus, Perilla, Mentha, Lavandula, Picea, Solanum, Vitis, Ocimum*, and *Malus*, and actinomycete, and a plant belonging to the genus *Actinidia, Coriandrum, Artemisia, Backhousia, Citrus, Malus, Perilla, Vitis, Lavandula, Mentha*, or *Ocimum*, or actinomycete are particular examples.

Examples of the plant belonging to the genus *Actinidia* can include hardy kiwifruit (*Actinidia arguta*) and silver vine (*Actinidia polygama*), and hardy kiwifruit is a particular example. Examples of the plant belonging to the genus *Coriandrum* can include coriander (*Coriandrum sativum*). Examples of the plant belonging to the genus *Artemisia* can include annual wormwood (*Artemisia annua*). Examples of the plant belonging to the genus *Backhousia* can include lemon myrtle (*Backhousia citriodora*). Examples of the plant belonging to the genus *Fragaria* can include strawberries (*Fragaria×ananassa*). Examples of the plant belonging to the genus *Clarkia* can include *clarkia* (*Clarkia breweri*). Examples of the plant belonging to the genus *Arabidopsis* can include thale-cress (*Arabidopsis thaliana*). Examples of the plant belonging to the genus *Citrus* can include unshu mikan (*Citrus unshiu*). Examples of the plant belonging to the genus *Perilla* can include Japanese basil (*Perilla hirtella; Perilla setoensis; Perilla frutescens* var. *crispa; Perilla frutescens* var. *hirtella*), and *Perilla frutescens* var. *crispa* is a particular example. Examples of the plant belonging to the genus *Mentha* can include bergamot Mint (*Mentha citrata*) and Water Mint (*Mentha aquatica*), and bergamot Mint is a particular example. Examples of the plant belonging to the genus *Lavandula* can include lavender (*Lavandula angustifolia*). Examples of the plant belonging to the genus *Picea* can include Sitka spruce (*Picea sitchensis*) and Norway spruce (*Picea abies*). Examples of the plant belonging to the genus *Solanum* can include tomatoes (*Solanum lycopersicum*). Examples of the plant belonging to the genus *Malus* can include apples (*Malus domestica*). Examples of the plant belonging to the genus *Vitis* can include European grapes (*Vitis vinifera*). Examples of the plant belonging to the genus *Ocimum* can include Basilico (*Ocimum basilicum*).

Examples of the actinomycete can include microorganisms belonging to the genera *Streptomyces, Kitasatospora, Streptacidiphilus, Pseudonocardia, Actinoalloteichus, Actinokineospora, Actinomycetospora, Actinophytocola, Actinosynnema, Alloactinosynnema, Allokutzneria, Amycolatopsis, Crossiella, Goodfellowiella, Haloechinothrix, Kibdelosporangium, Kutzneria, Labedaea, Lechevalieria, Lentzea, Longimycelium, Prauserella, Saccharomonospora, Saccharopolyspora, Saccharothrix, Sciscionella, Streptoalloteichus, Tamaricihabitans, Thermobispora, Thermocrispum, Thermotunica, Umezawaea*, and *Yuhushiella*, and microorganisms belonging to the genus *Streptomyces* (for example, *Streptomyces clavuligerus, Streptomyces griseus, Streptomyces antibioticus, Streptomyces avermitilis, Streptomyces verticillus, Streptomyces peuceticus, Streptomyces tsukubaensis,* or *Stereptomyces hygroscopicus* var. *limoneus*) are particular examples.

The linalool synthase can be native to a plant belonging to the genus *Actinidia, Coriandrum, Artemisia, Backhousia, Citrus, Malus, Perilla, Vitis, Lavandula, Mentha,* or *Ocimum*, or it can be native to an actinomycete.

The linalool synthase native to a living organism may have the above-described motif, and the linalool synthase native to a plant may also the above-described motif. Incidentally, the linalool synthase may have at least one motif described above and is not limited to the linalool synthase native to the living organism.

The microorganism expressing linalool synthase can be obtained, for example, by transforming a microorganism with an expression vector containing a heterologous expression unit that contains a polynucleotide encoding the linalool synthase native to a living substance and a promoter operably linked to the polynucleotide.

The phrase "native to", "derived from", or "in which it exists natively, when referring to a nucleic acid sequence such as a gene, a promoter, and the like, or an amino acid sequence such as a protein, can mean a nucleic acid molecule or an amino acid molecule that are naturally or natively synthesized by a microorganism or can be isolated from the natural or wild-type microorganism.

The polynucleotide encoding linalool synthase can include one or more polynucleotides designated as (a1)-(C23), for example:

(a1) a polynucleotide having (i1) the nucleotide sequence represented by SEQ ID NO:2, (ii1) the nucleotide sequence having the nucleotide residues at positions 79 to 1725 in the nucleotide sequence represented by SEQ ID NO:2, or (iii1) the nucleotide sequence represented by SEQ ID NO:3;

(b1) a polynucleotide that has a nucleotide sequence having 90% or more identity to the nucleotide sequence of (i1), (ii1) or (iii1) above, and encodes a protein having a linalool synthase activity;

(c1) a polynucleotide that hybridizes under stringent conditions with a polynucleotide having a nucleotide sequence complementary to the nucleotide sequence of (i1), (ii1), or (iii1) above, and encodes a protein having a linalool synthase activity;

(a2) a polynucleotide having (i2) the nucleotide sequence represented by SEQ ID NO:5, (ii2) the nucleotide sequence having the nucleotide residues at positions 115 to 1773 in the nucleotide sequence represented by SEQ ID NO:5, or (iii2) the nucleotide sequence represented by SEQ ID NO:6;

(b2) a polynucleotide that has a nucleotide sequence having 90% or more identity to the nucleotide sequence of (i2), (ii2) or (iii2) above, and encodes a protein having a linalool synthase activity;

(c2) a polynucleotide that hybridizes under stringent conditions with a polynucleotide having a nucleotide sequence complementary to the nucleotide sequence of (i2), (ii2), or (iii2) above, and encodes a protein having a linalool synthase activity;

(a3) a polynucleotide having (i3) the nucleotide sequence represented by SEQ ID NO:62, or (ii3) the nucleotide sequence represented by SEQ ID NO:63;

(b3) a polynucleotide that has a nucleotide sequence having 90% or more identity to the nucleotide sequence of (i3) or (ii3) above, and encodes a protein having a linalool synthase activity;

(c3) a polynucleotide that hybridizes under stringent conditions with a polynucleotide having a nucleotide sequence complementary to the nucleotide sequence of (i3) or (ii3) above, and encodes a protein having a linalool synthase activity;

(a4) a polynucleotide having (i4) the nucleotide sequence represented by SEQ ID NO: 70, (ii4) the nucleotide sequence having the nucleotide residues at positions 85 50 1704 in the nucleotide sequence represented by SEQ ID NO:70, or (iii4) the nucleotide sequence represented by SEQ ID NO:71;

(b4) a polynucleotide that has a nucleotide sequence having 90% or more identity to the nucleotide sequence of (i4), (ii4) or (iii4) above, and encodes a protein having a linalool synthase activity;

(c4) a polynucleotide that hybridizes under stringent conditions with a polynucleotide having a nucleotide sequence complementary to the nucleotide sequence of (i4), (ii4), or (iii4) above, and encodes a protein having a linalool synthase activity;

(a5) a polynucleotide having (i5) the nucleotide sequence represented by SEQ ID NO: 73, (ii5) the nucleotide sequence having the nucleotide residues at positions 169 to 1785 in the nucleotide sequence represented by SEQ ID NO:73, or (iii5) the nucleotide sequence represented by SEQ ID NO:74;

(b5) a polynucleotide that has a nucleotide sequence having 90% or more identity to the nucleotide sequence of (i5), (ii5) or (iii5) above, and encodes a protein having a linalool synthase activity;

(c5) a polynucleotide that hybridizes under stringent conditions with a polynucleotide having a nucleotide sequence complementary to the nucleotide sequence of (i5), (ii5), or (iii5) above, and encodes a protein having a linalool synthase activity;

(a6) a polynucleotide having (i6) the nucleotide sequence represented by SEQ ID NO:89 (M1), or (ii6) the nucleotide sequence represented by SEQ ID NO:102 (M14);

(b6) a polynucleotide that has a nucleotide sequence having 90% or more identity to the nucleotide sequence of (i6) or (ii6) above, and encodes a protein having a linalool synthase activity;

(c6) a polynucleotide that hybridizes under stringent conditions with a polynucleotide having a nucleotide sequence complementary to the nucleotide sequence of (i6) or (ii6) above, and encodes a protein having a linalool synthase activity;

(a7) a polynucleotide having (i7) the nucleotide sequence represented by SEQ ID NO:90 (M2), or (ii7) the nucleotide sequence represented by SEQ ID NO:104 (M16);

(b7) a polynucleotide that has a nucleotide sequence having 90% or more identity to the nucleotide sequence of (i7) or (ii7) above, and encodes a protein having a linalool synthase activity;

(c7) a polynucleotide that hybridizes under stringent conditions with a polynucleotide having a nucleotide sequence complementary to the nucleotide sequence of (i7) or (ii7) above, and encodes a protein having a linalool synthase activity;

(a8) a polynucleotide having (i8) the nucleotide sequence represented by SEQ ID NO:91 (M3), or (ii8) the nucleotide sequence represented by SEQ ID NO:106 (M18);

(b8) a polynucleotide that has a nucleotide sequence having 90% or more identity to the nucleotide sequence of (i8) or (ii8) above, and encodes a protein having a linalool synthase activity;

(c8) a polynucleotide that hybridizes under stringent conditions with a polynucleotide having a nucleotide sequence complementary to the nucleotide sequence of (i8) or (ii8) above, and encodes a protein having a linalool synthase activity;

(a9) a polynucleotide having (i9) the nucleotide sequence represented by SEQ ID NO:92 (M4), or (ii9) the nucleotide sequence represented by SEQ ID NO:108 (M20);

(b9) a polynucleotide that has a nucleotide sequence having 90% or more identity to the nucleotide sequence of (i9) or (ii9) above, and encodes a protein having a linalool synthase activity;

(c9) a polynucleotide that hybridizes under stringent conditions with a polynucleotide having a nucleotide sequence complementary to the nucleotide sequence of (i9) or (ii9) above, and encodes a protein having a linalool synthase activity;

(a10) a polynucleotide having (i10) the nucleotide sequence represented by SEQ ID NO:93 (M5), or (ii10) the nucleotide sequence represented by SEQ ID NO:110 (M22);

(b10) a polynucleotide that has a nucleotide sequence having 90% or more identity to the nucleotide sequence of (i10) or (ii10) above, and encodes a protein having a linalool synthase activity;

(c10) a polynucleotide that hybridizes under stringent conditions with a polynucleotide having a nucleotide sequence complementary to the nucleotide sequence of (i10) or (ii10) above, and encodes a protein having a linalool synthase activity;

(a11) a polynucleotide having (i11) the nucleotide sequence represented by SEQ ID NO:94 (M6), or (ii11) the nucleotide sequence represented by SEQ ID NO:112 (M24);

(b11) a polynucleotide that has a nucleotide sequence having 90% or more identity to the nucleotide sequence of (i11) or (ii11) above, and encodes a protein having a linalool synthase activity;

(c11) a polynucleotide that hybridizes under stringent conditions with a polynucleotide having a nucleotide sequence complementary to the nucleotide sequence of (i11) or (ii11) above, and encodes a protein having a linalool synthase activity;

(a12) a polynucleotide having (i12) the nucleotide sequence represented by SEQ ID NO:95 (M7), or (ii12) the nucleotide sequence represented by SEQ ID NO:114 (M26);

(b12) a polynucleotide that has a nucleotide sequence having 90% or more identity to the nucleotide sequence of (i12) or (ii12) above, and encodes a protein having a linalool synthase activity;

(c12) a polynucleotide that hybridizes under stringent conditions with a polynucleotide having a nucleotide sequence complementary to the nucleotide sequence of (i12) or (ii12) above, and encodes a protein having a linalool synthase activity;

(a13) a polynucleotide having (i13) the nucleotide sequence represented by SEQ ID NO:96 (M18), or (ii13) the nucleotide sequence represented by SEQ ID NO:116 (M28);

(b13) a polynucleotide that has a nucleotide sequence having 90% or more identity to the nucleotide sequence of (i13) or (ii13) above, and encodes a protein having a linalool synthase activity;

(c13) a polynucleotide that hybridizes under stringent conditions with a polynucleotide having a nucleotide sequence complementary to the nucleotide sequence of (i13) or (ii13) above, and encodes a protein having a linalool synthase activity;

(a14) a polynucleotide having (i14) the nucleotide sequence represented by SEQ ID NO:97 (M9), or (ii14) the nucleotide sequence represented by SEQ ID NO:118 (M30);

(b14) a polynucleotide that has a nucleotide sequence having 90% or more identity to the nucleotide sequence of (i14) or (ii14) above, and encodes a protein having a linalool synthase activity;

(c14) a polynucleotide that hybridizes under stringent conditions with a polynucleotide having a nucleotide sequence complementary to the nucleotide sequence of (i14) or (ii14) above, and encodes a protein having a linalool synthase activity;

(a15) a polynucleotide having (i15) the nucleotide sequence represented by SEQ ID NO:98 (M10), or (ii15) the nucleotide sequence represented by SEQ ID NO:120 (M32);

(b15) a polynucleotide that has a nucleotide sequence having 90% or more identity to the nucleotide sequence of (i15) or (ii15) above, and encodes a protein having a linalool synthase activity;

(c15) a polynucleotide that hybridizes under stringent conditions with a polynucleotide having a nucleotide sequence complementary to the nucleotide sequence of (i15) or (ii15) above, and encodes a protein having a linalool synthase activity;

(a16) a polynucleotide having (i16) the nucleotide sequence represented by SEQ ID NO:99 (M11), or (ii16) the nucleotide sequence represented by SEQ ID NO:122 (M34);

(b16) a polynucleotide that has a nucleotide sequence having 90% or more identity to the nucleotide sequence of (i16) or (ii16) above, and encodes a protein having a linalool synthase activity;

(c16) a polynucleotide that hybridizes under stringent conditions with a polynucleotide having a nucleotide sequence complementary to the nucleotide sequence of (i16) or (ii16) above, and encodes a protein having a linalool synthase activity;

(a17) a polynucleotide having (i17) the nucleotide sequence represented by SEQ ID NO:100 (M12), or (ii17) the nucleotide sequence represented by SEQ ID NO:124 (M36);

(b17) a polynucleotide that has a nucleotide sequence having 90% or more identity to the nucleotide sequence of (i17) or (ii17) above, and encodes a protein having a linalool synthase activity;

(c17) a polynucleotide that hybridizes under stringent conditions with a polynucleotide having a nucleotide sequence complementary to the nucleotide sequence of (i17) or (ii17) above, and encodes a protein having a linalool synthase activity;

(a18) a polynucleotide having (i18) the nucleotide sequence represented by SEQ ID NO:101 (M13), or (ii18) the nucleotide sequence represented by SEQ ID NO:126 (M38);

(b18) a polynucleotide that has a nucleotide sequence having 90% or more identity to the nucleotide sequence of (i18) or (ii18) above, and encodes a protein having a linalool synthase activity;

(c18) a polynucleotide that hybridizes under stringent conditions with a polynucleotide having a nucleotide sequence complementary to the nucleotide sequence of (i18) or (ii18) above, and encodes a protein having a linalool synthase activity;

(a19) a polynucleotide having (i19) the nucleotide sequence represented by SEQ ID NO:170, or (ii19) the nucleotide sequence represented by SEQ ID NO:171;

(b19) a polynucleotide that has a nucleotide sequence having 90% or more identity to the nucleotide sequence of (i19) or (ii19) above, and encodes a protein having a linalool synthase activity;

(c19) a polynucleotide that hybridizes under stringent conditions with a polynucleotide having a nucleotide sequence complementary to the nucleotide sequence of (i19) or (ii19) above, and encodes a protein having a linalool synthase activity;

(a20) a polynucleotide having (i20) the nucleotide sequence represented by SEQ ID NO:173, or (ii20) the nucleotide sequence represented by SEQ ID NO:174;

(b20) a polynucleotide that has a nucleotide sequence having 90% or more identity to the nucleotide sequence of (i20) or (ii20) above, and encodes a protein having a linalool synthase activity;

(c20) a polynucleotide that hybridizes under stringent conditions with a polynucleotide having a nucleotide sequence complementary to the nucleotide sequence of (i20) or (ii20) above, and encodes a protein having a linalool synthase activity;

(a21) a polynucleotide having (i21) the nucleotide sequence represented by SEQ ID NO:176, or (ii21) the nucleotide sequence represented by SEQ ID NO:177;

(b21) a polynucleotide that has a nucleotide sequence having 90% or more identity to the nucleotide sequence of (i21) or (ii21) above, and encodes a protein having a linalool synthase activity;

(c21) a polynucleotide that hybridizes under stringent conditions with a polynucleotide having a nucleotide sequence complementary to the nucleotide sequence of (i21) or (ii21) above, and encodes a protein having a linalool synthase activity;

(a22) a polynucleotide having (i22) the nucleotide sequence represented by SEQ ID NO:179, or (ii22) the nucleotide sequence represented by SEQ ID NO:180;

(b22) a polynucleotide that has a nucleotide sequence having 90% or more identity to the nucleotide sequence of (i22) or (ii22) above, and encodes a protein having a linalool synthase activity;

(c22) a polynucleotide that hybridizes under stringent conditions with a polynucleotide having a nucleotide sequence complementary to the nucleotide sequence of (i22) or (ii22) above, and encodes a protein having a linalool synthase activity;

(a23) a polynucleotide having (i23) the nucleotide sequence represented by SEQ ID NO:182, or (ii23) the nucleotide sequence represented by SEQ ID NO:183;

(b23) a polynucleotide that has a nucleotide sequence having 90% or more identity to the nucleotide sequence of (i23) or (ii23) above, and encodes a protein having a linalool synthase activity; and/or (c23) a polynucleotide that hybridizes under stringent conditions with a polynucleotide having a nucleotide sequence complementary to the nucleotide sequence of (i23) or (ii23) above, and encodes a protein having a linalool synthase activity.

The nucleotide sequence represented by SEQ ID NO: 2 is a full-length nucleotide sequence of a linalool synthase gene native to hardy kiwifruit. The nucleotide sequence represented by SEQ ID NO: 2 may encode the amino acid sequence represented by SEQ ID NO: 1, the nucleotide sequence having nucleotide residues at positions 1 to 78 may encode a putative chloroplast localization signal, and the nucleotide sequence having nucleotide residues at positions 79 to 1725 (1722) may encode an amino acid sequence of mature linalool synthase. The nucleotide sequence represented by SEQ ID NO: 3 has a nucleotide sequence in which codons in the nucleotide sequence at positions 79 to 1725 (1722) of SEQ ID NO: 2 are modified, and methionine codons are further added at the 5' terminus thereof.

The nucleotide sequence represented by SEQ ID NO: 5 is a full-length of a linalool synthase gene native to coriander. The nucleotide sequence represented by SEQ ID NO: 5 may encode the amino acid sequence represented by SEQ ID NO: 4, the nucleotide sequence having nucleotide residues at positions 1 to 114 may encode a putative chloroplast localization signal, and the nucleotide sequence having nucleotide residues at positions 115 to 1773 (1770) may encode an amino acid sequence of mature linalool synthase. The nucleotide sequence represented by SEQ ID NO: 6 has a nucleotide sequence in which codons in the nucleotide sequence at positions 115 to 1773 (1770) of SEQ ID NO: 5 are modified.

The nucleotide sequence represented by SEQ ID NO: 62 is a full-length of a linalool synthase gene native to *Streptomyces clavuligerus*. The nucleotide sequence represented by SEQ ID NO: 62 may encode the amino acid sequence represented by SEQ ID NO: 61 and can include a coding region of the amino acid sequence of mature linalool synthase. The nucleotide sequence represented by SEQ ID NO:

63 has a nucleotide sequence in which codons in the nucleotide sequence represented by SEQ ID NO: 62 are modified. Incidentally, in the linalool synthase of *Streptomyces clavuligerus*, a putative chloroplast localization signal does not exist.

The nucleotide sequence represented by SEQ ID NO: 70 is a full-length of a linalool synthase gene native to annual wormwood. The nucleotide sequence represented by SEQ ID NO: 70 may encode the amino acid sequence represented by SEQ ID NO: 69, the nucleotide sequence having nucleotide residues at positions 1 to 84 may encode a putative chloroplast localization signal, and the nucleotide sequence having nucleotide residues at positions 85 to 1704 (1701) may encode an amino acid sequence of mature linalool synthase. The nucleotide sequence represented by SEQ ID NO: 71 has a nucleotide sequence in which codons in the nucleotide sequence at positions 85 to 1704 of SEQ ID NO: 70 are modified.

The nucleotide sequence represented by SEQ ID NO: 73 is a full-length of a linalool synthase gene native to lemon myrtle. The nucleotide sequence represented by SEQ ID NO: 73 may encode the amino acid sequence represented by SEQ ID NO: 72, the nucleotide sequence having nucleotide residues at positions 1 to 168 may encode a putative chloroplast localization signal, and the nucleotide sequence having nucleotide residues at positions 169 to 1785 (1782) may encode an amino acid sequence of mature linalool synthase. The nucleotide sequence represented by SEQ ID NO: 74 has a nucleotide sequence in which codons in the nucleotide sequence at positions 169 to 1785 (1782) of SEQ ID NO: 73 are modified.

The nucleotide sequence represented by SEQ ID NO: 89 (M1) is a full-length of a linalool synthase gene native to thale-cress. The nucleotide sequence represented by SEQ ID NO: 89 (M1) may encode an amino acid sequence of mature linalool synthase represented by SEQ ID NO: 103 (M15). The nucleotide sequence represented by SEQ ID NO: 102 (M14) has a nucleotide sequence in which codons in the nucleotide sequence having nucleotide residues at positions 70 to 1644 (1641) in the nucleotide sequence represented by SEQ ID NO: 89 (M1) are modified.

The nucleotide sequence represented by SEQ ID NO: 90 (M2) is a full-length of a linalool synthase gene native to thale-cress. The nucleotide sequence represented by SEQ ID NO: 90 (M2) may encode an amino acid sequence of mature linalool synthase represented by SEQ ID NO: 105 (M17). The nucleotide sequence represented by SEQ ID NO: 104 (M16) has a nucleotide sequence in which codons in the nucleotide sequence represented by SEQ ID NO: 90 (M2) are modified.

The nucleotide sequence represented by SEQ ID NO: 91 (M3) is a full-length of a linalool synthase gene native to *Citrus unshiu* (unshu mikan). The nucleotide sequence represented by SEQ ID NO: 91 (M3) may encode an amino acid sequence of mature linalool synthase represented by SEQ ID NO: 107 (M19). The nucleotide sequence represented by SEQ ID NO: 106 (M18) has a nucleotide sequence in which codons in the nucleotide sequence represented by SEQ ID NO: 91 (M3) are modified.

The nucleotide sequence represented by SEQ ID NO: 92 (M4) is a full-length of a linalool synthase gene native to *Citrus unshiu* (unshu mikan). The nucleotide sequence represented by SEQ ID NO: 92 (M4) may encode an amino acid sequence of mature linalool synthase represented by SEQ ID NO: 109 (M21). The nucleotide sequence represented by SEQ ID NO: 108 (M20) has a nucleotide sequence in which codons in the nucleotide sequence represented by SEQ ID NO: 92 (M4) are modified.

The nucleotide sequence represented by SEQ ID NO: 93 (M5) is a full-length of a linalool synthase gene native to *Citrus unshiu* (unshu mikan). The nucleotide sequence represented by SEQ ID NO: 93 (M5) may encode an amino acid sequence of mature linalool synthase represented by SEQ ID NO: 111 (M23). The nucleotide sequence represented by SEQ ID NO: 110 (M22) has a nucleotide sequence in which codons in the nucleotide sequence represented by SEQ ID NO: 93 (M5) are modified.

The nucleotide sequence represented by SEQ ID NO: 94 (M6) is a full-length of a linalool synthase gene native to apple. The nucleotide sequence represented by SEQ ID NO: 94 (M6) may encode an amino acid sequence of mature linalool synthase represented by SEQ ID NO: 113 (M25). The nucleotide sequence represented by SEQ ID NO: 112 (M24) has a nucleotide sequence in which codons in the nucleotide sequence represented by SEQ ID NO: 94 (M6) are modified.

The nucleotide sequence represented by SEQ ID NO: 95 (M7) is a full-length of a linalool synthase gene native to shiso. The nucleotide sequence represented by SEQ ID NO: 95 (M7) may encode an amino acid sequence of mature linalool synthase represented by SEQ ID NO: 115 (M27). The nucleotide sequence represented by SEQ ID NO: 114 (M26) has a nucleotide sequence in which codons in the nucleotide sequence represented by SEQ ID NO: 95 (M7) are modified.

The nucleotide sequence represented by SEQ ID NO: 96 (M8) is a full-length of a linalool synthase gene native to European grape. The nucleotide sequence represented by SEQ ID NO: 96 (M8) may encode an amino acid sequence of mature linalool synthase represented by SEQ ID NO: 117 (M29). The nucleotide sequence represented by SEQ ID NO: 116 (M28) has a nucleotide sequence in which codons in the nucleotide sequence represented by SEQ ID NO: 96 (M8) are modified.

The nucleotide sequence represented by SEQ ID NO: 97 (M9) is a full-length of a linalool synthase gene native to European grape. The nucleotide sequence represented by SEQ ID NO: 97 (M9) may encode an amino acid sequence of mature linalool synthase represented by SEQ ID NO: 119 (M31). The nucleotide sequence represented by SEQ ID NO: 118 (M30) has a nucleotide sequence in which codons in the nucleotide sequence represented by SEQ ID NO: 97 (M9) are modified.

The nucleotide sequence represented by SEQ ID NO: 98 (M10) is a full-length of a linalool synthase gene native to lavender. The nucleotide sequence represented by SEQ ID NO: 98 (M10) may encode an amino acid sequence of mature linalool synthase represented by SEQ ID NO: 121 (M33). The nucleotide sequence represented by SEQ ID NO: 120 (M32) has a nucleotide sequence in which codons in the nucleotide sequence represented by SEQ ID NO: 98 (M10) are modified.

The nucleotide sequence represented by SEQ ID NO: 99 (M11) is a full-length of a linalool synthase gene native to bergamot mint. The nucleotide sequence represented by SEQ ID NO: 99 (M11) may encode an amino acid sequence of mature linalool synthase represented by SEQ ID NO: M35. The nucleotide sequence represented by SEQ ID NO: M34 has a nucleotide sequence in which codons in the nucleotide sequence represented by SEQ ID NO: 99 (M11) are modified.

The nucleotide sequence represented by SEQ ID NO: 100 (M12) is a full-length of a linalool synthase gene native to basilico. The nucleotide sequence represented by SEQ ID NO: 100 (M12) may encode an amino acid sequence of mature linalool synthase represented by SEQ ID NO: 125 (M37). The nucleotide sequence represented by SEQ ID NO: 124 (M36) has a nucleotide sequence in which codons in the nucleotide sequence represented by SEQ ID NO: 100 (M12) are modified.

The nucleotide sequence represented by SEQ ID NO: 101 (M13) is a full-length of a linalool synthase gene native to *clarkia*. The nucleotide sequence represented by SEQ ID NO: 101 (M13) may encode an amino acid sequence of mature linalool synthase represented by SEQ ID NO: 127 (M39). The nucleotide sequence represented by SEQ ID NO: 126 (M38) has a nucleotide sequence in which codons in the nucleotide sequence represented by SEQ ID NO: 101 (M13) are modified.

The nucleotide sequence represented by SEQ ID NO: 170 is a full-length of a linalool synthase gene native to *Arabidopsis thaliana* (thale-cress). The nucleotide sequence represented by SEQ ID NO: 170 may encode the amino acid sequence represented by SEQ ID NO: 169 and can include a coding region of the amino acid sequence of mature linalool synthase. The nucleotide sequence represented by SEQ ID NO: 171 has a nucleotide sequence in which codons in the nucleotide sequence represented by SEQ ID NO: 170 are modified. Incidentally, in the respective sequences represented by SEQ ID NOs: 169 to 171, a sequence portion corresponding to a putative chloroplast localization signal is not present.

The nucleotide sequence represented by SEQ ID NO: 173 is a full-length of a linalool synthase gene native to *Perilla frutescens* var. *crispa* (shiso). The nucleotide sequence represented by SEQ ID NO: 173 may encode the amino acid sequence represented by SEQ ID NO: 172 and can include a coding region of the amino acid sequence of mature linalool synthase. The nucleotide sequence represented by SEQ ID NO: 174 has a nucleotide sequence in which codons in the nucleotide sequence represented by SEQ ID NO: 173 are modified. Incidentally, in the sequences represented by SEQ ID NOs: 172 to 174, a sequence portion corresponding to a putative chloroplast localization signal is not present.

The nucleotide sequence represented by SEQ ID NO:176 is a full-length of a linalool synthase gene native to *Vitis vinifera* (European grape). The nucleotide sequence represented by SEQ ID NO: 176 may encode the amino acid sequence represented by SEQ ID NO: 175 and can include a coding region of the amino acid sequence of mature linalool synthase. The nucleotide sequence represented by SEQ ID NO: 177 has a nucleotide sequence in which codons in the nucleotide sequence represented by SEQ ID NO: 176 are modified. Incidentally, in the sequences represented by SEQ ID NOs: 175 to 177, a sequence portion corresponding to a putative chloroplast localization signal is not present.

The nucleotide sequence represented by SEQ ID NO: 179 is a full-length of a linalool synthase gene native to *Mentha citrata* (bergamot Mint). The nucleotide sequence represented by SEQ ID NO: 179 may encode the amino acid sequence represented by SEQ ID NO: 178 and can include a coding region of the amino acid sequence of mature linalool synthase. The nucleotide sequence represented by SEQ ID NO: 180 has a nucleotide sequence in which codons in the nucleotide sequence represented by SEQ ID NO: 179 are modified. Incidentally, in the sequences represented by SEQ ID NOs: 178 to 180, a sequence portion corresponding to a putative chloroplast localization signal is not present.

The nucleotide sequence represented by SEQ ID NO: 182 is a full-length of a linalool synthase gene native to *Ocimum Basilicum* (Basilico). The nucleotide sequence represented by SEQ ID NO: 182 may encode the amino acid sequence represented by SEQ ID NO: 181 and can include a coding region of the amino acid sequence of mature linalool synthase. The nucleotide sequence represented by SEQ ID NO: 183 has a nucleotide sequence in which codons in the nucleotide sequence represented by SEQ ID NO: 182 are modified. Incidentally, in the sequences represented by SEQ ID NOs: 181 to 183, a sequence portion corresponding to a putative chloroplast localization signal is not present.

The percent identity to the nucleotide sequence may be 90%, 91%, 92%, 93%, 94%, 95%, 96%, 97%, 98%, or 99% or more. The linalool synthase activity can refer to an activity to produce linalool from geranyl diphosphate (GPP) (the same meaning shall apply hereinafter).

The percent identity of the nucleotide sequences, and the percent identity of the amino acid sequences as described herein can be determined using algorithm BLAST (Pro. Natl. Acad. Sci. USA, 90, 5873 (1993)) by Karlin and Altschul, and FASTA (Methods Enzymol., 183, 63 (1990)) by Pearson. The programs referred to as BLASTP and BLASTN were developed based on this algorithm BLAST (see ncbi.nlm.nih.gov). Thus, the percent identity of the nucleotide sequences and the amino acid sequences may be calculated using these programs with their default setting. Also, for example, a numerical value obtained by calculating similarity as a percentage at a setting of "unit size to compare=2" using the full-length of a polypeptide portion encoded in ORF with the software GENETYX Ver. 7.0.9 from Genetyx Corporation employing Lipman-Pearson method may be used as the homology of the amino acid sequences. The lowest value among the values derived from these calculations may be employed as the percent identity of the nucleotide sequences and the amino acid sequences.

The "stringent conditions" can refer to conditions where a so-called specific hybrid is formed and a non-specific hybrid is not formed. It is difficult to clearly quantify such a condition. However, these conditions can be when substantially the same polynucleotides having high identity, for example, the polynucleotides having the percent identity described above, hybridize with each other and polynucleotides having lower identity than above do not hybridize with each other. Specifically, such conditions can include hybridization in 6×SCC (sodium chloride/sodium citrate) at about 45° C. followed by one or two or more washings in 0.2×SCC and 0.1% SDS at 50 to 65° C. DNAs that hybridize with each other may have identity of more than 90%, 91%, 92%, 93%, 94%, 95%, 96%, 97%, 98%, or 99%.

The (a1) to (c23) polynucleotides may be DNA or RNA obtained from the corresponding DNA by substituting a thymine base with a uracil base, but are preferably DNA.

Linalool synthase can be one or more of the proteins designated as (A1)-(C31):

(A1) a protein having (i1') the full-length amino acid sequence represented by SEQ ID NO: 1, or (ii1') the amino acid sequence having the amino acid residues at positions 27 to 574 in the amino acid sequence represented by SEQ ID NO:1;

(B1) a protein that has an amino acid sequence having 90% or more identity to the amino acid sequence of (i1') or (ii1'), and has a linalool synthase activity;

(C1) a protein that has an amino acid sequence having a deletion, substitution, addition, or insertion of one or several amino acids in the amino acid sequence of (i1') or (ii1'), and has a linalool synthase activity;

(A2) a protein having (i2') the full-length amino acid sequence represented by SEQ ID NO: 4, or (ii2') the amino acid sequence having the amino acid residues at positions 39 to 590 in the amino acid sequence represented by SEQ ID NO:4;

(B2) a protein that has an amino acid sequence having 90% or more identity to the amino acid sequence of (i2') or (ii2'), and has a linalool synthase activity;

(C2) a protein that has an amino acid sequence having a deletion, substitution, addition, or insertion of one or several amino acids in the amino acid sequence of (i2') or (ii2'), and has a linalool synthase activity;

(A3) a protein having (i3') the full-length amino acid sequence represented by SEQ ID NO: 61;

(B3) a protein that has an amino acid sequence having 90% or more identity to the amino acid sequence of (i3'), and has a linalool synthase activity;

(C3) a protein that has an amino acid sequence having a deletion, substitution, addition, or insertion of one or several amino acids in the amino acid sequence of (i3'), and has a linalool synthase activity;

(A4) a protein having (i4') the full-length amino acid sequence represented by SEQ ID NO:69, or (ii4') the amino acid sequence having the amino acid residues at positions 29 to 567 in the amino acid sequence represented by SEQ ID NO: 69;

(B4) a protein that has an amino acid sequence having 90% or more identity to the amino acid sequence of (i4') or (ii4'), and has a linalool synthase activity;

(C4) a protein that has an amino acid sequence having a deletion, substitution, addition, or insertion of one or several amino acids in the amino acid sequence of (i4') or (ii4'), and has a linalool synthase activity;

(A5) a protein having (i5') the full-length amino acid sequence represented by SEQ ID NO:72, or (ii5') the amino acid sequence having the amino acid residues at positions 57 to 594 in the amino acid sequence represented by SEQ ID NO: 72;

(B5) a protein that has an amino acid sequence having 90% or more identity to the amino acid sequence of (i5') or (ii5'), and has a linalool synthase activity;

(C5) a protein that has an amino acid sequence having a deletion, substitution, addition, or insertion of one or several amino acids in the amino acid sequence of (i5') or (ii5'), and has a linalool synthase activity;

(A6) a protein having (i6') the full-length amino acid sequence represented by SEQ ID NO: 103 (M15);

(B6) a protein that has an amino acid sequence having 90% or more identity to the amino acid sequence of (i6'), and has a linalool synthase activity;

(C6) a protein that has an amino acid sequence having a deletion, substitution, addition, or insertion of one or several amino acids in the amino acid sequence of (i6'), and has a linalool synthase activity;

(A7) a protein having (i7') the full-length amino acid sequence represented by SEQ ID NO: 105 (M17);

(B7) a protein that has an amino acid sequence having 90% or more identity to the amino acid sequence of (i7'), and has a linalool synthase activity;

(C7) a protein that has an amino acid sequence having a deletion, substitution, addition, or insertion of one or several amino acids in the amino acid sequence of (i7'), and has a linalool synthase activity;

(A8) a protein having (i8') the full-length amino acid sequence represented by SEQ ID NO: 107 (M19);

(B8) a protein that has an amino acid sequence having 90% or more identity to the amino acid sequence of (i8'), and has a linalool synthase activity;

(C8) a protein that has an amino acid sequence having a deletion, substitution, addition, or insertion of one or several amino acids in the amino acid sequence of (i8'), and has a linalool synthase activity;

(A9) a protein having (i9') the full-length amino acid sequence represented by SEQ ID NO: 109 (M21);

(B9) a protein that has an amino acid sequence having 90% or more identity to the amino acid sequence of (i9'), and has a linalool synthase activity;

(C9) a protein that has an amino acid sequence having a deletion, substitution, addition, or insertion of one or several amino acids in the amino acid sequence of (i9'), and has a linalool synthase activity;

(A10) a protein having (i10') the full-length amino acid sequence represented by SEQ ID NO: 111 (M23);

(B10) a protein that has an amino acid sequence having 90% or more identity to the amino acid sequence of (i10'), and has a linalool synthase activity;

(C10) a protein that has an amino acid sequence having a deletion, substitution, addition, or insertion of one or several amino acids in the amino acid sequence of (i10'), and has a linalool synthase activity;

(A11) a protein having (i11') the full-length amino acid sequence represented by SEQ ID NO: 113 (M25);

(B11) a protein that has an amino acid sequence having 90% or more identity to the amino acid sequence of (i11'), and has a linalool synthase activity;

(C11) a protein that has an amino acid sequence having a deletion, substitution, addition, or insertion of one or several amino acids in the amino acid sequence of (i11'), and has a linalool synthase activity;

(A12) a protein having (i12') the full-length amino acid sequence represented by SEQ ID NO: 115 (M27);

(B12) a protein that has an amino acid sequence having 90% or more identity to the amino acid sequence of (i12'), and has a linalool synthase activity;

(C12) a protein that has an amino acid sequence having a deletion, substitution, addition, or insertion of one or several amino acids in the amino acid sequence of (i12'), and has a linalool synthase activity;

(A13) a protein having (i13') the full-length amino acid sequence represented by SEQ ID NO: 117 (M29);

(B13) a protein that has an amino acid sequence having 90% or more identity to the amino acid sequence of (i13'), and has a linalool synthase activity;

(C13) a protein that has an amino acid sequence having a deletion, substitution, addition, or insertion of one or several amino acids in the amino acid sequence of (i13'), and has a linalool synthase activity;

(A14) a protein having (i14') the full-length amino acid sequence represented by SEQ ID NO: 119 (M31);

(B14) a protein that has an amino acid sequence having 90% or more identity to the amino acid sequence of (i14'), and has a linalool synthase activity;

(C14) a protein that has an amino acid sequence having a deletion, substitution, addition, or insertion of one or several amino acids in the amino acid sequence of (i14'), and has a linalool synthase activity;

(A15) a protein having (i15') the full-length amino acid sequence represented by SEQ ID NO: 121 (M33);

(B15) a protein that has an amino acid sequence having 90% or more identity to the amino acid sequence of (i15'), and has a linalool synthase activity;

(C15) a protein that has an amino acid sequence having a deletion, substitution, addition, or insertion of one or several amino acids in the amino acid sequence of (i15'), and has a linalool synthase activity;

(A16) a protein having (i16') the full-length amino acid sequence represented by SEQ ID NO: 123 (M35);

(B16) a protein that has an amino acid sequence having 90% or more identity to the amino acid sequence of (i16'), and has a linalool synthase activity;

(C16) a protein that has an amino acid sequence having a deletion, substitution, addition, or insertion of one or several amino acids in the amino acid sequence of (i16'), and has a linalool synthase activity;

(A17) a protein having (i17') the full-length amino acid sequence represented by SEQ ID NO: 125 (M37);

(B17) a protein that has an amino acid sequence having 90% or more identity to the amino acid sequence of (i17'), and has a linalool synthase activity;

(C17) a protein that has an amino acid sequence having a deletion, substitution, addition, or insertion of one or several amino acids in the amino acid sequence of (i17'), and has a linalool synthase activity;

(A18) a protein having (i18') the full-length amino acid sequence represented by SEQ ID NO: 127 (M39);

(B18) a protein that has an amino acid sequence having 90% or more identity to the amino acid sequence of (i18'), and has a linalool synthase activity;

(C18) a protein that has an amino acid sequence having a deletion, substitution, addition, or insertion of one or several amino acids in the amino acid sequence of (i18'), and has a linalool synthase activity;

(A19) a protein having (i19') the full-length amino acid sequence represented by SEQ ID NO: 161;

(B19) a protein that has an amino acid sequence having 90% or more identity to the amino acid sequence of (i19'), and has a linalool synthase activity;

(C19) a protein that has an amino acid sequence having a deletion, substitution, addition, or insertion of one or several amino acids in the amino acid sequence of (i19'), and has a linalool synthase activity;

(A20) a protein having (i20') the full-length amino acid sequence represented by SEQ ID NO: 162;

(B20) a protein that has an amino acid sequence having 90% or more identity to the amino acid sequence of (i20'), and has a linalool synthase activity;

(C20) a protein that has an amino acid sequence having a deletion, substitution, addition, or insertion of one or several amino acids in the amino acid sequence of (i20'), and has a linalool synthase activity;

(A21) a protein having (i21') the full-length amino acid sequence represented by SEQ ID NO: 163;

(B21) a protein that has an amino acid sequence having 90% or more identity to the amino acid sequence of (i21'), and has a linalool synthase activity;

(C21) a protein that has an amino acid sequence having a deletion, substitution, addition, or insertion of one or several amino acids in the amino acid sequence of (i21'), and has a linalool synthase activity;

(A22) a protein having (i22') the full-length amino acid sequence represented by SEQ ID NO: 164;

(B22) a protein that has an amino acid sequence having 90% or more identity to the amino acid sequence of (i22'), and has a linalool synthase activity;

(C22) a protein that has an amino acid sequence having a deletion, substitution, addition, or insertion of one or several amino acids in the amino acid sequence of (i22'), and has a linalool synthase activity;

(A23) a protein having (i23') the full-length amino acid sequence represented by SEQ ID NO: 165;

(B23) a protein that has an amino acid sequence having 90% or more identity to the amino acid sequence of (i23'), and has a linalool synthase activity;

(C23) a protein that has an amino acid sequence having a deletion, substitution, addition, or insertion of one or several amino acids in the amino acid sequence of (i23'), and has a linalool synthase activity;

(A24) a protein having (i24') the full-length amino acid sequence represented by SEQ ID NO: 166;

(B24) a protein that has an amino acid sequence having 90% or more identity to the amino acid sequence of (i24'), and has a linalool synthase activity;

(C24) a protein that has an amino acid sequence having a deletion, substitution, addition, or insertion of one or several amino acids in the amino acid sequence of (i24'), and has a linalool synthase activity;

(A25) a protein having (i25') the full-length amino acid sequence represented by SEQ ID NO: 167;

(B25) a protein that has an amino acid sequence having 90% or more identity to the amino acid sequence of (i25'), and has a linalool synthase activity;

(C25) a protein that has an amino acid sequence having a deletion, substitution, addition, or insertion of one or several amino acids in the amino acid sequence of (i25'), and has a linalool synthase activity;

(A26) a protein having (i26') the full-length amino acid sequence represented by SEQ ID NO: 168;

(B26) a protein that has an amino acid sequence having 90% or more identity to the amino acid sequence of (i26'), and has a linalool synthase activity;

(C26) a protein that has an amino acid sequence having a deletion, substitution, addition, or insertion of one or several amino acids in the amino acid sequence of (i26'), and has a linalool synthase activity;

(A27) a protein having (i27') the full-length amino acid sequence represented by SEQ ID NO: 169;

(B27) a protein that has an amino acid sequence having 90% or more identity to the amino acid sequence of (i27'), and has a linalool synthase activity;

(C27) a protein that has an amino acid sequence having a deletion, substitution, addition, or insertion of one or several amino acids in the amino acid sequence of (i27'), and has a linalool synthase activity;

(A28) a protein having (i28') the full-length amino acid sequence represented by SEQ ID NO: 172;

(B28) a protein that has an amino acid sequence having 90% or more identity to the amino acid sequence of (i28'), and has a linalool synthase activity;

(C28) a protein that has an amino acid sequence having a deletion, substitution, addition, or insertion of one or several amino acids in the amino acid sequence of (i28'), and has a linalool synthase activity;

(A29) a protein having (i29') the full-length amino acid sequence represented by SEQ ID NO: 175;

(B29) a protein that has an amino acid sequence having 90% or more identity to the amino acid sequence of (i29'), and has a linalool synthase activity;

(C29) a protein that has an amino acid sequence having a deletion, substitution, addition, or insertion of one or several amino acids in the amino acid sequence of (i29'), and has a linalool synthase activity;

(A30) a protein having (i30') the full-length amino acid sequence represented by SEQ ID NO: 178;

(B30) a protein that has an amino acid sequence having 90% or more identity to the amino acid sequence of (i30'), and has a linalool synthase activity;

(C30) a protein that has an amino acid sequence having a deletion, substitution, addition, or insertion of one or several amino acids in the amino acid sequence of (i30'), and has a linalool synthase activity;

(A31) a protein having (i31') the full-length amino acid sequence represented by SEQ ID NO: 181;

(B31) a protein that has an amino acid sequence having 90% or more identity to the amino acid sequence of (i31'), and has a linalool synthase activity;

(C31) a protein that has an amino acid sequence having a deletion, substitution, addition, or insertion of one or several amino acids in the amino acid sequence of (i31'), and has a linalool synthase activity.

The amino acid sequence having amino acid residues at positions 1 to 26 in the amino acid sequence represented by SEQ ID NO: 1 can include a putative chloroplast localization signal. The amino acid sequence having amino acid residues at positions 27 to 574 can include mature linalool synthase. When mature linalool synthase is expressed in the microorganism, usually, a sequence with methionine residues at the N terminus can be used.

The amino acid sequence having amino acid residues at positions 1 to 38 in the amino acid sequence represented by SEQ ID NO: 4 can include a putative chloroplast localization signal, and the amino acid sequence having amino acid residues at positions 39 to 590 can include mature linalool synthase.

The full-length amino acid sequence represented by SEQ ID NO: 61 can include mature linalool synthase.

The amino acid sequence having amino acid residues at positions 1 to 28 in the amino acid sequence represented by SEQ ID NO: 69 can include a putative chloroplast localization signal, and the amino acid sequence having amino acid residues at positions 29 to 567 can include mature linalool synthase.

The amino acid sequence having amino acid residues at positions 1 to 56 in the amino acid sequence represented by SEQ ID NO: 72 can include a putative chloroplast localization signal, and the amino acid sequence having amino acid residues at positions 57 to 594 can include mature linalool synthase.

The full-length amino acid sequences represented by SEQ ID NOs: 103 and 105 (M15 and M17) each can include mature linalool synthase native to *Arabidopsis thaliana* (thale-cress) (SEQ ID NO: 103 (M15) is terpene synthase 10 and SEQ ID NO: 105 (M17) is terpene synthase 14). The amino acid sequences represented by SEQ ID NOs: 107, 109, and 111 (M19, M21, and M23) each can include mature linalool synthase native to *Citrus unshiu* (unshu mikan). The amino acid sequence represented by SEQ ID NO: 113 (M25) can include mature linalool synthase native to *Malus domestica* (apple). The amino acid sequence represented by SEQ ID NO: 115 (M27) can include mature linalool synthase native to *Perilla frutescens* var. *crispa* (shiso). The amino acid sequences represented by SEQ ID NOs: 117 and 119 (M29 and M31) each can include mature amino acid sequence of mature linalool synthase native to *Vitis vinifera* (European grape) (respectively, (3S)-linalool/(E)-nerolidol synthase and (3R)-linalool synthase). The amino acid sequence represented by SEQ ID NO: 121 (M33) can include mature linalool synthase of *Lavandula angustifolia* (lavender). The amino acid sequence represented by SEQ ID NO: 123 (M35) can include mature linalool synthase of *Mentha citrata* (Bergamot Mint). The amino acid sequence represented by SEQ ID NO: 125 (M37) can include mature linalool synthase (R-linalool synthase) of *Ocimum basilicum* (basilico). The amino acid sequence represented by SEQ ID NO: 127 (M39) can include mature linalool synthase (S-linalool synthase) of *Clarkia brewer/(clarkia)*. The amino acid sequence of SEQ ID NO: 161 can include mature linalool synthase (R-linalool synthase) of *Solanum lycopersicum* (tomato). The amino acid sequence of SEQ ID NO: 162 can include mature linalool synthase of *Backhousia citriodora* (lemon myrtle). The amino acid sequences of SEQ ID NOs: 163 and 164 can include mature linalool synthase of *Artemisia annua* (annual wormwood). The amino acid sequence of SEQ ID NO: 165 can include mature linalool synthase (S-linalool synthase) of *Actinidia arguta* (hardy kiwifruit). The amino acid sequence of SEQ ID NO: 166 can include mature linalool synthase (S-linalool synthase) of *Actinidia polygama* (silver vine). The amino acid sequences of SEQ ID NO: 167 can include mature amino acid synthase (S-linalool synthase) of *Perilla frutescens* var. *hirtella* (shiso). The amino acid sequence of SEQ ID NO: 168 can include mature amino acid synthase (S-linalool synthase) of *Perilla setoensis* (shiso).

The full-length amino acid sequences represented by SEQ ID NOs: 169, 172, 175, 178, and 181 can include mature linalool synthase (R-linalool synthase) native to *Arabidopsis thaliana* (thale-cress), *Perilla frutescens* var. *crispa* (shiso), *Vitis vinifera* (European grape), *Mentha citrata* (bergamot mint), and *Ocimum basilicum* (basilico), respectively.

The amino acid sequences of SEQ ID NOs: 103, 105, 107, 109, 111, 113, 115, 117, 119, 121, 123, 125, 127 (M15, M17, M19, M21, M23, M25, M27, M29, M31, M33, M35, M37, M39), 161 to 168, 169, 172, 175, 178, and 181 each have a motif represented by a formula:

$DDX_1[F/Y][D/Y]X_2X_3G$ (SEQ ID NO: 184).

The percent identity to the amino acid sequence may be 90%, 91%, 92%, 93%, 94%, 95%, 96%, 97%, 98%, or 99% or more.

Examples of the mutation of the amino acid residues can include deletion, substitution, addition, and insertion of amino acid residues. The mutation of one or several amino acids may be introduced into one region or multiple different regions in the amino acid sequence. The term "one or several" can indicate a range in which a three-dimensional structure and an activity of the protein are not greatly impaired. In these, the number represented by "one or several" can be, for example, 1 to 100, 1 to 80, 1 to 50, 1 to 30, 1 to 20, 1 to 10, or 1 to 5. The above protein of (A1)-(C26) may have a methionine residue at the N-terminus. The above protein of (A1)-(C26) may have a tag at the C-terminus for purification, such as a histidine tag.

The proteins designated as (B1) and (C1) can have a linalool synthase activity that is 50% or more, 60% or more, 70% or more, 80% or more, 90% or more, or 95% or more of the linalool synthase activity of the protein that includes the amino acid sequence designated as either one of (i') or (ii') above when measured under the same conditions.

The proteins designated as (B2) and (C2) can have a linalool synthase activity that is 50% or more, 60% or more, 70% or more, 80% or more, 90% or more, or 95% or more of the linalool synthase activity of the protein that includes the amino acid sequence of either one of (i2') or (ii2') above when measured under the same conditions.

The proteins designated as (B3) and (C3) can have a linalool synthase activity that is 50% or more, 60% or more, 70% or more, 80% or more, 90% or more, or 95% or more of the linalool synthase activity of the protein that includes the amino acid sequence of (i3') above when measured under the same conditions.

The proteins designated as (B4) and (C4) can have a linalool synthase activity that is 50% or more, 60% or more, 70% or more, 80% or more, 90% or more, or 95% or more of the linalool synthase activity of the protein that includes the amino acid sequence of either one of (i4') or (ii4') above when measured under the same conditions.

The proteins designated as (B5) and (C5) can have a linalool synthase activity that is 50% or more, 60% or more, 70% or more, 80% or more, 90% or more, or 95% or more of the linalool synthase activity of the protein that includes the amino acid sequence of either one of (i5') or (ii5') above when measured under the same conditions.

The proteins designated as (B6) and (C6) can have a linalool synthase activity that is 50% or more, 60% or more, 70% or more, 80% or more, 90% or more, or 95% or more of the linalool synthase activity of the protein that includes the amino acid sequence of either one of (i6') or (ii6') above when measured under the same conditions. The proteins designated as (B6) and (C6) can maintain a motif included in the protein of (A6).

The protein designated as (B7) and (C7) can have a linalool synthase activity that is 50% or more, 60% or more, 70% or more, 80% or more, 90% or more, or 95% or more of the linalool synthase activity of the protein that includes the amino acid sequence of either one of (i7') or (ii7') above when measured under the same conditions. The proteins designated as (B7) and (C7) can maintain a motif included in the protein of (A7).

The protein designated as (B8) and (C8) can have a linalool synthase activity that is 50% or more, 60% or more, 70% or more, 80% or more, 90% or more, or 95% or more of the linalool synthase activity of the protein that includes the amino acid sequence of (i8') above when measured under the same conditions. The proteins designated as (B8) and (C8) can maintain a motif included in the protein of (A8).

The protein designated as (B9) and (C9) can have a linalool synthase activity that is 50% or more, 60% or more, 70% or more, 80% or more, 90% or more, or 95% or more of the linalool synthase activity of the protein that includes the amino acid sequence of either one of (i9') or (ii9') above when measured under the same conditions. The proteins of (B9) and (C9) can maintain a motif included in the protein of (A9).

The protein designated as (B10) and (C10) can have a linalool synthase activity that is 50% or more, 60% or more, 70% or more, 80% or more, 90% or more, or 95% or more of the linalool synthase activity of the protein that includes the amino acid sequence of either one of (i10') or (ii10') above when measured under the same conditions. The proteins designated as (B10) and (C10) can maintain a motif included in the protein of (A10).

The protein designated as (B11) and (C11) can have a linalool synthase activity that is 50% or more, 60% or more, 70% or more, 80% or more, 90% or more, or 95% or more of the linalool synthase activity of the protein that includes the amino acid sequence of either one of (i11') or (ii11') above when measured under the same conditions. The proteins designated as (B11) and (C11) can maintain a motif included in the protein of (A11).

The protein designated as (B12) and (C12) can have a linalool synthase activity that is 50% or more, 60% or more, 70% or more, 80% or more, 90% or more, or 95% or more of the linalool synthase activity of the protein that includes the amino acid sequence of either one of (i12') or (ii12') above when measured under the same conditions. The proteins designated as (B12) and (C12) can maintain a motif included in the protein of (A12).

The protein designated as (B13) and (C13) can have a linalool synthase activity that is 50% or more, 60% or more, 70% or more, 80% or more, 90% or more, or 95% or more of the linalool synthase activity of the protein that includes the amino acid sequence of (i13') above when measured under the same conditions. The proteins designated as (B13) and (C13) can maintain a motif included in the protein of (A13).

The protein designated as (B14) and (C14) can have a linalool synthase activity that is 50% or more, 60% or more, 70% or more, 80% or more, 90% or more, or 95% or more of the linalool synthase activity of the protein that includes the amino acid sequence of either one of (i14') or (ii14') above when measured under the same conditions. The proteins designated as (B14) and (C14) can maintain a motif included in the protein of (A14).

The protein designated as (B15) and (C15) can have a linalool synthase activity that is 50% or more, 60% or more, 70% or more, 80% or more, 90% or more, or 95% or more of the linalool synthase activity of the protein that includes the amino acid sequence of either one of (i15') or (ii15') above when measured under the same conditions. The proteins designated as (B15) and (C15) can maintain a motif included in the protein of (A15).

The protein designated as (B16) and (C16) can have a linalool synthase activity that is 50% or more, 60% or more, 70% or more, 80% or more, 90% or more, or 95% or more of the linalool synthase activity of the protein that includes the amino acid sequence of either one of (i16') or (ii16') above when measured under the same conditions. The proteins designated as (B16) and (C16) can maintain a motif included in the protein of (A16).

The protein designated as (B17) and (C17) can have a linalool synthase activity that is 50% or more, 60% or more, 70% or more, 80% or more, 90% or more, or 95% or more of the linalool synthase activity of the protein that includes the amino acid sequence of either one of (i17') or (ii17') above when measured under the same conditions. The proteins designated as (B17) and (C17) can maintain a motif included in the protein of (A17).

The protein designated as (B18) and (C18) can have a linalool synthase activity that is 50% or more, 60% or more, 70% or more, 80% or more, 90% or more, or 95% or more of the linalool synthase activity of the protein that includes the amino acid sequence of (i18') above when measured under the same conditions. The proteins designated as (B18) and (C18) can maintain a motif included in the protein of (A18).

The protein designated as (B19) and (C19) can have a linalool synthase activity that is 50% or more, 60% or more, 70% or more, 80% or more, 90% or more, or 95% or more of the linalool synthase activity of the protein that includes the amino acid sequence of either one of (i19') or (ii19') above when measured under the same conditions. The proteins designated as (B19) and (C19) can maintain a motif included in the protein of (A19).

The protein designated as (B20) and (C20) can have a linalool synthase activity that is 50% or more, 60% or more, 70% or more, 80% or more, 90% or more, or 95% or more of the linalool synthase activity of the protein that includes the amino acid sequence of either one of (i20') or (ii20') above when measured under the same conditions. The proteins designated as (B20) and (C20) can maintain a motif included in the protein of (A20).

The protein designated as (B21) and (C21) can have a linalool synthase activity that is 50% or more, 60% or more, 70% or more, 80% or more, 90% or more, or 95% or more of the linalool synthase activity of the protein that includes the amino acid sequence of either one of (i21') or (ii21') above when measured under the same conditions. The proteins designated as (B21) and (C21) can maintain a motif included in the protein of (A21).

The protein designated as (B22) and (C22) can have a linalool synthase activity that is 50% or more, 60% or more, 70% or more, 80% or more, 90% or more, or 95% or more of the linalool synthase activity of the protein that includes the amino acid sequence of either one of (i22') or (ii22') above when measured under the same conditions. The proteins designated as (B22) and (C22) can maintain a motif included in the protein of (A22).

The protein designated as (B23) and (C23) can have a linalool synthase activity that is 50% or more, 60% or more, 70% or more, 80% or more, 90% or more, or 95% or more of the linalool synthase activity of the protein that includes the amino acid sequence of (i23') above when measured under the same conditions. The proteins designated as (B23) and (C23) can maintain a motif included in the protein of (A23).

The protein designated as (B24) and (C24) can have a linalool synthase activity that is 50% or more, 60% or more, 70% or more, 80% or more, 90% or more, or 95% or more of the linalool synthase activity of the protein that includes the amino acid sequence of either one of (i24') or (ii24') above when measured under the same conditions. The proteins designated as (B24) and (C24) can maintain a motif included in the protein of (A24).

The protein designated as (B25) and (C25) can have a linalool synthase activity that is 50% or more, 60% or more, 70% or more, 80% or more, 90% or more, or 95% or more of the linalool synthase activity of the protein that includes the amino acid sequence of either one of (i25') or (ii25') above when measured under the same conditions. The proteins designated as (B25) and (C25) can maintain a motif included in the protein of (A25).

The protein designated as (B26) and (C26) can have a linalool synthase activity that is 50% or more, 60% or more, 70% or more, 80% or more, 90% or more, or 95% or more of the linalool synthase activity of the protein that includes the amino acid sequence of either one of (i26') or (ii26') above when measured under the same conditions. The proteins designated as (B26) and (C26) can maintain a motif included in the protein of (A26).

The protein designated as (B27) and (C27) can have a linalool synthase activity that is 50% or more, 60% or more, 70% or more, 80% or more, 90% or more, or 95% or more of the linalool synthase activity of the protein that includes the amino acid sequence of either one of (i27') or (ii27') above when measured under the same conditions. The proteins designated as (B27) and (C27) can maintain a motif included in the protein of (A27).

The protein designated as (B28) and (C28) can have a linalool synthase activity that is 50% or more, 60% or more, 70% or more, 80% or more, 90% or more, or 95% or more of the linalool synthase activity of the protein that includes the amino acid sequence of either one of (i28') or (ii28') above when measured under the same conditions. The proteins designated as (B28) and (C28) can maintain a motif included in the protein of (A28).

The protein designated as (B29) and (C29) can have a linalool synthase activity that is 50% or more, 60% or more, 70% or more, 80% or more, 90% or more, or 95% or more of the linalool synthase activity of the protein that includes the amino acid sequence of either one of (i29') or (ii29') above when measured under the same conditions. The proteins designated as (B29) and (C29) can maintain a motif included in the protein of (A29).

The protein designated as (B30) and (C30) can have a linalool synthase activity that is 50% or more, 60% or more, 70% or more, 80% or more, 90% or more, or 95% or more of the linalool synthase activity of the protein that includes the amino acid sequence of either one of (i30') or (ii30') above when measured under the same conditions. The proteins designated as (B30) and (C30) can maintain a motif included in the protein of (A30).

The protein designated as (B31) and (C31) can have a linalool synthase activity that is 50% or more, 60% or more, 70% or more, 80% or more, 90% or more, or 95% or more of the linalool synthase activity of the protein that includes the amino acid sequence of either one of (i31') or (ii31') above when measured under the same conditions. The proteins designated as (B31) and (C31) can maintain a motif included in the protein of (A31).

In the protein, the mutation may be introduced into sites in a catalytic domain and sites other than the catalytic domain as long as an objective activity is retained. The positions of amino acid residues to be mutated in the protein, which is capable of retaining the objective activity, would be understood by a person of ordinary skill in the art. Specifically, the person of ordinary skill in the art would be able to recognize the correlation between structure and function, since a person skilled in the art can 1) compare the amino acid sequences of multiple proteins having the same type of activity, for example, the amino acid sequence represented by SEQ ID NO: 1 or 4 and the amino acid sequences of other linalool synthases, 2) determine regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, a person skilled in the art can identify the positions of the amino acid residues that can be mutated in the amino acid sequence of the linalool synthase.

When the amino acid residue is mutated by substitution, the substitution of the amino acid residue may be conservative substitution. The term "conservative substitution" can refer to substitution of a certain amino acid residue with an amino acid residue having a similar side chain. Families of amino acid residues having the similar side chain are well-known in the art. Examples of such families can include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group-containing side chain (e.g., alkoxy, phenoxy group-containing side chain) (e.g., serine, threonine, tyrosine), and amino acids having a sulfur-containing side chain (e.g., cysteine, methionine). The conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

The microorganism expressing linalool synthase may also express geranyl diphosphate synthase, and the microorganism can express geranyl diphosphate synthase depending on the linalool synthase to be introduced. Dimethylallyl diphosphate (DMAPP) is known as a precursor of peptide glycan and an electron acceptor, such as menaquinone and the like, and is essential for growth of microorganisms (Fujisaki et al., J. Biochem., 1986; 99: 1137-1146). The geranyl diphosphate synthase activity can refer to an activity to produce geranyl diphosphate from IPP and DMAPP. Examples of the geranyl diphosphate synthase and farnesyl diphosphate synthase can include the farnesyl diphosphate synthase native to *Escherichia coli*. Alternatively, examples thereof can include geranyl diphosphate synthase native to microorganisms such as *Pantoea ananatis* (e.g., WO 2007/029577 A1), *Bacillus stearothermophilus* (e.g., JP2000-245482), and *Geobacillus stearothermophilus*. Examples thereof also can include geranyl diphosphate synthases native to plants such as grand fir (*Abies grandis*), peppermint (*Mentha×piperita*), Norway spruce (*Picea abies*), Madagascar periwinkle (*Catharanthus roseus*), thale-cress (*Arabidopsis thaliana*), snapdragon (*Antirrhinum majus*) or hop (*Humulus lupulus*).

The polynucleotide encoding geranyl diphosphate synthase can be one or more of the polynucleotides designated as [p], [q], or [r]:

[p] a polynucleotide having [xi] the nucleotide sequence represented by SEQ ID NO: 7, or [xii] the nucleotide sequence represented by SEQ ID NO: 8;

[q] a polynucleotide that has a nucleotide sequence having 90% or more identity to the nucleotide sequence of [xi], or [xii] above, and encodes a protein having a geranyl diphosphate synthase activity; or

[r] a polynucleotide that hybridizes under stringent conditions with a polynucleotide having a nucleotide sequence complementary to the nucleotide sequence of [xi], or [xii] above, and encodes a protein having a geranyl diphosphate synthase activity.

The nucleotide sequence represented by SEQ ID NO: 7 is a nucleotide sequence of a farnesyl diphosphate/geranyl diphosphate synthase gene native to *Escherichia coli*. The nucleotide sequence represented by SEQ ID NO: 8 may encode the amino acid sequence represented by SEQ ID NO: 87 and can include a coding region of a mature farnesyl diphosphate/geranyl diphosphate synthase gene. In the nucleotide sequence represented by SEQ ID NO: 8, codons in the nucleotide sequence represented by SEQ ID NO: 7 are modified and codons encoding serine at position 80 in the protein represented by SEQ ID NO: 87 are mutated into codons encoding phenylalanine (S80F mutation). That is, the nucleotide sequence represented by SEQ ID NO: 8 encodes the amino acid sequence represented by SEQ ID NO: 88 and the protein represented by SEQ ID NO: 88 is a (S80F) mutated protein in which the serine residue at position 80 in the protein represented by SEQ ID NO: 87 is substituted with a phenylalanine residue. It is known that the farnesyl diphosphate synthase having S80F mutation has improved function as a geranyl diphosphate synthase (Reiling K K et al. (2004) Biotechnol Bioeng. 87(2) 200-212). The polynucleotide encoding geranyl diphosphate synthase can be the above-designated [q] or [r]. For this reason, the polynucleotide may have one or more mutations, which may obtain the same effect as the S80F mutation, although it is not limited to the S80F mutation, and mutation is not limited to the S80F mutation. Furthermore, derivation of the farnesyl diphosphate synthase gene is not limited to *Escherichia coli*, and for example, mutation to increase the concentration of geranyl diphosphate in the microbial cell is clearly known in farnesyl diphosphate synthase native to *Bacillus stearothermophilus* (Narita K., et al. (1999) J Biochem 126(3) 566-571.). Furthermore, although not limited to geranyl diphosphate synthase obtained by introducing a mutation to the farnesyl diphosphate synthase gene, a gene functioning as the original geranyl diphosphate synthase may be used. For example, a geranyl diphosphate synthase gene native to periwinkle (Rai A., et al. (2013) Mol Plant. 6(5) 1531-49), a geranyl diphosphate synthase gene native to thale-cress (Camara B., (2000) Plant J. 24(2), 241-252), a geranyl diphosphate synthase gene native to actinomycete (WO 2007/029577 A1), and the like may be used. The farnesyl diphosphate synthase activity can refer to an activity of producing farnesyl diphosphate from geranyl diphosphate (GPP) and IPP. The identity of the nucleotide sequence, the stringent conditions, and the definition of polynucleotide are the same as those described in the above polynucleotides designated as (a1) to (c23).

The geranyl diphosphate synthase can be one or more proteins designated as [P]-[R]:

[P] a protein that includes the full-length amino acid sequence represented by SEQ ID NO: 87 or 88;

[Q] a protein that has an amino acid sequence having 90% or more identity to the above amino acid sequence, and has a geranyl diphosphate synthase activity; and

[R] a protein that has an amino acid sequence having a deletion, substitution, addition, or insertion of one or several amino acids in the amino acid sequence, and has a geranyl diphosphate synthase activity.

The amino acid sequence represented by SEQ ID NO: 87 can include mature farnesyl diphosphate/geranyl diphosphate synthase. The amino acid sequence represented by SEQ ID NO: 88 can include mutated mature farnesyl diphosphate/geranyl diphosphate synthase. The [Q] and [R] proteins can have an activity of 50% or more, 60% or more, 70% or more, 80% or more, 90% or more, or 95% or more of the geranyl diphosphate synthase activity of the protein that includes the amino acid sequence represented by SEQ ID NO: 87 or 88, and the geranyl diphosphate synthase activity and the farnesyl diphosphate synthase activity when they are measured under the same conditions. The definition of deletion, substitution, addition, or insertion, the identity of amino acid, and the like are the same as those described in the proteins designated as (A1) to (C31).

Neither the polynucleotide encoding the desired protein nor the promoter operably linked thereto, which make up an expression unit, are necessarily inherent to the microorganism chosen as the host cell. Therefore, the entire expression unit may be a heterologous expression unit. Also, both the polynucleotide encoding linalool synthase and the promoter may not be inherent to the chosen host cell. The promoter may be homologous or heterologous relative to the polynucleotide encoding the desired protein. The expression unit may further include elements such as a terminator, a ribosomal binding site, and a drug resistance gene. The expression unit may be DNA or RNA, but is preferably DNA. The heterologous expression unit can include a gene encoding a protein other than a polynucleotide encoding linalool synthase. Examples of such a protein can include linalool synthase and one or more enzymes involved in the mevalonate pathway and one or more enzymes involved in the methylerythritol phosphate pathway, but are not limited thereto.

The microorganism can be obtained, for example, by transformation with the following expression vectors: an expression vector that includes an expression unit including a polynucleotide encoding linalool synthase and a promoter operably linked to the polynucleotide; an expression vector that includes an expression unit including a polynucleotide encoding linalool synthase, polynucleotide encoding geranyl diphosphate synthase, and a promoter operably linked to the polynucleotide; an expression vector that includes a first expression unit including a polynucleotide encoding linalool synthase and a promoter operably linked to the polynucleotide and a second expression unit including a polynucleotide encoding geranyl diphosphate synthase and a promoter operably linked to the polynucleotide; and a combination of a first expression vector that includes a polynucleotide encoding linalool synthase and a promoter operably linked to the polynucleotide and a second expression vector that includes an expression unit including a polynucleotide encoding geranyl diphosphate synthase and a promoter operably linked to the polynucleotide. The expression vector may be an integrative vector or a non-integrative vector. In the expression vector, the gene encoding linalool synthase may be placed under the control of a constitutive promoter or inducible promoter. Examples of the constitutive promoter can include the tac promoter, the lac promoter, the trp promoter, the trc promoter, the T7 promoter, the T5 promoter, the T3 promoter, and the SP6 promoter. Examples of the inducible promoter can include a promoter which is inversely dependent on a growth promoting agent to be described herein. The term "operably linked" can mean that a nucleotide sequence in the regulatory region is linked to a nucleotide sequence of a nucleic acid molecule or gene (that is, polynucleotide) in the form capable of expressing the polynucleotide, and thus an expression product of the polynucleotide encoded by the nucleotide sequence is produced.

The microorganism expressing linalool synthase can have an ability to synthesize dimethyl diphosphate via a dimethylallyl diphosphate supply pathway from the viewpoint of supplying IPP and DMAPP for efficient production of linalool. Examples of the dimethylallyl diphosphate supply pathway can include a methylerythritol phosphate (MEP) pathway and a mevalonate (MVA) pathway.

The methylerythritol phosphate (MEP) pathway, also called non-mevalonate pathway, is a biosynthesis pathway of isopentenyldiphosphate (IPP) and dimethylallyl pyrophosphate (DMAPP), which are precursors of linalool. Examples of the enzymes involved in the methylerythritol phosphate (MEP) pathway can include 1-deoxy-D-xylulose-5-phosphate synthase (EC: 2.2.1.7, example 1, Dxs, ACCESSION ID NP_414954; example 2, AT3G21500, ACCESSION ID NP_566686; example 3, AT4G15560, ACCESSION ID NP_193291; example 4, AT5G11380, ACCESSION ID NP_001078570), 1-deoxy-D-xylulose-5-phosphate reductoisomerase (EC: 1.1.1.267; example 1, Dxr, ACCESSION ID NP_414715; example 2, AT5G62790, ACCESSION ID NP_001190600), 4-diphosphocytidyl-2-C-methyl-D-erythritol synthase (EC: 2.7.7.60; example 1, IspD, ACCESSION ID NP_417227; example 2, AT2G02500, ACCESSION ID NP_565286), 4-diphosphocytidyl-2-C-methyl-D-erythritol kinase (EC: 2.7.1.148; example 1, IspE, ACCESSION ID NP_415726; example 2, AT2G26930, ACCESSION ID NP_180261), 2-C-methyl-D-erythritol-2,4-cyclodiphosphate synthase (EC: 4.6.1.12; example 1, IspF, ACCESSION ID NP_417226; example 2, AT1G63970, ACCESSION ID NP_564819), 1-hydroxy-2-methyl-2-(E)-butenyl-4-diphosphate synthase (EC: 1.17.7.1; example 1, IspG, ACCESSION ID NP_417010; example 2, AT5G60600, ACCESSION ID NP_001119467), and 4-hydroxy-3-methyl-2-butenyl diphosphate reductase (EC: 1.17.1.2; example 1, IspH, ACCESSION ID NP_414570; example 2, AT4G34350, ACCESSION ID NP_567965). In the expression vector, the gene(s) encoding one or more enzymes involved in the methylerythritol phosphate (MEP) pathway may be placed under the control of the promoter which is inversely dependent on the growth-promoting agent.

Examples of the enzymes involved in the mevalonate (MVA) pathway can include mevalonate kinase (EC: 2.7.1.36; example 1, Erg12p, ACCESSION ID NP_013935; example 2, AT5G27450, ACCESSION ID NP_001190411), phosphomevalonate kinase (EC: 2.7.4.2; example 1, Erg8p, ACCESSION ID NP_013947; example 2, AT1G31910, ACCESSION ID NP_001185124), diphosphomevalonate decarboxylase (EC: 4.1.1.33; example 1, Mvd1p, ACCESSION ID NP_014441; example 2, AT2G38700, ACCESSION ID NP_181404; example 3, AT3G54250, ACCESSION ID NP_566995), acetyl-CoA-C-acetyltransferase (EC: 2.3.1.9; example 1, Erg10p, ACCESSION ID NP_015297; example 2, AT5G47720, ACCESSION ID NP_001032028; example 3, AT5G48230, ACCESSION ID NP_568694), hydroxymethylglutaryl-CoA synthase (EC: 2.3.3.10; example 1, Erg13p, ACCESSION ID NP_013580; example 2, AT4G11820, ACCESSION ID NP_192919; example 3, MvaS, ACCESSION ID AAG02438), hydroxymethylglutaryl-CoA reductase (EC: 1.1.1.34; example 1, Hmg2p, ACCESSION ID NP_013555; example 2, Hmg1p, ACCESSION ID NP_013636; example 3, AT1G76490, ACCESSION ID NP_177775; example 4, AT2G17370, ACCESSION ID NP_179329, EC: 1.1.1.88, example, MvaA, ACCESSION ID P13702), and acetyl-CoA-C-acetyltransferase/hydroxymethylglutaryl-CoA reductase (EC: 2.3.1.9/1.1.1.34, example, MvaE, ACCESSION ID AAG02439).

IPP and DMAPP, which are the building-blocks of linalool, are typically biosynthesized via either a methylerythritol phosphate pathway or a mevalonate pathway inherent or native to a microorganism, as described above. Therefore, to supply IPP and DMAPP for efficient production of R-linalool or S-linalool, the methylerythritol phosphate pathway and/or the mevalonate pathway may be enhanced in the chosen microorganism, as described herein.

To enhance these pathways, the chosen microorganism may further express an enzyme of a mevalonate pathway or a methylerythritol phosphate pathway, for example, mevalonate kinase in addition to the linalool synthase. Therefore, one or more enzymes involved in the mevalonate pathway or the methylerythritol phosphate pathway may also be introduced into the microorganism expressing linalool synthase. In other words, the microorganism expressing linalool synthase can include an expression unit containing a gene that encodes one or more enzymes involved in the mevalonate pathway or the methylerythritol phosphate pathway and a promoter operably linked to the gene. Examples of the mevalonate kinase gene can include genes from microorganisms belonging to the genus *Methanosarcina* such as *Methanosarcina mazei*, the genus *Methanocella* such as *Methanocella paludicola*, the genus *Corynebacterium* such as *Corynebacterium variabile*, the genus *Methanosaeta* such as *Methanosaeta concilii*, and the genus *Nitrosopumilus* such as *Nitrosopumilus maritimus*.

The microorganism expressing linalool synthase may be transformed with one or more expression vectors encoding enzymes involved in the mevalonate pathway or the methylerythritol phosphate pathway. The expression vector may be an integrative vector or a non-integrative vector. In the expression vector, the gene encoding the mevalonate kinase may be placed under the control of a constitutive promoter or inducible promoter (e.g., the promoter which is inversely dependent on the growth-promoting agent). Specifically, the gene encoding the mevalonate kinase may be placed under the control of the constitutive promoter. Examples of the constitutive promoter can include the tac promoter, the lac promoter, the trp promoter, the trc promoter, the T7 promoter, the T5 promoter, the T3 promoter, and the SP6 promoter. Examples of the inducible promoter can include the promoter which is inversely dependent on the growth-promoting agent described below.

The expression vector for such an enzyme may express further a plurality of enzymes, one or more, two or more, three or more or four or more, involved in the mevalonate pathway and/or the methylerythritol phosphate pathway, and may be, for example, an expression vector for polycistronic mRNA.

The one or more enzymes involved in the mevalonate pathway and/or the methylerythritol phosphate pathway may be homologous or heterologous relative to the host. When the origin of the enzyme involved in the mevalonate pathway and/or the methylerythritol phosphate pathway is heterologous to the host, for example, the host may be a bacterium as described above (e.g., *Escherichia coli*) and the enzyme involved in the mevalonate pathway may be native to a fungus (e.g., *Saccharomyces cerevisiae*). In addition, when the host inherently produces the enzyme involved in the methylerythritol phosphate pathway, an expression vector to be introduced into the host may express an enzyme involved in the mevalonate pathway.

In the expression vector, the gene encoding one or more enzymes involved in the mevalonate (MVA) pathway or the methylerythritol phosphate (MEP) pathway may be placed under the control of the promoter which is inversely dependent on the growth-promoting agent.

To enhance the mevalonate pathway and/or methylerythritol phosphate pathway, an isopentenyl-diphosphate delta isomerase having an ability to convert isopentenyl diphosphate (IPP) into dimethylallyl diphosphate (DMAPP) may be introduced into the microorganism.

Examples of the isopentenyl-diphosphate delta isomerase (EC: 5.3.3.2) can include Idi1p (ACCESSION ID NP_015208), AT3G02780 (ACCESSION ID NP_186927), AT5G16440 (ACCESSION ID NP_197148) and Idi (ACCESSION ID NP_417365). In the expression vector, the gene encoding the isopentenyl-diphosphate delta isomerase may be placed under the control of the promoter which is inversely dependent on the growth-promoting agent.

The transformation of a host with an expression vector containing the gene(s) described above can be carried out using one or more known methods. Examples of such methods can include a competent cell method using a microbial cell treated with calcium, an electroporation method, and the like. The gene may also be introduced by infecting the microbial cell with a phage vector other than the plasmid vector.

The microorganism expressing linalool synthase can have a dimethylallyl diphosphate supply pathway, and the 2-ketogluconate formation pathway can be blocked.

The microorganism can be a microorganism in which a 2-ketogluconate formation pathway is blocked. In the 2-ketogluconate formation pathway, glucose is oxidized by glucose dehydrogenase to produce gluconate and then the gluconate is oxidized by 2-keto gluconate dehydrogenase to produce NADPH and 2-ketogluconate. Thus, a microorganism in which the 2-ketogluconate formation pathway is blocked can be obtained by reducing the activity of one or more of glucose dehydrogenase (GCD) and 2-keto gluconate dehydrogenase. The 2-ketogluconate formation pathway can be blocked by reduction of the enzyme activity. That is, in the microorganism, the enzyme activity of one or more of glucose dehydrogenase and 2-ketogluconate dehydrogenase is/are reduced and thus the 2-ketogluconate formation pathway is blocked in the microorganism.

Reduced enzymatic activity in a microorganism can mean a decrease and/or a complete loss of the activity of the enzyme. Also, the reduced enzymatic activity in a microorganism can include a decrease and/or a complete loss of the expression amount of an enzyme in a microorganism since such a decrease or a complete loss leads to a decrease or a complete loss of the enzymatic activity possessed by the microorganism. Reduction of enzymatic activity in a microorganism can be accomplished by, for example, disrupting one or more of the following: a gene encoding the enzyme, a gene encoding a factor capable of regulating an expression or activity of the enzyme, an expression regulatory region such as a transcriptional regulatory region located upstream to these genes and a translational regulatory region (e.g., promoter and Shine-Dalgarno (SD) sequence), or an untranslated region. The disruption of the above gene or region can be performed by modifying a genomic region corresponding to the gene or region so as to decrease or completely eliminate expression or activity of the enzyme. Examples of such a modification can include, but are not limited to, deletion of a part or all of the genomic region, insertion of a polynucleotide into the genomic region, and replacement of the genomic region with another polynucleotide.

The microorganism expressing linalool synthase can be a microorganism that is capable of synthesizing pyrroloquinoline quinone (PQQ) or using PQQ supplied in culture environment.

The microorganism expressing linalool synthase can be a microorganism having reduced activity of glucose dehydrogenase, and can be a microorganism having reduced activity of glucose dehydrogenase that uses PQQ as a coenzyme.

When the microorganism expressing linalool synthase is a microorganism obtained by transforming a host microorganism originally having the 2-ketogluconate formation pathway with an expression vector that includes the gene encoding an isoprenoid compound-synthetic enzyme, the microorganism can be modified to block the 2-ketogluconate formation pathway.

For example, microorganism belonging to the family Enterobacteriaceae such as *Escherichia coli* has a gene encoding glucose dehydrogenase and produces GCD apoenzyme, but since the microorganism does not have production ability of PQQ, it does not have GCD activity in the absence of PQQ. However, it is known that if a foreign gene is expressed in a microbial cell, an alternative substance of PQQ is generated and the substance exhibits GCD activity (WO2006/183898). The above host microorganism "originally having 2-ketogluconate formation pathway" can include microorganisms such as the microorganism belonging to the family Enterobacteriaceae that acquire GCD activity.

The modification to block the 2-ketogluconate formation pathway can be a modification to reduce the activity of the glucose dehydrogenase, and more preferably, a modification to reduce the activity of the glucose dehydrogenase that uses PQQ as coenzyme. The modification can be performed so that GCD activity per cell of the modified microorganism is lower than that of an unmodified strain such as a wild-type strain belonging to the family Enterobacteriaceae. For example, it may be confirmed that a molecular weight of GCD per cell or GCD activity per molecule of the modified strain is lower than that of the wild-type strain. The GCD activity per cell of the modified strain and the wild strain can be compared, for example, by comparing GCD activity contained in a cell extract composition of both strains cultured under the same condition. Examples of the wild-type of the microorganism belonging to the family Enterobacteriaceae that can be used as comparison (control) can include *Pantoea ananatis* AJ13355 (FERM BP-6614), *Pantoea ananatis* SC17 strain (FERM BP-11091), and *Pantoea ananatis* SC17 (0) strain (Katashkina J I et al., BMC Mol Biol., 2009; 10:34 VKPM B-9246).

The activity of the glucose dehydrogenase that uses PQQ as a coenzyme can refer to an activity catalyzing the following reaction:

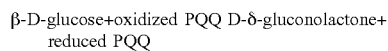

β-D-glucose+oxidized PQQ D-δ-gluconolactone+ reduced PQQ

The GCD activity can be measured, for example, on the basis of detection of generation of the reduced DCPIP through the following reactions by measuring absorbance in 600 nm (JP2007-129965):

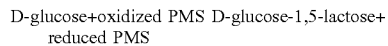

D-glucose+oxidized PMS D-glucose-1,5-lactose+ reduced PMS

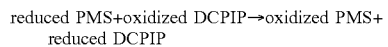

reduced PMS+oxidized DCPIP→oxidized PMS+ reduced DCPIP

PMS: phenazine methosulfate
DCPIP: 2,6-dichlorophenol-indophenol

The activity of the glucose dehydrogenase can be reduced by disrupting a gene encoding a glucose dehydrogenase (gcd gene), a gene encoding a factor capable of regulating an expression or activity of GCD, or a transcriptional regulatory region located upstream to these genes.

The gcd gene can be one or more polynucleotide designated as (x)-(z):

(x) a polynucleotide that includes [i] the nucleotide sequence represented by SEQ ID NO: 59, or [ii] the nucleotide sequence having the nucleotide residues at positions 301 to 2691 in the nucleotide sequence represented by SEQ ID NO: 59;

(y) a polynucleotide that has a nucleotide sequence having 90% or more identity to the nucleotide sequence of [i] or [ii] above, and encodes a protein having a GCD activity; and (z) a polynucleotide that hybridizes under stringent conditions with a polynucleotide having a nucleotide sequence complementary to the nucleotide sequence of [i] or [ii] above, and encodes a protein having a GCD activity.

The nucleotide sequence represented by SEQ ID NO: 59 can include a full-length nucleotide sequence of the gcd gene from *Pantoea ananatis*. The nucleotide sequence represented by SEQ ID NO: 59 can encode the amino acid sequence represented by SEQ ID NO: 60, and the nucleotide sequence having the nucleotide residues at positions 301 to 2691 (2688) can encode an amino acid sequence of mature GCD. The identity of the gene, the stringent condition and polynucleotide are the same as the corresponding definitions of the polynucleotide designated as (a1) to (c23) described below.

GCD can be one or more proteins designated as (X)-(Z):

(X) a protein that includes the full-length amino acid sequence represented by SEQ ID NO: 60;

(Y) a protein that has an amino acid sequence having 90% or more identity to the amino acid sequence represented by SEQ ID NO: 60, and has a GCD activity; or (Z) a protein that has an amino acid sequence having a deletion, substitution, addition, or insertion of one or several amino acids in the amino acid sequence represented by SEQ ID NO: 60, and has a GCD activity.

The amino acid sequence represented by SEQ ID NO: 60 can include the mature GCD. The protein of (Y) or (Z) can have GCD activity that is 50% or more, 60% or more, 70% or more, 80% or more, 90% or more, or 95% or more of the GCD activity of the protein that includes the amino acid sequence represented by SEQ ID NO: 60 when measured under the same conditions. The deletion, substitution, addition or insertion, and the identity of the amino acid are the same as the corresponding definitions of the proteins designated as (A1) to (C31) described below.

The gcd gene can be cloned by synthesizing an oligonucleotide based on these sequences, and carrying out PCR reaction using a chromosome of *Pantoea ananatis* as a template. The gcd gene may be disrupted by homologous recombination. In this case, a gene having for example 80% or more, 90% or more, or 95% or more identity to the gcd gene on a chromosome may be used. Also, a gene that hybridizes under a stringent condition with the gcd gene on the chromosome may be used. Example of the stringent condition can include washing once, or 2-3 times, at salt concentrations corresponding to 1×SCC and 0.1% SDS, or 0.1×SCC and 0.1% SDS, at 60° C.

The gcd gene may be disrupted, for example, by deletion of an entire target gene and a upstream and downstream portion of the target gene on a chromosome; introducing a substitution of an amino acid (missense mutation) or a insertion of a terminating codon (nonsense mutation); or introducing a frame shift mutation of addition or deletion of one or two nucleotide (Journal of Biological Chemistry 272:8611-8617 (1997) Proceedings of the National Academy of Sciences, USA 95 5511-5515 (1998), Journal of Biological Chemistry 266, 20833-20839 (1991)).

The disruption of each gene can be performed by genetic recombination. Examples of the method using gene recombination can include deleting all or part of an expression regulatory region, such as promoter region, coding region, or non-coding region, or insertion a polynucleotide into the region by utilizing homologous recombination.

Disruption of the expression regulatory region can be performed for one or more, two or more, or three or more, times. In the deletion of the coding region, the region to be deleted may be an N-terminal region, an internal region, or a C-terminal region, or even the entire coding region, so long as the function of the protein to be produced by the gene is reduced. Generally, deletion of a longer region will more certainly disrupt a target gene. It is preferable that reading frames upstream and downstream of the region to be deleted are not the same.

When a polynucleotide is inserted into a coding region, the polynucleotide may be inserted into any region of a target gene. However, insertion of a longer polynucleotide will more certainly disrupt the target gene. It is preferable that reading frames upstream and downstream of the region to be deleted are not the same. The polynucleotide is not limited so long as the polynucleotide reduces a function of the protein encoded by the target gene. However, examples of it can include a transposon carrying an antibiotic-resistant gene or a gene useful for L-amino acid production.

Examples of method for mutating the target gene on the chromosome can include the following method. First, a part of the target gene is deleted to produce a mutated gene that cannot produce a functional protein. Next, a microorganism is transformed by the DNA containing the mutated gene to cause a homologous recombination between the mutated gene and the target gene on the chromosome, and thereby, replace the target gene on the chromosome with the mutated gene. The protein encoded by the obtained mutated target gene, even if it is produced, has a stereostructure different from that of a wild-type protein, and thus, the function thereof is reduced. Such gene disruption based on gene replacement utilizing homologous recombination has been already reported. Examples of this method can include: methods using linear DNA such as the method called Red-driven integration (Datsenko, K. A, and Wanner, B. L. Proc. Natl. Acad. Sci. USA. 97: 6640-6645 (2000)), a method utilizing Red-driven integration in combination with the delivering system derived from λ phage (Cho, E. H., Gumport, R. I., Gardner, J. F. J. Bacteriol. 184: 5200-5203 (2002)) (WO2005/010175); a method using a plasmid having thermosensitive replication origin or a plasmid capable having conjugation transfer ability; or a method utilizing a suicide vector having no replication origin in a host (U.S. Pat. No. 6,303,383 or Japanese Patent Laid Open No. H5-007491). Decrease in transcription amount of a target gene can be confirmed by comparing the amount of mRNA transcribed from the target gene with that in a wild-type strain or unmodified strain. Examples of the method for evaluating the amount of mRNA can include northern hybridization and RT-PCR (Molecular cloning (Cold spring Harbor Laboratory Press, Cold spring Harbor (USA), 2001)). The transcription amount may be decreased to any extent so long as it is decreased compared with that observed in a wild-type strain or unmodified strain, and, for example, it can be decreased to at least 75% or less, 50% or less, 25% or less, or 10% or less, of that observed in a wild-type strain or unmodified strain, and it is more preferable that the gene is not expressed at all. Decrease in amount of a protein encoded by a target gene can be confirmed by Western blotting using an antibody that binds to the protein (Molecular cloning (Cold spring Harbor Laboratory Press, Cold spring Harbor (USA), 2001). The amount of protein may be decreased to any extent so long as it is decreased compared with that observed in a wild-type strain or unmodified strain, for example, it is can be decreased to at least 75% or less, 50% or less, 25% or less, or 10% or less of that observed in a wild-type strain or unmodified strain, and it is more preferable that the protein is not produced at all (the activity is completely eliminated).

Examples of the method for decreasing the activity of GCD can include, besides the aforementioned genetic manipulation techniques, a method of treating a microorganism belonging to the family Enterobacteriaceae, such as a bacteria belonging to the genus *Pantoea* with ultraviolet irradiation or a mutagen used for a typical mutagenesis treatment such as N-methyl-N'-nitro-N-nitrosoguanidine (NTG) or nitrous acid, and selecting a strain having decreased GCD activity.

The activity of GCD can also be reduced by reducing PQQ biosynthesis. The PQQ biosynthesis can be reduced, for example, by deleting part or all of pqqABCDEF that is operon required for PQQ biosynthesis of (J. S. Velterop, P. W. Postma, J. Bacteriology 177(17): 5088-5098 (1995)).

The microorganism chosen as a host usually can be a bacterium. The bacterium may be a gram-positive bacterium or a gram-negative bacterium. Examples of the microorganism can include a microorganism belonging to the family Enterobacteriaceae and a microorganism containing blue-green algae to be described herein, and the family Enterobacteriaceae or blue-green algae is a particular example.

Examples of the gram-positive bacterium can include bacteria belonging to the genera *Bacillus, Listeria, Staphylococcus, Streptococcus, Enterococcus, Clostridium, Corynebacterium*, and *Streptomyces*. Bacteria belonging to the genera *Bacillus* and *Corynebacterium* are particular examples.

Examples of the bacteria belonging to the genus *Bacillus* can include *Bacillus subtilis, Bacillus anthracis*, and *Bacillus cereus. Bacillus subtilis* is a particular example.

Examples of the bacteria belonging to the genus *Corynebacterium* can include *Corynebacterium glutamicum, Corynebacterium efficiens*, and *Corynebacterium callunae. Corynebacterium glutamicum* is a particular example.

Examples of the gram-negative bacterium can include bacteria belonging to the genera *Escherichia, Pantoea, Salmonella, Vibrio, Serratia, Enterobacter*, and Cyanobacteria. The bacteria belonging to the genera *Escherichia, Pantoea, Enterobacter*, and Cyanobacteria are particular examples.

*Escherichia coli* is a particular example as the bacterium belonging to the genus *Escherichia*. Examples thereof can include *Escherichia coli* MG1655 and *Escherichia coli* W3110.

Examples of the bacteria belonging to the genus *Pantoea* can include *Pantoea ananatis, Pantoea stewartii, Pantoea agglomerans*, and *Pantoea citrea. Pantoea ananatis* and *Pantoea citrea* are particular examples. Strains exemplified in the European Patent Application Publication EP0952221 may be used as the bacteria belonging to the genus *Pantoea*. Examples of representative strains of the bacteria belonging to the genus *Pantoea* can include *Pantoea ananatis* AJ13355 strain (FERM BP-6614) and *Pantoea ananatis* AJ13356 strain (FERM BP-6615) disclosed in the European Patent Application Publication EP0952221, *Pantoea ananatis* SC17 strain (FERM BP-11091), and *Pantoea ananatis* SC17 (0) strain (Katashikina J I et al., BMC Mol Biol 2009; 10:34 VKPM B-9246).

Examples of the bacteria belonging to the genus *Enterobacter* can include *Enterobacter agglomerans* and *Enterobacter aerogenes*, and *Enterobacter aerogenes* is a particular example. The bacterial strains exemplified in the European Patent Application Publication EP0952221 may be used as the bacteria belonging to the genus *Enterobacter*. Examples of representative strains of the bacteria belonging to the genus *Enterobacter* can include *Enterobacter agglomerans* ATCC12287 strain, *Enterobacter aerogenes* ATCC13048 strain, *Enterobacter aerogenes* NBRC12010 strain (Biotechnol. Bioeng., 2007 Mar. 27; 98(2) 340-348), *Enterobacter aerogenes* AJ110637 (FERM BP-10955), and the like. The *Enterobacter aerogenes* AJ110637 strain was deposited at the International Patent Organism Depositary (IPOD), National Institute of Advanced Industrial Science and Technology (AIST) (Chuo No. 6, Higashi 1-1-1, Tsukuba City, Ibaraki Pref., JP, Postal code 305-8566; currently, International Patent Organism Depositary, National Institute of Technology and Evaluation (NITE-IPOD), #120, 2-5-8 Kazusakamatari, Kisarazu-shi, Chiba, 292-0818, Japan) on Aug. 22, 2007, and was converted to an international deposition under the provisions of the Budapest Treaty on Mar. 13, 2008, and the deposit number FERM BP-10955 was given thereto.

Examples of the blue-green algae (Cyanobacteria) can include blue-green algae belonging to the genera *Anabaena, Arthrospira, Cyanothece, Nostoc, Prochlorococcus, Syn-*

*echococcus*, and *Thermosynechococcus*, and blue-green algae belonging to the genus *Synechocystis* is a particular example.

Examples of strains of the bacteria belonging to the genus *Synechocystis* can include *Synechocystis* sp. (e.g., *Synechocystis*. sp. PCC6803, PCC6701, PCC6714, PCC6902, PCC7008), and *Synechocystis* sp. PCC6803 is a particular example. Examples of representative strains of the bacteria belonging to the genus *Synechocystis* can include *Synechocystis* sp. PCC6803 GT strain (WO2014/142051A1).

*Synechocystis* sp. PCC6803 is available from Pasteur Institute, France, and ATCC27184 is available from American Type Culture Collection. The strains such as *Synechocystis* sp. PCC6803 GT can be derived from the PCC6803 strain based on the methods described in Qinglong D., et al. Int. J. Mol. Sci. 2015, 16, 24081-24093.

Furthermore, linalool can accumulate in the culture medium. The amount of linalool that can accumulate can be 200 mg/L or more or 500 mg/L or more, or 500 mg/L or more. Linalool typically is toxic to a microorganism producing linalool, and the microorganism will not grow, or barely grow, when a large amount of linalool accumulates. However, in the method as described herein, linalool can accumulate in the culture medium, and even at amounts of 200 mg/L or more or 500 mg/L or more, the bacterium can grow. In the method as described herein, the amount of linalool that accumulates in the culture medium can be 200 mg/L or more or 500 mg/L or more, or 600 mg/L or more, and even 625 mg/L or 700 mg/L or more. The linalool can accumulate at a high concentration. Examples of the culture conditions such as culture components, which may make up the culture medium, will be described herein.

The amount of linalool that can accumulate in the culture medium can mean the content (mg) of linalool per 1 L of the culture medium. The content of linalool in the total content of linalool and other volatile components can mean the content (mg) of linalool per total amount of 1 L of linalool and other volatile components.

Examples of the volatile components other than linalool can include volatile flavor components (flavor volatile components) such as 3-methyl-1-butanol, 1-pentanol, 3-methyl-2-buten-1-ol, β-citronellol, (R)-(+)-β-citronellol, geraniol, nerol, trans-nerolidol, nerolidyl acetate, linalyl acetate, limonene, and caryophyllin, but these may not be present in the culture medium. The total content of linalool and other volatile components in the total content of linalool and other volatile components can mean the total weight of volatile organic compounds contained in the composition.

Examples of the identification and quantification method of the volatile organic compounds and the linalool present in the linalool composition can include gas chromatography and a headspace method.

The headspace method is generally widely used for analyzing volatile components (Yumi Nagai, "Improved Analysis of Flavor Components in Alcoholic Beverages by Headspace Gas Chromatography," Journal of Food Science and Technology, 39(3), 264-270, 1992). When the total content of volatile components in the linalool composition is measured by the headspace method, the measurement may be carried out according to the following procedure, for example. A solution containing a linalool composition is enclosed in a headspace vial and heated under a certain condition, and then the identification of the volatile components is determined by separation and mass analysis by gas chromatography. A standard curve of the identified compound is generated so that the concentration of the compound present in the solution can be calculated and based on this, the total content of the volatile components and the constituent ratio of each component can be determined. In this way, the total content of volatile components in the composition can be measured.

When the total content of volatile components in the linalool composition is measured by gas chromatography, the measurement may be carried out according to the following procedure, for example. A method or the like has been reported in which volatile components are sampled, for example, using a Tenax TA (registered trademark) adsorbent (produced by GL Sciences Inc.) and the total chromatogram peak area, which is eluted and detected in a range of n-hexane and n-hexadecane using a hydrogen flame ionization detector or a mass spectrometer by a non-polar capillary column, is converted in a toluene equivalent amount (Japanese Industrial Standards JIS A 1965).

The method as described herein can include the following steps:

1) culturing a microorganism expressing linalool synthase in the presence of a growth-promoting agent at a sufficient concentration to grow the linalool-producing microorganism;

2) decreasing the concentration of the growth-promoting agent to induce production of linalool by the microorganism; and 3) culturing the microorganism to produce linalool.

For efficient production of linalool, step 1) which corresponds to a growth phase of a microorganism and the step 3) which corresponds to a formation phase of linalool can be conducted separately. The step 2) which corresponds to an induction phase of linalool formation functions to move the microorganism from the growth phase to the formation phase of linalool.

The growth-promoting agent can refer to a factor essential for the growth of a microorganism or a factor having an activity of promoting the growth of the microorganism, which can be consumed by the microorganism, the consumption of which causes reduction of its amount in a culture medium, and consequent loss or reduction of the growth of the microorganism. For example, when the growth-promoting agent in a certain amount is used, a microorganism continues to grow until the certain amount of growth-promoting agent is consumed, and once the growth-promoting agent is entirely consumed, the microorganism cannot grow or the growth rate decreases. Therefore, the degree of the growth of the microorganism can be regulated by the growth-promoting agent. Examples of such a growth-promoting agent can include, but are not limited to, substances such as oxygen (gas); minerals such as ions of iron, magnesium, potassium and calcium; phosphorus compounds such as monophosphoric acid, diphosphoric acid, and polyphosphoric acid, or salt thereof; nitrogen compounds such as ammonia, nitrate, nitrite, nitrogen (gas), and urea; sulfur compounds such as ammonium sulfate and thiosulfuric acid; and nutrients such as vitamins (e.g., vitamin A, vitamin D, vitamin E, vitamin K, vitamin B1, vitamin B2, vitamin B6, vitamin B12, niacin, pantothenic acid, biotin, ascorbic acid), and amino acids (e.g., alanine, arginine, asparagine, aspartic acid, cysteine, glutamine, glutamic acid, glycine, histidine, leucine, isoleucine, lysine, methionine, phenylalanine, proline, serine, threonine, tryptophan, tyrosine, valine, selenocysteine). One kind of growth-promoting agent may be used or two or more kinds of growth-promoting agents may be used in combination in the method.

When the method as described herein includes the above steps 1) to 3), the microorganism expressing linalool synthase can have an ability to grow depending on the growth-promoting agent and an ability to produce linalool depending on a promoter that is inversely dependent on the growth-promoting agent, and to which an ability to synthesize linalool by an enzymatic reaction has been conferred. Such an microorganism can grow in the presence of the growth-promoting agent at a concentration sufficient for the growth of the microorganism. Here, the "sufficient concentration" of the growth-promoting agent can refer to a concentration that is effective for the growth of the microorganism. The expression "ability to produce linalool depending on a promoter that is inversely depending on the growth-promoting agent" can mean that linalool cannot be produced at all or at a very low efficiency in the presence of a relatively high concentration of growth-promoting agent; whereas, linalool can be produced or of linalool can be produced at high efficiency in the presence of the growth-promoting agent at a relatively low concentration or in the absence of the growth-promoting agent. Therefore, the chosen microorganism can grow well but cannot produce linalool or produces linalool at a low efficiency in the presence of the growth-promoting agent at the sufficient concentration. The chosen microorganism cannot grow well but can produce linalool at high efficiency in the presence of the growth-promoting agent at insufficient concentration or in the absence of the growth-promoting agent.

When the method as described herein includes the above steps 1) to 3), a gene encoding linalool synthase and expressing linalool synthase can be under the control of a promoter that is inversely dependent on the growth-promoting agent. The expression "promoter that is inversely dependent on the growth-promoting agent" can mean a promoter that does not induce transcription of the gene at all, or only at very low amounts, in the presence of relatively high concentration of the growth-promoting agent; but is able to induce transcription of the gene at a medium to high rate in the presence of the growth-promoting agent at relatively low concentration or in the absence of the growth-promoting agent. Therefore, the promoter that is inversely dependent on the growth-promoting agent can suppress the expression of the gene encoding linalool synthase in the presence of the growth-promoting agent at a concentration sufficient for the growth of the microorganism; whereas, the promoter can promote the expression of the gene encoding linalool synthase in the presence of the growth-promoting agent at a concentration insufficient for the growth of the microorganism. Specifically, the growth of the microorganism is under the control of the promoter which is inversely dependent on the growth-promoting agent.

For example, when the growth-promoting agent is a phosphorus compound, a phosphorus deficiency-inducible promoter can be utilized. The expression "phosphorus deficiency-inducible promoter" can refer to a promoter that can promote the expression of a downstream gene at a low concentration of the phosphorus compound. The low concentration of the phosphorus compound can mean 100 mg/L or less. The expression "phosphorus" is synonymous to the expression "phosphorus compound", and they can be used interchangeably. The concentration of total phosphorus can be quantified by decomposing all of the phosphorus compounds in the liquid to orthophosphoric acid by a strong acid or oxidizing agent. The total phosphorus concentration under phosphorus-deficient conditions may be 100 mg/L or less, 50 mg/L or less, 10 mg/L or less, 5 mg/L or less, 1 mg/L or less, 0.1 mg/L or less, or 0.01 mg/L or less. Examples of the phosphorus deficiency-inducible promoter can include a promoter of the gene encoding alkali phosphatase, for example, phoA, a promoter of the gene encoding an acid phosphatase, for example, pho), a promoter of the gene encoding a sensor histidine kinase, for example, phoR, a promoter of the gene encoding a response regulator, for example, phoB, and a promoter of the gene encoding a phosphorus uptake carrier, pstS.

In the above step 1), the microorganism expressing linalool synthase can be grown in the presence of the growth-promoting agent at the sufficient concentration. More specifically, the microorganism expressing linalool synthase can be grown by culturing the isoprenoid compound-producing microorganism in a culture medium in the presence of the growth-promoting agent at the sufficient concentration.

For example, when a phosphorus compound is used as the growth-promoting agent, the microorganism expressing linalool synthase can grow well in the presence of the phosphorus compound at a sufficient concentration, and thus, the phosphorus compound can act as the growth-promoting agent. When the growth-promoting agent is the phosphorus compound, the concentration of the phosphorus compound that is sufficient for the growth in step 1) is not particularly limited, and may be, for example, 200 mg/L or more, 300 mg/L or more, 500 mg/L or more, 1000 mg/L or more, or 2000 mg/L or more. The concentration of the phosphorus compound for the growth may be, for example, 20 g/L or less, 10 g/L or less, or 5 g/L or less.

In the above step 2), the production of the isoprenoid compound by the microorganism is induced by decreasing the concentration of the growth-promoting agent. More specifically, the concentration of the growth-promoting agent can be decreased by decreasing the amount of the growth-promoting agent supplied to the culture medium. Even if the amount of the growth-promoting agent supplied to the culture medium is kept constant throughout steps 1) and 2), the concentration of the growth-promoting agent can be decreased by utilizing the growth of the microorganism. In the early phase of the growth of the microorganism in step 1), the microorganism does not grow sufficiently and the cell number in the culture medium is small. Thus, consumption of the growth-promoting agent by the microorganism is relatively low. Therefore, the concentration of the growth-promoting agent in the culture medium is relatively high in the early phase of the growth. On the other hand, in the late phase of the growth of the microorganism in step 1), the microorganism grows sufficiently and the cell number is large, and thus, the consumption of the growth-promoting agent by the microorganism is relatively high. Therefore, the concentration of the growth-promoting agent in the culture medium becomes relatively low in the late phase of the growth. As described above, when a constant amount of the growth-promoting agent is supplied to the culture medium throughout steps 1) and 2), the concentration of the growth-promoting agent in the culture medium decreases in inverse proportion to the growth of the microorganism. This decreased concentration can be used as a trigger to induce the production of linalool by the microorganism.

For example, when a phosphorus compound or an amino acid is used as the growth-promoting agent, the concentration of the phosphorus compound or the amino acid in the culture medium, which can induce the production of linalool by the microorganism, can be, for example, 100 mg/L or less, 50 mg/L or less, or 10 mg/L or less.

In the above step 3), linalool is produced by culturing the microorganism. More specifically, linalool can be produced by culturing the microorganism in the culture medium under the conditions described in step 2) where the concentration of the growth-promoting agent is decreased. The concentration of the growth-promoting agent in the culture medium can be maintained at the concentration described in step 2) in order to make the production of linalool by the microorganism possible.

In the method as described herein, it is also possible that the period of time for culturing the microorganism in step 3) is set so that it is longer than the period of time for culturing period in step 1). In conventional methods, an inducer is used to obtain linalool in a higher amount, and it is necessary to culture a microorganism for a longer period of time using the inducer in the formation phase of linalool. However, when the cultivation is continued for a long period of time, the inducer decomposes, and the microorganism fails to maintain the ability to produce linalool. Thus, it is necessary to continuously add the inducer into culture medium. As the inducer may be expensive, the cost for producing linalool possibly is prohibitive. Therefore, culturing a microorganism for a long period of time using the inducer in the formation phase of linalool is problematic in that the cost for producing linalool is increased depending on the duration of the cultivation period. On the other hand, in the method as described herein that does not use a particular substance such as the inducer in step 3), the decomposition of the particular substance is not an issue, and the prohibitive cost issue that occurs in conventional methods due to long cultivation times in the formation phase of linalool is avoided. Therefore, in the method as described herein, the period of time for step 3) can easily be longer, in contrast to the conventional methods that utilize the inducer. In the method as described herein, the longer the period of time in step 3), the more linalool that can be produced.

The method as described herein may be combined with another method in terms of enhancing the amount of produced linalool. Examples of such a method can include a method of utilizing an environmental factor such as light (Pia Lindberg, Sungsoon Park, Anastasios Melis, Metabolic Engineering 12 (2010): 70-79) or temperature (Norma A Valdez-Cruz, Luis Caspeta, Néstor O Pérez, Octavio T Ramirez, Mauricio A Trujillo-Roldán, Microbial Cell Factories 2010, 9:1), change of pH (EP 1233068 A2), addition of surfactant (JP H11-009296 A), and auto-inducible expression system (WO2013/151174).

The culture medium used in the method as described herein may contain a carbon source for producing linalool. The carbon source can include carbohydrates such as monosaccharides, disaccharides, oligosaccharides and polysaccharides; invert sugars obtained by hydrolyzing sucrose; glycerol; compounds having one carbon atom (hereinafter referred to as a C1 compound) such as methanol, formaldehyde, formate, carbon monoxide and carbon dioxide; oils such as corn oil, palm oil and soybean oil; acetate; animal fats; animal oils; fatty acids such as saturated fatty acids and unsaturated fatty acids; lipids; phospholipids; glycerolipids; glycerol fatty acid esters such as monoglyceride, diglyceride and triglyceride; polypeptides such as microbial proteins and plant proteins; renewable carbon sources such as hydrolyzed biomass carbon sources; yeast extracts, or combinations thereof. For a nitrogen source, inorganic ammonium salts such as ammonium sulfate, ammonium chloride and ammonium phosphate, organic nitrogen such as hydrolyzed soybeans, ammonia gas, ammonia water, and the like can be used The culture medium can contain required substances such as vitamin B1 and L-homoserine, or the yeast extract and the like in an appropriate amount as an organic trace nutrient source. In addition thereto, potassium phosphate, magnesium sulfate, iron ion, manganese ion, and the like are added in a small amount if necessary. The culture medium employed in the method as described herein can be a natural medium or a synthesized medium as long as it contains a carbon source, a nitrogen source, inorganic ions, and optionally other organic trace ingredients.

Examples of the monosaccharide can include triose such as ketotriose (dihydroxyacetone) and aldotriose (glyceraldehyde); tetrose such as ketotetrose (erythrulose) and aldotetrose (erythrose, threose); pentose such as ketopentose (ribulose, xylulose), aldopentose (ribose, arabinose, xylose, lyxose) and deoxysaccharide (deoxyribose); hexose such as ketohexose (psichose, fructose, sorbose, tagatose), aldohexose (allose, altrose, glucose, mannose, gulose, idose, galactose, talose), and deoxysaccharide (fucose, fuculose, rhamnose); and heptose such as sedoheptulose. C6 sugars such as fructose, mannose, galactose and glucose; and C5 sugars such as xylose and arabinose are particular examples.

Examples of the disaccharide can include sucrose, lactose, maltose, trehalose, turanose, and cellobiose. Sucrose and lactose are particular examples.

Examples of the oligosaccharide can include trisaccharides such as raffinose, melezitose and maltotriose; tetrasaccharides such as acarbose and stachyose; and other oligosaccharides such as fructooligosaccharide (FOS), galactooligosaccharide (GOS) and mannan-oligosaccharide (MOS).

Examples of the polysaccharide can include glycogen, starch (amylose, amylopectin), cellulose, dextrin, and glucan (β-1,3-glucan), and starch and cellulose are particular examples.

Examples of the microbial protein can include polypeptides native to a yeast or bacterium.

Examples of the plant protein can include polypeptides native to soybean, corn, canola, Jatropha, palm, peanut, sunflower, coconut, mustard, cotton seed, palm kernel oil, olive, safflower, sesame, and linseed.

Examples of the lipid can include substances containing one or more saturated or unsaturated fatty acids of C4 or more.

The oil can be a lipid that contains one or more saturated or unsaturated fatty acids of C4 or more and is liquid at room temperature, and examples of the oil can include lipids native to soybean, corn, canola, Jatropha, palm, peanut, sunflower, coconut, mustard, cotton seed, palm kernel oil, olive, safflower, sesame, linseed, oily microbial cells, Chinese tallow tree, and a combination of two or more thereof.

Examples of the fatty acid can include compounds represented by a formula RCOOH ("R" represents a hydrocarbon group having two or more carbon atoms).

The unsaturated fatty acid can be a compound having at least one double bond between two carbon atoms in the group "R" as described above, and examples of the unsaturated fatty acid can include oleic acid, vaccenic acid, linoleic acid, palmitelaidic acid, and arachidonic acid.

The saturated fatty acid is a compound where the "R" is a saturated aliphatic group, and examples of the saturated fatty acid can include docosanoic acid, eicosanoic acid, octadecanoic acid, hexadecanoic acid, tetradecanoic acid, and dodecanoic acid. Of these, saturated fatty acids containing one or more C2 to C22 fatty acids are particular examples, and a C12 fatty acid, C14 fatty acid, C16 fatty acid, C18 fatty acid, C20 fatty acid, and C22 fatty acid are even more particular examples.

The carbon source can include salts, such as isopropyl myristate, and derivatives of these fatty acids and salts of these derivatives. Examples of the salt can include lithium salts, potassium salts, sodium salts, and so forth.

Examples of the carbon source also can include combinations of carbohydrates such as glucose with lipids, oils, fats, fatty acids, and glycerol fatty acid esters.

Examples of the renewable carbon source can include hydrolyzed biomass carbon sources.

Examples of the biomass carbon source can include cellulose-based substrates such as waste materials of woods, papers and pulps, leafy plants, and fruit pulps; and partial plants such as stalks, grain particles, roots, and tubers.

Examples of the plant employed as the biomass carbon source can include corn, wheat, rye, sorghum, triticale, rice, millet, barley, cassava, legume such as pea, potato, sweet potato, banana, sugar cane, and tapioca.

When a renewable carbon source such as biomass is added to the culture medium, the carbon source can be pretreated. Examples of the pretreatment can include an enzymatic pretreatment, a chemical pretreatment, and a combination of the enzymatic pretreatment and the chemical pretreatment.

It is preferred that the renewable carbon source is entirely or partially hydrolyzed before being added to the culture medium.

Examples of the carbon source also can include a yeast extract and a combination of a yeast extract with another carbon source such as glucose. The combination of the yeast extract with a C1 compound such as carbon dioxide and methanol is a particular example.

In the method as described herein, a particular example is to culture the microorganism expressing linalool synthase in a standard culture medium containing saline and nutrients.

The culture medium is not particularly limited, and examples of the culture medium can include ready-made general media that is commercially available such as Luria Bertani (LB) broth, Sabouraud dextrose (SD) broth, and yeast medium (YM) broth. A medium suitable for the cultivation of a specific host can be selected appropriately.

The cell medium can contain appropriate minerals, salts, supplemental elements, buffers, and ingredients known to those of ordinary skill in the art that are suitable for the cultivation and to facilitate the production of the linalool in addition to the appropriate carbon source.

The standard cell culture conditions are regulated as described above and can be used as the culture conditions for the microorganism.

The culture temperature can be 20 to 40° C., and the pH value can be about 4.5 to about 9.5.

The microorganism as described herein can be cultured under aerobic, oxygen-free, or anaerobic conditions depending on a nature of the host for the isoprenoid compound-producing microorganism. A known fermentation method such as a batch cultivation method, a feeding cultivation method, or a continuous cultivation method can appropriately be used as the cultivation method.

Incidentally, linalool has low solubility in water and thus can be collected while being dissolved in an organic layer by forming an organic layer in a culture medium and culturing with two phases. As a material to be added for forming an organic layer, for example, dodecane, methyl oleate, oleyl alcohol, dibutyl phthalate, isopropyl myristate, or the like can be used.

EXAMPLES

Hereinafter, the present invention will be described in detail with reference to Examples, but the Present Invention is not Limited to the Following Examples.

Reference Example 1: Linalool Addition Test

The glycerol stock of the SWITCH-PphoC Δgcd/pSTV28 strain obtained by transforming the SWITCH-PphoC Δgcd strain constructed in Example 4 below with the commercially available plasmid vector pSTV28 (produced by Takara Bio Inc.) was thawed, and 50 μL of a microbial cell suspension was uniformly applied onto an LB plate containing 60 mg/L of chloramphenicol and cultured at 34° C. for 18 hours while left to stand (without agitation). The resulting microbial cells on the plate were collected and inoculated into a small-sized L-type culture tube (model type: TV100030, produced by Advantec Toyo Kaisha, Ltd.) injected with 4 mL of a culture medium described below containing 60 mg/L of chloramphenicol such that the initial O.D. was within a range of 0.01 to 0.02, and cap-type SILICOSEN was used as a culture plug. The minimum culture medium was used as a growing medium, 10 mL of 20% (w/v) glucose, 0.05 mL of 1 M $CaCl_2$, and 1.0 mL of 1 M $MgSO_4$ separately sterilized (AC 120° C., 20 minutes, 1 M $CaCl_2$ was subjected to filtration) were added after being cooled (50° C. or lower) to 50 mL of the 10×M9 Salts described in Table 1 and mixed with sterilized water to prepare 500 mL. The culture temperature was set to 34° C. and the shaking speed was set to 70 rpm. Cultivation was carried out using a small-sized shaking culture apparatus TVS062CA (produced by Advantec Toyo Kaisha, Ltd.) for 23 hours, the shaking was stopped for 5.0 sec every 15 minutes, and the O.D. values were automatically measured.

TABLE 1

| 10×M9 salts | |
| --- | --- |
| $Na_2HPO_4 \cdot 7H_2O$ | 128 g/L |
| $KH_2PO_4$ | 30 g/L |
| NaCl | 5.0 g/L |
| $NH_4Cl$ | 10 g/L |

Not adjusted pH, AC 120° C., 15 minutes

After the start of the cultivation, at the time point when the O.D. value reached 0.6 to 0.7, a linalool solution was added to each small-sized L-type culture tube such that concentrations of the reagent Linalool in respective culture mediums became 1251 mg/L, 837 mg/L, 626 mg/L, and 417 mg/L. The linalool solution was diluted with ethanol (produced by Wako Pure Chemical Industries, Ltd.) such that the reagent Linalool (produced by Wako Pure Chemical Industries, Ltd.) was present at 15%, 10%, 7.5%, 5.0%, and 0.0% (v/v), and then 40 μL of the resulting solution was added to each small-sized L-type culture tube. The concentration of linalool in the culture medium was calculated from the specific gravity of the reagent Linalool, 0.86 (20/4° C.) (reference literature: actual values produced by Wako Pure Chemical Industries, Ltd.).

Figure 14:
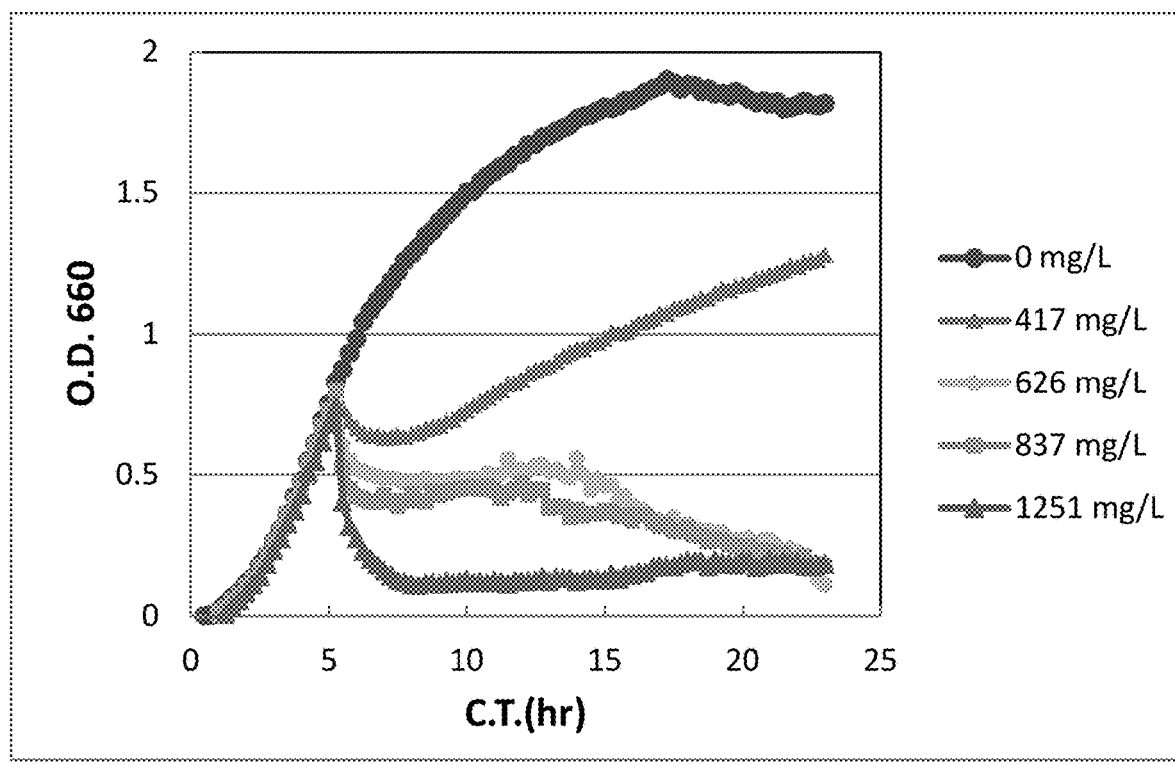
FIG. 14 shows a diagram illustrating a result of a linalool addition test.

The graph showing changes of the O.D. value over time measured using TVS062CA communication software (TV100070, produced by Advantec Toyo Kaisha, Ltd.) is illustrated in FIG. 14.

In general, it is known that a plurality of kinds of monoterpenoid including linalool exhibit antibiotic properties (Park et al., Anaerobe, 18(3), 369-372, 2012). It was recognized that in the case of the SWITCH-PphoC Δgcd/pSTV28 strain, the O.D. value is decreased by adding 626 mg/L or more of linalool to the culture medium (FIG. 14). These results show that the concentration of linalool in the culture medium should be less than 626 mg/L so that microbial cell growth inhibition is suppressed.

Example 1: Construction of Linalool Synthase-Expression Plasmid 1-1) Obtaining Linalool Synthase Gene Native to *Actinidia arguta* (Hardy Kiwifruit)

The nucleotide sequence (GenBank accession number: GQ338153) and the amino acid sequence (GenPept accession number: ADD81294) of a linalool synthase gene native to *Actinidia arguta* (AaLINS) have been already known (Chen, X. et al., (2010) Functional Plant Biology, 37, 232-243). The amino acid sequence of a linalool synthase protein and the nucleotide sequence of its gene native to *Actinidia arguta* are shown in SEQ ID NO: 1 and SEQ ID NO: 2. In order to efficiently express the AaLINS gene, codons were optimized, an AaLINS gene in which the chloroplast localization signal had been cleaved was designed, and this was designated as opt_AaLINS. The nucleotide sequence of opt_AaLINS is shown in SEQ ID NO: 3. DNA in which a tac promoter region (deBoer et al., (1983) Proc. Natl. Acad. Sci. U.S.A., 80: 21-25) had been added to the opt_AaLINS gene was chemically synthesized, subsequently cloned into pMW119 (produced by NIPPON GENE CO., LTD.) and the resulting plasmid was designated as pMW119-Ptac-opt_AaLINS.

1-2) Obtaining a Linalool Synthase Gene Native to *Coriandrum sativum* (Coriander)

A nucleotide sequence (GenBank accession number: KF700700) and an amino acid sequence (GenPept accession number: AHC54051) of a linalool synthase (CsLINS) gene native to *Coriandrum sativum* have been reported (Galata M et al., (2014) Phytochemistry, 102, 64-73). The amino acid sequence of a linalool synthase protein and the nucleotide sequence of its gene native to *Coriandrum sativum* are shown in SEQ ID NO: 4 and SEQ ID NO: 5. In order to efficiently express the CsLINS gene, codons were optimized, a CsLINS gene in which the chloroplast localization signal had been cleaved was designed, and this was designated as opt_CsLINS. A nucleotide sequence of opt_CsLINS is shown in SEQ ID NO: 6. DNA in which the tac promoter region (deBoer, et al., (1983) Proc. Natl. Acad. Sci. U.S.A., 80, 21-25) had been added to the opt_CsLINS gene was chemically synthesized, cloned into pMW119 (produced by NIPPON GENE CO., LTD.), and the resulting plasmid was designated as pMW119-Ptac-opt_CsLINS.

1-3) Obtaining a Mutated Farnesyl Diphosphate Synthase Gene Native to *Escherichia coli*

Farnesyl diphosphate synthase native to *Escherichia coli* is encoded by an ispA gene (SEQ ID NO: 7) (Fujisaki et al. (1990) J. Biochem. (Tokyo) 108:995-1000). A mutation that increases the concentration of geranyl diphosphate in microbial cells has been demonstrated in farnesyl diphosphate synthase native to *Bacillus stearothemophilus* (Narita et al. (1999) J Biochem 126(3):566-571).

Based on this finding, the similar mutant has been also produced in farnesyl diphosphate synthase native to *Escherichia coli* (Reiling et al. (2004) Biotechnol Bioeng. 87(2): 200-212). In order to efficiently express an ispA mutant (S80F) gene having a high activity for producing geranyl diphosphate, a sequence in which the codons were optimized was designed and designated as ispA*. A nucleotide sequence of ispA* is shown in SEQ ID NO: 8. The ispA* gene was chemically synthesized, subsequently cloned into pMW119 (produced by NIPPON GENE CO., LTD.), and the resulting plasmid was designated as pMW119-ispA*.

1-4) Construction of Co-Expression Plasmid for Opt_AaLINS and the ispA* Genes

PCR with pMW119-Ptac-opt_AaLINS as a template was carried out using primers shown in SEQ ID NO: 9 and SEQ ID NO: 11 to obtain a Ptac-opt_AaLINS fragment. Furthermore, PCR with pMW119-ispA* as a template was carried out using primers shown in SEQ ID NO: 12 and SEQ ID NO: 13 to obtain an ispA* fragment. The purified Ptac-opt_AaLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_AaLINS-ispA*.

1-5) Construction of Co-Expression Plasmid for Opt_CsLINS and ispA* Genes

PCR with pMW119-Ptac-opt_CsLINS as a template was carried out using primers shown in SEQ ID NO: 9 and SEQ ID NO: 14 to obtain a Ptac-opt_CsLINS fragment. Furthermore, PCR with pMW119-ispA* as a template was carried out using primers shown in SEQ ID NO: 15 and SEQ ID NO: 13 to obtain an ispA* fragment. The purified Ptac-opt_CsLINS fragment and ispA* fragment were ligated to pACYC177 (produced by NIPPON GENE CO., LTD.) and digested with restriction enzymes PstI and ScaI using In-Fusion HD cloning kit (produced by Clontech Laboratories, Inc.) to construct pACYC177-Ptac-opt_CsLINS-ispA*.

1-6) Construction of Opt_AaLINS Gene-Expressing Plasmid

PCR with pMW119-Ptac-opt_AaLINS as a template was carried out using the primer shown in SEQ ID NO: 9 and the primer shown in SEQ ID NO: 10 to obtain a Ptac-opt_AaLINS fragment. The purified Ptac-opt_AaLINS fragment was ligated to pACYC177 (produced by NIPPON GENE CO., LTD.) and digested with restriction enzymes Pst I and Sca I using In-Fusion HD cloning kit (produced by Clontech Laboratories, Inc.) to construct pACYC177-Ptac-opt_AaLINS.

Example 2: Linalool Fermentation of *E. coli* Wild Type Strain 2-1) Introduction of Linalool Synthase Expression Plasmid into *E. coli* MG1655 Strain Competent cells of *E. coli* MG1655 were prepared, and pACYC177-Ptac-opt_AaLINS-ispA*, pACYC177-Ptac-opt_AaLINS, or pACYC177 strains were introduced into the cells by an electroporation method. Resulting strains were designated as *E. coli* MG1655/AaLINS-ispA*, *E. coli* MG1655/AaLINS, and *E. coli* MG1655/pACYC177 strains.

The strains obtained as above were cultured in an LB liquid culture medium containing 50 mg/L of kanamycin at 37° C. such that the final O.D. 600≈0.3, a 40% glycerol solution was added thereto in an amount equal to the culture solution and then stirred, and the resulting solution was dispensed in each appropriate amount and then stored at −80° C.

2-2) Evaluation of Ability to Produce Linalool by Linalool Synthase-Expressing Strains Derived from *E. coli* MG1655

The glycerol stocks of *E. coli* MG1655/AaLINS-ispA*, *E. coli* MG1655/AaLINS, and *E. coli* MG1655/pACYC177 strains were thawed. Subsequently 50 μL of a microbial cell suspension from each strain was uniformly applied onto an LB plate containing 50 mg/L of kanamycin, and cultured at 37° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium (Table 2) containing 50 mg/L of kanamycin in a test tube produced by AGC Techno Glass Co., Ltd. (diameter×length×thickness=25× 200×1.2 mm), and cultured at 30° C. on a reciprocal shaking culture apparatus at 120 rpm for 24 hours.

TABLE 2

Fermentation medium for *E. coli* MG1655, host strain for expression of linalool

| Group A | |
| --- | --- |
| D-Glucose | 40 g/L |
| $MgSO_4 \cdot 7H_2O$ | 1 g/L |

Not adjusted pH, AC 115° C., 10 minutes

| Group B | |
| --- | --- |
| $(NH_4)_2SO_4$ | 20 g/L |
| $KH_2PO_4$ | 0.5 g/L |
| Yeast Extract | 2 g/L |
| $FeSO_4 \cdot 7H_2O$ | 0.01 g/L |
| $MnSO_4 \cdot 5H_2O$ | 0.01 g/L |

After adjusting pH to 7.0 with KOH, AC 115° C., 10 minutes

| Group C | |
| --- | --- |
| $CaCO_3$ | 20 g/L |

Dry-heat sterilization 180° C., 2 hours

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the following conditions using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd.). The O.D. value was measured at 620 nm using a spectrophotometer (HITACHI U-2900). Hereinafter, unless otherwise stated, the O.D. value was measured using this instrument.

| | |
| --- | --- |
| Temperature in vaporization chamber | 360.0° C. |
| Injection amount | 1.0 μL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
| --- | --- | --- |
| | 65.0 | 5.0 |
| 5.0 | 105.0 | 0.5 |
| 35.0 | 297.5 | 2.5 |

| | |
| --- | --- |
| Detector temperature | 375.0° C. |
| Detector | FID |
| Make-up gas | He (30.0 mL/min) |
| Hydrogen flow | 40.0 mL/min |
| Air | 400.0 mL/min |

The concentration of linalool is shown in terms of medium amount. A mean value obtained from two test tubes is shown in Table 3. No linalool production was observed in the control strain having the control vector pACYC177, whereas linalool production was confirmed in *E. coli* MG1655/AaLINS and *E. coli* MG1655/CsLINS-ispA* strains.

TABLE 3

Accumulation of linalool when linalool synthase native to *A. arguta* and mutant ispA were introduced

| Strain | O.D. 620 nm | Linalool (mg/L) |
| --- | --- | --- |
| *E. coli* MG1655/pACYC177 | 40.0 | 0.0 |
| *E. coli* MG1655/AaLINS | 35.4 | 1.0 |
| *E. coli* MG1655/AaLINS-ispA* | 36.7 | 2.3 |

Example 3: Linalool Fermentation of *P. ananatis* SC17

3-1) Introduction of Linalool Synthase Expression Plasmid into *P. ananatis* SC17 Strain Competent cells of *P. ananatis* SC17 strain were prepared, and pACYC177-Ptac-opt_AaLINS-ispA*, pACYC177-Ptac-opt_AaLINS, or pACYC177 were introduced into the cells by an electroporation method. Resulting strains were designated as *P. ananatis* SC17/AaLINS-ispA*, *P. ananatis* SC17/AaLINS, and *P. ananatis* SC17/pACYC177 strains, respectively.

3-2) Evaluation of Ability to Produce Linalool by Linalool Synthase-Expressing Strains Derived from *P. ananatis* SC17

The glycerol stocks of *P. ananatis* SC17/AaLINS-ispA*, *P. ananatis* SC17 AaLINS, and *P. ananatis* SC17/pACYC177 strains were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated into 5 mL of fermentation medium (Table 4) described below containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours.

TABLE 4

Fermentation medium for *P. ananatis* SC17, host strain for production of linalool

| Group A | |
| --- | --- |
| D-Glucose | 40 g/L |
| $MgSO_4 \cdot 7H_2O$ | 1 g/L |

Not adjusted pH, AC 115° C., 10 minutes

| Group B | |
| --- | --- |
| $(NH_4)_2SO_4$ | 20 g/L |
| $KH_2PO_4$ | 0.5 g/L |
| Yeast Extract | 2 g/L |
| $FeSO_4 \cdot 7H_2O$ | 0.01 g/L |
| $MnSO_4 \cdot 5H_2O$ | 0.01 g/L |

After adjusting pH to 7.0 with KOH, AC 115° C., 10 minutes

| Group C | |
| --- | --- |
| $CaCO_3$ | 20 g/L |

Dry-heat sterilization 180° C., 2 hours

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the following condition using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd.).

| | |
|---|---|
| Temperature in vaporization chamber | 360.0° C. |
| Injection amount | 1.0 µL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

The concentration of linalool is shown in terms of medium amount. A mean value obtained from two test tubes is shown in Table 5. No linalool production was observed in the control strain having the control vector pACYC177, whereas linalool production was confirmed in *P. ananatis* SC17/AaLINS and *P. ananatis* SC17/CsLINS-ispA* strains.

TABLE 5

Accumulation of linalool when linalool synthase native to *A. arguta* and mutant ispA were introduced in *P. ananatis* SC17

| Strain | O.D. 620 nm | Linalool (mg/L) |
|---|---|---|
| *P. ananatis* SC17/pACYC177 | 31.8 | 0.0 |
| *P. ananatis* SC17/AaLINS | 20.9 | 1.8 |
| *P. ananatis* SC17/AaLINS-ispA* | 30.2 | 5.8 |

Reference Practical Example 1

Construction of microaerobically inducible isoprenoid compound-producing microorganism (SWITCH-Plld/IspSM), phosphate deficiency-inducible isoprenoid compound-producing microorganism (SWITCH-PphoC/IspSM, SWITCH-PpstS/IspSM) and arabinose-inducible isoprenoid compound-producing microorganism (SWITCH-Para/IspSM)

1-1) Construction of pMW-Para-mvaES-Ttrp 1-1-1) Chemical Synthesis of mvaE Gene Native to *Enterococcus faecalis*

A nucleotide sequence and an amino acid sequence of mvaE encoding acetyl-CoA acetyltransferase and hydroxymethylglutaryl-CoA reductase and native to *Enterococcus faecalis* have been reported (Accession number of nucleotide sequence: AF290092.1, (1479 . . . 3890), Accession number of amino acid sequence: AAG02439) (J. Bacteriol. 182 (15): 4319-4327 (2000)). The amino acid sequence of the mvaE protein native to *Enterococcus faecalis* and the nucleotide sequence of its gene are shown as SEQ ID NO: 20 and SEQ ID NO: 21, respectively. In order to efficiently express the mvaE gene in *E. coli*, an mvaE gene in which codon usage in *E. coli* had been optimized was designed, and this was designated as EFmvaE. This nucleotide sequence is shown as SEQ ID NO: 22. The mvaE gene was chemically synthesized, then was cloned into pUC57 (produced by GenScript), and the resulting plasmid was designated as pUC57-EFmvaE.

1-1-2) Chemical Synthesis of mvaS Gene Native to *Enterococcus faecalis*

A nucleotide sequence of mvaS native to *Enterococcus faecalis* encoding hydroxymethylglutaryl-CoA synthase, and its amino acid sequence have been already known (Accession number of nucleotide sequence: AF290092.1, complement (142 . . . 1293), Accession number of amino acid sequence: AAG02438) (J. Bacteriol. 182(15): 4319-4327 (2000)). The amino acid sequence of the mvaS protein native to *Enterococcus faecalis* and the nucleotide sequence of its gene are shown as SEQ ID NO: 23 and SEQ ID NO: 24, respectively. In order to efficiently express the mvaS gene in *E. coli*, an mvaS gene optimized to the codon usage in *E. coli* was designed, and this was designated as EFmvaS. This nucleotide sequence is shown as SEQ ID NO: 25. The mvaS gene was chemically synthesized, then was cloned into pUC57 (produced by GenScript), and the resulting plasmid was designated as pUC57-EFmvaS.

1-1-3) Construction of Expression Vector for Arabinose-Inducible mvaES

An expression vector for an arabinose-inducible gene upstream of the mevalonate pathway was constructed by the following procedure. PCR with plasmid pKD46 as the template was carried out using synthesized oligonucleotides shown as SEQ ID NO: 26 and SEQ ID NO: 27 as primers to obtain a PCR fragment containing Para composed of araC and an araBAD promoter native to *E. coli*. PCR with plasmid pUC57-EFmvaE as the template was carried out using synthesized oligonucleotides shown as SEQ ID NO: 28 and SEQ ID NO: 29 as primers to obtain a PCR fragment containing the EFmvaE gene. PCR with plasmid pUC57-EFmvaS as the template was carried out using synthesized oligonucleotides shown as SEQ ID NO: 30 and SEQ ID NO: 31 as primers to obtain a PCR fragment containing the EFmvaS gene. PCR with plasmid pSTV-Ptac-Ttrp (WO2013/069634 A1) as the template was carried out using synthesized oligonucleotides shown as SEQ ID NO: 32 and SEQ ID NO: 33 as primers to obtain a PCR fragment containing a Ttrp sequence. Prime Star polymerase (produced by Takara Bio Inc.) was used for PCR to obtain these four PCR fragments. A reaction solution was prepared according to a composition attached to a kit, and DNA was amplified through 30 cycles of reactions at 98° C. for 10 seconds, 55° C. for 5 seconds and 72° C. for one minute per kb. PCR with the purified PCR product containing Para and PCR product containing the EFmvaE gene as the template was carried out using synthesized oligonucleotides shown as SEQ ID NO: 26 and SEQ ID NO: 29 as primers, and PCR with the purified PCR product containing the EFmvaS gene and PCR product containing Ttrp as the template was carried out using synthesized oligonucleotides shown in SEQ ID NO: 30 and SEQ ID NO: 33 as primers. As a result, a PCR product containing Para and the EFmvaE gene and a PCR product containing the EFmvaS gene and Ttrp were obtained. A plasmid pMW219 (produced by NIPPON GENE CO., LTD.) was digested with SmaI according to a standard method. pMW219 digested with SmaI was ligated to the purified PCR product containing Para and the EFmvaE gene and the purified PCR product containing the EFmvaS gene and Ttrp using In-Fusion HD Cloning Kit (produced by Clontech Laboratories, Inc.). The resulting plasmid was designated as pMW-Para-mvaES-Ttrp.

1-2) Construction of the Integrative Conditionally Replicated Plasmids Carrying Upstream and Downstream Genes in Mevalonate Pathways 1-2-1) Construction of Plasmids Containing the mvaES Gene Under the Control of a Different Promoter To construct integrative plasmids carrying upstream and downstream genes of mevalonate pathways, the pAH162-λattL-TcR-λattR vector (Minaeva et al., BMC Biotechnol., 2008; 8: 63) was used.

KpnI-SalI fragment of pMW-Para-mvaES-Ttrp was cloned into SphI-SalI recognition sites of pAH162-λattL-TcR-λattR. As a result, the pAH162-Para-mvaES plasmid carrying mvaES operon from E. faecalis under control of the E. coli Para promoter and repressor gene araC have been constructed (FIG. 1).

Figure 2:
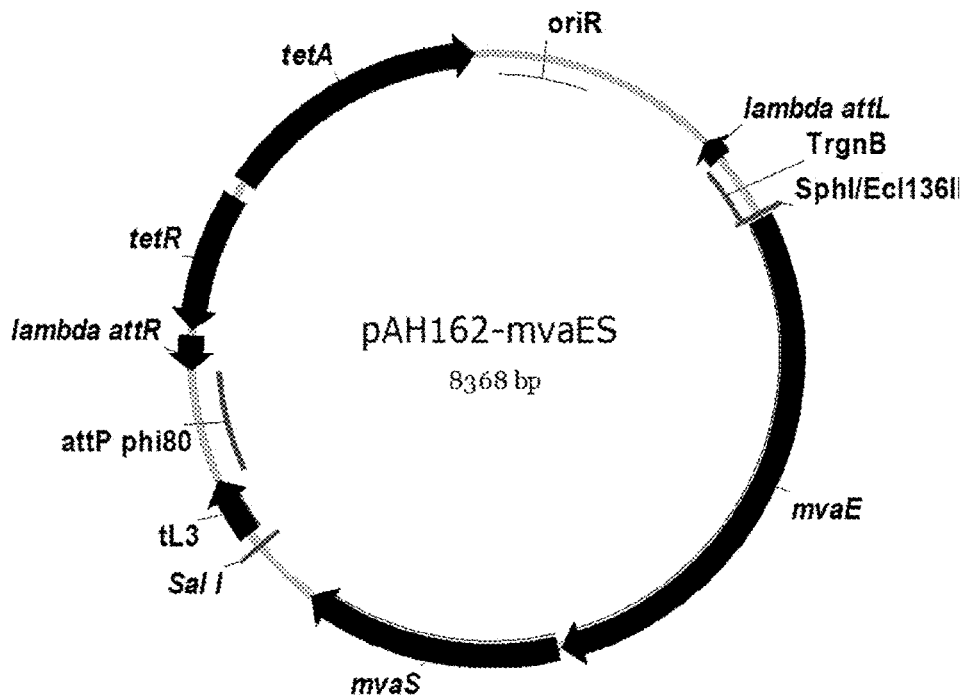
FIG. 2 shows a map of pAH162-mvaES.

In order to obtain a variant of promoter-deficient operon, an Ecl136II-SalI fragment of pMW219-Para-mvaES-Ttrp was subcloned into the same integrative vector. A map of the resulting plasmid is shown in FIG. 2.

Figure 3:
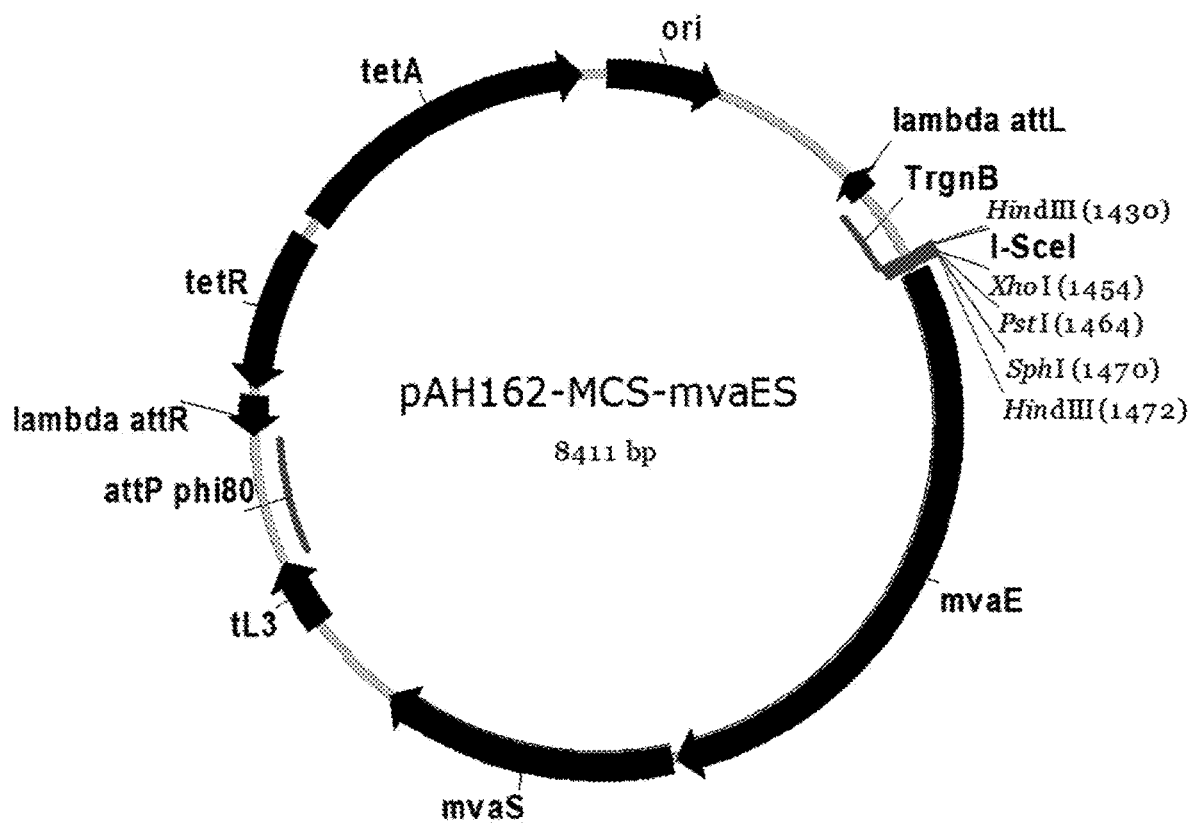
FIG. 3 shows a plasmid for chromosome fixation of pAH162-MCS-mvaES.
Figure 4A:
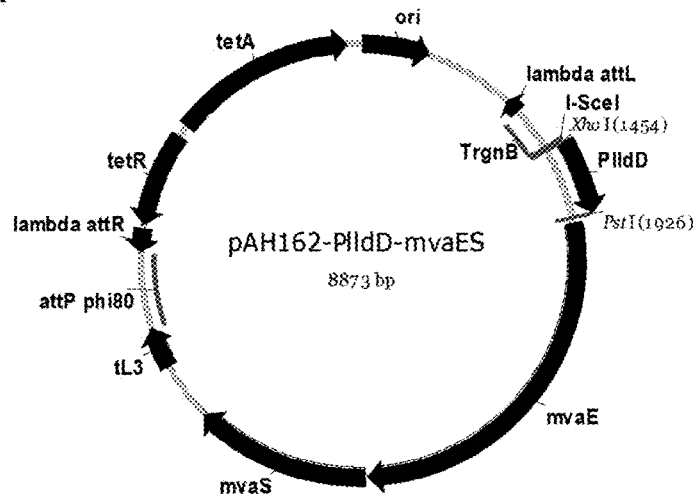
FIGS. 4A, 4B, and 4C show a set of plasmids for chromosome fixation which possess an mvaES gene under transcription control of (A) $P_{lldD}$, (B) $P_{phoC}$, or (C) $P_{pstS}$.
Figure 4B:
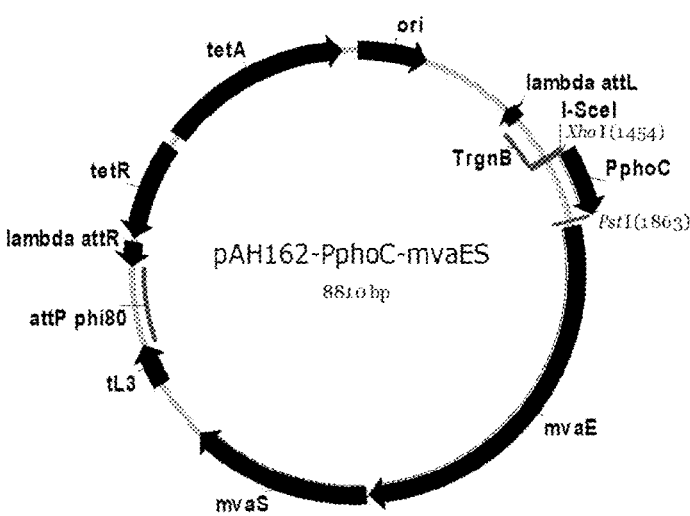
Figure 4C:
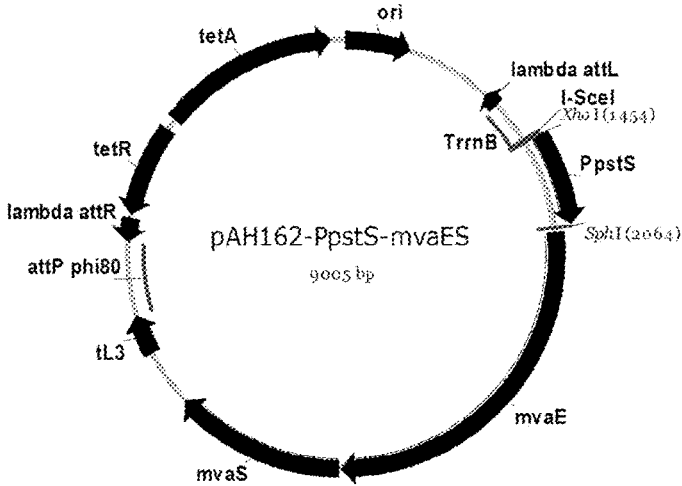

A set of plasmids for chromosome fixation, which retains the mvaES gene under the control of a different promoter was constructed. For this purpose, a polylinker containing I-SceI, XhoI, PstI and SphI recognition sites was inserted into the unique HindIII recognition site located upstream of the mvaES gene. In order to accomplish this purpose, annealing was carried out using the primers 1, 2 (Table 6) and polynucleotide kinase. After that, the resulting double-stranded DNA fragment was 5' phosphorylated with polynucleotide kinase and the resulting phosphorylated fragment was inserted into a pAH162-mvaES plasmid cleaved with HindIII by a ligation reaction. The resulting pAH162-MCS-mvaES plasmid (FIG. 3) is convenient for cloning of a promoter with a desired orientation before the mvaES gene. DNA fragments retaining a regulatory region of a lldD, phoC and pstS genes were generated by PCR with genomic DNA from P. ananatis SC17(0) strain (Katashkina et al., BMC Mol Biol., 2009; 10: 34) as the template using primers 3 and 4, primers 5 and 6, and primers 7 and 8 (Table 6), respectively, and cloned into an appropriate restriction enzyme recognition site of pAH162-MCS-mvaES. The resulting plasmids are shown in FIG. 4. The cloned promoter fragments were sequenced and confirmed to exactly correspond to predicted nucleotide sequences.

1-2-2) Construction of pAH162-Km-Ptac-KDyI Plasmid for Chromosome Fixation

Figure 5:
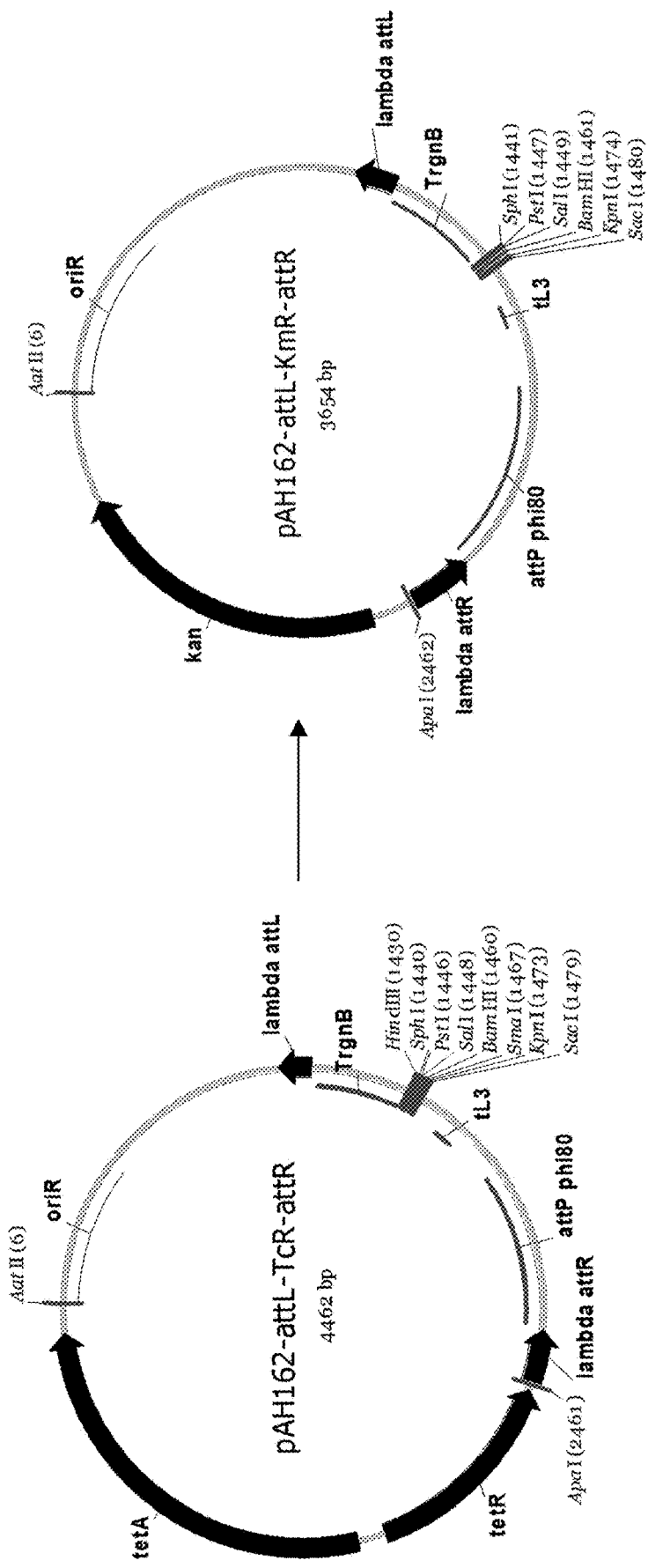
FIG. 5 shows an outline for construction of a pAH162-λattL-$Km^R$-λattR vector.

An AatII-ApaI fragment of pAH162-λattL-Tc$^R$-λattR containing a tetAR gene (Minaeva et al., BMC Biotechnol., 2008; 8: 63) was replaced with a DNA fragment obtained by PCR with a pUC4K plasmid (Taylor L A and Rose R E., Nucleic Acids Res., 16: 358, 1988) as the template using the primers 9 and 10 (Table 6). As a result, pAH162-λattL-Km$^R$-λattR was obtained (FIG. 5).

Figure 6:
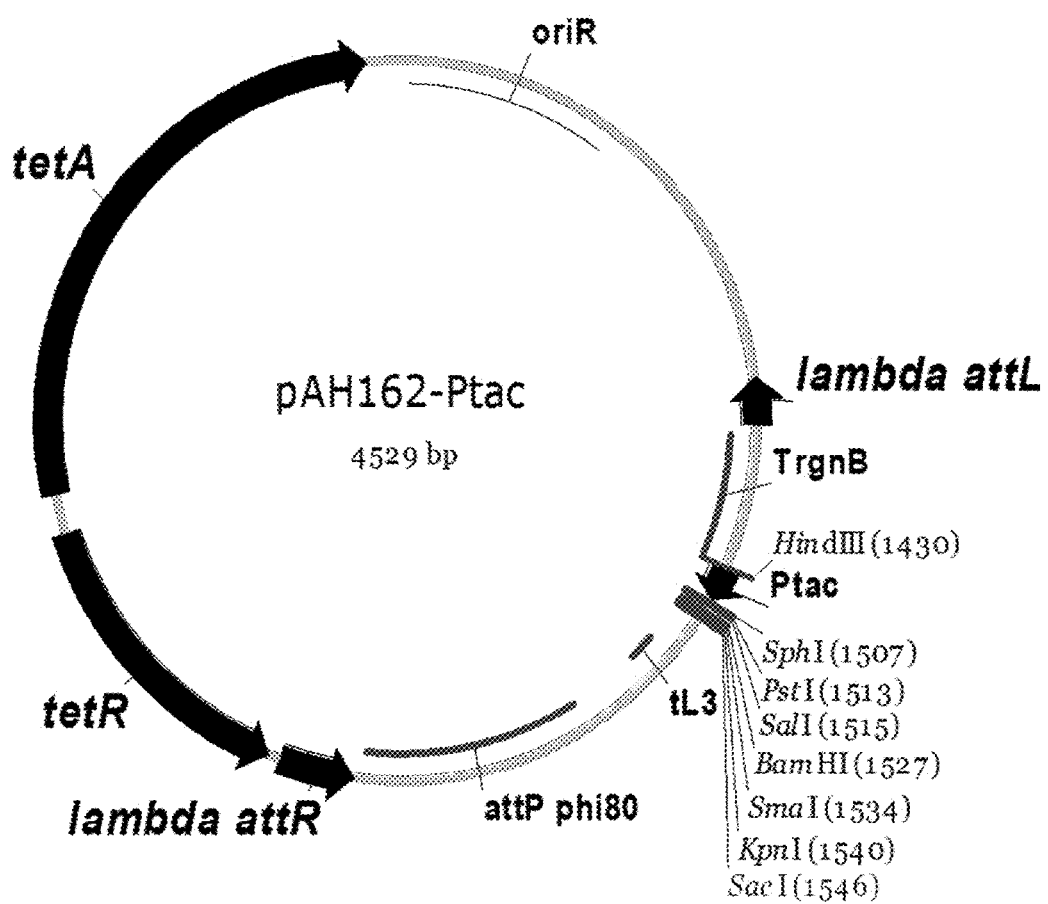
FIG. 6 shows a pAH162-Ptac expression vector for chromosome fixation.

A Ptac promoter was inserted into a HindIII-SphI recognition site of the pAH162-λattL-Tc$^R$-λattR vector (Minaeva N I et al., BMC Biotechnol., 2008; 8: 63). As a result, the expression vector pAH162-Ptac for chromosome fixation was constructed. The cloned promoter fragment was sequenced and confirmed to be the sequence as designed. A map of pAH162-Ptac is shown in FIG. 6.

Figure 7:
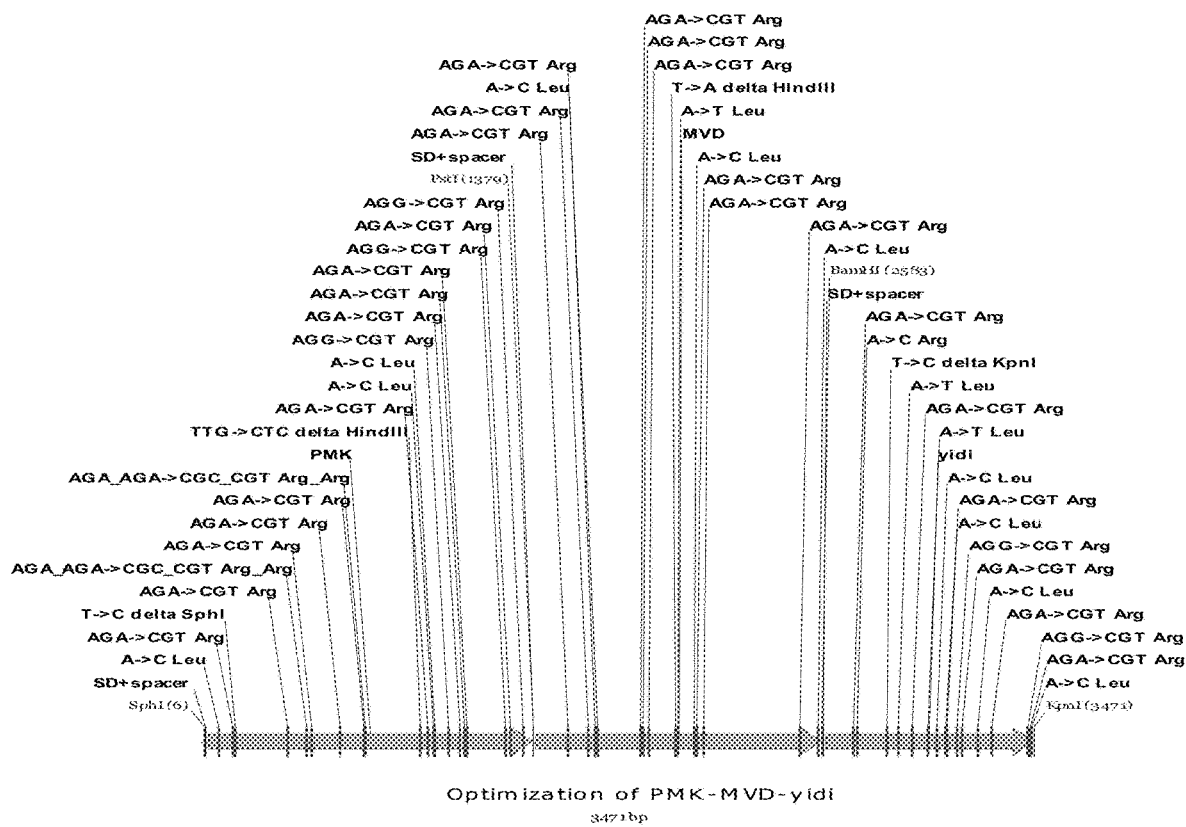
FIG. 7 shows codon optimization in a KDyI operon obtained by chemical synthesis.
Figure 8A:
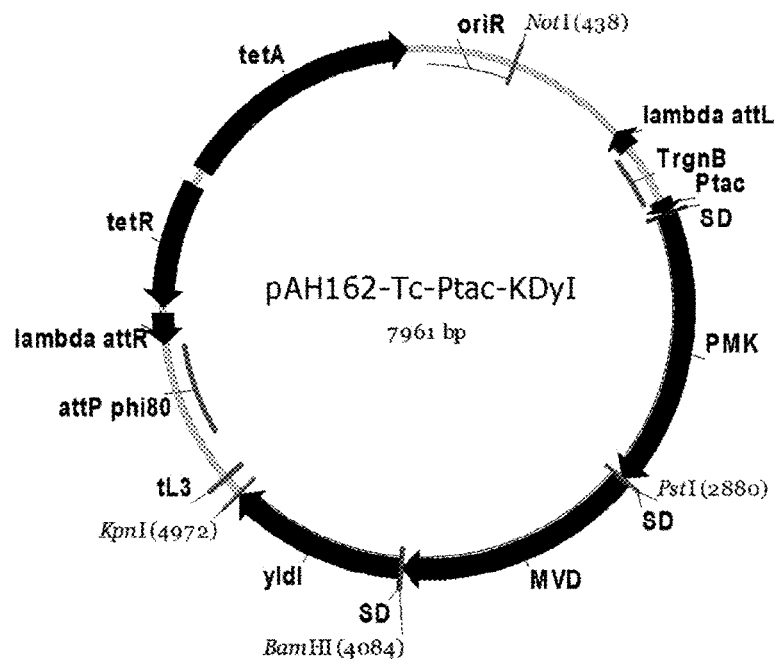
FIGS. 8A and 8B show plasmids (A) pAH162-Tc-Ptac-KDyI and (B) pAH162-Km-Ptac-KDyI for chromosome fixation, which retain the KDyI operon with codon optimization.
Figure 8B:
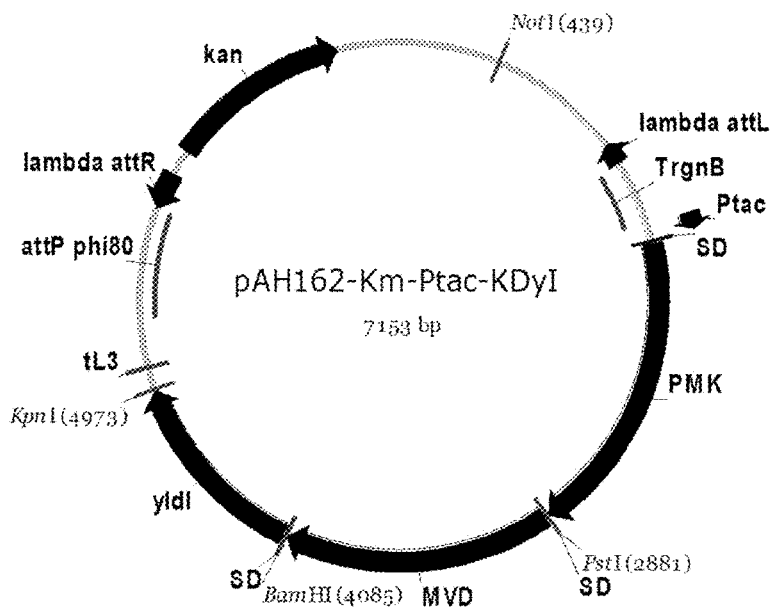

A DNA fragment that retained the PMK, MVD and yldI genes native to S. cerevisiae, in which rare codons had been replaced with synonymous codons, and had been chemically synthesized by ATG Service Gene (Russia) (FIG. 7) was subcloned into a SphI-KpnI restriction enzyme recognition site of the vector pAH162-Ptac for the chromosome fixation. The DNA sequence including the chemically synthesized KDyI operon is shown in SEQ ID NO:58. The resulting plasmid pAH162-Tc-Ptac-KDyI retaining a Ptac-KDyI expression cassette is shown in FIG. 8(A). Subsequently, for the purpose of replacing a drug resistant marker gene, a NotI-KpnI fragment of pAH162-Tc-Ptac-KDyI retaining the tetAR gene was replaced with a corresponding fragment of pAH162-λattL-Km$^R$-λattR. As a result, a plasmid pAH162-Km-Ptac-KDyI having a kanamycin resistant gene, kan, as a marker was obtained (FIG. 8(B)).

Figure 9:
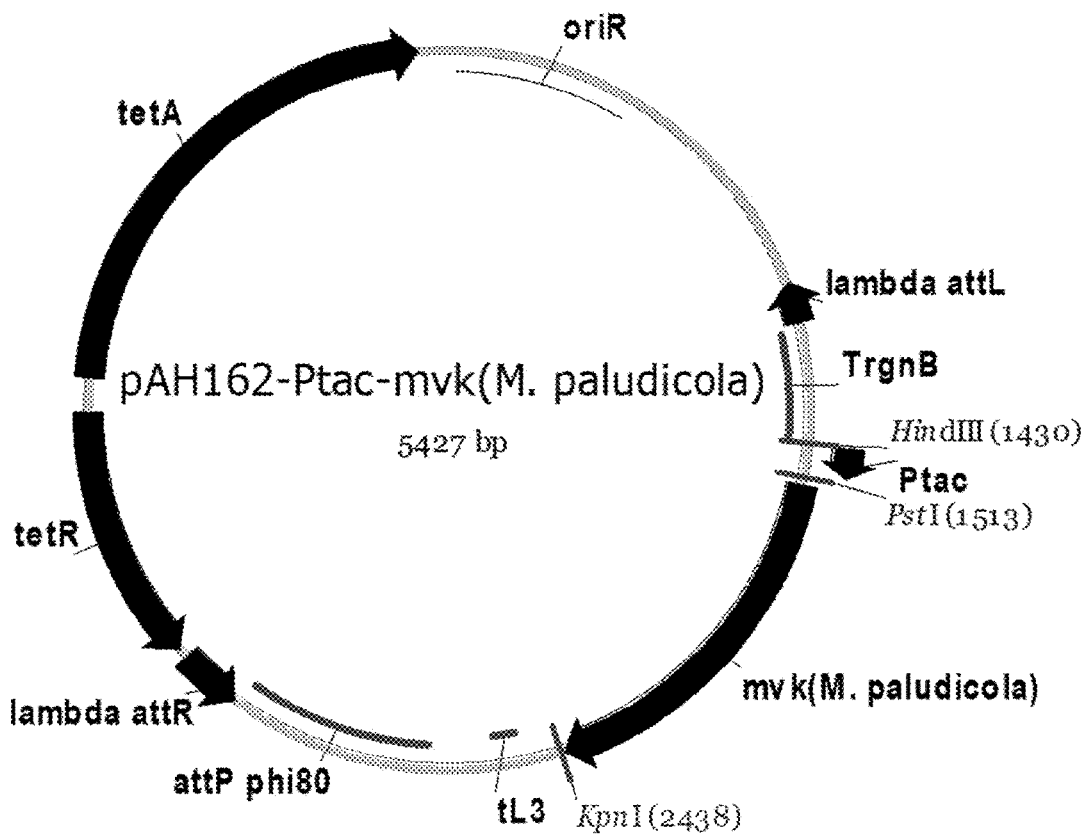
FIG. 9 shows a plasmid for chromosome fixation, which retains a mevalonate kinase gene native to *M. paludicola.*

A chemically synthesized DNA fragment containing a coding region of a putative mvk gene native to SANAE (for full-length genomic sequence, see GenBank Accession Number AP011532) that is strain of Methanocella paludicola, which had been ligated to a classical SD sequence, was cloned into a PstI-KpnI recognition site of the above integrative expression vector pAH162-Ptac. A map of the plasmid for the chromosome fixation retaining the mvk gene is shown in FIG. 9.

1-3) Construction of Recipient Strain SC17(0) ΔampC::attB$_{phi80}$ ΔampH::attB$_{phi80}$ Δcrt::Ptac-mvk (M. paludicola)

Using a two-stage technique of λ-Red dependent integration of a PCR amplified DNA fragment containing the kan gene flanked by attL$_{phi80}$ and attR$_{phi80}$ and 40 bp sequences homologous to a target chromosome site (Katashkina et al., BMC Mol Biol., 2009; 10: 34), and subsequent phage phi80 Int/Xis-dependent removal of the kanamycin resistant marker (Andreeva et al., FEMS Microbiol Lett., 2011; 318(1): 55-60), chromosomal modifications of ΔampH::attB$_{phi80}$ and ΔampC::attB$_{phi80}$ were introduced into P. ananatis SC17(0) strain in a stepwise fashion. SC17(0) is a λ-Red resistant derivative of P. ananatis AJ13355 (Katashkina et al., BMC Mol Biol., 2009; 10: 34); an annotated full-length genomic sequence of P. ananatis AJ13355 is available as PRJDA162073 or GenBank Accession Numbers AP012032.1 and AP012033.1. Using pMWattphi plasmid (Minaeva et al., BMC Biotechnol., 2008; 8:63) as the template, and using primers 11 and 12, and primers 13 and 14 (Table 6), DNA fragments used for integration into an ampH and ampC gene regions, respectively, were generated. The primers 15 and 16, and the primers 17 and 18 (Table 6) were used to verify the resulting chromosome modifications by PCR.

Figure 10A:
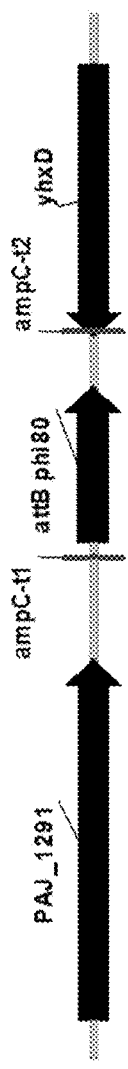
FIGS. 10A, 10B, and 10C show maps of genome modifications of (A) ΔampC::attB$_{phi80}$, (B) ΔampH::attB$_{phi80}$, and (C) Δcrt::attB$_{phi80}$.
Figure 10B:
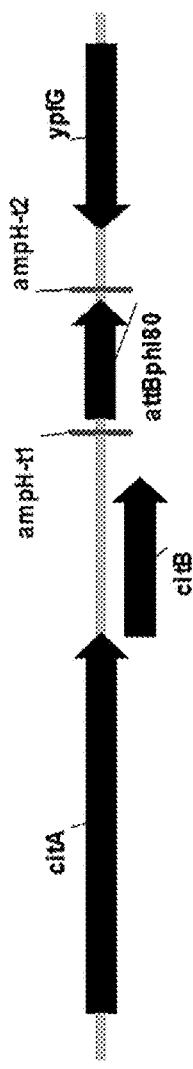
Figure 10C:

In parallel, a derivative of P. ananatis SC17(0) retaining the attB site of phi80 phage in place of the crt operon located on the pEA320 320 kb megaplasmid, which is a part of P. ananatis AJ13355 genome, was constructed. In order to obtain this strain, λ-Red dependent integration of PCR-amplified DNA fragment retaining attL$_{phi80}$-kan-attR$_{phi80}$ flanked by a 40 bp region homologous to a target site in the genome was carried out according to the previously described technique (Katashkina et al., BMC Mol Biol., 2009; 10: 34). Therefore, a DNA fragment to be used in the replacement of the crt operon with attL$_{phi80}$-kan-attR$_{phi80}$ was amplified in the reaction using the primers 19 and 20 (Table 6). The pMWattphi plasmid (Minaeva et al., BMC Biotechnol., 2008; 8: 63) was used as the template in this reaction. The resulting integrated product was designated as SC17(0) Δcrt::attL$_{phi80}$-kan-attR$_{phi80}$. The primers 21 and 22 (Table 6) were used to verify the chromosome structure of SC17(0) Δcrt::attL$_{phi80}$-kan-attR$_{phi80}$ by PCR. The kanamycin resistance marker was removed from the constructed strain according to the reported technique using a pAH129-cat helper plasmid (Andreeva I G et al., FEMS Microbiol Lett., 2011; 318(1): 55-60). The primers 21 and 22 were used to verify the resulting SC17(0) Δcrt::attB$_{phi80}$ strain by PCR. Maps of the resulting genome-modified products, ΔampC::attB$_{phi80}$, ΔampH::attB$_{phi80}$ and Δcrt::attB$_{phi80}$ are shown in FIGS. 10 (A), (B) and (C), respectively.

Figures 11A, 11B:
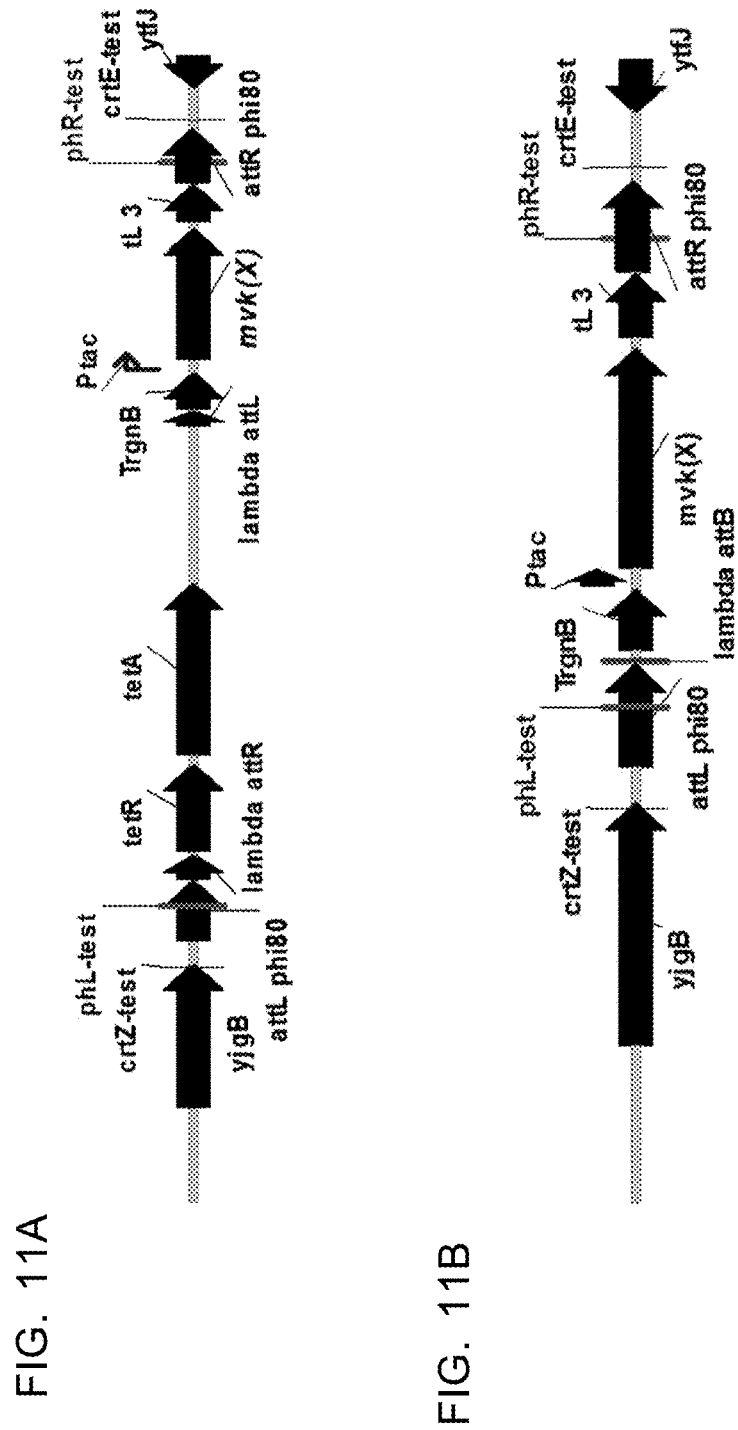
FIGS. 11A and 11B show maps of genome modifications of (A) Δcrt::pAH162-Ptac-mvk(X) and (B) Δcrt::Ptac-mvk (X).

The aforementioned pAH162-Ptac-mvk (*M. paludicola*) plasmid was integrated into an attB$_{phi80}$ site of SC17(0) Δcrt::attB$_{phi80}$ according to the reported protocol (Andreeva et al., FEMS Microbiol Lett., 2011; 318(1): 55-60). The integration of the plasmid was confirmed by PCR using the primers 21 and 23 and the primers 22 and 24 (Table 6). As a result, the SC17(0) Δcrt::pAH162-Ptac-mvk (*M. paludicola*) strain was obtained. A map of the modified genome of Δcrt::pAH162-Ptac-mvk (*M. paludicola*) is shown in FIG. 11(A).

Subsequently, a genetic trait of SC17(0) Δcrt::pAH162-Ptac-mvk (*M. paludicola*) was transferred to SC17(0) ΔampC::attB$_{phi80}$ ΔampH::attB$_{phi80}$ via a genome DNA electroporation method (Katashkina et al., BMC Mol Biol., 2009; 10: 34). The resulting strain utilizes a tetracycline resistant gene, tetRA as the marker. The vector part of the pAH162-Ptac-mvk (*M. paludicola*) integrative plasmid including tetRA marker genes was eliminated using the reported pMW-intxis-cat helper plasmid (Katashkina et al., BMC Mol Biol., 2009; 10: 34). As a result, a marker gene deficient strain, SC17(0) ΔampH::attB$_{φ80}$ ΔampC::attB$_{φ80}$ Δcrt::Ptac-mvk (*M. paludicola*) was obtained. A map of the modified genome of Δcrt::Ptac-mvk (*M. paludicola*) is shown in FIG. 11(B).

1-4) Construction of Set of SWITCH Strains

Figure 12A:
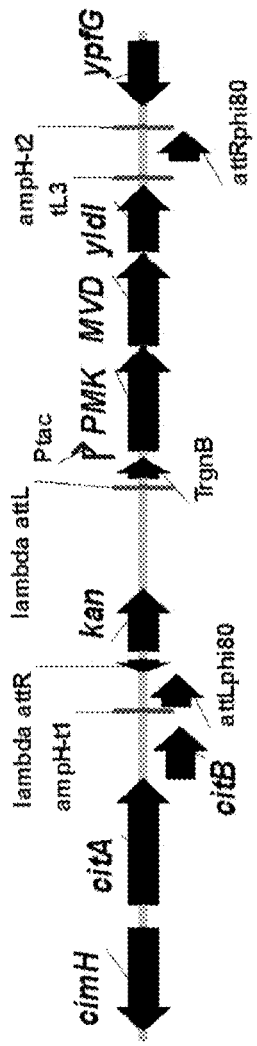
FIGS. 12A, 12B, and 12C show maps of chromosome modifications of (A) ΔampH::pAH162-Km-Ptac-KDyI, (B) ΔampC::pAH162-Km-Ptac-KDyI and (C) ΔampC::Ptac-KDyI.
Figure 12B:
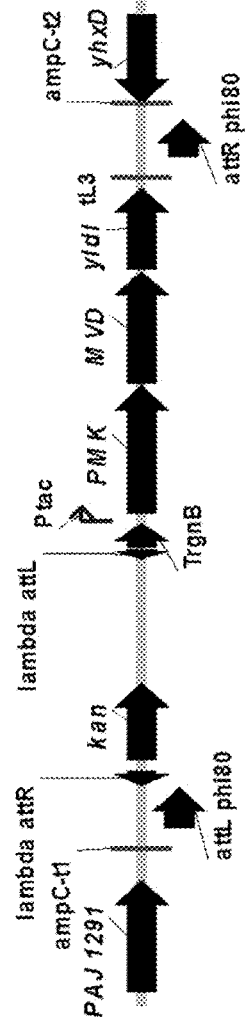
Figure 12C:
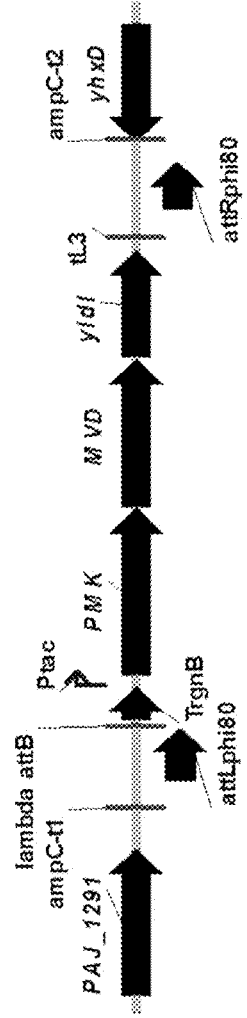
Figure 13A:
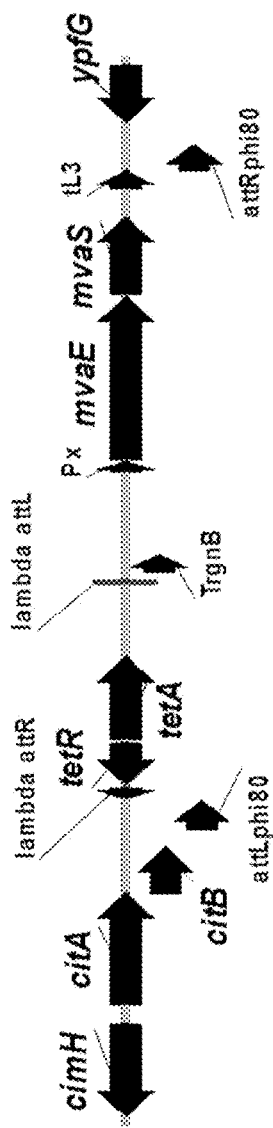
FIGS. 13A and 13B show maps of chromosome modifications of (A) ΔampH::pAH162-Px-mvaES and (B) ΔampC::pAH162-Px-mvaES.
Figure 13B:
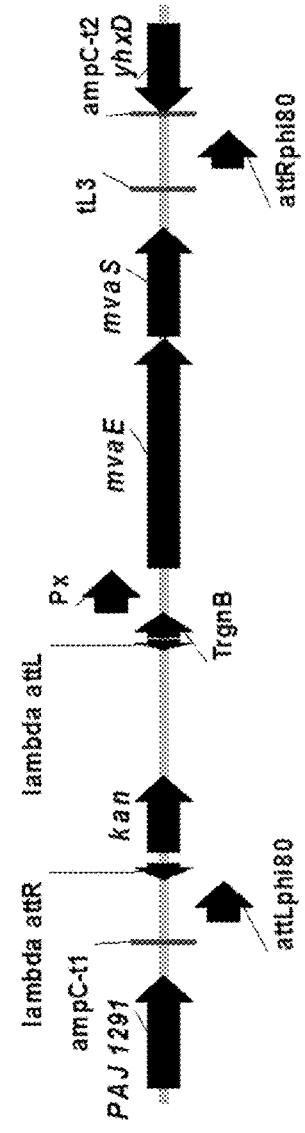

The pAH162-Km-Ptac-KDyI plasmid was integrated into the chromosome of SC17(0) ΔampH::attB$_{φ80}$ ΔampC::attB$_{φ80}$ Δcrt::Ptac-mvk (*M. paludicola*)/pAH123-cat strain according to the reported protocol (Andreeva et al., FEMS Microbiol Lett. 2011; 318(1): 55-60). The cells were seeded on LB agar containing 50 mg/L of kanamycin. A grown Km$^R$ clone was examined by PCR reaction using the primers 11 and 15 and the primers 11 and 17 (Table 6). Strains retaining the pAH162-Km-Ptac-KDyI plasmid integrated into ΔampH::attB$_{φ80}$ or ΔampC::attB$_{φ80}$m were chosen. Maps of the modified chromosomes of ΔampH::pAH162-Km-Ptac-KDyI, ΔampC::pAH162-Km-Ptac-KDyI and ΔampC::Ptac-KDyI are shown in FIGS. 12(A), (B) and (C).

pAH162-Px-mvaES (Px is one of the following regulatory regions: araC-P$_{ara}$ (*E. coli*), P$_{lldD}$, P$_{phoC}$, P$_{pstS}$) was inserted into the attB$_{phi80}$ site of SC17(0) ΔampC::pAH162-Km-Ptac-KDyI ΔampH::attB$_{phi80}$ Δcrt::Ptac-mvk(*M. paludicola*) and SC17(0) ΔampC::attB$_{phi80}$ ΔampH::pAH162-Km-Ptac-KDyI Δcrt::Ptac-mvk (*M. paludicola*) recipient strains using a pAH123-cat helper plasmid according to the reported protocol (Andreeva et al., FEMS Microbiol Lett., 2011; 318(1): 55-60). As a result, two sets of strains designated as SWITCH-Px-1 and SWITCH-Px-2 were obtained. Maps of the modified chromosomes of ΔampH::pAH162-Px-mvaES and ΔampC::pAH162-Px-mvaES are shown in FIG. 13.

TABLE 6

Primer sequences utilized in Reference Practical Example 1

| No | Name | Sequence 5'->3' |
|---|---|---|
| 1 | Linker-F | AGCTTTAGGGATAACAGGGTAATCTCGAGCTGCAGGCATGCA (SEQ ID NO: 34) |
| 2 | Linker-R | AGCTTGCATGCCTGCAGCTCGAGATTACCCTGTTATCCCTAA (SEQ ID NO: 35) |
| 3 | lldD5'CAs | TTTTTAAGCTTTAGGGATAACAGGGTAATCTCGAGATTTAAAGCGGCTGCTTTAC (SEQ ID NO: 36) |
| 4 | lldD3'CAs | TTTTTAAGCTTGCATGCCTGCAGTATTTAATAGAATCAGGTAG (SEQ ID NO: 37) |
| 5 | phoC5'CAS | TTTTTAAGCTTTAGGGATAACAGGGTAATCTCGAGTGGATAACCTCATGTAAAC (SEQ ID NO: 38) |
| 6 | phoC3'CAS | TTTTTAAGCTTGCATGCCTGCAGTTGATGTCTGATTATCTCTGA (SEQ ID NO: 39) |
| 7 | pstS5'CAs | TTTTTAAGCTTTAGGGATAACAGGGTAATCTCGAGAGCCTCTCACGCGTGAATC (SEQ ID NO: 40) |
| 8 | pstS3'CAs | TTTTTAAGCTTGCATGCCTGCAGAGGGGAGAAAAGTCAGGCTAA (SEQ ID NO: 41) |
| 9 | n67 | TGCGAAGACGTCCTCGTGAAGAAGGTGTTGCTG (SEQ ID NO: 42) |
| 10 | n68 | TGCGAAGGGCCCCGTTGTGTCTCAAAATCTCTGATG (SEQ ID NO: 43) |
| 11 | ampH-attL-phi80 | ATGCGCACTCCTTACGTACTGGCTCTACTGGTTTCTTTGCGAAAGGTCATTTTTCCTGAATATGCTCACA (SEQ ID NO: 44) |
| 12 | ampH-attR-phi80 | TTAAGGAATCGCCTGGACCATCATCGGCGAGCCGTTCTGACGTTTGTTGACAGCTGGTCCAATG (SEQ ID NO: 45) |
| 13 | DampC-phL | CTGATGAACTGTCACCTGAATGAGTGCTGATGAAAATATAGAAAGGTCATTTTTCCTGAATATGCTCA (SEQ ID NO: 46) |
| 14 | DampC-phR | ATTCGCCAGCATAACGATGCCGCTGTTGAGCTGAGGAACACGTTTGTTGACAGCTGGTCCAATG (SEQ ID NO: 47) |
| 15 | ampH-t1 | GCGAAGCCCTCTCCGTTG (SEQ ID NO: 48) |
| 16 | ampH-t2 | AGCCAGTCAGCCTCATCAGCG (SEQ ID NO: 49) |
| 17 | ampC-t1 | GATTCCCACTTCACCGAGCCG (SEQ ID NO: 50) |
| 18 | ampC-t2 | GGCAGGTATGGTGCTCTGACG (SEQ ID NO: 51) |
| 19 | crtE-attRphi80 | ATGACGGTCTGCGCAAAAAAACACGTTCATCTCACTCGCGCGTTTGTTGACAGCTGGTCCAATG (SEQ ID NO: 52) |
| 20 | crtZ-attLphi80 | ATGTTGTGGATTTGGAATGCCCTGATCGTTTTCGTTACCGGAAAGGTCATTTTTCCTGAATATGCTCA (SEQ ID NO: 53) |
| 21 | crtZ-test | CCGTGTGGTTCTGAAAGCCGA (SEQ ID NO: 54) |
| 22 | crtE-test | CGTTGCCGTAAATGTATCCGT (SEQ ID NO: 55) |
| 23 | phL-test | GGATGTAAACCATAACACTCTGCGAAC (SEQ ID NO: 56) |

TABLE 6-continued

Primer sequences utilized in Reference Practical Example 1

| No | Name | Sequence 5'->3' |
|---|---|---|
| 24 | phR-test | GATTGGTGGTTGAATTGTCCGTAAC (SEQ ID NO: 57) |

Example 4: Construction of SC17(0)Δgcd and SWITCH-PphoC Δgcd

The gcd gene in *P. ananatis* codes for glucose dehydrogenase, and it has been reported that *P. ananatis* produces gluconate during aerobic growth (Andreeva et al., FEMS Microbiol Lett. 2011 May; 318(1):55-60).

The SC17(0)Δgcd strain in which the gcd gene is disrupted is constructed using λRed-dependent integration of DNA fragments obtained in PCRs with the primers gcd-attL and gcd-attR (Table 7) and the pMW118-attL-kan-attR plasmid (Minaeva et al., BMC Biotechnol. 2008; 8:63) as the template. To verify the integrant, the primers gcd-t1 and gcd-t2 (Table 7) are used.

Genomic DNA of the SC17(0)Δgcd strain is isolated using the Wizard Genomic DNA Purification Kit (Promega) and electro-transformed into the marker-less derivative of the SWITCH-PphoC strain according to the previously described method (Katashkina et al., BMC Mol Biol. 2009; 10:34). As a result, the SWITCH-PphoC-Δgcd (Km$^R$) strain is obtained. The primers gcd-t1 and gcd-t2 (Table 7) are used for PCR analysis of the obtained integrant. The kanamycin resistant marker gene is obtained according to the standard λInt/Xis-mediated procedure (Katashkina et al., BMC Mol Biol. 2009; 10:34). The obtained strain is designated as SWITCH-PphoC Δgcd strain.

TABLE 7

Primer List

| Primer | Nucleotide sequence (SEQ ID NO:) |
|---|---|
| gcd-attL | GGTCAACATTATGGGGAAAAACTCCTCATCCTTTAGCGTGTG AAGCCTGCTTTTTTATACTAAGTTGG (SEQ ID NO: 16) |
| gcd-attR | TTACTTCTGGTCGGGCAGCGCATAGGCAATCACGTAATCGCG CTCAAGTTAGTATAAAAAAGCTGAAC (SEQ ID NO: 17) |
| gcd-t1 | TGACAACAATCTATCTGATT (SEQ ID NO: 18) |
| gcd-t2 | TGCGCCTGGTTAAGCTGGCG (SEQ ID NO: 19) |

Competent cells of SWITCH-PphoC were prepared, and pACYC177, pACYC177-Ptac-opt_AaLINS-ispA*, or pACYC177-Ptac-opt_CsLINS-ispA* was introduced into the cells by electroporation. The resulting strains were designated as SWITCH-PphoC/pACYC177, SWITCH-PphoC/AaLINS-ispA* and SWITCH-PphoC/CsLINS-ispA*, respectively.

Example 5: Evaluation of Ability to Produce Linalool by Linalool Synthase-Expressing Strains Derived from the SWITCH-PphoC Strain The glycerol stocks of SWITCH-PphoC/AaLINS-ispA*, and SWITCH-PphoC/CsLINS-ispA* strains, and SWITCH-PphoC/pACYC177 strains obtained in Example 4 were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated into 5 mL of fermentation medium described in Table 8 containing 50 mg/L of kanamycin in a test tube produced by AGC Techno Glass Co., Ltd. (diameter×length×thickness=25× 200×1.2 mm), and cultured at 30° C. on a reciprocal shaking culture apparatus at 120 rpm for 24 hours.

TABLE 8

Fermentation medium for SWITCH-PphoC, host strain for production of linalool

| Group A | |
|---|---|
| D-Glucose | 40 g/L |
| MgSO$_4$•7H$_2$O | 1 g/L |
| Not adjusted pH, AC 115° C., 10 minutes | |
| Group B | |
| (NH$_4$)$_2$SO$_4$ | 20 g/L |
| KH$_2$PO$_4$ | 0.5 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |

Dry-heat sterilization 180° C., 2 hours

After the completion of sterilization, the above Groups A, B and C were mixed. Then, 1 mL of isopropyl myristate (produced by Tokyo Chemical Industry Co., Ltd.) was added to 5 mL of the fermentation medium in the test tube.

24 hours after starting the cultivation, the concentrations of isopropyl myristate and linalool in the culture supernatant were measured under the following conditions using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd.).

| | |
|---|---|
| Temperature in vaporization chamber | 360.0° C. |
| Injection amount | 1.0 μL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

The concentration of linalool is shown in terms of medium amount. A mean value obtained from two test tubes is shown in Table 9. It was shown that linalool is produced in the linalool synthase-expressing strain.

TABLE 9

Accumulation of linalool when linalool synthase native to *Actinidia arguta* and *Coriandrum sativum* were introduced

| Strain | O.D. (620 nm) | Linalool (mg/L) |
|---|---|---|
| SWITCH-PphoC/pACYC177 | 17.5 | 0.0 |
| SWITCH-PphoC/CsLINS-ispA* | 25.8 | 0.7 |
| SWITCH-PphoC/AaLINS-ispA* | 26.4 | 805.3 |

Example 6: Evaluation of Ability to Produce Linalool by Linalool Synthase-Expressing Strains Derived from SWITCH-PphoC Δgcd Strain Competent cells of SWITCH-PphoC Δgcd obtained in Example 4 were prepared, and pACYC177, pACYC177-Ptac-opt_AaLINS-ispA* or pACYC177-Ptac-opt_CsLINS-ispA* was introduced into the cells by electroporation. Resulting strains were designated as SWITCH-PphoC Δgcd/pACYC177, SWITCH-PphoC Δgcd/AaLINS-ispA* and SWITCH-PphoC Δgcd/CsLINS-ispA*, respectively.

The glycerol stocks of resulting SWITCH-PphoC Δgcd/AaLINS-ispA*, SWITCH-PphoC Δgcd/CsLINS-ispA* and SWITCH-PphoC Δgcd/pACYC177 strains were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium described in Table 10 containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours.

TABLE 10

Fermentation medium for SWITCH-PphoC Δgcd, host strain for production of linalool

| Group A | |
|---|---|
| D-Glucose | 40 g/L |
| MgSO$_4$•7H$_2$O | 1 g/L |
| Not adjusted pH, AC 115° C., 10 minutes | |
| Group B | |
| (NH$_4$)$_2$SO$_4$ | 20 g/L |
| KH$_2$PO$_4$ | 0.5 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |
| Dry-heat sterilization 180° C., 2 hours | |

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after the start of the cultivation, the concentrations of isopropyl myristate and linalool in the culture supernatant were measured under the following condition using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd.).

| | |
|---|---|
| Temperature in vaporization chamber | 360.0° C. |
| Injection amount | 1.0 μL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

The concentration of linalool is shown in terms of medium amount. A mean value obtained from two test tubes is shown in Table 11. No linalool production was observed in the control strain having the introduced control vector pACYC177, whereas linalool production was confirmed in SWITCH-PphoC Δgcd/AaLINS-ispA* and SWITCH-PphoC Δgcd/CsLINS-ispA* strains.

TABLE 11

Accumulation of linalool when linalool synthase native to *Actinidia arguta* and *Coriandrum sativum* were introduced

| Strain | O.D. (620 nm) | Linalool (mg/L) |
|---|---|---|
| SWITCH-PphoC Δgcd/pACYC177 | 15.9 | 0.0 |
| SWITCH-PphoC Δgcd/CsLINS-ispA* | 20.2 | 2.6 |
| SWITCH-PphoC Δgcd/AaLINS-ispA* | 12.0 | 1328.2 |

Example 7: Construction of Linalool Synthase-Expressing Plasmid 7-1) Obtaining of Linalool Synthase Gene Native to *Streptomyces clavuligerus*

A nucleotide sequence (GenBank accession number: DS570692) and an amino acid sequence (GenPept accession number: EDY52263) of a linalool synthase gene and protein native to *Streptomyces clavuligerus* (ScLINS) have been reported (Nakano C et al. (2011) ChemBiochem. 12(16): 2403-2407). The amino acid sequence of a linalool synthase protein and the nucleotide sequence of its gene native to *Streptomyces clavuligerus* are shown in SEQ ID NO: 61 and SEQ ID NO: 62, respectively. In order to efficiently express the ScLINS gene, codons of the ScLINS gene were optimized, and this was designated as opt_ScLINS. A nucleotide sequence of opt_ScLINS is shown in SEQ ID NO: 63. DNA in which a tac promoter region (deBoer et al., (1983) Proc. Natl. Acad. Sci. U.S.A., 80, 21-25) had been added to the opt_ScLINS gene was chemically synthesized, cloned into pMW119 (produced by NIPPON GENE CO., LTD.), and the resulting plasmid was designated as pMW119-Ptac-opt_ScLINS.

7-2) Construction of Co-Expression Plasmid for Opt_ScLINS and ispA* Gene

PCR with pMW119-Ptac-opt_ScLINS as a template was carried out using primers shown in SEQ ID NO: 9 and SEQ ID NO: 64 to obtain a Ptac-opt_ScLINS fragment. Furthermore, PCR with pMW119-ispA* as a template was carried out using primers shown in SEQ ID NO: 65 and SEQ ID NO: 13 to obtain an ispA* fragment. The purified Ptac-opt_ScLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_ScLINS-ispA*.

7-3) Construction of Opt_ScLINS Gene-Expressing Plasmid

PCR with pUC57-Ptac-opt_ScLINS as a template was carried out using a primer shown in SEQ ID NO: 9 and a primer shown in SEQ ID NO: 66 to obtain a Ptac-opt_ScLINS fragment. The purified Ptac-opt_ScLINS fragment was ligated to pACYC177 (produced by NIPPON GENE CO., LTD.) digested with restriction enzymes Pst I and Sca I using In-Fusion HD cloning kit (produced by Clontech Laboratories, Inc.) to construct pACYC177-Ptac-opt_ScLINS.

7-4) Construction of Co-Expression Plasmid for Opt_CsLINS and ispA* Genes with Optimized Expression Amount PCR with pACYC177-Ptac-opt_CsLINS-ispA* constructed in Example 1 as a template was carried out using a primer shown in SEQ ID NO: 67 and a primer shown in SEQ ID NO: 13 to obtain an opt_CsLINS-ispA* fragment in which a part of the sequence of the upstream of CsLINS had been changed. The purified opt_CsLINS-ispA* fragment in which a part of the sequence of the upstream of CsLINS had been changed was ligated to pACYC177 (produced by NIPPON GENE CO., LTD.) digested with restriction enzymes PstI and ScaI using In-Fusion HD cloning kit (produced by Clontech Laboratories, Inc.), and the constructed opt_CsLINS-ispA* expression plasmid was designated as pACYC177-Ptac2-opt_CsLINS-ispA*.

7-5) Construction of Opt_CsLINS Gene-Expressing Plasmid with Optimized Expression Amount PCR with pMW119-Ptac-opt_CsLINS obtained in Example 1 as a template was carried out using a primer shown in SEQ ID NO: 67 and a primer shown in SEQ ID NO: 68 to obtain an opt_CsLINS fragment in which a part of the sequence of the upstream of CsLINS had been changed. The purified opt_CsLINS fragment in which a part of the sequence of the upstream of CsLINS had been changed was ligated to pACYC177 (produced by NIPPON GENE CO., LTD.) digested with restriction enzymes PstI and ScaI using In-Fusion HD cloning kit (produced by Clontech Laboratories, Inc.), and the constructed promoter-modified opt_CsLINS expression plasmid was designated as pACYC177-Ptac2-opt_CsLINS.

7-6) Obtaining of Linalool Synthase Gene Native to *Artemisia annua* (Annual Mugwort)

A nucleotide sequence (GenBank accession number: AF154125) and an amino acid sequence (GenPept accession number: AAF13357) of a linalool synthase gene and protein native to *Artemisia annua* (AnLINS) have been reported (Jia et al., (1999) Archives of Biochemistry and Biophysics, Volume 372, 143-149). Furthermore, a nucleotide sequence (GenBank accession number: AF154124) and an amino acid sequence (GenPept accession number: AAF13356) of a linalool synthase gene and protein native to *Artemisia annua* have been reported. The amino acid sequence of a linalool synthase protein and the nucleotide sequence of its gene native to *Artemisia annua* in the former case are shown in SEQ ID NO: 69 and SEQ ID NO: 70. In order to efficiently express the AnLINS gene, codons were optimized, an AaLINS gene in which the chloroplast localization signal had been cleaved was designed, and this was designated as opt_AnLINS. A nucleotide sequence of opt_AnLINS is shown in SEQ ID NO: 71. DNA in which a tac promoter region (deBoer et al., (1983) Proc. Natl. Acad. Sci. U.S.A., 80, 21-25) had been added to the opt_ScLINS gene was chemically synthesized, cloned into pMW119 (produced by NIPPON GENE CO., LTD.), and the resulting plasmid was designated as pMW119-Ptac-opt_AnLINS.

7-7) Obtaining of Linalool Synthase Gene Native to *Backhousia citriodora* (Lemon Myrtle)

A nucleotide sequence (GenBank accession number: AB438045) and an amino acid sequence (GenPept accession number: BAG82825) of a linalool synthase (BcLINS) gene and protein native to *Backhousia citriodora* have been reported (Sugiura M et al., (2011) Biosci Biotechnol Biochem., 75, 1245-8). The amino acid sequence of a linalool synthase protein and the nucleotide sequence of its gene native to *Backhousia citriodora* are shown in SEQ ID NO: 72 and SEQ ID NO: 73, respectively. In order to efficiently express the BcLINS gene, codons were optimized, a BcLINS gene in which the chloroplast localization signal had been cleaved was designed, and this was designated as opt_BcLINS. A nucleotide sequence of opt_BcLINS is shown in SEQ ID NO: 74. DNA in which a tac promoter region (deBoer et al., (1983) Proc. Natl. Acad. Sci. U.S.A., 80, 21-25) had been added to the opt_BcLINS gene was chemically synthesized, cloned into pMW119 (produced by NIPPON GENE CO., LTD.) and the resulting plasmid was designated as pMW119-Ptac-opt_BcLINS.

7-8) Construction of Co-Expression Plasmid for Opt_AnLINS and ispA* Gene

PCR with pMW119-Ptac-opt_AnLINS as a template was carried out using primers shown in SEQ ID NO: 9 and SEQ ID NO: 75 to obtain a Ptac-opt_AnLINS fragment. Furthermore, PCR with pMW119-ispA* as a template was carried out using primers shown in SEQ ID NO: 76 and SEQ ID NO: 13 to obtain an ispA* fragment. The purified Ptac-opt_AnLINS fragment and ispA* fragment were ligated to pACYC177 (produced by NIPPON GENE CO., LTD.) digested with restriction enzymes PstI and ScaI using In-Fusion HD cloning kit (produced by Clontech Laboratories, Inc.) to construct pACYC177-Ptac-opt_AnLINS-ispA*.

7-9) Construction of Co-Expression Plasmid for Opt_BcLINS and ispA* Gene

PCR with pMW119-Ptac-opt_BcLINS as a template was carried out using primers shown in SEQ ID NO: 9 and SEQ ID NO:77 to obtain a Ptac-opt_BcLINS fragment. Furthermore, PCR with pMW119-ispA* as a template was carried out using primers shown in SEQ ID NO: 78 and SEQ ID NO: 13 to obtain an ispA* fragment. The purified Ptac-opt_BcLINS fragment and ispA* fragment were ligated to pACYC177 (produced by NIPPON GENE CO., LTD.) digested with restriction enzymes PstI and ScaI using In- Fusion HD cloning kit (produced by Clontech Laboratories, Inc.) to construct pACYC177-Ptac-opt_BcLINS-ispA*.

Example 8: Linalool Fermentation of *P. ananatis* SC17

8-1) Introduction of Linalool Synthase Expression Plasmid into *P. ananatis* SC17

Competent cells of *P. ananatis* SC17 were prepared, and pACYC177-Ptac-opt_ScLINS-ispA*, pACYC177-Ptac-opt_ScLINS, pACYC177-Ptac-opt_CsLINS-ispA*, or pACYC177-Ptac-opt_CsLINS that were constructed in Example 7 were introduced into the cells by an electroporation method. Resulting strains were designated as *P. ananatis* SC17/ScLINS-ispA*, *P. ananatis* SC17/ScLINS, *P. ananatis* SC17/Ptac2-CsLINS-ispA*, and *P. ananatis* SC17/Ptac2-CsLINS strains, respectively.

The strains obtained as above were cultured in an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

8-2) Evaluation of Ability to Produce Linalool by Linalool Synthase-Expressing Strains Native to *P. ananatis* SC17

The glycerol stocks of *P. ananatis* SC17/ScLINS-ispA*, *P. ananatis* SC17/ScLINS, *P. ananatis* SC17/Ptac2-CsLINS-ispA*, and *P. ananatis* SC17/Ptac2-CsLINS strains, as well as the *P. ananatis* SC17/pACYC177 and *P. ananatis* SC17/AaLINS-ispA*, *P. ananatis* SC17/AaLINS strains constructed in Example 3 were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium described below (Table 12) containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours.

TABLE 12

| Fermentation medium for linalool | |
|---|---|
| Group A | |
| D-Glucose | 40 g/L |
| MgSO$_4$•7H$_2$O | 1 g/L |
| Not adjusted pH, AC 115° C., 10 minutes | |
| Group B | |
| (NH$_4$)$_2$SO$_4$ | 20 g/L |
| KH$_2$PO$_4$ | 0.5 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |
| Dry-heat sterilization 180° C., 2 hours | |

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the following conditions using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd). A sample for measurement was appropriately diluted with ethanol (supplid from Wako Pure Chemical Industries, Ltd.).

| | |
|---|---|
| Temperature in vaporization chamber | 360.0° C. |
| Injection amount | 1.0 μL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

The linalool is shown in terms of accumulated concentration in the fermentation liquor. A mean value obtained from two test tubes is shown in Table 13. Linalool production was observed in all strains other than the control strain having the introduced control vector pACYC177.

TABLE 13

Accumulation of linalool when linalool synthase native to *S. clavuligerus*, *C. sativum*, and *A. arguta*, and mutant ispA were introduced in *P. ananatis* SC17

| Strain | O.D. 620 nm | Linalool (mg/L) |
|---|---|---|
| *P. ananatis* SC17/pACYC177 | 36.4 | 0.0 |
| *P. ananatis* SC17/ScLINS | 35.4 | 0.1 |
| *P. ananatis* SC17/ScLINS-ispA* | 37.8 | 0.3 |
| *P. ananatis* SC17/Ptac2-CsLINS | 31.7 | 0.4 |
| *P. ananatis* SC17/Ptac2-CsLINS-ispA* | 27.2 | 1.4 |
| *P. ananatis* SC17/AaLINS | 25.1 | 1.9 |
| *P. ananatis* SC17/AaLINS-ispA* | 32.0 | 6.8 |

Example 9: Evaluation of Ability to Produce Linalool of Linalool Synthase-Expressing Strains Derived from SWITCH-PphoC Strain 9-1) Introduction of Linalool Synthase Expression Plasmid into Switch-PphoC Strain After a marker was removed from the SWITCH-PphoC strain obtained in Reference Practical Example 1 by a standard method, competent cells were prepared, and the pACYC177-Ptac-opt_ScLINS-ispA*, pACYC177-Ptac-opt_ScLINS, pACYC177-Ptac2-opt_CsLINS-ispA*, or pACYC177-Ptac2-opt_CsLINS constructed in Example 7, or otherwise the pACYC177-Ptac-opt_AaLINS constructed in Example 1 was introduced into the cells by an electroporation method. Resulting strains were designated as SWITCH-PphoC/ScLINS-ispA* strain, a SWITCH-PphoC/ScLINS strain, SWITCH-PphoC/Ptac2-CsLINS-ispA* strain, SWITCH-PphoC/Ptac2-CsLINS strain, and SWITCH-PphoC/AaLINS strain, respectively.

The strains obtained as above were cultured in an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

9-2) Evaluation of Ability to Produce Linalool by Linalool Synthase-Expressing Strains Derived from SWITCH-PphoC The glycerol stocks of SWITCH-PphoC/ScLINS-ispA*, SWITCH-PphoC/ScLINS, SWITCH-PphoC/Ptac2-CsLINS-ispA*, SWITCH-PphoC/Ptac2-CsLINS, SWITCH-PphoC/AaLINS strains, as well as the SWITCH-PphoC/pACYC177 and SWITCH-PphoC/AaLINS-ispA* strains obtained in Example 4 were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium (Table 12) described in Example 8 containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours.

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the conditions described in Example 8 using gas chromatograph GC-2025AF (produced by SHIMADZU CORPORATION). DB-5 (produced by Agilent Technologies, length 30 m, internal diameter 0.25 mm, thickness 0.25 μm) was used as a column, and a linalool standard solution was prepared using a reagent Linalool (produced by Wako Pure Chemical Industries Ltd). A sample for measurement was appropriately diluted with ethanol (produced by Wako Pure Chemical Industries, Ltd.).

The linalool is shown in terms of accumulated concentration in the fermentation liquor. A mean value obtained from two test tubes is shown in Table 14.

TABLE 14

Accumulation of linalool when linalool synthase native to *S. clavuligerus*, *C. sativum*, and *A. arguta*, and mutant ispA were introduced in SWITCH-PphoC

| Strain | O.D. 620 nm | Linalool (mg/L) |
|---|---|---|
| SWITCH-PphoC/pACYC177 | 13.2 | 0.0 |
| SWITCH-PphoC/ScLINS | 9.2 | 56.1 |
| SWITCH-PphoC/ScLINS-ispA* | 36.7 | 891.4 |

TABLE 14-continued

Accumulation of linalool when linalool synthase native to *S. clavuligerus*, *C. sativum*, and *A. arguta*, and mutant ispA were introduced in SWITCH-PphoC

| Strain | O.D. 620 nm | Linalool (mg/L) |
|---|---|---|
| SWITCH-PphoC/Ptac2-CsLINS | 11.7 | 80.7 |
| SWITCH-PphoC/Ptac2-CsLINS-ispA* | 21.6 | 820.8 |
| SWITCH-PphoC/AaLINS | 12.3 | 37.2 |
| SWITCH-PphoC/AaLINS-ispA* | 21.1 | 1053.1 |

Example 10: Evaluation of Ability to Produce Linalool by Linalool Synthase-Expressing Strains Derived from SWITCH-PphoC Δgcd Strain 10-1) Introduction of Linalool Synthase Expression Plasmid into SWITCH-PphoC Δgcd Competent cells of SWITCH-PphoC Δgcd strain obtained in Example 4 were prepared, and pACYC177-Ptac-opt_ScLINS-ispA*, pACYC177-Ptac-opt_ScLINS, pACYC177-Ptac2-opt_CsLINS-ispA*, or pACYC177-Ptac2-opt_CsLINS constructed in Example 7, or pACYC177-Ptac-opt_AaLINS obtained in Example 1 were introduced into the cells by an electroporation method. Resulting strains were designated as SWITCH-PphoC Δgcd/ScLINS-ispA*, SWITCH-PphoC Δgcd/ScLINS, SWITCH-PphoC Δgcd/Ptac2-CsLINS-ispA*, SWITCH-PphoC Δgcd/Ptac2-CsLINS, and SWITCH-PphoC Δgcd/AaLINS strains, respectively.

The strains obtained above were cultured on an LB plate containing 50 mg/L of kanamycin at 34° C. for 16 hours, the microbial cells on the plate were then scraped in an appropriate amount using a 10 μL inoculating loop (produced by Thermo Fisher Scientific Inc.) and suspended in a 20% glycerol solution, and the resulting solution was dispensed in each appropriate amount and then stored at −80° C.

10-2) Evaluation of Ability to Produce Linalool by Linalool Synthase-Expressing Strains Derived from SWITCH-PphoC Δgcd Strain The glycerol stocks of SWITCH-PphoC Δgcd/ScLINS-ispA*, SWITCH-PphoC Δgcd/ScLINS, SWITCH-PphoC Δgcd/Ptac2-CsLINS-ispA*, SWITCH-PphoC Δgcd/Ptac2-CsLINS, SWITCH-PphoC Δgcd/AaLINS strains, and SWITCH-PphoC Δgcd/pACYC177 and SWITCH-PphoC Δgcd/AaLINS-ispA* strains constructed in Example 6 were thawed. Subsequently 50 μL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 μL inoculating loop (produced by Thermo Fisher Scientific Inc.). The picked up microbial cells were inoculated to 5 mL of fermentation medium (Table 12) described in Example 8 containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours.

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the condition described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd). A sample for measurement was appropriately diluted with ethanol (produced by Wako Pure Chemical Industries, Ltd.).

The linalool is shown in terms of accumulated concentration in the fermentation liquor. A mean value obtained from two test tubes is shown in Table 15.

TABLE 15

Accumulation of linalool when linalool synthase native to S. clavuligerus, C. sativum, and A. arguta, and mutant ispA were introduced in SWITCH-PphoC Δgcd

| Strain | O.D. 620 nm | Linalool (mg/L) |
|---|---|---|
| SWITCH-PphoC Δgcd/pACYC177 | 8.9 | 0.0 |
| SWITCH-PphoC Δgcd/ScLINS | 7.5 | 84.6 |
| SWITCH-PphoC Δgcd/ScLINS-ispA* | 14.9 | 1179.0 |
| SWITCH-PphoC Δgcd/Ptac2-CsLINS | 12.3 | 92.3 |
| SWITCH-PphoC Δgcd/Ptac2-CsLINS-ispA* | 21.5 | 1108.1 |
| SWITCH-PphoC Δgcd/AaLINS | 13.7 | 50.0 |
| SWITCH-PphoC Δgcd/AaLINS-ispA* | 17.4 | 1575.7 |

Example 11: Construction of Linalool Synthase-Expressing Plasmid 11-1) Plasmid that can be Transformed into Synechocystis sp. PCC6803 GT Strain It has been reported that Synechocystis sp. PCC6803 can be subjected to natural transformation. The plasmid pTCP2031V can include the sequences of parts of coding regions of slr2030 and slr2031, the sequence of a chloramphenicol resistance gene, the sequence of a psbA2 (slr1311) promoter, and the like, and when the coding regions of slr2030 and slr2031 are set to homologous sequences, the genomic recombination of the Synechocystis sp. PCC6803 strain can be carried out (Horiuchi M., et al. (2010) J Biochem 431: 135-140). The plasmid pTKHT0846-slr0846 can include the sequences of parts of coding regions of sll0822, slr0846, and sll0821, the sequence of a kanamycin resistance gene, and the like, and when the coding regions of slr0846 and sll0821 are set to homologous sequences, the genomic recombination of the Synechocystis sp. PCC6803 strain can be carried out (Midorikawa T., et al. (2012) Plant Cell Physiol. 53(1): 164-172). These plasmids were furnished by Prof. Masahiko Ikeuchi, Graduate School of Arts and Sciences, the University of Tokyo.

11-2) Construction of Opt_AaLINS Gene-Expressing Plasmid

PCR with pMW119-Ptac-opt_AaLINS obtained in Example 1 as a template was carried out using a primer shown in SEQ ID NO: 79 and a primer shown in SEQ ID NO: 80 to obtain an opt_AaLINS fragment. The purified opt_AaLINS fragment was ligated to pTCP2031V digested with a restriction enzyme NdeI using In-Fusion HD cloning kit (produced by Clontech Laboratories, Inc.) to construct pTCP2031V-PpsbA2-opt_AaLINS.

11-3) Construction of ispA* Gene-Expressing Plasmid

PCR with pMW119-ispA* obtained in Example 1 as a template was carried out using a primer shown in SEQ ID NO: 81 and a primer shown in SEQ ID NO: 82 to obtain a Ptac-ispA* fragment. The purified ispA* fragment was ligated to pTKHT0846-slr0846 digested with restriction enzymes AatII and HpaI using In-Fusion HD cloning kit (produced by Clontech Laboratories, Inc.) to construct pTKHT0846-Ptac-ispA*.

Example 12: Linalool Production in Synechocystis sp. PCC6803 GT Strain 12-1) Introduction of Opt_AaLINS Gene-Expressing Plasmid into Synechocystis Sp. PCC6803 GT Strain The transformation of the Synechocystis sp. PCC6803 GT strain was carried out according to the previously described method (WO 2015/115520 A1). 1 to 2 µg of the constructed plasmid pTCP2031V-PpsbA2-opt_AaLINS was mixed to 1 mL of the culture solution of the Synechocystis sp. PCC6803 GT strain (O.D 730=0.5 to 1.0) and the resulting solution was used as a cell-DNA mixture solution. The O.D. value was measured by a 96-well plate reader (Molecular Devices Spectra Max M2e) at 720 nm. Hereinafter, the O.D. value of cultivation using the Synechocystis sp. PCC6803 GT strain was measured by this instrument. A nitrocellulose membrane (Millipore Corporation, surfactant free, pore size 0.2 µm, model number: HATF08250) was placed on a BG-11 agar medium (Table 16) without addition of a drug, and then the cell-DNA mixture solution was applied thereto. After cultivation under conditions of 18 to 24 hours, 34° C., $CO_2$ concentration 1%, and light intensity 50 µE/m$^2$/s, the nitrocellulose membrane was transferred to the BG-11 agar medium (Table 16) added with 20 mg/L of chloramphenicol. Thereafter, cultivation was carried out under conditions of 2 to 4 weeks, 34° C., $CO_2$ concentration 1%, and light intensity 50 µE/m$^2$/s, and then emerging colonies were subcultured to a new BG-11 agar medium (Table 16) added with 20 mg/L of chloramphenicol. This subculturing operation was repeated three to four times, and colony PCR was carried out to resulting colonies using a primer shown in SEQ ID NO: 83 and a primer shown in SEQ ID NO: 84. It was confirmed that a DNA fragment having a target size was inserted to a target position in genome, and the resulting strain was designated as a GT2031C-AaLINS strain.

The strain obtained above was grown on the BG-11 agar medium (Table 16) added with 20 mg/L of chloramphenicol. The microbial cells were scraped in an appropriate amount using a 1 µL inoculating loop (produced by Thermo Fisher Scientific Inc.) and inoculated into 5 mL of a BG-11 liquid culture medium (Table 16) containing 20 mg/L of chloramphenicol in a 6-well plate (produced by Corning Incorporated, model number: 351146). Cultivation was carried out for about 3 days under conditions of 60 rpm, 34° C., $CO_2$ concentration 1%, and light intensity 50 µE/m$^2$/s with a whirl shaking culture apparatus provided with an LED light emitting unit (LC-LED 450 W (white)) (TAITEC CORPORATION NR-20 or NR-30). Cells were collected by centrifugation of about 1 mL of this culture solution at 7,000 rpm, for 5 min, and at room temperature, a stocked solution prepared by removing the supernatant and adding dimethylsulfoxide to the BG-11 liquid culture medium (Table 16) to have a final concentration of 5% was added and suspended, and the resulting solution was dispensed in each appropriate amount and then stored as a frozen stock at −80° C.

12-2) Introduction of ispA* Gene-Expressing Plasmid into GT2031C-AaLINS Strain

The transformation was carried out according to the same method as in 12-1. 1 to 2 μg of the constructed plasmid pTKHT0846-Ptac-ispA* was mixed to 1 mL of the culture solution of the GT2031C-AaLINS strain (O.D 730=0.5 to 1.0) and the resulting solution was used as a cell-DNA mixture solution. A nitrocellulose membrane (Millipore Corporation, surfactant free, pore size 0.2 μm, model number: HATF08250) was placed on a BG-11 agar medium (Table 16) without addition of a drug, and then the cell-DNA mixture solution was applied thereto. After cultivation under conditions of 18 to 24 hours, 34° C., $CO_2$ concentration 1%, and light intensity 50 μE/m$^2$/s, the nitrocellulose membrane was transferred to the BG-11 agar medium (Table 16) added with 20 mg/L of each of chloramphenicol and kanamycin. Thereafter, cultivation was carried out under conditions of 2 to 4 weeks, 34° C., $CO_2$ concentration 1%, and light intensity 50 μE/m$^2$/s, and then emerging colonies were subcultured to a new BG-11 agar medium (Table 16) added with 20 mg/L of each of chloramphenicol and kanamycin. This subculturing operation was repeated three to four times, and colony PCR was carried out to resulting colonies using a primer shown in SEQ ID NO: 85 and a primer shown in SEQ ID NO: 86. It was confirmed that a DNA fragment having a target size was inserted to a target position in genome, and the resulting strain was designated as a GT2031C-AaLINS_0846K-ispA* strain.

The strain obtained above was grown on the BG-11 agar medium (Table 16) added with 20 mg/L of chloramphenicol and kanamycin. The microbial cells were scraped therefrom in an appropriate amount using a 1 μL inoculating loop (produced by Thermo Fisher Scientific Inc.) and inoculated to 5 mL of a BG-11 liquid culture medium (Table 16) added with 20 mg/L of each of chloramphenicol and kanamycin in a 6-well plate (produced by Corning Incorporated, model number: 351146). Cultivation was carried out for about 3 days under conditions of 60 rpm, 34° C., $CO_2$ concentration 1%, and light intensity 50 μE/m$^2$/s with a whirl shaking culture apparatus provided with an LED light emitting unit (LC-LED 450 W (white)) (TAITEC CORPORATION NR-20 or NR-30). Cells were collected by centrifugation of about 1 mL of this culture solution at 7,000 rpm, for 5 min, and at room temperature, a stocked solution prepared by removing the supernatant and adding dimethylsulfoxide to the BG-11 liquid culture medium (Table 16) to have a final concentration of 5% was added and suspended, and the resulting solution was dispensed in each appropriate amount and then stored as a frozen stock at −80° C.

12-3) Evaluation of Ability to Produce Linalool by Linalool Synthase-Expressing Strain Native to *Synechocystis* sp. PCC6803 GT Strain The frozen stocks of the *Synechocystis* sp. PCC6803 GT strain, the GT2031C-AaLINS strain, and the GT2031C-AaLINS_0846K-ispA* strain were thawed, 50 μL of a microbial cell suspension from each strain was uniformly applied onto a BG-11 agar medium (Table 16) containing a necessary drug, and cultivation was carried out for about 7 days under conditions of 34° C., $CO_2$ concentration 1%, and light intensity 50 μE/m$^2$/s. The *Synechocystis* sp. PCC6803 GT strain was cultured without addition of a drug, the GT2031C-AaLINS strain was cultured with addition of 20 mg/L of chloramphenicol, and the GT2031C-AaLINS_0846K-ispA* strain was cultured with addition of 20 mg/L of each of chloramphenicol and kanamycin. The resulting microbial cells on the agar medium were scraped in an appropriate amount using a loop of a 1 μL inoculating loop (produced by Thermo Fisher Scientific Inc.) and inoculated to 5 mL of a BG-11 liquid culture medium (Table 16) containing a necessary drug in a 6-well plate (produced by Corning Incorporated, model number: 351146). Cultivation was carried out for about 3 days under culture conditions of 60 rpm, 30° C., $CO_2$ concentration 1%, and light intensity 50 μE/m$^2$/s with a whirl shaking culture apparatus provided with an LED light emitting unit (LC-LED 450 W (white)) (TAITEC CORPORATION NR-20 or NR-30). The microbial cells were inoculated to 10 mL of a BG-11 liquid culture medium for cultivation (Table 16) containing a necessary drug in an Erlenmeyer flask (HARIO) having a capacity of 50 mL to satisfy O.D 730=0.05 using the culture solution, and cultivation was carried out for about 6 days under conditions of 60 rpm, 30° C., $CO_2$ concentration 1%, and light intensity 100 μE/m$^2$/s with a whirl shaking culture apparatus provided with an LED light emitting unit (LC-LED 450 W (white)) (TAITEC CORPORATION NR-20 or NR-30).

TABLE 16

BG-11 culture Medium for cultivation

Stock solution
Solution I

| | |
|---|---|
| Citric acid (anhydride) | 0.3 g/100 mL |
| Ferric Ammonium Citrate | 0.3 g/100 mL |
| Na$_2$ EDTA | 0.05 g/100 mL |

Not adjusted pH; adjusted to 100 mL by using water treated with reverse osmosis membrane (RO water)
Solution II

| | |
|---|---|
| NaNO$_3$ | 30 g/L |
| K$_2$HPO$_4$ | 0.78 g/L |
| MgSO$_4$•7H$_2$O | 1.5 g/L |

Not adjusted pH; adjusted to 1 L by RO water
Solution III

| | |
|---|---|
| CaCl$_2$•2H$_2$O | 1.9 g/100 mL |

Not adjusted pH; adjusted to 100 mL by RO water
Solution IV

| | |
|---|---|
| Na$_2$CO$_3$ | 2 g/100 mL |

Not adjusted pH; after adjusted to 100 mL by RO water, sterilized by filter
Solution A6

| | |
|---|---|
| H$_3$BO$_3$ | 2.86 g/L |
| MnCl$_2$•4H$_2$O | 1.81 g/L |
| ZnSO$_4$•7H$_2$O | 0.22 g/L |
| CuSO$_4$•5H$_2$O | 0.08 g/L |
| Na$_2$MoO$_4$ | 0.021 g/L |
| Concentrated sulfuric acid | one droplet/L |
| Co(No3)$_2$•6H$_2$O | 0.0494 g/L |

Not adjusted pH; adjusted to 1 L by RO water

As for the liquid culture medium, 50 mL of Solution II, 2 mL of Solution III, 1 mL of Solution IV, 1 mL of Solution A6, 20 mL of 1 M TES-KOH (pH 8.2), and 926 mL of RO water were mixed and subjected to treatment at AC 121° C./20 min, and 2 mL of Solution I similarly subjected to treatment at AC 121° C./20 min was mixed thereto.

As for the agar medium, 1 mL of Solution I, 25 mL of Solution II, 1 mL of Solution III, 0.5 mL of Solution IV, 0.5 mL of Solution A6, 1.5 g of sodium thiosulfate (anhydride), 10 mL of 1 M TES-KOH (pH 7.8), and 261 mL of RO water were mixed, and a solution subjected to treatment at AC 121° C./20 min and the total amount of a mixed solution of 7.5 g of BactoAgar (produced by Nippon Becton, Dickinson and Company) similarly subjected to treatment at AC 121° C./20 min and 200 mL of RO water were mixed thereto.

Two mL of isopropyl myristate (produced by Tokyo Chemical Industry Co., Ltd.) was added to 10 mL of BG-11 liquid culture medium for cultivation (Table 16) dispensed in the Erlenmeyer flask.

About 6 days after starting the cultivation, the concentration of linalool in the isopropyl myristate was measured under the condition described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd).

The linalool is shown in terms of amount accumulated in culture solution. A mean value of results obtained from two test tubes is shown in Table 17. No linalool production was observed in the control strain Synechocystis sp. PCC6803 GT, whereas linalool production was confirmed in GT2031C-AaLINS and GT2031C-AaLINS_0846K-ispA* strains.

TABLE 17

Accumulation of linalool when linalool synthase native to A. arguta and mutant ispA were introduced

| strain | O.D 730 nm | Linalool (mg/L) |
|---|---|---|
| Synechocystis sp. PCC6803 GT | 9.69 | 0.0 |
| GT2031C-AaLINS | 9.60 | 0.7 |
| GT2031C-AaLINS_0846K-ispA* | 9.82 | 1.3 |

Example 13: Evaluation of Ability to Produce Linalool by Linalool Synthase-Expressing Strains Derived from SWITCH-PphoC Δgcd Strain 13-1) Introduction of Linalool Synthase Expression Plasmid into SWITCH-PphoC Δgcd Strain Competent cells of SWITCH-PphoC Δgcd strain obtained in Example 4 were prepared, and the pACYC177-Ptac-opt_AnLINS-ispA* or pACYC177-Ptac-opt_BcLINS-ispA* constructed in Example 7 were introduced into the cells by an electroporation method. Resulting strains were designated as SWITCH-PphoC Δgcd/AnLINS-ispA* and SWITCH-PphoC Δgcd/BcLINS-ispA* strains, respectively.

The strains obtained above were cultured in an LB plate containing 50 mg/L of kanamycin at 34° C. for 16 hours, the microbial cells on the plate were then scraped in an appropriate amount using a 10 µL inoculating loop (produced by Thermo Fisher Scientific Inc.) and suspended in a 20% glycerol solution, and the resulting solution was dispensed in each appropriate amount and then stored at −80° C.

13-2) Evaluation of Ability to Produce Linalool by Linalool Synthase-Expressing Strains Derived from SWITCH-PphoC ΔGcd The glycerol stocks of SWITCH-PphoC Δgcd/AnLINS-ispA* and SWITCH-PphoC Δgcd/BcLINS-ispA* strains, as well as the SWITCH-PphoC Δgcd/pACYC177 strain obtained in Example 6 were thawed. Subsequently 50 µL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 µL inoculating loop (produced by Thermo Fisher Scientific Inc.). The picked up microbial cells were inoculated to 5 mL of fermentation medium described below (Table 18) containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 48 hours.

TABLE 18

Linalool fermentation medium for linalool synthase-expressing strains native to Artemisia annua and B. citriodora

| Group A | |
|---|---|
| D-Glucose | 60 g/L |
| MgSO$_4$•7H$_2$O | 1 g/L |
| Not adjusted pH, AC 115° C., 10 minutes | |
| Group B | |
| (NH$_4$)$_2$SO$_4$ | 20 g/L |
| KH$_2$PO$_4$ | 0.5 g/L |
| Yeast Extract | 2 g/L |
| FeSO$_4$•7H$_2$O | 0.01 g/L |
| MnSO$_4$•5H$_2$O | 0.01 g/L |
| After adjusting pH to 7.0 with KOH, AC 115° C., 10 minutes | |
| Group C | |
| CaCO$_3$ | 20 g/L |
| Dry-heat sterilization 180° C., 2 hours | |

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

48 hours after starting the cultivation, the concentrations of isopropyl myristate and linalool in the culture supernatant were measured under the condition described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd). A sample for measurement was appropriately diluted with ethanol (produced by Wako Pure Chemical Industries, Ltd.).

The linalool is shown in terms of accumulated concentration in the fermentation liquor. A mean value of results obtained from two test tubes is shown in Table 19.

TABLE 19

Accumulation of linalool when linalool synthase native to Artemisia annua, linalool synthase native to B. citriodora, and mutant ispA were introduced in SWITCH-PphoC Δgcd

| Strain | O.D. 620 nm | Linalool (mg/L) |
|---|---|---|
| SWITCH-PphoC Δgcd/pACYC177 | 45.9 | 0.0 |
| SWITCH-PphoC Δgcd/AnLINS-ispA* | 19.0 | 0.1 |
| SWITCH-PphoC Δgcd/BcLINS-ispA* | 19.3 | 0.5 |

Example 14: Linalool Fermentation without Addition of Isopropyl Myristate (Under Single Phase Condition) Using Jar Fermenter The SWITCH-PphoC Δgcd/pACYC177, SWITCH-PphoC Δgcd/AaLINS-ispA* strains constructed in Example 6, and the SWITCH-PphoC Δgcd/ScLINS-ispA* strain constructed in Example 10 were used in a test. The glycerol stocks were thawed, 50 µL of a microbial cell suspension from each strain was uniformly applied onto an LB plate containing 50 mg/L of kanamycin, and cultured at 34° C. for 18 hours. The resulting microbial cells were recovered from the plate. Subsequently, 300 mL of a fermentation medium (Table 20) described below containing 50 mg/L of kanamycin was injected into a jar fermenter having a capacity of 1 L. Then, inoculation was carried out such that the initial O.D. was 0.1. As for the fermentation medium, Group A and Group B described in Table 20 were mixed after the completion of sterilization. Cultivation was carried out for 30 hours while the culture temperature was set to 30° C., the ventilation volume was set to 1 vvm, the dissolved oxygen level was adjusted to 6% or more by stirring, and the culture pH was controlled to 6.5 using ammonia gas.

TABLE 20

Linalool fermentation medium for jar fermenter cultivation

| Group A | |
|---|---|
| D-Glucose | 100 g/L |
| $MgSO_4 \cdot 7H_2O$ | 1 g/L |
| Not adjusted pH, AC 120° C., 20 minutes | |
| Group B | |
| Citate $3Na \cdot 2H_2O$ | 1 g/L |
| $(NH_4)_2SO_4$ | 1 g/L |
| $KH_2PO_4$ | 1.25 g/L |
| Betaine anhydride | 2 g/L |
| $FeSO_4 \cdot 7H_2O$ | 30 mg/L |
| $MnSO_4 \cdot 5H_2O$ | 30 mg/L |
| Yeast Extract | 2 g/L |
| Disfoam GD-113K | 0.01 mL/L |
| Not adjusted pH, AC 120° C., 20 minutes | |

After the start of the cultivation, sampling was appropriately carried out, and then analysis of the O.D. value and linalool was carried out. The concentration of linalool was measured under the conditions described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries, Ltd.). A sample for measurement was appropriately diluted with ethanol (produced by Wako Pure Chemical Industries, Ltd.).

Figure 15:
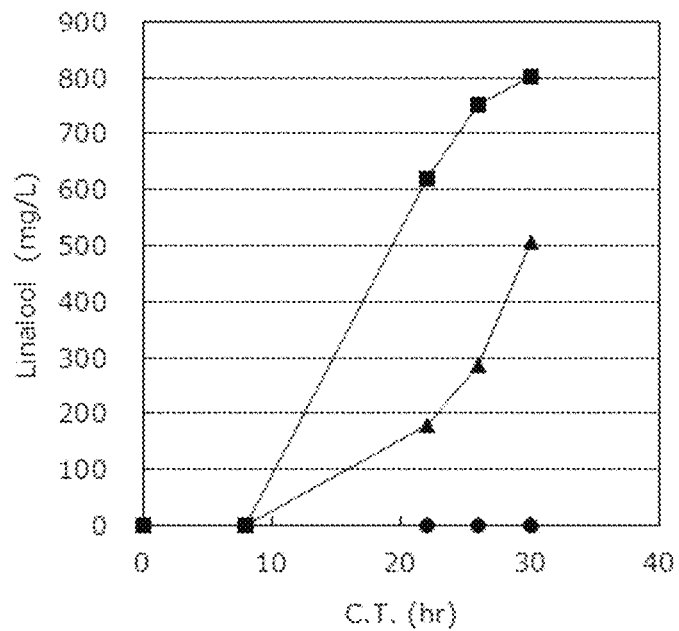
FIG. 15 shows a diagram illustrating a result of changes in linalool accumulation over time.
Figure 16:
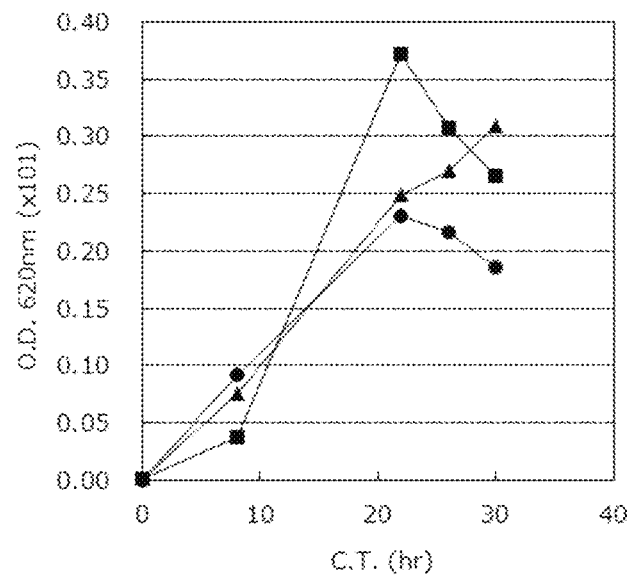
FIG. 16 shows a diagram illustrating a result of changes at O.D. 620 nm over time.
Figure 17:
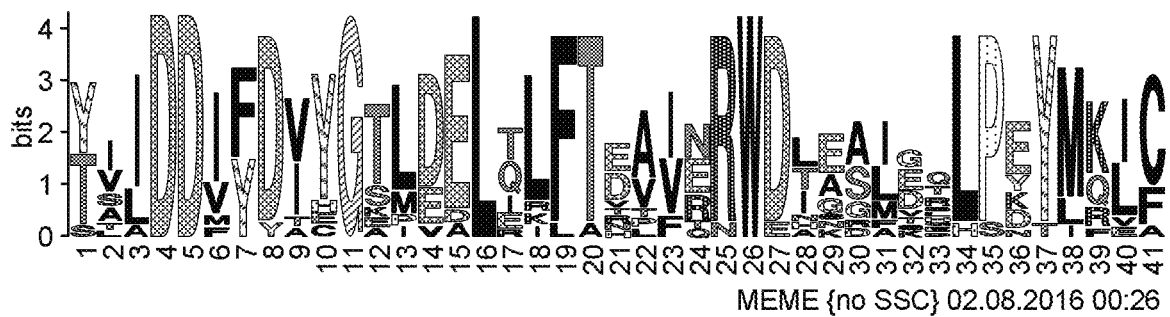
FIG. 17 shows a diagram illustrating the sequence logo of motif 1.
Figure 18:
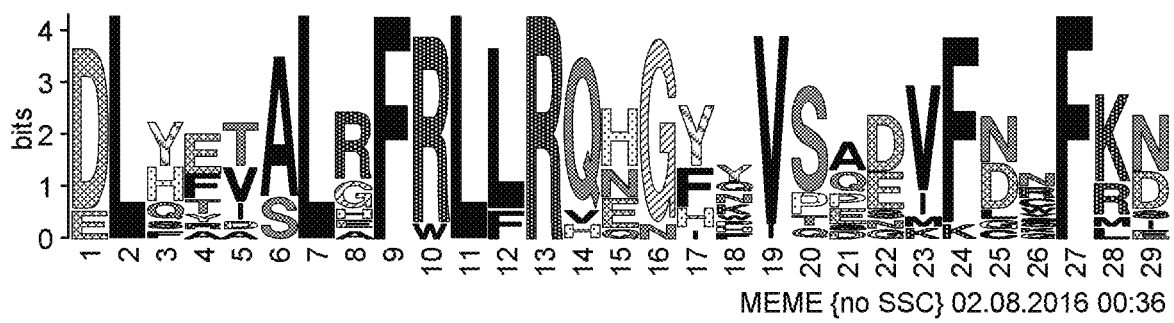
FIG. 18 shows a diagram illustrating the sequence logo of motif 2.
Figure 19:
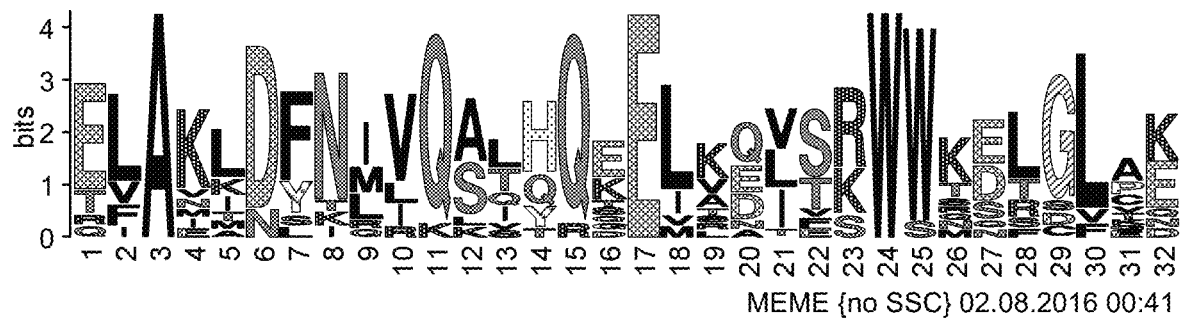
FIG. 19 shows a diagram illustrating the sequence logo of motif 3.

The concentration of linalool and the O.D. value at the time of the completion of cultivation are presented in Table 21, and graphs showing changes over time are illustrated in FIGS. 15 and 16, respectively.

TABLE 21

Fermentation result of SWITCH-PphoC Δgcd strain native to *S. clavuligerus*, linalool synthase native to *A. arguta*, and mutated ispA-introduced strain under the single phase condition using jar fermenter

| Strain | Symbol | O.D. 620 nm (x101) | Linalool (mg/L) |
|---|---|---|---|
| SWITCH-PphoC Δgcd/pACYC177 | ● | 0.19 | 0.0 |
| SWITCH-PphoC Δgcd/ScLINS-ispA* | ▲ | 0.31 | 507.3 |
| SWITCH-PphoC Δgcd/AaLINS-ispA* | ■ | 0.27 | 801.0 |

From Table 21 and FIGS. 15 and 16 (results of jar cultivation), it was shown that linalool fermentation can be carried out even when the concentration of linalool reaches 626 mg/L, which typically can inhibit growth of the SWITCH-PphoC Δgcd strain. While Reference Example 1 suggests that the concentration of linalool in the culture medium should be kept to 625 mg/L or less, the SWITCH-PphoC Δgcd/AaLINS-ispA* strain allows for linalool accumulation up to a concentration equal to or more than a typically toxic concentration, which allows for sufficient growth during cultivation. These results of Example 14 show that growth inhibition is virtually eliminated regardless of culture conditions and efficient hence linalool fermentation can be carried out.

TABLE 22

Sequence Information used in Examples 10-14

| No. | SEQ ID NO | Sequence |
|---|---|---|
| H1 | 61 | Amino acid sequence of linalool synthase native to *S. clavuligerus* |
| H2 | 62 | Nucleotide sequence of linalool synthase native to *S. clavuligerus* |
| H3 | 63 | Codon modified nucleotide sequence of linalool synthase native to *S. clavuligerus* |
| H4 (446) | 64 | GTGTGAAATTAGCCAGAGCTGCGGGCCACC |
| H5 (447) | 65 | TGGCTAATTTCACACAGGAGACTGCCatggattttccc cagcag |
| H6 (509) | 66 | ATGACTTGGTTGAGTTTAGCCAGAGCTGCGGGC |
| H7 (510) | 67 | ACGTTGTTGCCATTGCCCTGTTTGCAATTAATCA TCG |
| H8 (431) | 68 | ATGACTTGGTTGAGTTTATAAGGGAATGGGTTC AAC |
| 654 | 79 | AAGGAATTATAACCAAATGTCCACCGCCGTGCC CTCTATGCCCACTACCCAAAAAT |
| 655 | 80 | GGCATGGAGGACATATTAGCTACTGGAATCATA CAACATGGTTTTCATGTGTTCT |
| 671 | 81 | TCTAGAGTCGACGTCCCCTGTTGACAATTAATC ATCGGCTCGTATAATGTGTGGA |
| 678 | 82 | ATCCAATGTGAGGTTCTATTTGTTGCGCTGGAT GATGTAATCGGCCAGGGCTTCC |
| 614 | 83 | TTGGAACATTGTGTTCAGCCCATGGCTGTCTCC CGCCATTGCTAA |
| 615 | 84 | TTGTTCCCGGTACAACTTAGCCACCAACTCCTT GAGAATGACCAC |
| 683 | 85 | GGAGGATTGGGTTACCCTCAGTGTG |
| 684 | 86 | CGCCATATCAATCCCAACGCTCTGG |
| H9 | 69 | Amino acid sequence of linalool synthase native to *Artemisia annua* |
| H10 | 70 | Nucleotide sequence of linalool synthase native to *Artemisia annua* |
| H11 | 71 | Codon modified nucleotide sequence of linalool synthase native to *Artemisia annua* |
| H12 | 72 | Amino acid sequence of linalool synthase native to *B. citriodora* |

TABLE 22-continued

Sequence Information used in Examples 10-14

| No. | SEQ ID NO | Sequence |
|---|---|---|
| H13 | 73 | Nucleotide sequence of linalool synthase native to B. citriodora |
| H14 | 74 | Codon modified nucleotide sequence of linalool synthase native to B. citriodora |
| H15 (425) | 75 | TGTGAAATTAAATACCTTGAATGGGGG |
| H16 (433) | 76 | GTATTTAATTTCACACAGGAGACTGCCATGGAT TTTCCCCAGCAG |
| H17 (408) | 77 | TGTGAAATTAATCTAAAGACACGCTTTC |
| H18 (435) | 78 | TAGATTAATTTCACACAGGAGACTGCCATGGAT TTTCCCCAGCAG |

Example 15: Database Search of Linalool Synthase

A homology search on a non-redundant database was carried out using an amino acid sequence of linalool synthase (GenPept accession number ADD81294.1) native to hardy kiwifruit as a query sequence and by the BLASTP program (Altschul et al., "Basic local alignment search tool." J. Mol. Biol. 215, 403-410, 1990). Furthermore, plant names which are reported to produce linalool were searched by Essential oil database (Kumari et al., "EssOilDB: a database of essential oils reflecting terpene composition and variability in the plant kingdom" Database, 2014, 1-12 doi: 10. 1093/database/bau120). By comparing these results, candidates of linalool synthase were extracted from plants which are known to have an ability to produce linalool. Furthermore, literature references disclosing candidate sequences were reviewed and 13 distinct enzymes that are expected to have linalool synthase function were chosen (Table 23). Regarding the amino acid sequences of these 13 distinct enzymes, chloroplast localization signal sequences were investigated according to SignalP or literature information described in Table 24. Regarding those in which the presence of the signal sequence is indicated, the predicated signal sequence was eliminated to obtain mature amino acid sequences. The sequences of genes encoding these amino acid sequences are shown in SEQ ID NOs: 89 to 101 (Table 23: M1 to M13). As for these, gene synthesis was carried out on the based on sequences optimized for use of codons in *Pantoea ananatis*. The DNA sequences after the codon optimization are shown in SEQ ID NOs: 102, 104, 106, 108, 110, 112, 114, 116, 118, 120, 122, 124, and 126 (Table 24: M14, M16, M18, M20, M22, M24, M26, M28, M30, M32, M34, M36, and M38). Gene names presented in Table 25 are applied to these DNA sequences. The amino acid sequences encoded by these DNA sequences are shown in SEQ ID NOs: 103, 105, 107, 109, 111, 113, 115, 117, 119, 121, 123, 125, and 127 (Table 24: M15, M17, M19, M21, M23, M25, M27, M29, M31, M33, M35, M37, and M39). The DNA of each gene after the codon optimization was obtained by chemical synthesis and then cloned into pUC57. The names of the resulting plasmids are described in Table 25.

TABLE 23

Extracted linalool synthase candidates

| # | Origin | GenPept accession number | DDBJ/EMBL/ Genbank accession number | No | SEQ ID NO |
|---|---|---|---|---|---|
| 1 | Arabidopsis thaliana | NP_001185286 | NM_001198357 | M1 | 89 |
| 2 | Arabidopsis thaliana | ACF41947 | BT033153 | M2 | 90 |
| 3 | Citrus unshiu | BAP75561 | AB857232 | M3 | 91 |
| 4 | Citrus unshiu | BAP75560 | AB857231 | M4 | 92 |
| 5 | Citrus unshiu | BAP75559 | AB857230 | M5 | 93 |
| 6 | Malus domestica | AGB14629 | JX848734 | M6 | 94 |
| 7 | Perilla frutescens var. crispa | AAL38029 | AF444798 | M7 | 95 |
| 8 | Vitis vinifera | AEY82696 | JQ062931 | M8 | 96 |
| 9 | Vitis vinifera | ADR74209 | HM807390 | M9 | 97 |
| 10 | Lavandula angustifolia | ABB73045 | DQ263741 | M10 | 98 |
| 11 | Mentha citrata | AAL99381 | AY083653 | M11 | 99 |
| 12 | Ocimum basilicum | AAV63789 | AY693647 | M12 | 100 |
| 13 | Clarkia breweri | AAC49395 | U58314 | M13 | 101 |

TABLE 24

Literatures of linalool synthase candidates described in Table 23 and annotation information

| # | Definition | literature | DNA sequence number [1] | Amino acid sequence number [2] |
|---|---|---|---|---|
| 1 | terpene synthase 14 | Nature 408, 816-820 (2000) | 102 (M14) | 103 (M15) |
| 2 | At2g24210, terpene synthase 10, TPS10 | Plant Cell. 25, 4640-4657 (2013), Arch Biochem Biophys. 375, 261-269 (2000) | 104 (M16) | 105 (M17) |
| 3 | linalool synthase | Plant Sci. 229, 154-166 (2014) | 106 (M18) | 107 (M19) |
| 4 | linalool synthase | Plant Sci. 229, 154-166 (2014) | 108 (M20) | 109 (M21) |
| 5 | linalool synthase | Plant Sci. 229, 154-166 (2014) | 110 (M22) | 111 (M23) |
| 6 | linalool synthase | Plant Physiol. 161, 787-804 (2013) | 112 (M24) | 113 (M25) |

TABLE 24-continued

Literatures of linalool synthase candidates described in Table 23 and annotation information

| # | Definition | literature | DNA sequence number [1] | Amino acid sequence number [2] |
|---|---|---|---|---|
| 7 | linalool synthase | Phytochemistry 71, 1068-1075 (2010) | 114 (M26) | 115 (M27) |
| 8 | (3S)-linalool/(E)-nerolidol synthase | Int J Mol Sci 15, 21992-22010 (2014) | 116 (M28) | 117 (M29) |
| 9 | (3R)-linalool synthase | BMC Plant Biol. 10, 226 (2010) | 118 (M30) | 119 (M31) |
| 10 | linalool synthase | Arch. Biochem. Biophys. 465, 417-429 (2007) | 120 (M32) | 121 (M33) |
| 11 | linalool synthase | Arch. Biochem. Biophys. 405, 112-121 (2002) | 122 (M34) | 123 (M35) |
| 12 | R-linalool synthase | Plant Physiol. 136, 3724-3736 (2004) | 124 (M36) | 125 (M37) |
| 13 | S-linalool synthase | Plant Cell 8, 1137-1148 (1996) | 126 (M38) | 127 (M39) |

[1] sequence number in the sequence listing corresponding to DNA sequence after codon optimization [number]
[2] sequence number in the sequence listing corresponding to the amino acid sequence of linalool synthase used in test

TABLE 25

Vectors obtained by cloning sequences after codon optimization of Table 24 into pUC57

| # | Insert UNA sequence number | Gene name after codon optimization | Vector name |
|---|---|---|---|
| 1 | 102(M14) | At1LINS | pUC57-At1LINS |
| 2 | 104(M16) | At2LINS | pUC57-At2LINS |
| 3 | 106(M18) | Cu1LINS | pUC57-Cu1LINS |
| 4 | 108(M20) | Cu2LINS | pUC57-Cu2LINS |
| 5 | 110(M22) | Cu3LINS | pUC57-Cu3LINS |
| 6 | 112(M24) | MdLINS | pUC57-MdLINS |
| 7 | 114(M26) | PfLINS | pUC57-PfLINS |
| 8 | 116(M28) | Vv1LINS | pUC57-Vv1LINS |
| 9 | 118(M30) | Vv2LINS | pUC57-Vv2LINS |
| 10 | 120(M32) | LaLINS | pUC57-LaLINS |
| 11 | 122(M34) | McLINS | pUC57-McLINS |
| 12 | 124(M36) | ObLINS | pUC57-ObLINS |
| 13 | 126(M38) | CbLINS | pUC57-CbLINS |

Example 16: Construction of Various Linalool Synthase-Expressing Plasmids 16-1) Construction of Co-Expression Plasmid for At1LINS and ispA* Genes PCR with pUC57-At1LINS described in Table 25 as a template was carried out using primer Q28 (SEQ ID NO:128) and primer Q29 (SEQ ID NO:129) to obtain At1LINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-At1LINS-ispA*.

16-2) Construction of Co-Expression Plasmid for At2LINS and ispA* Genes

PCR with pUC57-At2LINS described in Table 25 as a template was carried out using primer Q30 (SEQ ID NO:130) and primer Q31 (SEQ ID NO:131) to obtain At2LINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer, et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-At2LINS-ispA*.

16-3) Construction of Co-Expression Plasmid for MdLINS and ispA* Genes

PCR with pUC57-MdLINS described in Table 25 as a template was carried out using primer Q32 (SEQ ID NO:132) and primer Q33 (SEQ ID NO:133) to obtain MdLINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-MdLINS-ispA*.

16-4) Construction of Co-Expression Plasmid for PfLINS and ispA* Genes

PCR with pUC57-PfLINS described in Table 25 as a template was carried out using primer Q34 (SEQ ID NO:134) and primer Q35 (SEQ ID NO:135) to obtain PfLINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-PfLINS-ispA*.

16-5) Construction of Co-Expression Plasmid for VvLINS and ispA* Genes

PCR with pUC57-Vv1LINS described in Table 25 as a template was carried out using primer Q36 (SEQ ID NO:136) and primer Q37 (SEQ ID NO:137) to obtain Vv1LINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-Vv1LINS-ispA*.

16-6) Construction of Co-Expression Plasmid for Vv2LINS and ispA* Genes

PCR with pUC57-Vv2LINS described in Table 25 as a template was carried out using primer Q38 (SEQ ID NO:138) and primer Q39 (SEQ ID NO:139) to obtain Vv2LINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-Vv2LINS-ispA*.

16-7) Construction of Co-Expression Plasmid for McLINS and ispA* Genes

PCR with pUC57-McLINS described in Table 25 as a template was carried out using primer Q40 (SEQ ID NO:140) and primer Q41 (SEQ ID NO:141) to obtain McLINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-McLINS-ispA*.

16-8) Construction of Co-Expression Plasmid for ObLINS and ispA* Genes

PCR with pUC57-ObLINS described in Table 25 as a template was carried out using primer Q42 (SEQ ID NO:142) and primer Q43 (SEQ ID NO:143) to obtain ObLINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-ObLINS-ispA*.

16-9) Construction of Co-Expression Plasmid for CbLINS and ispA* Genes

PCR with pUC57-CbLINS described in Table 25 as a template was carried out using primer Q44 (SEQ ID NO:144) and primer Q45 (SEQ ID NO:145) to obtain CbLINS fragment. Furthermore, PCR with pACYC177-Ptac-opt_AaLINS-ispA* constructed in Example 1 as a template was carried out using primer Q46 (SEQ ID NO:146) and primer Q47 (SEQ ID NO:147) to obtain a DNA fragment including pACYC177, tac promoter region (deBoer et al., (1983) Proc. Natl. Acad. Sci. U.S.A., 80, 21-25), and ispA*. These two fragments were ligated using In-Fusion HD cloning kit (produced by Clontech Laboratories, Inc.) to construct pACYC177-CbLINS-ispA*.

Example 17: Evaluation of Ability to Produce Linalool by Linalool Synthase-Expressing Strains Derived from SWITCH-PphoC ΔGcd Strain 17-1) Introduction of Linalool Synthase Expression Plasmid into SWITCH-PphoC Δgcd Strain Competent cells of the SWITCH-PphoC Δgcd obtained in Example 4 were prepared, and the pACYC177-At1LINS-ispA*, pACYC177-At2LINS-ispA*, pACYC177-MdLINS-ispA*, pACYC177-PfLINS-ispA*, pACYC177-Vv1LINS-ispA*, pACYC177-Vv2LINS-ispA*, pACYC177-McLINS-ispA*, pACYC177-ObLINS-ispA*, or the pACYC177-CbLINS-ispA* constructed in Example 16, and pACYC177 were introduced into the cells by an electroporation method. Resulting strains were designated as SWITCH-PphoC Δgcd/At1LINS-ispA*, SWITCH-PphoC Δgcd/At2LINS-ispA*, SWITCH-PphoC Δgcd/MdLINS-ispA*, SWITCH-PphoC Δgcd/PfLINS-ispA*, SWITCH-PphoC Δgcd/Vv1LINS-ispA*, SWITCH-PphoC Δgcd/Vv2LINS-ispA*, SWITCH-PphoC Δgcd/McLINS-ispA*, SWITCH-PphoC Δgcd/ObLINS-ispA*, SWITCH-PphoC Δgcd/CbLINS-ispA*, and SWITCH-PphoC Δgcd/pACYC177 strains, respectively.

The strains obtained above were cultured on an LB plate containing 50 mg/L of kanamycin at 34° C. for 16 hours, the microbial cells on the plate were then scraped in an appropriate amount using a 10 µL inoculating loop (produced by Thermo Fisher Scientific Inc.) and suspended in a 20% glycerol solution, and the resulting solution was dispensed in each appropriate amount and then stored at −80° C.

17-2) Evaluation of Ability to Produce Linalool by Linalool Synthase-Expressing Strains Derived from SWITCH-PphoC Δgcd Strain The glycerol stocks of SWITCH-PphoC Δgcd/At1LINS-ispA*, SWITCH-PphoC Δgcd/At2LINS-ispA*, SWITCH-PphoC Δgcd/MdLINS-ispA*, SWITCH-PphoC Δgcd/PfLINS-ispA*, SWITCH-PphoC Δgcd/Vv1LINS-ispA*, SWITCH-PphoC Δgcd/Vv2LINS-ispA*, SWITCH-PphoC Δgcd/McLINS-ispA*, SWITCH-PphoC Δgcd/ObLINS-ispA*, SWITCH-PphoC Δgcd/CbLINS-ispA*, and SWITCH-PphoC Δgcd/pACYC177 strains were thawed. Subsequently, 50 µL of a microbial cell suspension from each strain was uniformly applied onto an LB plate containing 50 mg/L of kanamycin, and cultured at 34° C. for 16 hours. The resulting microbial cells on the plate were picked up in an amount corresponding to about ¼ of a 10 µL inoculating loop (produced by Thermo Fisher Scientific Inc.). The picked up microbial cells were inoculated into 5 mL of fermentation medium described below containing 50 mg/L of kanamycin in a test tube produced by AGC Techno Glass Co., Ltd. (diameter×length×thickness=25×200×1.2 mm), and cultured at 30° C. on a reciprocal shaking culture apparatus at 120 rpm for 24 hours. The fermentation medium is showed in Table 26.

TABLE 26

Fermentation medium for linalool-producing host SWITCH-PphoC Δgcd strain (with addition of isopropyl myristate)

| Group A | |
|---|---|
| D-Glucose | 40 g/L |
| MgSO$_4$•7H$_2$O | 1 g/L |
| Not adjusted pH, AC 115° C., 10 minutes | |

TABLE 26-continued

Fermentation medium for linalool-producing host SWITCH-PphoC Δgcd strain (with addition of isopropyl myristate)

| Group B | |
|---|---|
| $(NH_4)_2SO_4$ | 20 g/L |
| $KH_2PO_4$ | 0.5 g/L |
| Yeast Extract | 2 g/L |
| $FeSO_4 \cdot 7H_2O$ | 0.01 g/L |
| $MnSO_4 \cdot 5H_2O$ | 0.01 g/L |
| After adjusting pH to 7.0 with KOH, AC 115° C., 10 minutes | |
| Group C | |
| $CaCO_3$ | 20 g/L |
| Dry-heat sterilization 180° C., 2 hours | |

After the completion of sterilization, the above Groups A, B and C were mixed. Then, 1 mL of isopropyl myristate (produced by Tokyo Chemical Industry Co., Ltd.) was added to 5 mL of the fermentation medium dispensed in the test tube.

24 hours after starting the cultivation, the concentrations of isopropyl myristate and linalool in the culture supernatant were measured under the following conditions using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd.). A sample for measurement was appropriately diluted with ethanol (supplied from Wako Pure Chemical Industries, Ltd.).

| | |
|---|---|
| Temperature in vaporization chamber | 360.0° C. |
| Injection amount | 1.0 µL |
| Injection mode | Split 1:10 |
| Carrier gas | He |
| Control mode | Line velocity |
| Pressure | 125.5 kPa |
| Total flow | 20.5 mL/minute |
| Column flow | 1.59 mL/minute |
| Line velocity | 36.3 cm/sec |
| Purge flow | 3.0 mL/minute |
| Column oven temperature program Total time | 21.5 minutes |

| Rate (° C./minute) | Temperature (° C.) | Hold time (min) |
|---|---|---|
| | 65.0 | 5.0 |
| 5.0 | 105.0 | 0.5 |
| 35.0 | 297.5 | 2.5 |

| | |
|---|---|
| Detector temperature | 375.0° C. |
| Detector | FID |
| Make-up gas | He (30.0 mL/min) |
| Hydrogen flow | 40.0 mL/min |
| Air | 400.0 mL/min |

The linalool is shown in terms of accumulated concentration in the fermentation liquor. A mean value of results obtained from two test tubes with addition of isopropyl myristate is shown in Table 27.

TABLE 27

Accumulation of linalool when various linalool synthases and mutated ispA were introduced in SWITCH-PphoC Δgcd (with addition of isopropyl myristate)Strain

| | O.D. 620 nm | Linalool (mg/L) |
|---|---|---|
| SWITCH-PphoC Δgcd/pACYC177 | 13.6 | 0.0 |
| SWITCH-PphoC Δgcd/At1LINS-ispA* | 20.2 | 13.3 |
| SWITCH-PphoC Δgcd/At2LINS-ispA* | 18.9 | 30.8 |
| SWITCH-PphoC Δgcd/MdLINS-ispA* | 11.5 | 116.7 |
| SWITCH-PphoC Δgcd/PfLINS-ispA* | 14.6 | 29.2 |
| SWITCH-PphoC Δgcd/Vv1LINS-ispA* | 16.5 | 37.3 |
| SWITCH-PphoC Δgcd/Vv2LINS-ispA* | 16.6 | 2.6 |
| SWITCH-PphoC Δgcd/McLINS-ispA* | 16.4 | 19.0 |
| SWITCH-PphoC Δgcd/ObLINS-ispA* | 21.7 | 519.8 |
| SWITCH-PphoC Δgcd/CbLINS-ispA* | 19.7 | 44.3 |

Example 18: Construction of Linalool Synthase-Expressing Plasmid

*Corynebacterium glutamicum* (*C. glutamicum*) 2256 strain (ATCC13869) was used as a coryneform bacterium (Okumura et al., 1962, Santamaria et al., 1984, Tsuchida et al., 1986). A plasmid for expressing an opt_AaLINS gene and an ispA gene in *C. glutamicum* was constructed by the following procedure. PCR with pACYC177-Ptac-optAa-LINS-ispA* obtained in Example 1 as a template was carried out using primers 814 and 815 shown in SEQ ID NOs: 148 and 149 to obtain an optAaLINS-ispA* fragment. Then, PCR with chromosomal DNA of the *C. glutamicum* 2256 strain as a template was carried out using primers 812 and 813 shown in SEQ ID NOs: 150 and 151 for the purpose of obtaining a promoter sequence of Elongation Factor Tu (hereinafter, described as P0480) (WO 2013/179722 A1) to obtain a P0480 fragment. Subsequently, a shuttle vector pVK9 of *C. glutamicum* and *E. coli* (WO 2013/179722A1) was digested with a restriction enzyme XbaI (produced by Takara Bio Inc.) (Miwa et al., 1985). The purified optAa-LINS-ispA* fragment, the PCR product of P0480, and pVK9 digested with XbaI and then purified were ligated using In-Fusion HD cloning kit (produced by Clontech Laboratories, Inc.). The resulting plasmid for expressing an optAaLINS-ispA* gene was designated as pVK9-P0480-optAaLINS-ispA* and the sequence information of this plasmid was shown in SEQ ID NO: 152.

Example 19: Linalool Production in *C. glutamicum* 2256 Strain 19-1) Introduction of Opt_AaLINS-ispA* Gene-Expressing Plasmid to *C. Glutamicum* 2256 Strain The transformation of the *C. glutamicum* 2256 strain was carried our according to the previously described method (WO 2013/179722 A1). The respective plasmid DNAs of pVK9 and pVK9-P0480-optAaLINS-ispA* were introduced, applied onto a CM-Dex plate culture medium containing 25 µg/ml of kanamycin (WO 2013/179722 A1), and cultured at 30° C. for 48 hours. The transformant exhibiting kanamycin resistance was obtained from the plate after cultivation, and a strain in which pVK9 is introduced into the *C. glutamicum* 2256 strain was designated as a 2256/pVK9 strain and a strain in which pVK9-P0480-optAa-LINS-ispA* is introduced into the *C. glutamicum* 2256 strain was designated as 2256/pVK9-P0480-optAaLINS-ispA*.

19-2) Evaluation of Ability to Produce Linalool by Linalool Synthase-Expressing Strains Derived from *C. glutamicum* 2256 Strain The 2256/pVK9 strain and the 2256/pVK9-P0480-optAaLINS-ispA* strain were uniformly applied onto a CM-Dex plate containing 25 (mg/L) of kanamycin and cultured at 30° C. for about 18 hours. The microbial cells corresponding to ⅙ part of the plate were inoculated from the plate after the cultivation to a large diameter test tube containing 5 ml of the culture medium for coryne_linalool production (Table 28) containing 25 (mg/L) of kanamycin, and cultured at 30° C. for 24 hours.

TABLE 28

Culture medium for coryne_linalool production

| | |
|---|---|
| Glucose | 80 g/L |
| $(NH_4)_2SO_4$ | 30 g/L |
| $KH_2PO_4$ | 1 g/L |
| $MgSO_4 \cdot 7H_2O$ | 0.4 g/L |
| $FeSO_4 \cdot 7H_2O$ | 0.01 g/L |
| $MnSO_4 \cdot 4\text{-}5H_2O$ | 0.01 g/L |
| VB1·HCl | 200 µg/L |
| Biotin | 60 µg/L |
| Mameno | 0.48 g/L |
| pH 8.0(KOH) | |
| Autoclave 115° C. 10 min | |
| $CaCO_3$ | 50 g/L |
| 180° C. 90 min | |

One mL of isopropyl myristate (produced by Tokyo Chemical Industry Co., Ltd.) was added to 5 mL of a culture medium for coryne_linalool production (Table 28) dispensed in the large diameter test tube.

24 hours after starting the cultivation, the concentrations of isopropyl myristate and linalool in the culture supernatant were measured under the same conditions as Example 8. DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd).

The concentration of linalool is shown in terms of medium amount. A mean value obtained from three large diameter test tubes is shown in Table 30. No linalool production was observed in the control strain 2256/pVK9, whereas linalool production was confirmed in 2256/pVK9-P0480-opt_AaLINS-ispA* strain (Table 29).

TABLE 29

Accumulation of linalool when linalool synthase native to *A. arguta* and mutant ispA were introduced

| Strain | O.D. 620 nm | Linalool (mg/L) |
|---|---|---|
| 2256/pVK9 | 73.4 | 0.00 |
| 2256/pVK9-$P_{0480}$-sLINS2-ispA* | 86.3 | 4.32 |

Example 20: Construction of Linalool Synthase-Expressing Plasmid 20-1) Plasmid that can be Transformed into *Synechocystis* sp. PCC6803 GT Strain It is known that *Synechocystis* sp. PCC6803 can be subjected to natural transformation. The plasmids pTKHT0846-slr0846 and pUC57-slr0846 contain the sequences of parts of coding regions of sll0822, slr0846, and sll0821, the sequence of a kanamycin resistance gene, and the like, and when the coding regions of slr0846 and sll0821 are set to homologous sequences, the genomic recombination of the *Synechocystis* sp. PCC6803 strain can be carried out (Midorikawa et al. (2012) Plant Cell Physiol. 53(1): 164-172). The plasmid of pTKHT0846-slr0846 was furnished by Prof. Masahiko Ikeuchi, Graduate School of Arts and Sciences, the University of Tokyo, and the total synthesis of pUC57-slr0846 was entrusted to GenScript.

20-2) Construction of Expression Plasmid for Opt_AaLINS

PCR with pMW119-Ptac-opt_AaLINS obtained in Example 1 as a template was carried out using primer 671 shown in SEQ ID NO:153 and primer 691 shown in SEQ ID NO:154 to obtain a Ptac-opt_AaLINS fragment. The purified Ptac-opt_AaLINS fragment was ligated to pTKHT0846-slr0846 digested with restriction enzymes AatII and HpaI using In-Fusion HD cloning kit (produced by Clontech Laboratories, Inc.) to construct pTKHT0846-Ptac-opt_AaLINS.

20-3) Construction of Expression Plasmid for Opt_AaLINS-ispA*

PCR with pACYC177-Ptac-opt_AaLINS-ispA* obtained in Example 1 as a template was carried out using primer 719 shown in SEQ ID NO:155 and primer 721 shown in SEQ ID NO:156 to obtain a Ptac-opt_AaLINS-ispA* fragment. The purified Ptac-opt_AaLINS-ispA* fragment was ligated to pUC57-slr0846-PpsbA2 digested with restriction enzymes NheI using In-Fusion HD cloning kit (produced by Clontech Laboratories, Inc.) to construct pUC57-slr0846-PpsbA2-opt_AaLINS-ispA*.

Example 21: Linalool Production in *Synechocystis* sp. PCC6803 GT Strain 21-1) Introduction of Opt_AaLINS Gene-Expressing Plasmid into *Synechocystis* Sp. PCC6803 GT Strain The *Synechocystis* sp. PCC6803 GT strain was transformed according to the method described in Example 11. A medium (Table 16) added with 20 mg/L of kanamycin as a reagent for selection of a transformant introduced with pTKHT0846-Ptac-opt_AaLINS was used. Colony PCR was carried out to resulting colonies using a primer 683 shown in SEQ ID NO: 157 and a primer 684 shown in SEQ ID NO: 158. It was confirmed that a DNA fragment having a target size was inserted to a target position in genome, and the resulting strain was designated as a GT0846K-Ptac-AaLINS strain.

The strain obtained above was grown on the BG-11 agar medium (Table 16) added with 20 mg/L of kanamycin. A frozen stock was prepared by the method described in Example 12, and stocked at −80° C.

21-2) Introduction of Opt_AaLINS-ispA* Gene-Expressing Plasmid into *Synechocystis* sp. PCC6803 GT Strain The transformation was carried out by the same method as in Example 11. As a drug for selecting a transformant into which pUC57-slr0846-PpsbA2-opt_AaLINS-ispA* is introduced, a culture medium added with 20 mg/L of kanamycin (Table 16) was used. Colony PCR was carried out to resulting colonies using a primer 683 shown in SEQ ID NO: 157 and a primer 684 shown in SEQ ID NO: 158. It was confirmed that a DNA fragment having a target size was inserted to a target position in genome, and the resulting strain was designated as a GT0846K-PpsbA2-AaLINS-ispA* strain.

The strain obtained above was grown on the BG-11 agar medium (Table 16) containing 20 mg/L of kanamycin. The frozen stock was prepared by the method described in Example 12 and stored at −80° C.

21-3) Evaluation of Ability to Produce Linalool by Linalool Synthase-Expressing Strain Derived from *Synechocystis* sp. PCC6803 GT Strain The ability to produce linalool was evaluated in the *Synechocystis* sp. PCC6803 GT strain, the GT0846K-Ptac-AaLINS strain, and the GT0846K-PpsbA2-AaLINS-ispA* strain by the method described in Example 12. The *Synechocystis* sp. PCC6803 GT strain was cultured without addition of a drug, and the GT0846K-Ptac-AaLINS strain and the GT0846K-PpsbA2-AaLINS-ispA* strain were cultured with addition of 20 mg/L of kanamycin.

About 6 days after starting the cultivation, the concentration of linalool in the isopropyl myristate was measured under the conditions described in Example 8 using gas chromatograph GC-2025AF (produced by SHIMADZU CORPORATION). DB-5 (produced by Agilent Technologies, length 30 m, internal diameter 0.25 mm, thickness 0.25 µm) was used as a column, and a linalool standard solution was prepared using a reagent Linalool (produced by Wako Pure Chemical Industries Ltd).

The linalool is shown in terms of amount accumulated in culture solution. A mean value obtained from three conical flasks is shown in Table 30. No linalool production was observed in the control strain *Synechocystis* sp. PCC6803 GT, whereas linalool production was confirmed in GT0846K-Ptac-AaLINS and GT0846K-PpsbA2-AaLINS-ispA* strains.

TABLE 30

Accumulation of linalool when linalool synthase native to *A. arguta* and mutant ispA were introduced

| Strain | O.D 730 nm | Linalool (mg/L) |
|---|---|---|
| *Synechocystis* sp. PCC6803 GT | 8.2 | 0.0 |
| GT0846K-Ptac-AaLINS | 8.7 | 11.4 |
| GT0846K-PpsbA2-AaLINS-ispA* | 3.4 | 11.6 |

Example 22: Construction of Linalool Synthase-Expressing Plasmid-Introduced Strain Derived from *Actinidia arguta* (Hardy Kiwifruit) from Yeast 22-1) Construction of Plasmid for Expressing Linalool Synthase Plasmid Native to *Actinidia arguta* in Yeast PCR with pACYC177-Ptac-opt_AaLINS-ispA* constructed in Example 1 as a template was carried out using primer Q48 (SEQ ID NO:159) and primer Q49 (SEQ ID NO:160) to obtain AaLINS-ispA* fragment. The digested AaLINS-ispA* fragments were ligated to pYES2 (produced by Invitrogen) digested with restriction enzymes KpnI and BamHI using In-Fusion HD cloning kit (produced by Clontech Laboratories, Inc.) to construct pYES2-Ptac-opt-AaLINS-ispA*.

22-2) Introduction of Linalool Expression Plasmid Derived from *Actinidia arguta* into Yeast The pYES2-Ptac-opt_AaLINS-ispA* was introduced into *Saccharomyces cerevisiae* S288C ura3Δ0 strain described in JP 5857973 B2.

The S288C ura3Δ0 strain was inoculated to a YPD liquid culture medium and cultured at 30° C. for 16 hours, and then 0.6 ml of the culture solution was transferred to 10 ml of the culture medium. Furthermore, cultivation was carried out at 30° C. for 2 hours and then the total amount of cells was collected to prepare competent cells using Frozen-EZ Yeast Transformation II™ kit (produced by ZYMO RESEARCH CORP.). The prepared competent cells were transformed with pYES2-Ptac-opt_AaLINS-ispA*, uniformly applied onto an SD-Ura plate, and then cultured at 30° C. for 3 days to obtain a transformant. The resulting strain was designated as S288C ura3Δ0/pYES2-Ptac-opt_AaLINS-ispA*. The composition of the YPD culture medium is presented in Table 31 and the composition of the SD-Ura culture medium is presented in Table 32.

TABLE 31

YPD culture medium

| Group A | |
|---|---|
| Polypeptone | 10 g/L |
| Yeast Extract | 10 g/L |
| Not adjusted pH, AC 120° C., 15 minutes | |
| Group B | |
| Glucose | 20 g/L |
| Not adjusted pH, AC 120° C., 20 minutes | |

Group A and Group B were mixed after sterilization
In the case of the plate, Agar was added to a concentration of 20 g/L.

TABLE 32

Ura culture medium

| Group A | |
|---|---|
| Difco Yeast Nitrogen Base W/O AA (Becton Dickinson Cat. No. 291940) | 6.7 g/L |
| Ura DO supplement (Clontech Cat. No. 630416) | 0.77 g/L |
| After adjusting pH to 5.7 with KOH, AC 120° C., 15 minutes | |
| Group B | |
| Glucose | 20 g/L |
| Not adjusted pH, AC 120° C., 20 minutes | |

Group A and Group B were mixed after sterilization
In the case of the plate, Agar was added to a concentration of 20 g/L.

Example 23: Linalool Production in Yeast

The S288C ura3Δ0/pYES2-Ptac-opt_AaLINS-ispA* strain obtained in Example 22 is uniformly applied onto an SD-Ura plate having the composition presented in Table 33 and cultured at 30° C. for about 24 hours. The resulting microbial cells on the plate are scraped in an amount corresponding to about ½ of a 10 µL inoculating loop (produced by Thermo Fisher Scientific Inc.). The scraped microbial cells are inoculated into 5 mL of SD-Ura-Gal culture medium in a test tube produced by AGC Techno Glass Co., Ltd. (diameter×length×thickness (mm)=25×200×1.2), and cultured at 30° C. on a reciprocal shaking culture apparatus at 120 rpm for 48 hours so that linalool can be obtained. The composition of the SD-Ura-Gal culture medium is presented in Table 33.

TABLE 33

SD-Ura-Gal culuture medium

| Group A | |
|---|---|
| Difco Yeast Nitrogen Base W/O AA (Becton Dickinson Cat. No. 291940) | 6.7 g/L |

TABLE 33-continued

SD-Ura-Gal culuture medium

| | |
|---|---|
| Ura DO supplement (Clontech Cat. No. 630416) | 0.77 g/L |
| After adjusting pH to 5.8 with KOH, filter sterilization | |
| Group B | |
| Galactose | 20 g/L |
| Not adjusted pH, filter sterilization | |

Group A and Group B were mixed after sterilizatio
1 mL of isopropyl myristate (produced by Tokyo Chemical Industry Co., Ltd.) was added to 5 mL of the SD-Ura-Gal culture medium dispensed in the test tube after inoculation.

Example 24: Searching for an Amino Acid Sequence Motif Locally Present in Linalool Synthase Thirteen distinct linalool synthase genes were synthesized and used as input sequences, and motif searching was carried out using MEME capable of finding locally stored sequences (Timothy L. Bailey and Charles Elkan, "Fitting a mixture model by expectation maximization to discover motifs in biopolymers", Proceedings of the Second International Conference on Intelligent Systems for Molecular Biology, pp. 28-36, AAAI Press, Menlo Park, Calif., 1994, meme-suite.org.). As the searching option of MEME, as for the site distribution condition, a condition that one similar motif is present in each sequence (One occurrence of a contributing motif site per sequence) was employed, and other than that condition, the default conditions were used. As a result, five motifs were obtained as output (FIGS. 17 to 21). The alignments configuring respective motif sequences are illustrated in FIGS. 22 to 26. The distribution positions of respective motifs in the 13 linalool synthases are illustrated in FIG. 27.

Subsequently, in order to define the found motifs as character strings, unique amino acid residues in the motif are determined, or residues that only appear twice, and residues other than those residues were classified. Thereafter, the motif length was defined as 8 to 20 amino acids, and the six amino acid sequence motifs are presented in Table 34.

The detection sensitivity of these six amino acid sequence motifs was examined. As a false-negative examination, the preserved properties of the six amino acid motif sequences as compared to the 168 amino acid sequences found using the keyword search "linalool synthase" from GenPept database were examined with fuzzpro. As a false-positive examination, whether the six amino acid motif-like sequences as compared to the 151 kinds of amino acid sequences found using the keyword search "limonene synthase" from GenPept database are found was examined with fuzzpro (Table 34).

TABLE 34

Detection of linalool synthase and limonene synthase by amino acid sequence motif

| Amino acid motif | With respect to linalool synthase | With respect to limonene synthase |
|---|---|---|
| DDx[F/Y][D/Y]xxG | 140/168, 83% | 86/151, 57% |
| Lxx[FL][TA]x(4)[RN]W[DE] | 117/168, 70% | 75/151, 50% |
| [DE]Lx(4)LxF[RW]L[LF]R | 65/168, 39% | 55/151, 36% |
| Axx[DN]x(4)[QK]xxx[QR]xEx(6)W[WS] | 72/168, 43% | 50/151, 33% |
| [EV]Yxxx[AG]xx[ST] | 121/168, 72% | 60/151, 40% |
| R[LI]x[DN]D[LI]x[ST]xxxExxxG | 103/168, 61% | 70/151, 46% |

Some of the sequences extracted by keyword search "linalool synthase" contain about 10 to 20 enzymes having an extremely short sequence, or are practically different from linalool synthase. On the other hand, it was found that each linalool synthase presented in Table 24 contains the DDx[F/Y][D/Y]xxG motif (FIGS. 28 to 40). Also, in other linalool synthases (Table 35) not presented in Table 24, the DDx[F/Y][D/Y]xxG motif was observed (FIGS. 41 to 48). From these points, it was found that DDx[F/Y][D/Y]xxG is an amino acid sequence motif capable of detecting linalool synthase. On the other hand, with a high false positive of 86/161 (57%), linalool synthase cannot be accurately detected using only the DDx[F/Y][D/Y]xxG motif. It was found that Lxx[FL][TA]x(4)[RN]W[DE], [EV]Yxxx[AG]xx[ ST], and R[LI]x[DN]D[LI]x[ST]xxxExxxG also have the same feature as DDx[F/Y][D/Y]xxG in terms of generating a large number of false positives.

As motifs found in terpene synthase, DDxxD motif, NSE motif, and DxDD motif have been reported (Chen et al., The Plant Journal (2011) 66, 212-229). The DDx[F/Y][D/Y]xxG motif can includes the DDxxD motif, but is not limited thereto, and is a motif which can more specifically define sequences.

TABLE 35

Linalool synthase having DDx[F/Y][D/Y]xxG motif

| SEQ ID NO | Microorganism name and accession number |
|---|---|
| 161 | Q1XBU5\|R-linalool synthase\|EC 4.2.3.26\|*Solanum lycopersicum*\|TrEMBL |
| 162 | gi\|211970992\|dbj\|BAG82825.1\| linalool synthase [*Backhousia citriodora*] |
| 163 | gi\|6469618\|gb\|AAF13357.1\|AF154125_1 (3R)-linalool synthase, partial [*Artemisia annua*] |
| 164 | gi\|6469616\|gb\|AAF13356.1\|AF154124_1 (3R)-linalool synthase [*Artemisia annua*] |
| 165 | D4N3A0\|S-linalool synthase\|EC 4.2.3.25\|*Actinidia arguta*\|TrEMBL |
| 166 | D4N3A1\|S-linalool synthase\|EC 4.2.3.25\|*Actinidia polygama*\|TrEMBL |
| 167 | C0KWV5\|S-linalool synthase\|EC 4.2.3.25\|*Perilla frutescens* var. *hirtella*\|TrEMBL |
| 168 | C0KWV3\|S-linalool synthase\|EC 4.2.3.25\|*Perilla setoyensis*\|TrEMBL |

TABLE 36

Sequences of primer used in Example 16 and later Examples (part 1)

| Seq ID No | No. | Sequence |
|---|---|---|
| 128 | Q28 | CACAAGGAGACTGCCATGGCGAACACGGCGAAGCGTAGTATCC |
| 129 | Q29 | GTCTCCTGTGTGAAATTACATCAGGCTTTTCAGATACTCATCGG |
| 130 | Q30 | CACAAGGAGACTGCCATGCGTCGTAGTGCGAATTACCAGCCGAG |
| 131 | Q31 | GTCTCCTGTGTGAAATTAGTCCAGCGGGATAGGGTTAAACAGC |
| 132 | Q32 | CACAAGGAGACTGCCATGGAGTTTAGCATTAGCCAGAGTAGTTTTGCG |
| 133 | Q33 | GTCTCCTGTGTGAAATTAGGCGTGCAGCATACTCTTCATGTACTC |

TABLE 36-continued

Sequences of primer used in Example 16 and later Examples (part 1)

| Seq ID No | No. | Sequence |
|---|---|---|
| 134 | Q34 | CACAAGGAGACTGCCATGTATAGCCTGCGTATTTATGTGGCG |
| 135 | Q35 | GTCTCCTGTGTGAAATTAGGCATAGGGTTCAAACAGCAGGCAGGCG |
| 136 | Q36 | CACAAGGAGACTGCCATGGGTTTTAGTCCTGCCTTTTATGCGTG |
| 137 | Q37 | GTCTCCTGTGTGAAATTACAGGGGAAACGCTTCAAACAGCAGACTC |
| 138 | Q38 | CACAAGGAGACTGCCATGGAACTGACCCTGACGAGTCTGAGCCCG |
| 139 | Q39 | GTCTCCTGTGTGAAATTAGCGGCGGTTACTCATCTTCATGCCATCC |
| 140 | Q40 | CACAAGGAGACTGCCATGTGTACCATCATTAGCGTCAATCATC |
| 141 | Q41 | GTCTCCTGTGTGAAATTAGACGTAGGGCTTAAACAGCAGATTGGC |
| 142 | Q42 | CACAAGGAGACTGCCATGGCGAGTGCGGTCCCCCTGAGTAGTACG |
| 143 | Q43 | GTCTCCTGTGTGAAATTAACTACTCAGCAGGGGCGTAAAAACAGGG |
| 144 | Q44 | CACAAGGAGACTGCCATGCGTGAGAGCCTGAGCAGTAGCAGTAGC |
| 145 | Q45 | GTCTCCTGTGTGAAATTAACTAAAGCACAGTTTGATATTCGGAC |
| 146 | Q46 | GGCAGTCTCCTTGTGTGAAATTGTTATCCGCTCA |
| 147 | Q47 | TTTCACACAGGAGACTGCCATGGATTTTCCCCAGC |
| 148 | 814 | ATGTCCACCGCCGTGCCCTCTATGCCCACTACCCAAAAATG |
| 149 | 815 | gcaggtcgactctagCTATTTGTTGCGCTGGATGATGTAATC |
| 150 | 812 | ggtacccggggatcctctagAGATCGTTTAGATCCGAAGG |
| 151 | 813 | CACGGCGGTGGACATTGTATGTCCTCCTGGACTTCGTGGT |
| 152 | xx | pVK9-P0480-opt_AaLINS-ispA* 4363-4724: P0480; 4725-6374: opt_AaLINS; 6375-6393: spacer; 6394-7293: ispA* |

TABLE 37

Sequences of primer used in Example 16 and later Examples (part 2)

| Seq ID No | No. | Sequence |
|---|---|---|
| 153 | 671 | tctagagtcgacgtcCCCTGTTGACAATTAATCATCGGCTCGTATAATGTGTGGA |
| 154 | 691 | tccaatgtgaggttTTAGCTACTGGAATCATACAACATGGTTTTCATGTGTTCT |
| 155 | 719 | aaggaattataaccaaATGTCCACCGCCGTGCCCTCTATGCCCACTACCCAAAAATG |
| 156 | 721 | gatggggaagtttaggctagcCTATTTGTTGCGCTGGATGATGTAATCGGCCAGG |
| 157 | 683 | ggaggattgggttaccctcagtgtg |
| 158 | 684 | cgccatatcaatcccaacgctctgg |
| 159 | Q48 | GGAATATTAAGCTTGGTACCATGTCCACCGCCGTGCCCTCTATG |
| 160 | Q49 | GTGGATCCGAGCTCGGTACCCTATTTGTTGCGCTGGATGATG |

Example 25: Evaluation of Cultivation of SWITCH-PphoC Δgcd Strains Respectively Expressing ScLINS, CsLINS, and AaLINS with 60 g/L of Glucose The SWITCH-PphoC Δgcd/AaLINS-ispA* strain obtained in Example 6 and the SWITCH-PphoC Δgcd/ScLINS-ispA* strain and the SWITCH-PphoC Δgcd/Ptac2-CsLINS-ispA* strain obtained in Example 10 were cultured under the conditions described in Example 13. Furthermore, the quantification of linalool was carried out under the conditions described in Example 3.

The value of linalool is shown in terms of accumulated concentration in the fermentation liquor. An average value obtained from three test tubes is presented in Table 38. The linalool production was not observed in the control strain having the control vector pACYC177, whereas a significantly large amount of linalool production that had not been achieved before was confirmed in the SWITCH-PphoC Δgcd/AaLINS-ispA* strain, the SWITCH-PphoC Δgcd/ScLINS-ispA* strain, and the SWITCH-PphoC Δgcd/Ptac2-CsLINS-ispA* strain.

TABLE 38

Accumulation of linalool when ScLINS, CsLINS, AaLINS, and mutated ispA were introduced in SWITCH-PphoC Δgcd strain (cultivation result with 60 g/L of glucose)

| Strain | Linalool (mg/L) |
|---|---|
| SWITCH-PphoC Δgcd/pACYC177 | 0.0 |
| SWITCH-PphoC Δgcd/ScLINS-ispA* | 3714.8 |
| SWITCH-PphoC Δgcd/Ptac2-CsLINS-ispA* | 4341.5 |
| SWITCH-PphoC Δgcd/AaLINS-ispA* | 5603.9 |

While the invention has been described in detail with reference to preferred embodiments thereof, it will be apparent to the person skilled in the art that various changes can be made, and equivalents employed, without departing from the scope of the invention. All the cited references herein are incorporated by reference as a part of this application.

INDUSTRIAL APPLICABILITY

The method as described herein is useful for the production of linalool.

The invention claimed is:

1. A method for producing linalool, the method comprising:

(i) culturing a bacterium in a culture medium so that it is able to produce and cause accumulation of linalool, wherein the bacterium has an ability to synthesize dimethylallyl diphosphate via a methylerythritol phosphate pathway and/or an ability to synthesize dimethylallyl diphosphate via a mevalonate pathway, and the bacterium belongs to the genus *Escherichia, Pantoea, Synechocystis,* or *Corynebacterium,* and a 2-ketogluconate formation pathway is blocked in the bacterium, and (ii) collecting linalool from the culture medium or the bacterium;

wherein said bacterium expresses linalool synthase; and wherein said linalool synthase has a property selected from the group consisting of:

(a) amino acid sequence of said linalool synthase has at least one motif represented by the following formula: DDX$_1$[F/Y][D/Y]X$_2$X$_3$G (SEQ ID NO: 184), wherein D represents aspartic acid, F represents phenylalanine, Y represents tyrosine, G represents glycine, X$_1$, X$_2$, and X$_3$ each independently represent an arbitrary amino acid, [F/Y] represents F or Y, and [D/Y] represents D or Y, and wherein the at least one motif is selected from the group consisting of:

a combination in which X$_1$ is I, [F/Y] is F, [D/Y] is D, X$_2$ is V, and X$_3$ is Y;

a combination in which X$_1$ is I, [F/Y] is F, [D/Y] is D, X$_2$ is V, and X$_3$ is Y;

a combination in which X$_1$ is I, [F/Y] is F, [D/Y] is D, X$_2$ is V, and X$_3$ is H;

a combination in which X$_1$ is I, [F/Y] is F, [D/Y] is D, X$_2$ is T, and X$_3$ is Y;

a combination in which X$_1$ is I, [F/Y] is F, [D/Y] is Y, X$_2$ is V, and X$_3$ is C;

a combination in which X$_1$ is I, [F/Y] is Y, [D/Y] is D, X$_2$ is I, and X$_3$ is Y;

a combination in which X$_1$ is I, [F/Y] is Y, [D/Y] is D, X$_2$ is A, and X$_3$ is Y;

a combination in which X$_1$ is I, [F/Y] is Y, [D/Y] is D, X$_2$ is V, and X$_3$ is Y;

a combination in which X$_1$ is V, [F/Y] is Y, [D/Y] is D, X$_2$ is I, and X$_3$ is Y;

a combination in which X$_1$ is V, [F/Y] is Y, [D/Y] is D, X$_2$ is V, and X$_3$ is F;

a combination in which X$_1$ is M, [F/Y] is Y, [D/Y] is D, X$_2$ is I, and X$_3$ is Y; and a combination in which X$_1$ is F, [F/Y] is F, [D/Y] is D, X$_2$ is V, and X$_3$ is E, (b) said linalool synthase is native to *Streptomyces clavuligerus,* and (c) combinations thereof.

2. The method according to claim 1, wherein the linalool synthase is native to an actinomycete or a plant belonging to the genus *Actinidia, Coriandrum, Artemisia, Backhousia, Arabidopsis, Citrus, Malus, Perilla, Vitis, Lavandula, Mentha, Ocimum,* or *Clarkia.*

3. The method according to claim 2, wherein the actinomycete is a bacterium belonging to the genus *Streptomyces.*

4. The method according to claim 1, wherein the linalool synthase is native to *Actinidia arguta, Coriandrum sativum, Artemisia annua, Backhousia citriodora, Arabidopsis thaliana, Citrus unshiu, Malus domestica, Perilla frutescens* var. *crispa, Vitis vinifera, Lavandula angustifolia, Mentha citrata, Ocimum basilicum, Clarkia breweri,* or *Streptomyces clavuligerus.*

5. The method according to claim 1, wherein the bacterium comprises a heterologous expression unit comprising a polynucleotide encoding the linalool synthase and a promoter operably linked thereto.

6. The method according to claim 5, wherein the polynucleotide is selected from the group consisting of:

(a1) a polynucleotide that comprises:

(i1) a nucleotide sequence of SEQ ID NO: 2, (ii1) a nucleotide sequence consisting of nucleotide residues at positions 79 to 1725 in the nucleotide sequence of SEQ ID NO: 2, or (iii1) a nucleotide sequence of SEQ ID NO: 3;

(b1) a polynucleotide that comprises a nucleotide sequence having an identity of 90% or more to the nucleotide sequence of (i1), (ii1), or (iii1), and encodes a protein having a linalool synthase activity;

(c1) a polynucleotide that hybridizes under stringent conditions with a polynucleotide comprising a nucleotide sequence complementary to the nucleotide sequence of (i1), (ii1), or (iii1), and encodes a protein having a linalool synthase activity;

(a2) a polynucleotide that comprises:
  (i2) a nucleotide sequence of SEQ ID NO: 5,
  (ii2) a nucleotide sequence consisting of nucleotide residues at positions 115 to 1773 in the nucleotide sequence of SEQ ID NO: 5, or
  (iii2) a nucleotide sequence of SEQ ID NO: 6;
(b2) a polynucleotide that comprises a nucleotide sequence having an identity of 90% or more to the nucleotide sequence of (i2), (ii2), or (iii2), and encodes a protein having a linalool synthase activity;
(c2) a polynucleotide that hybridizes under stringent conditions with a polynucleotide comprising a nucleotide sequence complementary to the nucleotide sequence of (i2), (ii2), or (iii2), and encodes a protein having a linalool synthase activity;
(a3) a polynucleotide that comprises:
  (i3) a nucleotide sequence of SEQ ID NO: 62 or
  (ii3) a nucleotide sequence of SEQ ID NO: 63;
(b3) a polynucleotide that comprises a nucleotide sequence having an identity of 90% or more to the nucleotide sequence of (i3) or (ii3), and encodes a protein having a linalool synthase activity;
(c3) a polynucleotide that hybridizes under stringent conditions with a polynucleotide comprising a nucleotide sequence complementary to the nucleotide sequence of (i3) or (ii3), and encodes a protein having a linalool synthase activity;
(a4) a polynucleotide that comprises:
  (i4) a nucleotide sequence of SEQ ID NO: 70,
  (ii4) a nucleotide sequence consisting of nucleotide residues at positions 85 to 1704 in the nucleotide sequence of SEQ ID NO: 70, or (iii4) a nucleotide sequence of SEQ ID NO: 71;
(b4) a polynucleotide that comprises a nucleotide sequence having an identity of 90% or more to the nucleotide sequence of (i4), (ii4), or (iii4), and encodes a protein having a linalool synthase activity;
(c4) a polynucleotide that hybridizes under stringent conditions with a polynucleotide comprising a nucleotide sequence complementary to the nucleotide sequence of (i4), (ii4), or
  (iii4), and encodes a protein having a linalool synthase activity;
(a5) a polynucleotide that comprises:
  (i5) a nucleotide sequence of SEQ ID NO: 73,
  (ii5) a nucleotide sequence consisting of nucleotide residues at positions 169 to 1785 in the nucleotide sequence of SEQ ID NO: 73, or
  (iii5) a nucleotide sequence of SEQ ID NO: 74;
(b5) a polynucleotide that comprises a nucleotide sequence having an identity of 90% or more to the nucleotide sequence of (i5), (ii5), or (iii5), and encodes a protein having a linalool synthase activity;
(c5) a polynucleotide that hybridizes under stringent conditions with a polynucleotide comprising a nucleotide sequence complementary to the nucleotide sequence of (i5), (ii5), or (iii5), and encodes a protein having a linalool synthase activity;
(a6) a polynucleotide that comprises:
  (i6) a nucleotide sequence of SEQ ID NO: 89 (M1) or
  (ii6) a nucleotide sequence of SEQ ID NO: 102 (M14);
(b6) a polynucleotide that comprises a nucleotide sequence having an identity of 90% or more to the nucleotide sequence of (i6) or (ii6), and encodes a protein having a linalool synthase activity;
(c6) a polynucleotide that hybridizes under stringent conditions with a polynucleotide comprising a nucleotide sequence complementary to the nucleotide sequence of (i6) or (ii6), and encodes a protein having a linalool synthase activity;
(a7) a polynucleotide that comprises:
  (i7) a nucleotide sequence of SEQ ID NO: 90 (M2) or
  (ii7) a nucleotide sequence of SEQ ID NO: 104 (M16);
(b7) a polynucleotide that comprises a nucleotide sequence having an identity of 90% or more to the nucleotide sequence of (i7) or (ii7), and encodes a protein having a linalool synthase activity;
(c7) a polynucleotide that hybridizes under stringent conditions with a polynucleotide comprising a nucleotide sequence complementary to the nucleotide sequence of (i7) or (ii7), and encodes a protein having a linalool synthase activity;
(a8) a polynucleotide that comprises:
  (i8) a nucleotide sequence of SEQ ID NO: 91 (M3) or
  (ii8) a nucleotide sequence of SEQ ID NO: 106 (M18);
(b8) a polynucleotide that comprises a nucleotide sequence having an identity of 90% or more to the nucleotide sequence of (i8) or (ii8), and encodes a protein having a linalool synthase activity;
(c8) a polynucleotide that hybridizes under stringent conditions with a polynucleotide comprising a nucleotide sequence complementary to the nucleotide sequence of (i8) or (ii8), and encodes a protein having a linalool synthase activity;
(a9) a polynucleotide that comprises:
  (i9) a nucleotide sequence of SEQ ID NO: 92 (M4) or
  (ii9) a nucleotide sequence of SEQ ID NO: 108 (M20);
(b9) a polynucleotide that comprises a nucleotide sequence having an identity of 90% or more to the nucleotide sequence of (i9) or (ii9), and encodes a protein having a linalool synthase activity;
(c9) a polynucleotide that hybridizes under stringent conditions with a polynucleotide comprising a nucleotide sequence complementary to the nucleotide sequence of (i9) or (ii9), and encodes a protein having a linalool synthase activity;
(a10) a polynucleotide that comprises:
  (i10) a nucleotide sequence of SEQ ID NO: 93 (M5) or
  (ii10) a nucleotide sequence of SEQ ID NO: 110 (M22);
(b10) a polynucleotide that comprises a nucleotide sequence having an identity of 90% or more to the nucleotide sequence of (i10) or (ii10), and encodes a protein having a linalool synthase activity;
(c10) a polynucleotide that hybridizes under stringent conditions with a polynucleotide comprising a nucleotide sequence complementary to the nucleotide sequence of (i10) or (ii10), and encodes a protein having a linalool synthase activity;
(a11) a polynucleotide that comprises:
  (i11) a nucleotide sequence of SEQ ID NO: 94 (M6) or
  (ii11) a nucleotide sequence of SEQ ID NO: 112 (M24);
(b11) a polynucleotide that comprises a nucleotide sequence having an identity of 90% or more to the nucleotide sequence of (i11) or (ii11), and encodes a protein having a linalool synthase activity;
(c11) a polynucleotide that hybridizes under stringent conditions with a polynucleotide comprising a nucleotide sequence complementary to the nucleotide sequence of (i11) or (ii11), and encodes a protein having a linalool synthase activity;

(a12) a polynucleotide that comprises:
  (i12) a nucleotide sequence of SEQ ID NO: 95 (M7) or
  (ii12) a nucleotide sequence of SEQ ID NO: 114 (M26);
(b12) a polynucleotide that comprises a nucleotide sequence having an identity of 90% or more to the nucleotide sequence of (i12) or (ii12), and encodes a protein having a linalool synthase activity;
(c12) a polynucleotide that hybridizes under stringent conditions with a polynucleotide comprising a nucleotide sequence complementary to the nucleotide sequence of (i12) or (ii12), and encodes a protein having a linalool synthase activity;
(a13) a polynucleotide that comprises (i13) a nucleotide sequence of SEQ ID NO: 96 (M8) or (ii13) a nucleotide sequence of SEQ ID NO: 116 (M28);
(b13) a polynucleotide that comprises a nucleotide sequence having an identity of 90% or more to the nucleotide sequence of (i13) or (ii13), and encodes a protein having a linalool synthase activity;
(c13) a polynucleotide that hybridizes under stringent conditions with a polynucleotide comprising a nucleotide sequence complementary to the nucleotide sequence of (i13) or (ii13), and encodes a protein having a linalool synthase activity;
(a14) a polynucleotide that comprises:
  (i14) a nucleotide sequence of SEQ ID NO: 97 (M9) or
  (ii14) a nucleotide sequence of SEQ ID NO: 118 (M30);
(b14) a polynucleotide that comprises a nucleotide sequence having an identity of 90% or more to the nucleotide sequence of (i14) or (ii14), and encodes a protein having a linalool synthase activity;
(c14) a polynucleotide that hybridizes under stringent conditions with a polynucleotide comprising a nucleotide sequence complementary to the nucleotide sequence of (i14) or (ii14), and encodes a protein having a linalool synthase activity;
(a15) a polynucleotide that comprises:
  (i15) a nucleotide sequence of SEQ ID NO: 98 (M10) or
  (ii15) a nucleotide sequence of SEQ ID NO: 120 (M32);
(b15) a polynucleotide that comprises a nucleotide sequence having an identity of 90% or more to the nucleotide sequence of (i15) or (ii15), and encodes a protein having a linalool synthase activity;
(c15) a polynucleotide that hybridizes under stringent conditions with a polynucleotide comprising a nucleotide sequence complementary to the nucleotide sequence of (i15) or (ii15), and encodes a protein having a linalool synthase activity;
(a16) a polynucleotide that comprises:
  (i16) a nucleotide sequence of SEQ ID NO: 99 (M11) or
  (ii16) a nucleotide sequence of SEQ ID NO: 122 (M34);
(b16) a polynucleotide that comprises a nucleotide sequence having an identity of 90% or more to the nucleotide sequence of (i16) or (ii16), and encodes a protein having a linalool synthase activity;
(c16) a polynucleotide that hybridizes under stringent conditions with a polynucleotide comprising a nucleotide sequence complementary to the nucleotide sequence of (i16) or (ii16), and encodes a protein having a linalool synthase activity;
(a17) a polynucleotide that comprises:
  (i17) a nucleotide sequence of SEQ ID NO: 100 (M12) or
  (ii17) a nucleotide sequence of SEQ ID NO: 124 (M36);
(b17) a polynucleotide that comprises a nucleotide sequence having an identity of 90% or more to the nucleotide sequence of (i17) or (ii17), and encodes a protein having a linalool synthase activity;
(c17) a polynucleotide that hybridizes under stringent conditions with a polynucleotide comprising a nucleotide sequence complementary to the nucleotide sequence of (i17) or (ii17), and encodes a protein having a linalool synthase activity;
(a18) a polynucleotide that comprises:
  (i18) a nucleotide sequence of SEQ ID NO: 101 (M13) or
  (ii18) a nucleotide sequence of SEQ ID NO: 126 (M38);
(b18) a polynucleotide that comprises a nucleotide sequence having an identity of 90% or more to the nucleotide sequence of (i18) or (ii18), and encodes a protein having a linalool synthase activity;
(c18) a polynucleotide that hybridizes under stringent conditions with a polynucleotide comprising a nucleotide sequence complementary to the nucleotide sequence of (i18) or (ii18), and encodes a protein having a linalool synthase activity;
(a19) a polynucleotide that comprises:
  (i19) a nucleotide sequence of SEQ ID NO: 170 or
  (ii19) a nucleotide sequence of SEQ ID NO: 171;
(b19) a polynucleotide that comprises a nucleotide sequence having an identity of 90% or more to the nucleotide sequence of (i19) or (ii19), and encodes a protein having a linalool synthase activity;
(c19) a polynucleotide that hybridizes under stringent conditions with a polynucleotide comprising a nucleotide sequence complementary to the nucleotide sequence of (i19) or (ii19), and encodes a protein having a linalool synthase activity;
(a20) a polynucleotide that comprises:
  (i20) a nucleotide sequence of SEQ ID NO: 173 or
  (ii20) a nucleotide sequence of SEQ ID NO: 174;
(b20) a polynucleotide that comprises a nucleotide sequence having an identity of 90% or more to the nucleotide sequence of (i20) or (ii20), and encodes a protein having a linalool synthase activity;
(c20) a polynucleotide that hybridizes under stringent conditions with a polynucleotide comprising a nucleotide sequence complementary to the nucleotide sequence of (i20) or (ii20), and encodes a protein having a linalool synthase activity;
(a21) a polynucleotide that comprises:
  (i21) a nucleotide sequence of SEQ ID NO: 176 or
  (ii21) a nucleotide sequence of SEQ ID NO: 177;
(b21) a polynucleotide that comprises a nucleotide sequence having an identity of 90% or more to the nucleotide sequence of (i21) or (ii21), and encodes a protein having a linalool synthase activity;
(c21) a polynucleotide that hybridizes under stringent conditions with a polynucleotide comprising a nucleotide sequence complementary to the nucleotide sequence of (i21) or (ii21), and encodes a protein having a linalool synthase activity;

(a22) a polynucleotide that comprises:
(i22) a nucleotide sequence of SEQ ID NO: 179 or
(ii22) a nucleotide sequence of SEQ ID NO: 180;
(b22) a polynucleotide that comprises a nucleotide sequence having an identity of 90% or more to the nucleotide sequence of (i22) or (ii22), and encodes a protein having a linalool synthase activity;
(c22) a polynucleotide that hybridizes under stringent conditions with a polynucleotide comprising a nucleotide sequence complementary to the nucleotide sequence of (i22) or (ii22), and encodes a protein having a linalool synthase activity;
(a23) a polynucleotide that comprises:
(i23) a nucleotide sequence of SEQ ID NO: 182 or
(ii23) a nucleotide sequence of SEQ ID NO: 183;
(b23) a polynucleotide that comprises a nucleotide sequence having an identity of 90% or more to the nucleotide sequence of (i23) or (ii23), and encodes a protein having a linalool synthase activity;
(c23) a polynucleotide that hybridizes under stringent conditions with a polynucleotide comprising a nucleotide sequence complementary to the nucleotide sequence of (i23) or (ii23), and encodes a protein having a linalool synthase activity; and
(a24) combinations thereof;
wherein the stringent conditions are hybridization in 6×SCC (sodium chloride/sodium citrate) at about 45° C. followed by one or two or more washings in 0.2×SCC and 0.1% SDS at 50 to 65° C.

7. The method according to claim 1, wherein the linalool synthase is a protein selected from the group consisting of:
(A1) a protein that comprises (i1') a full-length amino acid sequence of SEQ ID NO: 1 or (ii1') an amino acid sequence consisting of amino acid residues at positions 27 to 574 in the amino acid sequence of SEQ ID NO: 1;
(B1) a protein that comprises an amino acid sequence having an identity of 90% or more to the amino acid sequence of (i1') or (ii1'), and has a linalool synthase activity;
(C1) a protein that comprises an amino acid sequence having a deletion, substitution, addition, or insertion of one or several amino acids in the amino acid sequence of (i1') or (ii1'), and has a linalool synthase activity;
(A2) a protein that comprises (i2') a full-length amino acid sequence of SEQ ID NO: 4 or (ii2') an amino acid sequence consisting of amino acid residues at positions 39 to 590 in the amino acid sequence of SEQ ID NO: 4;
(B2) a protein that comprises an amino acid sequence having an identity of 90% or more to the amino acid sequence of (i2') or (ii2'), and has a linalool synthase activity;
(C2) a protein that comprises an amino acid sequence having a deletion, substitution, addition, or insertion of one or several amino acids in the amino acid sequence of (i2') or (ii2'), and has a linalool synthase activity;
(A3) a protein that comprises (i3') a full-length amino acid sequence of SEQ ID NO: 61;
(B3) a protein that comprises an amino acid sequence having an identity of 90% or more to the amino acid sequence of (i3'), and has a linalool synthase activity;
(C3) a protein that comprises an amino acid sequence having a deletion, substitution, addition, or insertion of one or several amino acids in the amino acid sequence of (i3'), and has a linalool synthase activity;

(A4) a protein that comprises (i4') a full-length amino acid sequence of SEQ ID NO: 69 or (ii4') an amino acid sequence consisting of amino acid residues at positions 29 to 567 in the amino acid sequence of SEQ ID NO: 69;
(B4) a protein that comprises an amino acid sequence having an identity of 90% or more to the amino acid sequence of (i4') or (ii4'), and has a linalool synthase activity;
(C4) a protein that comprises an amino acid sequence having a deletion, substitution, addition, or insertion of one or several amino acids in the amino acid sequence of (i4') or (ii4'), and has a linalool synthase activity;
(A5) a protein that comprises (i5') a full-length amino acid sequence of SEQ ID NO: 72 or (ii5') an amino acid sequence consisting of amino acid residues at positions 57 to 594 in the amino acid sequence of SEQ ID NO: 72;
(B5) a protein that comprises an amino acid sequence having an identity of 90% or more to the amino acid sequence of (i5') or (ii5'), and has a linalool synthase activity;
(C5) a protein that comprises an amino acid sequence having a deletion, substitution, addition, or insertion of one or several amino acids in the amino acid sequence of (i5') or (ii5'), and has a linalool synthase activity;
(A6) a protein that comprises (i6') an amino acid sequence consisting of a full-length amino acid sequence of SEQ ID NO: 103 (M15);
(B6) a protein that comprises an amino acid sequence having an identity of 90% or more to the amino acid sequence of (i6'), and has a linalool synthase activity;
(C6) a protein that comprises an amino acid sequence having a deletion, substitution, addition, or insertion of one or several amino acids in the amino acid sequence of (i6'), and has a linalool synthase activity;
(A7) a protein that comprises (i7') an amino acid sequence consisting of a full-length amino acid sequence of SEQ ID NO: 105 (M17);
(B7) a protein that comprises an amino acid sequence having an identity of 90% or more to the amino acid sequence of (i7'), and has a linalool synthase activity;
(C7) a protein that comprises an amino acid sequence having a deletion, substitution, addition, or insertion of one or several amino acids in the amino acid sequence of (i7'), and has a linalool synthase activity;
(A8) a protein that comprises (i8') an amino acid sequence consisting of a full-length amino acid sequence of SEQ ID NO: 107 (M19);
(B8) a protein that comprises an amino acid sequence having an identity of 90% or more to the amino acid sequence of (i8'), and has a linalool synthase activity;
(C8) a protein that comprises an amino acid sequence having a deletion, substitution, addition, or insertion of one or several amino acids in the amino acid sequence of (i8'), and has a linalool synthase activity;
(A9) a protein that comprises (i9') a full-length amino acid sequence of SEQ ID NO: 109 (M21);
(B9) a protein that comprises an amino acid sequence having an identity of 90% or more to the amino acid sequence of (i9'), and has a linalool synthase activity;
(C9) a protein that comprises an amino acid sequence having a deletion, substitution, addition, or insertion of one or several amino acids in the amino acid sequence of (i9'), and has a linalool synthase activity;

(A10) a protein that comprises (i10') an amino acid sequence consisting of a full-length amino acid sequence of SEQ ID NO: 111 (M23);
(B10) a protein that comprises an amino acid sequence having an identity of 90% or more to the amino acid sequence of (i10'), and has a linalool synthase activity;
(C10) a protein that comprises an amino acid sequence having a deletion, substitution, addition, or insertion of one or several amino acids in the amino acid sequence of (i10'), and has a linalool synthase activity;
(A11) a protein that comprises (i11') a full-length amino acid sequence of SEQ ID NO: 113 (M25);
(B11) a protein that comprises an amino acid sequence having an identity of 90% or more to the amino acid sequence of (i11'), and has a linalool synthase activity;
(C11) a protein that comprises an amino acid sequence having a deletion, substitution, addition, or insertion of one or several amino acids in the amino acid sequence of (i11'), and has a linalool synthase activity;
(A12) a protein that comprises (i12') a full-length amino acid sequence of SEQ ID NO: 115 (M27);
(B12) a protein that comprises an amino acid sequence having an identity of 90% or more to the amino acid sequence of (i12'), and has a linalool synthase activity;
(C12) a protein that comprises an amino acid sequence having a deletion, substitution, addition, or insertion of one or several amino acids in the amino acid sequence of (i12'), and has a linalool synthase activity;
(A13) a protein that comprises (i13') a full-length amino acid sequence of SEQ ID NO: 117 (M29);
(B13) a protein that comprises an amino acid sequence having an identity of 90% or more to the amino acid sequence of (i13'), and has a linalool synthase activity;
(C13) a protein that comprises an amino acid sequence having a deletion, substitution, addition, or insertion of one or several amino acids in the amino acid sequence of (i13'), and has a linalool synthase activity;
(A14) a protein that comprises (i14') a full-length amino acid sequence of SEQ ID NO: 119 (M31);
(B14) a protein that comprises an amino acid sequence having an identity of 90% or more to the amino acid sequence of (i14'), and has a linalool synthase activity;
(C14) a protein that comprises an amino acid sequence having a deletion, substitution, addition, or insertion of one or several amino acids in the amino acid sequence of (i14'), and has a linalool synthase activity;
(A15) a protein that comprises (i15') a full-length amino acid sequence of SEQ ID NO: 121 (M33);
(B15) a protein that comprises an amino acid sequence having an identity of 90% or more to the (i15') amino acid sequence and has a linalool synthase activity;
(C15) a protein that comprises an amino acid sequence having a deletion, substitution, addition, or insertion of one or several amino acids in the amino acid sequence of (i15'), and has a linalool synthase activity;
(A16) a protein that comprises (i16') a full-length amino acid sequence of SEQ ID NO: 123 (M35);
(B16) a protein that comprises an amino acid sequence having an identity of 90% or more to the amino acid sequence of (i16'), and has a linalool synthase activity;
(C16) a protein that comprises an amino acid sequence having a deletion, substitution, addition, or insertion of one or several amino acids in the amino acid sequence of (i16'), and has a linalool synthase activity;
(A17) a protein that comprises (i17') a full-length amino acid sequence of SEQ ID NO: 125 (M37);
(B17) a protein that comprises an amino acid sequence having an identity of 90% or more to the amino acid sequence of (i17'), and has a linalool synthase activity;
(C17) a protein that comprises an amino acid sequence having a deletion, substitution, addition, or insertion of one or several amino acids in the amino acid sequence of (i17'), and has a linalool synthase activity;
(A18) a protein that comprises (i18') a full-length amino acid sequence of SEQ ID NO: 127 (M39);
(B18) a protein that comprises an amino acid sequence having an identity of 90% or more to the amino acid sequence of (i18'), and has a linalool synthase activity;
(C18) a protein that comprises an amino acid sequence having a deletion, substitution, addition, or insertion of one or several amino acids in the amino acid sequence of (i18'), and has a linalool synthase activity;
(A19) a protein that comprises (i19') an amino acid sequence consisting of a full-length amino acid sequence of SEQ ID NO: 161;
(B19) a protein that comprises an amino acid sequence having an identity of 90% or more to the amino acid sequence of (i19'), and has a linalool synthase activity;
(C19) a protein that comprises an amino acid sequence having a deletion, substitution, addition, or insertion of one or several amino acids in the amino acid sequence of (i19'), and has a linalool synthase activity;
(A20) a protein that comprises (i20') a full-length amino acid sequence of SEQ ID NO: 162;
(B20) a protein that comprises an amino acid sequence having an identity of 90% or more to the amino acid sequence of (i20'), and has a linalool synthase activity;
(C20) a protein that comprises an amino acid sequence having a deletion, substitution, addition, or insertion of one or several amino acids in the amino acid sequence of (i20'), and has a linalool synthase activity;
(A21) a protein that comprises (i21') an amino acid sequence consisting of a full-length amino acid sequence of SEQ ID NO: 163;
(B21) a protein that comprises an amino acid sequence having an identity of 90% or more to the amino acid sequence of (i21'), and has a linalool synthase activity;
(C21) a protein that comprises an amino acid sequence having a deletion, substitution, addition, or insertion of one or several amino acids in the amino acid sequence of (i21'), and has a linalool synthase activity;
(A22) a protein that comprises (i22') a full-length amino acid sequence of SEQ ID NO: 164;
(B22) a protein that comprises an amino acid sequence having an identity of 90% or more to the amino acid sequence of (i22'), and has a linalool synthase activity;
(C22) a protein that comprises an amino acid sequence having a deletion, substitution, addition, or insertion of one or several amino acids in the amino acid sequence of (i22'), and has a linalool synthase activity;
(A23) a protein that comprises (i23') a full-length amino acid sequence of SEQ ID NO: 165;
(B23) a protein that comprises an amino acid sequence having an identity of 90% or more to the amino acid sequence of (i23'), and has a linalool synthase activity;
(C23) a protein that comprises an amino acid sequence having a deletion, substitution, addition, or insertion of one or several amino acids in the amino acid sequence of (i23'), and has a linalool synthase activity;
(A24) a protein that comprises (i24') a full-length amino acid sequence of SEQ ID NO: 166;

(B24) a protein that comprises an amino acid sequence having an identity of 90% or more to the amino acid sequence of (i24'), and has a linalool synthase activity;
(C24) a protein that comprises an amino acid sequence having a deletion, substitution, addition, or insertion of one or several amino acids in the amino acid sequence of (i24'), and has a linalool synthase activity;
(A25) a protein that comprises (i25') a full-length amino acid sequence of SEQ ID NO: 167;
(B25) a protein that comprises an amino acid sequence having an identity of 90% or more to the amino acid sequence of (i25'), and has a linalool synthase activity;
(C25) a protein that comprises an amino acid sequence having a deletion, substitution, addition, or insertion of one or several amino acids in the amino acid sequence of (i25'), and has a linalool synthase activity;
(A26) a protein that comprises (i26') a full-length amino acid sequence of SEQ ID NO: 168;
(B26) a protein that comprises an amino acid sequence having an identity of 90% or more to the amino acid sequence of (i26'), and has a linalool synthase activity;
(C26) a protein that comprises an amino acid sequence having a deletion, substitution, addition, or insertion of one or several amino acids in the amino acid sequence of (i26'), and has a linalool synthase activity;
(A27) a protein that comprises (i27') a full-length amino acid sequence of SEQ ID NO: 169;
(B27) a protein that comprises an amino acid sequence having an identity of 90% or more to the amino acid sequence of (i27'), and has a linalool synthase activity;
(C27) a protein that comprises an amino acid sequence having a deletion, substitution, addition, or insertion of one or several amino acids in the amino acid sequence of (i27'), and has a linalool synthase activity;
(A28) a protein that comprises (i28') a full-length amino acid sequence of SEQ ID NO: 172;
(B28) a protein that comprises an amino acid sequence having an identity of 90% or more to the amino acid sequence of (i28'), and has a linalool synthase activity;
(C28) a protein that comprises an amino acid sequence having a deletion, substitution, addition, or insertion of one or several amino acids in the amino acid sequence of (i28'), and has a linalool synthase activity;
(A29) a protein that comprises (i29') a full-length amino acid sequence of SEQ ID NO: 175;
(B29) a protein that comprises an amino acid sequence having an identity of 90% or more to the amino acid sequence of (i29'), and has a linalool synthase activity;
(C29) a protein that comprises an amino acid sequence having a deletion, substitution, addition, or insertion of one or several amino acids in the amino acid sequence of (i29'), and has a linalool synthase activity;
(A30) a protein that comprises (i30') a full-length amino acid sequence of SEQ ID NO: 178;
(B30) a protein that comprises an amino acid sequence having an identity of 90% or more to the amino acid sequence of (i30'), and has a linalool synthase activity;
(C30) a protein that comprises an amino acid sequence having a deletion, substitution, addition, or insertion of one or several amino acids in the amino acid sequence of (i30'), and has a linalool synthase activity;
(A31) a protein that comprises (i31') a full-length amino acid sequence of SEQ ID NO: 181;
(B31) a protein that comprises an amino acid sequence having an identity of 90% or more to the amino acid sequence of (i31'), and has a linalool synthase activity;
(C31) a protein that comprises an amino acid sequence having a deletion, substitution, addition, or insertion of one or several amino acids in the amino acid sequence of (i31'), and has a linalool synthase activity; and
(A32) combinations thereof.

8. The method according to claim 1, wherein the bacterium expresses geranyl diphosphate synthase.

9. The method according to claim 1, wherein the bacterium is *Escherichia coli*, *Pantoea ananatis*, *Synechocystis* sp., or *Corynebacterium glutamicum*.

10. The method according to claim 1, wherein a 2-ketogluconate formation pathway is blocked in the bacterium.

11. The method according to claim 10, wherein the 2-ketogluconate formation pathway is blocked by reduction of a glucose dehydrogenase activity.

12. The method according to claim 11, wherein a glucose dehydrogenase gene is disrupted in the microorganism.

13. The method according to claim 12, wherein the polynucleotide is selected from the group consisting of:
(x) a polynucleotide that comprises:
[i] a nucleotide sequence of SEQ ID NO: 59 or
[ii] a nucleotide sequence consisting of nucleotide residues at positions 301 to 2691 in the nucleotide sequence of SEQ ID NO: 59;
(y) a polynucleotide that comprises a nucleotide sequence having an identity of 90% or more to the nucleotide sequence of [i] or [ii], and encodes a protein having a glucose dehydrogenase activity;
(z) a polynucleotide that hybridizes under stringent conditions with a polynucleotide comprising a nucleotide sequence complementary to the nucleotide sequence of [i] or [ii], and encodes a protein having a glucose dehydrogenase activity, wherein the stringent conditions are hybridization in 6×SCC (sodium chloride/sodium citrate) at about 45° C. followed by one or two or more washings in 0.2×SCC and 0.1% SDS at 50 to 65° C.; and
(z') combinations thereof.

14. The method according to claim 11, wherein the glucose dehydrogenase is a protein selected from the group consisting of:
(X) a protein that comprises a full-length amino acid sequence of SEQ ID NO: 60;
(Y) a protein that comprises an amino acid sequence having an identity of 90% or more to the amino acid sequence of SEQ ID NO: 60, and has a glucose dehydrogenase activity;
(Z) a protein that comprises an amino acid sequence having a deletion, substitution, addition, or insertion of one or several amino acids in the amino acid sequence of SEQ ID NO: 60, and has a glucose dehydrogenase activity; and
(Z') combinations thereof.

15. The method according to claim 1, wherein an amount of linalool accumulated in the culture medium is 200 mg/L or more.

16. The method according to claim 1, wherein an amount of linalool accumulated in the culture medium is 500 mg/L or more.

* * * * *